US008450522B2

(12) United States Patent
Brown et al.

(10) Patent No.: US 8,450,522 B2
(45) Date of Patent: May 28, 2013

(54) CONFORMATIONALLY CONSTRAINED CARBOXYLIC ACID DERIVATIVES USEFUL FOR TREATING METABOLIC DISORDERS

(75) Inventors: Sean P. Brown, San Francisco, CA (US); Paul J. Dransfield, San Francisco, CA (US); Jonathan Houze, San Mateo, CA (US); Todd J. Kohn, San Mateo, CA (US); Jiwen Liu, Foster City, CA (US); Julio Medina, San Carlos, CA (US); Vatee Pattaropong, Burlingame, CA (US); Wang Shen, San Mateo, CA (US); Marc Vimolratana, San Mateo, CA (US); Yingcai Wang, Millbrae, CA (US); Ming Yu, Foster City, CA (US); Liusheng Zhu, Foster City, CA (US)

(73) Assignee: Amgen Inc., Thousand Oaks, CA (US)

( * ) Notice: Subject to any disclaimer, the term of this patent is extended or adjusted under 35 U.S.C. 154(b) by 137 days.

(21) Appl. No.: 12/863,578

(22) PCT Filed: Mar. 4, 2009

(86) PCT No.: PCT/US2009/001435
§ 371 (c)(1),
(2), (4) Date: Jul. 19, 2010

(87) PCT Pub. No.: WO2009/111056
PCT Pub. Date: Sep. 11, 2009

(65) Prior Publication Data

US 2010/0298367 A1 Nov. 25, 2010

Related U.S. Application Data

(60) Provisional application No. 61/068,733, filed on Mar. 6, 2008, provisional application No. 61/196,249, filed on Oct. 15, 2008.

(51) Int. Cl.
*C07C 63/00* (2006.01)
*A61K 31/185* (2006.01)

(52) U.S. Cl.
USPC ............................ 562/405; 514/576; 514/577

(58) Field of Classification Search
None
See application file for complete search history.

(56) References Cited

U.S. PATENT DOCUMENTS

| | | | |
|---|---|---|---|
| 3,507,881 | A | 4/1970 | Sandberg et al. |
| 4,760,089 | A | 7/1988 | Chambers et al. |
| 5,312,960 | A | 5/1994 | Krämer et al. |
| 6,037,367 | A | 3/2000 | Christensen, IV et al. |
| 6,506,757 | B1 | 1/2003 | Tajima et al. |
| 6,620,832 | B2 | 9/2003 | Eastwood |
| 6,645,939 | B1 | 11/2003 | Durette et al. |
| 6,710,063 | B1 | 3/2004 | Chao et al. |
| 6,723,740 | B2 | 4/2004 | Chao et al. |
| 6,875,780 | B2 | 4/2005 | Auerbach et al. |
| 6,906,046 | B2 | 6/2005 | Jackson et al. |
| 6,939,875 | B2 | 9/2005 | Auerbach et al. |
| 6,964,983 | B2 | 11/2005 | Auerbach et al. |
| 7,326,732 | B2 | 2/2008 | Oxford et al. |
| 7,338,960 | B2 | 3/2008 | Bell et al. |

(Continued)

FOREIGN PATENT DOCUMENTS

| | | |
|---|---|---|
| AU | A 27141/77 | 1/1979 |
| AU | A 52306/93 | 6/1994 |

(Continued)

OTHER PUBLICATIONS

International Search Report and Written Opinion from parent PCT Application No. PCT/US2009/001435 mailed on Jul. 15, 2009.

(Continued)

*Primary Examiner* — Sreeni Padmanabhan
*Assistant Examiner* — Svetlana M Ivanova
(74) *Attorney, Agent, or Firm* — Bernard P. Friedrichsen

(57) ABSTRACT

The present invention provides compounds useful, for example, for treating metabolic disorders in a subject. Such compounds have the general formula I or the general formula III:

I

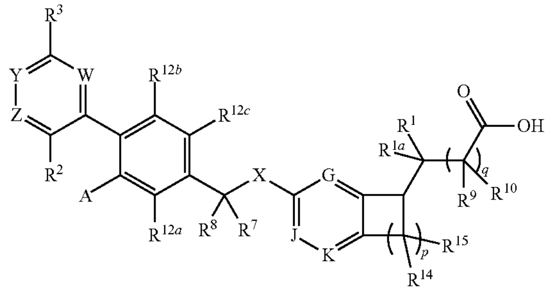

III

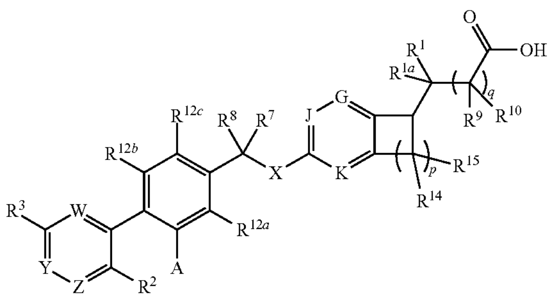

where the definitions of the variables are provided herein. The present invention also provides compositions that include, and methods for using, the compounds in preparing medicaments and for treating metabolic disorders such as, for example, type II diabetes.

17 Claims, 1 Drawing Sheet

U.S. PATENT DOCUMENTS

| | | | |
|---|---|---|---|
| 7,345,068 | B2 | 3/2008 | Endou et al. |
| 7,572,934 | B2 | 8/2009 | Brown et al. |
| 2004/0058965 | A1 | 3/2004 | Momose et al. |
| 2005/0089866 | A1 | 4/2005 | Hinuma et al. |
| 2005/0119256 | A1 | 6/2005 | Endo et al. |
| 2006/0003344 | A1 | 1/2006 | Houseknecht et al. |
| 2006/0004012 | A1 | 1/2006 | Akerman et al. |
| 2006/0270724 | A1 | 11/2006 | Houze et al. |
| 2007/0066647 | A1 | 3/2007 | Akerman et al. |
| 2007/0149608 | A1 | 6/2007 | Yasuma et al. |
| 2007/0244155 | A1 | 10/2007 | Sharma et al. |
| 2007/0265332 | A1 | 11/2007 | Ge et al. |
| 2008/0020148 | A1 | 1/2008 | Klein et al. |
| 2008/0090840 | A1 | 4/2008 | Beck et al. |
| 2008/0119511 | A1 | 5/2008 | Brown et al. |
| 2009/0137561 | A1 | 5/2009 | Brown et al. |

FOREIGN PATENT DOCUMENTS

| | | | |
|---|---|---|---|
| CA | 2111035 | | 6/1994 |
| DE | 199 41 567 | A1 | 4/2000 |
| DE | 199 41567 | A1 | 4/2000 |
| DE | 10 2005 045 849 | A1 | 9/2005 |
| EP | 0 250 264 | A1 | 12/1987 |
| EP | 0 414 289 | B1 | 2/1994 |
| EP | 1 357 115 | A1 | 10/2003 |
| EP | 1 380 562 | A1 | 1/2004 |
| EP | 1 535 915 | A1 | 6/2005 |
| EP | 1 559 422 | A1 | 8/2005 |
| EP | 1 630 152 | A1 | 3/2006 |
| EP | 1630152 | A1 * | 3/2006 |
| EP | 1 731 505 | A1 | 12/2006 |
| JP | 10316641 | A | 2/1998 |
| JP | 2001242165 | | 9/2001 |
| JP | 2002003368 | | 1/2002 |
| WO | WO 93/23040 | | 11/1993 |
| WO | WO 93/23041 | | 11/1993 |
| WO | WO 95/01326 | | 1/1995 |
| WO | WO 95/01348 | | 1/1995 |
| WO | WO 97/12867 | | 4/1997 |
| WO | WO 99/11255 | | 3/1999 |
| WO | WO 01/00603 | A1 | 1/2001 |
| WO | WO 01/36351 | A2 | 5/2001 |
| WO | WO 01/36365 | A2 | 5/2001 |
| WO | WO 02/057783 | A2 | 7/2002 |
| WO | WO 02/062774 | A1 | 8/2002 |
| WO | WO 00/63196 | | 10/2002 |
| WO | WO 02/100403 | A1 | 12/2002 |
| WO | WO 03/074050 | A1 | 9/2003 |
| WO | WO 03/099793 | A1 | 12/2003 |
| WO | WO 2004/000315 | A1 | 12/2003 |
| WO | WO 2004/092117 | A1 | 10/2004 |
| WO | WO 2004/106276 | A1 | 12/2004 |
| WO | WO 2005/051890 | A1 | 6/2005 |
| WO | WO 2005/058848 | A1 | 6/2005 |
| WO | WO 2005/063725 | A1 | 7/2005 |
| WO | WO 2005/063729 | A1 | 7/2005 |
| WO | WO 2005/087710 | A1 | 9/2005 |
| WO | WO 2006/001092 | A1 | 1/2006 |
| WO | WO 2006/011615 | A1 | 2/2006 |
| WO | WO 2006/083612 | A1 | 8/2006 |
| WO | WO 2006/083781 | A1 | 8/2006 |
| WO | WO 2007/008541 | A2 | 1/2007 |
| WO | WO 2007106469 | A2 * | 9/2007 |
| WO | WO 2007/123225 | A1 | 11/2007 |
| WO | WO 2007/131619 | A1 | 11/2007 |
| WO | WO 2007/131620 | A1 | 11/2007 |
| WO | WO 2007/131622 | A1 | 11/2007 |
| WO | WO 2007/147516 | A1 | 12/2007 |
| WO | WO 2008001931 | A2 * | 1/2008 |

OTHER PUBLICATIONS

Bachmann, W. E. et al., "The Synthesis of an Analog of the Sex Hormones," *J. Am. Chem. Soc.*, 64, 94-97 (1942).

Berthelot et al., "Synthesis and Pharmacological Evaluation of γ-Aminobutyric Acid Analogues. New Ligand for GABA$_B$ Sites," *J. Med. Chem.*, 30, 743-746 (1987).

Booth, C. J. et al., "The Synthesis and Transition Temperatures of Novel Low Molar Mass Cholesteric materials Derives from (R)-2-(4-Hydroxyphenoxy)propanoic Acid," Mol. Cryst. Liq. Cryst., vol. 210, pp. 31-57 (1992).

Booth, C. J. et al., "The Influence of the Liquid Crystalline Core Geometry on the Mesogenicity of Novel Chiral 2-(4-Substituted-phenoxy)propanonitriles," Liquid Crystals, vol. 16(6), pp. 925-940, (1994).

Boyle, Thomas F. et al., "Applications of the Spiroannulation of Tetralins with Alkynes; Towards New Anti-Estrogenic Compounds," *J. Chem. Soc. Perkin Trans. I: Organic and Bioorganic Chem.*, 18, 2707-2711 (1997).

Briscoe et al., "The Orphan G Protein-Coupled Receptor GPR40 is Activated by Medium and Long Chain Fatty Acids," *J. of Biol. Chem.*, 278(13), 11303-11311 (2003).

Briscoe, C. P. et al., "Pharmacological Regulation of Insulin Secretion in MIN6 Cells Through the Fatty Acid Receptor GPR40: Identification of Agonist and Antagonist Small Molecules," *Brit. J. of Pharmacology*, 148, 619-628 (2006).

Burnop, V.C.E. et al., "Fused Carbon Rings. Part XIX. Experiments on the Synthesis of Tetracyclic Compounds of the Sexual Hormonal Type," *J. Chem. Soc.*, 727-735 (1940).

Chatterjee, A., et al., "Studies on Nucleophilic Ring Opening of Some Epoxides in Polar Protic Solvents," *Tetrahedron*, 33, 85-94 (1977).

Collins, David J. et al., "The Structure and Function of Oestrogens. IX*. Synthesis of the trans Isomer of 5,5,10b-Trimtehyl-4b,5,6,10b,11,12-hexahydrocvhrysene-2,8-diol," *Aust. J. Chem.*, 41, 735-744 (1988).

Deb, Soumitra et al., "A Stereocontrolled Synthesis of (1'RS,2'SR)-3-oxo-3',4'-dihydrospiro[cyclopentane-1,1'(2'H)-naphthalen]-2-yl Acetic Acid and its Methoxy Derivatives," *J. Chem. Res. Synops.*, 12, 406 (1985).

DeWolf et al., "Inactivation of Dopamine β-Hydroxylase by β-Ethynyltyramine: Kinetic Characterization and Covalent Modification of an Active Site Peptide," *Biochemistry*, 28, 3833-3842 (1989).

Egan, R. W. et al., "Naphthalenes as Inhibitors of Myeloperoxidase: Direct and Indirect Mechanisms of Inhibition," *Agents and Actions*, 29 3/4 266-276 (1990).

Frey et al., "Total Synthesis of Pentacyclic Diterpenoid Tropone Hainanolidol," *Aust. J. Chem.*, 53, 819-830 (2000).

Galemmo et al., "The Development of a Novel Series of (Quinolin-2-ylmethoxy) phenyl-Containing Compounds as High-Affinity Leukotriene Receptor Antagonists. 3. Structural Variation of the Acidic Side Chain to Give Antagonists of Enhanced Potency," *J. Med. Chem.*, 33, 2828-2841 (1990).

Garrido, D. M., et al., "Synthesis and Activity of Small Molecule GPR40 Agonists," *Bioorg. and Med. Chem. Lett.*, 16, 1840-1845 (2006).

Ghosal, Probir Kumar, et al., "Stereospecific Synthesis of 9bβ-Carbomethoxy-7-methoxy-2,3,3aα,4,5,9bβ-Hexahydro-1H-Benz[e]-Inden-2-one; An Intermediate Towards Physiologically Active Compounds," *Tet. Lett.*, 17, 1463-1464 (1977).

Guthrie, R. W. et al., "Synthesis in the Series of Diterpene Alkaloids VI. A Simple Synthesis of Atisine," *Tet. Lett.*, 38, 4645-4654 (1966).

Haigh et al., "Non-thiazolidinedione Antihyperglycaemic Agents. Part 3: The Effects of Stereochemistry on the Potency of α-Methoxy-β-phenylpropanoic Acids," *Bioorg. and Med. Chem.*, 7, 821-830 (1999).

Hares, Owen et al., "Synthetic Studies of Tricyclospirodienones: Model Chemistry for Novel Mimics of Steroid Substrates," *J. Chem. Soc. Perkin Trans. I: Organic and Bioorganic Chem.*, 13, 1481-1492 (1993).

Houze, J. et al., "Beta-substituted Carboxylic Acids as Potent, Bioavailable Agonists of GPR40", 234$^{th}$ ACS National Meeting Boston, MA Aug. 19-23, 2007.

Iizuka et al., "β-Substituted Phenethylamines as High Affinity Mechanism-Based Inhibitors of Dopamine β-Hydroxylase," *J. Med. Chem.*, 31, 704-706 (1988).

Ishikawa et al., "Actions of the Novel Oral Antidiabetic Agent HQL-975 in Insulin-Resistant Non-Insulin—Dependent Diabetes Mellitus Model Animals," *Diabetes Res. and Clin. Pract.*, 41, 101-111 (1998).

Ishikawa et al., "Effects of the Novel Oral Antidiabetic Agent HQL-975 on Glucose and Lipid Metabolism in Diabetic db/db Mice," *Arzneim. Forsch. Drug Res.*, 48(3), 245-250 (1998).
Itoh et al., "Free Fatty Acids Regulate Insulin Secretion from Pancreatic β Cells Through GPR40," *Nature*, 422, 173-176 (2003).
Johns, William F. et al., "Total Synthesis of Estrajervatetraene," *J. Org. Chem.*, 44(6), 958-961 (1979).
Kao et al., "One-Pot Synthesis of the Hydroximoyl Chlorides and [3.3.0] Bicyclic Compounds from the Reactions of β-Nitrostyrenese with Stabilized Nucleophiles," Tetrahedron, 54(46), 13997-14014 (1998).
Kolasa et al., "Symmetrical Bis (heteroarylmethoxyphenyl) alkylcarboxylic Acids as Inhibitors of Leukotriene Biosynthesis," *J. Med. Chem.*, 43, 3322-3334 (2000).
Kotarsky et al., "A Human Cell Surface Receptor Activated by Free Fatty Acids and Thiazolidinedione Drugs", *Biochem. and Biophys. Res. Comm.*, 301, 406-410 (2003).
Kuchar et al., "Benzyloxyarylaliphatic Acids: Synthesis and Quantitative Relations Between Structure and Antiinflammatory Activity," *Collection Czechoslovak Chem, Comm.*, 47, 2514-2524 (1982).
Kuchar et al., "The Effects of Lopophilicity on the Inhibition of Denaturation of Serum Albumin and on the Activation of Fibrionolysis Observed with a Serixes of Benzyloxyarylaliphatic Acids," *Collection Czechoslovak Chem, Comm.*, 48, 1077-1088 (1983).
Lin, Llnus S. et al., "The Discovery of Acylated β-Amino Acids as Potent and Orally Bioavailable VLA-4 Antagonists," *Bioorg. and Med. Chem. Lett.*, 12, 611-614 (2002).
Liu et al., "Synthesis and Biological Activity of L-Tyrosine-based PPARγ Agonists with Reduced Molecular Weight," *Bioorg. and Med. Chem. Lett.*, 11, 3111-3113 (2001).
McKeown, S.C. et al., "Solid Phase Synthesis and SAR of Small Molecule Agonists for the GPR40 Receptor," *Bioorg. and Med. Chem. Lett.*, 17, pp. 1584-1589 (2007).
Nilsson, N. E. et al., "Identification of a Free Fatty Acid Receptor, $FFA_2R$, Expressed on Leukocytes and Activated by Short-Chain Fatty Acids," *Biochem. and Biophys. Res. Comm.*, 303 1047-1052 (2003).
Oliver et al., "A Selective Peroxisome Proliferator-Activated Receptor δ Agonist Promotes Reverse Cholesterol Transport," *PNAS*, 98(9), 5306-5311 (2001).
Poitout, Vincent, "The Ins and Outs of Fatty Acids on the Pancreatic β Cells," *Trends in Endocrinology and Metabolism*, 14(5), 201-203 (2003).
Ray, Chhanda et al., "Synthesis of some angularly cyclopentanone fused hydrophenanthrene and hydrofluorene derivatives by acid-catalyzed intramolecular C-alkylation of γ, δ-unsaturated α'-diazomethyl ketones," *Synthetic Commun.*, 21(10-11), 1223-1242 (1991).
Sandberg, Rune et al., "N-Aminoalkylsuccinimides as Local Anaesthetics," *Acta Pharmaceutica Suecica*, 17(4) 169-176 (1980).
Sanyal, Utpal et al., "A Novel Synthesis of a Tricyclo ($7.5.0^{1,5}.0^{1,9}$) Tetradecane Ring System Related to Gascardic Acid," *Tet. Lett.*, 25, 2187-2190 (1978).
Sarma, Aluru Sudarsana et al., "Synthetic Studies on Terpenoids. Parts XVIII. Stereocontrolled Synthesis of (+/−)-1,2,3,4,4a,9,10,10aα-Octahydro-1α-methylenephenanthrene-1β,4aβ-dicarboxylic acid and the 7-Methoxy Analog: A Potential Intermediate for Diterpinoid Synthesis," *J. Chem. Soc. Perkin Trans. I: Organic and Bioorganic Chem.*, 7, 722-727 (1976).
Sawzdargo et al., "A Cluster of Four Novel Human G Protein-Coupled Receptor Genes Occurring in Close Proximity to CD22 Gene on Chromosome 19q13.1", *Biochem. and Biophys. Res. Comm.*, 239, 543-547 (1997).
Shaw et al., "Enantioselective Synthesis of (+)-(2S, 3S)-3-Ethyltyrosine," *Tet. Lett.*, 31(35), 5081-84 (1990).
Shiotani, Shunsaku et al., "Synthesis of 1,3-Bridged 1,2,3,4,5,6-Hexahydro-2,6-methano-3-benzazocine Derivatives," *Chem. Pharm. Bull.*, 28(6), 1928-1931 (1980).
Song, F. et al., "Synthesis and Biological Evaluation of 3-Aryl-3-(4-phenoxy)-propionic Acid as a Novel Series of G Protein-Coupled REceptor 40 Agonists," J. Med. Chem. 50 pp. 2807-2817 (2007).
Waid et al., "Constrained Amino Acids. An Approach to the Synthesis of 3-Substituted Prolines," *Tet. Lett.*, 37(24), 4091-4094 (1996).

* cited by examiner

GPR40 Binding Displacement Assay
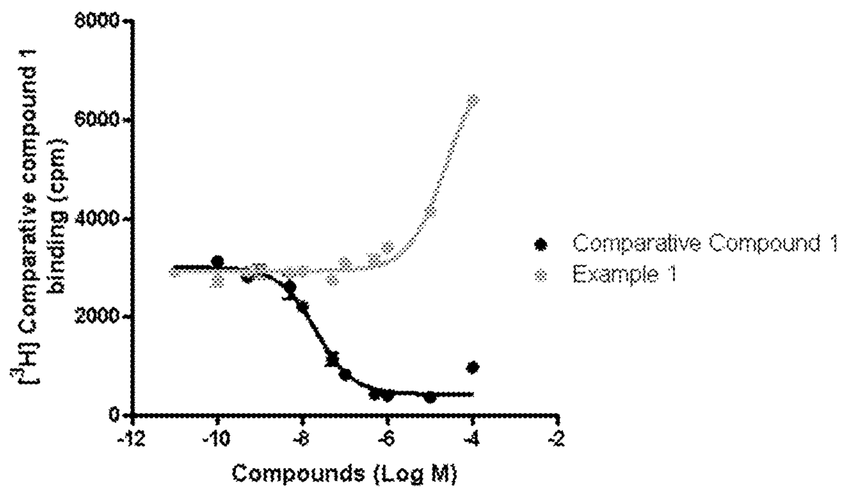
| | Comparative Compound 1 | Example 1 |
|---|---|---|
| BOTTOM | 438.1 | 7164 |
| TOP | 3010 | 2939 |
| LOGEC50 | -7.680 | -4.634 |
| EC50 | 2.087e-008 | 2.322e-005 |
| Ki | 1.392e-008 | 1.548e-005 |

CONFORMATIONALLY CONSTRAINED CARBOXYLIC ACID DERIVATIVES USEFUL FOR TREATING METABOLIC DISORDERS

1. CROSS REFERENCES TO RELATED APPLICATIONS

This application is a national stage application under 35 U.S.C. §371 of International Application No. PCT/US2009/001435, having an international filing date of Mar. 4, 2009, which claims the benefit of, and priority to, U.S. Provisional Application No. 61/068,733, filed on Mar. 6, 2008, and U.S. Provisional Application No. 61/196,249, filed on Oct. 15, 2008, each of which is hereby incorporated by reference in their entireties and for all purposes as if fully set forth herein.

2. FIELD OF THE INVENTION

The present invention relates to compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

3. BACKGROUND OF THE INVENTION

The production of insulin is central to the regulation of carbohydrate and lipid metabolism. Insulin imbalances lead to conditions such as type II diabetes mellitus, a serious metabolic disease that afflicts around 5% of the population in Western Societies and over 150 million people worldwide. Insulin is secreted from pancreatic β cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors ("GPCRs"). GPCRs are membrane proteins characterized as having seven putative transmembrane domains that respond to a variety of molecules by activating intra-cellular signaling pathways critical to a diversity of physiological functions. GPR40 was first identified as an orphan receptor (i.e., a receptor without a known ligand) from a human genomic DNA fragment. Sawzdargo et al. (1997) *Biochem. Biophys. Res. Commun.* 239: 543-547. GPR40 is highly expressed in pancreatic β cells and insulin-secreting cell lines. GPR40 activation is linked to modulation of the $G_q$ family of intra-cellular signaling proteins and concomitant induction of elevated calcium levels. It has been recognized that fatty acids serve as ligands for GPR40, and that fatty acids regulate insulin secretion through GPR40. Itoh et al. (2003) *Nature* 422:173-176; Briscoe et al. (2003) *J. Biol. Chem.* 278: 11303-11311; Kotarsky et al. (2003) *Biochem. Biophys. Res. Commun.* 301: 406-410.

Various documents have disclosed compounds reportedly having activity with respect to GPR40. For example, WO 2004/041266 and EP 1559422 disclose compounds that purportedly act as GPR40 receptor function regulators. WO 2004/106276 and EP 1630152 are directed to condensed ring compounds that purportedly possess GPR40 receptor function modulating action. More recently, WO 2005/086661 U.S. Patent Publication No. 2006/0004012, US Patent Publication No. 2006/0270724, and US Patent Publication No. 2007/0066647 disclose compounds useful for modulating insulin levels in subjects and useful for treating type II diabetes.

Although a number of compounds have been disclosed that reportedly modulate GPR40 activity, the prevalence of type II diabetes, obesity, hypertension, cardiovascular disease and dyslipidemia underscores the need for new therapies to effectively treat or prevent these conditions.

4. SUMMARY OF THE INVENTION

Provided herein are compounds, pharmaceutical compositions, and methods useful for treating or preventing a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema.

In one aspect, the present invention provides a compound of formula I or a compound of formula III or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof:

I

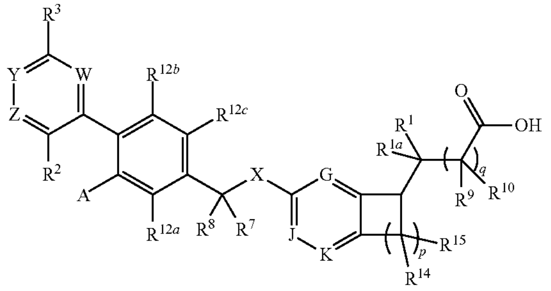

III

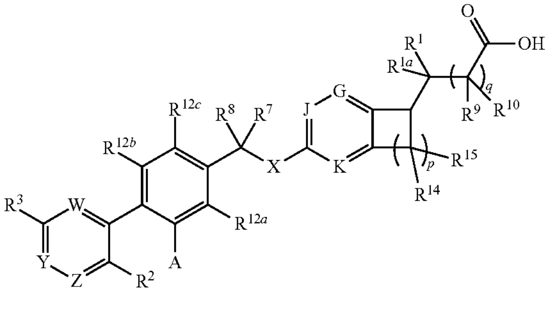

where

G is selected from N or $CR^{11a}$;

J is selected from N or $CR^{11b}$;

K is selected from N or $CR^{11c}$;

wherein 0 or 1 of G, J, and K is N;

A is selected from ($C_1$-$C_{12}$)alkyl, ($C_2$-$C_{12}$)alkenyl, —O—($C_1$-$C_{12}$)alkyl, —O—($C_2$-$C_{12}$)alkenyl, —O—($C_1$-$C_4$)alkyl-aryl, or a 4 to 7 membered heterocycle comprising 1 or 2 heteroatoms selected from N or O, wherein the heterocycle comprises 0 or 1 one double bond between ring members;

X is O or S;

W, Y, and Z are selected from N or $CR^{13}$; wherein 0 or 1 of W, Y, and Z is N; and further wherein Z is not N if $R^2$ is F;

$R^1$ is selected from H, $(C_1-C_6)$alkyl, $(C_2-C_6)$alkenyl, $(C_2-C_6)$alkynyl, —$(C_1-C_4)$alkyl-O—$(C_1-C_4)$alkyl, heterocyclyl, aryl, or heteroaryl;

$R^{1a}$ is selected from H and $(C_1-C_4)$alkyl;

$R^2$ is selected from H, F, $CF_3$, or $(C_1-C_6)$alkoxy;

$R^3$ is H, —OH, —$O(C_1-C_2)$alkyl, or —$S(C_1-C_2)$alkyl;

$R^7$ and $R^8$ are independently selected from H and $(C_1-C_4)$alkyl;

$R^9$, $R^{10}$, $R^{14}$, and $R^{15}$ are, in each instance independently selected from H and $(C_1-C_4)$alkyl and $R^9$ and $R^{10}$ are absent if q is 0;

Each of $R^{11a}$, $R^{11b}$, and $R^{11c}$ is independently selected from H, F, Cl, $(C_1-C_4)$alkyl, or $(C_1-C_4)$alkoxy; and $R^{11a}$ is absent if G is N; $R^{11b}$ is absent if J is N; or $R^{11c}$ is absent if K is N;

Each of $R^{12a}$, $R^{12b}$, and $R^{12c}$ is independently selected from H, F, Cl, $(C_1-C_4)$alkyl, or $(C_1-C_4)$alkoxy;

$R^{13}$ is selected from H, F, $(C_1-C_4)$alkyl, and —O—$(C_1-C_4)$alkyl;

q is 0 or 1; and p is 1, 2, 3, or 4.

In some embodiments, the compound of formula I or formula III, is a compound of formula I.

In some embodiments, the compound of formula I or formula III, is a compound of formula III.

In some embodiments of the compound of formula I or formula III, G is $CR^{11a}$; J is $CR^{11b}$; and K is $CR^{11c}$. In some such embodiments, each of $R^{11a}$, $R^{11b}$, and $R^{11c}$ is H.

In some embodiments of the compound of formula I or formula III, G is $CR^{11a}$; J is $CR^{11b}$; and K is N. In other embodiments, G is $CR^{11a}$; J is N; and K is $CR^{11}$. In still other embodiments, G is N; J is $CR^{11b}$; and K is $CR^{11}$.

In some embodiments of the compound of formula I or formula III, $R^3$ is selected from —OH, —$O(C_1-C_2)$alkyl, or —$S(C_1-C_2)$alkyl. In some such embodiments, $R^3$ is —$O(C_1-C_2)$alkyl. In some such embodiments, $R^3$ is —$OCH_3$.

In some embodiments of the compound of formula I or formula III, $R^1$ is selected from H and $(C_1-C_4)$alkyl. In some such embodiments, $R^1$ and $R^{1a}$ are independently selected from H and $CH_3$. In some such embodiments, $R^1$ and $R^{1a}$ are both H. In other such embodiments, one of $R^1$ and $R^{1a}$ is H and the other of $R^1$ and $R^{1a}$ is $CH_3$. In still other such embodiments, $R^1$ and $R^{1a}$ are both $CH_3$.

In some embodiments of the compound of formula I or formula III, each instance of $R^{14}$ and $R^{15}$ is selected from H and $CH_3$.

In some embodiments of the compound of formula I or formula III, $R^2$ is selected from F, $CF_3$, or $(C_1-C_6)$alkoxy. In some such embodiments, $R^2$ is F.

In some embodiments of the compound of formula I formula III, $R^2$ is H or F.

In some embodiments of the compound of formula I or formula III, $R^2$ is butoxy In some embodiments of the compound of formula I or formula III, each of $R^{11a}$, $R^{11b}$, $R^{11c}$, $R^{12a}$, $R^{12b}$, and $R^{12c}$ is H.

In some embodiments of the compound of formula I or formula III, q is 0.

In some embodiments of the compound of formula I or formula III, W, Y, and Z are all C—H In some embodiments of the compound of formula I or formula III, X is O.

In some embodiments of the compound of formula I or formula III, A is selected from $(C_3-C_{10})$alkyl or $(C_4-C_{10})$alkenyl.

In some embodiments of the compound of formula I or formula III, A is a group of formula A'

A'

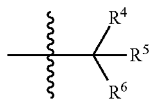

where the wavy line indicates the point of attachment; and $R^4$, $R^5$, and $R^6$ are independently selected from H, F, or $(C_1-C_4)$alkyl, wherein at least two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring.

In some embodiments of the compound of formula I or formula III, $R^7$ and $R^8$ are both H. In other embodiments, at least one of $R^7$ and $R^8$ is $CH_3$.

In some embodiments of the compound of formula I or formula III, G is $CR^{11a}$; J is $CR^{11b}$; K is $CR^{11c}$; $R^{11a}$, $R^{11b}$, $R^{11c}$, $R^{12a}$, $R^{12b}$, and $R^{12c}$ are all H; W is C—H; Y, is C—H; Z is C—H; $R^2$ is F; $R^3$ is methoxy; $R^7$ is H; $R^8$ is H; X is O, q is 0, and p is 1, 2, or 3.

In some embodiments of the compound of formula I or formula III, A is a branched chain $(C_4-C_8)$alkyl group. In some such embodiments, A is a t-butyl group.

In some embodiments of the compound of formula I or formula III, A is an optionally substituted $(C_5-C_7)$cycloalkyl group or an optionally substituted $(C_5-C_7)$cycloalkenyl group. In some such embodiments, the $(C_5-C_7)$cycloalkyl group or the $(C_5-C_7)$cycloalkenyl group is substituted with 1, 2, 3, or 4 methyl groups.

In some embodiments of the compound of formula I or formula III, A is a group of formula

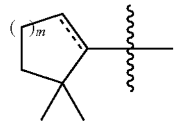

wherein m is 1, 2, or 3, and the dashed line indicates a single or double bond In some such embodiments, A is a group of formula

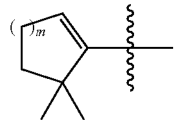

wherein m is 1, 2, or 3.

In some embodiments of the compound of formula I or formula III, A is —$OCF_3$.

In some embodiments of the compound of formula I or formula III, A is —O—$(C_3-C_{10})$alkyl or —O—$(C_3-C_{10})$alkenyl.

In some embodiments of the compound of formula I or formula III, A is —O—$(C_3-C_8)$cycloalkyl optionally substituted with 1 or 2 methyl groups.

In some embodiments, the compound of formula I is a compound of formula IIA, IIB, or IIC, or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula IIA, IIB, and IIC have the following structures where each of the variables has any of the values of any of the embodiments described herein:

IIA

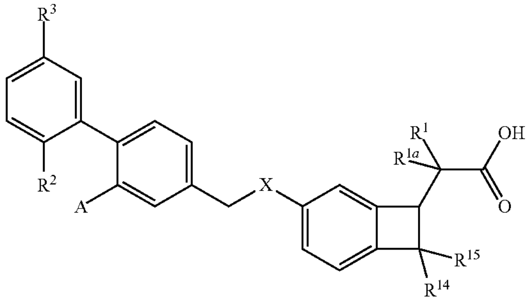

IIB

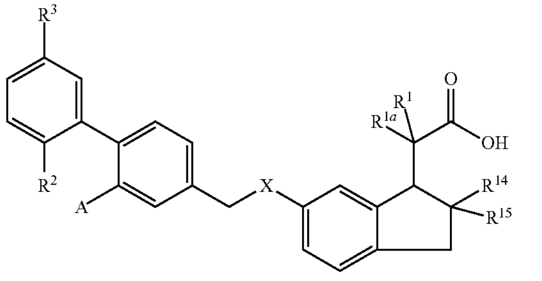

IIC

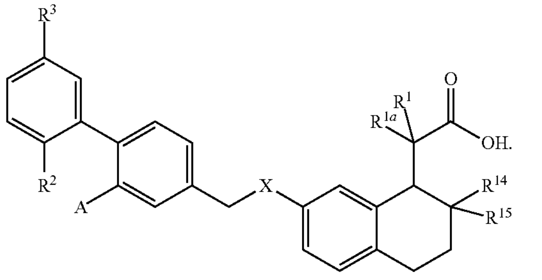

In some embodiments, the compound of formula IIA, IIB, or IIC, is a compound of formula IIA', IIB', or IIC' or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula IIA', IIB', and IIC' have the following structures where each of the variables has any of the values of any of the embodiments described herein:

IIA'

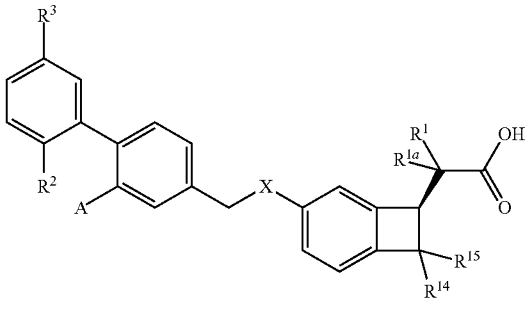

-continued

IIB'

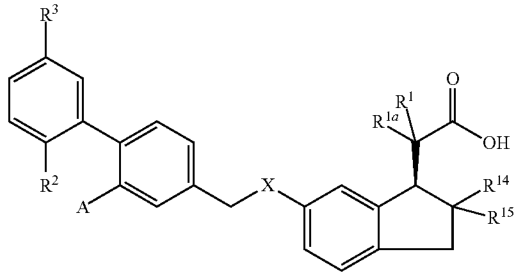

IIC'

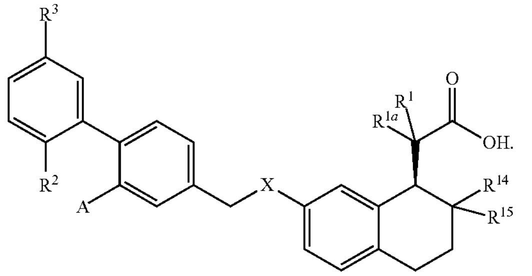

In some embodiments, the compound of formula IIA, IIB, or IIC, is a compound of formula IIA", IIB", or IIC" or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula IIA", IIB", and IIC" have the following structures where each of the variables has any of the values of any of the embodiments described herein:

IIA"

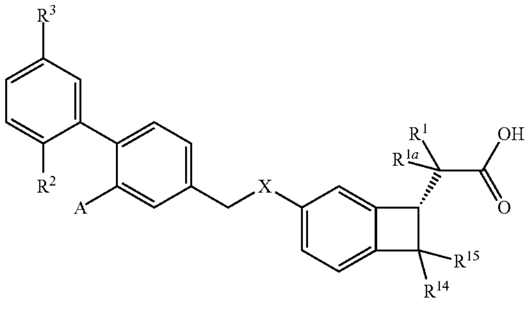

IIB"

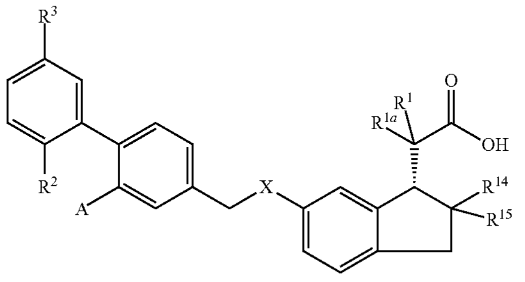

-continued

IIC″

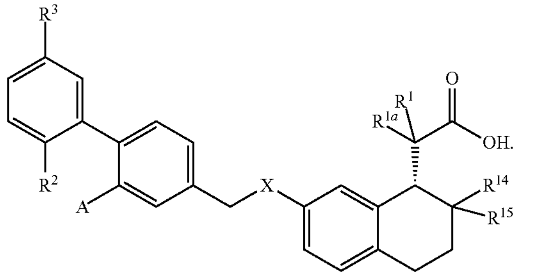

In another aspect, the present invention provides a compound of formula IV or a compound of formula VI or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof:

IV

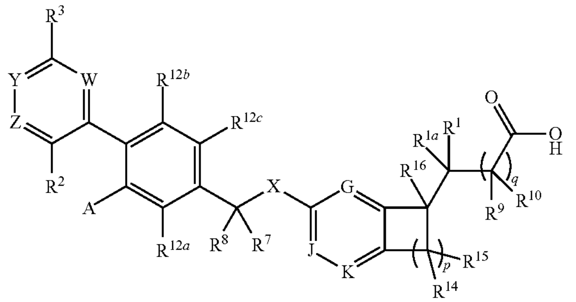

VI

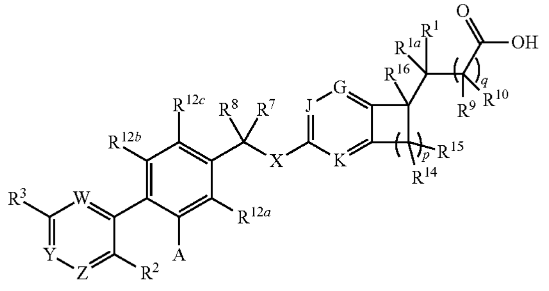

where

G is selected from N or $CR^{11a}$;

J is selected from N or $CR^{11b}$;

K is selected from N or $CR^{11c}$;

wherein 0 or 1 of G, J, and K is N;

A is selected from —($C_1$-$C_{12}$)alkyl; —($C_2$-$C_{12}$)alkenyl; —($C_1$-$C_{12}$)alkyl-O—($C_1$-$C_4$)alkyl; —($C_1$-$C_{12}$)alkyl-OH; —($C_1$-$C_{12}$)alkyl-O—($C_2$-$C_4$)alkenyl; —($C_2$-$C_{12}$)alkenyl-O—($C_1$-$C_4$)alkyl; —($C_2$-$C_{12}$)alkenyl-OH; —($C_2$-$C_{12}$)alkenyl-O—($C_2$-$C_4$)alkenyl; —O—($C_1$-$C_{12}$)alkyl; —O—($C_2$-$C_{12}$)alkenyl; —O—($C_1$-$C_4$)alkyl-aryl; —S—($C_1$-$C_{12}$)alkyl; —S—($C_2$-$C_{12}$)alkenyl; —S(O)—($C_1$-$C_{12}$)alkyl; —S(O)—($C_2$-$C_{12}$)alkenyl; —$S(O)_2$—($C_1$-$C_{12}$)alkyl; —$S(O)_2$—($C_2$-$C_{12}$)alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$)alkyl groups; a —($C_1$-$C_4$)alkyl-heterocyclyl wherein the heterocyclyl of the —($C_1$-$C_4$)alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 ($C_1$-$C_2$)alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$)alkyl groups; further wherein the alkyl and alkenyl groups of —($C_1$-$C_{12}$)alkyl, —($C_2$-$C_{12}$)alkenyl, —($C_1$-$C_{12}$)alkyl-O—($C_1$-$C_4$)alkyl, —($C_1$-$C_{12}$)alkyl-O—H, —($C_1$-$C_{12}$)alkyl-O—($C_2$-$C_4$)alkenyl, —($C_2$-$C_{12}$)alkenyl-O—($C_1$-$C_4$)alkyl, —($C_2$-$C_{12}$)alkenyl-OH, —($C_2$-$C_{12}$)alkenyl-O—($C_2$-$C_4$)alkenyl, —O—($C_1$-$C_{12}$)alkyl, —O—($C_2$-$C_{12}$)alkenyl, and —O—($C_1$-$C_4$)alkyl-aryl are unsubstituted or are substituted with from 1 to 4 substituents selected from —F, —Cl, —OH, (═O), —$NH_2$, NH($C_1$-$C_4$)alkyl, —N(($C_1$-$C_4$)alkyl)$_2$, aryl, unsubstituted —($C_1$-$C_2$)alkyl, or unsubstituted —O—($C_1$-$C_2$)alkyl;

X is O or S;

W, Y, and Z are selected from N or $CR^{13}$; wherein 0 or 1 of W, Y, and Z is N; and further wherein Z is not N if $R^2$ is F;

$R^1$ is selected from H, ($C_1$-$C_6$)alkyl, ($C_2$-$C_6$)alkenyl, ($C_2$-$C_6$)alkynyl, —($C_1$-$C_4$)alkyl-O—($C_1$-$C_4$)alkyl, heterocyclyl, aryl, or heteroaryl;

$R^{1a}$ is selected from H and ($C_1$-$C_4$)alkyl;

$R^2$ is selected from H, F, $CF_3$, or ($C_1$-$C_6$)alkoxy;

$R^3$ is H, —OH, —O($C_1$-$C_2$)alkyl, or —S($C_1$-$C_2$)alkyl;

$R^7$ and $R^8$ are independently selected from H and ($C_1$-$C_4$)alkyl;

$R^9$, $R^{10}$, $R^{14}$, $R^{15}$, and $R^{16}$ are, in each instance independently selected from H and ($C_1$-$C_4$)alkyl and $R^9$ and $R^{10}$ are absent if q is 0;

Each of $R^{11a}$, $R^{11b}$, and $R^{11c}$ is independently selected from H, F, Cl, ($C_1$-$C_4$)alkyl, or ($C_1$-$C_4$)alkoxy; and $R^{11a}$ is absent if G is N; $R^{11b}$ is absent if J is N; or $R^{11c}$ is absent if K is N;

Each of $R^{12a}$, $R^{12b}$, and $R^{12c}$ is independently selected from H, F, Cl, ($C_1$-$C_4$)alkyl, or ($C_1$-$C_4$)alkoxy;

$R^{13}$ is selected from H, F, ($C_1$-$C_4$)alkyl, and —O—($C_1$-$C_4$)alkyl;

q is 0 or 1; and p is 1, 2, 3, or 4.

In some embodiments of the compounds of formula IV or VI, A is selected from ($C_1$-$C_{12}$)alkyl, ($C_2$-$C_{12}$)alkenyl, —O—($C_1$-$C_{12}$)alkyl, —O—($C_2$-$C_{12}$)alkenyl, —O—($C_1$-$C_4$)alkyl-aryl, or a 4 to 7 membered heterocycle comprising 1 or 2 heteroatoms selected from N or O, wherein the heterocycle comprises 0 or 1 one double bond between ring members.

In some embodiments, the compound of formula IV or formula VI, is a compound of formula IV.

In some embodiments, the compound of formula IV or formula VI, is a compound of formula VI.

In some embodiments of the compound of formula IV or formula VI, G is $CR^{11a}$; J is $CR^{11b}$; and K is $CR^{11c}$. In some such embodiments, each of $R^{11a}$, $R^{11b}$, and $R^{11c}$ is H.

In some embodiments of the compound of formula IV or formula VI, G is $CR^{11a}$; J is $CR^{11b}$; and K is N. In other embodiments, G is $CR^{11a}$; J is N; and K is $CR^{11}$. In still other embodiments, G is N; J is $CR^{11b}$; and K is $CR^{11}$.

In some embodiments of the compound of formula IV or formula VI, $R^3$ is selected from —OH, —O($C_1$-$C_2$)alkyl, or —S($C_1$-$C_2$)alkyl. In some such embodiments, $R^3$ is —O($C_1$-$C_2$)alkyl. In some such embodiments, $R^3$ is —$OCH_3$.

In some embodiments of the compound of formula IV or formula VI, $R^1$ is selected from H and $(C_1\text{-}C_4)$alkyl. In some such embodiments, $R^1$ and $R^{1a}$ are independently selected from H and $CH_3$. In some such embodiments, $R^1$ and $R^{1a}$ are both H. In other such embodiments, one of $R^1$ and $R^{1a}$ is H and the other of $R^1$ and $R^{1a}$ is $CH_3$. In still other such embodiments, $R^1$ and $R^{1a}$ are both $CH_3$.

In some embodiments of the compound of formula IV or formula VI, each instance of $R^{14}$ and $R^{15}$ is selected from H and $CH_3$.

In some embodiments of the compound of formula IV or formula VI, $R^2$ is selected from F, $CF_3$, or $(C_1\text{-}C_6)$alkoxy. In some such embodiments, $R^2$ is F.

In some embodiments of the compound of formula IV or formula VI, $R^2$ is H or F.

In some embodiments of the compound of formula IV or formula VI, $R^2$ is butoxy In some embodiments of the compound of formula IV or formula VI, each of $R^{11a}$, $R^{11b}$, $R^{11c}$, $R^{12a}$, $R^{12b}$, and $R^{12c}$ is H.

In some embodiments of the compound of formula IV or formula VI, q is 0.

In some embodiments of the compound of formula IV or formula VI, W, Y, and Z are all C—H In some embodiments of the compound of formula IV or formula VI, X is O.

In some embodiments of the compound of formula IV or formula VI, A is selected from $(C_3\text{-}C_{10})$alkyl or $(C_4\text{-}C_{10})$alkenyl.

In some embodiments of the compound of formula IV or formula VI, A is a group of formula A'

A'

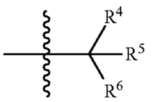

where the wavy line indicates the point of attachment; and $R^4$, $R^5$, and $R^6$ are independently selected from H, F, or $(C_1\text{-}C_4)$alkyl, wherein at least two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring.

In some embodiments of the compound of formula IV or formula VI, $R^7$ and $R^8$ are both H. In other embodiments, at least one of $R^7$ and $R^8$ is $CH_3$.

In some embodiments of the compound of formula IV or formula VI, $R^{16}$ is H. In other embodiments, $R^{16}$ is a $(C_1\text{-}C_4)$ alkyl group such as, in some embodiments, a methyl, ethyl, propyl, or butyl group. In some such embodiments, $R^{16}$ is a methyl group.

In some embodiments of the compound of formula IV or formula VI, G is $CR^{11a}$; J is $CR^{11b}$; K is $CR^{11c}$; $R^{11a}$, $R^{11b}$, $R^{11c}$, $R^{12a}$, $R^{12b}$, and $R^{12c}$ are all H; W is C—H; Y, is C—H; Z is C—H; $R^2$ is F; $R^3$ is methoxy; $R^7$ is H; $R^8$ is H; X is O, q is 0, and p is 1, 2, or 3. In some such embodiments, $R^{16}$ is H. In other such embodiments, $R^{16}$ is a $(C_1\text{-}C_4)$alkyl group such as, in some embodiments, a methyl group.

In some embodiments of the compound of formula IV or formula VI, A is a branched chain $(C_4\text{-}C_8)$alkyl group. In some such embodiments, A is a t-butyl group.

In some embodiments of the compound of formula IV or formula VI, A is an optionally substituted $(C_5\text{-}C_7)$cycloalkyl group or an optionally substituted $(C_5\text{-}C_7)$cycloalkenyl group. In some such embodiments, the $(C_5\text{-}C_7)$cycloalkyl group or the $(C_5\text{-}C_7)$cycloalkenyl group is substituted with 1, 2, 3, or 4 methyl groups.

In some embodiments of the compound of formula IV or formula VI, A is a group of formula

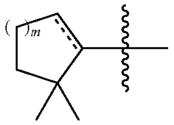

wherein m is 1, 2, or 3, and the dashed line indicates a single or double bond In some such embodiments, A is a group of formula

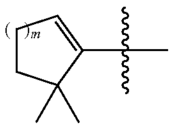

wherein m is 1, 2, or 3.

In some embodiments of the compound of formula IV or formula VI, A is $—OCF_3$.

In some embodiments of the compound of formula IV or formula VI, A is $—O—(C_3\text{-}C_{10})$alkyl or $—O—(C_3\text{-}C_{10})$alkenyl.

In some embodiments of the compound of formula IV or formula VI, A is $—O—(C_3\text{-}C_8)$cycloalkyl optionally substituted with 1 or 2 methyl groups.

In some embodiments, the compound of formula IV is a compound of formula VA, VB, or VC, or a pharmaceutically acceptable salt, solvate, stereoisomer, or $C_1\text{-}C_6$ alkyl ester thereof; or a tautomer or a pharmaceutically acceptable salt, solvate, stereoisomer, or $C_1\text{-}C_6$ alkyl ester thereof; or a mixture thereof. The compound of formula VA, VB, and VC have the following structures where each of the variables has any of the values of any of the embodiments described herein:

VA

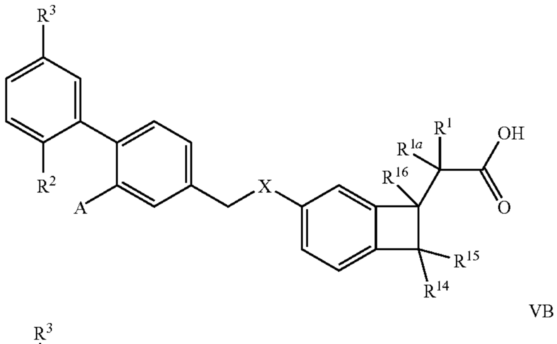

VB

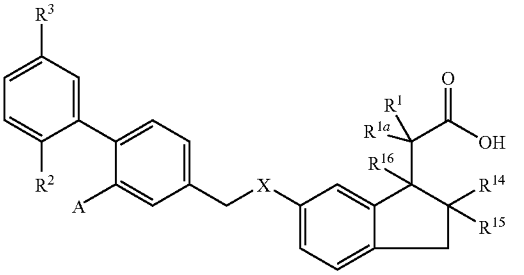

-continued

VC

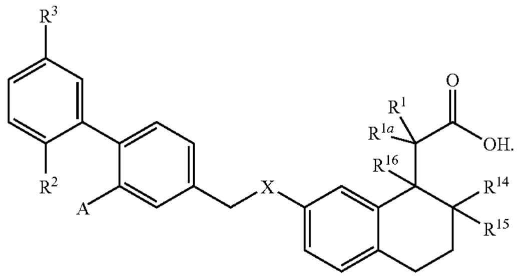

In some embodiments, the compound of formula VA, VB, or VC, is a compound of formula VA', VB', or VC' or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula VA', VB', and VC' have the following structures where each of the variables has any of the values of any of the embodiments described herein:

VA′

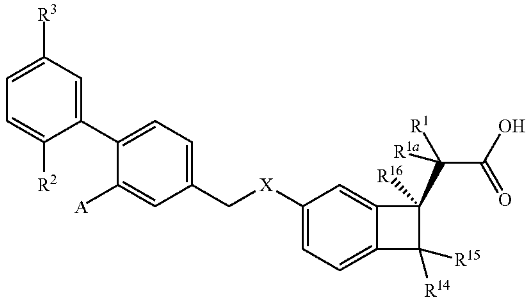

VB′

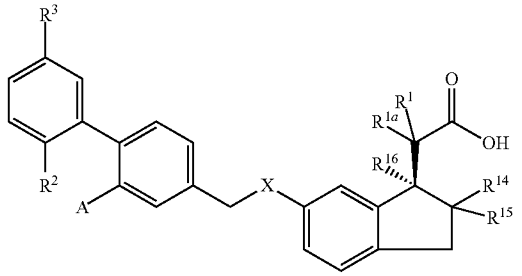

VC′

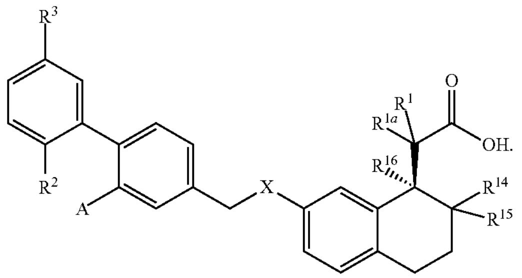

In some embodiments, the compound of formula VA, VB, or VC, is a compound of formula VA", VB", or VC" or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula VA", VB", and VC" have the following structures where each of the variables has any of the values of any of the embodiments described herein:

VA″

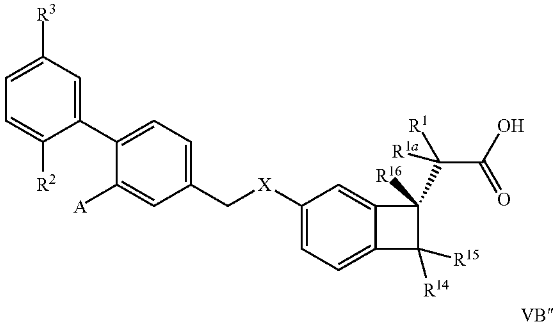

VB″

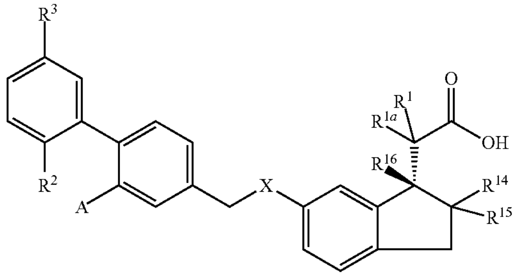

VC″

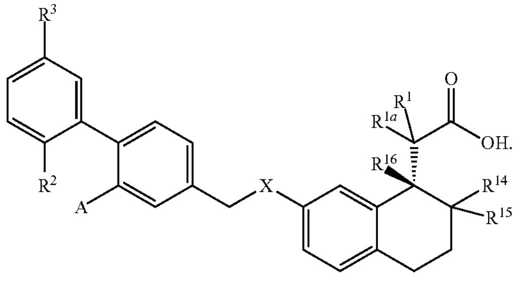

In some embodiments, the compound of any of the embodiments is a salt. In other embodiments, the compound of any of the embodiments is a $C_1$-$C_6$ alkyl ester. In some such embodiments, the $C_1$-$C_6$ alkyl ester is a methyl, ethyl, propyl, butyl, isopropyl, pentyl, or hexyl ester. In some such embodiments, the ester is a methyl or ethyl ester.

In some embodiments, where two or more chiral centers are present, the compound is a mixture of diastereomers. In some such embodiments, the percentage of one diastereomer is greater than 75%, greater than 80%, greater than 85%, greater than 90%, greater than 95%, greater than 98%, or greater than 99% based on the total diastereomers present in the mixture. In other embodiments, the compound is one specific diastereomer. In some embodiments, the compound is a mixture of enantiomers. In some such embodiments, the mixture comprises both enantiomers where the percent of one enantiomer with respect to both enantiomers is greater than 75%, greater than 80%, greater than 85%, greater than 90%, greater than 95%, greater than 98%, or greater than 99%. In other embodiments, the compound is a pure single enantiomer. In some embodiments with a single chiral center, the compound comprises a stereomerically pure S-enantiomer. In other embodiments with a single chiral center, the compound comprises a stereomerically pure R-enantiomer. In yet other embodiments with a single chiral center, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

In another aspect, the invention provides methods for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. Such methods include administering to a subject in need thereof, a therapeutically effective amount of a compound of any of the embodiments. In some such embodiments, the disease or condition is type II diabetes. In some embodiments, a compound of any of the embodiments is administered in combination with a second therapeutic agent. In some such embodiments, the second therapeutic agent is metformin, is a thiazolidinedione, or is a DPP-IV inhibitor. The second therapeutic agent may be administered before, during, or after administration of the compound of any of the embodiments.

In another aspect, the invention provides methods for treating or preventing a disease or condition responsive to the modulation of GPR40. Such methods include administering to a subject in need thereof, a therapeutically effective amount of a compound of any of the embodiments.

In another aspect, the invention provides methods for treating or preventing a disease or condition mediated, regulated, or influenced by pancreatic β cells. Such methods include administering to a subject in need thereof, a therapeutically effective amount of a compound of any of the embodiments.

In another aspect, the invention provides methods for modulating GPR40 function in a cell. Such methods include contacting a cell with a compound of any of the embodiments. In some such embodiments, the method is a method for activating GPR40 function in a cell.

In another aspect, the invention provides methods for modulating GPR40 function. Such methods include contacting GPR40 with a compound of any of the embodiments. In some such embodiments, the method is a method for activating GPR40 function.

In another aspect, the invention provides methods for modulating circulating insulin concentration in a subject. Such methods include administering a compound of any of the embodiments to the subject. In some such embodiments, the circulating insulin concentration is increased in the subject after administration whereas in other such embodiments, the circulating insulin concentration is decreased in the subject after administration.

In another aspect, the invention provides the use of a compound of any of the embodiments for treating a disease or condition or for preparing a medicament for treating a disease or condition where the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes. The compounds of the invention may also be used to prepare medicaments that include a second therapeutic agent such as metformin, a thiazolidinedione, or a DPP-IV inhibitor.

In another aspect, the invention provides the use of a compound of any of the embodiments for modulating GPR40 or for use in the preparation of a medicament for modulating GPR40. In some such embodiments, the use of the compound is for activating GPR40 or for preparation of a medicament for activating GPR40.

In another aspect, the invention provides a therapeutic composition that includes a compound of any of the embodiments and a second therapeutic agent such as those described herein, for example, metformin a thiazolidinedione, or a DPP-IV inhibitor, as a combined preparation for simultaneous, separate, or sequential use in the treatment of a disease or condition mediated by GPR40. In some such embodiments, the disease or condition is type II diabetes. In some embodiments, the compound of any of the embodiments and the second therapeutic agent are provided as a single composition, whereas in other embodiments they are provided separately as parts of a kit.

In some embodiments, the invention features a compound of any of the embodiments described herein for use as a medicament.

In other embodiments, the invention features a compound of any of the embodiments described herein for use in modulating GPR40. In some such embodiments, the compound is for use in activating GPR40 function.

In still other embodiments, the invention features a compound of any of the embodiments described herein for use in a method for treating a disease or condition selected from type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, or edema.

Other objects, features and advantages of the invention will become apparent to those skilled in the art from the following description and claims.

5. BRIEF DESCRIPTION OF THE DRAWINGS

FIG. 1 is a graph showing displacement of $^{3}$H-labeled Comparative Compound 1 by various unlabeled compounds, including Examples 1 and unlabeled Comparative Compound 1. Unlabeled Comparative Compound 1 displaced the $^{3}$H-labeled Comparative Compound. In direct contrast, Example 1 enhanced the total binding of $^{3}$H-labeled Comparative Compound 1. These results indicate that Example 1 interact with the GPR40 receptor in a manner that is different from Comparative Compound 1.

6. DETAILED DESCRIPTION OF THE INVENTION

6.1 Abbreviations and Definitions

The terms "treat", "treating" and "treatment", as used herein, are meant to include alleviating or abrogating a condition or disease and/or its attendant symptoms. The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity, and the age, weight, etc., of the subject to be treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

As used herein, the phrases "GPR40-mediated condition or disorder", "disease or condition mediated by GPR40", and the like refer to a condition or disorder characterized by inappropriate, for example, less than or greater than normal, GPR40 activity. A GPR40-mediated condition or disorder may be completely or partially mediated by inappropriate GPR40 activity. However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia, and edema.

The term "alkyl", by itself or as part of another substituent, means, unless otherwise stated, a straight or branched chain, or cyclic hydrocarbon radical, or combination thereof, which is fully saturated, having the number of carbon atoms designated (e.g., $C_1$-$C_{10}$ means one to ten carbons). Examples of alkyl groups include, but are not limited to, methyl, ethyl, n-propyl, isopropyl, n-butyl, t-butyl, isobutyl, sec-butyl, pentyl, cyclohexyl, (cyclohexyl)methyl, methylcyclohexyl, dimethylcyclohexyl, cyclopropyl, cyclopropylmethyl, methylcyclopropyl, cyclobutyl, cyclobutylmethyl, methylcyclobutyl, cyclopentyl, methylcyclopentyl, cyclopentylmethyl, dimethylcyclopentyl, and homologs and isomers thereof, for example, n-pentyl, n-hexyl, n-heptyl, n-octyl, and the like. Alkyl groups may be substituted or unsubstituted.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include, but are not limited to, vinyl, 2-propenyl, crotyl, 2-isopentenyl, 2-(butadienyl), 2,4-pentadienyl, 3-(1,4-pentadienyl), cyclopentenyl, cyclohexenyl, 5,5-dimethylcyclopentenyl, 6,6-dimethylcyclohexenyl, cycloheptenyl, cycloheptadienyl, and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include, but are not limited to, ethynyl, 1- and 3-propynyl, 3-butynyl, and higher homologs and isomers thereof.

The term "alkoxy" refers to a group of formula —O-alkyl where alkyl has the definition provided above. An alkoxy group can have a specified number of carbon atoms. For example, a methoxy group (—$OCH_3$) is a $C_1$ alkoxy group. Alkoxy groups typically have from 1 to 10 carbon atoms. Examples of alkoxy group include, but are not limited to, methoxy, ethoxy, propoxy, butoxy, pentoxy, hexoxy, heptoxy, and the like.

The term "cycloalkyl" by itself, or in combination with other terms, represents, unless otherwise stated, a cyclic type of "alkyl" in which 3 or more carbon atoms form a ring. Thus, the term "cycloalkyl" is meant to be included in the term "alkyl". Examples of cycloalkyl include cyclopropyl, cyclobutyl, cyclopentyl, cyclohexyl, cycloheptyl, and the like. Cycloalkyl groups typically include from 3 to 14 or 3 to 10 ring members. Cycloalkyl groups may be monocyclic, bicyclic, or multicyclic. Therefore, in addition to the groups described above, cycloalkyl groups include norbornyl and adamantyl groups.

The term "cycloalkenyl" by itself, or in combination with other terms, represents, unless otherwise stated, a cyclic type of "alkenyl" in which 3 or more carbon atoms form a ring that includes at least one carbon-carbon double bond. Thus, the term "cycloalkenyl" is meant to be included in the term "alkenyl". Examples of cycloalkenyl include cyclopropenyl, cyclobutenyl, cyclopentenyl, cyclohexenyl, cycloheptenyl, and the like. Cycloalkenyl groups typically include from 3 to 14 or 3 to 10 ring members. Cycloalkenyl groups may be monocyclic, bicyclic, or multicyclic.

The term "heterocyclyl" by itself or in combination with other terms, represents, unless otherwise stated, a ring system in which one or more ring members is a heteroatom selected from N, O, or S. The heteroatom can occupy the position at which the heterocycle is attached to the remainder of the molecule. A heterocyclyl group can also be attached to the remainder of the molecule through a carbon atom of the ring. Heterocyclyl groups typically include from 3 to 10 ring members of which 1, 2, or 3 are heteroatoms. Heterocyclyl groups can be saturated or may include some unsaturation. Heterocyclyl groups may also be substituted or unsubstituted. Examples of heterocyclyl groups include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 4,5-dihydroisoxazol-3-yl, and the like.

The term "heteroalkyl," by itself or in combination with another term, means, unless otherwise stated, a stable straight or branched chain, or cyclic hydrocarbon radical, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S may be placed at any position of the heteroalkyl group. Examples include $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2—S(O)—CH_3$, $—CH_2—CH_2—S(O)_2—CH_3$, and $—CH_2—CH=N—OCH_3$. Up to two heteroatoms may be consecutive, such as, for example, $—CH_2—NH—OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, $—CH_2OH$ (one carbon atom and one heteroatom replacing a carbon atom) and $—CH_2SH$.

To further illustrate the definition of a heteroalkyl group, where the heteroatom is oxygen, a heteroalkyl group is a oxyalkyl group. For instance, ($C_2$-$C_5$)oxyalkyl is meant to include, for example $—CH_2—O—CH_3$ (a $C_3$-oxyalkyl group with two carbon atoms and one oxygen replacing a carbon atom), $—CH_2CH_2CH_2CH_2OH$, and the like.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2 m'+1), where m' is the total number of carbon atoms in the alkyl group. For example, the term "halo($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2 m'+1) halogen atoms). The term "perhaloalkyl" means, unless otherwise stated, alkyl substituted with (2 m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, aromatic, hydrocarbon substituent which can be a single ring or multiple rings (up to three rings) which are fused together or linked covalently. The term "heteroaryl" refers to aryl groups (or rings) that contain from one to four heteroatom ring members selected from the group consisting of N, O and S, wherein the nitrogen and sulfur atoms are optionally oxidized, and the nitrogen atom(s) are optionally quaternized. Heteroaryl groups can be unsubstituted or substituted. In some embodiments, a heteroaryl group includes 1 or 2 heteroatoms. A heteroaryl group can be attached to the remainder of the molecule through a heteroatom or through a carbon atom of the ring. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, dibenzofuryl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl. Typically an aryl group refers to an aromatic group that includes from 6-10 ring members such that it is a ($C_6$-$C_{10}$)aryl group. Typically, heteroaryl groups include 5 to 10 ring members of which 1 or 2 is selected from O, N, or S.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, oxadiazolyl, isoxazolyl, thiazolyl, furyl, thienyl (thiophenyl), pyridyl, pyrimidyl, benzothiazolyl, purinyl, benzimidazolyl, indolyl, isoquinolyl, triazolyl, tetrazolyl, quinoxalinyl. or quinolyl group which is unsubstituted or substituted.

For brevity, the term "aryl" when used in combination with other terms (e.g., aryloxy, arylalkoxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). As another example, the term "aryl($C_1$-$C_4$)alkoxy" is mean to include radicals in which an aryl group is attached to an alkyl group having 1 to 4 carbon atoms that is bonded to an 0 which is attached to the rest of the molecule. Examples include substituted and unsubstituted phenylmethoxy, phenylethoxy, phenylpropoxy, pyridylmethoxy, and the like.

Each of the above terms (e.g., "alkyl," "alkenyl," "aryl," "heterocyclyl" and "heteroaryl") is meant to include both substituted and unsubstituted forms of the indicated radical, unless otherwise indicated. Preferred substituents for each type of radical are provided below.

Substituents for the alkyl radicals (as well as those groups referred to as alkenyl, alkynyl, cycloalkyl, and heterocyclyl) can be a variety of groups selected from: —OR', =O, =NR', =N—OR', —NR'R", R', —SR', halogen, —OC(O)R', —C(O)R', $—CO_2R'$, —CONR'R", —OC(O)NR'R", —NR"C(O)R', —NR'—C(O)NR"R'", $—NR'—SO_2NR"R'"$, $—NR"CO_2R'$, $—NH—C(NH_2)=NH$, $—NR'C(NH_2)=NH$, $—NH—C(NH_2)=NR'$, —SiR'R"R'", —S(O)R', $—SO_2R'$, $—SO_2NR'R"$, $—NR"SO_2R$, —CN, —($C_2$-$C_5$) alkynyl, —($C_2$-$C_5$) alkenyl, and $—NO_2$, in a number ranging from zero to three, with those groups having zero, one or two substituents being particularly preferred. R', R" and R'" each independently refer to hydrogen; unsubstituted ($C_1$-$C_8$)alkyl, ($C_2$-$C_8$)alkenyl, and heteroalkyl; unsubstituted aryl; unsubstituted heterocyclyl; heterocyclyl substituted with up to three unsubstituted ($C_1$-$C_2$)alkyl groups; aryl substituted with one to three halogens, unsubstituted ($C_1$-$C_2$)alkyl, —O—($C_1$-$C_4$)alkyl, and —S—($C_1$-$C_4$)alkyl groups; unsubstituted halo($C_1$-$C_4$)alkyl; unsubstituted —($C_1$-$C_4$)alkyl-O—($C_1$-$C_4$)alkyl; unsubstituted —($C_1$-$C_4$)alkyl-aryl; or unsubstituted aryl-($C_1$-$C_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl group will have from zero to three substituents, with those groups having two or fewer substituents being preferred in the present invention. More preferably, an alkyl radical will be unsubstituted or monosubstituted. Most preferably, an alkyl radical will be unsubstituted.

From the above discussion of substituents, one of skill in the art will understand that the term "alkyl" is meant to include groups such as trihaloalkyl (e.g., —$CF_3$ and —$CH_2CF_3$).

Preferred substituents for the alkyl radicals are selected from: —OR', ═O, —NR'R", —SR', halogen, —OC(O)R', —C(O)R', —$CO_2$R', —CONR'R", —OC(O)NR'R", —NR"C(O)R', —NR"$CO_2$R', —NR'—$SO_2$NR"R'", —S(O)R', —$SO_2$R', —$SO_2$NR'R", —NR"$SO_2$R, —CN, —($C_2$-$C_5$) alkynyl, —($C_2$-$C_5$) alkenyl, R', and —$NO_2$, where R' and R" are as defined above. Further preferred substituents are selected from: —OR', ═O, —NR'R", halogen, —OC(O)R', —$CO_2$R', —CONR'R", —OC(O)NR'R", —NR"C(O)R', —NR"$CO_2$R', —NR'—$SO_2$NR"R'", —$SO_2$R', —$SO_2$NR'R", —NR"$SO_2$R, —CN, —($C_2$-$C_5$) alkynyl, —($C_2$-$C_5$) alkenyl, and —$NO_2$.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)═NH, —NR'C($NH_2$)═NH, —NH—C($NH_2$)═NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, unsubstituted ($C_1$-$C_8$)alkyl and heteroalkyl; unsubstituted aryl and heteroaryl; unsubstituted aryl-($C_1$-$C_4$)alkyl; unsubstituted aryl-O—($C_1$-$C_4$)alkyl; unsubstituted —($C_2$-$C_5$) alkynyl; and unsubstituted —($C_2$-$C_5$) alkenyl.

Two of the substituents on adjacent atoms of the aryl or heteroaryl ring may optionally be replaced with a substituent of the formula -T-C(O)—$(CH_2)_q$—U—, wherein T and U are independently —NH—, —O—, —$CH_2$—, or a single bond, and q is an integer of from 0 to 2. Alternatively, two of the substituents on adjacent atoms of the aryl or heteroaryl ring may optionally be replaced with a substituent of the formula -A-$(CH_2)_r$—B—, wherein A and B are independently —$CH_2$—, —O—, —NH—, —S—, —S(O)—, —S(O)$_2$—, —S(O)$_2$NR'—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl. Otherwise, R' is as defined above.

As used herein, the term "heteroatom" is meant to include oxygen (O), nitrogen (N), and sulfur (S).

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate. In some embodiments, the compounds, salts of the compounds, tautomers of the compound, and salts of the tautomers may include a solvent or water such that the compound or salt is a solvate or hydrate.

Certain compounds of the invention may exist in multiple crystalline or amorphous forms. In general, all physical forms are equivalent for the uses contemplated by the invention and are intended to be within the scope of the invention.

As known by those skilled in the art, certain compounds of the invention may exist in one or more tautomeric forms. Because one chemical structure may only be used to represent one tautomeric form, it will be understood that convenience, referral to a compound of a given structural formula includes tautomers of the structure represented by the structural formula.

Certain compounds of the invention possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, N.Y., 1962); and Wilen, S. H., Tables of Resolving Agents and Optical Resolutions p. 268 (E. L. Eliel, Ed., Univ. of Notre Dame Press, Notre Dame, Ind., 1972).

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T).

6.2 Embodiments of the Invention

In one aspect, a class of compounds that modulates GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject. The compounds find use as therapeutic agents for modulating diseases and conditions responsive to modulation of GPR40 and/or mediated by GPR40 and/or mediated by pancreatic β cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglyceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema. Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

6.2.1 Compounds

In one aspect, the present invention provides a compound having the formula I or formula III or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof:

I

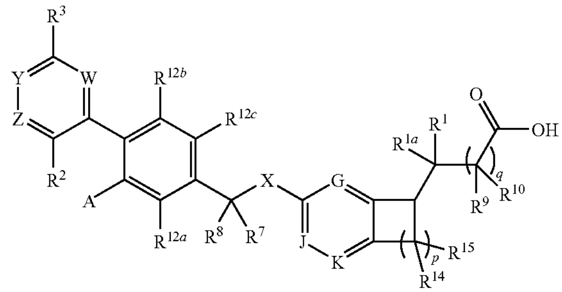

III

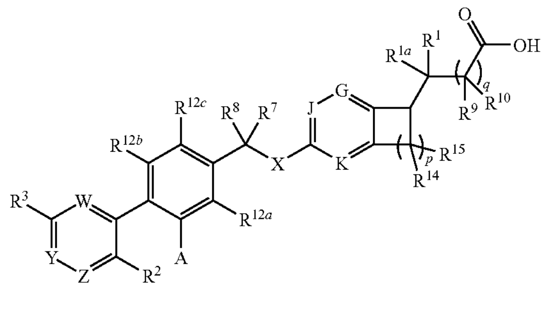

where

G is selected from N or $CR^{11a}$;

J is selected from N or $CR^{11b}$;

K is selected from N or $CR^{11c}$;

wherein 0 or 1 of G, J, and K is N;

A is selected from $(C_1\text{-}C_{12})$alkyl, $(C_2\text{-}C_{12})$alkenyl, —O—$(C_1\text{-}C_{12})$alkyl, —O—$(C_2\text{-}C_{12})$alkenyl, —O—$(C_1\text{-}C_4)$alkyl-aryl, or a 4 to 7 membered heterocycle comprising 1 or 2 heteroatoms selected from N or O, wherein the heterocycle comprises 0 or 1 one double bond between ring members;

X is O or S;

W, Y, and Z are selected from N or $CR^{13}$; wherein 0 or 1 of W, Y, and Z is N; and further wherein Z is not N if $R^2$ is F;

$R^1$ is selected from H, $(C_1\text{-}C_6)$alkyl, $(C_2\text{-}C_6)$alkenyl, $(C_2\text{-}C_6)$alkynyl, —$(C_1\text{-}C_4)$alkyl-O—$(C_1\text{-}C_4)$alkyl, heterocyclyl, aryl, or heteroaryl;

$R^{1a}$ is selected from H and $(C_1\text{-}C_4)$alkyl;

$R^2$ is selected from H, F, $CF_3$, or $(C_1\text{-}C_6)$alkoxy;

$R^3$ is H, —OH, —$O(C_1\text{-}C_2)$alkyl, or —$S(C_1\text{-}C_2)$alkyl;

$R^7$ and $R^8$ are independently selected from H and $(C_1\text{-}C_4)$ alkyl;

$R^9$, $R^{10}$, $R^{14}$, and $R^{15}$ are, in each instance independently selected from H and $(C_1\text{-}C_4)$alkyl and $R^9$ and $R^{10}$ are absent if q is 0;

Each of $R^{11a}$, $R^{11b}$, and $R^{11c}$ is independently selected from H, F, Cl, $(C_1\text{-}C_4)$alkyl, or $(C_1\text{-}C_4)$alkoxy; and $R^{11a}$ is absent if G is N; $R^{11b}$ is absent if J is N; or $R^{11c}$ is absent if K is N;

Each of $R^{12a}$, $R^{12b}$, and $R^{12c}$ is independently selected from H, F, Cl, $(C_1\text{-}C_4)$alkyl, or $(C_1\text{-}C_4)$alkoxy;

$R^{13}$ is selected from H, F, $(C_1\text{-}C_4)$alkyl, and —O—$(C_1\text{-}C_4)$ alkyl;

q is 0 or 1; and p is 1, 2, 3, or 4.

In some embodiments of the compound of formula I or the compound of formula III, the compound has the formula I. In other embodiments, the compound has the formula III.

In some embodiments of the compound of formula I or formula III, G is $CR^{11a}$; J is $CR^{11b}$; and K is $CR^{11c}$. In some such embodiments, each of $R^{11a}$, $R^{11b}$, and $R^{11c}$ is H. In some such embodiments, each of $R^{12a}$, $R^{12b}$, and $R^{12c}$ is H. Therefore, in some embodiments, each of $R^{11a}$, $R^{11b}$, $R^{11c}$, $R^{12a}$, $R^{12b}$, and $R^{12c}$ is H.

In some embodiments of the compound of formula I or formula III, G is $CR^{11a}$; J is $CR^{11b}$; and K is N. In other embodiments, G is $CR^{11a}$; J is N; and K is $CR^{11}$. In still other embodiments, G is N; J is $CR^{11b}$; and K is $CR^{11}$. In some such embodiments, two of $R^{11a}$, $R^{11b}$, and $R^{11c}$ are H. In some such embodiments, each of $R^{12a}$, $R^{12b}$, and $R^{12c}$ is H. In some such embodiments, W is C—H; Y, is C—H; Z is C—H; $R^7$ is H; $R^8$ is H; X is O, and q is 0. In still other such embodiments, $R^2$ is F. In some such embodiments, $R^3$ is methoxy or ethoxy.

In some embodiments of the compound of formula I or formula III, $R^2$ is selected from F, $CF_3$, or $(C_1\text{-}C_6)$alkoxy. In some such embodiments, $R^2$ is selected from F, $CF_3$, or $(C_4\text{-}C_6)$alkoxy. In some embodiments, $R^2$ is H or F. In other embodiments, $R^2$ is F. In still other embodiments, $R^2$ is H. In other embodiments, $R^2$ is propoxy, butoxy, or pentoxy. In some such embodiments, $R^2$ is butoxy.

In some embodiments, A is selected from $(C_1\text{-}C_{12})$alkyl, $(C_2\text{-}C_{12})$alkenyl, —O—$(C_1\text{-}C_{12})$alkyl, —O—$(C_2\text{-}C_{12})$alkenyl, or —O—$(C_1\text{-}C_4)$alkyl-aryl.

In some embodiments, $R^2$ is H or F, and A is selected from a branched $(C_4\text{-}C_{10})$alkyl group, a $(C_4\text{-}C_{10})$alkenyl group, a bicyclic $(C_7\text{-}C_{12})$alkyl group, an unsubstituted or a substituted $(C_5\text{-}C_7)$cycloalkyl group, or an unsubstituted or a substituted $(C_5\text{-}C_7)$cycloalkenyl group. In some embodiments, A is a an unsubstituted $(C_5\text{-}C_7)$cycloalkyl group, a $(C_5\text{-}C_7)$cycloalkyl group substituted with 1, 2, 3, or 4 methyl groups, an unsubstituted $(C_5\text{-}C_7)$cycloalkenyl group, or a $(C_5\text{-}C_7)$cycloalkenyl group substituted with 1, 2, 3, or 4 methyl groups. In some such embodiments, $R^1$ is selected from methyl, ethyl, propyl, cyclopropyl, cyclobutyl, or cyclopropylmethyl. In some such embodiments, $R^3$ is methoxy. In some such embodiments, A is selected from

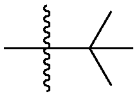, 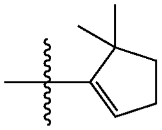, 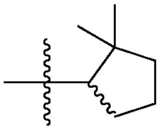,

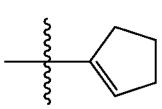, 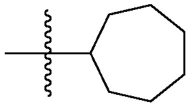,

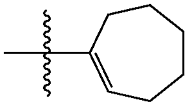, 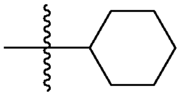,

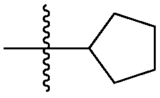, 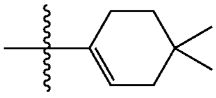,

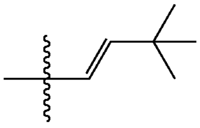, 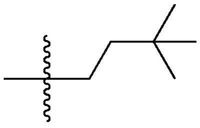,

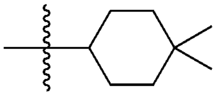, 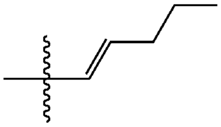,

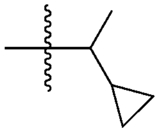, 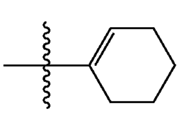,

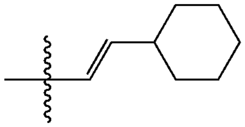, 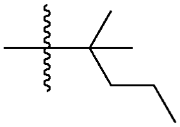,

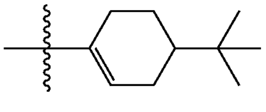, 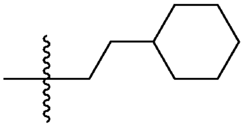,

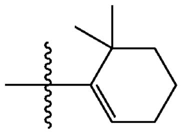, 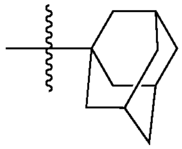,

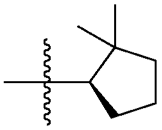, 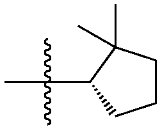, or

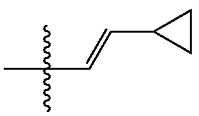.

In some such embodiments, A is selected from

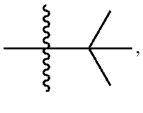, 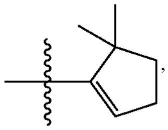, 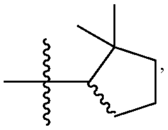, 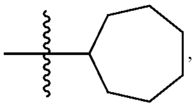, 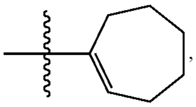, 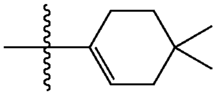, 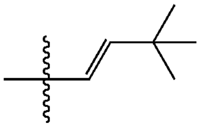, 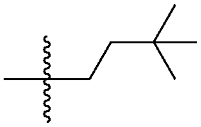, 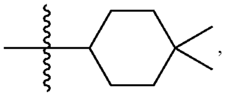, 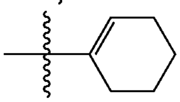, 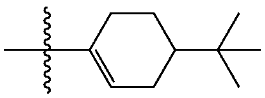, 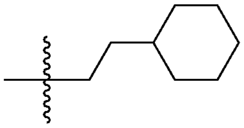, 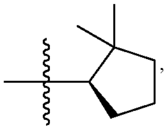, 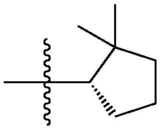, or 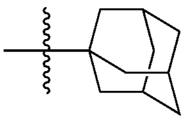.

In some embodiments of the compound of formula I or formula III, $R^3$ is selected from —OH, —O($C_1$-$C_2$)alkyl, or —S($C_1$-$C_2$)alkyl. In some such embodiments, $R^3$ is selected from —O($C_1$-$C_2$)alkyl or —S($C_1$-$C_2$)alkyl. In some such embodiments, $R^3$ is selected from —O($C_1$-$C_2$)alkyl. In some embodiments, $R^3$ is selected from —O—$CH_3$ or —S—$CH_3$. In some embodiments, $R^3$ is selected from —$OCH_3$ or —$OCH_2CH_3$. In some embodiments, $R^3$ is —$OCH_3$.

In some embodiments of the compound of formula I or formula III, q is 0.

In some embodiments of the compound of formula I or formula III, $R^1$ is selected from H and ($C_1$-$C_4$)alkyl. In some such embodiments, $R^1$ and $R^{1a}$ are independently selected from H and $CH_3$. In some such embodiments, $R^1$ and $R^{1a}$ are both H. In other such embodiments, one of $R^1$ and $R^{1a}$ is H and the other of $R^1$ and $R^{1a}$ is $CH_3$. In still other such embodiments, $R^1$ and $R^{1a}$ are both $CH_3$.

In some embodiments of the compound of formula I or formula III, each instance of $R^{14}$ and $R^{15}$ is selected from H and $CH_3$.

In some embodiments of the compound of formula I or formula III, W, Y, and Z are all C—H.

In some embodiments of the compound of formula I or formula III, A is selected from ($C_3$-$C_{10}$)alkyl or ($C_4$-$C_{10}$) alkenyl. In some such embodiments, A is t-butyl. In other such embodiments, A is an unsubstituted or optionally substituted cyclopentyl, cyclohexyl, or cycloheptyl group. In some such embodiments, A is an unsubstituted cyclopentyl, cyclohexyl, or cycloheptyl group. In some such embodiments, A is a cyclopentyl, cyclohexyl, or cycloheptyl group optionally substituted with 1, 2, 3, or 4 ($C_1$-$C_4$)alkyl groups. In some such embodiments, A is a cyclopentyl, cyclohexyl, or cycloheptyl group substituted with a t-butyl group. In other such embodiments A is a cyclopentyl, cyclohexyl, or cycloheptyl group substituted with 1 or 2 methyl groups. In some such embodiments, A is an unsubstituted or optionally substituted cyclopentenyl, cyclohexenyl, or cycloheptenyl group. In some such embodiments, A is an unsubstituted cyclopentenyl, cyclohexenyl, or cycloheptenyl group. In some such embodiments, A is a cyclopentenyl, cyclohexenyl, or cycloheptenyl group optionally substituted with 1, 2, 3, or 4 ($C_1$-$C_4$)alkyl groups. In some such embodiments, A is a cyclopentenyl, cyclohexenyl, or cycloheptenyl group substituted with a t-butyl group. In other such embodiments A is a cyclopentenyl, cyclohexenyl, or cycloheptenyl group substituted with 1 or 2 methyl groups.

In some embodiments of the compound of formula I or formula III, A is selected from

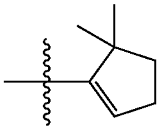, 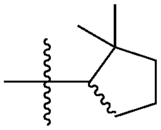, 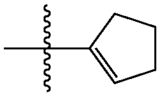, 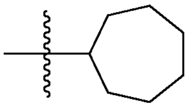, 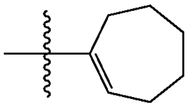, 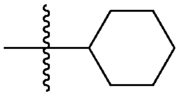, 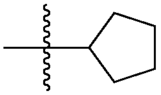, 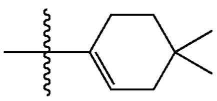, 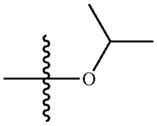 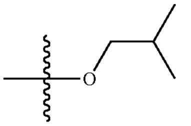, 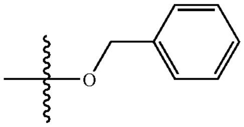, 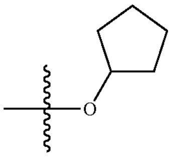, 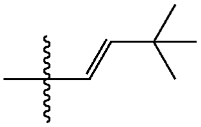, 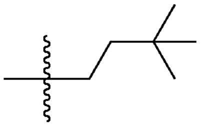, 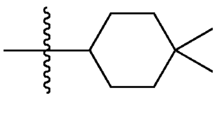, 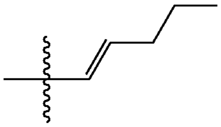, 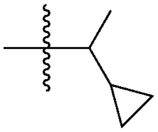, 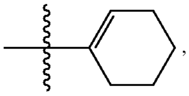, 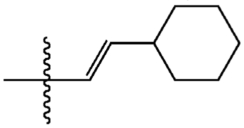, 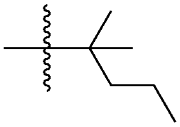, 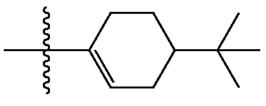, -continued

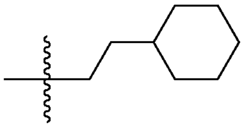, 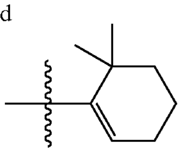,

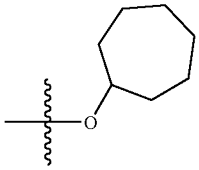, 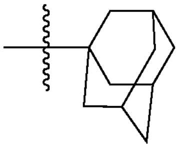,

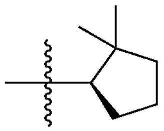, 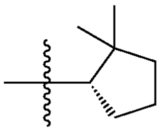, or

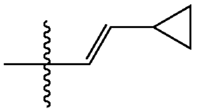.

In some embodiments of the compound of formula I or formula III, A is a group of formula A'.

A'

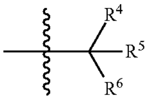

where the wavy line indicates the point of attachment and $R^4$, $R^5$, and $R^6$ are independently selected from H, F, ($C_1$-$C_4$) alkyl, and two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring. In some such embodiments, $R^4$, $R^5$, and $R^6$ are independently selected from H and ($C_1$-$C_4$) alkyl groups and at least two of $R^4$, $R^5$, and $R^6$ are ($C_1$-$C_4$) alkyl groups. In some such embodiments, all three of $R^4$, $R^5$, and $R^6$ are independently selected from ($C_1$-$C_4$)alkyl groups. In some such embodiments, two of $R^4$, $R^5$, and $R^6$ are methyl groups. In some such embodiments, each of $R^4$, $R^5$, and $R^6$ is a methyl group. In other embodiments, $R^4$, $R^5$, and $R^6$ are independently selected from H, ($C_1$-$C_4$)alkyl groups, or a substituted ($C_1$-$C_4$) alkyl group selected from ($C_1$-$C_4$)haloalkyl groups, ($C_1$-$C_4$)perhaloalkyl groups, or ($C_1$-$C_4$) alkoxy($C_1$-$C_4$)alkyl groups. In some such embodiments, at least one of $R^4$, $R^5$, and $R^6$ is a $CF_3$ group. In other embodiments at least one of $R^4$, $R^5$, and $R^6$ is a methoxymethyl group.

In some embodiments of the compound of formula I or formula III where A is a group of formula A', two of $R^4$, $R^5$, and $R^6$, together with the C atom to which they are attached, join to form a 3-8 or 3-7 membered ring, and the other of $R^4$, $R^5$, and $R^6$ is selected from H, an unsubstituted ($C_1$-$C_4$)alkyl, or a substituted ($C_1$-$C_4$)alkyl. In some embodiments the ring is a carbocyclic ring which may be a fully saturated cycloalkyl ring. In some such embodiments, the 3-8 membered ring is a 5-7 membered ring, a 3-6 membered ring, or a 3-5 membered ring. Examples of such rings include cyclopropyl, cyclobutyl, cyclopentyl, cyclohexyl, and cycloheptyl rings. In some such embodiments, two of $R^4$, $R^5$, and $R^6$ join to form a cyclopropyl ring. In some such embodiments, the other of $R^4$, $R^5$, and $R^6$ is H. In some embodiments two of $R^4$, $R^5$, and $R^6$, together with the C atom to which they are attached, join to form an optionally substituted saturated or partially unsaturated 3-8 or 3-7 membered ring which may be monocyclic or bicyclic, and the other of $R^4$, $R^5$, and $R^6$ is selected from H, an unsubstituted ($C_1$-$C_4$)alkyl, or a substituted ($C_1$-$C_4$)alkyl. In some embodiments the ring only includes carbon ring members. In some such embodiments, the ring includes 0 or 1 double bonds between ring members. In some such embodiments, the 3-7 membered ring is a 3-6, or a 3-5 membered ring. Examples of such rings include cyclopropyl, cyclobutyl, cyclobutenyl, cyclopentyl, cyclopentenyl, cyclohexyl, cyclohexenyl, cycloheptyl, and cycloheptenyl rings. In some such embodiments, two of $R^4$, $R^5$, and $R^6$ join to form an optionally substituted cyclopropyl ring. In some such embodiments, the other of $R^4$, $R^5$, and $R^6$ is H. In some such embodiments, two of $R^4$, $R^5$, and $R^6$ join to form an optionally substituted cyclopentenyl, cyclohexenyl, or cycloheptenyl ring. In some such embodiments, the other of $R^4$, $R^5$, and $R^6$ is H. In some embodiments all three of $R^4$, $R^5$, and $R^6$, together with the C atom to which they are attached, join to form an optionally substituted saturated or partially unsaturated 3-8 membered ring bicyclic ring system. For example, in some embodiments, A may comprise an adamantyl or another bicyclic ring system such as, but not limited to bicyclo[3.2.1]octane, bicyclo[2.2.1]heptane, and the like. In some such embodiments the ring only includes carbon ring members. In some such embodiments, the ring includes 0 or 1 double bonds between ring members. In some embodiments, A is a branched chain ($C_4$-$C_8$)alkyl group such as a t-butyl group. In other such embodiments, A is an optionally substituted ($C_5$-$C_7$)cycloalkyl group or an optionally substituted ($C_5$-$C_7$)cycloalkenyl group. In some such embodiments, the ($C_5$-$C_7$)cycloalkyl group or the ($C_5$-$C_7$)cycloalkenyl group are substituted with 1, 2, 3, or 4 methyl groups. In some other such embodiments, A has the formula

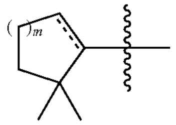

wherein m is 1, 2, or 3, and the dashed line indicates a single or double bond. In some such embodiments, A has the formula

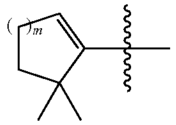

wherein m is 1, 2, or 3. In other such embodiments, A has the formula

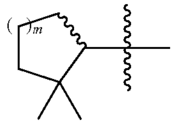

wherein m is 1, 2, or 3 and the wavy line indicates that the compound has the R stereochemistry, the S stereochemistry, or a mixture of the R and S stereochemistry with respect to the carbon attached to the rest of the molecule. In some such embodiments, A has the formula

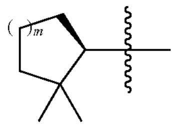

wherein m is 1, 2, or 3. In other embodiments, A has the formula

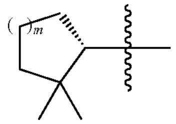

wherein m is 1, 2, or 3. In some embodiments, A is an —$OR^{4a}$ group, In some such embodiments, $R^{4a}$ is selected from a methyl, ethyl, propyl, butyl, pentyl, hexyl, isopropyl, t-butyl, or an isomer thereof. In some embodiments, $R^{4a}$ is selected from such an alkyl group that is substituted. For example, in some embodiments, $R^{4a}$ may a trihaloalkyl group such as a $CF_3$ group or another perhaloalkyl group.

In some embodiments of the compound of formula I or formula III, $R^2$ is F or butoxy. In some such embodiments, $R^2$ is F whereas in other such embodiments, $R^2$ is butoxy. In still other embodiments, $R^2$ is propoxy, pentoxy, or hexoxy. In still further embodiments, $R^2$ is selected from F or $(C_3$-$C_4)$ alkoxy. In some embodiments, $R^2$ is a —$CF_3$ group.

In some embodiments of the compound of formula I or formula III, $R^3$ is methoxy or ethoxy. In some such embodiments, $R^3$ is methoxy.

In some embodiments of the compound of formula I or formula III, X is O. In other embodiments, X is S.

In some embodiments of the compound of formula I or formula III, $R^7$ and $R^8$ are both H. In some embodiments one of $R^7$ and $R^8$ is H and the other of $R^7$ and $R^8$ is methyl. Therefore, in some embodiments $R^7$ and $R^8$ are independently selected from H and methyl.

In some embodiments of the compound of formula I or formula III, $R^9$ and $R^{10}$ are both H. In other embodiments, $R^9$ and $R^{10}$ are selected from H and methyl. In some such embodiments, one of $R^9$ and $R^{10}$ is H and the other of $R^9$ and $R^{10}$ is methyl. In some embodiments, q is 0 and $R^9$ and $R^{10}$ are absent.

In some embodiments of the compound of formula I or formula III, G is $CR^{11a}$; J is $CR^{11b}$; K is $CR^{11c}$; $R^{11a}$, $R^{11b}$, $R^{11c}$, $R^{12a}$, $R^{12b}$, and $R^{12c}$ are all H; W is C—H; Y, is C—H; Z is C—H; $R^2$ is F; $R^3$ is methoxy; $R^7$ is H; $R^8$ is H; X is O, q is 0, and p is 1, 2, or 3. In some such embodiments, A is a branched chain $(C_4$-$C_8)$alkyl group such as a t-butyl, —$CH_2CH_2C(CH_3)_3$, —$CH_2CH_2CH(CH_3)_2$, —$CH(CH_3)$(cyclopropyl), or —$C(CH_3)_2CH_2CH_2CH_3$ group. In some such embodiments, A is a t-butyl group. In other such embodiments, A is an optionally substituted $(C_5$-$C_7)$cycloalkyl group or an optionally substituted $(C_5$-$C_7)$cycloalkenyl group. In some such embodiments, the $(C_5$-$C_7)$cycloalkyl group or the $(C_5$-$C_7)$cycloalkenyl group are substituted with 1, 2, 3, or 4 methyl groups. In some other such embodiments, A has the formula

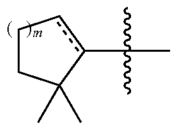

wherein m is 1, 2, or 3, and the dashed line indicates a single or double bond. In some such embodiments, A has the formula

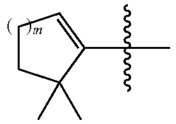

wherein m is 1, 2, or 3. In other such embodiments, A has the formula

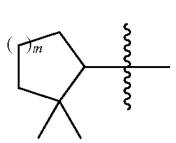

wherein m is 1, 2, or 3. In some such embodiments, A is a $(C_4$-$C_{10})$alkenyl group. In some such embodiments, A is selected from —CH═CH—$C(CH_3)_3$, —CH═CH—$CH_2CH_2CH_3$, —CH═CH-cyclopropyl, or —CH═CH-cyclohexyl groups.

In some embodiments of the compound of formula I or formula III, G is $CR^{11a}$; J is $CR^{11b}$; K is $CR^{11c}$; $R^{11a}$, $R^{11b}$, $R^{11c}$, $R^{12a}$, $R^{12b}$, and $R^{12c}$ are all H; W is C—H; Y, is C—H; Z is C—H; $R^2$ is F; $R^3$ is methoxy; $R^7$ is H; $R^8$ is H; X is O; q is 1; p is 1, 2, or 3; and A is —O—$(C_1$-$C_{12})$alkyl, —O—$(C_2$-$C_{12})$alkenyl, or —O—$(C_1$-$C_4)$alkyl-aryl. In some such embodiments, A is a —$OCH_2$-phenyl. In other embodiments, A is a —O—$CF_3$. In other such embodiments, A is a —O—$(C_3$-$C_{10})$alkyl or —O—$(C_3$-$C_{10})$alkenyl group. In other such embodiments, A is —O—$(C_3$-$C_8)$cycloalkyl optionally substituted with 1 or 2 methyl groups. In some such embodiments, A is an unsubstituted —O—$(C_3$-$C_8)$cycloalkyl group. In some such embodiments, A is a cyclopropyloxy, a cyclobutyloxy, a cyclopentyloxy, a cyclohexyloxy, or a cycloheptyloxy group. In some embodiments, A is a —O—$CH_2CH_2CH_3$, —O—$CH_2CH_2CH_2CH_3$, —O—$CH_2CH_2CH_2CH_2CH_3$, —O—$CH(CH_3)_2$, or —O—$CH_2CH(CH_3)_2$.

In some embodiments of the compound of formula I or formula III, $R^{11a}$, $R^{11b}$, $R^{11c}$, $R^{12a}$, $R^{12b}$, and $R^{12c}$ are all H; W is C—H; Y, is C—H; Z is C—H; $R^7$ is H; $R^8$ is H; X is O; q is 0; p is 1, 2, or 3; and A is —$OR^{4a}$. In other such embodiments, p is 1. In still other such embodiments, p is 2. In still further such embodiments, p is 3.

In some embodiments, the compound of formula I or formula III is a compound of formula I' or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof:

I'

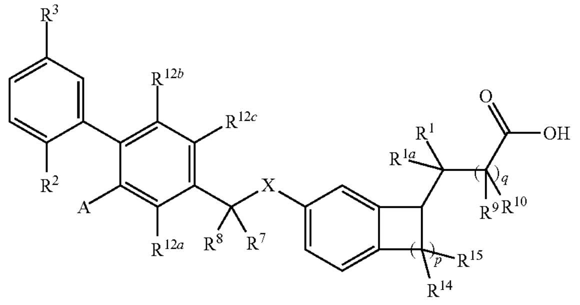

where the variables have the values described above with respect to the compound of formula I.

In some embodiments, the compound of formula I is a compound of formula I" or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof:

I"

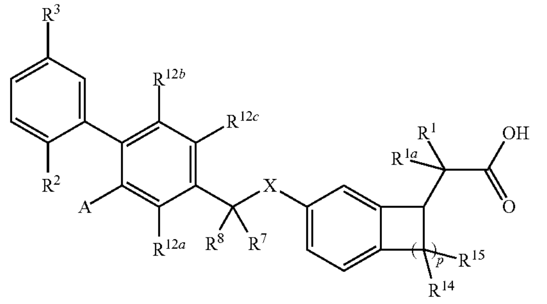

where the variables have the values described above with respect to the compound of formula I.

In some embodiments, the compound of formula I is a compound of formula IIA, IIB, or IIC, or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula IIA, IIB, and IIC have the following structures where each of the variables has any of the values of any of the embodiments described herein:

IIA

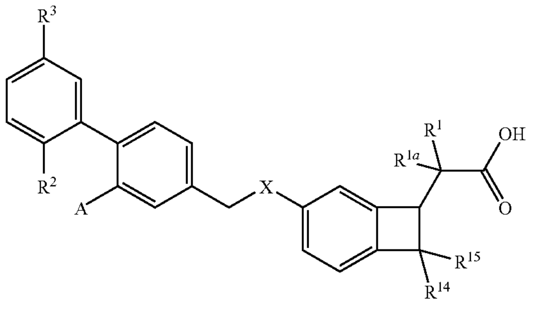

-continued

IIB

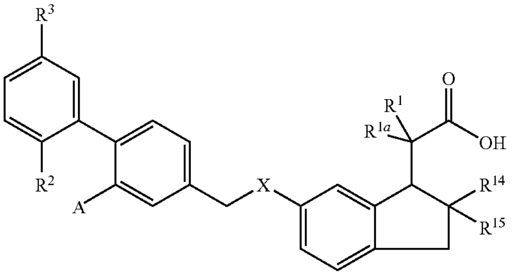

IIC

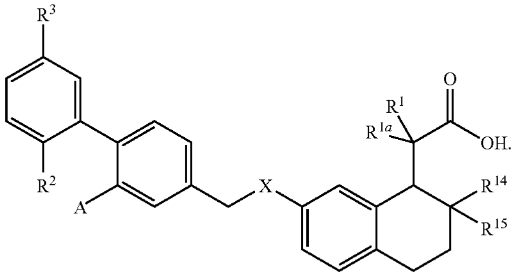

In some embodiments, the compound of formula IIA, IIB, or IIC, is a compound of formula IIA', IIB', or IIC' or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula IIA', IIB', and IIC' have the following structures where each of the variables has any of the values of any of the embodiments described herein:

IIA'

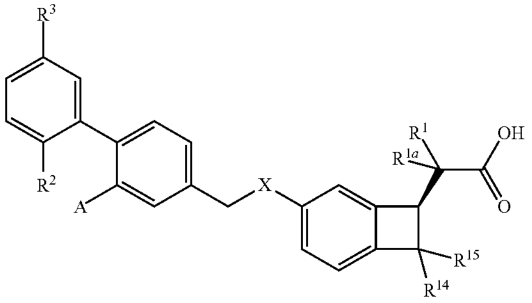

IIB'

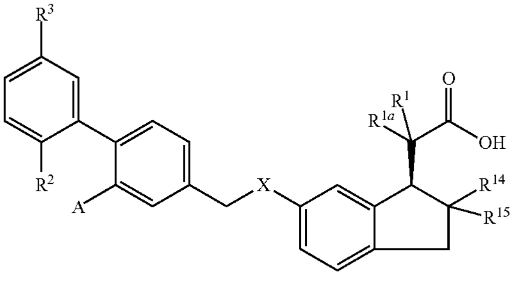

-continued

IIC'

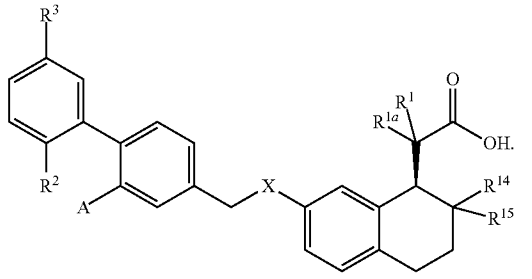

In some embodiments, the compound of formula IIA, IIB, or IIC, is a compound of formula IIA", IIB", or IIC" or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula IIA", IIB", and IIC" have the following structures where each of the variables has any of the values of any of the embodiments described herein:

IIA″

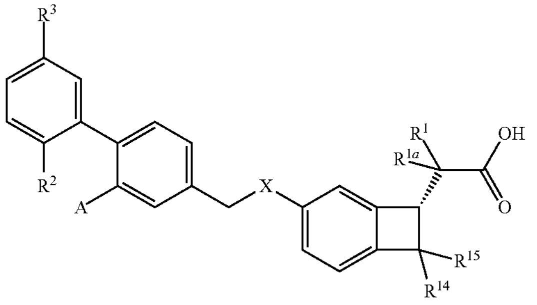

IIB″

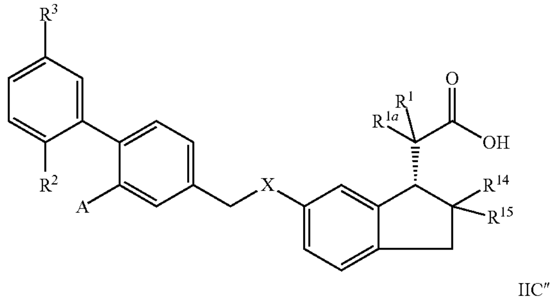

IIC″

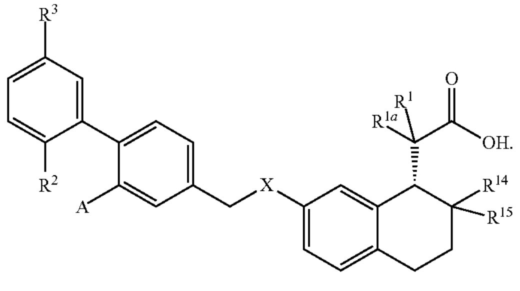

In some embodiments, the compound of formula I or formula III is selected from a group that includes each, all, or any one of the Example compounds set forth herein or is a pharmaceutically acceptable salt, solvate, or $C_1$-$C_6$ alkyl ester thereof. In some such embodiments where the compound has a chiral center, the compound exists as a single enantiomer whereas in other embodiments, the compound is a mixture of enantiomers of the compounds shown above.

In some embodiments, the compound is selected from any of the Example compounds set forth herein. Furthermore, in some embodiments, the compound of formula I or formula III has a variable corresponding to any of the groups in the Example compounds. For example, if an Example compound has a group corresponding to the A group, then in some embodiments of the compound of formula I or formula III, the A group will correspond to that set forth in the Example compound(s).

In some embodiments, the compound of any of the embodiments described herein does not displace a compound of the following formula that is bound to the GPR40 receptor

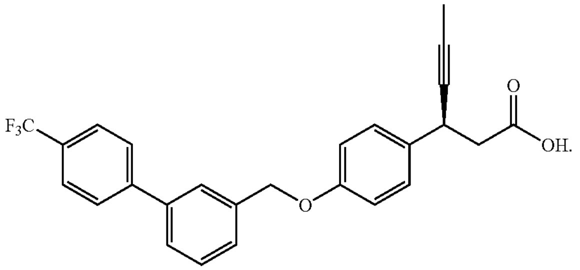 [SMILES: CC#C[C@@H](CC(=O)O)c1ccc(OCc2cccc(-c3ccc(C(F)(F)F)cc3)c2)cc1]

In some embodiments, the compound of any one of the embodiments described herein binds to a different site on the GPR40 receptor than does a compound of formula

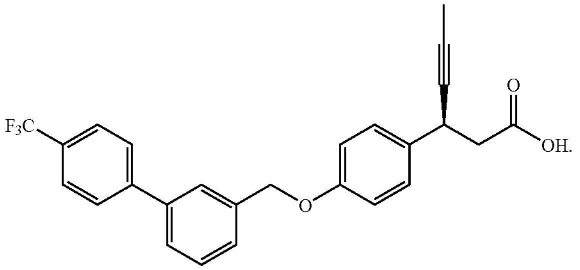 [SMILES: CC#C[C@@H](CC(=O)O)c1ccc(OCc2cccc(-c3ccc(C(F)(F)F)cc3)c2)cc1]

In another aspect, the present invention provides a compound of formula IV or a compound of formula VI or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof:

IV

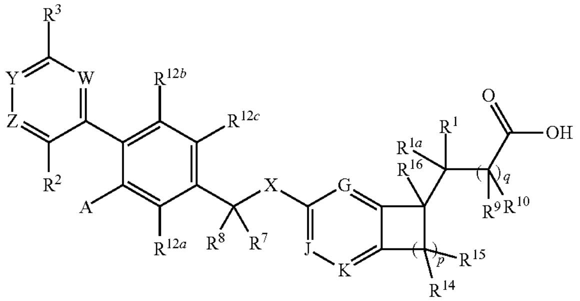

-continued

VI

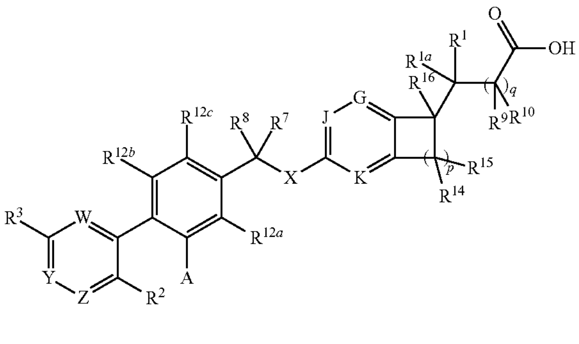

where

G is selected from N or $CR^{11a}$;

J is selected from N or $CR^{11b}$;

K is selected from N or $CR^{11c}$;

wherein 0 or 1 of G, J, and K is N;

A is selected from —$(C_1\text{-}C_{12})$alkyl; —$(C_2\text{-}C_{12})$alkenyl; —$(C_1\text{-}C_{12})$alkyl-O—$(C_1\text{-}C_4)$alkyl; —$(C_1\text{-}C_{12})$alkyl-OH; —$(C_1\text{-}C_{12})$alkyl-O—$(C_2\text{-}C_4)$alkenyl; —$(C_2\text{-}C_{12})$alkenyl-O—$(C_1\text{-}C_4)$alkyl; —$(C_2\text{-}C_{12})$alkenyl-OH; —$(C_2\text{-}C_{12})$alkenyl-O—$(C_2\text{-}C_4)$alkenyl; —O—$(C_1\text{-}C_{12})$alkyl; —O—$(C_2\text{-}C_{12})$alkenyl; —O—$(C_1\text{-}C_4)$alkyl-aryl; —S—$(C_1\text{-}C_{12})$alkyl; —S—$(C_2\text{-}C_{12})$alkenyl; —S(O)—$(C_1\text{-}C_{12})$alkyl; —S(O)—$(C_2\text{-}C_{12})$alkenyl; —$S(O)_2$—$(C_1\text{-}C_{12})$alkyl; —$S(O)_2$—$(C_2\text{-}C_{12})$alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 $(C_1\text{-}C_2)$alkyl groups; a —$(C_1\text{-}C_4)$alkyl-heterocyclyl wherein the heterocyclyl of the —$(C_1\text{-}C_4)$alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 $(C_1\text{-}C_2)$alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 $(C_1\text{-}C_2)$alkyl groups; further wherein the alkyl and alkenyl groups of —$(C_1\text{-}C_{12})$alkyl, —$(C_2\text{-}C_{12})$alkenyl, —$(C_1\text{-}C_{12})$alkyl-O—$(C_1\text{-}C_4)$alkyl, —$(C_1\text{-}C_{12})$alkyl-O—H, —$(C_1\text{-}C_{12})$alkyl-O—$(C_2\text{-}C_4)$alkenyl, —$(C_2\text{-}C_{12})$alkenyl-O—$(C_1\text{-}C_4)$alkyl, —$(C_2\text{-}C_{12})$alkenyl-OH, —$(C_2\text{-}C_{12})$alkenyl-O—$(C_2\text{-}C_4)$alkenyl, —O—$(C_1\text{-}C_{12})$alkyl, —O—$(C_2\text{-}C_{12})$alkenyl, and —O—$(C_1\text{-}C_4)$alkyl-aryl are unsubstituted or are substituted with from 1 to 4 substituents selected from —F, —Cl, —OH, (=O), —$NH_2$, $NH(C_1\text{-}C_4)$alkyl, —$N((C_1\text{-}C_4)alkyl)_2$, aryl, unsubstituted —$(C_1\text{-}C_2)$alkyl, or unsubstituted —O—$(C_1\text{-}C_2)$alkyl;

X is O or S;

W, Y, and Z are selected from N or $CR^{13}$; wherein 0 or 1 of W, Y, and Z is N; and further wherein Z is not N if $R^2$ is F;

$R^1$ is selected from H, $(C_1\text{-}C_6)$alkyl, $(C_2\text{-}C_6)$alkenyl, $(C_2\text{-}C_6)$alkynyl, —$(C_1\text{-}C_4)$alkyl-O—$(C_1\text{-}C_4)$alkyl, heterocyclyl, aryl, or heteroaryl;

$R^{1a}$ is selected from H and $(C_1\text{-}C_4)$alkyl;

$R^2$ is selected from H, F, $CF_3$, or $(C_1\text{-}C_6)$alkoxy;

$R^3$ is H, —OH, —$O(C_1\text{-}C_2)$alkyl, or —$S(C_1\text{-}C_2)$alkyl;

$R^7$ and $R^8$ are independently selected from H and $(C_1\text{-}C_4)$alkyl;

$R^9$, $R^{10}$, $R^{14}$, $R^{15}$, and $R^{16}$ are, in each instance independently selected from H and $(C_1\text{-}C_4)$alkyl and $R^9$ and $R^{10}$ are absent if q is 0;

Each of $R^{11a}$, $R^{11b}$, and $R^{11c}$ is independently selected from H, F, Cl, $(C_1\text{-}C_4)$alkyl, or $(C_1\text{-}C_4)$alkoxy; and $R^{11a}$ is absent if G is N; $R^{11b}$ is absent if J is N; or $R^{11c}$ is absent if K is N;

Each of $R^{12a}$, $R^{12b}$, and $R^{12c}$ is independently selected from H, F, Cl, $(C_1\text{-}C_4)$alkyl, or $(C_1\text{-}C_4)$alkoxy;

$R^{13}$ is selected from H, F, $(C_1\text{-}C_4)$alkyl, and —O—$(C_1\text{-}C_4)$alkyl;

q is 0 or 1; and p is 1, 2, 3, or 4.

In some embodiments of the compound of formula IV or formula VI, A is selected from —$(C_4\text{-}C_{12})$alkyl, —$(C_4\text{-}C_{12})$alkenyl, —$(C_3\text{-}C_{12})$alkyl-O—$(C_1\text{-}C_4)$alkyl, —$(C_3\text{-}C_{12})$alkyl-OH, —$(C_3\text{-}C_{12})$alkenyl-O—$(C_1\text{-}C_4)$alkyl, —$(C_3\text{-}C_{12})$alkenyl-OH, —O—$(C_4\text{-}C_{12})$alkyl, —O—$(C_4\text{-}C_{12})$alkenyl, a heterocycle comprising 4 to 7 ring members of which 1 or 2 are heteroatoms selected from N or O, wherein the heterocycle has 0 or 1 double bond between ring members and is unsubstituted or is substituted with from 1 to 4 $(C_1\text{-}C_2)$alkyl groups, a —$(C_1\text{-}C_4)$alkyl-heterocyclyl wherein the heterocyclyl of the —$(C_1\text{-}C_4)$alkyl-heterocyclyl comprises 4 to 7 ring members of which 1 or 2 are heteroatoms selected from N or O, wherein the heterocycle has 0 or 1 double bond between ring members and is unsubstituted or is substituted with from 1 to 4 $(C_1\text{-}C_2)$alkyl groups, or a —O-heterocyclyl wherein the heterocyclyl of the —O-heterocyclyl comprises 4 to 7 ring members of which 1 or 2 are heteroatoms selected from N or O, wherein the heterocycle has 0 or 1 double bond between ring members and is unsubstituted or is substituted with from 1 to 4 $(C_1\text{-}C_2)$alkyl groups, further wherein the alkyl and alkenyl groups of —$(C_4\text{-}C_{12})$alkyl, —$(C_4\text{-}C_{12})$alkenyl, —$(C_3\text{-}C_{12})$alkyl-O—$(C_1\text{-}C_4)$alkyl, —$(C_3\text{-}C_{12})$alkyl-O—H, —$(C_3\text{-}C_{12})$alkenyl-O—$(C_1\text{-}C_4)$alkyl, —$(C_3\text{-}C_{12})$alkenyl-OH, —O—$(C_4\text{-}C_{12})$alkyl, or —O—$(C_4\text{-}C_{12})$alkenyl are unsubstituted or are substituted with from 1 to 4 substituents selected from —F, —Cl, —OH, (=O), —$NH_2$, $NH(C_1\text{-}C_4)$alkyl, —$N((C_1\text{-}C_4)alkyl)_2$, aryl, unsubstituted —O—$(C_1\text{-}C_2)$alkyl, or unsubstituted —$(C_1\text{-}C_2)$alkyl. In some such embodiments, A is selected from —$(C_4\text{-}C_{12})$alkyl, —$(C_4\text{-}C_{12})$alkenyl, —$(C_3\text{-}C_{12})$alkyl-O—$(C_1\text{-}C_4)$alkyl, —$(C_3\text{-}C_{12})$alkyl-OH, —$(C_3\text{-}C_{12})$alkenyl-O—$(C_1\text{-}C_4)$alkyl, —$(C_3\text{-}C_{12})$alkenyl-OH, —O—$(C_4\text{-}C_{12})$alkyl, or —O—$(C_4\text{-}C_{12})$alkenyl, wherein the alkyl and alkenyl groups of —$(C_4\text{-}C_{12})$alkyl, —$(C_4\text{-}C_{12})$alkenyl, —$(C_3\text{-}C_{12})$alkyl-O—$(C_1\text{-}C_4)$alkyl, —$(C_3\text{-}C_{12})$alkyl-O—H, —$(C_3\text{-}C_{12})$alkenyl-O—$(C_1\text{-}C_4)$alkyl, —$(C_3\text{-}C_{12})$alkenyl-OH, —O—$(C_4\text{-}C_{12})$alkyl, or —O—$(C_4\text{-}C_{12})$alkenyl are unsubstituted or are substituted with from 1 to 4 substituents selected from —F, —Cl, —OH, (=O), —$NH_2$, $NH(C_1\text{-}C_4)$alkyl, -or $N((C_1\text{-}C_4)alkyl)_2$, unsubstituted —O—$(C_1\text{-}C_2)$alkyl, or unsubstituted —$(C_1\text{-}C_2)$alkyl. In some such embodiments, A is selected from —$(C_4\text{-}C_{12})$alkyl, —$(C_4\text{-}C_{12})$alkenyl, —$(C_3\text{-}C_{12})$alkyl-O—$(C_1\text{-}C_4)$alkyl, —$(C_3\text{-}C_{12})$alkyl-OH, —$(C_3\text{-}C_{12})$alkenyl-O—$(C_1\text{-}C_4)$alkyl, —$(C_3\text{-}C_{12})$alkenyl-OH, wherein the alkyl and alkenyl groups of —$(C_4\text{-}C_{12})$alkyl, —$(C_4\text{-}C_{12})$alkenyl, —$(C_3\text{-}C_{12})$alkyl-O—$(C_1\text{-}C_4)$alkyl, —$(C_3\text{-}C_{12})$alkyl-O—H, —$(C_3\text{-}C_{12})$alkenyl-O—$(C_1\text{-}C_4)$alkyl, or —$(C_3\text{-}C_{12})$alkenyl-OH, are unsubstituted or are substituted with from 1 to 4 substituents selected from —F, —OH, unsubstituted —O—$(C_1\text{-}C_2)$alkyl, or unsubstituted —$(C_1\text{-}C_2)$alkyl. In some such embodiments, A is selected from —$(C_4\text{-}C_{12})$alkyl, —$(C_4\text{-}C_{12})$alkenyl, —$(C_3\text{-}C_{12})$alkyl-O—$(C_1\text{-}C_4)$alkyl, —$(C_3\text{-}C_{12})$alkyl-OH, —$(C_3\text{-}C_{12})$alkenyl-O—$(C_1\text{-}C_4)$alkyl, —$(C_3\text{-}C_{12})$alkenyl-OH, wherein the alkyl and alkenyl groups of —$(C_4\text{-}$ $C_{12}$)alkyl, —($C_4$-$C_{12}$)alkenyl, —($C_3$-$C_{12}$)alkyl-O—($C_1$-$C_4$) alkyl, —($C_3$-$C_{12}$)alkyl-O—H, —($C_3$-$C_{12}$)alkenyl-O—($C_1$-$C_4$)alkyl, or —($C_3$-$C_{12}$)alkenyl-OH, are unsubstituted or are substituted with 1 to 4 substituent selected from —F, —OH, unsubstituted —O—($C_1$-$C_2$)alkyl, or unsubstituted —($C_1$-$C_2$)alkyl. In some such embodiments, A is a 5 to 7 membered cycloalkyl or cycloalkenyl group comprising from 1 to 4 methyl groups. In other embodiments, A is a —($C_3$-$C_{12}$) alkyl-O—($C_1$-$C_4$)alkyl, —($C_3$-$C_{12}$)alkyl-OH, —($C_3$-$C_{12}$) alkenyl-O—($C_1$-$C_4$)alkyl, or —($C_3$-$C_{12}$)alkenyl-OH. In some embodiments, each of the alkyl and alkenyl groups of the —($C_3$-$C_{12}$)alkyl-O—($C_1$-$C_4$)alkyl, —($C_3$-$C_{12}$)alkyl-OH, —($C_3$-$C_{12}$)alkenyl-O—($C_1$-$C_4$)alkyl, or —($C_3$-$C_{12}$)alkenyl-OH are unsubstituted whereas in other embodiments, each is substituted with 1 to 4 substituents selected from —OH, unsubstituted —O—($C_1$-$C_2$)alkyl, or unsubstituted —($C_1$-$C_2$)alkyl. In some embodiments, A is a —($C_4$-$C_8$)alkyl-O—($C_1$-$C_2$)alkyl, —($C_4$-$C_8$)alkyl-OH, —($C_4$-$C_8$)alkenyl-O—($C_1$-$C_2$)alkyl, or —($C_4$-$C_8$)alkenyl-OH and each of the alkyl and alkenyl groups of —($C_4$-$C_8$)alkyl-O—($C_1$-$C_2$)alkyl, —($C_4$-$C_8$)alkyl-OH, —($C_4$-$C_8$)alkenyl-O—($C_1$-$C_2$)alkyl, or —($C_4$-$C_8$)alkenyl-OH are unsubstituted or are substituted with 1 substituent selected from —OH, unsubstituted —O—($C_1$-$C_2$)alkyl, or unsubstituted —($C_1$-$C_2$)alkyl. In some such embodiments, at least one of the alkyl or alkenyl groups is branched or comprises a $C_3$-$C_7$ cycloalkyl ring. Therefore, in some embodiments, A is selected from

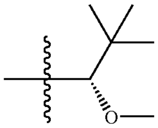 , 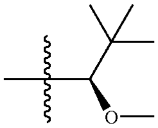 ,

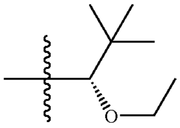 , 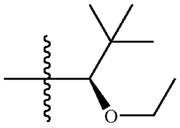 ,

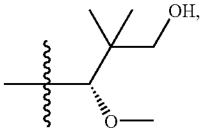 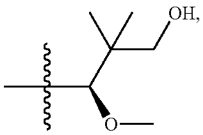

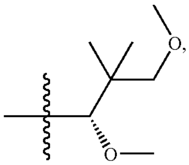 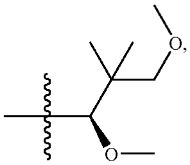

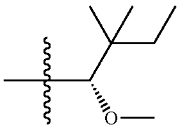 , 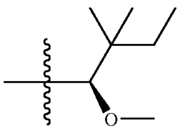 ,

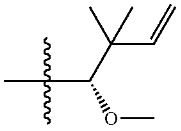 , 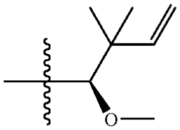 ,

-continued

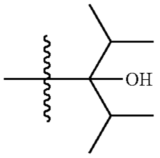 , 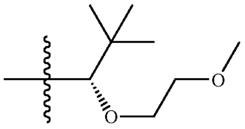 ,

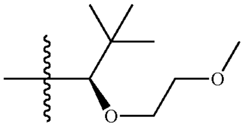 , 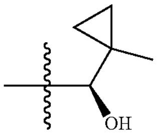 ,

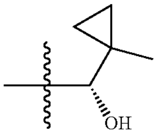 , 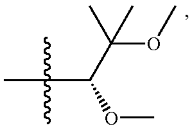 ,

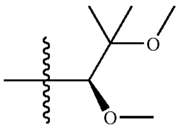 , 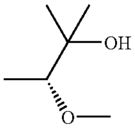 ,

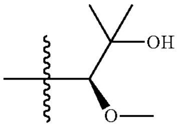 , or 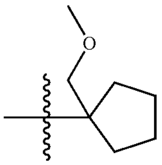 .

In some embodiments of the compound of formula IV or formula VI, A is selected from ($C_1$-$C_{12}$)alkyl, ($C_2$-$C_{12}$)alkenyl, —O—($C_1$-$C_{12}$)alkyl, —O—($C_2$-$C_{12}$)alkenyl, or —O—($C_1$-$C_4$)alkyl-aryl.

In some embodiments of the compound of formula IV or formula VI, A is selected from a branched ($C_4$-$C_{10}$)alkyl group, a ($C_4$-$C_{10}$)alkenyl group, a bicyclic ($C_7$-$C_{12}$)alkyl group, an unsubstituted or a substituted ($C_5$-$C_7$)cycloalkyl group, or an unsubstituted or a substituted ($C_5$-$C_7$)cycloalkenyl group. In some embodiments, A is a an unsubstituted ($C_5$-$C_7$)cycloalkyl group, a ($C_5$-$C_7$)cycloalkyl group substituted with 1, 2, 3, or 4 methyl groups, an unsubstituted ($C_5$-$C_7$)cycloalkenyl group, or a ($C_5$-$C_7$)cycloalkenyl group substituted with 1, 2, 3, or 4 methyl groups. In some such embodiments, $R^3$ is methoxy. In some such embodiments, $R^2$ is H whereas in other such embodiments, $R^2$ is F. In some such embodiments, A is selected from

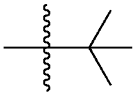 , 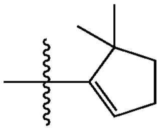 , 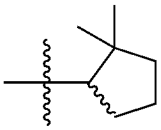 ,

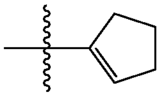 , 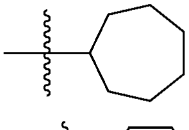 ,

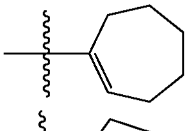 , 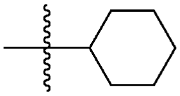 ,

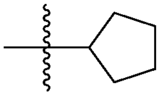 , 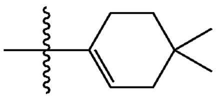 ,

-continued

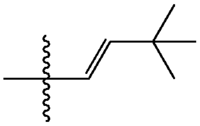, 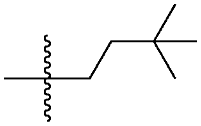,

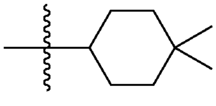, 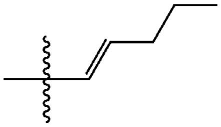,

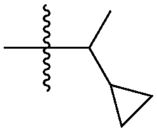, 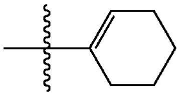,

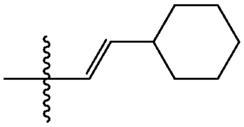, 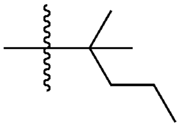,

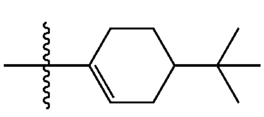, 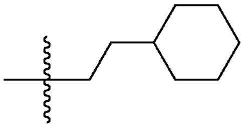,

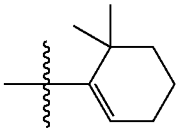, 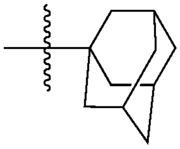,

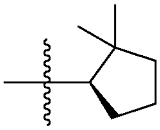, 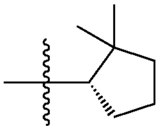, or

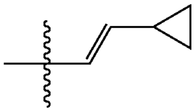.

In some such embodiments, A is selected from

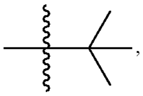, 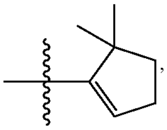, 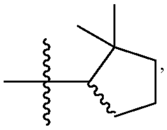,

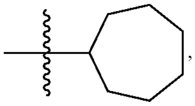, 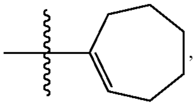,

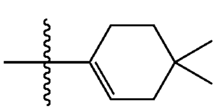, 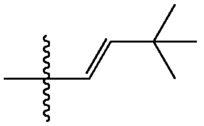,

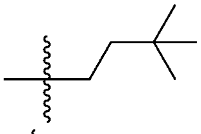, 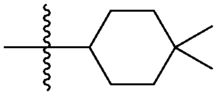,

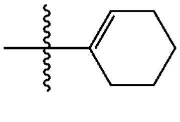, 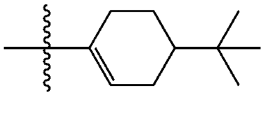,

-continued

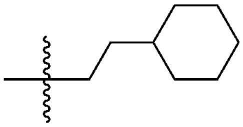, 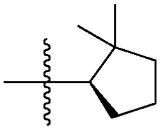,

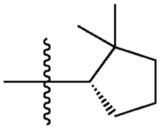, or 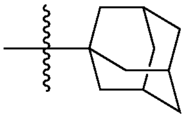.

In some embodiments of the compound of formula IV or formula VI, A is selected from ($C_3$-$C_{10}$)alkyl or ($C_4$-$C_{10}$) alkenyl. In some such embodiments, A is t-butyl. In other such embodiments, A is an unsubstituted or optionally substituted cyclopentyl, cyclohexyl, or cycloheptyl group. In some such embodiments, A is an unsubstituted cyclopentyl, cyclohexyl, or cycloheptyl group. In some such embodiments, A is a cyclopentyl, cyclohexyl, or cycloheptyl group optionally substituted with 1, 2, 3, or 4 ($C_1$-$C_4$)alkyl groups. In some such embodiments, A is a cyclopentyl, cyclohexyl, or cycloheptyl group substituted with a t-butyl group. In other such embodiments A is a cyclopentyl, cyclohexyl, or cycloheptyl group substituted with 1 or 2 methyl groups. In some such embodiments, A is an unsubstituted or optionally substituted cyclopentenyl, cyclohexenyl, or cycloheptenyl group. In some such embodiments, A is an unsubstituted cyclopentenyl, cyclohexenyl, or cycloheptenyl group. In some such embodiments, A is a cyclopentenyl, cyclohexenyl, or cycloheptenyl group optionally substituted with 1, 2, 3, or 4 ($C_1$-$C_4$)alkyl groups. In some such embodiments, A is a cyclopentenyl, cyclohexenyl, or cycloheptenyl group substituted with a t-butyl group. In other such embodiments A is a cyclopentenyl, cyclohexenyl, or cycloheptenyl group substituted with 1 or 2 methyl groups.

In some embodiments of the compound of formula IV or formula VI, A is selected from

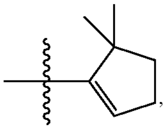, 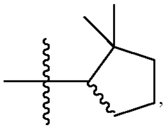, 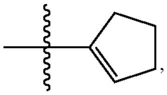,

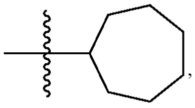, 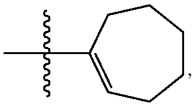,

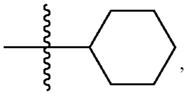, 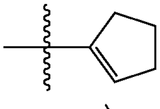,

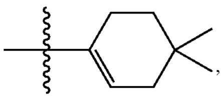, 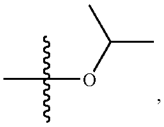,

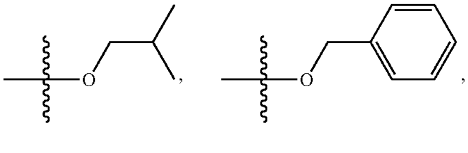,

-continued
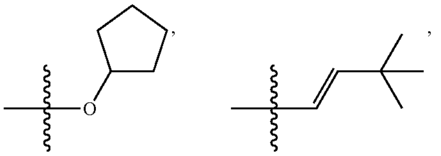
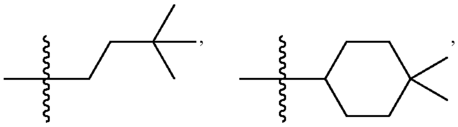
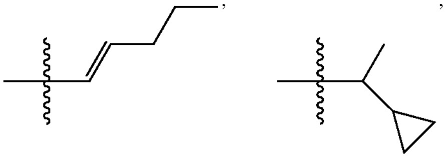
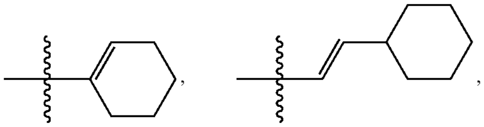
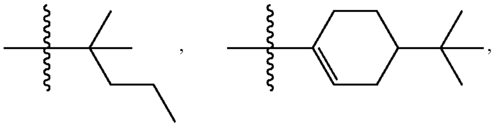
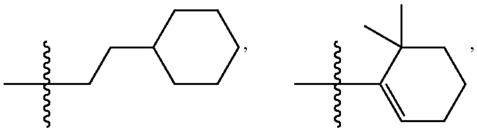
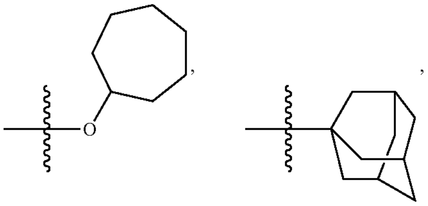
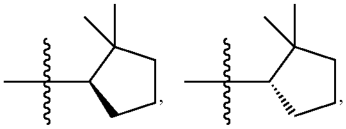 or
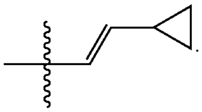
In some embodiments of the compound of formula IV or formula VI, A is selected from any one or more of
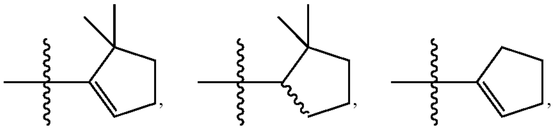
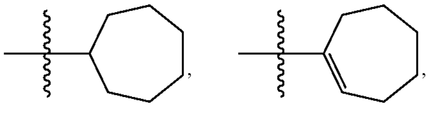
-continued
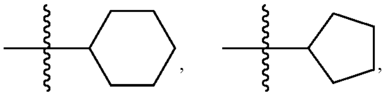
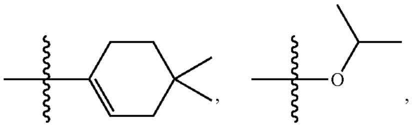
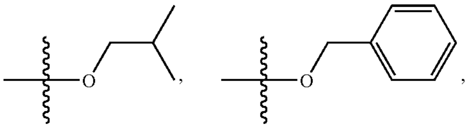
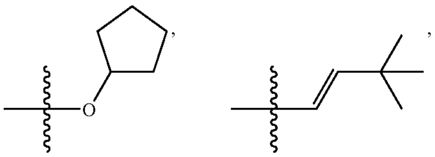
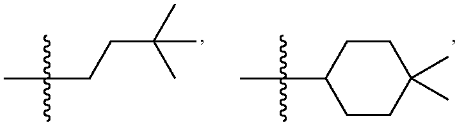
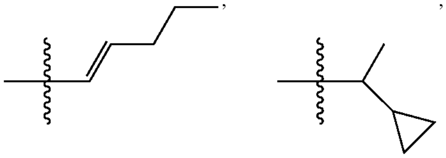
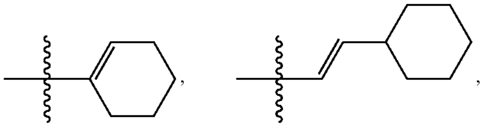
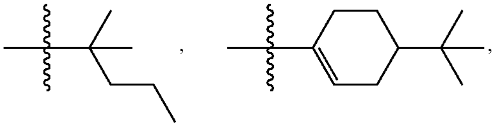
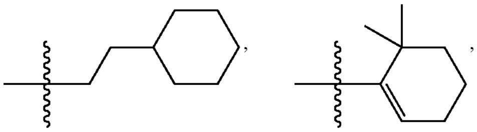
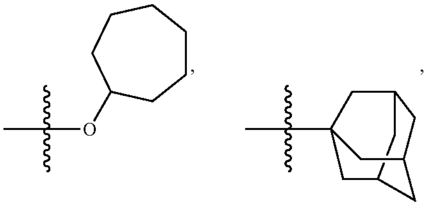
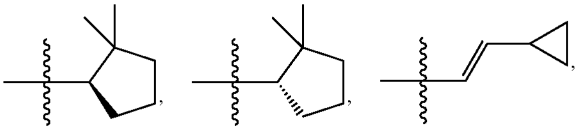
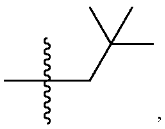
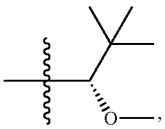
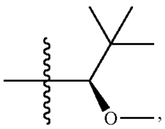

-continued
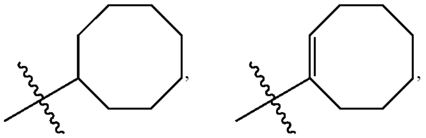
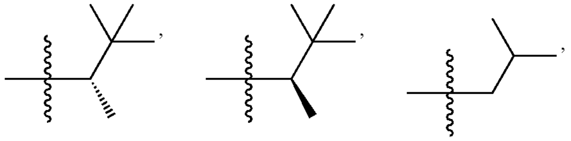
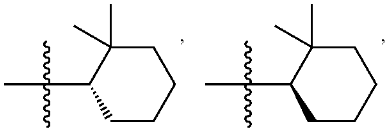
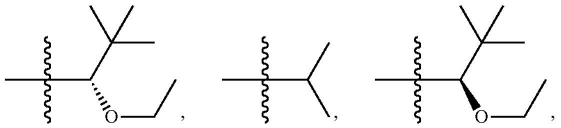
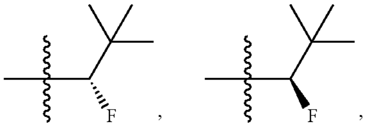
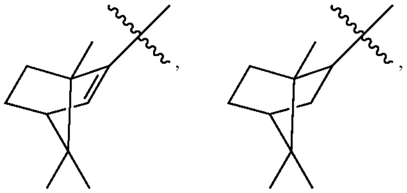
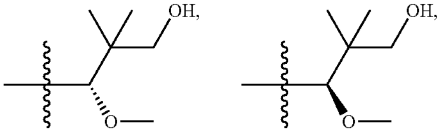
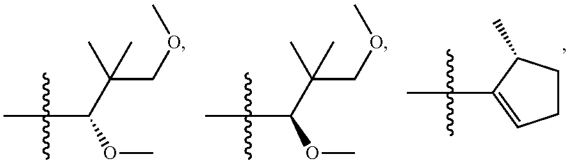
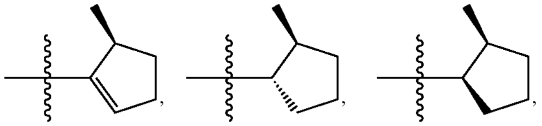
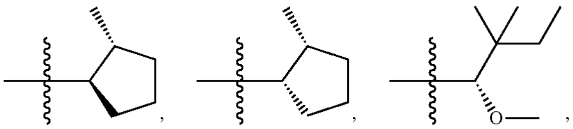
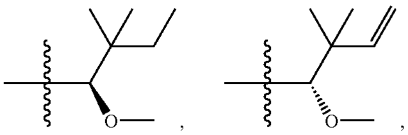
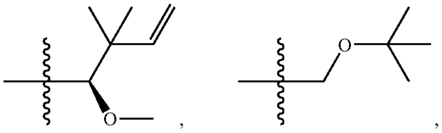
-continued
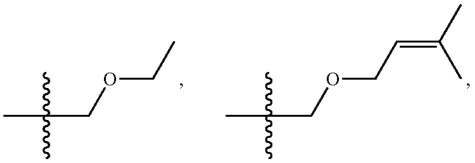
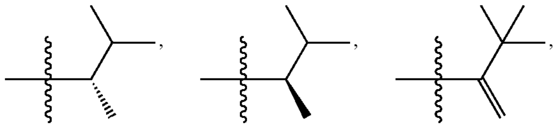
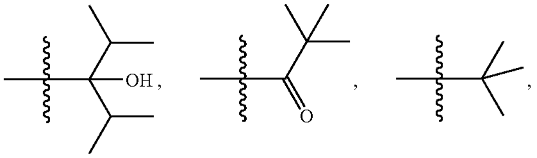
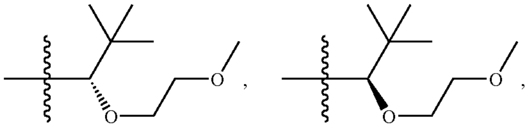
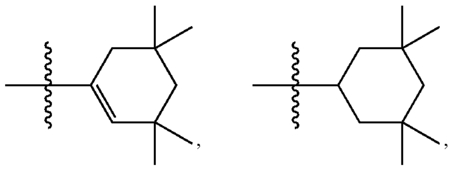
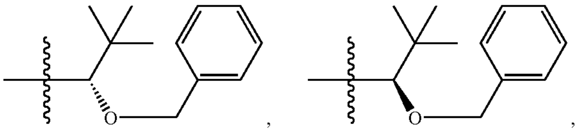
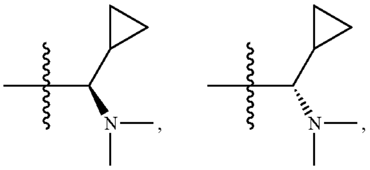
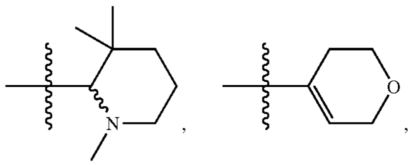
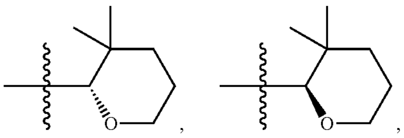
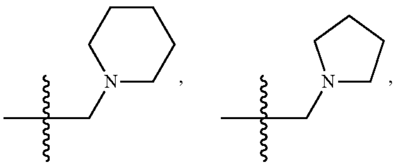
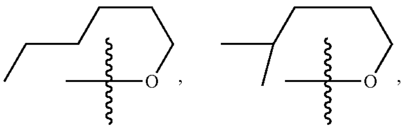

-continued

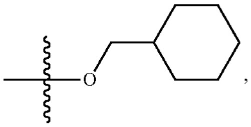, 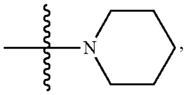,

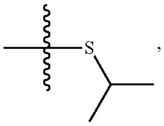, 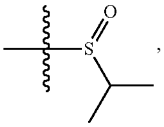, 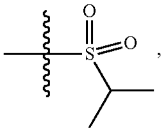,

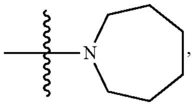, 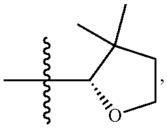, 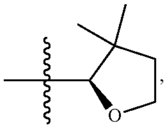,

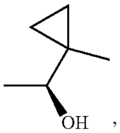, 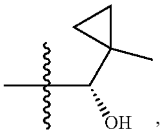, 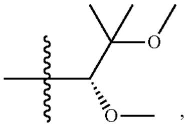,

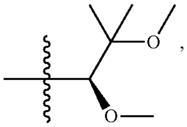, 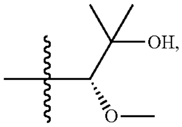

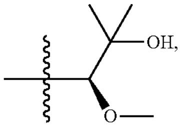 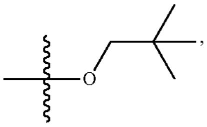,

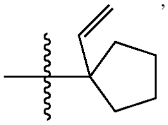, 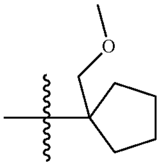,

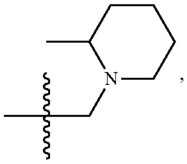, 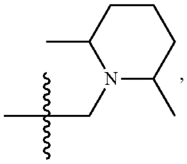,

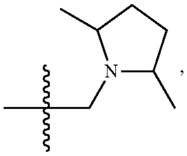, 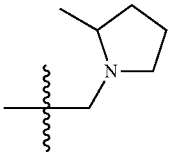, or

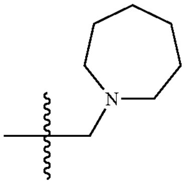.

In some embodiments of the compound of formula IV or formula VI, A is a group of formula A'.

A'

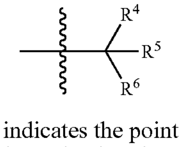

where the wavy line indicates the point of attachment and $R^4$, $R^5$, and $R^6$ are independently selected from H, F, ($C_1$-$C_4$) alkyl, and two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring. In some such embodiments, $R^4$, $R^5$, and $R^6$ are independently selected from H and ($C_1$-$C_4$) alkyl groups and at least two of $R^4$, $R^5$, and $R^6$ are ($C_1$-$C_4$) alkyl groups. In some such embodiments, all three of $R^4$, $R^5$, and $R^6$ are independently selected from ($C_1$-$C_4$)alkyl groups. In some such embodiments, two of $R^4$, $R^5$, and $R^6$ are methyl groups. In some such embodiments, each of $R^4$, $R^5$, and $R^6$ is a methyl group. In other embodiments, $R^4$, $R^5$, and $R^6$ are independently selected from H, ($C_1$-$C_4$)alkyl groups, or a substituted ($C_1$-$C_4$)alkyl group selected from ($C_1$-$C_4$)haloalkyl groups, ($C_1$-$C_4$)perhaloalkyl groups, or ($C_1$-$C_4$) alkoxy($C_1$-$C_4$)alkyl groups. In some such embodiments, at least one of $R^4$, $R^5$, and $R^6$ is a $CF_3$ group. In other embodiments at least one of $R^4$, $R^5$, and $R^6$ is a methoxymethyl group.

In some embodiments of the compound of formula IV or formula VI, A is a group of formula A' where the wavy line indicates the point of attachment and $R^4$, $R^5$, and $R^6$ are independently selected from H, F, OH, —O—($C_1$-$C_3$)alkyl, ($C_1$-$C_6$)alkyl and ($C_2$-$C_6$)alkenyl, and two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring. In some such embodiments, $R^4$, $R^5$, and $R^6$ are independently selected from H, OH, OMe, OEt, ($C_1$-$C_6$)alkyl, and ($C_2$-$C_6$)alkenyl groups and at least two of $R^4$, $R^5$, and $R^6$ are ($C_1$-$C_4$)alkyl groups. In some such embodiments, all three of $R^4$, $R^5$, and $R^6$ are independently selected from ($C_1$-$C_4$)alkyl groups. In some such embodiments, two of $R^4$, $R^5$, and $R^6$ are methyl groups. In some such embodiments, each of $R^4$, $R^5$, and $R^6$ is a methyl group. In other embodiments, $R^4$, $R^5$, and $R^6$ are independently selected from H, ($C_1$-$C_4$)alkyl groups, or a substituted ($C_1$-$C_4$)alkyl group selected from ($C_1$-$C_4$)haloalkyl groups, ($C_1$-$C_4$)perhaloalkyl groups, or ($C_1$-$C_4$) alkoxy($C_1$-$C_4$)alkyl groups. In some such embodiments, at least one of $R^4$, $R^5$, and $R^6$ is a $CF_3$ group. In other embodiments at least one of $R^4$, $R^5$, and $R^6$ is a methoxymethyl group. In other embodiments, at least one of $R^4$, $R^5$, and $R^6$ is selected from OH, methoxy, or is ethoxy. In some such embodiments one of $R^4$, $R^5$, and $R^6$ is a methoxy. In other such embodiments one of $R^4$, $R^5$, and $R^6$ is OH. In other such embodiments one of $R^4$, $R^5$, and $R^6$ is ethoxy.

In some embodiments of the compound of formula IV or formula VI where A is a group of formula A', two of $R^4$, $R^5$, and $R^6$, together with the C atom to which they are attached, join to form a 3-8 or 3-7 membered ring, and the other of $R^4$, $R^5$, and $R^6$ is selected from H, an unsubstituted ($C_1$-$C_4$)alkyl, or a substituted ($C_1$-$C_4$)alkyl. In some embodiments the ring is a carbocyclic ring which may be a fully saturated cycloalkyl ring. In some such embodiments, the 3-8 membered ring is a 5-7 membered ring, a 3-6 membered ring, or a 3-5 membered ring. Examples of such rings include cyclopropyl, cyclobutyl, cyclopentyl, cyclohexyl, and cycloheptyl rings. In some such embodiments, two of $R^4$, $R^5$, and $R^6$ join to form a cyclopropyl ring. In some such embodiments, the other of $R^4$, $R^5$, and $R^6$ is H. In some embodiments two of $R^4$, $R^5$, and $R^6$, together with the C atom to which they are attached, join to form an optionally substituted saturated or partially unsaturated 3-8 or 3-7 membered ring which may be monocyclic or bicyclic, and the other of $R^4$, $R^5$, and $R^6$ is selected from H, an unsubstituted ($C_1$-$C_4$)alkyl, or a substituted ($C_1$-$C_4$)alkyl. In some embodiments the ring only includes carbon ring members. In some such embodiments, the ring includes 0 or 1 double bonds between ring members. In some such embodiments, the 3-7 membered ring is a 3-6, or a 3-5 membered ring. Examples of such rings include cyclopropyl, cyclobutyl, cyclobutenyl, cyclopentyl, cyclopentenyl, cyclohexyl, cyclohexenyl, cycloheptyl, and cycloheptenyl rings. In some such embodiments, two of $R^4$, $R^5$, and $R^6$ join to form an optionally substituted cyclopropyl ring. In some such embodiments, the other of $R^4$, $R^5$, and $R^6$ is H. In some such embodiments, two of $R^4$, $R^5$, and $R^6$ join to form an optionally substituted cyclopentenyl, cyclohexenyl, or cycloheptenyl ring. In some such embodiments, the other of $R^4$, $R^5$, and $R^6$ is H. In some embodiments all three of $R^4$, $R^5$, and $R^6$, together with the C atom to which they are attached, join to form an optionally substituted saturated or partially unsaturated 3-8 membered ring bicyclic ring system. For example, in some embodiments, A may comprise an adamantyl or another bicyclic ring system such as, but not limited to bicyclo[3.2.1]octane, bicyclo[2.2.1]heptane, and the like. In some such embodiments the ring only includes carbon ring members. In some such embodiments, the ring includes 0 or 1 double bonds between ring members. In some embodiments, A is a branched chain $(C_4-C_8)$alkyl group such as a t-butyl group. In other such embodiments, A is an optionally substituted $(C_5-C_7)$cycloalkyl group or an optionally substituted $(C_5-C_7)$cycloalkenyl group. In some such embodiments, the $(C_5-C_7)$cycloalkyl group or the $(C_5-C_7)$cycloalkenyl group are substituted with 1, 2, 3, or 4 methyl groups. In some other such embodiments, A has the formula

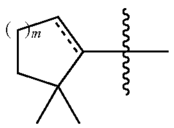

wherein m is 1, 2, or 3, and the dashed line indicates a single or double bond. In some such embodiments, A has the formula

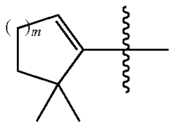

wherein m is 1, 2, or 3. In other such embodiments, A has the formula

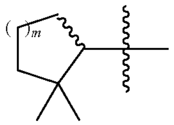

wherein m is 1, 2, or 3 and the wavy line indicates that the compound has the R stereochemistry, the S stereochemistry, or a mixture of the R and S stereochemistry with respect to the carbon attached to the rest of the molecule. In some such embodiments, A has the formula

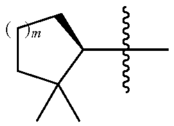

wherein m is 1, 2, or 3. In other embodiments, A has the formula

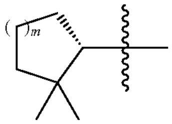

wherein m is 1, 2, or 3. In some embodiments, A is an —$OR^{4a}$ group, In some such embodiments, $R^{4a}$ is selected from a methyl, ethyl, propyl, butyl, pentyl, hexyl, isopropyl, t-butyl, or an isomer thereof. In some embodiments, $R^{4a}$ is selected from such an alkyl group that is substituted. For example, in some embodiments, $R^{4a}$ may a trihaloalkyl group such as a $CF_3$ group or another perhaloalkyl group.

In some embodiments of the compound of formula IV or formula VI, A is

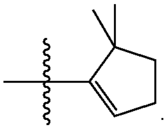 [SMILES: *C1=CCCC1(C)C]

In some embodiments of the compound of formula IV or formula VI, A is selected from

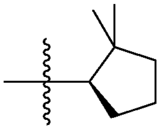

or

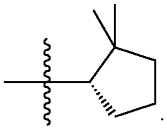

In some embodiments of the compound of formula IV or formula VI, A is

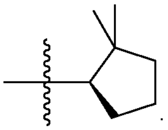 [SMILES: *[C@@H]1CCCC1(C)C]

In some embodiments of the compound of formula IV or formula VI, A is

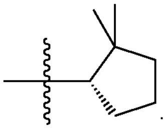

In some embodiments of the compound of formula IV or formula VI, A is a $(C_1-C_{12})$alkyl or is a $(C_2-C_{12})$alkenyl group and the $(C_1-C_{12})$alkyl or the $(C_2-C_{12})$alkenyl group is substituted with at least one A" group where A" is selected from —F, —OH, —O—$(C_1-C_4)$alkyl, —O$(C_1-C_4)$alkyl-aryl, —O$(C_2-C_8)$alkenyl, or —O—$(C_1-C_4)$alkyl-O—$(C_1-C_4)$ alkyl. Therefore, in some embodiments A is selected from any one or all of:

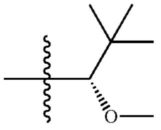 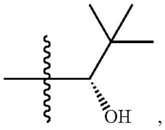 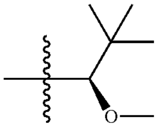
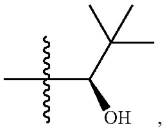 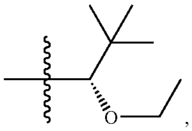 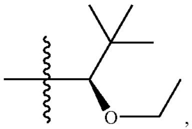
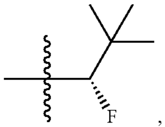 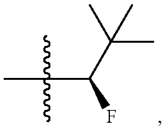 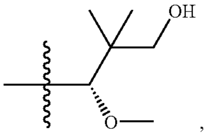
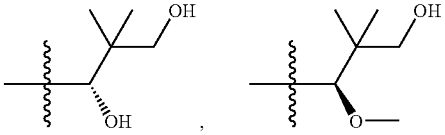
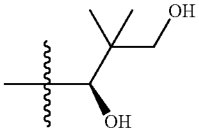 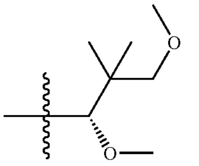
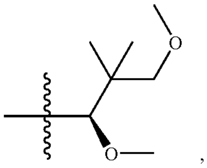 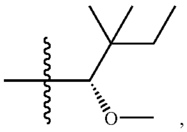
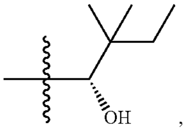 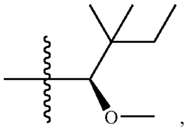
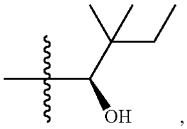 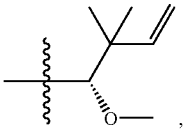
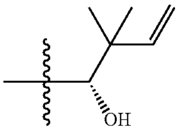 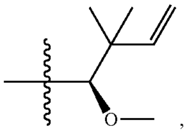
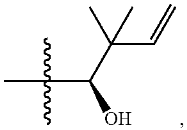 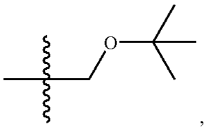
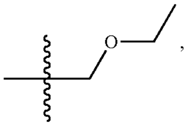 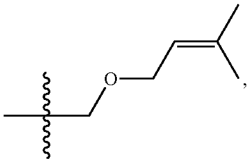
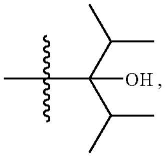 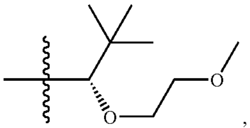
-continued
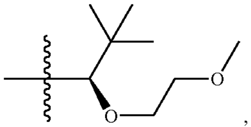 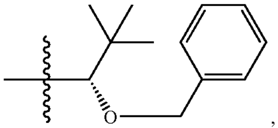
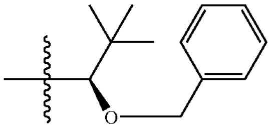 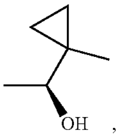
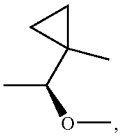 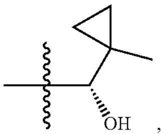 or 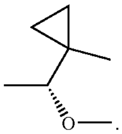
In some embodiments of the compound of formula IV or formula VI, A is selected from
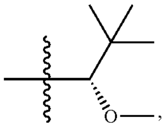 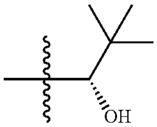 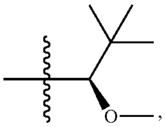 or
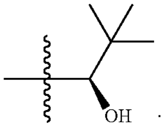
In some embodiments of the compound of formula IV or formula VI, A is selected from
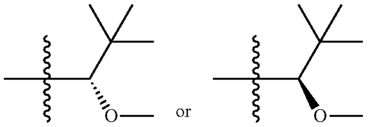
In some embodiments of the compound of formula IV or formula VI, A is
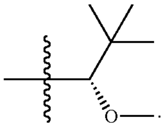 [SMILES: *[C@@H](OC)C(C)(C)C]
In some embodiments of the compound of formula IV or formula VI, A is
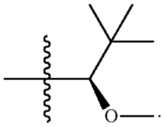 [SMILES: *[C@H](OC)C(C)(C)C]

In some embodiments of the compound of formula IV or formula VI, A is selected from

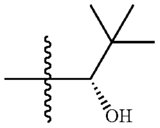

or

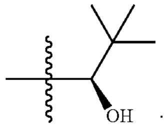

.

In some embodiments of the compound of formula IV or formula VI, A is

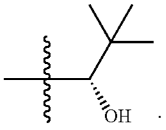 [SMILES: *[C@@H](O)C(C)(C)C]

.

In some embodiments of the compound of formula IV or formula VI, A is

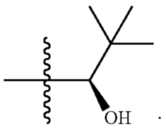 [SMILES: *[C@H](O)C(C)(C)C]

.

In some embodiments of the compound of formula IV or formula VI, A is selected from A is selected from $(C_1-C_{12})$alkyl, $(C_2-C_{12})$alkenyl, —O—$(C_1-C_{12})$alkyl, —O—$(C_2-C_{12})$alkenyl, —O—$(C_1-C_4)$alkyl-aryl, or a 4 to 7 membered heterocycle comprising 1 or 2 heteroatoms selected from N or O, wherein the heterocycle comprises 0 or 1 one double bond between ring members.

In some embodiments, the compound of formula IV or formula VI, is a compound of formula IV.

In some embodiments, the compound of formula IV or formula VI, is a compound of formula VI.

In some embodiments of the compound of formula IV or formula VI, G is $CR^{11a}$; J is $CR^{11b}$; and K is $CR^{11c}$. In some such embodiments, each of $R^{11a}$, $R^{11b}$, and $R^{11c}$ is H.

In some embodiments of the compound of formula IV or formula VI, G is $CR^{11a}$; J is $CR^{11b}$; and K is N. In other embodiments, G is $CR^{11a}$; J is N; and K is $CR^{11}$. In still other embodiments, G is N; J is $CR^{11b}$; and K is $CR^{11}$.

In some embodiments of the compound of formula IV or formula VI, $R^3$ is selected from —OH, —O$(C_1-C_2)$alkyl, or —S$(C_1-C_2)$alkyl. In some such embodiments, $R^3$ is —O$(C_1-C_2)$alkyl. In some such embodiments, $R^3$ is —$OCH_3$.

In some embodiments of the compound of formula IV or formula VI, $R^1$ is selected from H and $(C_1-C_4)$alkyl. In some such embodiments, $R^1$ and $R^{1a}$ are independently selected from H and $CH_3$. In some such embodiments, $R^1$ and $R^{1a}$ are both H. In other such embodiments, one of $R^1$ and $R^{1a}$ is H and the other of $R^1$ and $R^{1a}$ is $CH_3$. In still other such embodiments, $R^1$ and $R^{1a}$ are both $CH_3$.

In some embodiments of the compound of formula IV or formula VI, each instance of $R^{14}$ and $R^{15}$ is selected from H and $CH_3$.

In some embodiments of the compound of formula IV or formula VI, $R^2$ is selected from F, $CF_3$, or $(C_1-C_6)$alkoxy. In some such embodiments, $R^2$ is F.

In some embodiments of the compound of formula IV or formula VI, $R^2$ is H or F.

In some embodiments of the compound of formula IV or formula VI, $R^2$ is butoxy In some embodiments of the compound of formula IV or formula VI, each of $R^{11a}$, $R^{11b}$, $R^{11c}$, $R^{12a}$, $R^{12b}$, and $R^{12c}$ is H.

In some embodiments of the compound of formula IV or formula VI, q is 0.

In some embodiments of the compound of formula IV or formula VI, W, Y, and Z are all C—H In some embodiments of the compound of formula IV or formula VI, X is O.

In some embodiments of the compound of formula IV or formula VI, A is selected from $(C_3-C_{10})$alkyl or $(C_4-C_{10})$ alkenyl.

In some embodiments of the compound of formula IV or formula VI, A is a group of formula A'

A'

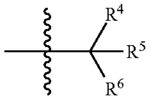

where the wavy line indicates the point of attachment; and $R^4$, $R^5$, and $R^6$ are independently selected from H, F, or $(C_1-C_4)$alkyl, wherein at least two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring.

In some embodiments of the compound of formula IV or formula VI, $R^7$ and $R^8$ are both H. In other embodiments, at least one of $R^7$ and $R^8$ is $CH_3$.

In some embodiments of the compound of formula IV or formula VI, $R^{16}$ is H. In other embodiments, $R^{16}$ is a $(C_1-C_4)$ alkyl group such as, in some embodiments, a methyl, ethyl, propyl, or butyl group. In some such embodiments, $R^{16}$ is a methyl group.

In some embodiments of the compound of formula IV or formula VI, G is $CR^{11a}$; J is $CR^{11b}$; K is $CR^{11c}$; $R^{11a}$, $R^{11b}$, $R^{11c}$, $R^{12a}$, $R^{12b}$, and $R^{12c}$ are all H; W is C—H; Y, is C—H; Z is C—H; $R^2$ is F; $R^3$ is methoxy; $R^7$ is H; $R^8$ is H; X is O, q is 0, and p is 1, 2, or 3. In some such embodiments, $R^{16}$ is H. In other such embodiments, $R^{16}$ is a $(C_1-C_4)$alkyl group such as, in some embodiments, a methyl group.

In some embodiments of the compound of formula IV or formula VI, A is a branched chain $(C_4-C_8)$alkyl group. In some such embodiments, A is a t-butyl group.

In some embodiments of the compound of formula IV or formula VI, A is an optionally substituted $(C_5-C_7)$cycloalkyl group or an optionally substituted $(C_5-C_7)$cycloalkenyl group. In some such embodiments, the $(C_5-C_7)$cycloalkyl group or the $(C_5-C_7)$cycloalkenyl group is substituted with 1, 2, 3, or 4 methyl groups.

In some embodiments of the compound of formula IV or formula VI, A is a group of formula

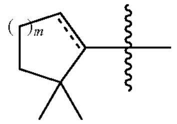

wherein m is 1, 2, or 3, and the dashed line indicates a single or double bond In some such embodiments, A is a group of formula

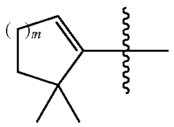

wherein m is 1, 2, or 3.

In some embodiments of the compound of formula IV or formula VI, A is —$OCF_3$.

In some embodiments of the compound of formula IV or formula VI, A is —O—($C_3$-$C_{10}$)alkyl or —O—($C_3$-$C_{10}$)alkenyl.

In some embodiments of the compound of formula IV or formula VI, A is —O—($C_3$-$C_8$)cycloalkyl optionally substituted with 1 or 2 methyl groups.

In some embodiments, the compound of formula IV is a compound of formula VA, VB, or VC, or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula VA, VB, and VC have the following structures where each of the variables has any of the values of any of the embodiments described herein:

VA

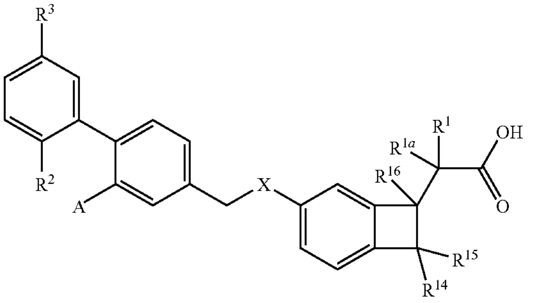

VB

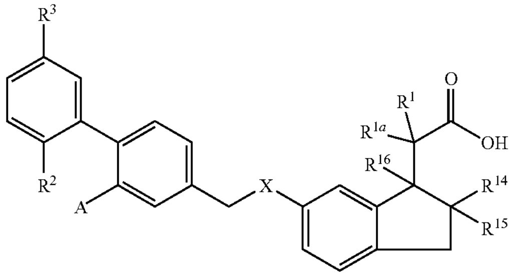

VC

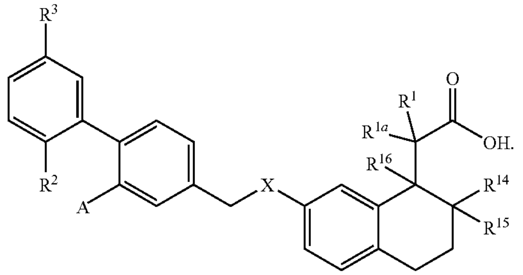

In some embodiments, the compound of formula VA, VB, or VC, is a compound of formula VA', VB', or VC' or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula VA', VB', and VC' have the following structures where each of the variables has any of the values of any of the embodiments described herein:

VA′

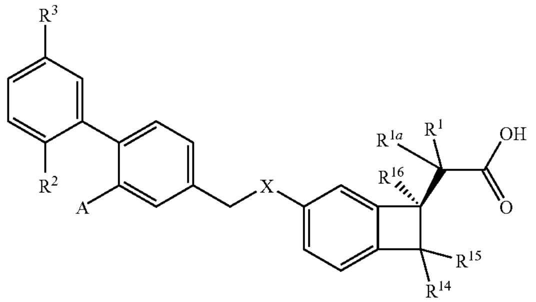

VB′

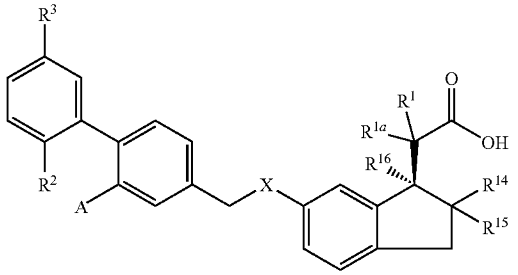

VC′

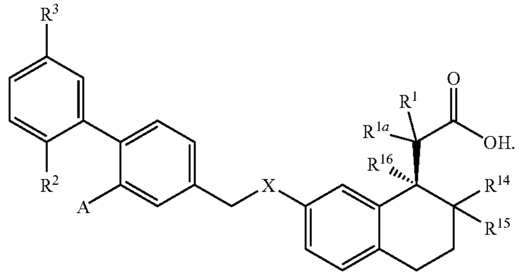

In some embodiments, the compound of formula VA, VB, or VC, is a compound of formula VA", VB", or VC" or a pharmaceutically acceptable salt, solvate, stereoisomer, or $C_1$-$C_6$ alkyl ester thereof; or a tautomer or a pharmaceutically acceptable salt, solvate, stereoisomer, or $C_1$-$C_6$ alkyl ester thereof; or a mixture thereof. The compound of formula VA", VB", and VC" have the following structures where each of the variables has any of the values of any of the embodiments described herein:

VA″

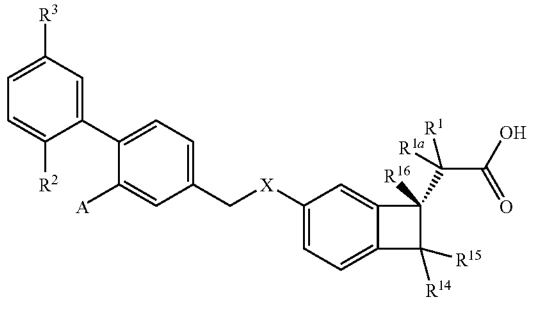

-continued

VB″

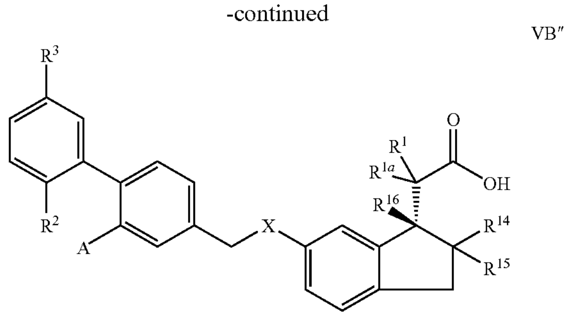

VC″

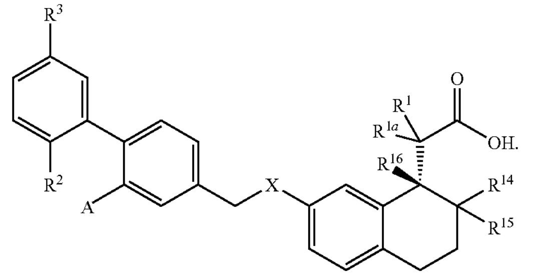

In some embodiments, the compound of any of the embodiments is a salt. In other embodiments, the compound of any of the embodiments is a $C_1$-$C_6$ alkyl ester. In some such embodiments, the $C_1$-$C_6$ alkyl ester is a methyl, ethyl, propyl, butyl, isopropyl, pentyl, or hexyl ester. In some such embodiments, the ester is a methyl or ethyl ester.

In some embodiments, the compound comprises a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

In another aspect, a compound of any of the embodiments described herein is used to prepare a medicament.

In yet another aspect, the invention provides a therapeutic composition that includes a compound of any of the embodiments and a second therapeutic agent as a combined preparation for simultaneous, separate, or sequential use in the treatment of a disease or condition mediated by GPR40. In some such embodiments, the disease or condition is type II diabetes. In some embodiments, the second therapeutic agent is selected from metformin, a thiazolidinedione, or a DPP-IV inhibitor. In some embodiments, the compound of any of the embodiments described herein and the second therapeutic agent are provided as single composition. In other embodiments, the compound of any of the embodiments described herein and the second therapeutic agent are provided separately as parts of a kit.

In some embodiments, the invention provides a compound of any of the embodiments described herein for use as a medicament.

In some embodiments, the invention provides a compound of any of the embodiments described herein for use in modulating GPR40.

In some embodiments, the invention provides a compound of any of the embodiments described herein for use in treating a disease or condition selected from type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, or edema. In some such embodiments, the compound is used for treating type II diabetes.

6.2.2 Preparation of the Compounds

The compounds of the invention can be prepared by a variety of synthetic or semisynthetic techniques. Scheme 1 provides a general synthetic scheme for exemplary compounds of the invention of formula I utilizing ester A where the variables in Scheme 1 have any of the values described above with respect to any of the embodiments, V is a OH or a halogen such as, but not limited to a Cl, Br, or I, or sulfonate ester such as, but not limited to OTs (tosylate) or OTf (triflate); and Alk is a straight or branched chain alkyl group having from 1-8 carbon atoms. It will be understood that the phenolic OH group of A can be replaced with an SH and reacted with a compound where V is a halogen to produce the analogous S-containing derivative (X═S) to the compounds shown. The synthesis of various biphenyl compounds is described in WO 2005/086661 and US 2006/0004012 which are both hereby incorporated by reference in their entireties and for all purposes as if fully set forth herein. Further relevant synthetic routes for related compounds are also described in these references. Appropriate starting materials can be prepared by techniques known or apparent to those of skill in the art or the starting materials may be commercially available. One of skill in the art will understand that the synthetic routes can be modified to use different starting materials or alternative reagents and that suitable adjustments in conditions (e.g., temperatures, solvents, etc.) can be made to accomplish the desired transformations. One of skill in the art will recognize that protecting groups may be necessary for the preparation of certain compounds and will be aware of those conditions compatible with a selected protecting group. Examples of such protecting groups include, for example, those set forth in Protective Groups in Organic Synthesis, Greene, T. W.; Wuts, P. G. M., John Wiley & Sons, New York, N.Y., (3rd Edition, 1999). Accordingly, the exemplary methods and the examples described herein are illustrative of the present invention and are not to be construed as limiting the scope thereof. It will be readily understood that the general synthetic route shown in Scheme 1 may also be used to prepare compounds of formula III by replacing A with B also shown in Scheme 1.

Scheme 1

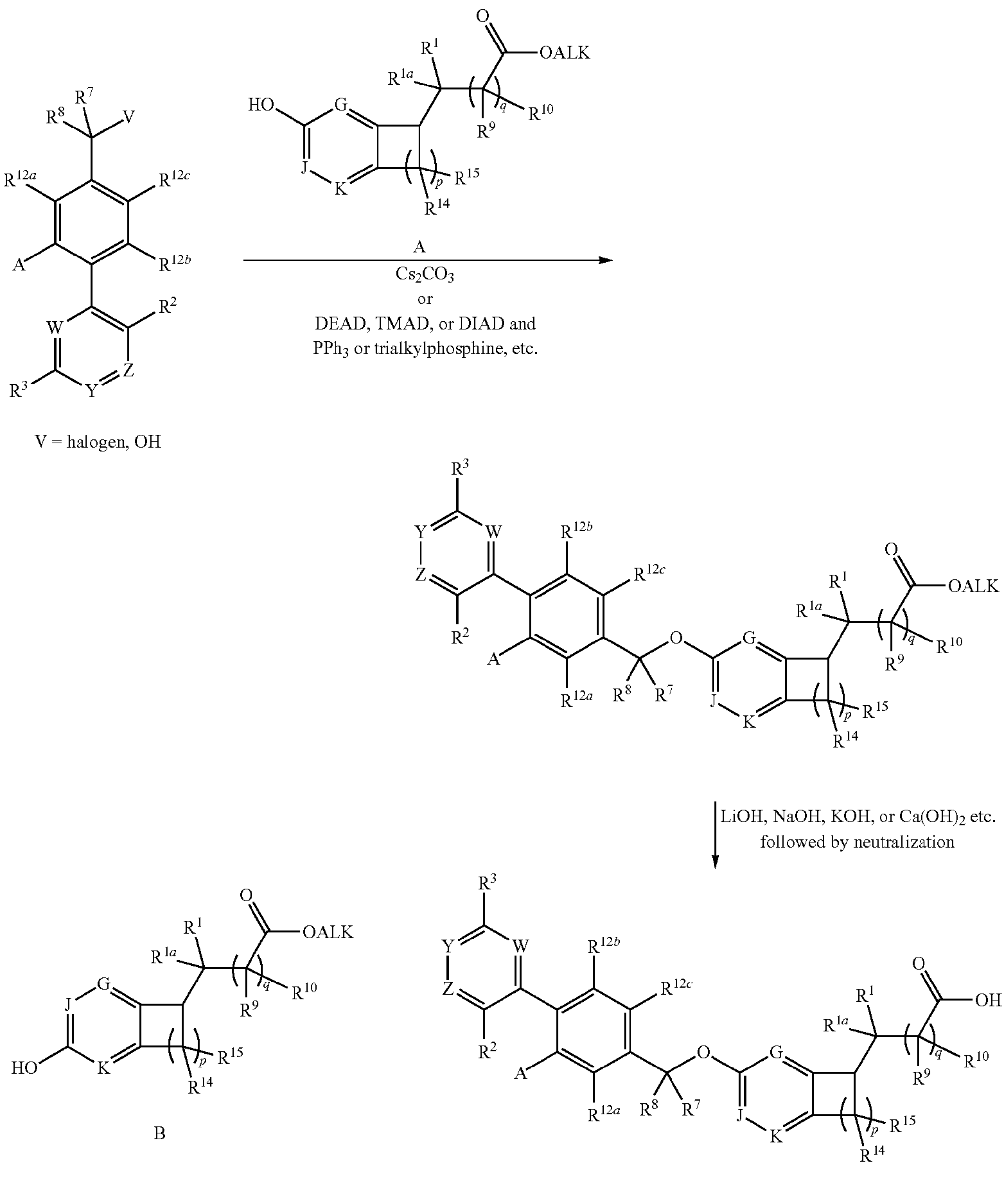

6.2.3 Compositions

In another aspect, the invention provides pharmaceutical compositions suitable for pharmaceutical use comprising one or more compounds of the invention and a pharmaceutically acceptable carrier, excipient, or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

6.2.4 Methods of Use

In another aspect, the invention provides methods of treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. The methods comprise administering to a subject in need thereof, a therapeutically effective amount of a compound or composition of any of the embodiments of the invention.

In one embodiment, the disease or condition is type II diabetes.

In another aspect, the present invention provides a method for treating a disease or condition responsive to the modulation of GPR40. Such methods comprise administering to a subject in need thereof a therapeutically effective amount of a compound or composition of the invention.

In some embodiments, the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, the disease or condition is type II diabetes.

In some embodiments, the disease or condition is obesity.

In some embodiments, the disease or condition is hypertension.

In some embodiments of administering the compounds or compositions of the invention, the compound or composition is administered orally, parenterally, or topically. In some embodiments, the compound or composition is administered orally. In other embodiments, the compound or composition is administered parenterally. In other embodiments, the compound or composition is administered topically.

The compounds of the invention may be administered alone or in combination with one or more other therapeutic agents. Therefore, in some embodiments, the compound or composition of any of the embodiments is administered in combination with a second therapeutic agent. In some such embodiments, the second therapeutic agent is an insulin sensitizing agent, such as metformin or a thiazolidinedione, for example. In some embodiments, the second therapeutic agent is a GLP-1 analog. In some embodiments, the second therapeutic agent is an inhibitor of DPP-IV such as, but not limited to, sitagliptin.

In another aspect, the invention provides methods of treating or preventing a disease or disorder responsive to modulation of GPR40 comprising administering to a subject having such a disease or disorder, a therapeutically effective amount of one or more of the subject compounds or compositions.

In yet another aspect, the invention provides methods of treating or preventing a GPR40-mediated condition, disease or disorder comprising administering to a subject having such a condition, disease or disorder, a therapeutically effective amount of one or more of the subject compounds or compositions.

In yet another aspect, the invention provides methods of modulating GPR40 comprising contacting a cell with one or more of the subject compounds or compositions.

For example, in some embodiments, a cell that constitutively expresses GPR40 is contacted with one or more of the subject compounds or compositions.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day. For oral administration, the compositions are preferably provided in the form of tablets containing from 1.0 to 1000 milligrams of the active ingredient, particularly 1.0, 3.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition mediated by GPR40. In some embodiments, therapeutic compositions are provided that include a compound of the invention and a second therapeutic agent as a combined preparation for simultaneous, separate or sequential use in the prophylactic treatment of a subject at risk for a disease or condition mediated by GPR40. In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat); and (c) antidiabetic agents such as insulin and insulin mimetics, sulfonylureas (e.g., glyburide, meglinatide), biguanides, e.g., metformin (GLUCOPHAGE®), α-glucosidase inhibitors (acarbose), insulin sensitizers, e.g., thiazolidinone compounds, rosiglitazone (AVANDIA®), troglitazone (REZULIN®), ciglitazone, pioglitazone (ACTOS®) and englitazone, DPP-IV inhibitors, e.g., vildagliptin (Galvus®), sitagliptin (Januvia™), and GLP-I analogs, e.g., exenatide (Byetta®). In some embodiments, a compound of the invention may be administered along with a DPP-IV inhibitor or a GLP-I analog. In some embodiments, a compound of the invention is administered with any of the DPP-IV inhibitors set forth in U.S. Patent Publication No. 2006/0270701 which is hereby incorporated by reference in its entirety and for all purposes as if specifically set forth herein.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject, comprising administering a compound or composition of the invention.

In some embodiments, the insulin concentration is increased after the compound is administered to the subject.

In other embodiments, the insulin concentration is decreased after the compound is administered to the subject.

The compounds and compositions described herein may be used to treat a variety of disease states and conditions. Therefore, in some embodiments, a compound of composition of any of the described embodiments is used for treating a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes.

The compounds of the invention may also be used to modulate GPR40. Therefore, in some embodiments, a compound or composition of any of the embodiments is used for modulating GPR40.

The compounds of any of the embodiments described herein may be used to prepare medicaments for treating the diseases or conditions described herein such as type II diabetes, obesity, hyperglycemia, glucose intolerance, insulin resistance, hyperinsulinemia, hypercholesterolemia, hypertension, hyperlipoproteinemia, hyperlipidemia, hypertriglyceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and/or edema. In some embodiment, the disease or condition is type II diabetes. The compounds of any of the embodiments may also be used to prepare medicaments for modulating GPR40 in a subject such as in a mammalian subject with type II diabetes.

The following examples are offered by way of illustration and are not intended to limit the scope of the invention. Those of skill in the art will readily recognize a variety of noncritical parameters that could be modified to yield essentially similar results.

7. EXAMPLES

Unless otherwise stated, all compounds were obtained from commercial sources or were prepared using the methods and experimental procedures described herein. Various procedures are also set forth in published U.S. Patent Application No. 2006/0004012 which is hereby incorporated by reference in its entirety and for all purposes as if set forth herein. The following abbreviations are used to refer to various reagents, solvents, experimental procedures, or analytical techniques that are described in the examples:

| | |
|---|---|
| DCM | Dichloromethane |
| DMF | N,N'-Dimethylformamide |
| DMAP | Dimethylaminopyridine |
| DME | Dimethoxyethane |
| DMSO | Dimethylsulfoxide |

-continued

| | |
|---|---|
| ESI | Electrospray Ionization |
| EtOAc | Ethyl acetate |
| EtOH | Ethanol |
| HMPA | Hexamethylphosphoramide |
| HPLC | High Performance Liquid Chromatography |
| HSA | Human Serum Albumin |
| IPA | Isopropanol |
| LAH | Lithium Aluminum Hydride |
| LDA | Lithium Diisopropylamide |
| MeOH | Methanol |
| MS | Mass Spectrometry |
| NMP | N-Methylpyrrolidinone |
| NMR | Nuclear Magnetic Resonance |
| PPTS | Pyridinium p-Toluenesulfonate |
| TEA | Triethlamine |
| THF | Tetrahydrofuran |
| THP | Tetrahydropyran |
| SPA | Scintilliation Proximity Assay |

Synthesis of Biphenyl Reagents

Method A

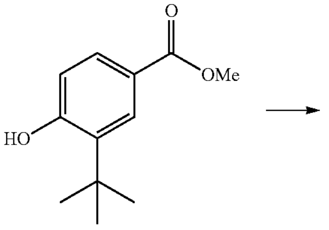

A.1

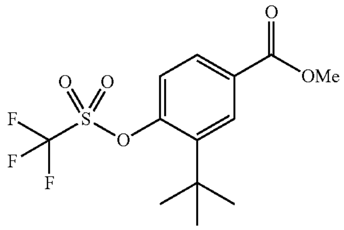

A.2

Methyl 3-tert-butyl-4-(trifluoromethylsulfonyloxy) benzoate (A.2)

To a stirred solution of commercially available methyl 3-tert-butyl-4-hydroxybenzoate (available from Apin Chemical Ltd, United Kingdom) (0.100 g, 0.48 mmol) in DCM (10 mL, 155 mmol) at 23° C., was added TEA (0.080 mL, 0.58 mmol) and DMAP (0.0059 g, 0.048 mmol), followed by triflic anhydride (0.097 mL, 0.58 mmol). The dark solution was stirred at room temperature and monitored by TLC and LC-MS. After 19 hours, the reaction was concentrated in vacuo. The residue was then purified by flash chromatography ($SiO_2$ gel 60, eluted with 0%-10% EtOAc in hexanes). Fractions containing the desired product were combined and concentrated to provide A.2 as a colorless oil (0.16 g, 98%). MS ESI (pos.) m/e: 341.0 $(M+H)^+$.

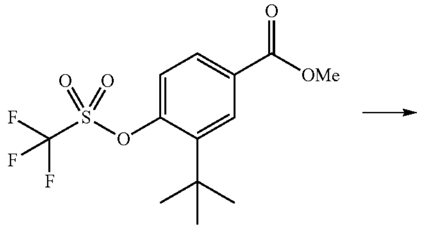

A.2

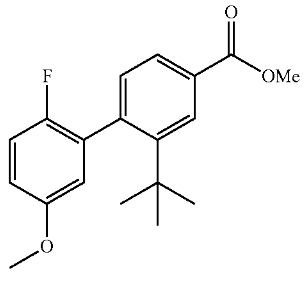

A.3

Methyl 2-(1,1-dimethylethyl)-2'-fluoro-5'-(methyloxy)-1,1'-biphenyl-4-carboxylate (A.3)

To a stirred solution of A.2 (0.100 g, 0.29 mmol) in DMF (2.00 mL, 26 mmol) at 23° C., was added 2-fluoro-5-methoxyphenylboronic acid (available from Aldrich) (0.100 g, 0.59 mmol), potassium carbonate (0.12 g, 0.88 mmol), followed by tetrakis(triphenylphosphine)palladium (0.034 g, 0.029 mmol). The mixture was heated to 100° C. After 2 hours, the reaction was cooled to room temperature and diluted with water. The mixture was extracted with EtOAc (3×50 mL) and concentrated in vacuo. The residue was then purified by flash chromatography ($SiO_2$ gel 60, eluted with 0%-15% EtOAc in hexanes). Fractions containing the desired product were combined and concentrated to provide A.3 as a colorless oil (0.85 g, 71%). MS ESI (pos.) m/e: 317.2 $(M+H)^+$.

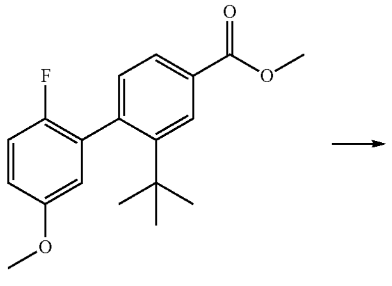

A.3

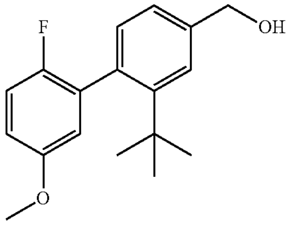

A.4

(2-(1,1-Dimethylethyl)-2'-fluoro-5'-(methyloxy)-1,1'-biphenyl-4-yl)methanol (A.4)

To a cooled solution of A.3 (0.85 g, 2.69 mmol) in dry THF (10.0 mL, 2.69 mmol) at 0° C., was added LAH (1.0 M solution in THF (6.0 mL, 6.0 mmol)). Upon complete addition, the reaction was allowed to warm to room temperature and monitored by TLC and LCMS. Upon completion, 1N NaOH (5 mL) was carefully added to quench the reaction. The resulting solution was extracted with EtOAc (3×10 mL). The combined organic layers were dried over $MgSO_4$, filtered, and concentrated in vacuo. The residue was then purified by flash chromatography ($SiO_2$ gel 60, eluted with 0%-40% EtOAc in hexanes). Fractions containing the desired product were combined and concentrated to provide A.4 as a colorless oil (0.56 g, 72%). MS ESI (pos.) m/e: 311.2 $(M+Na)^+$.

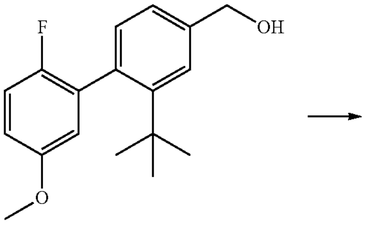

A.4

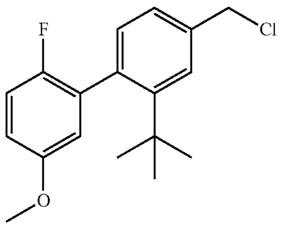

A 4-(Chloromethyl)-2-(1,1-dimethylethyl)-2'-fluoro-5'-(methyloxy)-1,1'-biphenyl (A)

To a cooled solution of A.4 (0.56 g, 1.93 mmol) in dry DCM (3.60 mL, 1.93 mmol) at 0° C., was added thionyl chloride (0.40 mL, 5.48 mmol) dropwise. Upon complete addition of thionyl chloride, the mixture was allowed to warm to room temperature. After 18 hours, the reaction was concentrated in vacuo. The residue was then purified by flash chromatography ($SiO_2$ gel 60, eluted with 0%-15% EtOAc in hexanes). Fractions containing the desired product were combined and concentrated to provide A as a colorless solid (0.44 g, 74%). $^1H$ NMR (500 MHz, $CDCl_3$) δ ppm 7.56 (1H, s), 7.25 (5H, dd, J=7.7, 1.6 Hz), 7.01 (2H, m), 6.86 (1H, dd, J=9.0, 3.2 Hz), 6.77 (1H, dd, J=5.9, 3.2 Hz), 4.65 (3H, s), 3.79 (3H, s), 1.24 (9H, s).

Method B

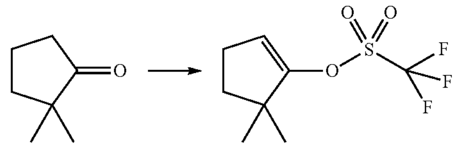

B.1 B.2

5,5-Dimethylcyclopent-1-enyl trifluoromethanesulfonate (B.2)

To a solution of 2,2-dimethylcyclopentanone B.1 (available from ChemSampCo) (3.00 g, 26.75 mmol) in THF (100 mL), was slowly added LDA (14.7 mL, 2.0 M, in heptane) at −78° C. The resulting mixture was stirred at −78° C. for 1 hour. A solution of N-phenyltriflamide (10.00 g, 28.00 mmol) was added to the mixture at −78° C., and stirring was continued at 0° C. for 2 hours and then at room temperature overnight. The reaction mixture was extracted with hexane (80×2 mL). The organic layer was washed with saturated $Na_2CO_3$ (30 mL), brine (20 mL), and dried with $MgSO_4$. The solvent was removed, and the residue was purified by CombiFlash® chromatography (eluent was EtOAc and hexane) to give B.2. $^1H$ NMR ($CDCl_3$) δ 1.16 (s, 6H), 1.86 (t, J=7.1 Hz, 2H), 2.36 (t, J=7.1 Hz, 2H), 5.56 (m, 1H).

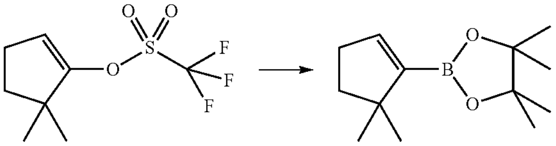

B.2 B.3

2-(5,5-Dimethylcyclopent-1-enyl)-4,4,5,5-tetramethyl-1,3,2-dioxaborolane (B.3)

$PdCl_2(PPh_3)_2$ (0.56 g, 0.80 mmol), $PPh_3$ (0.63 g, 2.40 mmol), bis(pinacolato)diboron (6.80 g, 26.75 mmol) and KOPh (fine powder, 5.30 g, 40.10 mmol) were added to a flask. The flask was flushed with nitrogen and charged with toluene (100 mL) and with B.2 (6.53 g, 26.75 mmol). The mixture was stirred at 50° C. for 2 hours. The reaction mixture was treated with water at room temperature and extracted with benzene (60×2 mL). The organic layer was dried over $MgSO_4$. The product was then purified by CombiFlash® chromatography to give intermediate B.3. $^1H$ NMR ($CDCl_3$) δ 1.04 (s, 6H), 1.18 (s, 12H), 1.57 (t, J=7.1 Hz, 2H), 2.29 (t, J=7.1 Hz, 2H), 6.29 (m, 1H).

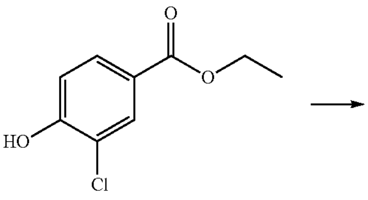

B.4

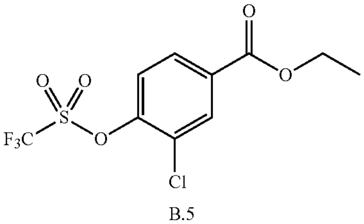

B.5

Ethyl 3-chloro-4-(((trifluoromethyl)sulfonyl)oxy)benzoate (B.5)

A mixture of ethyl 3-chloro-4-hydroxybenzoate (available from Aldrich) (5.00 g, 25.0 mmol), N-phenyltriflamide (9.30 g, 26.0 mmol) and TEA (4.2 mL, 30.0 mmol) in DCM (40 mL) with a catalytic amount of DMAP, was stirred at ambient temperature overnight. DCM (150 mL) was added, and the reaction mixture was washed with brine (30x3 mL), dried over $MgSO_4$, and the solvent was removed under reduced pressure. The product B.5 was used in the next step without further purification. MS ESI (pos.) m/e: 335.0 $(M+Na)^+$.

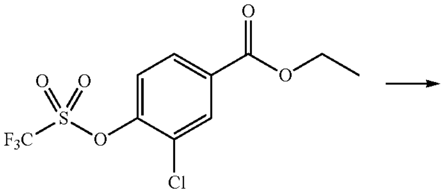

B.5

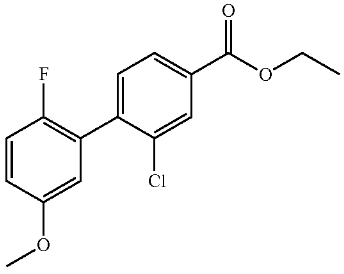

B.6

Ethyl 2-chloro-2'-fluoro-5'-(methyloxy)-1,1'-biphenyl-4-carboxylate (B.6)

A reaction mixture of ethyl 3-chloro-4-(trifluoromethylsulfonyloxy)benzoate (3.00 g, 9.02 mmol), 2-fluoro-5-methoxyphenylboronic acid (available from Aldrich) (1.84 g, 10.8 mmol), (t-4)-tetrakis(triphenylphosphine)palladium (0.521 g, 0.451 mmol) and potassium carbonate (2.49 g, 18.0 mmol) in DMF (20 mL), was purged with $N_2$ three times and then heated at 100° C. for 4 hours. The reaction was cooled to room temperature, and EtOAc (130 mL) was added. The mixture was then washed with brine (30×4 mL). The organic layer was dried over $MgSO_4$. The residue was purified by CombiFlash® silica gel column (eluent with hexane/EtOAc; 85/15) to give B.6. $^1$H NMR (400 MHz, $CDCl_3$) δ ppm 8.08 (d, 1H), 7.90 (d, 1H), 7.33 (dd, 1H), 6.96-7.02 (m, 1H), 6.82-6.85 (m, 1H), 6.74 (d, 1H), 4.33 (q, 2H), 4.31 (s, 3H), 1.34 (t, 3H). MS ESI (pos.) m/e: 309.1 $(M+H)^+$.

B.6

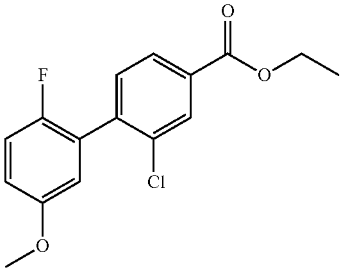

-continued

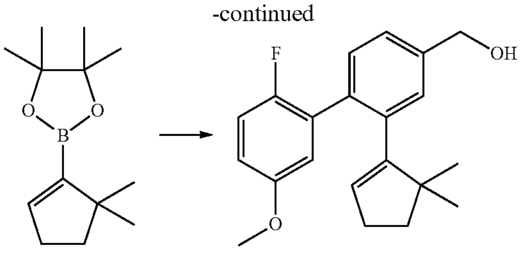

B.3 B.7

(2-(5,5-Dimethyl-1-cyclopenten-1-yl)-2'-fluoro-5'-(methyloxy)-1,1'-biphenyl-4-yl)methanol (B.7)

A reaction mixture of compound B.6 (1.80 g, 5.80 mmol), 2-(5,5-dimethylcyclopent-1-enyl)-4,4,5,5-tetramethyl-1,3,2-dioxaborolane (B.3) (1.40 g, 6.4 mmol), S-Phos (0.48 g, 1.20 mmol), tripotassium phosphate (3.10 g, 15.0 mmol) and palladium acetate (0.13 g, 0.58 mmol) in DMF (10.0 mL) and water (1.0 mL), was purged with $N_2$ three times. The resulting mixture was heated at 100° C. overnight. EtOAc (120 mL) was added, and the mixture was washed with brine (25×2 mL). The organic layer was dried with MgSO4. The residue was purified by CombiFlash® chromatography (silica gel, eluent with hexane/EtOAc, 9/1) to give Suzuki coupling product as an intermediate, ethyl 2-(5,5-dimethyl-1-cyclopenten-1-yl)-2'-fluoro-5'-(methyloxy)-1,1'-biphenyl-4-carboxylate. MS ESI (pos.) m/e: 369.1 $(M+H)^+$. To a solution of ethyl 2-(5,5-dimethyl-1-cyclopenten-1-yl)-2'-fluoro-5'-(methyloxy)-1,1'-biphenyl-4-carboxylate (1.00 g, 3.0 mmol) in THF (10.0 mL), was slowly added LAH, (1.0M solution in diethyl ether, 4.0 mL, 4.0 mmol) at 0° C. After the addition, the reaction mixture was stirred at 40° C. for 1.5 hours, and then at room temperature for 2 hours. A mixture of water (0.22 mL) in THF (2.0 mL) was slowly added and then 15% sodium hydroxide (0.22 mL) was added at 0° C. Finally, water (0.65 mL) was added at room temperature. The solid was removed by filtration, and the solvent was removed under reduced pressure. The residue was purified by CombiFlash® chromatography (silica gel column, eluent with hexane/EtOAc, 90/10 to 70/30) to give the title compound B.7. $^1$H NMR (400 MHz, $CDCl_3$) δ ppm. 7.24 (s, 2H), 7.09-7.21 (m, 1H), 6.84-6.96 (m, 1H), 6.68-6.72 (m, 2H), 5.43 (s, 1H), 4.65 (s, 2H), 3.66 (s, 3H), 2.17 (td, 2H), 1.77 (b, 1H), 1.58 (t, 2H), 0.78 (s, 6H). MS ESI (pos.) m/e: 309.1 $(M-HO)^+$, 345.2 $(M+H_3O)^+$.

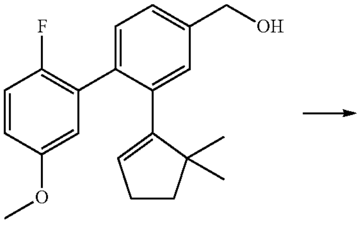

B.7

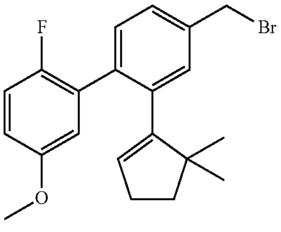

B.8

4-(Bromomethyl)-2-(5,5-dimethyl-1-cyclopenten-1-yl)-2'-fluoro-5'-(methyloxy)-1,1'-biphenyl (B.8)

To a solution of triphenylphosphine (0.13 g, 0.51 mmol) in DCM (1.0 mL), was slowly added bromine (0.081 g, 0.51 mmol, 0.25 mL, 2M in $CCl_4$) at 0° C. The resulting mixture was stirred at 0° C. for 15 minutes and then a mixture of compound B.7 (0.15 g, 0.46 mmol) and anhydrous pyridine (0.041 mL, 0.51 mmol) in DCM (3.0 mL) was added to the mixture. The reaction mixture was stirred at room temperature for 2 hours. DCM (80 mL) was added, and the mixture was washed with water (20×2 mL), and dried over $Na_2SO_4$. The solvent was removed under reduced pressure to provide product B.8. $^1H$ NMR (400 MHz, $CDCl_3$) δ ppm. 7.16-7.29 (m, 3H), 6.88 (t, 1H), 6.72 (m, 2H), 5.45 (s, 1H), 4.46 (s, 2H), 3.68 (s, 3H), 2.16-2.19 (m, 2H), 1.59 (t, 2H), 0.78 (s, 6H).

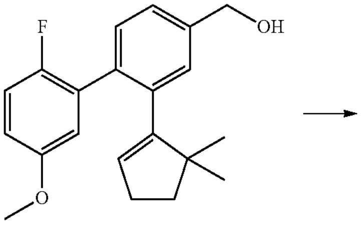

B.7

-continued

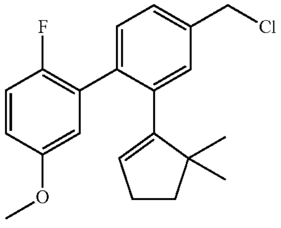

B.9

4-(Chloromethyl)-2-(5,5-dimethyl-1-cyclopenten-1-yl)-2'-fluoro-5'-(methyloxy)-1,1'-biphenyl (B.9)

To a solution of compound B.7 (1.10 g, 3.37 mmol) and a catalytic amount of DMF (0.10 mL) in DCM (12.0 mL), was slowly added thionyl chloride (0.802 g, 6.74 mmol) at 0° C. After addition, the reaction mixture was stirred at room temperature for 1 hour. The solvent was removed under reduced pressure, and the resulting residue was purified by Combi-Flash® chromatography (silica gel column eluted with hexane/EtOAc, 100/0 to 95/5) to give the title compound B.9 (1.15 g). $^1H$ NMR (400 MHz, $CDCl_3$) δ ppm. 7.32-7.39 (m, 2H), 7.28-7.29 (m, 1H), 6.88 (t, 1H), 6.80-6.82 (m, 2H), 5.56 (s, 1H), 4.66 (s, 2H), 3.78 (s, 3H), 2.27-2.29 (m, 2H), 1.69 (t, 2H), 0.89 (s, 6H)

Method C

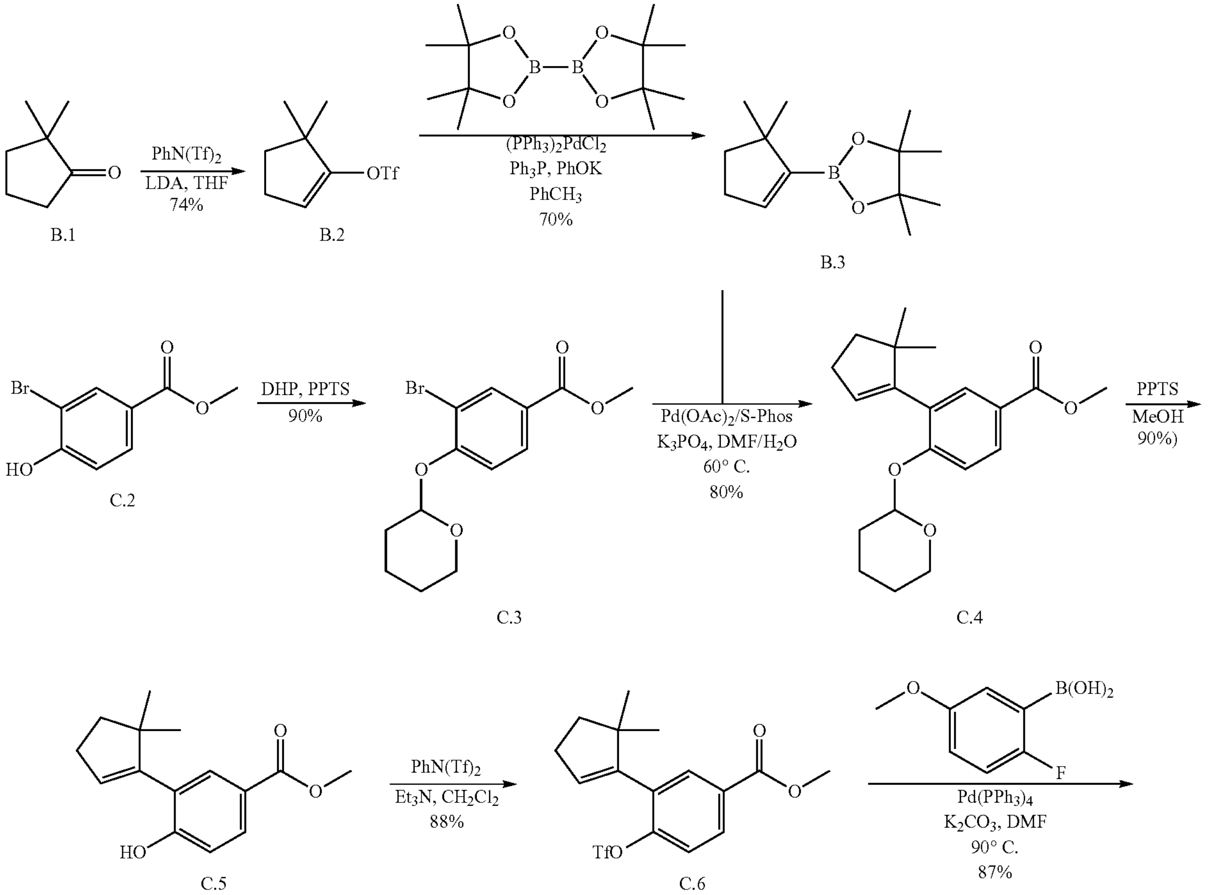

-continued

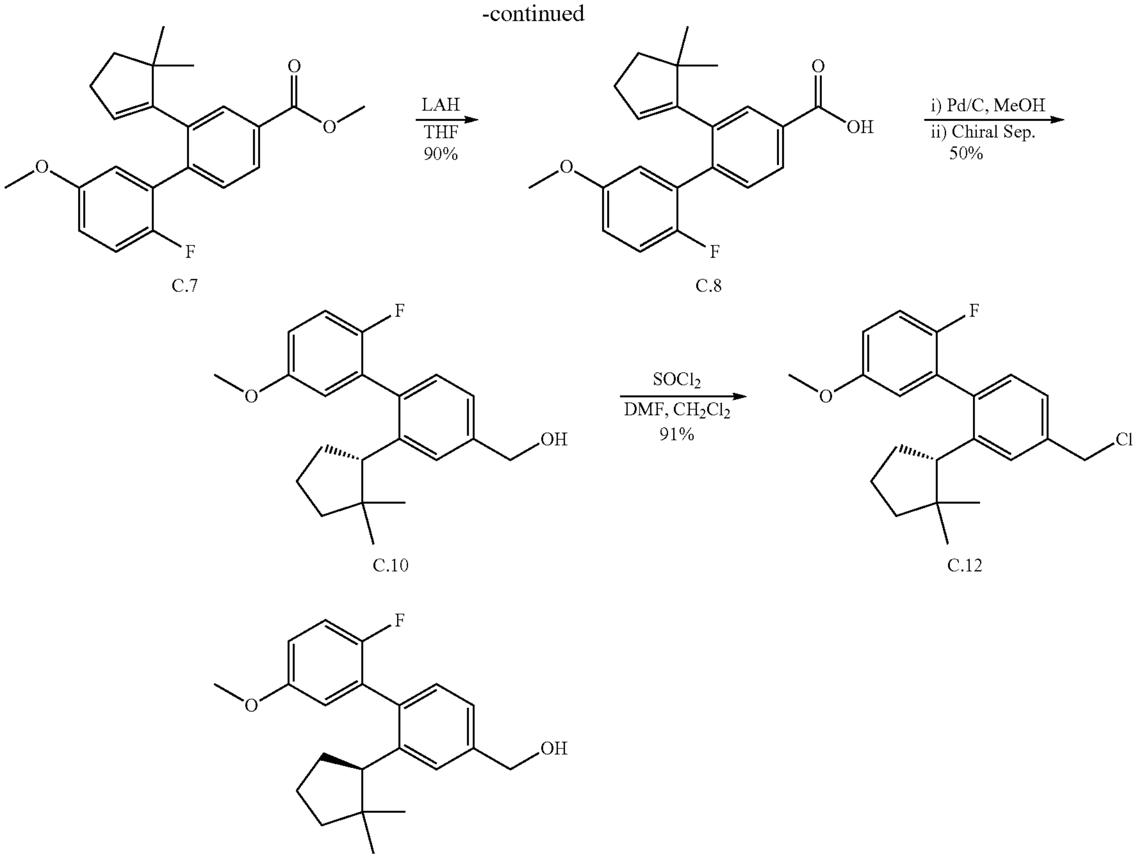

C.7 C.8 C.10 C.12 C.11

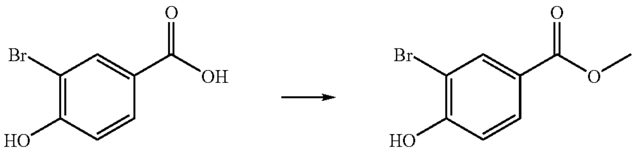

C.1 C.2

Methyl 3-bromo-4-hydroxybenzoate (C.2)

To a stirred solution of 3-bromo-4-hydroxybenzoic acid (C.1) (available from Alfa Aesar, Avocado, Lancaster) (50.0 g, 231 mmol) in MeOH (300 mL) was added a cold solution of sulfuric acid (2.50 mL, 47 mmol). The mixture was heated to 80° C. and monitored by TLC. After 16.5 hours, the solvent was removed and the reaction mixture was diluted with EtOAc. The organic phase was washed carefully two times with saturated aqueous $NaHCO_3$, once with brine, and then dried over anhydrous sodium sulfate. After filtration, the organic solvent was removed in vacuo to yield C.2 as a white solid (yield 100%) that was used without purification.

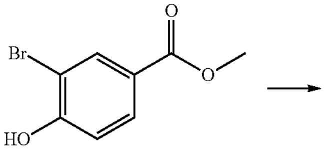

C.2

-continued

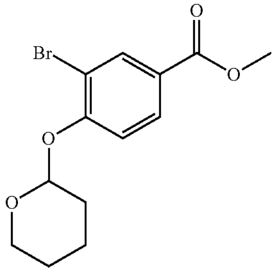

C.3

Methyl 3-bromo-4-(tetrahydro-2H-pyran-2-yloxy) benzoate (C.3)

To a stirred solution of C.2 (38 g, 164 mmol) and 3,4-dihydro-2H-pyran (45 mL, 493 mmol) in DCM (355 mL) was added 4-methylbenzenesulfonic acid hydrate (0.63 g, 3.30 mmol). The mixture was stirred at room temperature and monitored by TLC. After 2 hours, the solution was washed with a mixed aqueous solution of saturated aqueous sodium bicarbonate/brine/water (1:1:2). The aqueous layer was extracted three times with ether. After drying over anhydrous sodium sulfate and then filtering, the organic solvent was removed under reduced pressure. The residue was purified on silica gel (0-10% EtOAc in hexanes) to yield a white solid. The product was recrystallized from MeOH to provide C.3 (yield 90%). $^{1}$H NMR (400 MHz, $CDCl_3$) δ 8.24 (1H, d, J=2.0 Hz), 7.93 (1H, dd, J=8.6, 2.0 Hz), 7.17 (1H, d, J=8.6 Hz), 5.62 (1H, t, J=2.5 Hz), 3.90 (3H, s), 3.83 (1H, td, J=11.1, 2.9 Hz), 3.66 (1H, m), 2.18 (1H, m), 2.04 (1H, m), 1.94 (1H, m), 1.79 (2H, m), 1.67 (1H, m).)

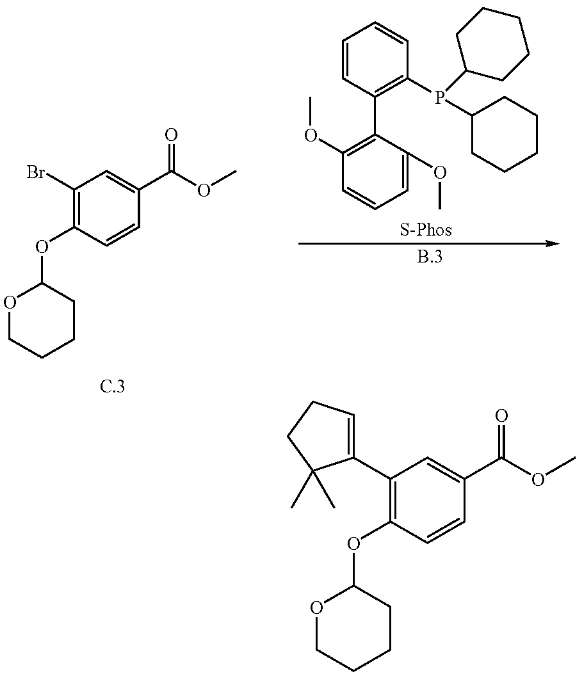

C.3

C.4

Methyl 3-(5,5-dimethylcyclopent-1-enyl)-4-(tetrahydro-2H-pyran-2-yloxy)benzoate (C.4)

A stirred mixture of C.3 (10.1 g, 31.9 mmol), grounded S-Phos (2.62 g, 6.39 mmol), palladium acetate (0.72 g, 3.2 mmol), and potassium phosphate, tribasic (17.0 g, 80.2 mmol) in DMF (70 mL) and water (3.5 mL) was purged three times with argon and placed under vacuum three times. Before heating, 2-(5,5-dimethylcyclopent-1-enyl)-4,4,5,5-tetramethyl-1,3,2-dioxaborolane (B.3) (8.50 g, 38.3 mmol) was added via syringe. The resulting mixture was then heated to 75° C. After 21 hours (black solution), the reaction was cooled to room temperature, diluted with water, and extracted three times with EtOAc. The organic layers were combined and washed twice with brine. After drying over anhydrous sodium sulfate and filtering, the organic solvent was removed under reduced pressure. The residue was purified on silica gel (0-20% EtOAc in hexanes) to yield C.4 as a colorless oil that solidified (yield 80%). $^{1}$H NMR (400 MHz) ($CDCl_3$) δ 7.91 (1H, dd, J=8.6, 2.3 Hz), 7.74 (1H, d, J=2.3 Hz), 7.15 (1H, d, J=8.6 Hz), 5.55 (1H, t, J=2.3 Hz), 5.49 (1H, t, J=2.9 Hz), 3.88 (3H, s), 3.82 (1H, td, J=11.1, 2.9 Hz), 3.64 (1H, m), 2.43 (2H, td, J=7.0, 2.3 Hz), 1.92 (5H, m), 1.69 (1H, m), 1.61 (2H, m), 1.09 (6H, d, J=13.7 Hz).

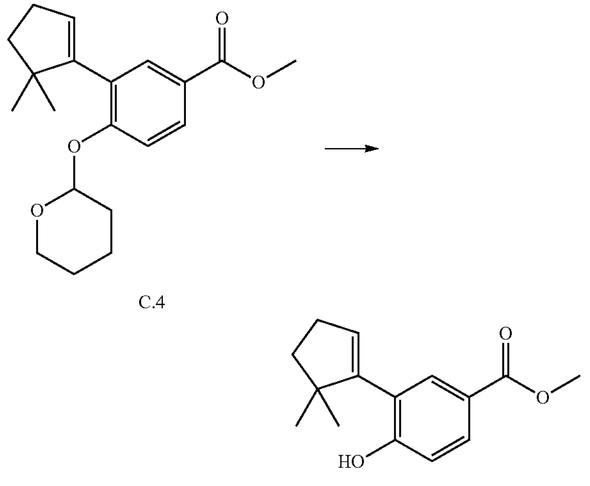

C.4

C.5

Methyl 3-(5,5-dimethylcyclopent-1-enyl)-4-hydroxybenzoate (C.5)

To a stirred solution of C.4 (19.0 g, 57.6 mmol) in MeOH (150 mL) was added pyridinium para-toluenesulfonate (PPTS) (1.46 g, 5.80 mmol). The mixture was heated to 50° C. and monitored with TLC. After 19 hours, the organic solvent was removed under reduced pressure and the product was then purified on silica gel (0-15% EtOAc in hexanes) to yield C.5 as a white solid (yield 90%). $^{1}$H NMR (400 MHz) ($CDCl_3$) δ 7.89 (1H, dd, J=8.6, 2.0 Hz), 7.79 (1H, d, J=2.3 Hz), 6.97 (1H, d, J=8.6 Hz), 5.87 (1H, s), 5.81 (1H, t, J=2.3 Hz), 3.89 (3H, s), 2.51 (2H, td, J=7.1, 2.5 Hz), 1.94 (2H, t, J=7.0 Hz), 1.12 (6H, s).

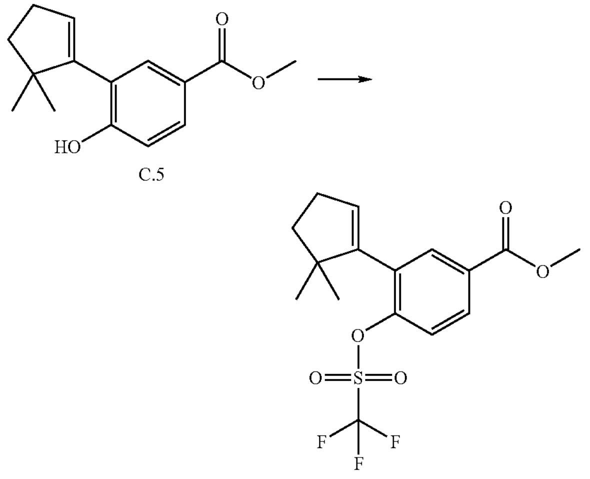

C.5

C.6

Methyl 3-(5,5-dimethylcyclopent-1-enyl)-4-(trifluoromethylsulfonyloxy)benzoate (C.6)

To a stirred solution of C.5 (6.00 g, 24.4 mmol) in dry DCM (35 mL) was added TEA (6.80 mL, 48.9 mmol) and 4-dimethylaminopyridine (0.30 g, 2.5 mmol). After about 20 minutes, N-phenyl bis-trifluoromethane sulfonimide (10.5 g, 29.3 mmol) was added in portion. Upon complete addition, the solution was stirred at room temperature and monitored with TLC. After 3 hours, the reaction was diluted with brine and extracted three times with DCM. After drying over anhydrous magnesium sulfate and filtering, the organic solvent was removed under reduced pressure and the product was then purified on silica gel (0-10% EtOAc in hexanes) to yield C.6 as a colorless oil (yield 88%). $^1$H NMR (400 MHz, $CDCl_3$) δ 8.02 (1H, dd, J=8.6, 2.0 Hz), 7.94 (1H, d, J=2.0 Hz), 7.35 (1H, d, J=8.6 Hz), 5.80 (1H, t, J=2.5 Hz), 3.94 (3H, s), 2.48 (2H, td, J=7.0, 2.3 Hz), 1.91 (2H, t, J=7.0 Hz), 1.09 (6H, s).

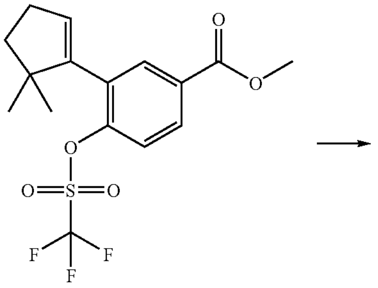

C.6

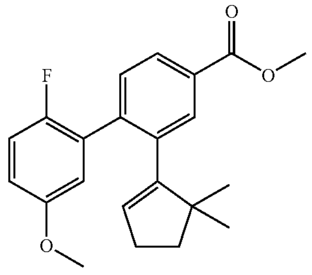

C.7

Synthesis of C.7

To a stirred solution of C.6 (8.71 g, 23.0 mmol) in DMF (20 mL) at 23° C. was added 2-fluoro-5-methoxyphenylboronic acid (7.84 g, 46.1 mmol) and potassium carbonate (9.56 g, 69.1 mmol) followed by tetrakis(triphenylphosphine)palladium (0) (2.67 g, 2.31 mmol). The mixture was heated to 90° C. After 15 hours, LCMS-showed that the reaction was complete. The mixture was then cooled to room temperature and then diluted with water. After extracting three times with EtOAc, the mixture was concentrated in vacuo and then purified on silica gel (0%-10% EtOAc/hexane) to give C.7 as a clear oil that solidified (yield 91%). $^1$H NMR (400 MHz, $CDCl_3$) δ 7.98 (1H, dd, J=8.0, 1.8 Hz), 7.91 (1H, d, J=2.0 Hz), 7.40 (1H, d, J=7.8 Hz), 6.98 (1H, t, J=8.8 Hz), 6.85 (2H, m), 5.55 (1H, s), 3.95 (3H, s), 3.77 (3H, s), 2.27 (2H, td, J=7.0, 2.7 Hz), 1.68 (2H, t, J=7.0 Hz), 0.87 (6H, s).

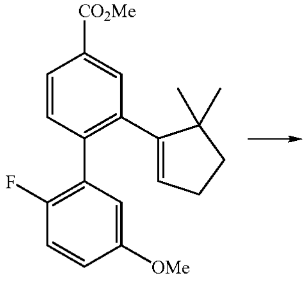

C.7

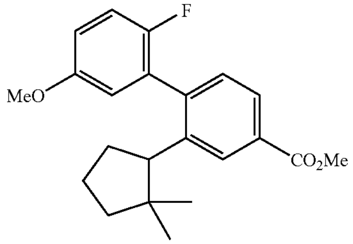

C.8

Synthesis of C.8

To a stirred solution of C.7 (0.660 g, 1.86 mmol) in MeOH (20.00 mL, 1.86 mmol) at 23° C. was added Pd/C (0.0198 g, 0.186 mmol). Stirring continued under an atmosphere of hydrogen (0.00375 g, 1.86 mmol) for 16 hours. The reaction mixture was then filtered and concentrated in vacuo to give C.8 as a clear oil (0.600 g, 90.4% yield).

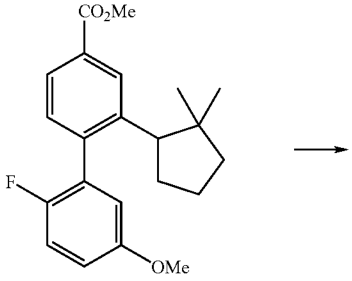

C.8

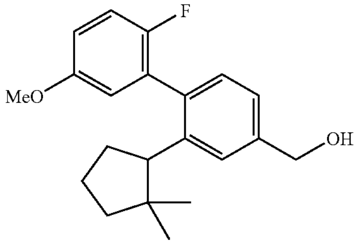

C.9

-continued

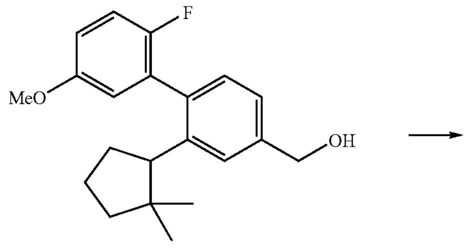

C.9

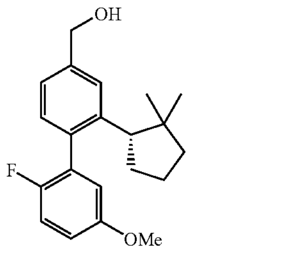

or

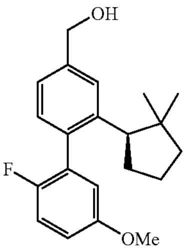

C.10 or C.11

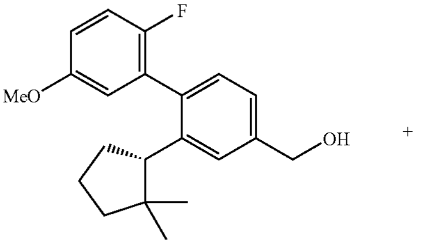

C.10

+

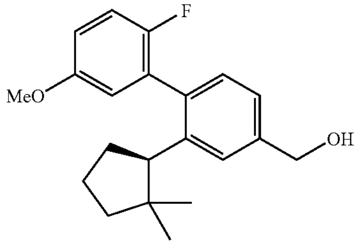

C.11

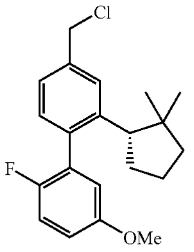

or

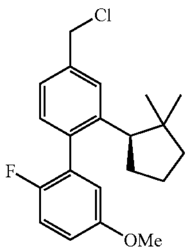

C

Synthesis of C.9, C.10, and C.11

To a stirred solution of C.8 (0.500 g, 1.4 mmol) in THF (7.0 mL, 1.4 mmol) at 0° C. was added LAH (1.4 mL, 1.4 mmol). After addition, the reaction was then stirred for 1.5 hours. 1N NaOH (aq) was then added to quench the reaction, and the mixture was then extracted with EtOAc. The organic layers were dried over magnesium sulfate, filtered, and concentrated in vacuo. The resulting product was then purified on silica gel (0%-20% EtOAc/hexane) to give C.9 (0.442 g, 96% yield). Chiral separation of C.9 was accomplished on Chiracel-OD (3% IPA in hexane) to provide C.10 and C.11. Both enantiomers were used to synthesize example compounds, and both enantiomers gave active example compounds. However, the enantiomer corresponding to peak 2 provided the most active example compounds. Analytical column (Chiracel-OD (2% IPA in hexane, 45 min run) Peak 1—15.5 mins, Peak 2—38.0 mins).[1]

Synthesis of C

Thionyl chloride (1.5 mL, 20 mmol) was added to a stirred solution of C.10 or C.11 (3.280 g, 10.0 mmol) in DCM (100 mL, 10.0 mmol) and DMF (0.77 mL, 10.0 mmol) at 0° C. Stirring was continued at room temperature for 2 hours. The reaction mixture was then concentrated in vacuo and purified on silica gel (0-10% EtOAc in hexane) to give the desired product C (3.00 g, 87% yield) as a clear oil.

Asymmetric Synthesis of C

The following procedures were used to synthesize C using a highly enantioselective procedure to hydrogenate C.5 to form C.12 or C.13.

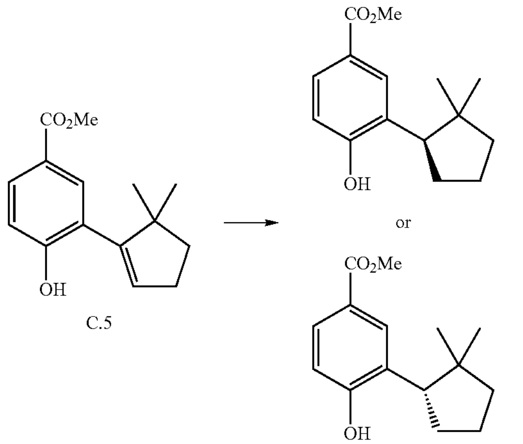

C.5 or

C.12 or C.13

(R)-methyl 3-(2,2-dimethylcyclopentyl)-4-hydroxybenzoate or (S)-methyl 3-(2,2-dimethylcyclopentyl)-4-hydroxybenzoate (C.12 or C.13)

A mixture of $Rh(COD)_2BF_4$ (Stern Chemical, 35138-22-8, 137.2 mg, 0.338 mmol) and (R)-1-[(S)-2-(R)-(ditertbutylphosphino)ferrocenyl]ethyl-bis-(3,5-bistrifluoromethylphenyl)phosphine (Solvias, SL-J210-1, 302 mg, 0.3718 mmol) was stirred in THF (300 mL) under $N_2$ for 60 minutes and a dark red solution formed. To the resulting solution was added methyl 3-(5,5-dimethylcyclopent-1-enyl)-4-hydroxybenzoate C.5 (41.64 g, 168.98 mmol) and TEA (10 mol %, 2.35 mL, 16.9 mmol). The resulting solution was filled with $H_2$ (200 psi) three times and stirred at room temperature/200 psi for 2 hours. The reaction mixture was then passed through a short plug of silica gel, eluting with 1:1 hexane/EtOAc, followed by concentration afforded the desired product as a white solid (98.9A % conversion, 99% yield (41.6 g), 99% ee).

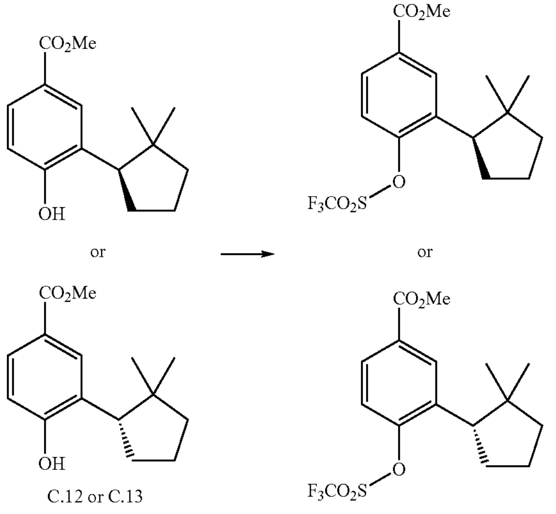

or or

C.12 or C.13

C.14 or C.15

(R)-methyl 3-(2,2-dimethylcyclopentyl)-4-(trifluoromethylsulfonyloxy)benzoate or (S)-methyl 3-(2,2-dimethylcyclopentyl)-4-(trifluoromethylsulfonyloxy)benzoate (C.14 or C.15)

To a stirred solution of (R)-methyl 3-(2,2-dimethylcyclopentyl)-4-hydroxybenzoate or (S)-methyl 3-(2,2-dimethylcyclopentyl)-4-hydroxybenzoate (C.12 or C.13) (18.00 g, 72 mmol) in DCM (181 mL, 72 mmol) at 23° C. was added TEA (12 mL, 87 mmol) and a catalytic amount of DMAP. N-phenyltriflimide (28 g, 80 mmol) was then added to the mixture and stirring was continued at room temperature for 16 hours. The reaction was concentrated in vacuo. The residue was purified on silica gel (0-10% EtOAc in hexanes) to yield C.14 or C.15 as a colorless oil (27.7 g, 100% yield). MS ESI (pos.) m/e: 381.1 $(M+H)^+$.

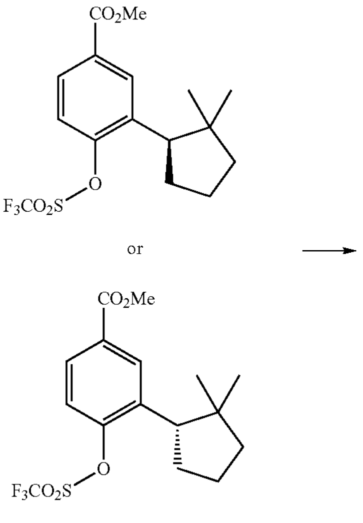

or

C.14 or C.15

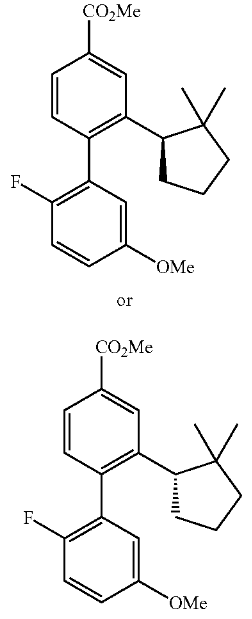

or

C.16 or C.17

Methyl 2-((1R)-2,2-dimethylcyclopentyl)-2'-fluoro-5'-(methyloxy)-1,1'-biphenyl-4-carboxylate or methyl 2-((1S)-2,2-dimethylcyclopentyl)-2'-fluoro-5'-(methyloxy)-1,1'-biphenyl-4-carboxylate (C.16 or C.17)

To a stirred solution of (S)-methyl 3-(2,2-dimethylcyclopentyl)-4-(trifluoromethylsulfonyloxy)benzoate or (R)-methyl 3-(2,2-dimethylcyclopentyl)-4-(trifluoromethylsulfonyloxy)benzoate (C.14 or C.15) (28.5 g, 75 mmol) in DMF (375 mL, 75 mmol) at 23° C. was added 2-fluoro-5-methoxyphenylboronic acid (19 g, 112 mmol) (commercially available from Aldrich), potassium carbonate (31 g, 225 mmol), and then tetrakis(triphenylphosphine)palladium (4 g, 4 mmol). The mixture was heated to 90° C. Stirring was continued for 20 hours, after which, the reaction was cooled to room temperature, diluted with water, and extracted three times with EtOAc. The organic layers were combined and washed twice with brine. After drying over anhydrous sodium sulfate and filtering, the organic solvent was removed under reduced pressure. The residue was purified on silica gel (0-10% EtOAc in hexanes) to yield C.16 or C.17 as a colorless oil (25.00 g, 94% yield). MS ESI (pos.) m/e: 357.1 $(M+H)^+$.

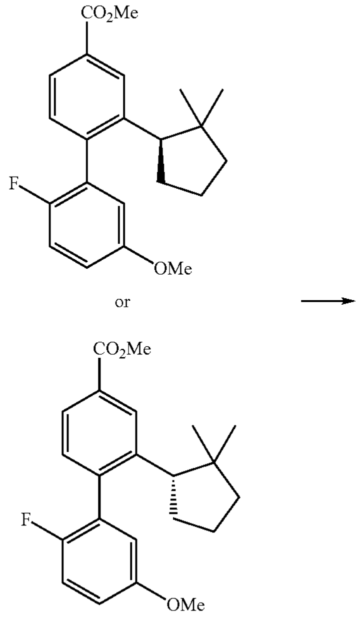
or

C.16 or C.17

-continued

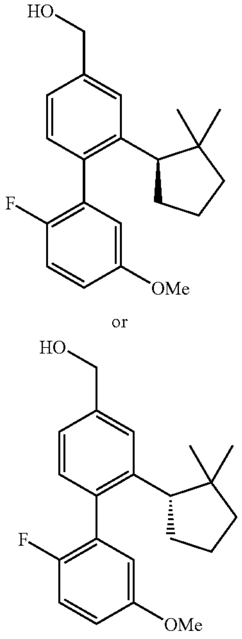
or

C.18 or C.19

(2-((1R)-2,2-Dimethylcyclopentyl)-2'-fluoro-5'-(methyloxy)-1,1'-biphenyl-4-yl)methanol or (2-((1S)-2,2-dimethylcyclopentyl)-2'-fluoro-5'-(methyloxy)-1,1'-biphenyl-4-yl)methanol (C.18 or C.19)

To a stirred solution of methyl 2-((1R)-2,2-dimethylcyclopentyl)-2'-fluoro-5'-(methyloxy)-1,1'-biphenyl-4-carboxylate or methyl 2-((1S)-2,2-dimethylcyclopentyl)-2'-fluoro-5'-(methyloxy)-1,1'-biphenyl-4-carboxylate (C.16 or C.17) (29.50 g, 83 mmol) in THF (414 mL, 83 mmol) at 0° C. was added LAH (124 mL, 124 mmol). Stirring was continued for 2 hours. Aqueous 1N NaOH was then added to quench the reaction, and the mixture was then extracted with EtOAc. The combined organic layers were dried over magnesium sulfate, filtered, and concentrated in vacuo. The residue was purified on silica gel (0-20% EtOAc in hexanes) to yield C.18 or C.19 as a colorless oil (23.66 g, 87% yield). MS ESI (pos.) m/e: 346.1 $(M+H_2O)^+$.

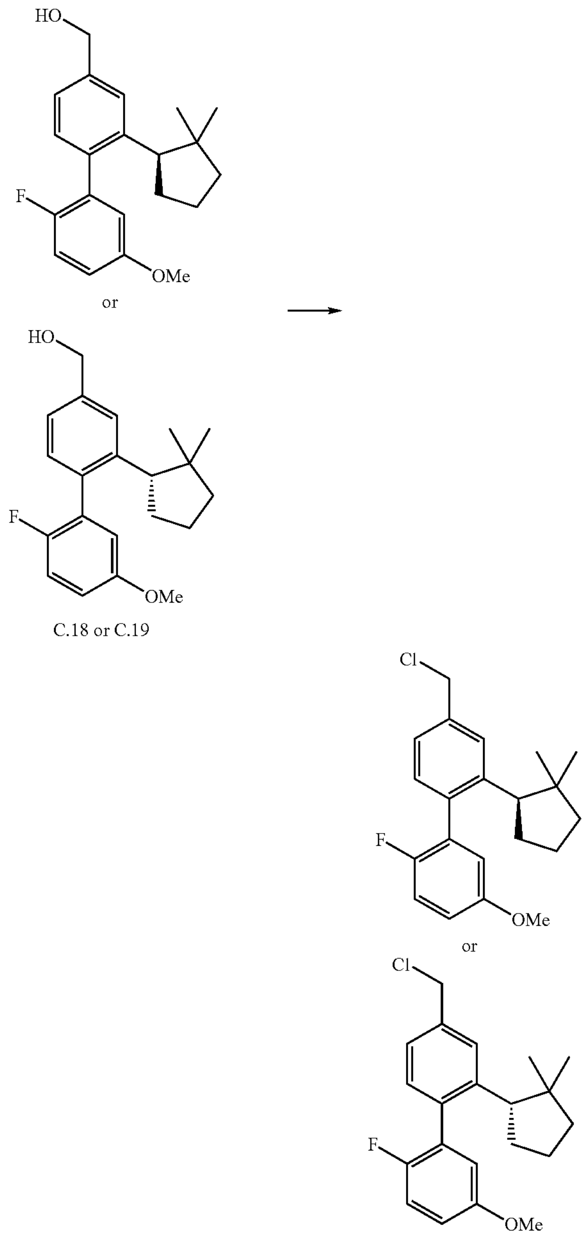

or

C.18 or C.19 or

C 4-(Chloromethyl)-2-((1R)-2,2-dimethylcyclopentyl)-2'-fluoro-5'-(methyloxy)-1,1'-biphenyl or 4-(chloromethyl)-2-((1S)-2,2-dimethylcyclopentyl)-2'-fluoro-5'-(methyloxy)-1,1'-biphenyl (C)

To a stirred solution of (2-((1R)-2,2-dimethylcyclopentyl)-2'-fluoro-5'-(methyloxy)-1,1'-biphenyl-4-yl)methanol or (2-((1S)-2,2-dimethylcyclopentyl)-2'-fluoro-5'-(methyloxy)-1,1'-biphenyl-4-yl)methanol (C.18 or C.19) (23.66 g, 72 mmol) in DCM (360 mL, 72 mmol) and DMF (0.56 mL, 7.2 mmol) at 0° C. was added thionyl chloride (11 mL, 144 mmol). Stirring was continued at room temperature for 1 hour. The reaction as then concentrated in vacuo, and the residue was purified on silica gel (0-10% EtOAc in hexanes) to yield C as a colorless oil (23.0 g, 92% yield). MS ESI (pos.) m/e: 364.1 $(M+H_2O)^+$.

Method D

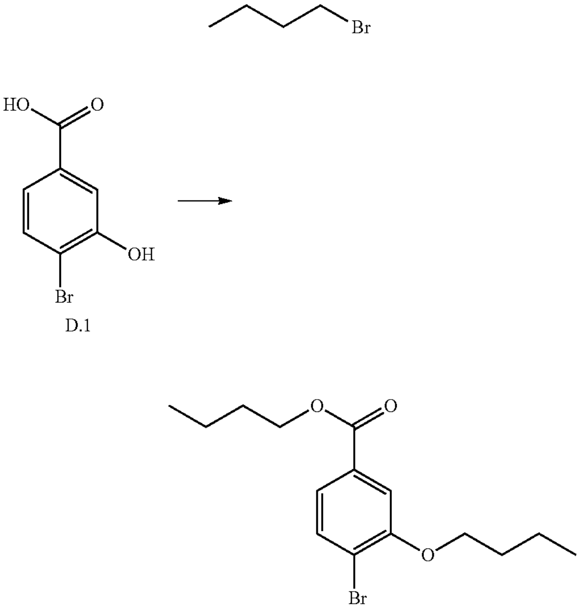

D.1

D.2

Butyl 4-bromo-3-(butyloxy)benzoate (D.2)

To a flask containing 4-bromo-3-hydroxybenzoic acid (D.1) (available from Combi-Blocks Inc.) (2.40 g, 11.06 mmol) and cesium carbonate (8.287 g, 25.44 mmol) in DMF (40 mL), was added 1-bromobutane (2.494 mL, 23.22 mmol), and the mixture was stirred overnight. The reaction was diluted with water and extracted with EtOAc. The organic layers were washed with brine, dried over $Na_2SO_4$, filtered, concentrated, and then purified by CombiFlash® chromatography (0 to 20% EtOAc/hexanes) to provide D.2 (2.4326 g, 66.81% yield).

D.2

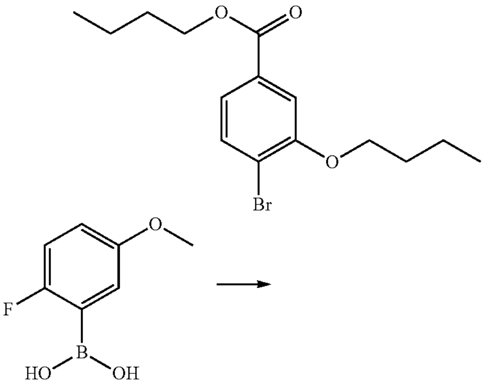

-continued

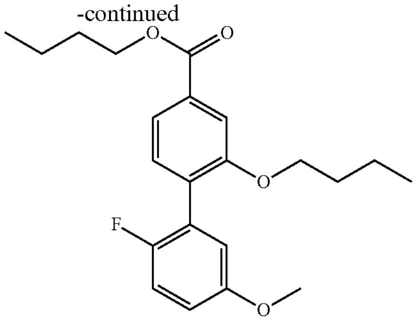

D.3

Butyl 2-(butyloxy)-2'-fluoro-5'-(methyloxy)-1,1'-biphenyl-4-carboxylate (D.3)

To a 2 dram vial charged with 2-fluoro-5-methoxyphenylboronic acid (available from Aldrich) (2.323 g, 13.67 mmol), tetrakis(triphenylphosphine) palladium(0) (0.7897 g, 0.6834 mmol), cesium fluoride (0.8409 mL, 22.78 mmol), and D.2 (1.50 g, 4.556 mmol), was added DME (20 mL), and the mixture was then heated at 90° C. overnight. The reaction was allowed to cool and then filtered and concentrated. The residue was purified by CombiFlash® chromatography (0 to 10% EtOAc/hexanes) yielding D.3 (1.1530 g, 67.58% yield).

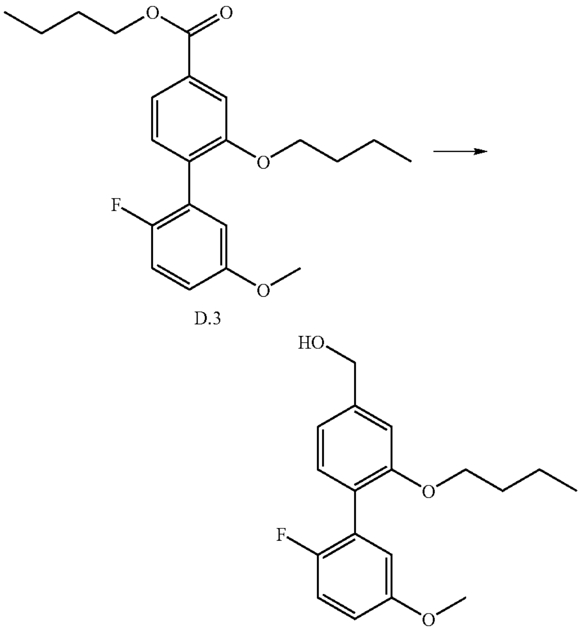

D.3

D.4

(2-(Butyloxy)-2'-fluoro-5'-(methyloxy)-1,1'-biphenyl-4-yl)methanol (D.4)

To D.3 (1.1530 g, 3.079 mmol) in THF (10 mL) at 0° C. was added LAH (1.0 M solution in THF (4.619 mL, 4.619 mmol)). The reaction was stirred for one hour and then carefully diluted with water, extracted with EtOAc, washed with brine, dried over sodium sulfate, filtered, and concentrated to provide D.4 (0.9050 g, 96.57% yield).

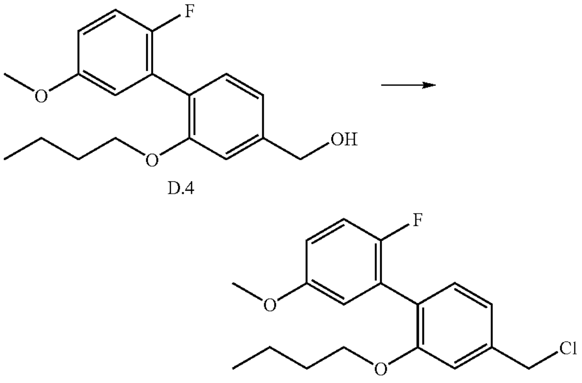

D.4

D 2-(Butyloxy)-4-(chloromethyl)-2'-fluoro-5'-(methyloxy)-1,1'-biphenyl (D)

To a stirred solution of D.4 (0.8800 g, 2.891 mmol) in DCM (15 mL) at 23° C. was added thionyl chloride (0.4218 mL, 5.783 mmol). The reaction mixture was then stirred overnight. The reaction was concentrated and then purified by CombiFlash® chromatography (0 to 10% EtOAc/Hexanes) to provide D (0.7980 g, 85.50% yield).

Method E

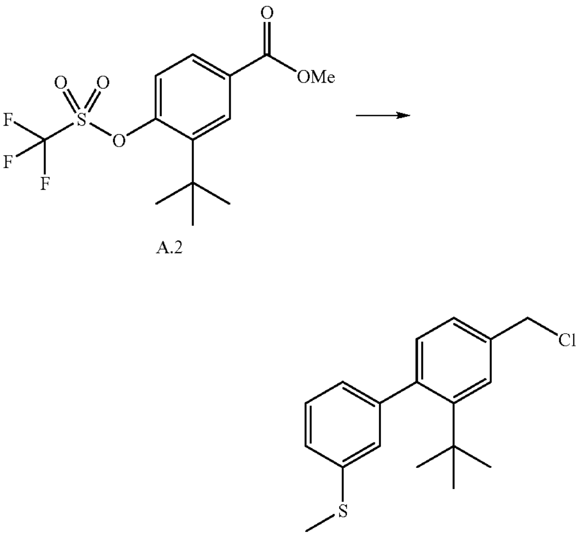

A.2

E 4-(Chloromethyl)-2-(1,1-dimethylethyl)-3'-(methylsulfanyl)-1,1'-biphenyl (E)

The title compound was synthesized in a similar manner as F starting from A.2 and 3-thiomethylphenylboronic acid (available from Aldrich). $^{1}H$ NMR (500 MHz, $CDCl_3$) δ ppm 7.54 (1H, d, J=2.0 Hz), 7.28 (4H, m), 7.15 (1H, t, J=1.7 Hz), 7.05 (2H, m), 4.65 (2H, s), 2.49 (3H, s), 1.22 (9H, s).

Method F

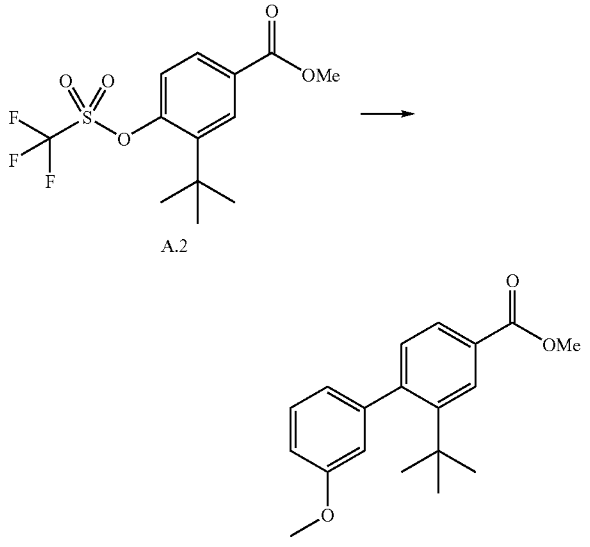

A.2

F.1

Methyl 2-(1,1-dimethylethyl)-3'-(methyloxy)-1,1'-biphenyl-4-carboxylate (F.1)

A dry round bottom flask containing A.2 (1.40 g, 4.1 mmol), 3-methoxyphenylboronic acid (available from Aldrich) (1.27 g, 8.34 mmol), tetrakis(triphenylphosphine)palladium (0.49 g, 0.42 mmol), and potassium carbonate (1.71 g, 12.36 mmol) was evacuated and backfilled three times with argon. Dry DMF (12.0 mL) was added via syringe under argon, and the mixture was then heated to 100° C. and monitored by TLC. After 2 hours, the reaction was cooled to room temperature and diluted with water. The mixture was extracted three times with EtOAc and then concentrated under reduced pressure. The residue was then purified by flash chromatography ($SiO_2$ gel 60, eluted with 0%-15% EtOAc in hexanes). Fractions containing the desired product were combined and concentrated to provide F.1 as a colorless oil (1.01, 82%). MS ESI (pos.) m/e: 299.2 $(M+H)^+$.

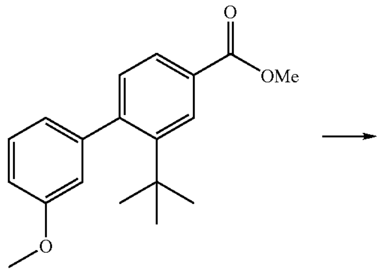

F.1

-continued

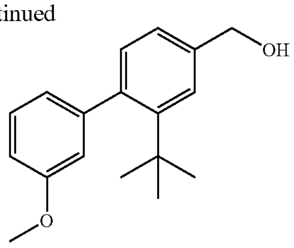

F.2

(2-(1,1-Dimethylethyl)-3'-(methyloxy)-1,1'-biphenyl-4-yl)methanol (F.2)

To a cooled solution of F.1 (1.01 g, 3.38 mmol) in dry THF (10.0 mL) at 0° C., was added LAH (1.0 M solution in THF (6.7 mL, 6.7 mmol)). Upon complete addition, the reaction was allowed to warm to room temperature and monitored by TLC and LCMS. Upon completion, 1N NaOH (5 mL) was carefully added to quench the reaction. The resulting solution was extracted with EtOAc (3×10 mL), dried over $MgSO_4$, filtered and concentrated in vacuo. The residue was then purified by flash chromatography ($SiO_2$ gel 60, eluted with 0%-40% EtOAc in hexanes). Fractions containing the desired product were combined and concentrated to provide F.2 as a colorless oil (0.82, 90%). $^1H$ NMR (500 MHz, $CDCl_3$) δ ppm 7.56 (1H, s), 7.29 (1H, t, J=3.8 Hz), 7.24 (1H, m), 7.07 (1H, d, J=7.6 Hz), 6.93 (2H, m), 6.86 (1H, d, J=1.5 Hz), 4.77 (2H, s), 3.85 (3H, s), 1.72 (1H, s), 1.26 (9H, s).

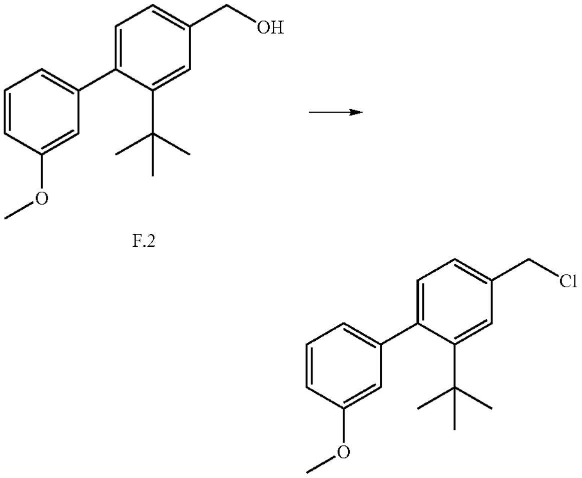

F.2

F 4-(Chloromethyl)-2-(1,1-dimethylethyl)-3'-(methyloxy)-1,1'-biphenyl (F)

A dry, round bottom flask containing F.2 (0.82 g, 3.04 mmol) and DCM (8.5 mL) was cooled to 0° C. After 15 minutes, thionyl chloride (1.50 mL, 20.56 mmol) was carefully added dropwise at 0° C. Upon complete addition of thionyl chloride, the mixture was allowed to warm to room temperature and stirred overnight. After 25 hours, the reaction was concentrated under reduced pressure. The residue was then purified by flash chromatography ($SiO_2$ gel 60, eluted with 0%-15% EtOAc in hexanes). Fractions containing the desired product were combined and concentrated to provide F as a colorless oil (0.82, 93%). $^1$H NMR (500 MHz, $CDCl_3$) δ ppm 7.53 (1H, d, J=1.7 Hz), 7.28 (3H, m), 7.03 (1H, d, J=7.8 Hz), 6.90 (3H, m), 4.65 (2H, s), 3.82 (3H, s), 1.23 (9H, s).

Method G

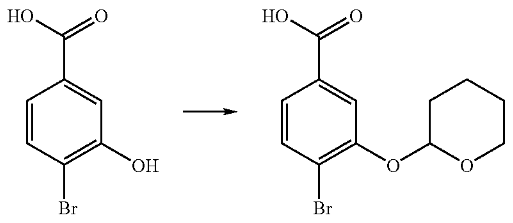

G.1 G.2

4-Bromo-3-(tetrahydro-2H-pyran-2-yloxy)benzoic acid 4-bromo-3-(tetrahydro-2H-pyran-2-yloxy)benzoic acid (G.2)

To solution of 4-bromo-3-hydroxybenzoic acid (G.1) (available from Combi-Blocks Inc.) (2.50 g, 115 mmol) in DCM (100 mL) at 23° C., was added 3,4-dihydro-2H-pyran (2.10 mL, 23.0 mmol) followed by PPTS (0.289 g, 1.15 mmol). The reaction gave a mixture of bis THP protected compound and G.2.

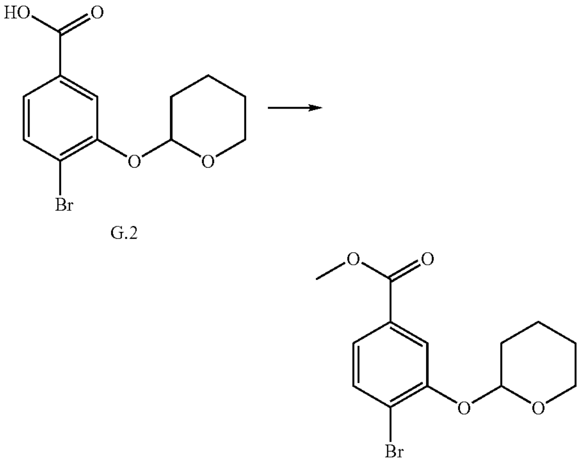

G.2

G.3

Methyl 4-bromo-3-(tetrahydro-2H-pyran-2-yloxy) benzoate (F.3)

To flask containing G.2 (2.15 g, 7.14 mmol) and cesium carbonate (3.95 g, 12.1 mmol) in acetone (50 mL), was added iodomethane (0.667 mL, 10.7 mmol). The resulting mixture was stirred overnight. The reaction was diluted with water and extracted with EtOAc. The organic layers were washed with brine, dried over $Na_2SO_4$, filtered, concentrated, and then purified by CombiFlash® chromatography (0 to 20% EtOAc/hexanes) to provide methyl G.3 (2.25 g, 99% yield).

G.3

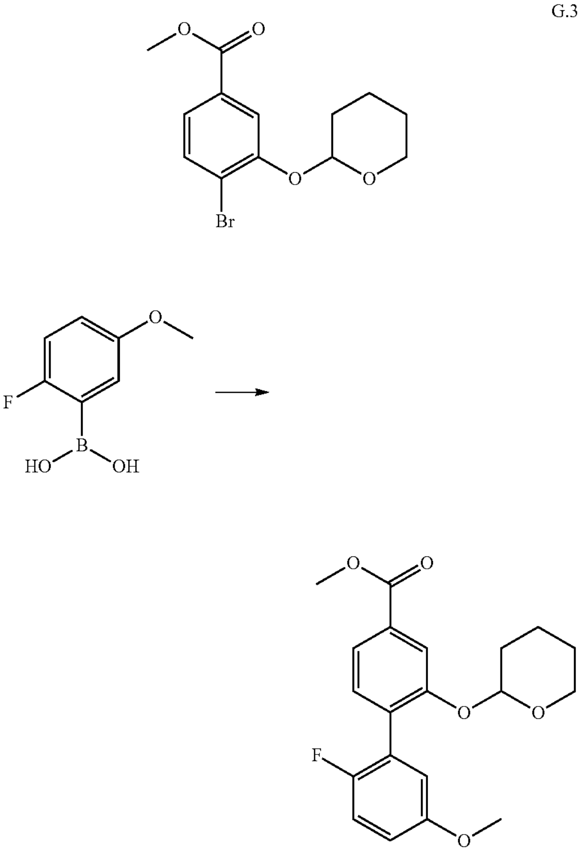

G.4

Methyl 2'-fluoro-5'-(methyloxy)-2-(tetrahydro-2H-pyran-2-yloxy)-1,1'-biphenyl-4-carboxylate (G.4)

To a 2 dram vial charged with 2-fluoro-5-methoxyphenylboronic acid (available from Aldrich) (3.17 g, 18.7 mmol), tetrakis(triphenylphosphine)palladium (0) (0.719 g, 0.622 mmol), cesium fluoride (1.15 mL, 31.1 mmol), and G.3 (1.96 g, 6.22 mmol), was added DME (20 mL). The reaction mixture was then heated at 90° C. overnight. The reaction was allowed to cool and then filtered and concentrated. The residue was purified by CombiFlash® chromatography (0 to 10% EtOAc/hexanes) yielding G.4 (1.61 g, 71.8% yield).

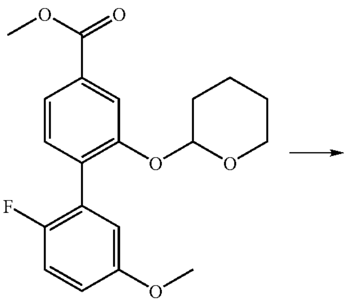

G.4

-continued

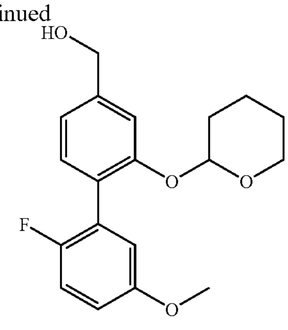

G (2'-Fluoro-5'-(methyloxy)-2-(tetrahydro-2H-pyran-2-yloxy)-1,1'-biphenyl-4-yl)methanol (G)

To G.4 (1.61 g, 4.47 mmol) in THF (10 mL) at 0° C., was added LAH (1.0M solution in THF, 6.70 mL, 6.70 mmol). The reaction was stirred for one hour and then carefully diluted with water, extracted with EtOAc, washed with brine, dried over sodium sulfate, filtered, and concentrated to provide G (0.990 g, 66.7% yield).

Method H

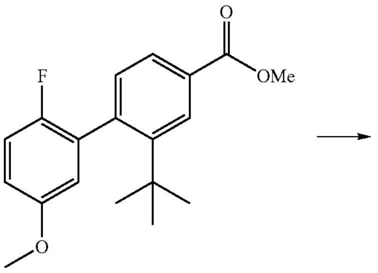

A.3

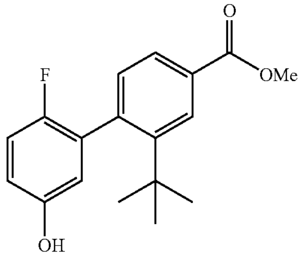

H.1

Methyl 2-(1,1-dimethylethyl)-2'-fluoro-5'-hydroxy-1,1'-biphenyl-4-carboxylate (H.1)

To a cooled solution of A.3 (0.500 g, 2.00 mmol) in dry DCM (32.0 mL) at 0° C. was added boron tribromide (7.00 mL, 7.00 mmol). Stirring was continued for 6 hours, and the reaction was monitored by TLC and LCMS. Upon completion, pH 7 buffer was added to the mixture at 0° C. The resulting solution was extracted with DCM (3x20 mL). The combined organic layers were dried over $MgSO_4$, filtered, and concentrated in vacuo. The residue was then purified by flash chromatography ($SiO_2$ gel 60, eluted with 0%-20% EtOAc in hexanes). Fractions containing the desired product were combined and concentrated to provide H.1 as a colorless oil (0.29 g, 61%). MS ESI (pos.) m/e: 335.1 $(M+Na)^+$, 320.1 $(M+H_2O)^+$, 303.1 $(M+H)^+$.

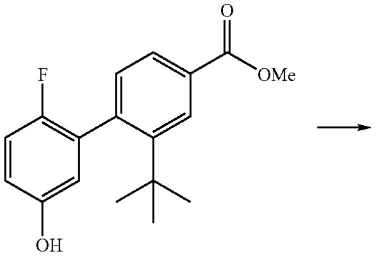

H.1

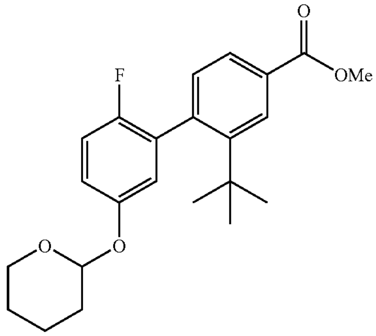

H.2

Methyl 2-(1,1-dimethylethyl)-2'-fluoro-5'-(tetrahydro-2H-pyran-2-yloxy)-1,1'-biphenyl-4-carboxylate (H.2)

To a stirred solution of H.1 (0.080 g, 0.30 mmol) in dry DCM (1.00 mL) at 23° C., was added 3,4-dihydro-2H-pyran (0.04 g, 0.50 mmol), followed by PPTS (0.007 g, 0.03 mmol). Stirring was continued for 14 hours. The resulting solution was concentrated in vacuo. Water was added, and the resulting mixture was extracted with EtOAc (3x10 mL). The combined organic layers were dried over $MgSO_4$, filtered, and concentrated in vacuo. The residue was then purified by flash chromatography ($SiO_2$ gel 60, eluted with 0%-20% EtOAc in hexanes). Fractions containing the desired product were combined and concentrated to provide H.2 as a colorless oil (0.100 g, 100%). MS ESI (pos.) m/e: 795.4 $(2M+Na)^+$.

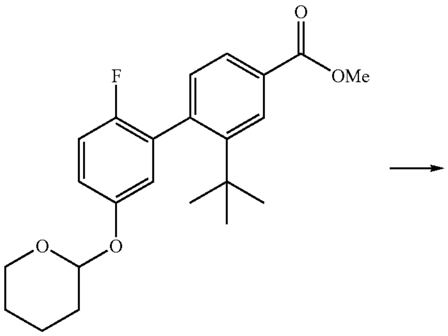

H.2

-continued

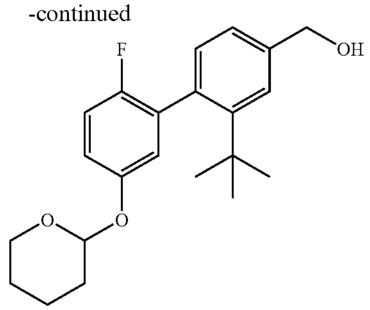

H (2-(1,1-Dimethylethyl)-2'-fluoro-5'-(tetrahydro-2H-pyran-2-yloxy)-1,1'-biphenyl-4-yl)methanol (H)

To a cooled solution of H.2 (0.080 g, 0.30 mmol) in THF (3.00 mL) at 0° C., was added LAH (1.0 M solution in THF, 0.60 mL, 0.60 mmol). Stirring was continued for 1 hour. 1N NaOH (5 mL) was carefully added to quench the reaction. The resulting solution was extracted with EtOAc (3×10 mL). The combined organic layers were dried over $MgSO_4$, filtered, and concentrated in vacuo. The residue was then purified by flash chromatography ($SiO_2$ gel 60, eluted with 0%-30% EtOAc in hexanes). Fractions containing the desired product were combined and concentrated to provide H as a colorless oil (0.055 g, 54%). MS ESI (pos.) m/e: 739.3 $(2M+Na)^+$, 376.1 $(M+H_2O)^+$.

Method J

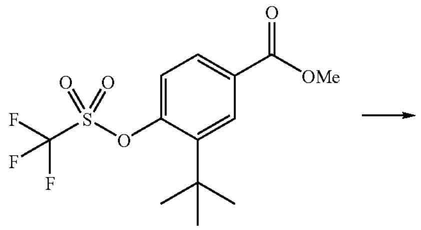

A.2

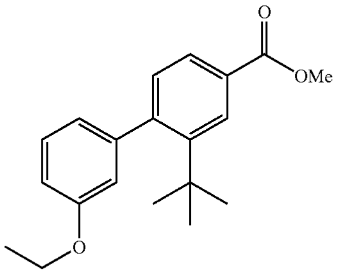

J.1

Methyl 2-(1,1-dimethylethyl)-3'-(ethyloxy)-1,1'-biphenyl-4-carboxylate (J.1)

A dry round bottom flask containing A.2 (1.13 g, 3.31 mmol), 3-ethoxyphenylboronic acid (available from Aldrich) (1.10 g, 6.63 mmol), tetrakis(triphenylphosphine)palladium (0.39 g, 0.340 mmol), and potassium carbonate (1.41 g, 10.20 mmol) was evacuated and backfilled three times with argon. Dry DMF (10.000 mL) was then added via syringe under argon. The mixture was then heated at 80° C. and monitored with TLC. After 20 hours, the reaction was cooled to room temperature and diluted with water. The mixture was extracted three times with EtOAc and then concentrated under reduced pressure. The residue was then purified by flash chromatography ($SiO_2$ gel 60, eluted with 0%-25% EtOAc in hexanes). Fractions containing the desired product were combined and concentrated to provide J.1 as a colorless oil (0.87, 84%). MS ESI (pos.) m/e: 313.1 $(M+H)^+$.

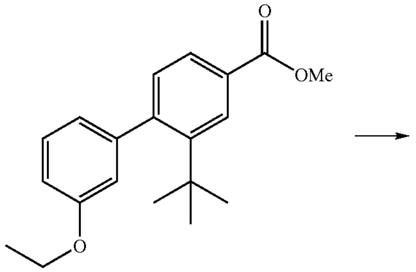

J.1

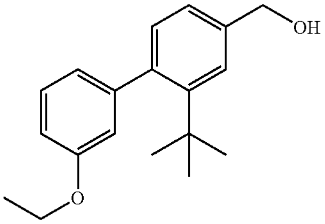

J.2

(2-(1,1-Dimethylethyl)-3'-(ethyloxy)-1,1'-biphenyl-4-yl)methanol (J.2)

To a cooled solution of J.1 (0.87 g, 2.79 mmol) in dry THF (10.0 mL) at 0° C., was added LAH (1.0 M solution in THF (5.5 mL, 5.5 mmol)). Upon complete addition, the reaction was allowed to warm to room temperature and monitored by TLC and LCMS. Upon completion, 1N NaOH (5 mL) was carefully added to quench the reaction. The resulting solution was extracted with EtOAc (3×10 mL). The combined organic layers were dried over $MgSO_4$, filtered, and concentrated in vacuo. The residue was then purified by flash chromatography ($SiO_2$ gel 60, eluted with 0%-40% EtOAc in hexanes). Fractions containing the desired product were combined and concentrated to provide J.2 as a colorless oil (0.72, 91%). $^1H$ NMR (500 MHz, $CDCl_3$) δ ppm 7.53 (1H, d, J=1.5 Hz), 7.26 (1H, m), 7.19 (1H, dd, J=7.7, 1.8 Hz), 7.04 (1H, d, J=7.6 Hz), 6.89 (3H, m), 4.74 (2H, d, J=3.2 Hz), 4.08 (2H, m), 1.71 (1H, s), 1.42 (3H, t, J=7.0 Hz), 1.23 (9H, s).

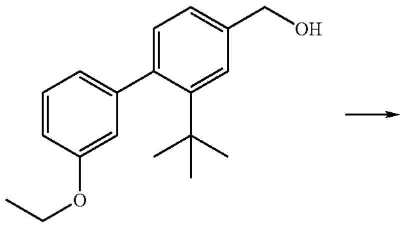

J.2

-continued

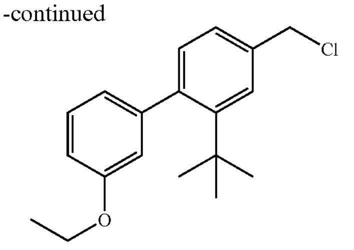

J

4-(Chloromethyl)-2-(1,1-dimethylethyl)-3'-(ethyloxy)-1,1'-biphenyl (J)

A dry, round bottom flask containing J.2 (0.72 g, 2.53 mmol) and DCM (9.0 mL) was cooled to 0° C. After 15 minutes, thionyl chloride (1.0 mL, 13.7 mmol) was carefully added dropwise at 0° C. Upon complete addition of thionyl chloride, the mixture was allowed to warm to room temperature and stirred overnight. After 20 hours, the reaction was concentrated under reduced pressure. The residue was then purified by flash chromatography ($SiO_2$ gel 60, eluted with 0%-15% EtOAc in hexanes). Fractions containing the desired product were combined and concentrated to provide J as a colorless oil (0.57, 74%). $^1$H NMR (500 MHz, $CDCl_3$) δ ppm 7.54 (1H, d, J=2.0 Hz), 7.25 (2H, m), 7.04 (1H, d, J=7.4 Hz), 6.90 (3H, m), 4.65 (2H, s), 4.05 (2H, m), 1.43 (3H, t, J=7.0 Hz), 1.24 (9H, s).

Method K

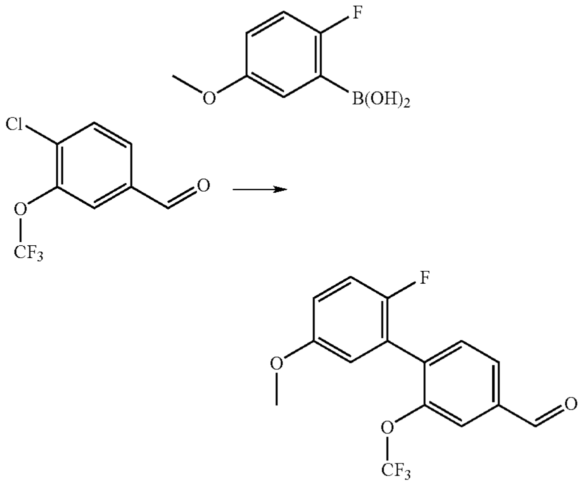

K.1

2'-Fluoro-5'-(methyloxy)-2-((trifluoromethyl)oxy)-1,1'-biphenyl-4-carbaldehyde (K.1)

A screw-cap vial was charged with 4-chloro-3-(trifluoromethoxy)benzaldehyde (available from Alfa Aesar, Avocado, Lancaster) (0.184 g, 0.82 mmol), 2-fluoro-5-methoxyphenylboronic acid (available from Aldrich) (0.278 g, 1.64 mmol), potassium phosphate (0.522 g, 2.46 mmol), 2-dicyclohexylphosphino-2',6'-dimethoxybiphenyl (0.101 g, 0.25 mmol), palladium(II) acetate (0.018 g, 0.082 mmol), and 5:1 THF/DMF (3.6 mL). The mixture was stirred overnight at 40° C., cooled to room temperature, diluted with EtOAc, washed with water and brine, dried ($MgSO_4$), and concentrated. The residue was chromatographed on silica gel (0-10% EtOAc/hexane) to afford K.1 (165 mg, 64%) as a colorless oil.

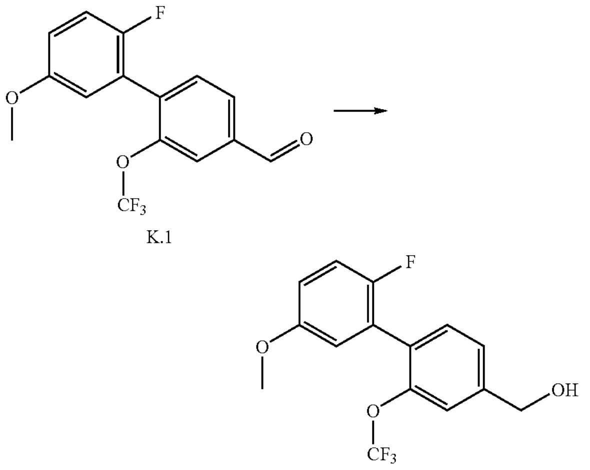

K.1

K.2

(2'-Fluoro-5'-(methyloxy)-2-((trifluoromethyl)oxy)-1,1'-biphenyl-4-yl)methanol (K.2)

To a solution of K.1 (0.165 g, 0.53 mmol) in MeOH (6 mL) was added sodium borohydride (0.040 g, 1.05 mmol) in one portion at room temperature. The mixture was stirred for 30 minutes, quenched with 1 N HCl, and extracted with EtOAc. The combined organic layers were washed with water and brine, dried ($MgSO_4$), and concentrated. The residue was chromatographed on silica gel (0-30% EtOAc/hexane) to afford K.2 (0.164 g, 99%) as a colorless oil.

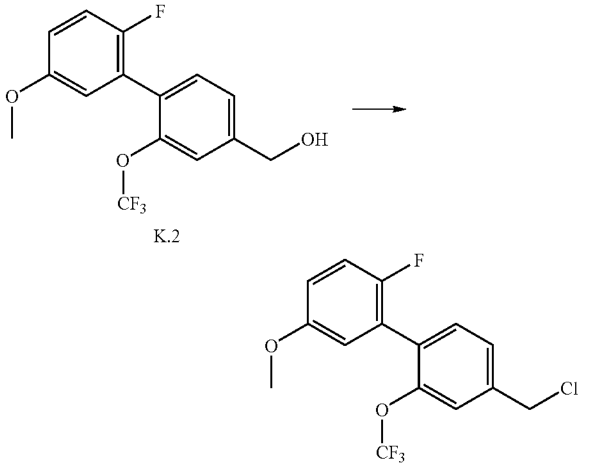

K.2

K

4-(Chloromethyl)-2'-fluoro-5'-(methyloxy)-2-((trifluoromethyl)oxy)-1,1'-biphenyl (K)

To a solution of K.2 (0.164 g, 0.52 mmol) in DCM (5 mL) was added thionyl chloride (76 μL, 1.04 mmol) in one portion at room temperature. The mixture was stirred overnight and concentrated. The residue was chromatographed on silica gel (0-10% EtOAc/hexane) to afford K (0.009 g, 5%) as a colorless oil.

Method L

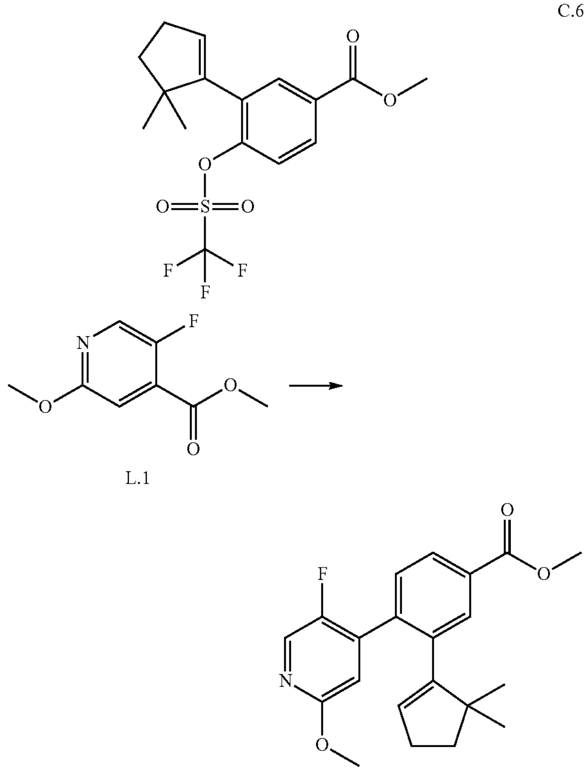

C.6

L.1

L.2

Methyl 3-(5,5-dimethylcyclopent-1-enyl)-4-(5-fluoro-2-methoxypyridin-4-yl)benzoate (L2)

To a flask with methyl 3-(5,5-dimethylcyclopent-1-enyl)-4-(trifluoromethylsulfonyloxy)benzoate C.6 (404 mg, 1068 μmol) was added $Pd(PPh_3)_4$ (123 mg, 107 μmol), potassium carbonate (443 mg, 3203 μmol), 5-fluoro-2-methoxypyridin-4-ylboronic acid L.1 (456 mg, 2669 μmol, commercially available from Asymchem). The mixture was then degassed, and DMF (3 mL) was added. The reaction was stirred overnight at 87° C. and worked up with EtOAc and water. Silica gel chromatography (0-50% EtOAc/Hexanes) afforded methyl 3-(5,5-dimethylcyclopent-1-enyl)-4-(5-fluoro-2-methoxypyridin-4-yl)benzoate L.2 295 mg (78%).

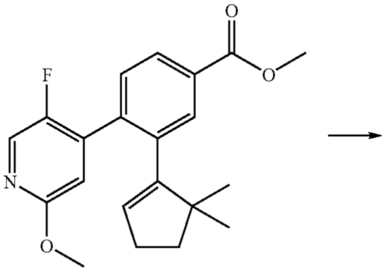

L.2

-continued

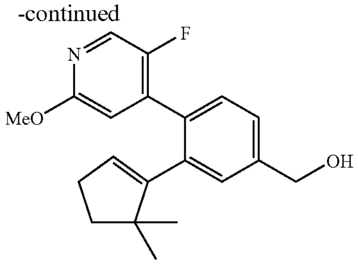

L.3

(3-(5,5-Dimethylcyclopent-1-enyl)-4-(5-fluoro-2-methoxypyridin-4-yl)phenyl)methanol (L.3)

To methyl 3-(5,5-dimethylcyclopent-1-enyl)-4-(5-fluoro-2-methoxypyridin-4-yl)benzoate L.2 (295 mg, 830 μmol) was added THF. The mixture was cooled to 0° C., and LAH (1660 μL, 1660 μmol) was added dropwise. The reaction was stirred at room temperature for 1 hour, and was quenched with water and a small amount of Rochelle's salt solution. Purification with silica gel chromatography afforded (3-(5,5-dimethylcyclopent-1-enyl)-4-(5-fluoro-2-methoxypyridin-4-yl)phenyl)methanol L.3 (201 mg) as an oil (74%).

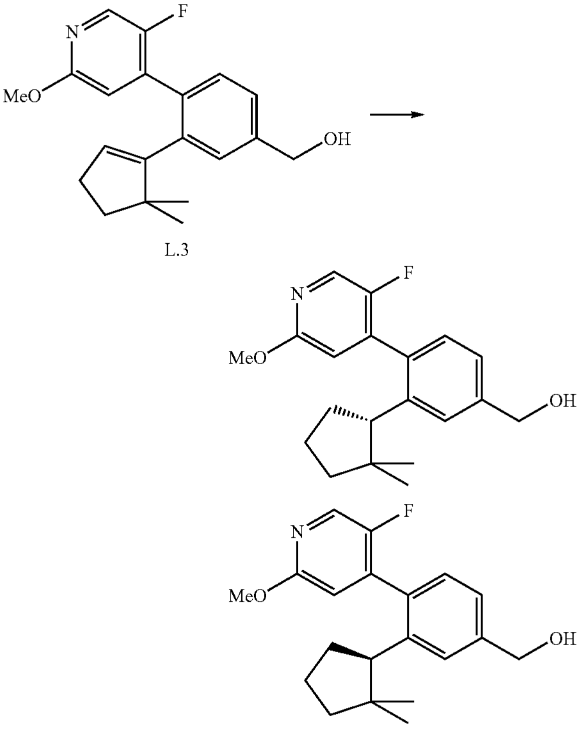

L.3

L.4A and L.4B (3-((S)-2,2-Dimethylcyclopentyl)-4-(5-fluoro-2-methoxypyridin-4-yl)phenyl)methanol and (3-((R)-2,2-dimethylcyclopentyl)-4-(5-fluoro-2-methoxypyridin-4-yl)phenyl)methanol (L.4A and L.4B)

To a flask with (3-(5,5-dimethylcyclopent-1-enyl)-4-(5-fluoro-2-methoxypyridin-4-yl)phenyl)methanol L.3 (50 mg, 0.153 mmol) was added 10 mg 10% Pd on Carbon, 1.2 mL EtOAc and 1.2 mL MeOH. The flask was purged with hydrogen and then stirred under a hydrogen balloon for 2 hours. LC/MS showed the completion of the reaction. The reaction was filtered through a pad of Celite® filter aid and rinsed with EtOAc. Two additional reactions were run with the same condition on 70 mg and 81 mg scale. Then the three batches of the reactions (a total of 201 mg of L.3) were combined and purified on chiral OD column in four equal portions with 3% IPA/Hexanes to afford L.4A (54 mg, 98% ee, the later-eluting enantiomer) and L.4B (78 mg, 100% ee). The mixed fraction was repurified on chiral column to afford an additional 28 mg of L.4A (>99% ee).

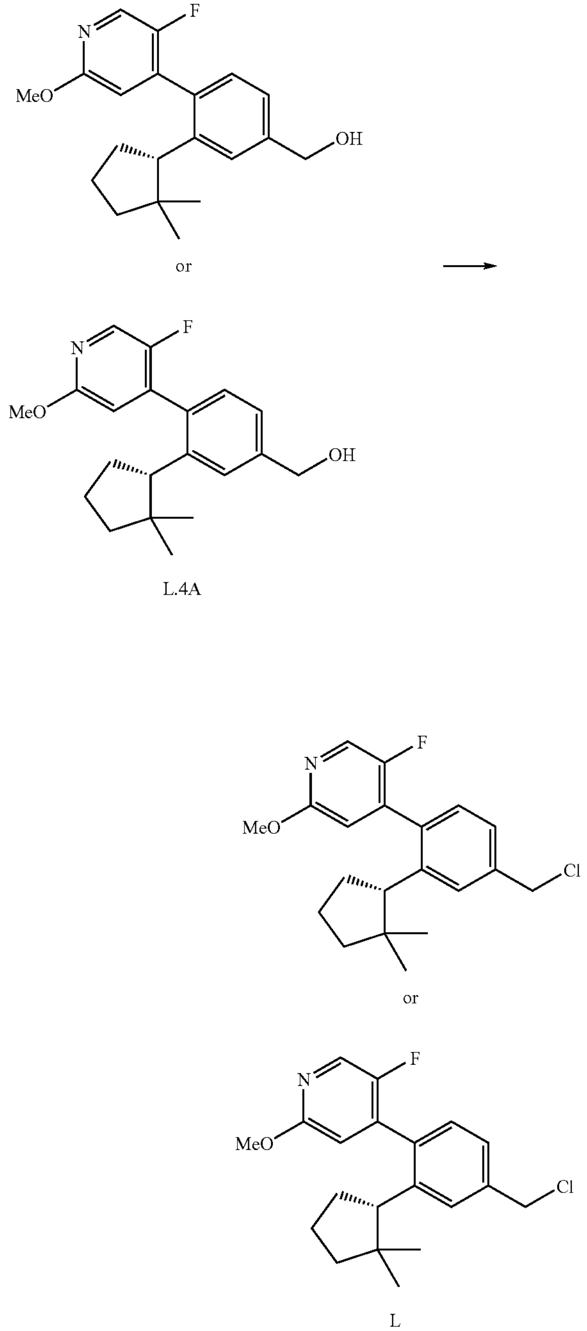 [SMILES: COc1cc(-c2ccc(CO)cc2[C@H]2CCCC2(C)C)c(F)cn1 ; COc1cc(-c2ccc(CO)cc2[C@H]2CCCC2(C)C)c(F)cn1 ; COc1cc(-c2ccc(CCl)cc2[C@H]2CCCC2(C)C)c(F)cn1 ; COc1cc(-c2ccc(CCl)cc2[C@H]2CCCC2(C)C)c(F)cn1]

or

L.4A or

L 4-(4-(Chloromethyl)-2-((S)-2,2-dimethylcyclopentyl)phenyl)-5-fluoro-2-methoxypyridine or 4-(4-(chloromethyl)-2-((R)-2,2-dimethylcyclopentyl)phenyl)-5-fluoro-2-methoxypyridine (L)

The same procedure used to prepare C from C.10 or C.11 was applied to make L from L.4A (28 mg, >99% ee). Compound L was obtained as an oil (27 mg, 91%).

Synthesis of Additional Tail Group Intermediates

The following examples describe the preparation of tail groups that may be used to prepare the compound of the present invention using the procedures described herein.

Example T1

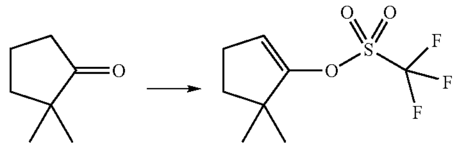

T1.1 T1.2

5,5-Dimethylcyclopent-1-enyl trifluoromethanesulfonate (T1.2)

To a solution of 2,2-dimethylcyclopentanone T1.1 (commercially available from ChemSampCo) (3.00 g, 26.75 mmol) in THF (100 mL), was slowly added LDA (14.7 mL, 2.0 M, in heptane) at −78° C. The resulting mixture was stirred at −78° C. for 1 hour. A solution of N-phenyltriflamide (10.00 g, 28.00 mmol) was added to the mixture at −78° C., and stirring was continued at 0° C. for 2 hours and then at room temperature for 16 hours. The reaction mixture was extracted with hexane (80×2 mL). The organic layer was then washed with saturated $Na_2CO_3$ (30 mL), brine (20 mL), and dried with $MgSO_4$. The solvent was removed, and the residue was purified by CombiFlash® silica gel chromatography (eluent was EtOAc and hexane) to give T1.2. $^1H$ NMR ($CDCl_3$) δ ppm 5.56 (m, 1H), 2.36 (t, J=7.1 Hz, 2H), 1.86 (t, J=7.1 Hz, 2H), 1.16 (s, 6H).

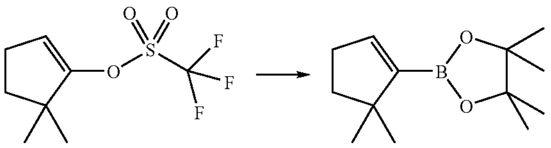

T1.2 T1.3

2-(5,5-Dimethylcyclopent-1-enyl)-4,4,5,5-tetramethyl-1,3,2-dioxaborolane (T1.3)

$PdCl_2(PPh_3)_2$ (0.56 g, 0.80 mmol), $PPh_3$ (0.63 g, 2.40 mmol), bis(pinacolato)diboron (6.80 g, 26.75 mmol) and KOPh (fine powder, 5.30 g, 40.10 mmol) were added to a flask. The flask was flushed with nitrogen and charged with toluene (100 mL) and T1.2 (6.53 g, 26.75 mmol). The mixture was stirred at 50° C. for 2 hours. The reaction mixture was treated with water at room temperature and extracted with benzene (60×2 mL). The organic layer was dried over $MgSO_4$. The product was then purified by CombiFlash® chromatography to give intermediate T1.3. $^1H$ NMR ($CDCl_3$) δ ppm 6.29 (m, 1H), 2.29 (t, J=7.1 Hz, 2H), 1.57 (t, J=7.1 Hz, 2H), 1.18 (s, 12H), 1.04 (s, 6H).

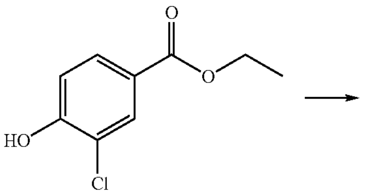

T1.4

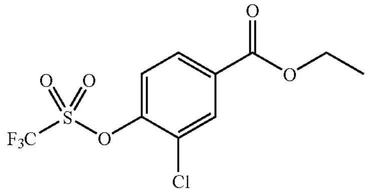

T1.5

Ethyl 3-chloro-4-(((trifluoromethyl)sulfonyl)oxy) benzoate (T1.5)

A mixture of ethyl 3-chloro-4-hydroxybenzoate (available from Aldrich) (5.00 g, 25.0 mmol), N-phenyltriflamide (9.30 g, 26.0 mmol) and TEA (4.2 mL, 30.0 mmol) in DCM (40 mL) with a catalytic amount of DMAP, was stirred at ambient temperature overnight. DCM (150 mL) was added, and the reaction mixture was washed with brine (30×3 mL), dried over $MgSO_4$, and the solvent was removed under reduced pressure. The product T1.5 was used in the next step without further purification. MS ESI (pos.) m/e: 335.0 $(M+Na)^+$.

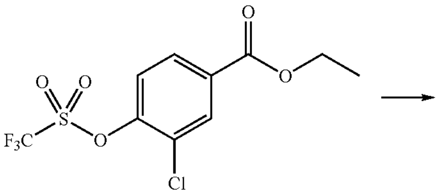

T1.5

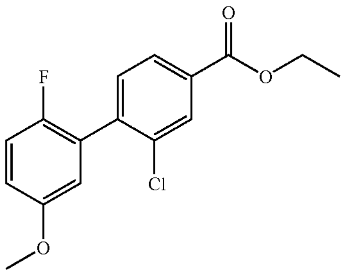

T1.6

Ethyl 2-chloro-2'-fluoro-5'-(methyloxy)-1,1'-biphenyl-4-carboxylate (T1.6)

A reaction mixture of ethyl 3-chloro-4-(trifluoromethylsulfonyloxy)benzoate (T1.5) (3.00 g, 9.02 mmol), 2-fluoro-5-methoxyphenylboronic acid (commercially available from Aldrich) (1.84 g, 10.8 mmol), tetrakis(triphenylphosphine) palladium (0.521 g, 0.451 mmol) and potassium carbonate (2.49 g, 18.0 mmol) in DMF (20 mL), was purged with $N_2$ three times and then heated at 100° C. for 4 hours. The reaction was cooled to room temperature, and EtOAc (130 mL) was added. The mixture was then washed with brine (30×4 mL). The organic layer was dried over $MgSO_4$. The residue was purified by CombiFlash® silica gel column (eluting with hexane/EtOAc; 85/15) to give T1.6. $^1H$ NMR (400 MHz, $CDCl_3$) δ ppm 8.08 (d, 1H), 7.90 (d, 1H), 7.33 (dd, 1H), 6.96-7.02 (m, 1H), 6.82-6.85 (m, 1H), 6.74 (d, 1H), 4.33 (q, 2H), 4.31 (s, 3H), 1.34 (t, 3H). MS ESI (pos.) m/e: 309.1 $(M+H)^+$.

T1.6

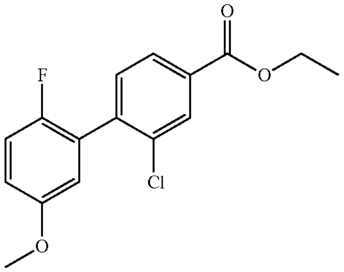

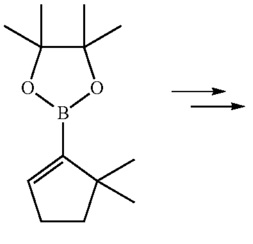

T1.3

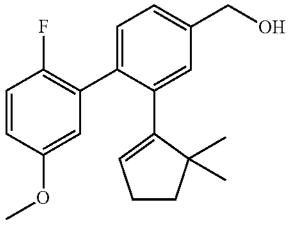

T1.7

(2-(5,5-Dimethyl-1-cyclopenten-1-yl)-2'-fluoro-5'-(methyloxy)-1,1'-biphenyl-4-yl)methanol (T1.7)

A reaction mixture of compound T1.6 (1.80 g, 5.80 mmol), 2-(5,5-dimethylcyclopent-1-enyl)-4,4,5,5-tetramethyl-1,3,2-dioxaborolane (T1.3) (1.40 g, 6.4 mmol), S-Phos (0.48 g, 1.20 mmol), tripotassium phosphate (3.10 g, 15.0 mmol) and palladium acetate (0.13 g, 0.58 mmol) in DMF (10.0 mL) and water (1.0 mL), was purged with $N_2$ three times. The resulting mixture was heated at 100° C. for 16 hours. EtOAc (120 mL) was added, and the mixture was washed with brine (25×2 mL). The organic layer was dried with $MgSO_4$. The residue was purified by CombiFlash® silica gel chromatography (eluting with hexane/EtOAc, 9/1) to give Suzuki coupling product as an intermediate, ethyl 2-(5,5-dimethyl-1-cyclopenten-1-yl)-2'-fluoro-5'-(methyloxy)-1,1'-biphenyl-4-carboxylate. MS ESI (pos.) m/e: 369.1 $(M+H)^+$. To a solution of ethyl 2-(5,5-dimethyl-1-cyclopenten-1-yl)-2'-fluoro-5'-(methyloxy)-1,1'-biphenyl-4-carboxylate (1.00 g, 3.0 mmol) in THF (10.0 mL), was slowly added LAH, (1.0M solution in diethyl ether, 4.0 mL, 4.0 mmol) at 0° C. After the addition, the reaction mixture was stirred at 40° C. for 1.5 hours, and then at room temperature for 2 hours. A mixture of water (0.22 mL) in THF (2.0 mL) was slowly added and then 15% sodium hydroxide (0.22 mL) was added at 0° C. Finally, water (0.65 mL) was added at room temperature. The solid was removed by filtration, and the solvent was removed under reduced pressure. The residue was purified by CombiFlash® chromatography (silica gel column, eluent with hexane/EtOAc, 90/10 to 70/30) to give the title compound T1.7. $^{1}H$ NMR (400 MHz, $CDCl_3$) δ ppm. 7.24 (s, 2H), 7.09-7.21 (m, 1H), 6.84-6.96 (m, 1H), 6.68-6.72 (m, 2H), 5.43 (s, 1H), 4.65 (s, 2H), 3.66 (s, 3H), 2.17 (td, 2H), 1.77 (b, 1H), 1.58 (t, 2H), 0.78 (s, 6H). MS ESI (pos.) m/e: 309.1 $(M-HO)^{1}$, 345.2 $(M+H_3O)^{1}$.

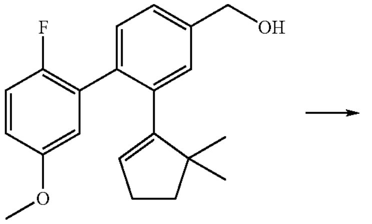

T1.7

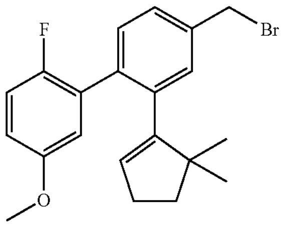

T1.8

4-(Bromomethyl)-2-(5,5-dimethyl-1-cyclopenten-1-yl)-2'-fluoro-5'-(methyloxy)-1,1'-biphenyl (T1.8)

To a solution of triphenylphosphine (0.13 g, 0.51 mmol) in DCM (1.0 mL), was slowly added bromine (0.081 g, 0.51 mmol, 0.25 mL, 2M in $CCl_4$) at 0° C. The resulting mixture was stirred at 0° C. for 15 minutes and then a mixture of compound T1.7 (0.15 g, 0.46 mmol) and anhydrous pyridine (0.041 mL, 0.51 mmol) in DCM (3.0 mL) was added to the mixture. The reaction mixture was stirred at room temperature for 2 hours. DCM (80 mL) was added, and the mixture was washed with water (20×2 mL), and dried over $Na_2SO_4$. The solvent was removed under reduced pressure to provide product T1.8. $^{1}H$ NMR (400 MHz, $CDCl_3$) δ ppm. 7.16-7.29 (m, 3H), 6.88 (t, 1H), 6.72 (m, 2H), 5.45 (s, 1H), 4.46 (s, 2H), 3.68 (s, 3H), 2.16-2.19 (m, 2H), 1.59 (t, 2H), 0.78 (s, 6H).

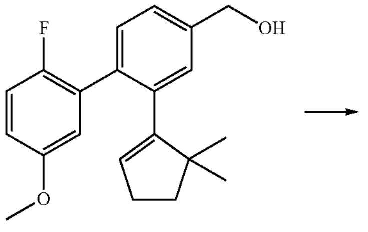

T1.7

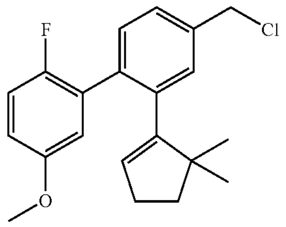

T1

4-(Chloromethyl)-2-(5,5-dimethyl-1-cyclopenten-1-yl)-2'-fluoro-5'-(methyloxy)-1,1'-biphenyl (C)

To a solution of compound T1.7 (1.10 g, 3.37 mmol) and a catalytic amount of DMF (0.10 mL) in DCM (12.0 mL), was slowly added thionyl chloride (0.802 g, 6.74 mmol) at 0° C. After addition, the reaction mixture was stirred at room temperature for 1 hour. The solvent was removed under reduced pressure, and the resulting residue was purified by CombiFlash® chromatography (silica gel column eluted with hexane/EtOAc, 100/0 to 95/5) to give the title compound T1 (1.15 g). $^{1}H$ NMR (400 MHz, $CDCl_3$) δ ppm. 7.32-7.39 (m, 2H), 7.28-7.29 (m, 1H), 6.88 (t, 1H), 6.80-6.82 (m, 2H), 5.56 (s, 1H), 4.66 (s, 2H), 3.78 (s, 3H), 2.27-2.29 (m, 2H), 1.69 (t, 2H), 0.89 (s, 6H).

Example T2

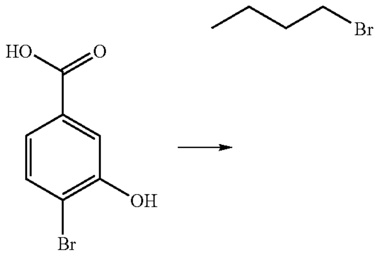

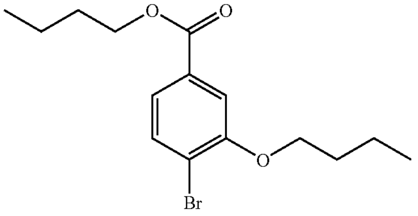

T2.1

Butyl 4-bromo-3-(butyloxy)benzoate (T2.1)

To a flask containing 4-bromo-3-hydroxybenzoic acid (available from Combi-Blocks Inc.) (2.40 g, 11.06 mmol) and cesium carbonate (8.287 g, 25.44 mmol) in DMF (40 mL), was added 1-bromobutane (available from Aldrich) (2.494 mL, 23.22 mmol), and the mixture was stirred overnight. The reaction was diluted with water and extracted with EtOAc. The organic layers were washed with brine, dried over $Na_2SO_4$, filtered, concentrated, and then purified by Combi-Flash® chromatography (0 to 20% EtOAc/Hexanes) to provide T2.1 (2.4326 g, 66.81% yield).

T2.1

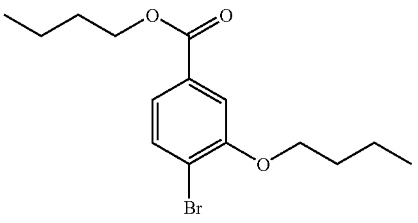

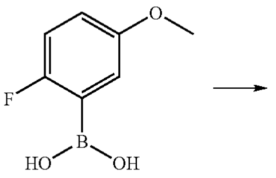

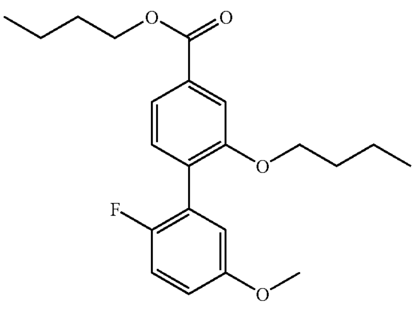

T2.2

Butyl 2-(butyloxy)-2'-fluoro-5'-(methyloxy)-1,1'-biphenyl-4-carboxylate (T2.2)

To a 2 dram vial charged with 2-fluoro-5-methoxyphenylboronic acid (available from Aldrich) (2.323 g, 13.67 mmol), tetrakis(triphenylphosphine) palladium(0) (0.7897 g, 0.6834 mmol), cesium fluoride (0.8409 mL, 22.78 mmol), and T2.1 (1.50 g, 4.556 mmol), was added DME (20 mL), and the mixture was then heated at 90° C. overnight. The reaction was allowed to cool and then filtered and concentrated. The residue was purified by CombiFlash® chromatography (0 to 10% EtOAc/hexanes) yielding T2.2 (1.1530 g, 67.58% yield).

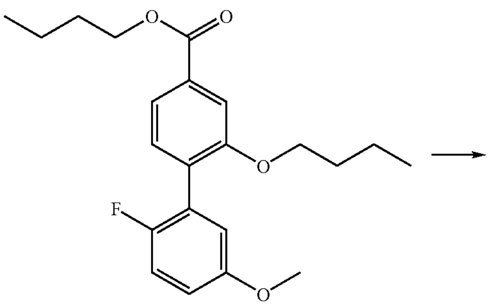

T2.2

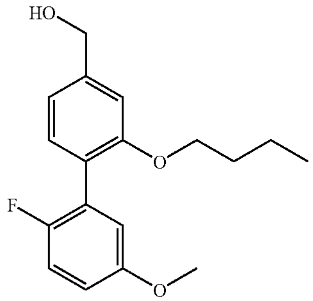

T2.3

(2-(Butyloxy)-2'-fluoro-5'-(methyloxy)-1,1'-biphenyl-4-yl)methanol (T2.3)

To T2.2 (1.1530 g, 3.079 mmol) in THF (10 mL) at 0° C. was added LAH (1.0 M solution in THF (4.619 mL, 4.619 mmol)). The reaction was stirred for one hour and then carefully diluted with water, extracted with EtOAc, washed with brine, dried over sodium sulfate, filtered, and concentrated to provide T2.3 (0.9050 g, 96.57% yield).

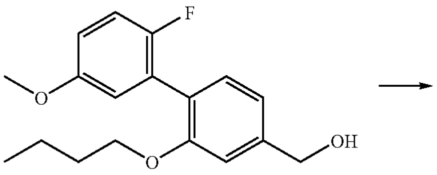

T2.3

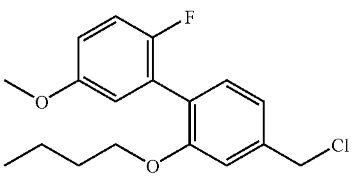

T2

2-(Butyloxy)-4-(chloromethyl)-2'-fluoro-5'-(methyloxy)-1,1'-biphenyl (T2)

To a stirred solution of T2.3 (0.8800 g, 2.891 mmol) in DCM (15 mL) at 23° C. was added thionyl chloride (0.4218 mL, 5.783 mmol). The reaction mixture was then stirred overnight. The reaction was concentrated and then purified by CombiFlash® chromatography (0 to 10% EtOAc/Hexanes) to provide T2 (0.7980 g, 85.50% yield).

Example T3

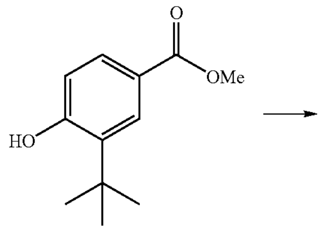

T3.1

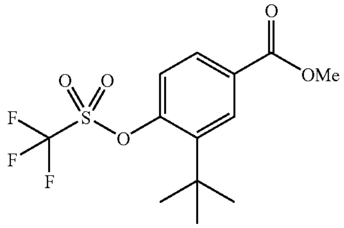

T3.2

Methyl 3-tert-butyl-4-(trifluoromethylsulfonyloxy) benzoate (T3.2)

To a stirred solution of methyl 3-tert-butyl-4-hydroxybenzoate (T3.1) (available from Apin Chemical Ltd, United Kingdom) (0.100 g, 0.48 mmol) in DCM (10 mL, 155 mmol) at 23° C., was added TEA (0.080 mL, 0.58 mmol) and DMAP (0.0059 g, 0.048 mmol), followed by triflic anhydride (0.097 mL, 0.58 mmol). The dark solution was stirred at room temperature and monitored by TLC and LC-MS. After 19 hours, the reaction was concentrated in vacuo. The residue was then purified by flash chromatography ($SiO_2$ gel 60, eluted with 0%-10% EtOAc in hexanes). Fractions containing the desired product were combined and concentrated to provide T3.2 as a colorless oil (0.16 g, 98%). MS ESI (pos.) m/e: 341.0 $(M+H)^+$.

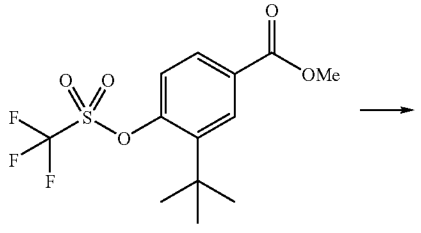

T3.2

-continued

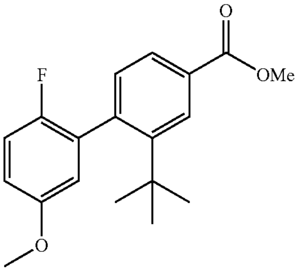

T3.3

Methyl 2-(1,1-dimethylethyl)-2'-fluoro-5'-(methyloxy)-1,1'-biphenyl-4-carboxylate (T3.3)

To a stirred solution of T3.2 (0.100 g, 0.29 mmol) in DMF (2.00 mL, 26 mmol) at 23° C., was added 2-fluoro-5-methoxyphenylboronic acid (available from Aldrich) (0.100 g, 0.59 mmol), potassium carbonate (0.12 g, 0.88 mmol), followed by tetrakis(triphenylphosphine)palladium (0.034 g, 0.029 mmol). The mixture was heated to 100° C. After 2 hours, the reaction was cooled to room temperature and diluted with water. The mixture was extracted with EtOAc (3×50 mL) and concentrated in vacuo. The residue was then purified by flash chromatography ($SiO_2$ gel 60, eluted with 0%-15% EtOAc in hexanes). Fractions containing the desired product were combined and concentrated to provide T3.3 as a colorless oil (0.85 g, 71%). MS ESI (pos.) m/e: 317.2 $(M+H)^+$.

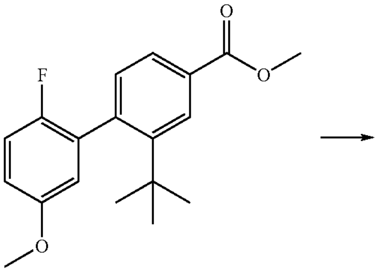

T3.3

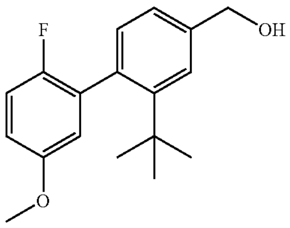

T3.4

(2-(1,1-Dimethylethyl)-2'-fluoro-5'-(methyloxy)-1,1'-biphenyl-4-yl)methanol (T3.4)

To a cooled solution of T3.3 (0.85 g, 2.69 mmol) in dry THF (10.0 mL, 2.69 mmol) at 0° C., was added LAH (1.0 M solution in THF (6.0 mL, 6.0 mmol)). Upon complete addition, the reaction was allowed to warm to room temperature and monitored by TLC and LCMS. Upon completion, 1N NaOH (5 mL) was carefully added to quench the reaction.

The resulting solution was extracted with EtOAc (3×10 mL). The combined organic layers were dried over $MgSO_4$, filtered, and concentrated in vacuo. The residue was then purified by flash chromatography ($SiO_2$ gel 60, eluted with 0%-40% EtOAc in hexanes). Fractions containing the desired product were combined and concentrated to provide T3.4 as a colorless oil (0.56 g, 72%). MS ESI (pos.) m/e: 311.2 $(M+Na)^+$.

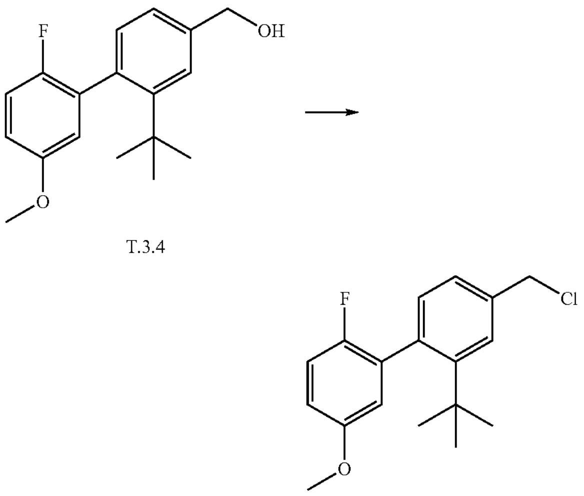

T.3.4

T3

4-(Chloromethyl)-2-(1,1-dimethylethyl)-2'-fluoro-5'-(methyloxy)-1,1'-biphenyl (T3)

To a cooled solution of T3.4 (0.56 g, 1.93 mmol) in dry DCM (3.60 mL, 1.93 mmol) at 0° C., was added thionyl chloride (0.40 mL, 5.48 mmol) dropwise. Upon complete addition of thionyl chloride, the mixture was allowed to warm to room temperature. After 18 hours, the reaction was concentrated in vacuo. The residue was then purified by flash chromatography ($SiO_2$ gel 60, eluted with 0%-15% EtOAc in hexanes). Fractions containing the desired product were combined and concentrated to provide T3 as a colorless solid (0.44 g, 74%). $^1H$ NMR (500 MHz, $CDCl_3$) δ ppm 7.56 (1H, s), 7.25 (5H, dd, J=7.7, 1.6 Hz), 7.01 (2H, m), 6.86 (1H, dd, J=9.0, 3.2 Hz), 6.77 (1H, dd, J=5.9, 3.2 Hz), 4.65 (3H, s), 3.79 (3H, s), 1.24 (9H, s).

Example T4

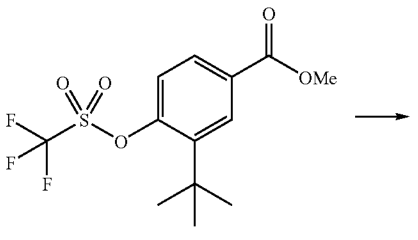

T3.2

-continued

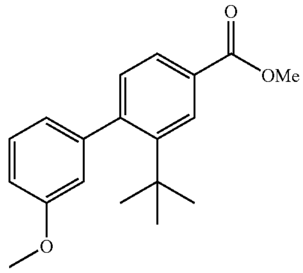

T4.1

Methyl 2-(1,1-dimethylethyl)-3'-(methyloxy)-1,1'-biphenyl-4-carboxylate (T4.1)

A dry round bottom flask containing T3.2 (1.40 g, 4.1 mmol), 3-methoxyphenylboronic acid (commercially available from Aldrich) (1.27 g, 8.34 mmol), tetrakis(triphenylphosphine)palladium (0.49 g, 0.42 mmol), and potassium carbonate (1.71 g, 12.36 mmol) was evacuated and backfilled three times with argon. Dry DMF (12.0 mL) was added via syringe under argon, and the mixture was then heated to 100° C. and monitored by TLC. After 2 hours, the reaction was cooled to room temperature and diluted with water. The mixture was extracted three times with EtOAc and then concentrated under reduced pressure. The residue was then purified by flash chromatography ($SiO_2$ gel 60, eluted with 0%-15% EtOAc in hexanes). Fractions containing the desired product were combined and concentrated to provide T4.1 as a colorless oil (1.01, 82%). MS ESI (pos.) m/e: 299.2 $(M+H)^+$.

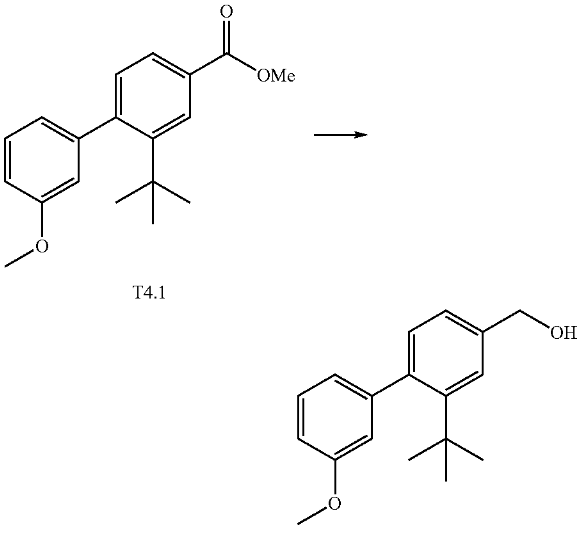

T4.1

T4.2

(2-(1,1-Dimethylethyl)-3'-(methyloxy)-1,1'-biphenyl-4-yl)methanol (T4.2)

To a cooled solution of T4.1 (1.01 g, 3.38 mmol) in dry THF (10.0 mL) at 0° C., was added LAH (1.0 M solution in THF (6.7 mL, 6.7 mmol)). Upon complete addition, the reaction was allowed to warm to room temperature and monitored by TLC and LCMS. Upon completion, 1N NaOH (5 mL) was carefully added to quench the reaction. The resulting solution was extracted with EtOAc (3×10 mL), dried over $MgSO_4$, filtered and concentrated in vacuo. The residue was then purified by flash chromatography ($SiO_2$ gel 60, eluted with 0%-40% EtOAc in hexanes). Fractions containing the desired product were combined and concentrated to provide T4.2 as a colorless oil (0.82, 90%). $^1H$ NMR (500 MHz, $CDCl_3$) δ ppm 7.56 (1H, s), 7.29 (1H, t, J=3.8 Hz), 7.24 (1H, m), 7.07 (1H, d, J=7.6 Hz), 6.93 (2H, m), 6.86 (1H, d, J=1.5 Hz), 4.77 (2H, s), 3.85 (3H, s), 1.72 (1H, s), 1.26 (9H, s).

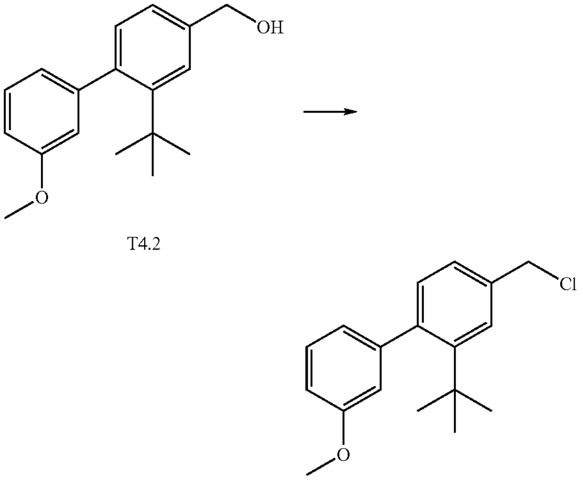

T4.2

T4

4-(Chloromethyl)-2-(1,1-dimethylethyl)-3'-(methyloxy)-1,1'-biphenyl (T4)

A dry, round bottom flask containing T4.2 (0.82 g, 3.04 mmol) and DCM (8.5 mL) was cooled to 0° C. After 15 minutes, thionyl chloride (1.50 mL, 20.56 mmol) was carefully added dropwise at 0° C. Upon complete addition of thionyl chloride, the mixture was allowed to warm to room temperature and stirred overnight. After 25 hours, the reaction was concentrated under reduced pressure. The residue was then purified by flash chromatography ($SiO_2$ gel 60, eluted with 0%-15% EtOAc in hexanes). Fractions containing the desired product were combined and concentrated to provide T4 as a colorless oil (0.82, 93%). $^1H$ NMR (500 MHz, $CDCl_3$) δ ppm 7.53 (1H, d, J=1.7 Hz), 7.28 (3H, m), 7.03 (1H, d, J=7.8 Hz), 6.90 (3H, m), 4.65 (2H, s), 3.82 (3H, s), 1.23 (9H, s).

Examples T5A and T5B

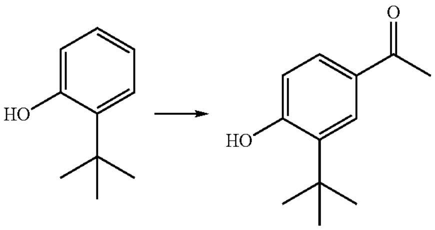

T5.1

1-(3-(1,1-Dimethylethyl)-4-hydroxyphenyl)ethanone (T5.1)

To a dry, round bottom flask was added aluminum chloride (4.402 g, 33.0 mmol). The flask was then cooled to −45° C. After 10 minutes, dry toluene (80 mL) was added followed by dropwise addition of 2-tert-butylphenol (5.00 mL, 32.7 mmol) (commercially available from Aldrich). The mixture was stirred and maintained at −4° C. After 1.5 hours, acetyl chloride (2.40 mL, 33.8 mmol) was carefully added dropwise. The mixture was allowed to warm to room temperature and monitored with TLC and LC-MS. After 18 hours, the mixture was slowly poured onto crushed ice. This mixture was stirred at room temperature and the crystals were collected by filtration. The light yellow solid was identified as T5.1 (4.2589 g, 68%). MS ESI (pos.) m/e: 193.1 $(M+H)^+$.

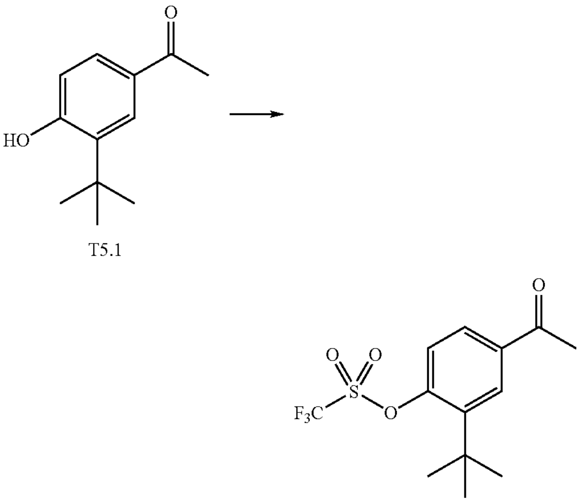

T5.1

T5.2

4-Acetyl-2-(1,1-dimethylethyl)phenyl trifluoromethanesulfonate (T5.2)

To a stirred solution of T5.1 (2.0006 g, 10.41 mmol) in dry DCM (37 mL) was added TEA (3.0 mL, 21.57 mmol) and DMAP (0.1309 g, 1.071 mmol). After 20 minutes, N-phenyl-trifluoromethanesulfonimide (5.5846 g, 15.63 mmol) was added in portions. Upon complete addition, the solution was stirred at room temperature and monitored with TLC and LC-MS. After 4.5 hours, the reaction was diluted with brine and extracted three times with DCM. After drying over anhydrous magnesium sulfate and filtration, the solvent was removed under reduced pressure. The residue was purified by silica gel flash chromatography (0-20% EtOAc/hexane) to yield T5.2 (3.0227 g, 90% yield). MS ESI (pos.) m/e: 325.1 $(M+H)^+$.

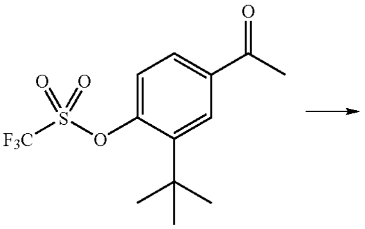

T5.2

-continued

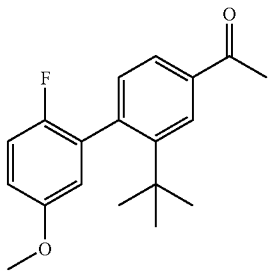

T5.3

1-(2-(1,1-Dimethylethyl)-2'-fluoro-5'-(methyloxy)-1,1'-biphenyl-4-yl)ethanone (T5.3)

A dry round bottom containing T5.2 (3.0227 g, 9.3202 mmol), 2-fluoro-5-methoxyphenylboronic acid (2.4005 g, 14.125 mmol) (commercially available from Aldrich), tetrakis(triphenylphosphine)palladium (1.0853 g, 0.93920 mmol), and potassium carbonate (3.9996 g, 28.940 mmol) was evacuated and backfilled three times with argon. Dry DMF (25 mL) was added via syringe under argon, then the mixture was heated to 100° C. and monitored with TLC. After 3 hours, the reaction was cooled to room temperature, then diluted with water. The mixture was extracted three times with EtOAc then concentrated under reduced pressure. The residue was purified by silica gel flash chromatography (0-15% EtOAc/hexane) to yield T5.3 (2.6053 g, 93% yield). MS ESI (pos.) m/e: 301.1 $(M+H)^+$.

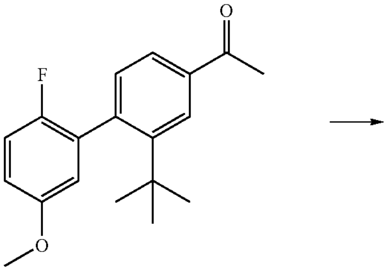

T5.3

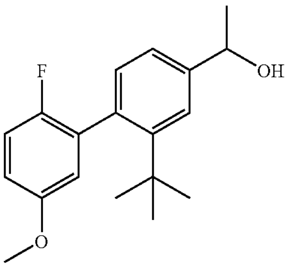

T5.4

-continued

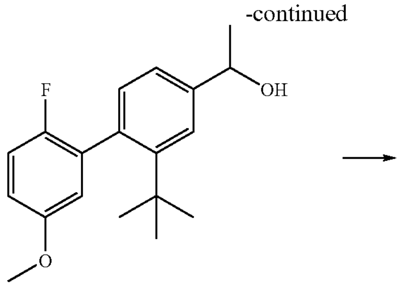

T5.4

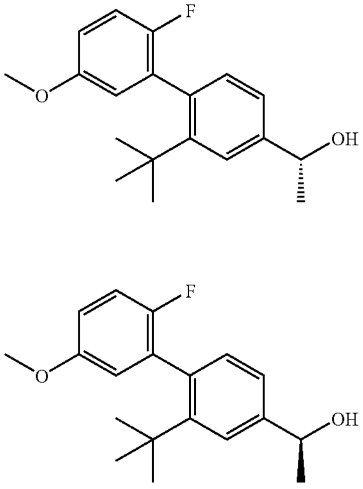

T5.5 and T5.6

1-(2-(1,1-Dimethylethyl)-2'-fluoro-5'-(methyloxy)-1,1'-biphenyl-4-yl)ethanol (T5.4)

To a dry round bottom flask containing T5.3 (2.5921 g, 8.630 mmol) was added a premixed solution of dry MeOH (10 mL) and dry DCM (10 mL). After stirring at 0° C. for about 15 minutes, sodium borohydride (0.6632 g, 17.53 mmol) was carefully added at 0° C. Upon complete addition, the reaction was allowed to warm to room temperature. After 2 hours, the reaction was cooled in an ice bath, then carefully quenched with water and extracted three times with DCM. After drying over anhydrous magnesium sulfate and filtration, the organic solvent was removed under reduced pressure. The residue was purified by silica gel flash chromatography (0-15% EtOAc/hexane) to yield T5.4 (2.5329 g, 97% yield). MS ESI (pos.) m/e: 285.1 $(M-H_2O)^+$. Chiral separation of T5.4 was accomplished using SFC with 9 g/min MeOH (0.6% DEA)+81 g/min $CO_2$ on a 250×30 mm OD-H column. The outlet pressure of the system was set to 140 bar, temperature at 25° C. and detector wavelength was 220 nm. Sample was dissolved to 54 mg/mL in MeOH and separations on 13.5 mg injections were performed at a rate of one injection per 1.65 minutes to provide T5.5 (peak 1) and T5.6 (peak 2).

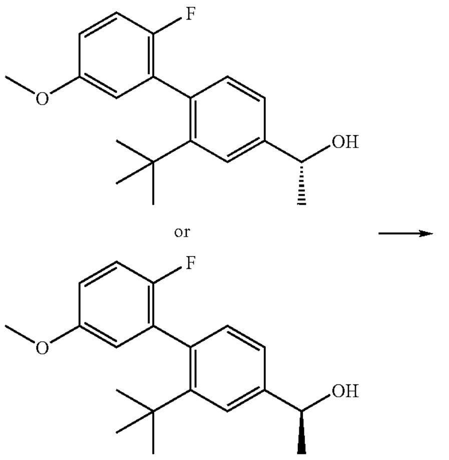

or

T5.6

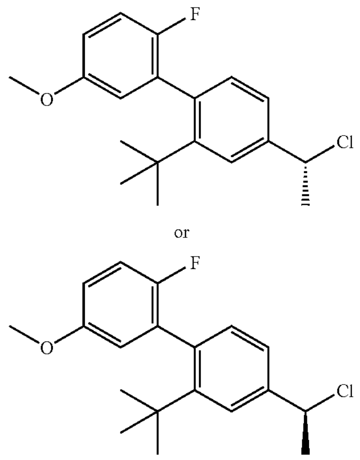

or

T5A 4-((1S)-1-Chloroethyl)-2-(1,1-dimethylethyl)-2'-fluoro-5'-(methyloxy)-1,1'-biphenyl or 4-((1R)-1-chloroethyl)-2-(1,1-dimethylethyl)-2'-fluoro-5'-(methyloxy)-1,1'-biphenyl (T5A)

A dry, round bottom flask containing T5.6 (1.0221 g, 3.380 mmol) was evacuated and backfilled with argon. Dry DCM (14 mL) was added under argon, and the homogeneous solution was cooled to 0° C. After 15 minutes, thionyl chloride (1.0 mL, 13.71 mmol) was carefully added dropwise at 0° C. Upon complete addition of thionyl chloride, the mixture was allowed to warm to room temperature and stirred overnight. After 2.5 hours, the reaction was concentrated under reduced pressure. The residue was purified by silica gel flash chromatography (0-15% EtOAc/hexane) to yield T5A (744.7 mg, 69% yield). MS ESI (pos.) m/e: 338.2 $(M+H_2O)^+$.

4-((1S)-1-Chloroethyl)-2-(1,1-dimethylethyl)-2'-fluoro-5'-(methyloxy)-1,1'-biphenyl or 4-((1R)-1-chloroethyl)-2-(1,1-dimethylethyl)-2'-fluoro-5'-(methyloxy)-1,1'-biphenyl (T5B)

This compound is prepared from T5.5 using the same procedure described above with respect to T5A.

Examples T6A and T6B

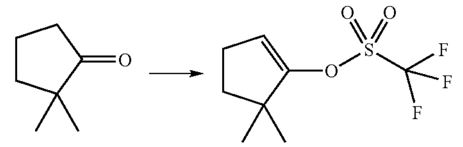

T6.1 T6.2

5,5-Dimethylcyclopent-1-enyl trifluoromethanesulfonate (T6.2)

To a solution of 2,2-dimethylcyclopentanone T6.1 (available from ChemSampCo) (3.00 g, 26.75 mmol) in THF (100 mL), was slowly added LDA (14.7 mL, 2.0 M, in heptane) at −78° C. The resulting mixture was stirred at −78° C. for 1 hour. A solution of N-phenyltriflamide (10.00 g, 28.00 mmol) was added to the mixture at −78° C., and stirring was continued at 0° C. for 2 hours and then at room temperature overnight. The reaction mixture was extracted with hexane (80×2 mL). The organic layer was washed with saturated $Na_2CO_3$ (30 mL), brine (20 mL), and dried with $MgSO_4$. The solvent was removed, and the residue was purified by CombiFlash® chromatography (eluant was EtOAc and hexane) to give T6.2. $^1$H NMR ($CDCl_3$) δ ppm 1.16 (s, 6H), 1.86 (t, J=7.1 Hz, 2H), 2.36 (t, J=7.1 Hz, 2H), 5.56 (m, 1H).

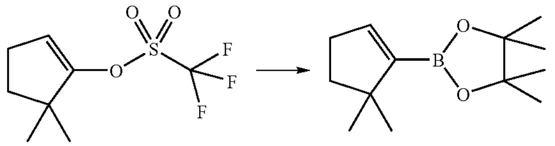

T6.2 T6.3

2-(5,5-Dimethylcyclopent-1-enyl)-4,4,5,5-tetramethyl-1,3,2-dioxaborolane (T6.3)

KOPh was prepared by dissolving commercially available phenol (100 g, 1063 mmol) in MeOH (300 mL) and then adding a mixture of potassium hydroxide (20 mL, 1052 mmol) dissolved in MeOH (80 mL) and water (80 mL). The resulting solution was mixed well and flushed with nitrogen. The solvent was then removed by rotary evaporator at 50-60° C. The resulting product was ground to fine powders and pumped on at high vacuum at 60° C. for 1 hour to give KOPh as an off white solid. $PdCl_2(PPh_3)_2$ (0.56 g, 0.80 mmol), $PPh_3$ (0.63 g, 2.40 mmol), bis(pinacolato)diboron (6.80 g, 26.75 mmol) and KOPh (fine powder, 5.30 g, 40.10 mmol) were added to a flask. The flask was flushed with nitrogen and charged with toluene (100 mL) and with T6.2 (6.53 g, 26.75 mmol). The mixture was stirred at 50° C. for 2 hours. The reaction mixture was treated with water at room temperature and extracted with benzene (60×2 mL). The organic layer was dried over $MgSO_4$. The product was then purified by CombiFlash® chromatography to give intermediate T6.3. $^1$H NMR ($CDCl_3$) δ ppm 1.04 (s, 6H), 1.18 (s, 12H), 1.57 (t, J=7.1 Hz, 2H), 2.29 (t, J=7.1 Hz, 2H), 6.29 (m, 1H).

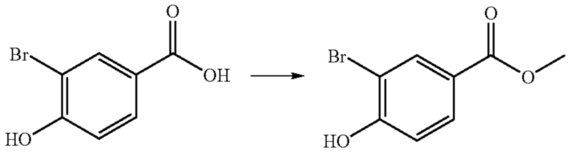

T6.4 T6.5

Methyl 3-bromo-4-hydroxybenzoate (T6.5)

To a stirred solution of 3-bromo-4-hydroxybenzoic acid (T6.4) (available from Alfa Aesar, Avocado, Lancaster) (50.0 g, 231 mmol) in MeOH (300 mL) was added a cold solution of sulfuric acid (2.50 mL, 47 mmol). The mixture was heated to 80° C. and monitored by TLC. After 16.5 hours, the solvent was removed and the reaction mixture was diluted with EtOAc. The organic phase was washed carefully two times with saturated aqueous $NaHCO_3$, once with brine, and then dried over anhydrous sodium sulfate. After filtration, the organic solvent was removed in vacuo to yield T6.5 as a white solid (yield 100%) that was used without purification.

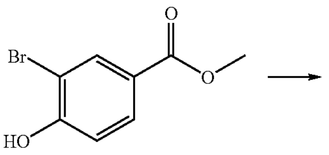

T6.5

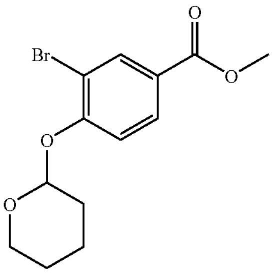

T6.6

Methyl 3-bromo-4-(tetrahydro-2H-pyran-2-yloxy) benzoate (T6.6)

To a stirred solution of T6.5 (38 g, 164 mmol) and 3,4-dihydro-2H-pyran (45 mL, 493 mmol) in DCM (355 mL) was added 4-methylbenzenesulfonic acid hydrate (0.63 g, 3.30 mmol). The mixture was stirred at room temperature and monitored by TLC. After 2 hours, the solution was washed with a mixed aqueous solution of saturated aqueous sodium bicarbonate/brine/water (1:1:2). The aqueous layer was extracted three times with ether. After drying over anhydrous sodium sulfate and then filtering, the organic solvent was removed under reduced pressure. The crude material was purified on silica gel (0-10% EtOAc in hexanes) to yield a white solid. The product was recrystallized from MeOH to provide T6.6 (yield 90%). $^1$H NMR (400 MHz, $CDCl_3$) δ ppm 8.24 (1H, d, J=2.0 Hz), 7.93 (1H, dd, J=8.6, 2.0 Hz), 7.17 (1H, d, J=8.6 Hz), 5.62 (1H, t, J=2.5 Hz), 3.90 (3H, s), 3.83 (1H, td, J=11.1, 2.9 Hz), 3.66 (1H, m), 2.18 (1H, m), 2.04 (1H, m), 1.94 (1H, m), 1.79 (2H, m), 1.67 (1H, m).)

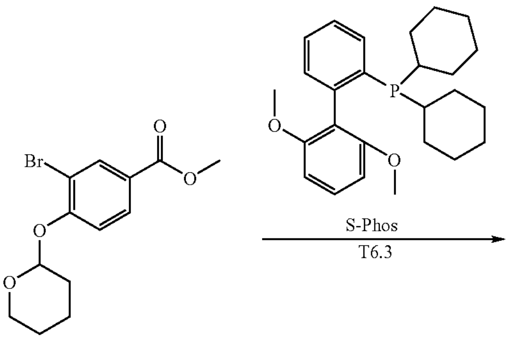

T6.6

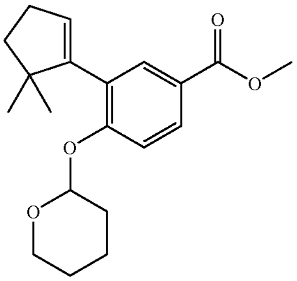

T6.7

Methyl 3-(5,5-dimethylcyclopent-1-enyl)-4-(tetrahydro-2H-pyran-2-yloxy)benzoate (T6.7)

A stirred mixture of T6.6 (10.1 g, 31.9 mmol), grounded S-Phos (2.62 g, 6.39 mmol), palladium acetate (0.72 g, 3.2 mmol), and potassium phosphate, tribasic (17.0 g, 80.2 mmol) in DMF (70 mL) and water (3.5 mL) was purged three times with argon and placed under vacuum three times. Before heating, 2-(5,5-dimethylcyclopent-1-enyl)-4,4,5,5-tetramethyl-1,3,2-dioxaborolane (T6.3) (8.50 g, 38.3 mmol) was added via syringe. The resulting mixture was then heated to 75° C. After 21 hours (black solution), the reaction was cooled to room temperature, diluted with water, and extracted three times with EtOAc. The organic layers were combined and washed twice with brine. After drying over anhydrous sodium sulfate and filtering, the organic solvent was removed under reduced pressure. The residue was purified on silica gel (0-20% EtOAc in hexanes) to yield T6.7 as a colorless oil that solidified (yield 80%). $^1$H NMR (400 MHz) ($CDCl_3$) δ ppm 7.91 (1H, dd, J=8.6, 2.3 Hz), 7.74 (1H, d, J=2.3 Hz), 7.15 (1H, d, J=8.6 Hz), 5.55 (1H, t, J=2.3 Hz), 5.49 (1H, t, J=2.9 Hz), 3.88 (3H, s), 3.82 (1H, td, J=11.1, 2.9 Hz), 3.64 (1H, m), 2.43 (2H, td, J=7.0, 2.3 Hz), 1.92 (5H, m), 1.69 (1H, m), 1.61 (2H, m), 1.09 (6H, d, J=13.7 Hz).

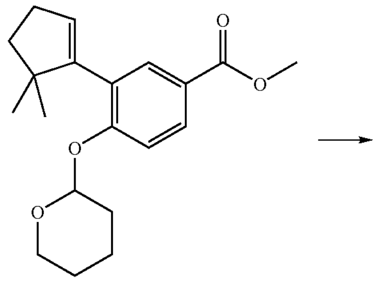

T6.7

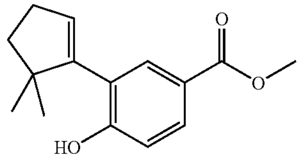

T6.8

Methyl 3-(5,5-dimethylcyclopent-1-enyl)-4-hydroxybenzoate (T6.8)

To a stirred solution of T6.7 (19.0 g, 57.6 mmol) in MeOH (150 mL) was added PPTS (1.46 g, 5.80 mmol). The mixture was heated to 50° C. and monitored with TLC. After 19 hours, the organic solvent was removed under reduced pressure and the product was then purified on silica gel (0-15% EtOAc in hexanes) to yield T6.8 as a white solid (yield 90%). $^{1}$H NMR (400 MHz) ($CDCl_3$) δ ppm 7.89 (1H, dd, J=8.6, 2.0 Hz), 7.79 (1H, d, J=2.3 Hz), 6.97 (1H, d, J=8.6 Hz), 5.87 (1H, s), 5.81 (1H, t, J=2.3 Hz), 3.89 (3H, s), 2.51 (2H, td, J=7.1, 2.5 Hz), 1.94 (2H, t, J=7.0 Hz), 1.12 (6H, s).

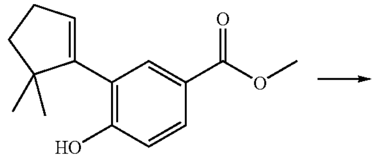

T6.8

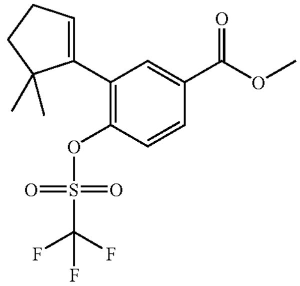

T6.9

Methyl 3-(5,5-dimethylcyclopent-1-enyl)-4-(trifluoromethylsulfonyloxy)benzoate (T6.9)

To a stirred solution of T6.8 (6.00 g, 24.4 mmol) in dry DCM (35 mL) was added TEA (6.80 mL, 48.9 mmol) and 4-dimethylaminopyridine (0.30 g, 2.5 mmol). After about 20 minutes, N-phenyl bis-trifluoromethane sulfonimide (10.5 g, 29.3 mmol) was added in portion. Upon complete addition, the solution was stirred at room temperature and monitored with TLC. After 3 hours, the reaction was diluted with brine and extracted three times with DCM. After drying over anhydrous magnesium sulfate and filtering, the organic solvent was removed under reduced pressure and the product was then purified on silica gel (0-10% EtOAc in hexanes) to yield T6.9 as a colorless oil (yield 88%). $^{1}$H NMR (400 MHz, $CDCl_3$) δ ppm 8.02 (1H, dd, J=8.6, 2.0 Hz), 7.94 (1H, d, J=2.0 Hz), 7.35 (1H, d, J=8.6 Hz), 5.80 (1H, t, J=2.5 Hz), 3.94 (3H, s), 2.48 (2H, td, J=7.0, 2.3 Hz), 1.91 (2H, t, J=7.0 Hz), 1.09 (6H, s).

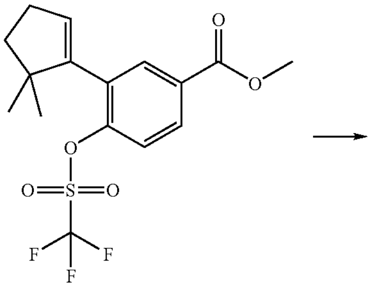

T6.9

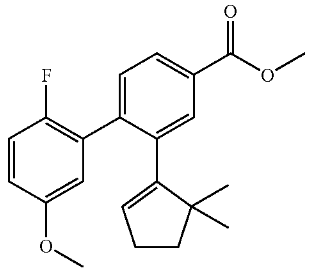

T6.10

Synthesis of T6.10

To a stirred solution of T6.9 (8.71 g, 23.0 mmol) in DMF (20 mL) at 23° C. was added 2-fluoro-5-methoxyphenylboronic acid (7.84 g, 46.1 mmol) (commercially available from Aldrich) and potassium carbonate (9.56 g, 69.1 mmol) followed by tetrakis(triphenylphosphine)palladium (0) (2.67 g, 2.31 mmol). The mixture was heated to 90° C. After 15 hours, LCMS-showed that the reaction was complete. The mixture was then cooled to room temperature and then diluted with water. After extracting three times with EtOAc, the mixture was concentrated in vacuo and then purified on silica gel (0%-10% EtOAc/hexane) to give T6.10 as a clear oil that solidified (yield 91%). $^{1}$H NMR (400 MHz, $CDCl_3$) δ ppm 7.98 (1H, dd, J=8.0, 1.8 Hz), 7.91 (1H, d, J=2.0 Hz), 7.40 (1H, d, J=7.8 Hz), 6.98 (1H, t, J=8.8 Hz), 6.85 (2H, m), 5.55 (1H, s), 3.95 (3H, s), 3.77 (3H, s), 2.27 (2H, td, J=7.0, 2.7 Hz), 1.68 (2H, t, J=7.0 Hz), 0.87 (6H, s).

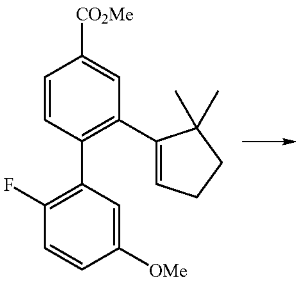

T6.10

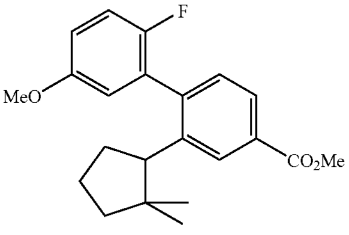

T6.11

Synthesis of T6.11

To a stirred solution of T6.10 (0.660 g, 1.86 mmol) in MeOH (20.00 mL, 1.86 mmol) at 23° C. was added Pd/C (0.0198 g, 0.186 mmol). The reaction was stirred under an atmosphere of hydrogen (0.00375 g, 1.86 mmol) for 16 hours. The reaction mixture was then filtered and concentrated in vacuo to give T6.11 as a clear oil (0.600 g, 90.4% yield).

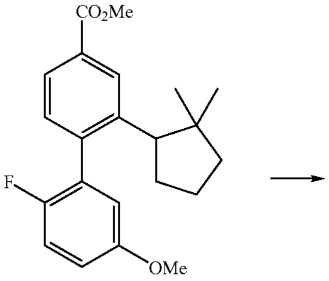

T6.11

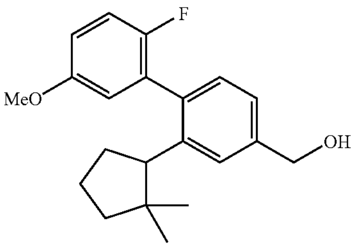

T6.12

-continued

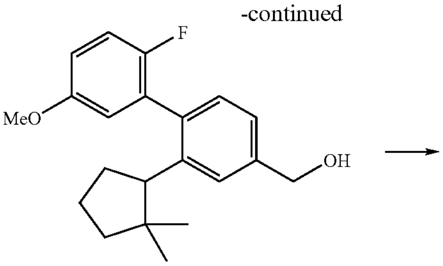

T6.12

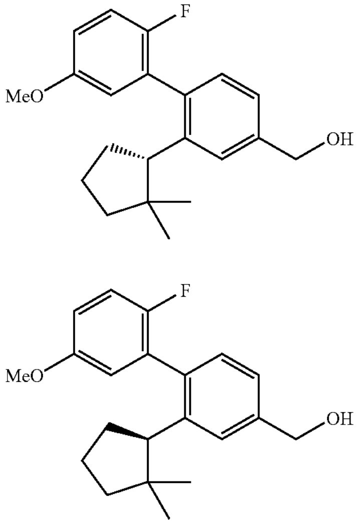

T6.13 and T6.14

Synthesis of T6.12, T6.13, and T6.14

To a stirred solution of T.6.11 (0.500 g, 1.4 mmol) in THF (7.0 mL, 1.4 mmol) at 0° C. was added LAH (1.4 mL, 1.4 mmol). After addition, the reaction was stirred for 1.5 hours. 1N NaOH (aq) was then added to quench the reaction, and the mixture was then extracted with EtOAc. The organic layers were dried over magnesium sulfate, filtered, and concentrated in vacuo. The resulting product was then purified on silica gel (0%-20% EtOAc/hexane) to give T6.12 (0.442 g, 96% yield). Chiral separation of T6.12 was accomplished on Chiracel-OD (3% IPA in hexane) to provide T6.13 and T6.14. Analytical column (Chiracel-OD (2% IPA in hexane, 45 min run) Peak 1—15.5 mins, Peak 2—38.0 mins).[1]

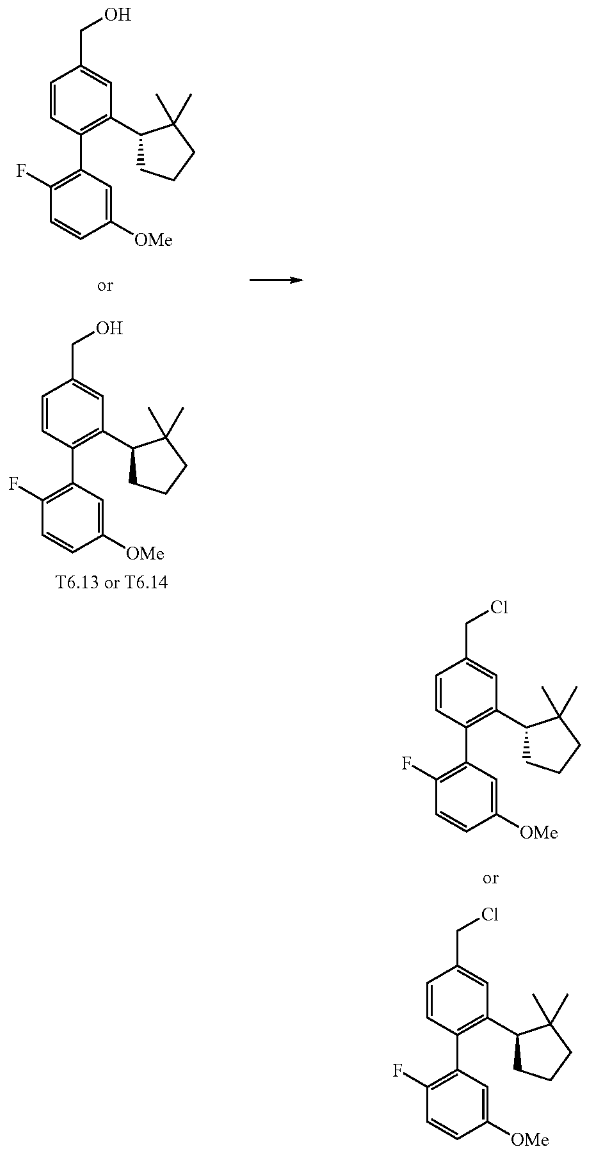

or

T6.13 or T6.14 or

T6A or T6B 4-(Chloromethyl)-2-((1R)-2,2-dimethylcyclopentyl)-2'-fluoro-5'-(methyloxy)-1,1'-biphenyl or 4-(chloromethyl)-2-((1S)-2,2-dimethylcyclopentyl)-2'-fluoro-5'-(methyloxy)-1,1'-biphenyl (T6A or T6B)

Thionyl chloride (1.5 mL, 20 mmol) was added to a stirred solution of T6.13 or T6.14 (3.280 g, 10.0 mmol) in DCM (100 mL, 10.0 mmol) and DMF (0.77 mL, 10.0 mmol) at 0° C. Stirring was continued at room temperature for 2 hours. The reaction mixture was then concentrated in vacuo and purified on silica gel (0-10% EtOAc in hexane) to give the desired product T6A or T6B (3.00 g, 87% yield) as a clear oil.

Asymmetric synthesis of T6A or T6B

The following procedures were used to synthesize T6A or T6B using a highly enantioselective procedure to hydrogenate T6.8 to form T6.15 or T6.16.

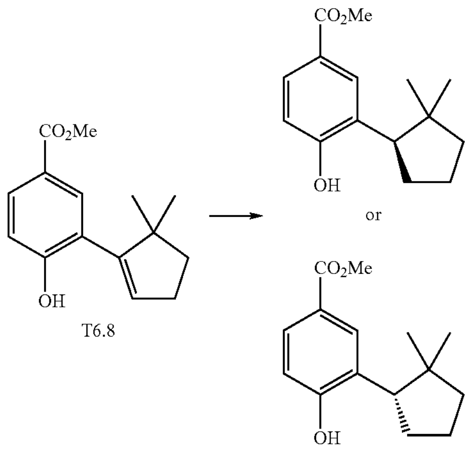

T6.8 or

T6.15 or T6.16

(R)-methyl 3-(2,2-dimethylcyclopentyl)-4-hydroxybenzoate or (S)-methyl 3-(2,2-dimethylcyclopentyl)-4-hydroxybenzoate (T6.15 or T6.16)

A mixture of $Rh(COD)_2BF_4$ (Stern Chemical, 35138-22-8, 137.2 mg, 0.338 mmol) and (R)-1-[(S)-2-(R)-(ditertbutylphosphino)ferrocenyl]ethyl-bis-(3,5-bistrifluoromethylphenyl)phosphine (Solvias, SL-J210-1, 302 mg, 0.3718 mmol) was stirred in THF (300 mL) under $N_2$ for 60 minutes and a dark red solution formed. To the resulting solution was added methyl 3-(5,5-dimethylcyclopent-1-enyl)-4-hydroxybenzoate T6.8 (41.64 g, 168.98 mmol) and TEA (10 mol %, 2.35 mL, 16.9 mmol). The resulting solution was filled with $H_2$ (200 psi) three times and stirred at room temperature/200 psi for 2 hours. The reaction mixture was then passed through a short plug of silica gel, eluting with 1:1 hexane/EtOAc, followed by concentration afforded the desired product as a white solid (98.9A % conversion, 99% yield (41.6 g), 99% ee).

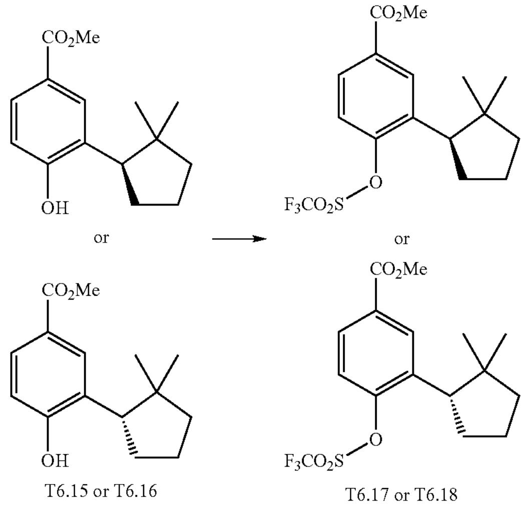

or or

T6.15 or T6.16

T6.17 or T6.18

(R)-methyl 3-(2,2-dimethylcyclopentyl)-4-(trifluoromethylsulfonyloxy)benzoate or (S)-methyl 3-(2,2-dimethylcyclopentyl)-4-(trifluoromethylsulfonyloxy) benzoate (T6.17 or T6.18)

To a stirred solution of (R)-methyl 3-(2,2-dimethylcyclopentyl)-4-hydroxybenzoate or (S)-methyl 3-(2,2-dimethylcyclopentyl)-4-hydroxybenzoate (T6.15 or T6.16) (18.00 g, 72 mmol) in DCM (181 mL, 72 mmol) at 23° C. was added TEA (12 mL, 87 mmol) and a catalytic amount of DMAP. N-phenyltriflamide (28 g, 80 mmol) was then added to the mixture and stirring was continued at room temperature for 16 hours. The reaction was concentrated in vacuo. The residue was purified on silica gel (0-10% EtOAc in hexanes) to yield T6.17 or T6.18 as a colorless oil (27.7 g, 100% yield). MS ESI (pos.) m/e: 381.1 $(M+H)^+$.

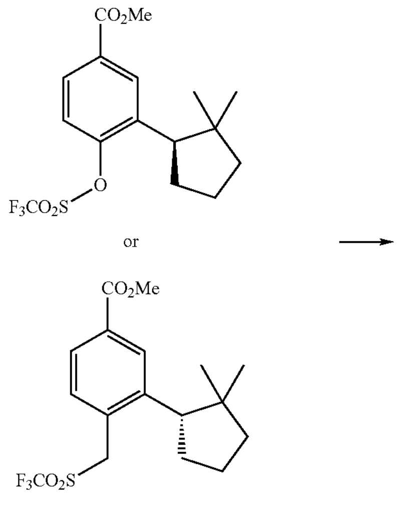

or

T6.17 or T6.18

Methyl 2-((1R)-2,2-dimethylcyclopentyl)-2'-fluoro-5'-(methyloxy)-1,1'-biphenyl-4-carboxylate or methyl 2-((1S)-2,2-dimethylcyclopentyl)-2'-fluoro-5'-(methyloxy)-1,1'-biphenyl-4-carboxylate (T6.19 or T6.20)

To a stirred solution of (S)-methyl 3-(2,2-dimethylcyclopentyl)-4-(trifluoromethylsulfonyloxy)benzoate or (R)-methyl 3-(2,2-dimethylcyclopentyl)-4-(trifluoromethylsulfonyloxy)benzoate (T6.17 or T6.18) (28.5 g, 75 mmol) in DMF (375 mL, 75 mmol) at 23° C. was added 2-fluoro-5-methoxyphenylboronic acid (19 g, 112 mmol) (commercially available from Aldrich), potassium carbonate (31 g, 225 mmol), and then tetrakis(triphenylphosphine)palladium (4 g, 4 mmol). The mixture was heated to 90° C. Stirring was continued for 20 hours, after which, the reaction was cooled to room temperature, diluted with water, and extracted three times with EtOAc. The organic layers were combined and washed twice with brine. After drying over anhydrous sodium sulfate and filtering, the organic solvent was removed under reduced pressure. The residue was purified on silica gel (0-10% EtOAc in hexanes) to yield T6.19 or T6.20 as a colorless oil (25.00 g, 94% yield). MS ESI (pos.) m/e: 357.1 $(M+H)^+$.

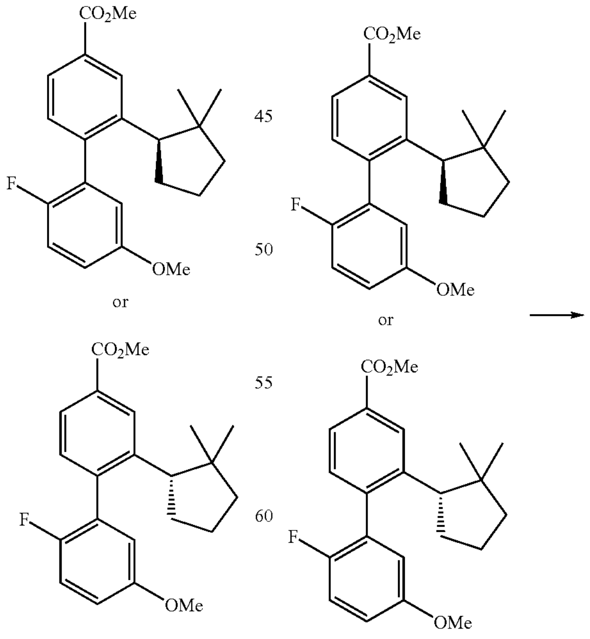

or or

T6.19 or T6.20

T6.19 or T6.20

-continued

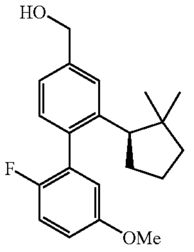

or

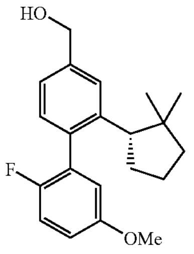

T6.21 or T6.22

(2-((1R)-2,2-Dimethylcyclopentyl)-2'-fluoro-5'-(methyloxy)-1,1'-biphenyl-4-yl)methanol or (2-((1S)-2,2-dimethylcyclopentyl)-2'-fluoro-5'-(methyloxy)-1,1'-biphenyl-4-yl)methanol (T6.21 or T6.22)

To a stirred solution of methyl 2-((1R)-2,2-dimethylcyclopentyl)-2'-fluoro-5'-(methyloxy)-1,1'-biphenyl-4-carboxylate or methyl 2-((1S)-2,2-dimethylcyclopentyl)-2'-fluoro-5'-(methyloxy)-1,1'-biphenyl-4-carboxylate (T6.19 or T6.20) (29.50 g, 83 mmol) in THF (414 mL, 83 mmol) at 0° C. was added LAH (124 mL, 124 mmol). Stirring was continued for 2 hours. Aqueous 1N NaOH was then added to quench the reaction, and the mixture was then extracted with EtOAc. The combined organic layers were dried over magnesium sulfate, filtered, and concentrated in vacuo. The residue was purified on silica gel (0-20% EtOAc in hexanes) to yield T6.21 or T6.22 as a colorless oil (23.66 g, 87% yield). MS ESI (pos.) m/e: 346.1 $(M+H_2O)^+$.

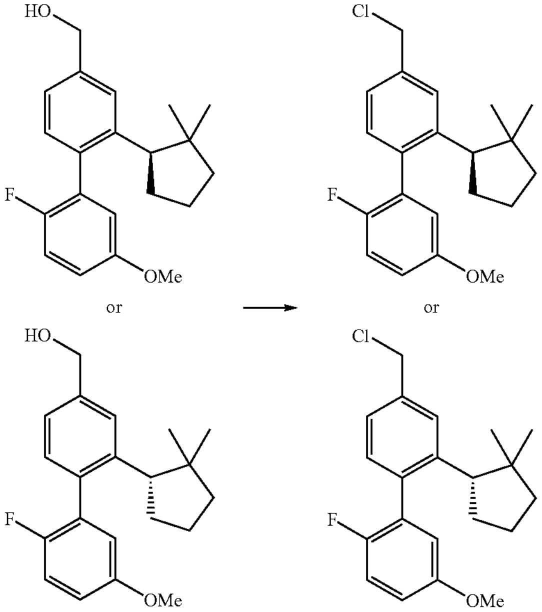

or or

T6.21 or T6.22 T6A or T6B 4-(Chloromethyl)-2-((1R)-2,2-dimethylcyclopentyl)-2'-fluoro-5'-(methyloxy)-1,1'-biphenyl or 4-(chloromethyl)-2-((1S)-2,2-dimethylcyclopentyl)-2'-fluoro-5'-(methyloxy)-1,1'-biphenyl (T6A or T6B)

To a stirred solution of (2-((1R)-2,2-dimethylcyclopentyl)-2'-fluoro-5'-(methyloxy)-1,1'-biphenyl-4-yl)methanol or (2-((1S)-2,2-dimethylcyclopentyl)-2'-fluoro-5'-(methyloxy)-1,1'-biphenyl-4-yl)methanol (T6.21 or T6.22) (23.66 g, 72 mmol) in DCM (360 mL, 72 mmol) and DMF (0.56 mL, 7.2 mmol) at 0° C. was added thionyl chloride (11 mL, 144 mmol). Stirring was continued at room temperature for 1 hour. The reaction as then concentrated in vacuo, and the residue was purified on silica gel (0-10% EtOAc in hexanes) to yield T6A or T6B as a colorless oil (23.0 g, 92% yield). MS ESI (pos.) m/e: 364.1 $(M+H_2O)^+$.

Examples T7A and T7B

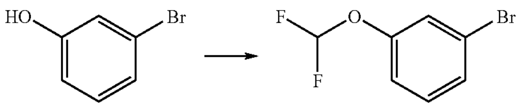

T7.1

1-Bromo-3-(difluoromethoxy)benzene (T7.1)

To a solution of 3-bromophenol (available from Sigma Aldrich) (1.28 g, 7.39 mmol) in DMF (12.0 mL) was added sodium 2-chloro-2,2-difluoroacetate (available from Sigma Aldrich) (2.82 g, 18.49 mmol) and cesium carbonate (4.82 g, 14.79 mmol). The reaction mixture was heated at 100° C. Gas was released from the reaction so care should be taken. After 2 hours, the reaction was cooled to room temperature then diluted with EtOAc, washed with water and then brine and re-extracted three times with EtOAc. The combined organic layers were dried over magnesium sulfate and then filtered, concentrated, and purified with silica gel chromatography (0-5% EtOAc in hexanes) to yield T7.1 as an oil that was used without further purification (yield 61%).

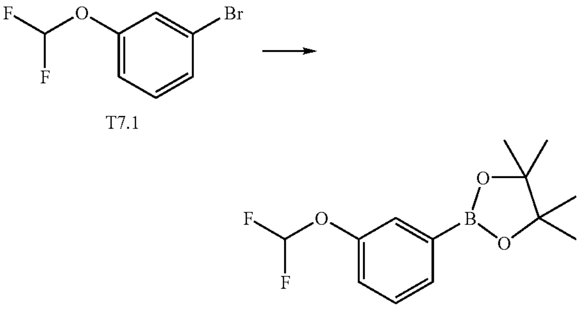

T7.1

T7.2

2-(3-(Difluoromethoxy)phenyl)-4,4,5,5-tetramethyl-1,3,2-dioxaborolane (T7.2)

A stirred mixture of T7.1 (1.00 g, 4.50 mmol), bis(pinacolato)diboron (1.26 g, 4.95 mmol), potassium acetate (1.34 g, 13.70 mmol), and dichloro[1,1'-bis(diphenylphosphino)ferrocene]dichloride palladium(II) DCM adduct (0.17 g, 0.23 mmol) in dry 1,4-dioxane (10.0 mL) was purged three times with argon and placed under vacuum three times. The mixture was heated to 100° C. and monitored with LC-MS and TLC. After 21 hours, the reaction was cooled to room temperature and then filtered through Celite® filter aid. The organic solvent was removed under reduced pressure, and the residue was purified on silica gel (0-10% EtOAc in hexanes) to yield T7.2 as a colorless oil (0.41 g, 34%). $^{1}$H NMR (400 MHz, $CDCl_3$) δ ppm 7.67 (1H, d, J=7.4 Hz), 7.56 (1H, d, J=2.3 Hz), 7.41 (1H, m), 7.22 (1H, dd, J=7.8, 2.3 Hz), 6.73 (1H, t, J=74 Hz), 1.36 (12H, s).

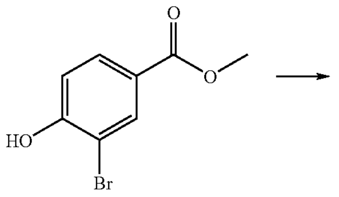

T6.5

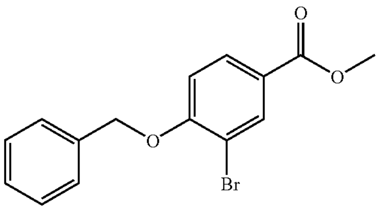

T7.3

Methyl 4-(benzyloxy)-3-bromobenzoate (T7.3)

To a solution of T6.5 (53.2 g, 230 mmol) in DMSO (45.0 mL) was added 1-(bromomethyl)benzene (35.6 mL, 299 mmol). After cooling in an ice water bath, cesium carbonate (128 g, 391 mmol) was carefully added to the mixture, and the mixture was allowed to warm to room temperature. After overnight stirring, the mixture was diluted with water and extracted three times with EtOAc. The organic layers were combined and then washed with brine. After drying over anhydrous magnesium sulfate and filtration, the organic solvent was removed under reduced pressure to yield T7.3 as a white solid.

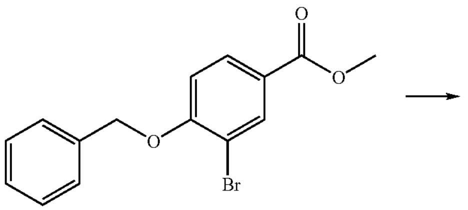

T7.3

-continued

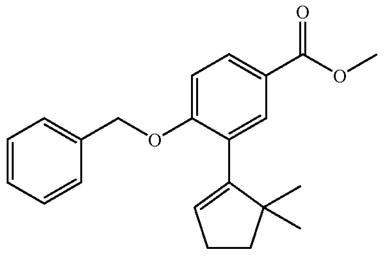

T7.4

Methyl 4-(benzyloxy)-3-(5,5-dimethylcyclopent-1-enyl)benzoate (T7.4)

A stirred mixture of T7.3 (3.75 g, 11.66 mmol), ground S-Phos (0.96 g, 2.33 mmol), palladium acetate (0.26 g, 1.17 mmol), and potassium phosphate, tribasic (6.19 g, 29.17 mmol) in DMF (28.0 mL) and water (1.50 mL) was purged three times with argon and placed under vacuum three times. Before heating, 2-(5,5-dimethylcyclopent-1-enyl)-4,4,5,5-tetramethyl-1,3,2-dioxaborolane (T6.3) (3.11 g, 13.99 mmol) was added via syringe, then the mixture was heated to 75° C. After 21 hours (black solution), the reaction was cooled to room temperature, diluted with water, and extracted three times with EtOAc. The combined organic layers were washed twice with brine. After drying over anhydrous sodium sulfate and filtration, the organic solvent was removed under reduced pressure. The residue was purified on silica gel (0-10% EtOAc in hexanes) to yield T7.4 as a colorless oil (3.03 g, 77%). MS ESI (pos.) m/e: 337.0 (M+H)$^{+}$.

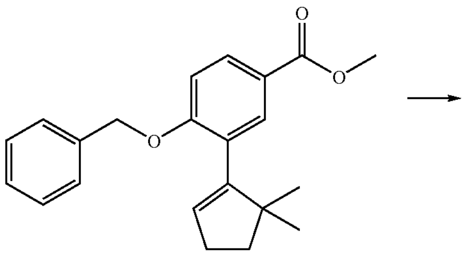

T7.4

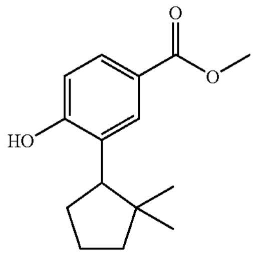

T7.5

Methyl 3-(2,2-dimethylcyclopentyl)-4-hydroxybenzoate (T7.5)

To a flask containing T7.4 (3.03 g, 9.0 mmol) in MeOH (25.0 mL) was added palladium, 10% wt. on activated carbon (0.48 g, 0.45 mmol). After purging, the mixture was stirred under an atmosphere of hydrogen at room temperature. The reaction was monitored with TLC and LC-MS. After 27.5 hours, the reaction was filtered through Celite® filter aid. After concentration, the residue was purified on silica gel using 0-50% EtOAc in hexanes to yield T7.5 as a colorless oil that solidified (1.99 g, 89%). $^1$H NMR (400 MHz, $CDCl_3$) δ ppm 7.91 (1H, d, J=2.3 Hz), 7.79 (1H, dd, J=8.4, 2.2 Hz), 6.82 (1H, d, J=8.2 Hz), 5.54 (1H, s), 3.90 (3H, s), 3.17 (1H, dd, J=10.4, 8.0 Hz), 2.17 (1H, m), 2.04 (1H, m), 1.92 (1H, m), 1.81 (1H, m), 1.68 (2H, m), 1.06 (3H, s), 0.72 (3H, s).

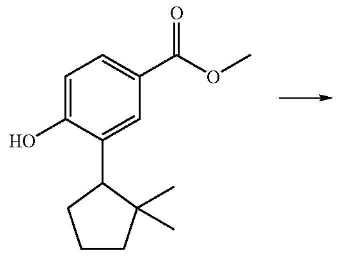

T7.5

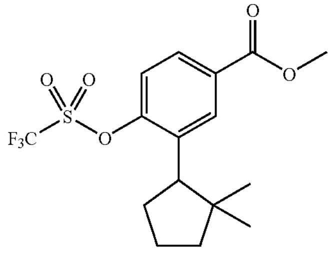

T7.6

Methyl 3-(2,2-dimethylcyclopentyl)-4-(trifluoromethylsulfonyloxy)benzoate (T7.6)

To a stirred solution of T7.5 (0.93 g, 3.74 mmol) in dry DCM (10.0 mL) was added TEA (1.1 mL, 7.89 mmol) and 4-(dimethylamino)pyridine (46.2 mg, 0.378 mmol). After about 20 minutes, N-phenyl-bis(trifluoromethanesulfonimide) (1.61 g, 4.51 mmol) was added in portions. Upon complete addition, the solution was stirred at room temperature and monitored with TLC and LC-MS. After 3.5 hours, the reaction was diluted with brine and extracted three times with DCM. After drying over anhydrous magnesium sulfate and filtration, the organic solvent was removed under reduced pressure and the residue was purified with silica gel chromatography using 0-10% EtOAc in hexanes to yield T7.6 as a colorless oil (1.21 g, 85%). $^1$H NMR (400 MHz, $CDCl_3$) δ ppm 8.08 (1H, d, J=2.2 Hz), 7.95 (1H, dd, J=8.6, 2.2 Hz), 7.35 (1H, d, J=8.6 Hz), 3.95 (3H, s), 3.21 (1H, dd, J=9.8, 8.4 Hz), 2.14 (2H, m), 1.95 (1H, m), 1.86 (1H, m), 1.69 (2H, m), 1.02 (3H, s), 0.70 (3H, s).

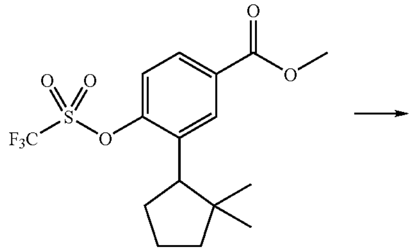

T7.6

-continued

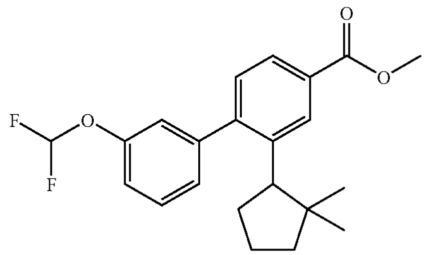

T7.7

Methyl 3'-((difluoromethyl)oxy)-2-(2,2-dimethylcyclopentyl)-1,1'-biphenyl-4-carboxylate (T7.7)

A stirred mixture of T7.6 (0.48 g, 1.26 mmol), ground S-Phos (104.8 mg, 0.255 mmol), palladium acetate (29.1 mg, 0.130 mmol), and potassium phosphate tribasic (0.6727 g, 3.17 mmol) in dry DMF (5.0 mL) was purged with argon and placed under vacuum (repeated three times). Before heating, T7.2 (0.512 g, 1.89 mmol) was added via syringe, and then the mixture was heated to 75° C. After 16 hours, the reaction was cooled to room temperature, diluted with water and extracted three times with EtOAc. The combined organic layers were washed twice with brine. After drying over anhydrous sodium sulfate and filtration, the organic solvent was removed under reduced pressure. The residue was purified on silica gel (0-20% EtOAc in hexanes) to yield T7.7 as a colorless oil (308.9 mg, 65%). $^1$H NMR (500 MHz, $CDCl_3$) δ ppm 8.11 (1H, d, J=1.7 Hz), 7.90 (1H, dd, J=7.9, 1.8 Hz), 7.44 (1H, m), 7.28 (1H, m), 7.16 (2H, m), 7.07 (1H, s), 6.57 (1H, t, J=75 Hz), 3.97 (3H, s), 3.10 (1H, t, J=9.4 Hz), 2.13 (2H, m), 1.90 (1H, m), 1.73 (1H, m), 1.61 (1H, m), 1.38 (1H, ddd, J=12.6, 9.4, 7.6 Hz), 0.75 (3H, s), 0.58 (3H, s).

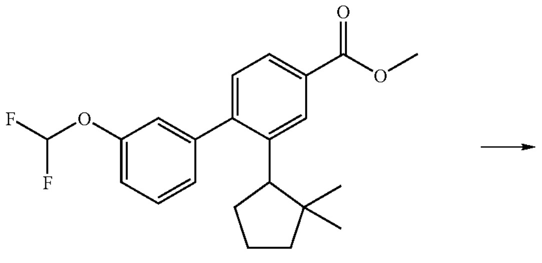

T7.7

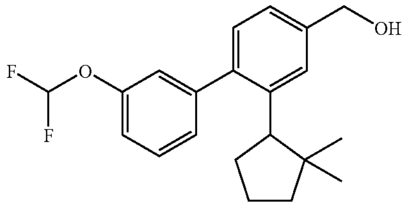

T7.8

-continued

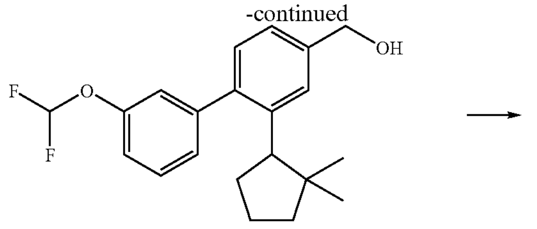

T7.8

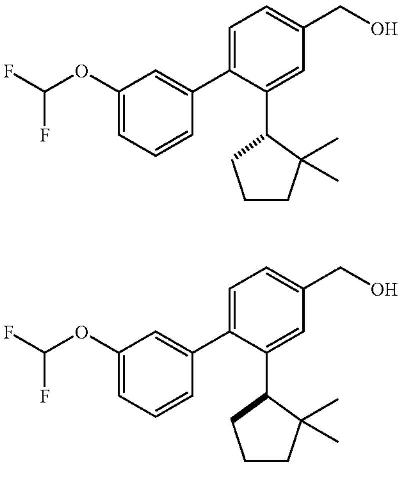

T7.9 and T7.10

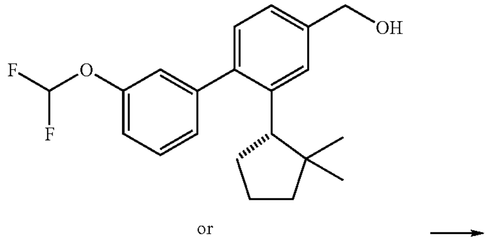

or

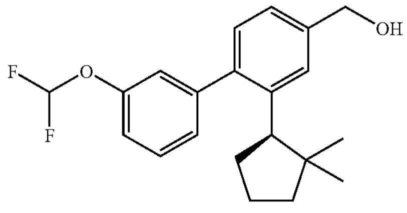

T7.9 or T7.10

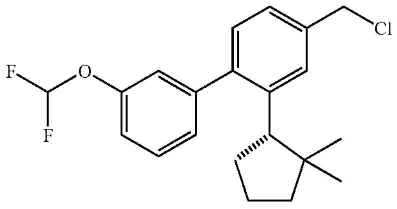

or

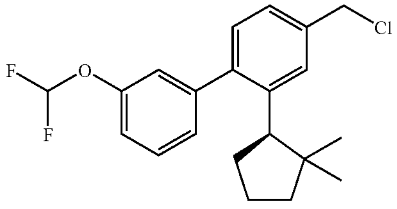

T7A or T7B (3'-((Difluoromethyl)oxy)-2-(2,2-dimethylcyclopentyl)-1,1'-biphenyl-4-yl)methanol (T7.8)

To a cooled solution of T7.7 (308.9 mg, 0.82 mmol) in dry THF (8.0 mL) at 0° C. was added LAH, 1.0 M in THF (1.70 mL, 1.70 mmol) dropwise. Upon complete addition, the reaction was maintained at 0° C. and was monitored by TLC and LCMS. After 45 minutes, 1N NaOH was added to quench the reaction. The resulting solution was extracted three times with EtOAc. After drying over anhydrous magnesium sulfate, filtration, and concentration, the residue was purified by flash chromatography ($SiO_2$ gel 60, eluted with 0%-50% EtOAc in hexanes). Fractions containing the desired product were combined and concentrated to yield T7.8 as a colorless oil (261.6 mg, 92%). $^1$H NMR (500 MHz, $CDCl_3$) δ ppm 7.41 (2H, m), 7.26 (1H, m), 7.21 (1H, m), 7.14 (2H, m), 7.05 (1H, s), 6.55 (1H, t, J=75 Hz), 4.76 (2H, m), 3.07 (1H, dd, J=10.3, 8.6 Hz), 2.10 (2H, m), 1.86 (1H, m), 1.71 (1H, m), 1.55 (1H, ddd, J=12.7, 8.1, 4.9 Hz), 1.37 (1H, ddd, J=12.5, 9.5, 7.6 Hz), 0.75 (3H, s), 0.60 (3H, s). Chiral separation of T7.8 was accomplished on Chiracel-OD (3% IPA in hexane) to provide T7.9 (peak 1) and T7.10 (peak 2).

4-(Chloromethyl)-3'-((difluoromethyl)oxy)-2-((1S)-2,2-dimethylcyclopentyl)-1,1'-biphenyl or 4-(chloromethyl)-3'-((difluoromethyl)oxy)-2-((1R)-2,2-dimethylcyclopentyl)-1,1'-biphenyl (T7A or T7B)

To a solution of T7.9 or T7.10 (112.7 mg, 0.325 mmol) in dry DCM (4.0 mL) and dry DMF (0.03 mL) was added thionyl chloride (0.06 mL, 0.823 mmol) at 0° C. The resulting solution was warmed to room temperature and monitored with TLC and LCMS. After 45 minutes, the reaction was concentrated then purified by silica gel flash chromatography (0-5% EtOAc/hexane) to yield T7A or T7B (99.5 mg, 84%). $^1$H NMR (400 MHz, $CDCl_3$) δ ppm 7.42 (2H, m), 7.25 (1H, d, J=2.0 Hz), 7.19 (1H, m), 7.11 (2H, dd, J=7.8, 2.0 Hz), 7.03 (1H, s), 6.54 (1H, t, J=74 Hz), 4.66 (2H, m), 3.04 (1H, dd, J=10.4, 8.4 Hz), 2.14 (2H, m), 1.88 (1H, m), 1.73 (1H, m), 1.54 (2H, ddd, J=12.7, 8.2, 4.9 Hz), 1.41 (1H, m), 0.73 (3H, s), 0.56 (3H, s).

Example T8

T6.9

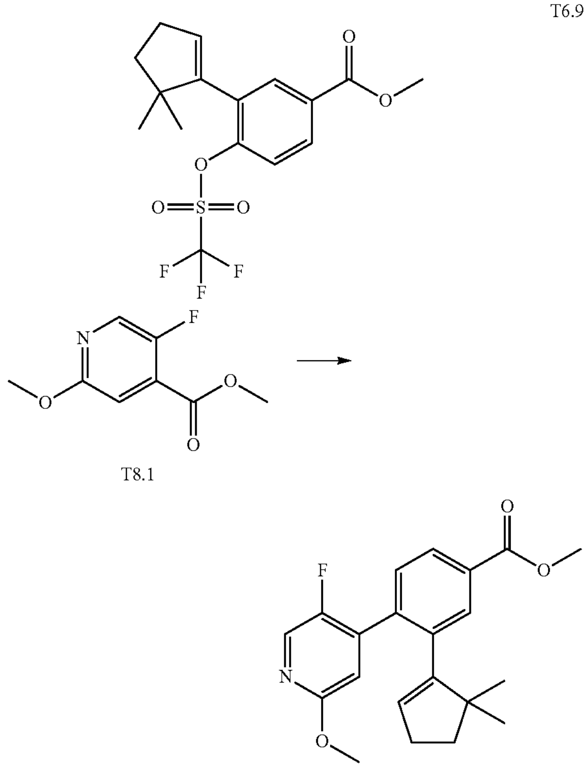

T8.1

T8.2

Methyl 3-(5,5-dimethylcyclopent-1-enyl)-4-(5-fluoro-2-methoxypyridin-4-yl)benzoate (T8.2)

To a flask with methyl 3-(5,5-dimethylcyclopent-1-enyl)-4-(trifluoromethylsulfonyloxy)benzoate T6.9 (404 mg, 1068 μmol) was added $Pd(PPh_3)_4$ (123 mg, 107 μmol), potassium carbonate (443 mg, 3203 μmol), 5-fluoro-2-methoxypyridin-4-ylboronic acid T8.1 (456 mg, 2669 μmol, commercially available from Asymchem). The mixture was then degassed, and DMF (3 mL) was added. The reaction was stirred overnight at 87° C. and worked up with EtOAc and water. Silica gel chromatography (0-50% EtOAc/Hexanes) afforded methyl 3-(5,5-dimethylcyclopent-1-enyl)-4-(5-fluoro-2-methoxypyridin-4-yl)benzoate T8.2 (295 mg. 78%).

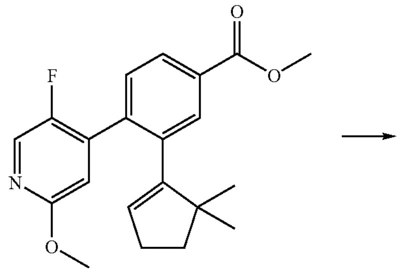

T8.2

-continued

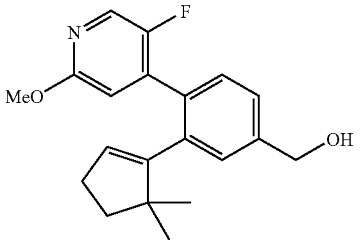

T8.3

(3-(5,5-Dimethylcyclopent-1-enyl)-4-(5-fluoro-2-methoxypyridin-4-yl)phenyl)methanol (T8.3)

To methyl 3-(5,5-dimethylcyclopent-1-enyl)-4-(5-fluoro-2-methoxypyridin-4-yl)benzoate T8.2 (295 mg, 830 μmol) was added THF. The mixture was cooled to 0° C., and LAH (1660 μL, 1660 μmol) was added dropwise. The reaction was stirred at room temperature for 1 hour, and was quenched with water and a small amount of Rochelle's salt solution. Purification with silica gel chromatography afforded (3-(5,5-dimethylcyclopent-1-enyl)-4-(5-fluoro-2-methoxypyridin-4-yl)phenyl)methanol T8.3 (201 mg) as an oil (74%).

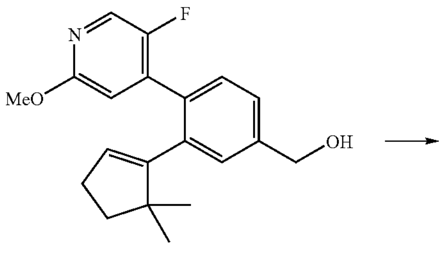

T8.3

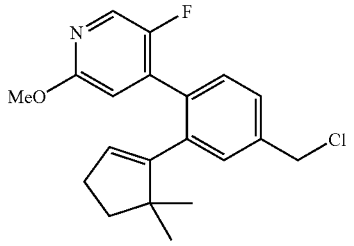

T8

4-(4-(Chloromethyl)-2-(5,5-dimethylcyclopent-1-enyl)phenyl)-5-fluoro-2-methoxypyridine (T8)

To (3-(5,5-dimethylcyclopent-1-enyl)-4-(5-fluoro-2-methoxypyridin-4-yl)phenyl)methanol T8.3 (34.5 mg, 105 μmol) was added DCM (1.1 mL) and DMF (8.2 μL, 105 μmol) followed by thionyl chloride (15 μL, 211 μmol) in an ice bath. The reaction was then stirred at room temperature for 1 hour. The reaction was concentrated and directly purified on silica gel to afford 4-(4-(chloromethyl)-2-(5,5-dimethylcyclopent-1-enyl)phenyl)-5-fluoro-2-methoxypyridine T8 (36 mg) as an oil (99%).

Examples T9A and T9B

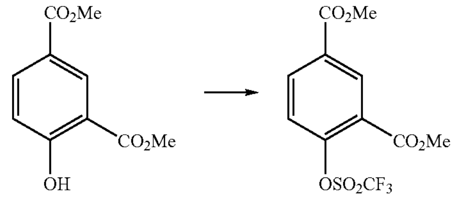

T9.1 T9.2

Dimethyl 4-(trifluoromethylsulfonyloxy)isophthalate (T9.2)

To a stirred solution of dimethyl 4-hydroxyisophthalate T9.1 (commercially available from Chem Service) (37.7 g, 179 mmol) in DCM (256 mL, 179 mmol) at 23° C. was added TEA (30 mL, 215 mmol), and a catalytic amount of DMAP. N-phenyltriflamide (70 g, 197 mmol) was then added, and stirring was continued at room temperature for 21 hours. The solvent was removed, and the residue was purified on silica gel (0-10% EtOAc in hexanes) to yield T9.2 dimethyl 4-(trifluoromethylsulfonyloxy)isophthalate as a colorless oil (59.00 g, 96% yield). MS ESI (pos.) m/e: 360.0 $(M+H_2O)^+$, 343.0 $(M+H)^+$.

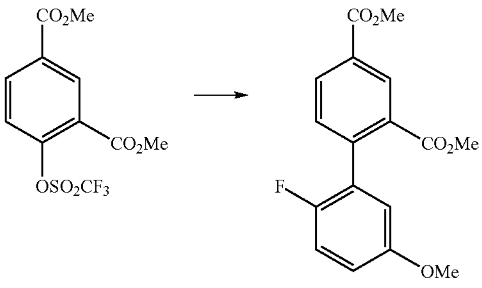

T9.2 T9.3

Dimethyl 2'-fluoro-5'-(methyloxy)-1,1'-biphenyl-2,4-dicarboxylate (T9.3)

To a stirred solution of dimethyl 4-(trifluoromethylsulfonyloxy)isophthalate T9.2 (39.00 g, 114 mmol) in DMF (228 mL, 114 mmol) at 23° C. was added 2-fluoro-5-methoxyphenylboronic acid (29 g, 171 mmol) (commercially available from Aldrich), potassium carbonate (47 g, 342 mmol), followed by tetrakis(triphenylphosphine)palladium (9.2 g, 8.0 mmol). The mixture was heated to 90° C. and stirring was continued for 18 hours. The reaction was cooled to room temperature. Water was added to the reaction, and the resulting mixture was extracted with EtOAc. The organic layer was dried over $MgSO_4$ and concentrated. The residue was purified by silica gel flash chromatography (0-20% EtOAc/hexane) to afford dimethyl 2'-fluoro-5'-(methyloxy)-1,1'-biphenyl-2,4-dicarboxylate T9.3 as a clear oil (32.00 g, 88% yield). MS ESI (pos.) m/e: 319.1 $(M+H)^+$.

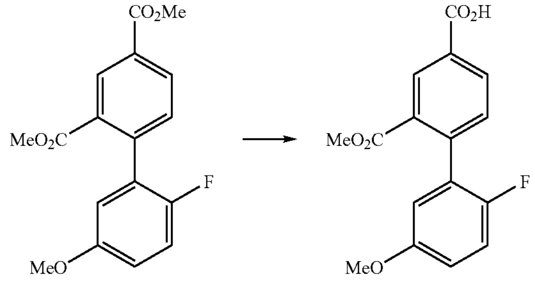

T9.3 T9.4

2'-Fluoro-5'-(methyloxy)-2-((methyloxy)carbonyl)-1,1'-biphenyl-4-carboxylic acid (T9.4)

To a stirred solution of T9.3 (36.50 g, 115 mmol) in THF (70.0 mL, 854 mmol) and MeOH (70.0 mL, 1730 mmol) at 0° C. was added potassium hydroxide (63 mL, 126 mmol) slowly to maintain the temperature below 6° C. The reaction mixture was allowed to warm to room temperature and stirring was continued for 15 hours. The reaction mixture was concentrated in vacuo. 1N HCl was added to the aqueous phase and the resulting mixture was extracted with EtOAc. The organic layer was dried over $MgSO_4$, and concentrated in vacuo to give 2'-fluoro-5'-(methyloxy)-2-((methyloxy)carbonyl)-1,1'-biphenyl-4-carboxylic acid T9.4 as a white solid (35.00 g, 100% yield). MS ESI (pos.) m/e: 322.1 $(M+H_2O)^+$, 305.0 $(M+H)^+$.

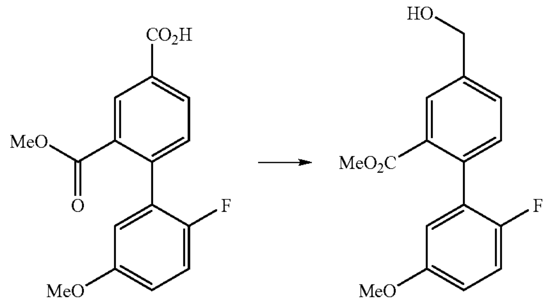

T9.4 T9.5

Methyl 2'-fluoro-4-(hydroxymethyl)-5'-(methyloxy)-1,1'-biphenyl-2-carboxylate (T9.5)

To a stirred solution of 2'-fluoro-5'-(methyloxy)-2-((methyloxy)carbonyl)-1,1'-biphenyl-4-carboxylic acid T9.4 (35.60 g, 117 mmol) in THF (1170 mL, 117 mmol) at 0° C. was added borane-THF (234 mL, 234 mmol). The reaction was warmed to 23° C. and stirring was continued for 6 hours. The mixture was then concentrated in vacuo. 1 N HCl was added to the reaction, and the mixture was extracted with EtOAc. The combined organic layers were dried over $MgSO_4$, filtered and concentrated in vacuo. The residue was purified on silica gel (0-40% EtOAc in hexane) to give methyl 2'-fluoro-4-(hydroxymethyl)-5'-(methyloxy)-1,1'-biphenyl-2-carboxylate T9.5 as a clear oil (30.00 g, 88% yield). MS ESI (pos.) m/e: 308.0 $(M+H_2O)^+$, 291.1 $(M+H)^+$.

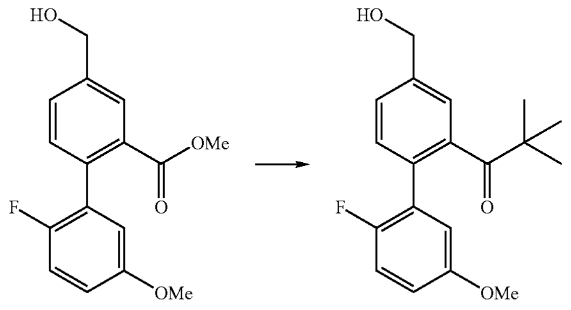

T9.5 T9.6

1-(2'-Fluoro-4-(hydroxymethyl)-5'-(methyloxy)-1,1'-biphenyl-2-yl)-2,2-dimethyl-1-propanone (T9.6)

To a stirred solution of methyl 2'-fluoro-4-(hydroxymethyl)-5'-(methyloxy)-1,1'-biphenyl-2-carboxylate T9.5 (2.00 g, 7 mmol) in THF (138 mL, 7 mmol) at −78° C. was added t-butyllithium (1.7 M in pentane, 9 mL, 14 mmol). Stirring was continued for 3 hours. A saturated solution of ammonium chloride was added to quench the reaction, and the resulting mixture was extracted with EtOAc. The combined organic layers were dried over $MgSO_4$, filtered, and concentrated in vacuo to give the residue. The residue was purified by silica gel flash chromatography (0-20% EtOAc/hexane) to afford 1-(2'-Fluoro-4-(hydroxymethyl)-5'-(methyloxy)-1,1'-biphenyl-2-yl)-2,2-dimethyl-1-propanone T9.6 as a clear oil (2.00 g, 92% yield). MS ESI (pos.) m/e: 334.1 $(M+H_2O)^+$, 317.2 $(M+H)^+$.

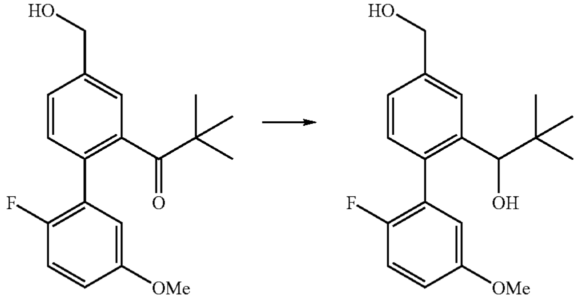

T9.6 T9.7

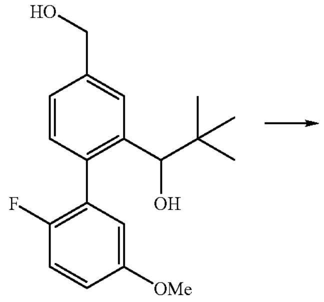

T9.7

-continued

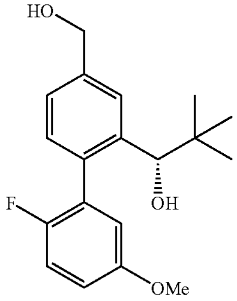

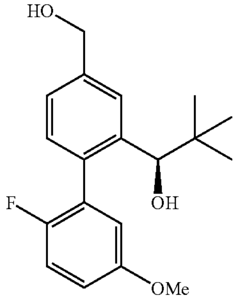

T9.8 and T9.9

1-(2'-Fluoro-4-(hydroxymethyl)-5'-(methyloxy)-1,1'-biphenyl-2-yl)-2,2-dimethyl-1-propanol (T9.7), and (1R)-1-(2'-fluoro-4-(hydroxymethyl)-5'-(methyloxy)-1,1'-biphenyl-2-yl)-2,2-dimethyl-1-propanol and (1S)-1-(2'-fluoro-4-(hydroxymethyl)-5'-(methyloxy)-1,1'-biphenyl-2-yl)-2,2-dimethyl-1-propanol (T9.8 and T9.9)

To a stirred solution of 1-(2'-fluoro-4-(hydroxymethyl)-5'-(methyloxy)-1,1'-biphenyl-2-yl)-2,2-dimethyl-1-propanone T9.6 (2.00 g, 6.3 mmol) in THF (63 mL, 6.3 mmol) at 0° C. was added LAH (1.0 M in THF, 13 mL, 13 mmol). Stirring was continued for 2 hours. 1N NaOH (aq) was added to the mixture, and the resulting mixture was extracted with EtOAc. The combined organic layers were dried over $MgSO_4$, filtered, and concentrated in vacuo to give the residue. The residue was purified by silica gel flash chromatography (0-30% EtOAc/hexane) to afford 1-(2'-fluoro-4-(hydroxymethyl)-5'-(methyloxy)-1,1'-biphenyl-2-yl)-2,2-dimethyl-1-propanol T9.7 (1.50 g, 75% yield) as a white solid. MS ESI (pos.) m/e: 336.2 $(M+H_2O)^+$. Chiral separation of T9.7 was accomplished on Chiracel-OD (4% IPA in hexane) to provide T9.8 and T9.9. Analytical column (Chiracel-OD (4% IPA in hexane, 45 min run) peak 1—18.5 mins, peak 2—24.5 mins).[1]

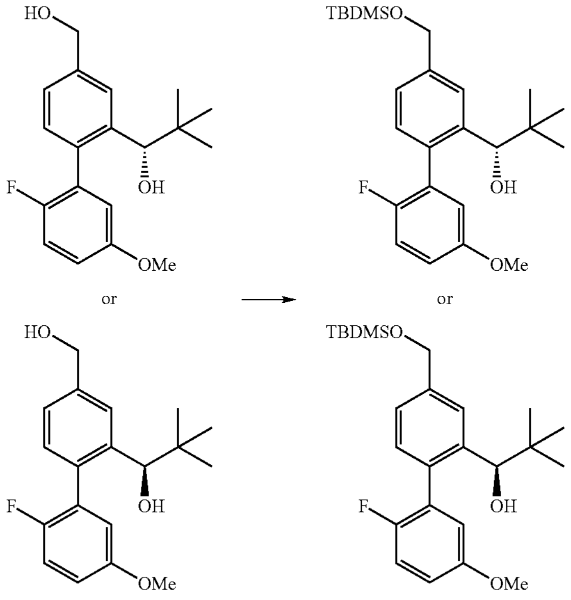

or → or

T9.8 or T9.9 T9.10 or T9.11

(1S)-1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanol or (1R)-1-(4-((((1,1-dimethylethyl)(dimethyl)silyl)oxy)methyl)-2'-fluoro-5'-(methyloxy)-1,1'-biphenyl-2-yl)-2,2-dimethyl-1-propanol (T9.10 or T9.11)

To a stirred solution of (1R)-1-(2'-fluoro-4-(hydroxymethyl)-5'-(methyloxy)-1,1'-biphenyl-2-yl)-2,2-dimethyl-1-propanol or (1S)-1-(2'-fluoro-4-(hydroxymethyl)-5'-(methyloxy)-1,1'-biphenyl-2-yl)-2,2-dimethyl-1-propanol (T9.8 or T9.9) (0.300 g, 0.9 mmol) in DCM (10.00 mL, 155 mmol) at 23° C. was added tert-butyldimethylsilyl chloride (0.2 mL, 1 mmol), followed by TEA (0.2 mL, 1 mmol) and DMAP (0.01 g, 0.09 mmol). Stirring was continued for 16 hours. The mixture was then concentrated in vacuo to give the residue. The residue was purified by silica gel flash chromatography (0-10% EtOAc/hexane) to afford (1S)-1-(4-((((1,1-dimethylethyl)(dimethyl)silyl)oxy)methyl)-2'-fluoro-5'-(methyloxy)-1,1'-biphenyl-2-yl)-2,2-dimethyl-1-propanol or (1R)-1-(4-((((1,1-dimethylethyl)(dimethyl)silyl)oxy)methyl)-2'-fluoro-5'-(methyloxy)-1,1'-biphenyl-2-yl)-2,2-dimethyl-1-propanol T9.10 or T9.11 (0.375 g, 92% yield). MS ESI (pos.) m/e: 450.2 $(M+H_2O)^+$.

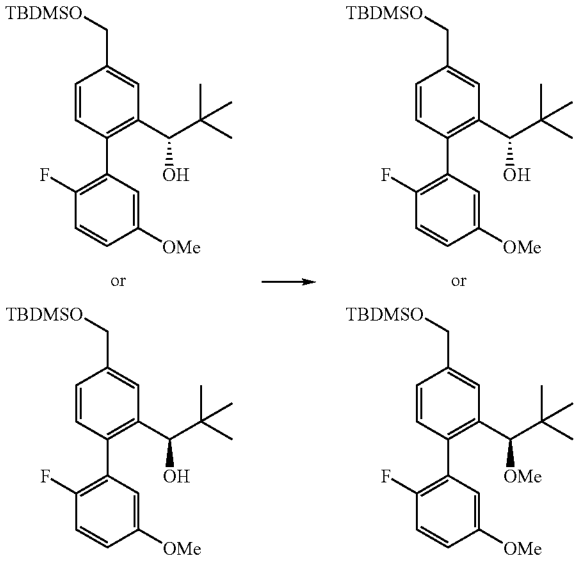

or → or

T9.10 or T9.11 T9.12 or T9.13

(1,1-Dimethylethyl)(((2-((1S)-2,2-dimethyl-1-(methyloxy)propyl)-2'-fluoro-5'-(methyloxy)-1,1'-biphenyl-4-yl)methyl)oxy)dimethylsilane or (1,1-dimethylethyl)(((2-((1R)-2,2-dimethyl-1-(methyloxy)propyl)-2'-fluoro-5'-(methyloxy)-1,1'-biphenyl-4-yl)methyl)oxy)dimethylsilane (T9.12 or T9.13)

To a stirred solution of T9.10 or T9.11 (0.110 g, 0.25 mmol) in DMF (2.00 mL, 26 mmol) at 23° C. was added iodomethane (0.069 g, 0.50 mmol), followed by sodium hydride (0.012 g, 0.50 mmol). Stirring was continued at 50° C. for 21 hours. Water was added to the mixture, and the resulting mixture was extracted with EtOAc. The combined organic layers were dried over $MgSO_4$, filtered, and concentrated in vacuo to give the residue. The residue was purified by silica gel flash chromatography (0-5% EtOAc/hexane) to afford T9.12 or T9.13 (0.051 g, 45% yield).

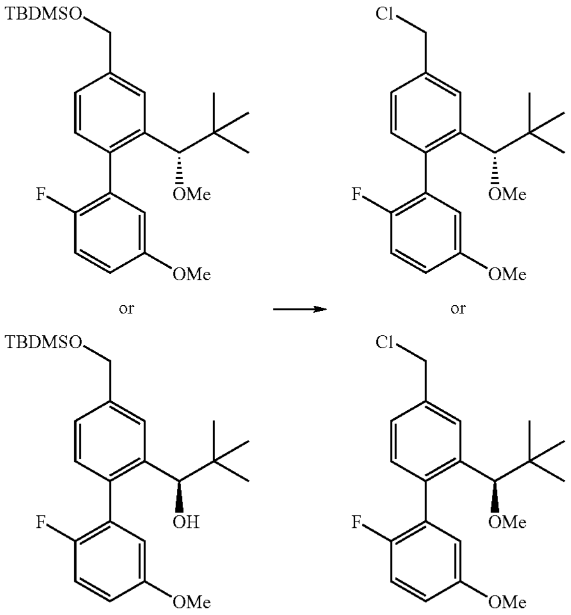

or → or

T9.12 to T9.13 T9A to T9B 4-(Chloromethyl)-2-((1S)-2,2-dimethyl-1-(methyloxy)propyl)-2'-fluoro-5'-(methyloxy)-1,1'-biphenyl or 4-(chloromethyl)-2-((1R)-2,2-dimethyl-1-(methyloxy)propyl)-2'-fluoro-5'-(methyloxy)-1,1'-biphenyl (T9A or T9B)

To a stirred solution of T9.12 or 6 T9.13 (0.082 g, 0.18 mmol) in DCM (2.00 mL, 31 mmol) at 23° C. was added DMF (0.0014 mL, 0.018 mmol) followed by thionyl chloride (0.027 mL, 0.37 mmol). Stirring was continued for one hour. The reaction mixture was then concentrated in vacuo. The residue was purified by silica gel flash chromatography (0-5% EtOAc/hexane) to afford T9A or T9B (0.063 g, 98% yield).

Asymmetric Synthesis of T9.8 or T9.9

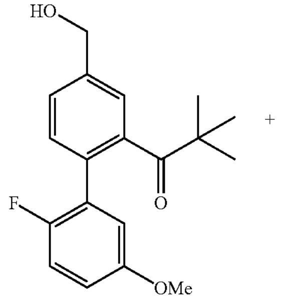

T9.6

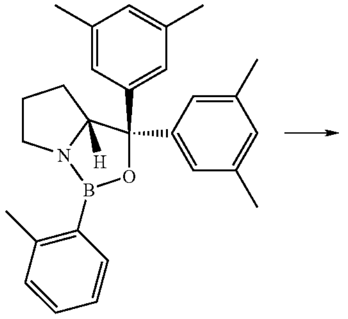

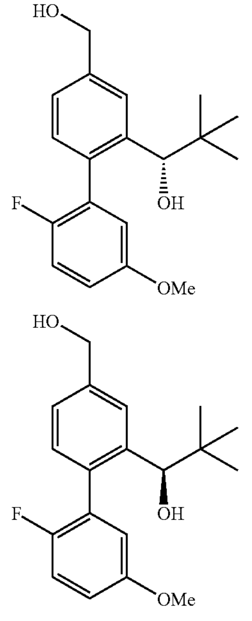

T9.8 and T9.9

(1R)-1-(2'-Fluoro-4-(hydroxymethyl)-5'-(methyloxy)-1,1'-biphenyl-2-yl)-2,2-dimethyl-1-propanol and (1S)-1-(2'-fluoro-4-(hydroxymethyl)-5'-(methyloxy)-1,1'-biphenyl-2-yl)-2,2-dimethyl-1-propanol (T9.8 and T9.9)

To a stirred solution of T9.6 (0.050 g, 0.2 mmol) in THF (2 mL, 0.2 mmol) at 0° C. was added (R)-3,3-bis(3,5-dimethylphenyl)-1-o-tolyl-hexahydropyrrolo[1,2-c][1,3,2]oxazaborole in toluene (0.02 mL, 0.02 mmol, 1.0M, commercially available from Aldrich), followed by dropwise addition of borane in THF (0.2 mL, 0.2 mmol). The reaction was then stirred at 23° C. for 4 hours. The reaction was then quenched with 1N HCl (aq). The reaction mixture was extracted with EtOAc, dried over $MgSO_4$, filtered, and concentrated in vacuo. The residue was purified on silica gel (0%-20% EtOAc/hexane) to yield T9.8 and T9.9 (0.045 g, 89% yield). Chiral HPLC determined that the major product was the desired more potent enantiomer with an enantiomeric excess of 85%.

Example T10

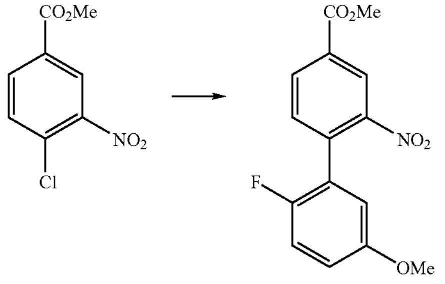

T10.1 T10.2

Methyl 2'-fluoro-5'-(methyloxy)-2-nitro-1,1'-biphenyl-4-carboxylate (T10.2)

To a stirred solution of methyl 4-chloro-3-nitrobenzoate T10.1 (10.00 g, 46 mmol) (commercially available from Aldrich) in DMF (15.00 mL, 194 mmol) at 23° C. was added 2-fluoro-5-methoxyphenylboronic acid (12 g, 70 mmol) (commercially available from Aldrich), and potassium carbonate (19 g, 139 mmol). Tetrakis(triphenylphosphine)palladium (2.1 g, 1.9 mmol) was then added to the mixture, and the mixture was heated at 90° C. for 18 hours. The mixture was then cooled to room temperature, diluted with brine and extracted three times with EtOAc. After drying over anhydrous magnesium sulfate and filtering, the organic solvent was removed under reduced pressure and the product was purified on silica gel (0-40% EtOAc in hexanes) to yield T10.2 as a colorless oil (14.00 g, 99% yield).

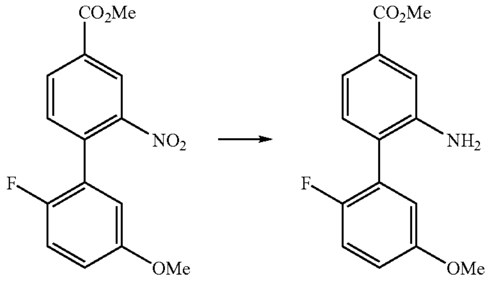

T10.2 T10.3

Methyl 2-amino-2'-fluoro-5'-(methyloxy)-1,1'-biphenyl-4-carboxylate (T10.3)

To a stirred solution of T10.2 (1.00 g, 3.3 mmol) in acetic acid (2.00 mL, 35 mmol) at 23° C. was added DME (15.00 mL, 144 mmol), EtOH (10.00 mL), followed by tin(II) chloride (4.7 g, 25 mmol). The mixture was heated at 60° C. for 17 hours. After which, the reaction was cooled to room temperature. The reaction was diluted with water and extracted three times with EtOAc. After drying over anhydrous magnesium sulfate and filtering, the organic solvent was removed under reduced pressure to give the product T10.3 (0.90 g, 100% yield).

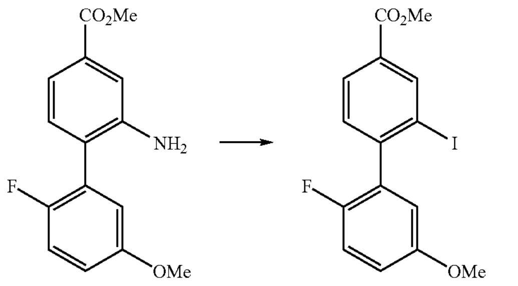

T10.3 T10.4

Methyl 2'-fluoro-2-iodo-5'-(methyloxy)-1,1'-biphenyl-4-carboxylate (T10.4)

To a stirred solution of T10.3 (1.00 g, 3.6 mmol) in DME (10.00 mL, 96 mmol) at 23° C. was added sulfuric acid (0.19 mL, 3.6 mmol) in water (8 mL), followed by dropwise addition of a solution of sodium nitrite (0.38 g, 5.4 mmol) in water (2 mL) at 0° C. over 30 minutes. The reaction was then stirred for 20 minutes. To the mixture was added a solution of sodium iodide (3.0 g, 20 mmol) in water (7 mL) at 0° C. The resulting mixture was then stirred for 1 hour. The reaction was quenched with sodium thiosulfate and extracted three times with diethyl ether. After drying over anhydrous magnesium sulfate and filtering, the organic solvent was removed under reduced pressure and the product was purified on silica gel (0-40% EtOAc in hexanes) to yield a colorless solid T10.4 (0.820 g, 58% yield).

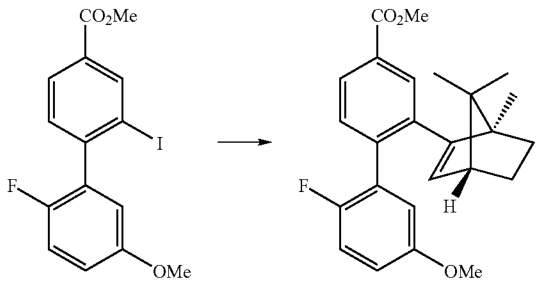

T10.4 T10.5

Methyl 2'-fluoro-5'-(methyloxy)-2-((1R,4R)-1,7,7-trimethylbicyclo[2.2.1]hept-2-en-2-yl)-1,1'-biphenyl-4-carboxylate (T10.5)

To a stirred solution of T10.4 (0.200 g, 0.52 mmol) in DMF (4.00 mL, 52 mmol) at 23° C. was added (1S,4R)-1,7,7-trimethylbicyclo[2.2.1]hept-2-en-2-ylboronic acid (0.19 g, 1.0 mmol, commercially available from Combi-Blocks, Cat. No. BB-2567), potassium carbonate (0.21 g, 1.6 mmol), and then tetrakis(triphenylphosphine)palladium (0.060 g, 0.052 mmol). The mixture was heated at 90° C. for 19 hours and then cooled to room temperature. The reaction was diluted with brine and extracted three times with EtOAc. After drying over anhydrous magnesium sulfate and filtering, the organic solvent was removed under reduced pressure and the product was purified on silica gel (0-10% EtOAc in hexanes) to yield T10.5 as a colorless oil (0.165 g, 81% yield).

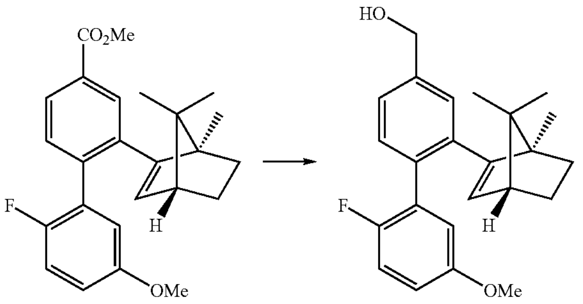

T10.5 T10.6

(2'-Fluoro-5'-(methyloxy)-2-((1R,4R)-1,7,7-trimethylbicyclo[2.2.1]hept-2-en-2-yl)-1,1'-biphenyl-4-yl)methanol (T10.6)

To a stirred solution of T10.5 (0.050 g, 0.1 mmol) in THF (4 mL) at 0° C. was added LAH in THF (0.3 mL, 0.3 mmol, 1.0M). The resulting mixture was stirred for 2 hours. 1N NaOH(aq) was added to the mixture to quench it. The reaction was then extracted three times with EtOAc. After drying over anhydrous magnesium sulfate and filtering, the organic solvent was removed under reduced pressure and the product was purified on silica gel (0-20% EtOAc in hexanes) to yield T10.6 as a colorless oil (0.035 g, 75% yield).

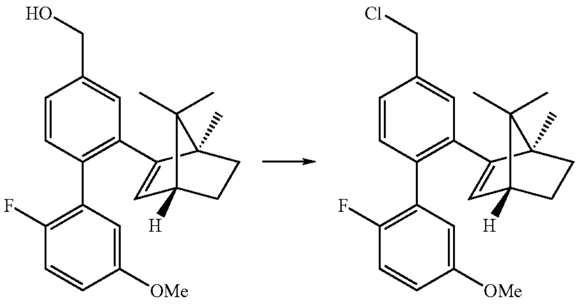

T10.6 T10

4'-(Chloromethyl)-6-fluoro-2'-((1R,4R)-1,7,7-trimethylbicyclo[2.2.1]hept-2-en-2-yl)-1,1'-biphenyl-3-yl methyl ether (T10)

To a stirred solution of T10.6 (0.035 g, 0.10 mmol) in DCM (2.00 mL) and DMF (0.01 mL) at 0° C. was added thionyl chloride (0.01 g, 0.10 mmol). The reaction was then stirred at room temperature for 2 hours and was then concentrated in vacuo. The resulting product was then purified on silica gel (0-10% EtOAc in hexanes) to yield T10 as a colorless oil (0.035 g, 95% yield).

Example T11

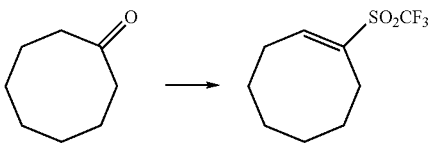

T11.1 T11.2

1-Cycloocten-1-yl trifluoromethyl sulfone (T11.2)

To a stirred solution of cyclooctanone (T11.1) (5.00 g, 40 mmol) (commercially available from Aldrich) in THF (35 mL) at −78° C. was added LDA (22 mL, 44 mmol, 2.0M). The resulting solution was stirred at −78° C. for 20 minutes. Then, a solution of N-phenyl-bis(trifluoromethane sulfonimide) (16 g, 44 mmol) in THF (15 mL) was added slowly at −78° C. The reaction mixture was allowed to warm to 23° C. over 3 hours and then was concentrated in vacuo. The residue was diluted with water and extracted three times with hexanes. After drying over anhydrous magnesium sulfate and filtering, the organic solvent was removed under reduced pressure and the product was then purified on silica gel (0-5% EtOAc in hexanes) to yield T11.2 as a colorless oil (10.00 g, 98% yield).

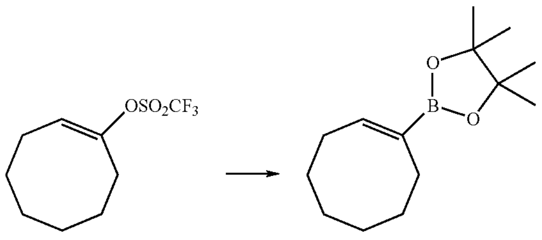

T11.2 T11.3

2-(1-Cycloocten-1-yl)-4,4,5,5-tetramethyl-1,3,2-dioxaborolane (T11.3)

A mixture of triphenylphosphine (1 g, 4 mmol), potassium phenolate (7 g, 54 mmol), 4,4,5,5-tetramethyl-2-(4,4,5,5-tetramethyl-1,3,2-dioxaborolan-2-yl)-1,3,2-dioxaborolane (10 g, 39 mmol) and T11.2 (10.00 g, 39 mmol) in toluene (194 mL) was degassed with nitrogen. Then, dichlorobis(triphenylphosphine)palladium(II) (1 g, 2 mmol) was added and the mixture was further degassed with nitrogen. The reaction mixture was stirred at 50° C. for 3.5 hours. The reaction mixture was diluted with water and extracted three times with EtOAc. After drying over anhydrous magnesium sulfate and filtering, the organic solvent was removed under reduced pressure and the product was then purified on silica gel (0-5% EtOAc in hexanes) to yield T11.3 as a colorless oil (7.00 g, 77% yield).

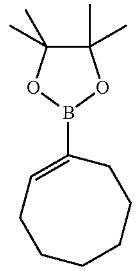

T11.3

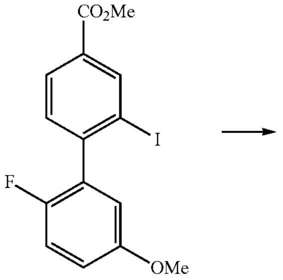

T10.4

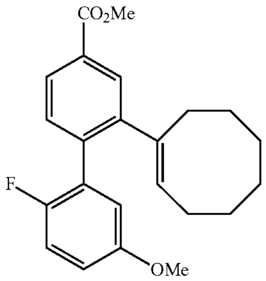

T11.4

Methyl 2-(1-cycloocten-1-yl)-2'-fluoro-5'-(methyloxy)-1,1'-biphenyl-4-carboxylate (T11.4)

To a stirred solution of T10.4 (0.750 g, 1.9 mmol) in DMF (4.00 mL, 52 mmol) at 23° C. was added (Z)-2-cyclooctenyl-4,4,5,5-tetramethyl-1,3,2-dioxaborolane T11.3 (0.92 g, 3.9 mmol), potassium carbonate (0.81 g, 5.8 mmol), and then tetrakis(triphenylphosphine)palladium (0.22 g, 0.19 mmol). The mixture was heated at 90° C. for 19 hours and then cooled to room temperature. The reaction was diluted with brine and extracted three times with EtOAc. After drying over anhydrous magnesium sulfate and filtering, the organic solvent was removed under reduced pressure and the product was purified on silica gel (0-10% EtOAc in hexanes) to yield T11.4 as a colorless oil (0.35 g, 49% yield).

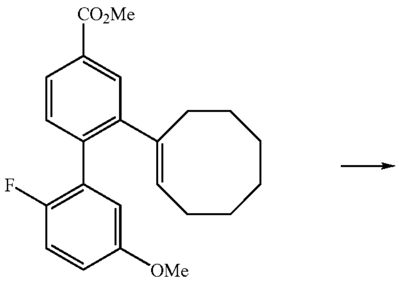

T11.4

-continued

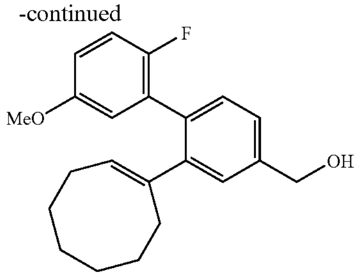

T11.5

(2-(1-Cycloocten-1-yl)-2'-fluoro-5'-(methyloxy)-1,1'-biphenyl-4-yl)methanol (T11.5)

To a stirred solution of T11.4 (0.350 g, 0.9 mmol) in THF (9 mL, 0.9 mmol) at 0° C. was added LAH in THF (2 mL, 2 mmol, 1.0M). The reaction was stirred for 1 hour. 1N NaOH (aq) was then added to quench the reaction. The reaction was extracted three times with EtOAc. After drying over anhydrous magnesium sulfate and filtering, the organic solvent was removed under reduced pressure and the product was then purified on silica gel (0-20% EtOAc in hexanes) to yield T11.5 as a colorless oil (0.387 g, 120% yield).

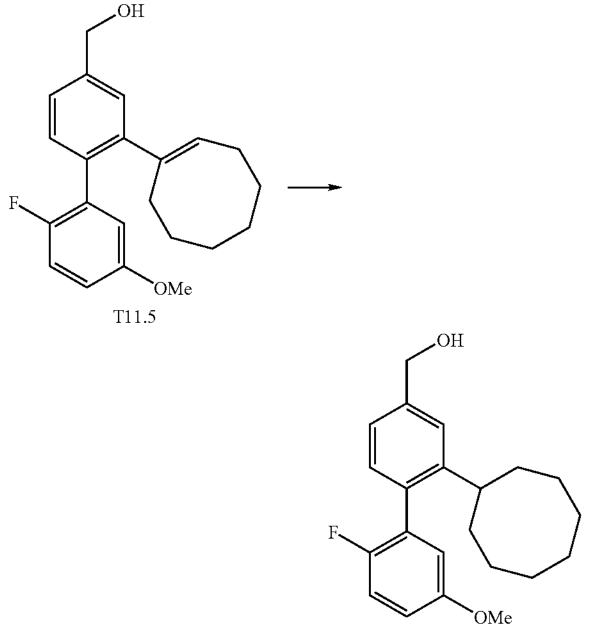

T11.5

T11.6

(2-Cyclooctyl-2'-fluoro-5'-(methyloxy)-1,1'-biphenyl-4-yl)methanol (T11.6)

To a stirred solution of T11.5 (0.387 g, 1 mmol) in EtOAc (11 mL) at 23° C. was added palladium on carbon (0.1 g, 1 mmol). The reaction was placed under an atmosphere of hydrogen and stirred for 2 hours. The reaction mixture was then filtered and concentrated in vacuo. The residue was purified on silica gel (0-20% EtOAc in hexanes) to yield T11.6 as a colorless oil (0.13 g, 33% yield).

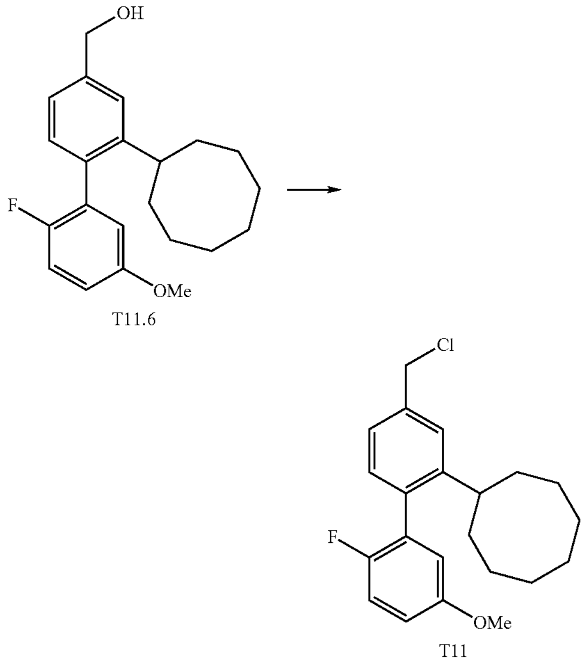

T11.6

T11

4-(Chloromethyl)-2'-fluoro-5'-(methyloxy)-2-cyclooctyl-1,1'-biphenyl (T11)

To a stirred solution of T11.6 (0.130 g, 0.4 mmol) in DCM (2.00 mL) and DMF (0.03 mL) at 0° C. was added thionyl chloride (0.06 mL, 0.8 mmol). The reaction was stirred at room temperature for 2 hours. After which, the reaction was concentrated in vacuo and the product was then purified on silica gel (0-10% EtOAc in hexanes) to yield T11 as a colorless oil (0.130 g, 95% yield).

Example T12A and T12B

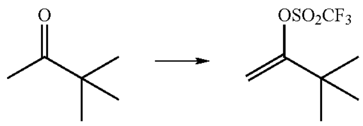

T12.1

Synthesis of T12.1

To a solution of 3,3-dimethylbutan-2-one (5.00 g, 50 mmol, commercially available from Aldrich) in THF (71 mL) at −78° C. was added dropwise a solution of LDA (28 mL, 56 mmol). The resulting solution was stirred at −78° C. for 20 minutes. A solution of N-phenyl-bis(trifluoromethane sulfonimide) (20 g, 55 mmol) in THF (15 mL) was then added slowly at −78° C. The reaction mixture was allowed to room temperature over 3 hours. The reaction was concentrated in vacuo. The reaction was then diluted with water and extracted three times with EtOAc. After drying over anhydrous magnesium sulfate and filtering, the organic solvent was removed under reduced pressure and the product was purified on silica gel (0-5% EtOAc in hexanes) to yield T12.1 as a colorless oil (10.00 g, 86% yield)

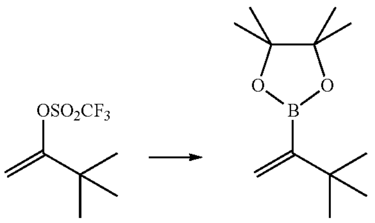

T12.1 T12.2

Synthesis of T12.2

A mixture of triphenylphosphine (0.90 g, 3.4 mmol), potassium phenolate (6.4 g, 48 mmol), 4,4,5,5-tetramethyl-2-(4,4,5,5-tetramethyl-1,3,2-dioxaborolan-2-yl)-1,3,2-dioxaborolane (8.7 g, 34 mmol) and T12.1 (8.00 g, 34 mmol) in toluene (172 mL) was degassed by $N_2$. Then dichlorobis(triphenylphosphine)palladium(II) (1.2 g, 1.7 mmol) was added, and the reaction mixture was further degassed with $N_2$. The reaction was then stirred at 50° C. for 3.5 hours. The reaction was then filtered and concentrated in vacuo. The product was purified on silica gel (0-5% EtOAc in hexanes) to yield T12.2 as a colorless oil (5.0 g, 69% yield).

T12.2

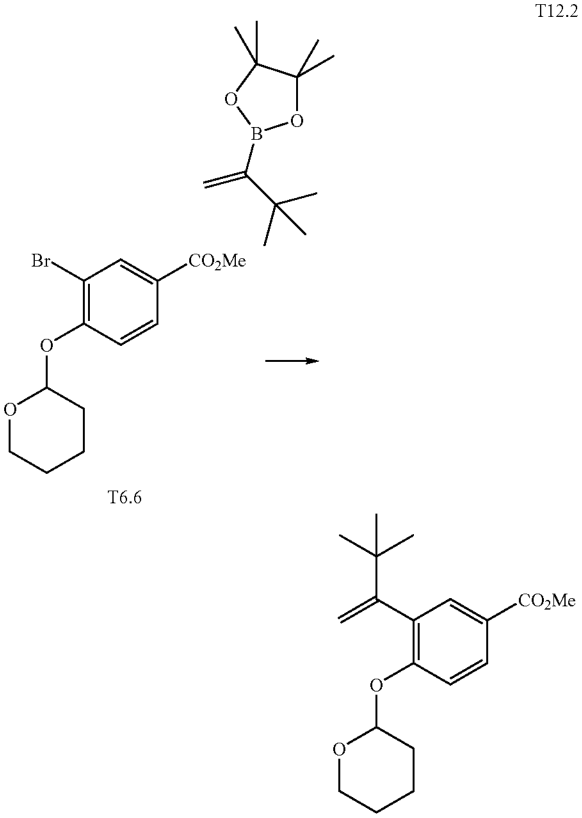

T6.6

T12.3

Methyl 3-(1-(1,1-dimethylethyl)ethenyl)-4-(tetrahydro-2H-pyran-2-yloxy)benzoate (T12.3)

A stirred solution of methyl 3-bromo-4-(tetrahydro-2H-pyran-2-yloxy)benzoate T6.6 (2.50 g, 7.9 mmol), palladium acetate (0.18 g, 0.79 mmol), S-Phos (0.65 g, 1.6 mmol), tripotassium phosphate (1.6 mL, 20 mmol) in DMF (15.00 mL, 194 mmol) and water (0.600 mL, 33 mmol) was purged 3 times with nitrogen and placed under vacuum and the process repeated three times. Before heating, T12.2 (2.0 g, 9.5 mmol) was added, and the mixture was heated to 70° C. and stirred for 19 hours. The resulting mixture was then cooled to room temperature, diluted with water and extracted three times with EtOAc. After drying over anhydrous magnesium sulfate and filtering, the organic solvent was removed under reduced pressure and the product was then purified on silica gel (0-20% EtOAc in hexanes) to yield T12.3 as a colorless oil (2.50 g, 99% yield).

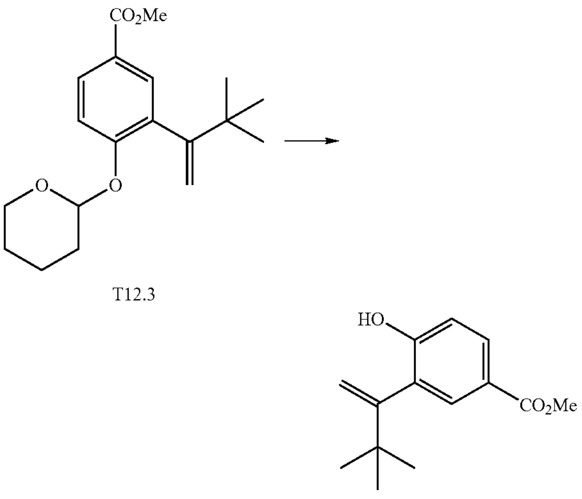

T12.3

T12.4

Methyl 3-(1-(1,1-dimethylethyl)ethenyl)-4-hydroxybenzoate (T12.4)

To a stirred solution of T12.3 (2.500 g, 7.85 mmol) in MeOH (10.00 mL, 7.85 mmol) at 23° C. was added PPTS (0.197 g, 0.785 mmol). The reaction was heated to 60° C. and stirred for 19 hours. The reaction was then concentrated in vacuo to give a clear oil. The product was then purified on silica gel (0-20% EtOAc in hexanes) to yield T12.4 as a colorless oil (1.50 g, 81.5% yield).

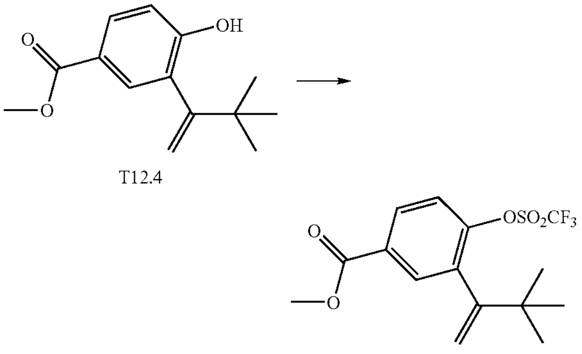

T12.4

T12.5

Methyl 3-(1-(1,1-dimethylethyl)ethenyl)-4-(((trifluoromethyl)sulfonyl)oxy)benzoate (T12.5)

To a stirred solution of T12.4 (0.500 g, 2 mmol) in DCM (11 mL) at 23° C. was added TEA (0.4 mL, 3 mmol), DMAP (catalytic), and then N-phenyltriflamide (0.8 g, 2 mmol). The reaction was further stirred for 19 hours and then concentrated in vacuo. The product was purified on silica gel (0-10% EtOAc in hexanes) to yield T12.5 as a colorless oil (0.1 g, 13% yield).

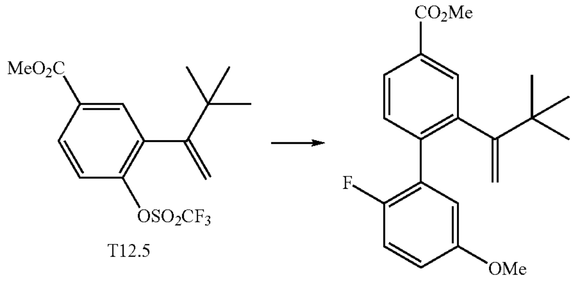

T12.5 T12.6

Methyl 2-(1-(1,1-dimethylethyl)ethenyl)-2'-fluoro-5'-(methyloxy)-1,1'-biphenyl-4-carboxylate (T12.6)

To a stirred solution of T12.5 (0.550 g, 1.5 mmol) in DMF (3.0 mL, 1.5 mmol) at 23° C. was added 2-fluoro-5-methoxyphenylboronic acid (0.38 g, 2.3 mmol) (commercially available from Aldrich), potassium carbonate (0.62 g, 4.5 mmol) and then tetrakis(triphenylphosphine)palladium (0.12 g, 0.11 mmol). The mixture was heated to 90° C. and stirred for 17 hours. The resulting mixture was then cooled to room temperature, diluted with water and extracted three times with EtOAc. After drying over anhydrous magnesium sulfate and filtering, the organic solvent was removed under reduced pressure and the product was then purified on silica gel (0-10% EtOAc in hexanes) to yield T12.6 as a colorless oil (0.100 g, 19% yield).

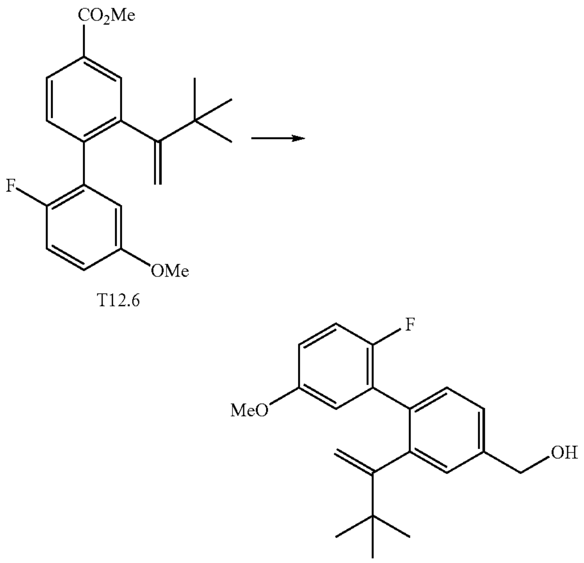

T12.6

T12.7

(2-(1-(1,1-Dimethylethyl)ethenyl)-2'-fluoro-5'-(methyloxy)-1,1'-biphenyl-4-yl)methanol (T12.7)

To a stirred solution of T12.6 (0.400 g, 1 mmol) in THF (6 mL) at 0° C. was added LAH in THF (2 mL, 2 mmol, 1.0M). The resulting mixture was stirred for 2 hours. 1N NaOH(aq) was then added to the mixture, and the resulting mixture was extracted three times with EtOAc. After drying over anhydrous magnesium sulfate and filtering, the organic solvent was removed under reduced pressure and the product was then purified on silica gel (0-20% EtOAc in hexanes) to yield T12.7 as a colorless oil (0.273 g, 74% yield).

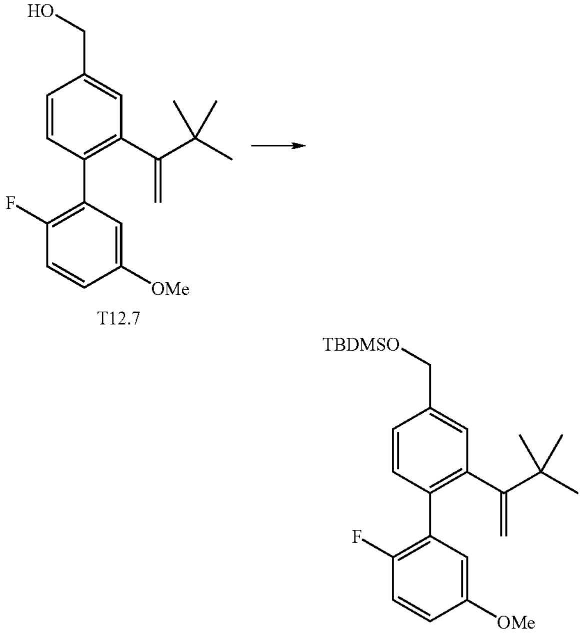

T12.7

T12.8

(1,1-Dimethylethyl)(((2-(1-(1,1-dimethylethyl)ethenyl)-2'-fluoro-5'-(methyloxy)-1,1'-biphenyl-4-yl)methyl)oxy)dimethylsilane (T12.8)

To a stirred solution of T12.7 (0.273 g, 0.9 mmol) in DCM (2.00 mL) at 23° C. was added tert-butyldimethylsilyl chloride (0.2 mL, 1 mmol), followed by TEA (0.1 mL, 1 mmol) and DMAP (0.01 g, 0.09 mmol). The resulting mixture was then stirred for 16 hours and then was concentrated in vacuo to give the product. The product was purified on silica gel (0-5% EtOAc in hexanes) to yield T12.8 as a colorless oil (0.374 g, 100% yield).

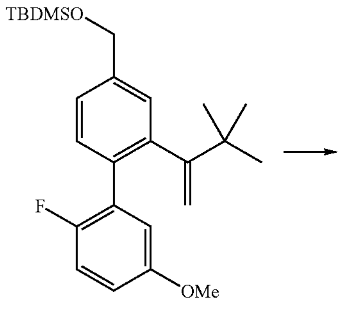

T12.8

-continued

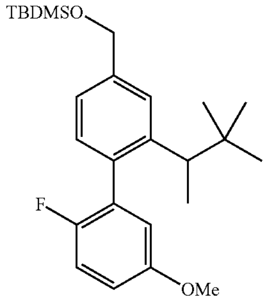

T12.9

(1,1-Dimethylethyl)(((2'-fluoro-5'-(methyloxy)-2-(1,2,2-trimethylpropyl)-1,1'-biphenyl-4-yl)methyl)oxy)dimethylsilane (T12.9)

To a stirred solution of T12.8 (0.400 g, 0.93 mmol) in EtOAc (2.00 mL) at 23° C. was added palladium on carbon (0.0099 g, 0.093 mmol). The resulting mixture was stirred under an atmosphere of hydrogen for 21 hours and then was filtered and concentrated in vacuo. The product was purified on silica gel (0-5% EtOAc in hexanes) to yield T12.9 as a colorless oil (0.400 g, 100% yield).

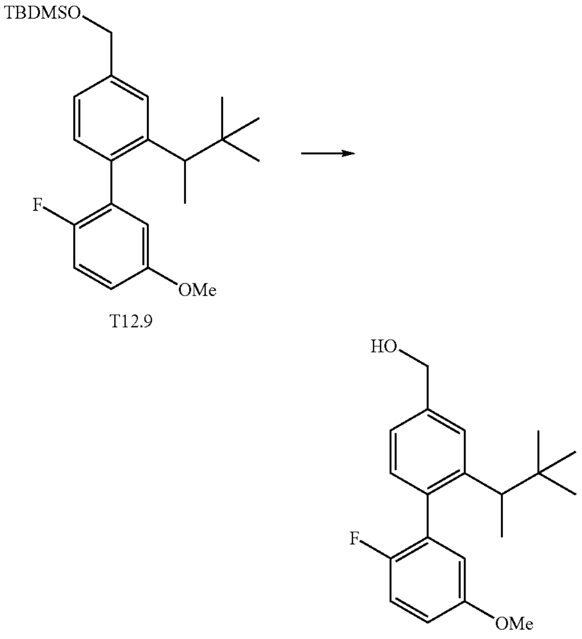

T12.9

T12.10

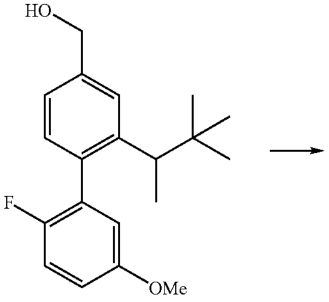

T12.10

-continued

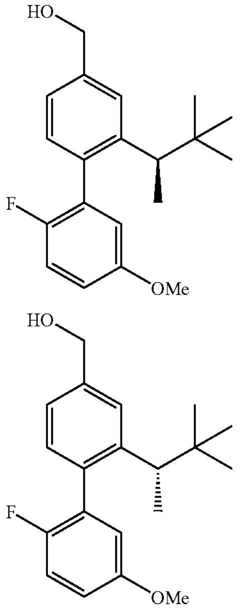

T12.11 and T12.12

(2'-Fluoro-5'-(methyloxy)-2-((1R)-1,2,2-trimethylpropyl)-1,1'-biphenyl-4-yl)methanol and (2'-fluoro-5'-(methyloxy)-2-((1S)-1,2,2-trimethylpropyl)-1,1'-biphenyl-4-yl)methanol (T12.11 and T12.12)

To a stirred solution of T12.9 (0.400 g, 0.929 mmol) in MeOH (10.00 mL, 0.929 mmol) at 23° C. was added PPTS (0.0233 g, 0.0929 mmol). The mixture was stirred for 19 hours and then was concentrated in vacuo to give a clear oil. The product was then purified on silica gel (0-20% EtOAc in hexanes) to yield T12.10 as a colorless oil (0.250 g, 85% yield). Chiral separation of T12.10 was accomplished on Chiracel-OD (3% IPA in hexane) to provide T12.11 (peak one) and T12.12 (peak two).[1]

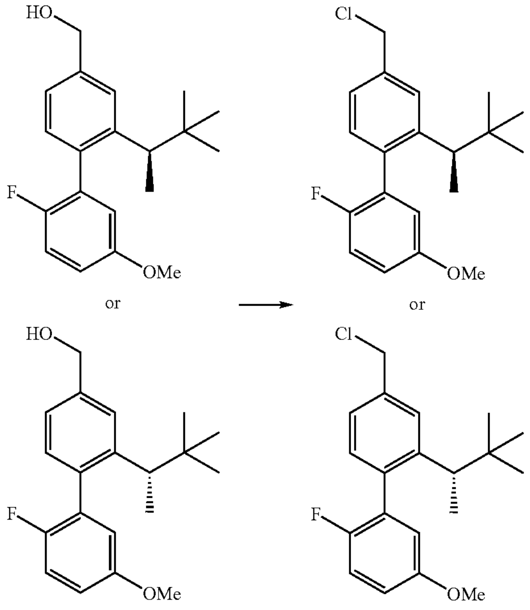

or or

T12.11 or T12.12

T12A or T12B 4-(Chloromethyl)-2'-fluoro-5'-(methyloxy)-2-((1R)-1,2,2-trimethylpropyl)-1,1'-biphenyl or 4-(chloromethyl)-2'-fluoro-5'-(methyloxy)-2-((1S)-1,2,2-trimethylpropyl)-1,1'-biphenyl (T12A or T12B)

To a stirred solution of T12.11 or T12.12 (0.050 g, 0.16 mmol) in DCM (2.00 mL) at 23° C. was added DMF (0.0012 mL) followed by thionyl chloride (0.023 mL, 0.32 mmol). The mixture was stirred for one hour and then was concentrated in vacuo. The resulting product was purified on silica gel (0-10% EtOAc in hexanes) to yield T12A or T12B as a colorless oil (0.050 g, 94% yield).

Example T13

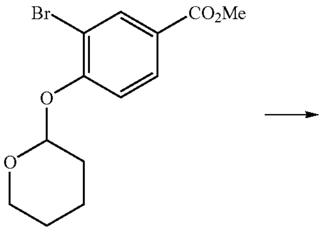

T6.6

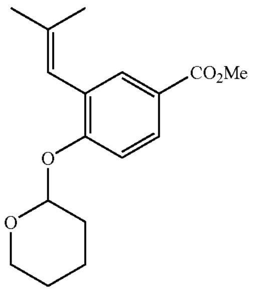

T13.1

Methyl 3-(2-methyl-1-propenyl)-4-(tetrahydro-2H-pyran-2-yloxy)benzoate (T13.1)

A mixture of methyl 3-bromo-4-(tetrahydro-2H-pyran-2-yloxy)benzoate T6.6 (0.500 g, 1.6 mmol), palladium acetate (0.036 g, 0.16 mmol), S-Phos (0.13 g, 0.32 mmol) and tripotassium phosphate (0.32 mL, 4.0 mmol) in DMF (10.00 mL, 129 mmol) and water (0.40 mL, 22 mmol) was stirred. The mixture was purged with nitrogen and placed under vacuum and the process repeated three times. Before heating, 2-methylprop-1-enylboronic acid (0.24 g, 2.4 mmol, commercially available from Synthonix, Cat. No. D3007G1) was added, and the mixture was heated to 70° C. and stirred for 23 hours. The mixture was then cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield T13.1 as a colorless oil (0.460 g, 100% yield).

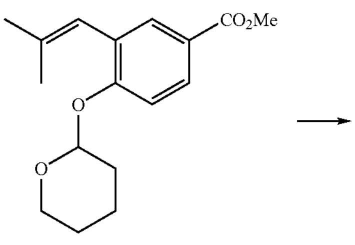

T13.1

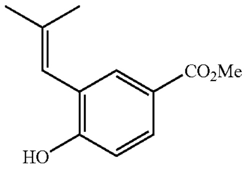

T13.2

Methyl 4-hydroxy-3-(2-methyl-1-propenyl)benzoate (T13.2)

To a stirred mixture of T13.1 (0.460 g, 2 mmol) in MeOH (8 mL) was added PPTS (0.04 g, 0.2 mmol). The reaction mixture was then stirred for 24 hours and then concentrated in vacuo. The residue was purified on silica gel (0-20% EtOAc in hexanes) to yield T13.2 as a colorless oil (0.320 g, 98% yield).

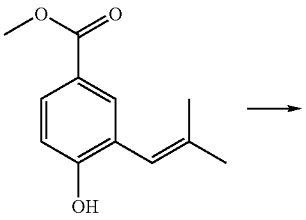

T13.2

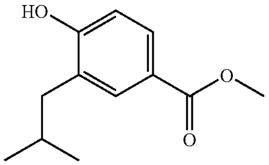

T13.3

Methyl 4-hydroxy-3-(2-methylpropyl)benzoate (T13.3)

To a stirred solution of methyl 4-hydroxy-3-(2-methyl-prop-1-enyl)benzoate T13.2 (0.320 g, 1.6 mmol) in EtOAc (2.00 mL, 20 mmol) at 23° C. was added palladium on carbon (0.017 g, 0.16 mmol). The reaction was stirred under an atmosphere of hydrogen (0.0031 g, 1.6 mmol) for 16 hours. The reaction mixture was then filtered and concentrated in vacuo to give a clear oil. The residue was purified on silica gel (0-20% EtOAc in hexanes) to yield T13.3 as a colorless oil (0.256 g, 79% yield)

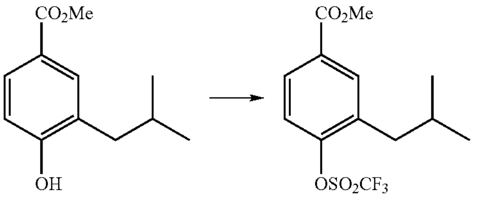

T13.3 T13.4

Methyl 3-(2-methylpropyl)-4-(((trifluoromethyl) sulfonyl)oxy)benzoate (T13.4)

To a stirred solution of T13.3 (0.256 g, 1 mmol) in DCM (12 mL, 1 mmol) at 0° C. was added TEA (0.2 mL, 1 mmol), and a catalytic amount of DMAP. N-phenyltriflamide (0.5 g, 1 mmol) was then added and the mixture was stirred at room temperature for 20 hours. The reaction was concentrated in vacuo, and the residue was purified on silica gel (0-10% EtOAc in hexanes) to yield T13.4 as a colorless oil (0.400 g, 96% yield).

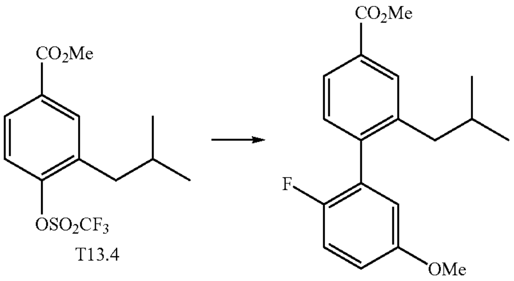

T13.4 T13.5

Methyl 2'-fluoro-5'-(methyloxy)-2-(2-methylpropyl)-1,1'-biphenyl-4-carboxylate (T13.5)

To a stirred solution of T13.4 (0.400 g, 1.2 mmol) in DMF (4.00 mL, 52 mmol) at 23° C. was added 2-fluoro-5-methoxyphenylboronic acid (0.40 g, 2.4 mmol) (commercially available from Aldrich), potassium carbonate (0.49 g, 3.5 mmol), and then tetrakis(triphenylphosphine)palladium (0.14 g, 0.12 mmol). The mixture was heated to 90° C. and stirred for 22 hours. The mixture was cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield T13.5 as a colorless oil (0.293 g, 79% yield).

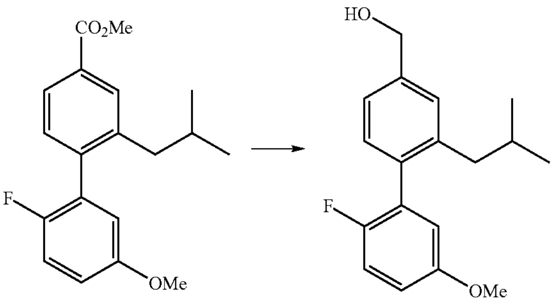

T13.5 T13.6

(2'-Fluoro-5'-(methyloxy)-2-(2-methylpropyl)-1,1'-biphenyl-4-yl)methanol (T13.6)

To a stirred solution of T13.5 (0.293 g, 0.9 mmol) in THF (5 mL, 0.9 mmol) at 0° C. was added LAH in THF (2 mL, 2 mmol, 1.0M). The reaction was stirred for one hour and then 1N NaOH(aq) was added to quench the mixture. The reaction was extracted three times with EtOAc. After drying over anhydrous magnesium sulfate and filtering, the organic solvent was removed under reduced pressure and the product was then purified on silica gel (0-20% EtOAc in hexanes) to yield T13.6 as a colorless oil (0.260 g, 97% yield).

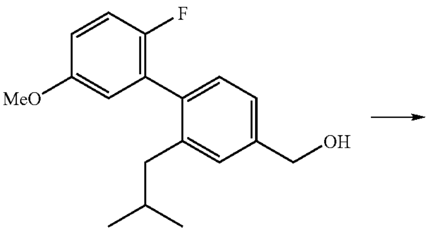

T13.6

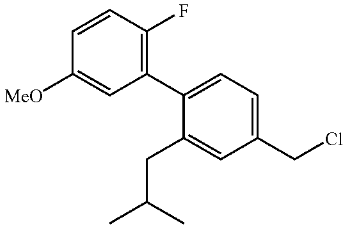

T13

4-(Chloromethyl)-2'-fluoro-5'-(methyloxy)-2-(2-methylpropyl)-1,1'-biphenyl (T13)

To a stirred solution of T13.6 (0.260 g, 0.90 mmol) in DCM (2.00 mL, 31 mmol) at 23° C. was added DMF (0.0070 mL, 0.090 mmol) followed by thionyl chloride (0.13 mL, 1.8 mmol). The reaction was stirred for one hour and then the reaction was concentrated in vacuo. The residue was then purified on silica gel (0-10% EtOAc in hexanes) to yield T13 as a colorless oil (0.252 g, 91% yield).

Examples T14A and T14B

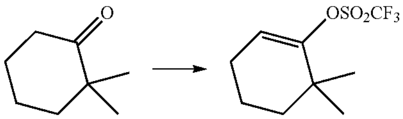

T14.1

6,6-Dimethyl-1-cyclohexen-1-yl trifluoromethanesulfonate (T14.1)

To a solution of 2,2-dimethylcyclohexanone (2.00 g, 16 mmol, commercially available from Aldrich) in THF (35 mL) at −78° C. was added dropwise LDA (9 mL, 18 mmol, 2.0 M). The resulting solution was stirred at −78° C. for 20 minutes. A solution of N-phenyl-bis(trifluoromethane sulfonimide) (6 g, 17 mmol) in THF (15 mL) was then added slowly at −78° C. The reaction mixture was allowed to warm to 23° C. over 3 hours and the reaction was then concentrated in vacuo. The reaction was diluted with brine and extracted three times with EtOAc. After drying over anhydrous magnesium sulfate and filtering, the organic solvent was removed under reduced pressure and the product was then purified on silica gel (0-10% EtOAc in hexanes) T14.1 as a clear oil (4.1 g, 100%).

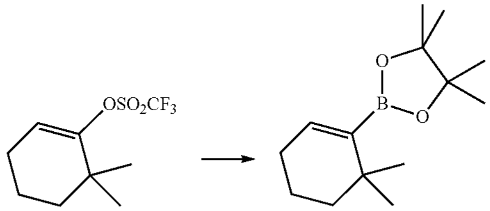

T14.1 T14.2

2-(6,6-Dimethyl-1-cyclohexen-1-yl)-4,4,5,5-tetramethyl-1,3,2-dioxaborolane (T14.2)

A mixture of triphenylphosphine (0.4 g, 2 mmol), potassium phenolate (3 g, 22 mmol), 4,4,5,5-tetramethyl-2-(4,4,5,5-tetramethyl-1,3,2-dioxaborolan-2-yl)-1,3,2-dioxaborolane (4 g, 16 mmol) and T14.1 (4.1 g, 16 mmol) in toluene (79 mL, 16 mmol) was degassed using $N_2$. Then dichlorobis(triphenylphosphine)-palladium(II) (0.6 g, 0.8 mmol) was added. The reaction mixture was further degassed with $N_2$. The reaction was stirred at 50° C. for 3.5 hours, and then it was diluted with brine and extracted three times with EtOAc. After drying over anhydrous magnesium sulfate and filtering, the organic solvent was removed under reduced pressure and the product was then purified on silica gel (0-10% EtOAc in hexanes) to yield T14.2 as a colorless oil (3.00 g, 80% yield).

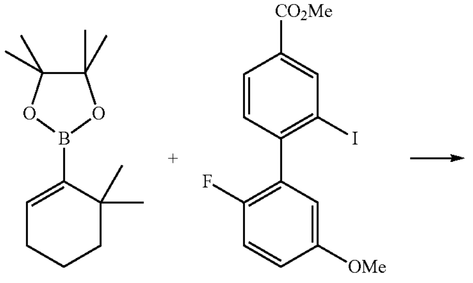

T14.2 T10.4

-continued

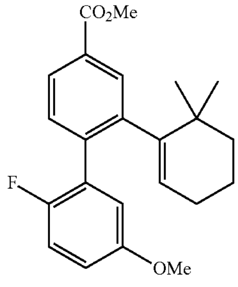

T14.3

Methyl 2-(6,6-dimethyl-1-cyclohexen-1-yl)-2'-fluoro-5'-(methyloxy)-1,1'-biphenyl-4-carboxylate (T14.3)

To a stirred solution of T10.4 (0.750 g, 1.9 mmol) in DMF (4.00 mL, 52 mmol) at 23° C. was added T14.2 (0.92 g, 3.9 mmol), potassium carbonate (0.81 g, 5.8 mmol), and then tetrakis(triphenylphosphine)palladium (0.22 g, 0.19 mmol). The mixture was heated to 90° C. and stirred for 24 hours. The reaction was then cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield T14.3 as a colorless oil (0.34 g, 48% yield).

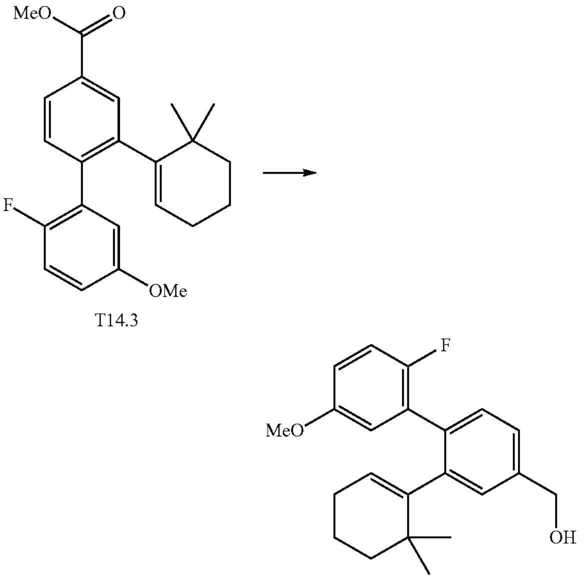

T14.3

T14.4

(2-(6,6-Dimethyl-1-cyclohexen-1-yl)-2'-fluoro-5'-(methyloxy)-1,1'-biphenyl-4-yl)methanol (T14.4)

To a stirred solution of T14.3 (0.300 g, 0.814 mmol) in THF (0.0587 g, 0.814 mmol) at 0° C. was added LAH in THF (1.63 mL, 1.63 mmol, 1.0M). The reaction was stirred for 4.5 hours and then 1N NaOH(aq) was added to quench the mixture. The reaction was extracted three times with EtOAc. After drying over anhydrous magnesium sulfate and filtering, the organic solvent was removed under reduced pressure and the product was then purified on silica gel (0-20% EtOAc in hexanes) to yield T14.4 as a colorless oil (0.250 g, 90.2% yield).

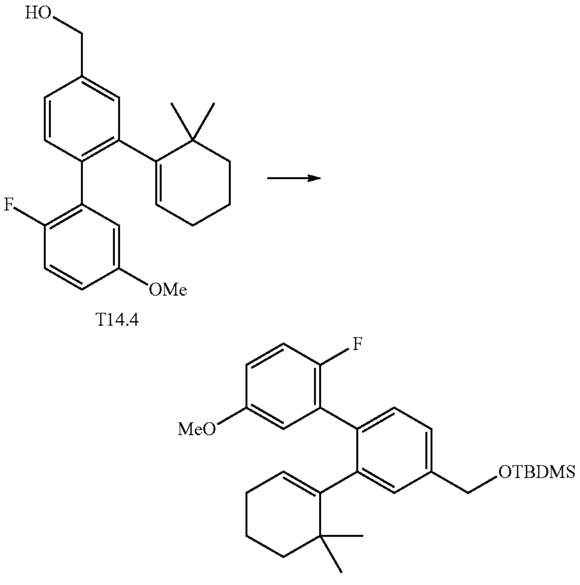

T14.4

T14.5

(((2-(6,6-Dimethyl-1-cyclohexen-1-yl)-2'-fluoro-5'-(methyloxy)-1,1'-biphenyl-4-yl)methyl)oxy)(1,1-dimethylethyl)dimethylsilane (T14.5)

To a stirred solution of T14.4 (0.160 g, 0.5 mmol) in DCM (10.00 mL, 155 mmol) at 23° C. was added tert-butyldimethylsilyl chloride (0.09 mL, 0.6 mmol), followed by TEA (0.08 mL, 0.6 mmol) and DMAP (0.006 g, 0.05 mmol). The reaction was stirred for one hour and then concentrated in vacuo. The residue was then purified on silica gel (0-5% EtOAc in hexanes) to yield T14.5 as a colorless oil (0.198 g, 93% yield).

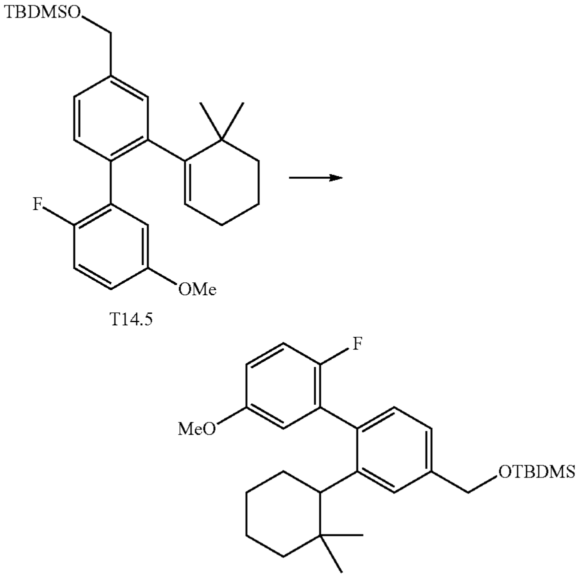

T14.5

T14.6

Synthesis of T14.6

To a stirred solution of T14.5 (0.090 g, 0.20 mmol) in EtOAc (2.00 mL, 20 mmol) at 23° C. was added palladium on carbon (0.0021 g, 0.020 mmol). The resulting mixture was stirred under an atmosphere of hydrogen for 4 days. The reaction mixture was filtered, and the filtrate was concentrated in vacuo to yield T14.6 as a colorless oil (0.090 g, 100% yield)

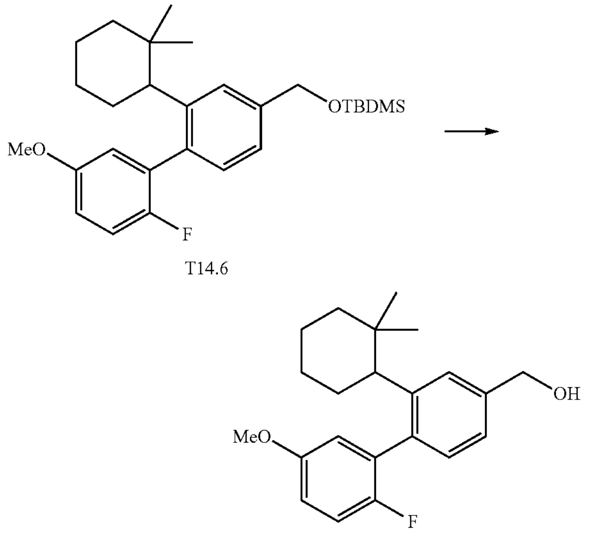

T14.6

T14.7

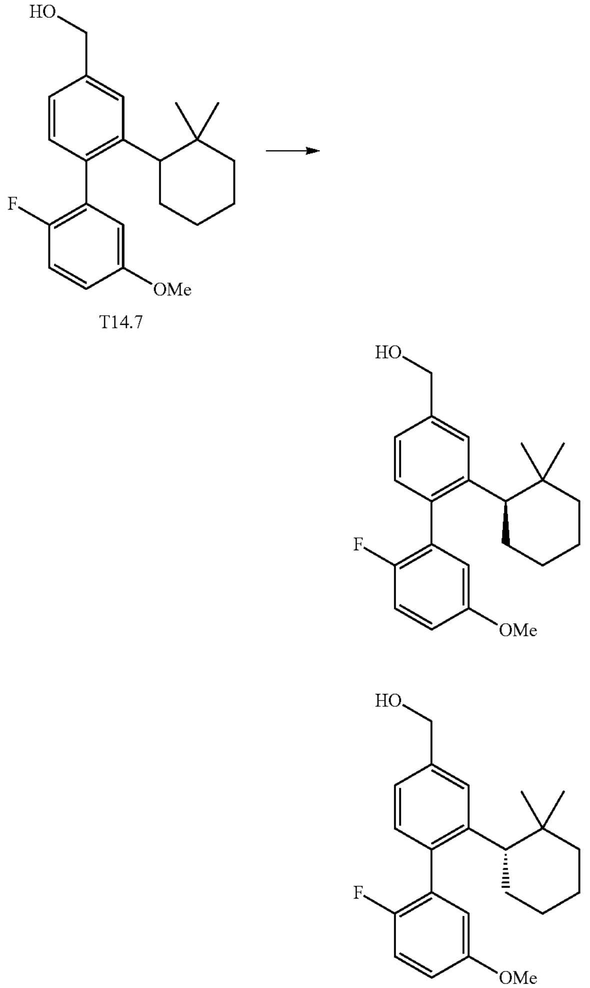

T14.7

T14.8 and T14.9

(2-((1R)-2,2-dimethylcyclohexyl)-2'-fluoro-5'-(methyloxy)-1,1'-biphenyl-4-yl)methanol and (2-((1S)-2,2-dimethylcyclohexyl)-2'-fluoro-5'-(methyloxy)-1,1'-biphenyl-4-yl)methanol (T14.8 and T14.9)

To a stirred mixture of T14.6 (0.090 g, 0.20 mmol) in MeOH (0.99 mL, 0.20 mmol) was added PPTS (0.0050 g, 0.020 mmol). The resulting mixture was stirred for 4.5 hours and then was concentrated in vacuo. The residue was purified on silica gel (0-15% EtOAc in hexanes) to yield a colorless oil (0.067 g, 99% yield). Chiral separation of T14.7 was accomplished on Chiracel-OD (3% IPA in hexane) to provide T14.8 (peak one) and T14.9 (peak two).[1]

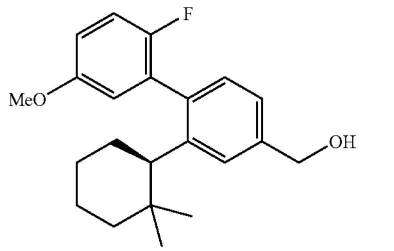

or

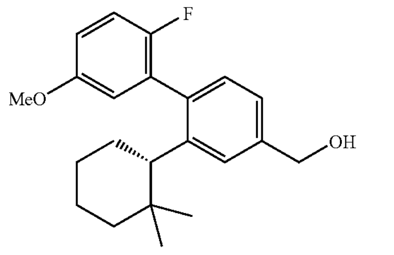

T14.8 or T14.9

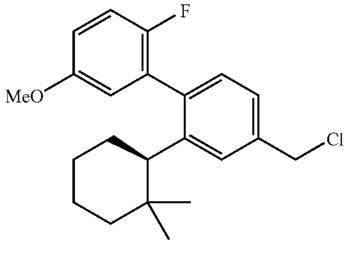

or

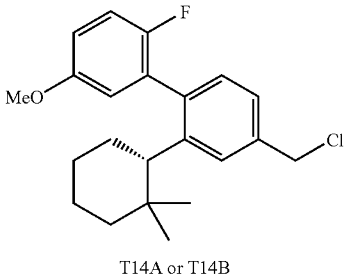

T14A or T14B 4-(Chloromethyl)-2-((1R)-2,2-dimethylcyclohexyl)-2'-fluoro-5'-(methyloxy)-1,1'-biphenyl or 4-(chloromethyl)-2-((1S)-2,2-dimethylcyclohexyl)-2'-fluoro-5'-(methyloxy)-1,1'-biphenyl (T14A or T14B)

To a stirred solution of T14.8 or T14.9 (0.035 g, 0.10 mmol) in DCM (2.00 mL, 31 mmol) at 23° C. was added DMF (0.00079 mL, 0.010 mmol) followed by thionyl chloride (0.015 mL, 0.20 mmol). The reaction was stirred for one hour. After which, the reaction mixture was concentrated in vacuo. The residue was then purified on silica gel (0-10% EtOAc in hexanes) to yield T14A or T14B as a colorless oil (0.025 g, 68% yield).

Example T15

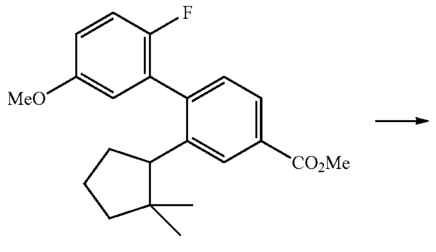

T6.11

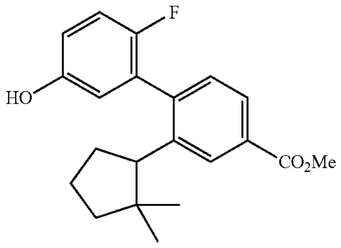

T15.1

Methyl 2-(2,2-dimethylcyclopentyl)-2'-fluoro-5'-hydroxy-1,1'-biphenyl-4-carboxylate (T15.1)

To a stirred solution of T6.11 (0.400 g, 1.12 mmol) in DCM (10.00 mL) at 0° C. was added boron tribromide (1.0M in DCM) (4.49 mL, 4.49 mmol). The reaction was stirred for one hour at 0° C. Water was then added, and the mixture was extracted three times with EtOAc. After drying over anhydrous magnesium sulfate and filtering, the organic solvent was removed under reduced pressure and the desired product was isolated. The initial product was dissolved in a 1/1 mixture of THF/ethanol and to this was added 1N NaOH (aq), the resulting solution was stirred for 16 hours, after which it was concentrated in vacuo. The reaction was acidified with 1N HCl and the resulting solution was extracted three times with EtOAc. After drying over anhydrous magnesium sulfate and filtering, the organic solvent was removed under reduced pressure. The resulting product was dissolved in MeOH and a drop of sulfuric acid was added. The mixture was heated at 70° C. for 16 hours. The reaction mixture was then concentrated in vacuo. The product was then purified on silica gel (0-20% EtOAc in hexanes) to yield T15.1 as a colorless oil (0.250 g, 65% yield).

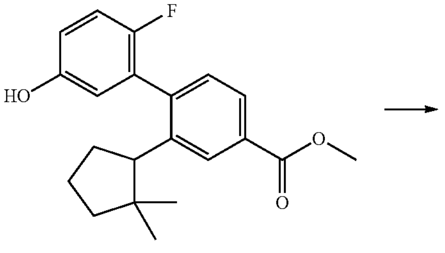

T15.1

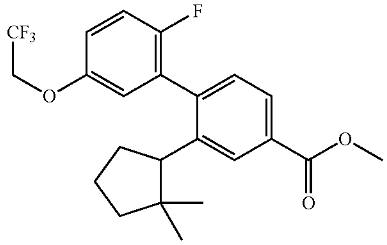

T15.2

Methyl 2-(2,2-dimethylcyclopentyl)-2'-fluoro-5'-((2,2,2-trifluoroethyl)oxy)-1,1'-biphenyl-4-carboxylate (T15.2)

To a flask containing T15.1 (0.100 g, 0.29 mmol) and cesium carbonate (0.29 g, 0.88 mmol) in DMF (2 mL) was added 1,1,1-trifluoro-2-iodoethane (0.12 g, 0.58 mmol) (commercially available from Aldrich), and stirring was continued for 5 hours. The reaction was diluted with water and extracted three times with EtOAc. After drying over anhydrous magnesium sulfate and filtering, the organic solvent was removed under reduced pressure and the product was then purified on silica gel (0-10% EtOAc in hexanes) to yield T15.2 as a colorless oil (0.113 g, 91% yield).

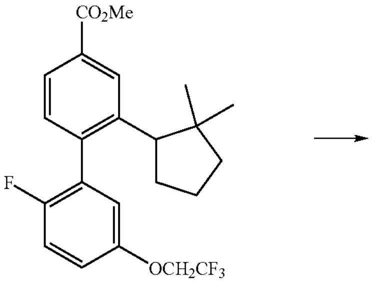

T15.2

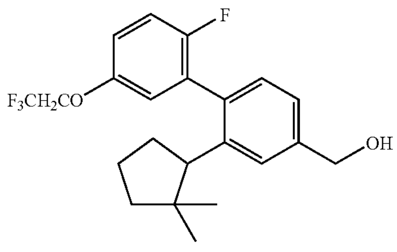

T15.3

-continued

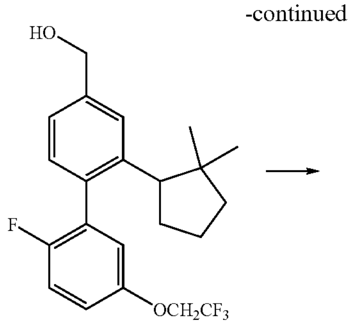

T15.3

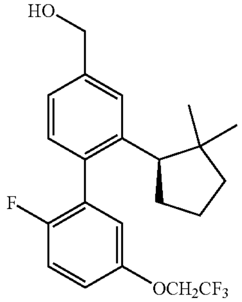

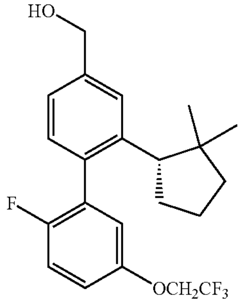

T15.4 and T15.5

(2-((1R)-2,2-Dimethylcyclopentyl)-2'-fluoro-5'-((2,2,2-trifluoroethyl)oxy)-1,1'-biphenyl-4-yl)methanol and (2-((1S)-2,2-dimethylcyclopentyl)-2'-fluoro-5'-((2,2,2-trifluoroethyl)oxy)-1,1'-biphenyl-4-yl)methanol (T15.4 and T15.5)

To a stirred solution of T15.2 (0.113 g, 0.3 mmol) in THF (5 mL) at 0° C. was added LAH in THF (0.5 mL, 0.5 mmol, 1.0M). The mixture was stirred for one hour and then 1N NaOH(aq) was added to quench the reaction. The reaction mixture was extracted three times with EtOAc. After drying over anhydrous magnesium sulfate and filtering, the organic solvent was removed under reduced pressure and the product was then purified on silica gel (0-20% EtOAc in hexanes) to yield T15.3 as a colorless oil (0.075 g, 71% yield). Chiral separation of T15.3 was accomplished on Chiracel-OD (3% IPA in hexane) to provide T15.4 (peak one) and T15.5 (peak two).[1]

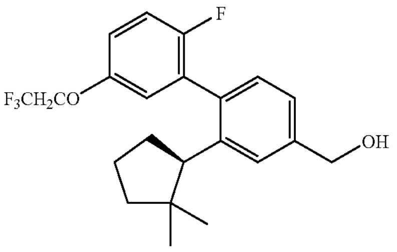

or

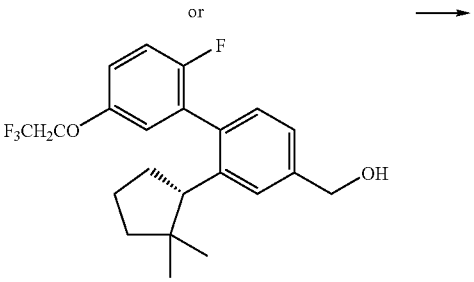

T15.4 or T15.5

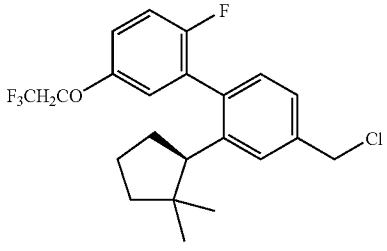

or

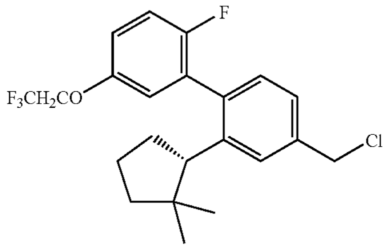

T15A or T15B 4-(Chloromethyl)-2-((1R)-2,2-dimethylcyclopentyl)-2'-fluoro-5'-((2,2,2-trifluoroethyl)oxy)-1,1'-biphenyl or 4-(chloromethyl)-2-((1S)-2,2-dimethylcyclopentyl)-2'-fluoro-5'-((2,2,2-trifluoroethyl)oxy)-1,1'-biphenyl (T15A or T15B)

To a stirred solution of T15.4 or T15.5 (0.022 g, 0.055 mmol) in DCM (2.00 mL) at 23° C. was added DMF (0.00043 mL) followed by thionyl chloride (0.0081 mL, 0.11 mmol). The reaction was stirred for two hours and then the reaction mixture was concentrated in vacuo. The product was then purified on silica gel (0-10% EtOAc in hexanes) to yield T15A or T15B as a colorless oil (0.019 g, 83% yield).

Examples T16A and T16B

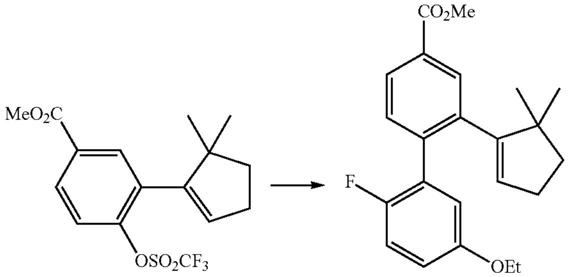

T6.9 T16.1

Methyl 2-(5,5-dimethyl-1-cyclopenten-1-yl)-5'-(ethyloxy)-2'-fluoro-1,1'-biphenyl-4-carboxylate (T16.1)

To a stirred solution of methyl 3-(5,5-dimethylcyclopent-1-enyl)-4-(trifluoromethylsulfonyloxy)benzoate T6.9 (0.400 g, 1.1 mmol) in DMF (4.00 mL) at 23° C. was added 5-ethoxy-2-fluorophenylboronic acid (0.29 g, 1.6 mmol, commercially available from Aldrich), potassium carbonate (0.44 g, 3.2 mmol), and then tetrakis(triphenylphosphine) palladium (0.12 g, 0.11 mmol). The mixture was heated to 90° C. and stirred for 21 hours. The mixture was then cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield T16.1 as a colorless oil (0.350 g, 90% yield).

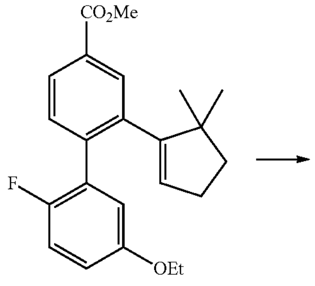

T16.1

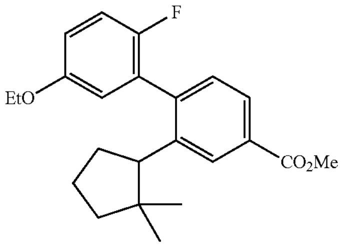

T16.2

Methyl 2-(2,2-dimethylcyclopentyl)-5'-(ethyloxy)-2'-fluoro-1,1'-biphenyl-4-carboxylate (T16.2)

To a stirred solution of T16.1 (0.400 g, 1.09 mmol) in MeOH (10.00 mL, 1.09 mmol) at 23° C. was added palladium on carbon (0.116 g, 1.09 mmol). The reaction was placed under an atmosphere of hydrogen and stirred for 23 hours. The mixture was then filtered and concentrated in vacuo. The initial product was then purified on silica gel (0-20% EtOAc in hexanes) to yield T16.2 as a colorless oil (0.400 g, 99.5% yield).

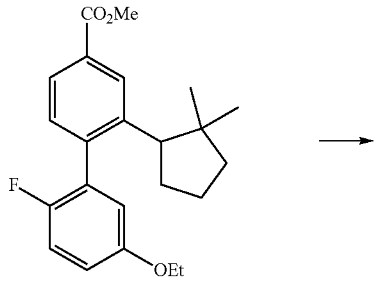

T16.2

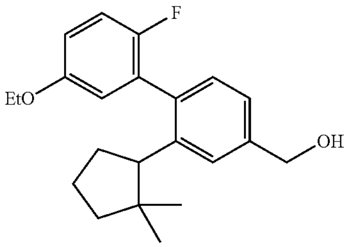

T16.3

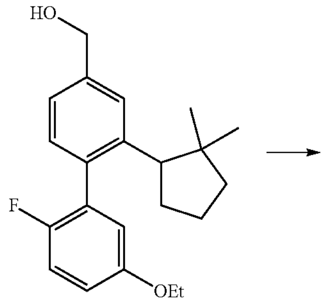

T16.3

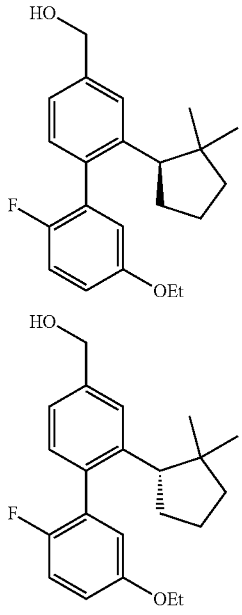

T16.4 and T16.5

(2-((1R)-2,2-Dimethylcyclopentyl)-5'-(ethyloxy)-2'-fluoro-1,1'-biphenyl-4-yl)methanol and (2-((1S)-2,2-dimethylcyclopentyl)-5'-(ethyloxy)-2'-fluoro-1,1'-biphenyl-4-yl)methanol (T16.4 and T16.5)

To a stirred solution of T16.2 (0.400 g, 1.1 mmol) in THF (15.00 mL, 183 mmol) at 0° C. was added LAH in THF (2.2 mL, 2.2 mmol, 1.0M). The mixture was stirred for one hour and then 1N NaOH(aq) was added to quench the reaction. The reaction mixture was extracted three times with EtOAc. After drying over anhydrous magnesium sulfate and filtering, the organic solvent was removed under reduced pressure and the product was then purified on silica gel (0-20% EtOAc in hexanes) to yield T16.3 as a colorless oil (0.320 g, 87% yield). Chiral separation of T16.3 was accomplished on Chiracel-OD (3% IPA in hexane) to provide T16.4 (peak one) and T16.5 (peak two).[1]

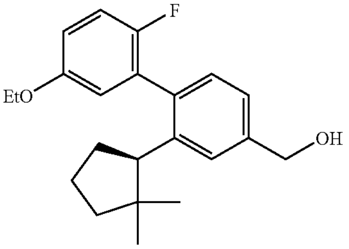

or

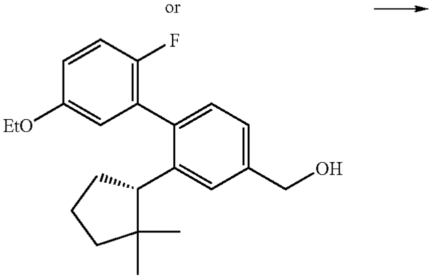

T16.4 or T16.5

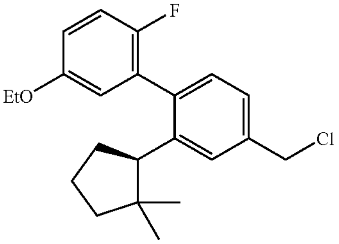

or

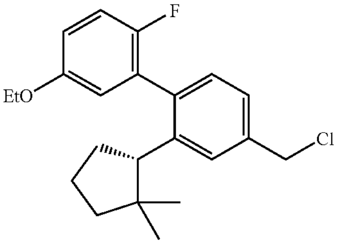

T16A or T16B 4-(Chloromethyl)-2-((1R)-2,2-dimethylcyclopentyl)-5'-(ethyloxy)-2'-fluoro-1,1'-biphenyl or 4-(chloromethyl)-2-((1S)-2,2-dimethylcyclopentyl)-5'-(ethyloxy)-2'-fluoro-1,1'-biphenyl (T16A or T16B)

To a stirred solution of T16.4 or T16.5 (0.147 g, 0.43 mmol) in DCM (2.00 mL) at 23° C. was added DMF (0.0033 mL) followed by thionyl chloride (0.063 mL, 0.86 mmol) The reaction was then stirred for 4 hours and then concentrated in vacuo. The initial product was then purified on silica gel (0-10% EtOAc in hexanes) to yield T16A or T16B as a colorless oil (0.120 g, 77% yield).

Examples T17A and T17B

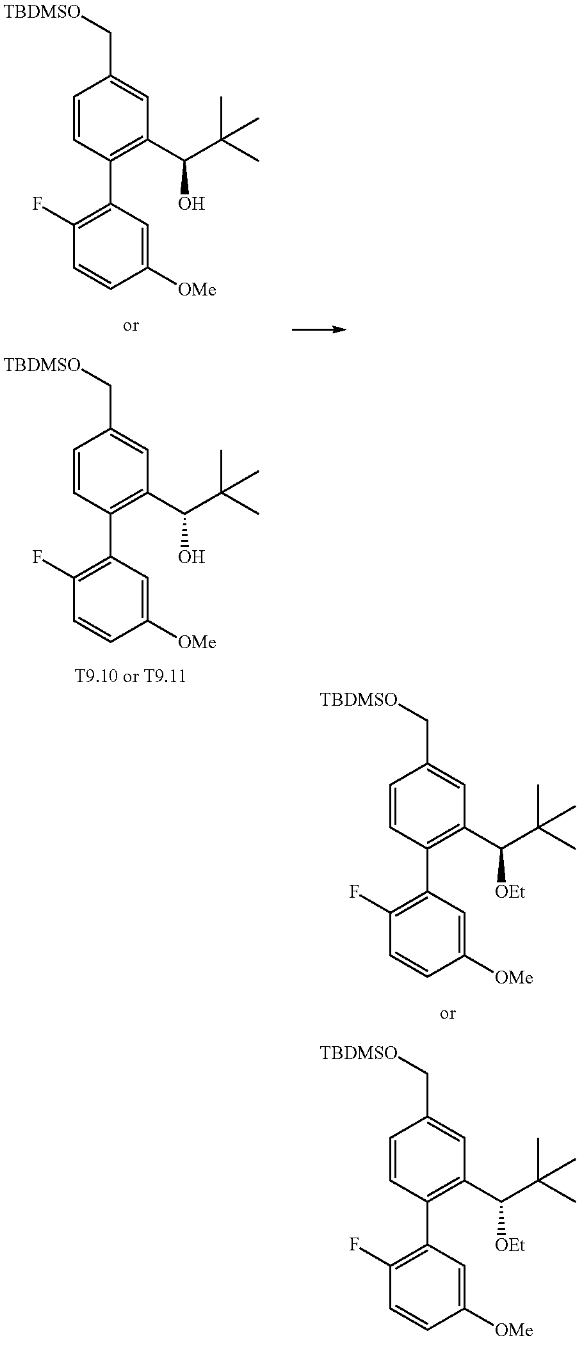

or

T9.10 or T9.11 or

T17.1 or T17.2

(1,1-Dimethylethyl)(((2-((1R)-1-(ethyloxy)-2,2-dimethylpropyl)-2'-fluoro-5'-(methyloxy)-1,1'-biphenyl-4-yl)methyl)oxy)dimethylsilane or (1,1-dimethylethyl)(((2-((1S)-1-(ethyloxy)-2,2-dimethylpropyl)-2'-fluoro-5'-(methyloxy)-1,1'-biphenyl-4-yl)methyl)oxy)dimethylsilane (T17.1 or T17.2)

To a stirred solution of T9.10 or T9.11 (derived from peak two from chiral separation of T9.7) (0.110 g, 0.25 mmol) in DMF (2.00 mL) at 23° C. was added iodoethane (0.048 g, 0.31 mmol), followed by sodium hydride (0.0073 g, 0.31 mmol). The mixture was stirred at 60° C. for 21 hours and then cooled to room temperature. The reaction was diluted with brine and extracted three times with EtOAc. After drying over anhydrous magnesium sulfate and filtering, the organic solvent was removed under reduced pressure and the product was then purified on silica gel (0-10% EtOAc in hexanes) to yield T17.1 or T17.2 as a colorless oil (0.065 g, 55% yield).

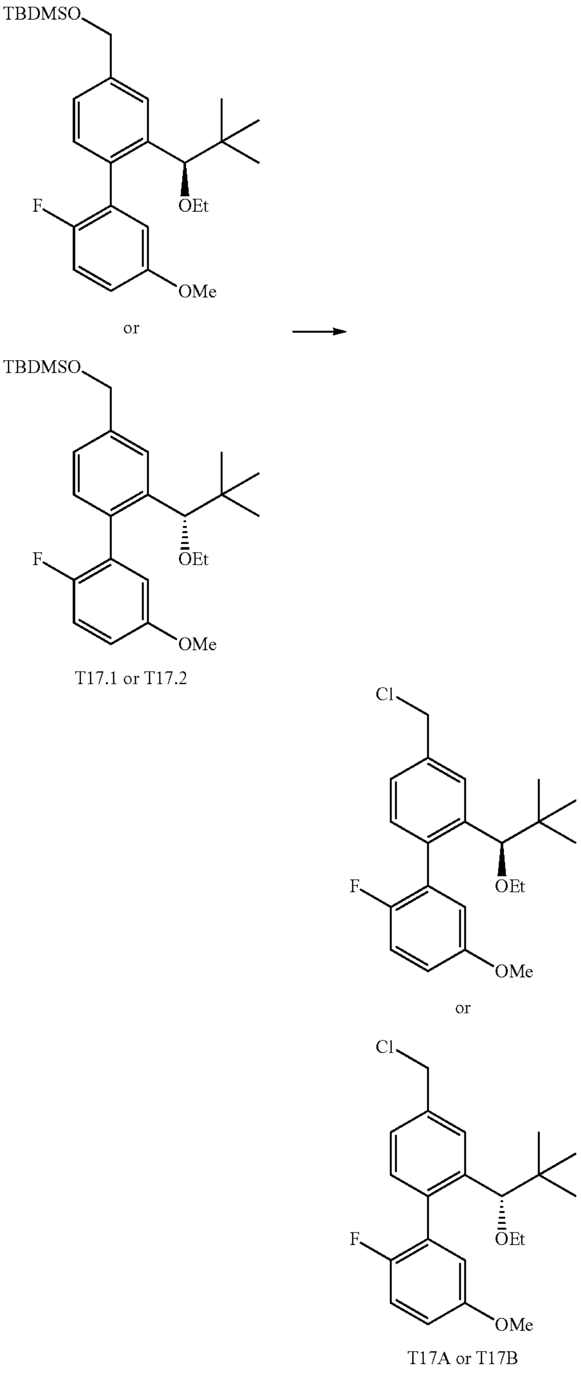

or

T17.1 or T17.2 or

T17A or T17B

4-(Chloromethyl)-2-((1R)-1-(ethyloxy)-2,2-dimethylpropyl)-2'-fluoro-5'-(methyloxy)-1,1'-biphenyl or 4-(chloromethyl)-2-((1S)-1-(ethyloxy)-2,2-dimethylpropyl)-2'-fluoro-5'-(methyloxy)-1,1'-biphenyl (T17A or T17B)

To a stirred solution of T17.1 or T17.2 (0.065 g, 0.1 mmol) in DCM (2.00 mL) at 23° C. was added DMF (0.001 mL) followed by thionyl chloride (0.02 mL, 0.3 mmol). The mixture was stirred for 2 hours and then concentrated in vacuo. The product was then purified on silica gel (0-10% EtOAc in hexanes) to yield T17A or T17B as a colorless oil (0.04 g, 78% yield).

Examples T18A and T18B

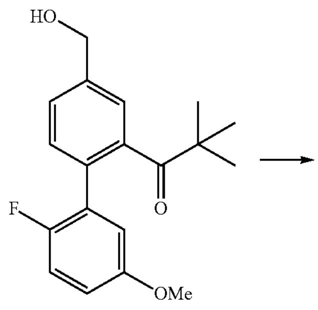

T9.6

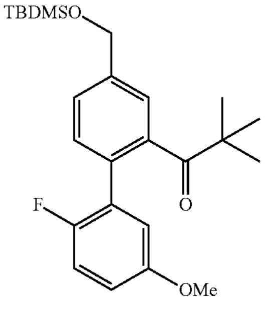

T18.1

1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanone (T18.1)

To a stirred solution of T9.6 (1.00 g, 3 mmol) in DCM (10.00 mL) at 23° C. was added tert-butyldimethylsilyl chloride (0.6 mL, 4 mmol), followed by TEA (0.5 mL, 4 mmol) and DMAP (0.04 g, 0.3 mmol). The reaction was stirred for 16 hours and then the reaction was concentrated in vacuo. The product was purified on silica gel (0-10% EtOAc in hexanes) to yield T18.1 as a colorless oil (1.30 g, 96% yield).

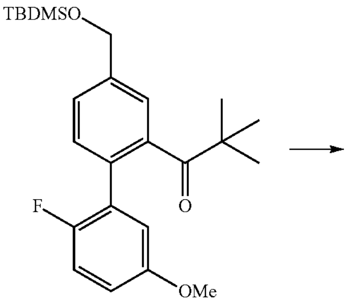

T18.1

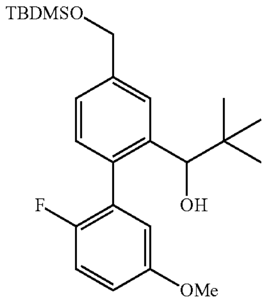

T18.2

1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanol (T18.2)

To a stirred solution of T18.1 (0.500 g, 1.2 mmol) in THF (15.00 mL, 183 mmol) at 0° C. was added LAH in THF (2.3 mL, 2.3 mmol, 1.0M). The reaction was stirred for two hours. 1N NaOH(aq) was added to quench the reaction mixture, and the reaction was then extracted three times with EtOAc. After drying over anhydrous magnesium sulfate and filtering, the organic solvent was removed under reduced pressure and the product was then purified on silica gel (0-10% EtOAc in hexanes) to yield T18.2 as a colorless oil (0.400 g, 80% yield).

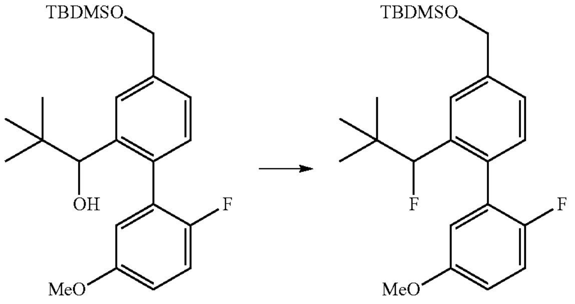

T18.2 T18.3

(1,1-Dimethylethyl)(((2'-fluoro-2-(1-fluoro-2,2-dimethylpropyl)-5'-(methyloxy)-1,1'-biphenyl-4-yl)methyl)oxy)dimethylsilane (T18.3)

To a solution of T18.2 (0.400 g, 0.925 mmol) in toluene (10 mL) at −78° C. was added DAST (0.209 g, 1.29 mmol) dropwise. The reaction was stirred at −78° C. for 30 minutes and then warmed to 23° C. and stirred for an additional 2 hours. Water was added to quench the reaction mixture. The reaction was then extracted three times with EtOAc. After drying over anhydrous magnesium sulfate and filtering, the organic solvent was removed under reduced pressure and the product was then purified on silica gel (0-10% EtOAc in hexanes) to yield T18.3 as a colorless oil (0.400 g, 99% yield).

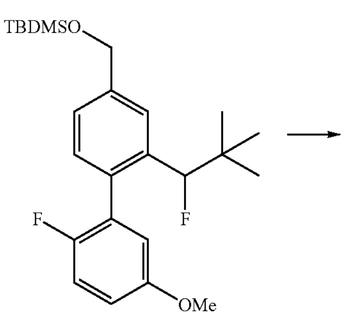

T18.3

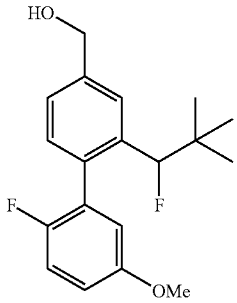

T18.4

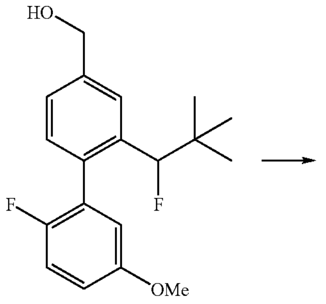

T18.4

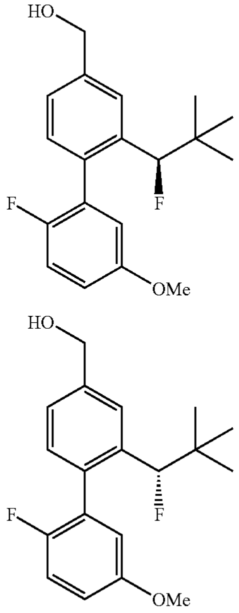

T18.5 and T18.6

(2'-Fluoro-2-((1R)-1-fluoro-2,2-dimethylpropyl)-5'-(methyloxy)-1,1'-biphenyl-4-yl)methanol and (2'-fluoro-2-((1S)-1-fluoro-2,2-dimethylpropyl)-5'-(methyloxy)-1,1'-biphenyl-4-yl)methanol (T18.5 and T18.6)

To a stirred solution of T18.3 (0.400 g, 0.920 mmol) in MeOH (10.00 mL) at 23° C. was added PPTS (0.0231 g, 0.0920 mmol). The reaction was stirred for 19 hours and then concentrated in vacuo to give a clear oil. The product was then purified on silica gel (0-20% EtOAc in hexanes) to yield T18.4 as a colorless oil (0.272 g, 92% yield). Chiral separation of T18.4 was accomplished on Chiracel-OD (3% IPA in hexane) to provide T18.5 and T18.6.

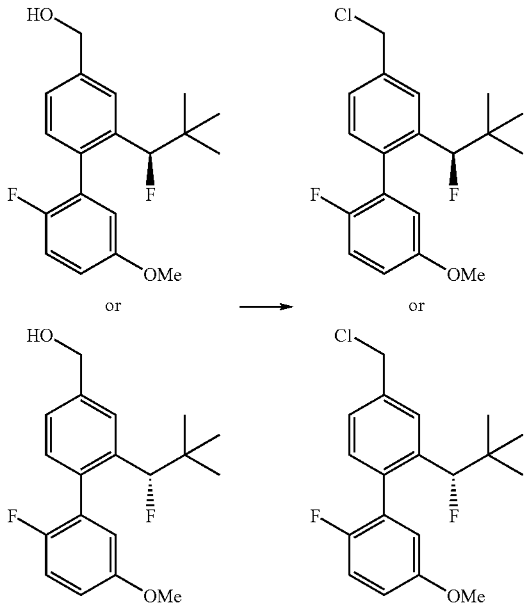

or or

T18.5 or T18.6

T18A or T18B 4-(Chloromethyl)-2'-fluoro-2-((1R)-1-fluoro-2,2-dimethylpropyl)-5'-(methyloxy)-1,1'-biphenyl or 4-(chloromethyl)-2'-fluoro-2-((1R)-1-fluoro-2,2-dimethylpropyl)-5'-(methyloxy)-1,1'-biphenyl (T18A or T18B)

To a stirred solution of T18.5 or T18.6 (0.102 g, 0.3 mmol) in DCM (2.00 mL) at 23° C. was added DMF (0.002 mL) followed by thionyl chloride (0.05 mL, 0.6 mmol). The reaction was stirred for 1.5 hours. The reaction was concentrated in vacuo. The product was then purified on silica gel (0-10% EtOAc in hexanes) to yield T18A or T18B as a colorless oil (0.09 g, 83% yield).

Examples T19A and T19B

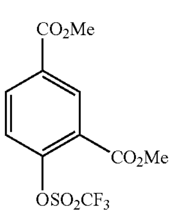

T9.2

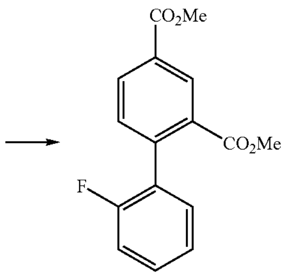

T19.1

Dimethyl 2'-fluoro-1,1'-biphenyl-2,4-dicarboxylate (T19.1)

To a stirred solution of dimethyl 4-(trifluoromethylsulfonyloxy)isophthalate T9.2 (1.60 g, 4.7 mmol) in DMF (9.4 mL, 4.7 mmol) at 23° C. was added 2-fluorophenylboronic acid (0.98 g, 7.0 mmol, commercially available from Aldrich), potassium carbonate (1.9 g, 14 mmol), and then tetrakis (triphenylphosphine)palladium (0.54 g, 0.47 mmol). The reaction mixture was heated to 90° C. and the reaction was stirred for 22 hours. The reaction was then cooled to room temperature, diluted with water, and extracted three times with EtOAc. After drying over anhydrous magnesium sulfate and filtering, the organic solvent was removed under reduced pressure and the product was then purified on silica gel (0-10% EtOAc in hexanes) to yield T19.1 as a colorless oil (1.10 g, 82% yield).

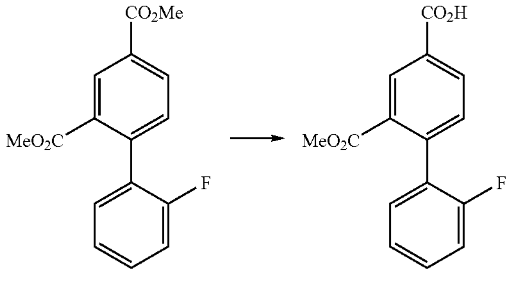

T19.1 T19.2

2'-Fluoro-2-((methyloxy)carbonyl)-1,1'-biphenyl-4-carboxylic acid (T19.2)

To a stirred solution of T19.1 (1.00 g, 3.5 mmol) in THF (70.0 mL) and MeOH (70.0 mL) at 0° C. was slowly added potassium hydroxide (1.9 mL, 3.8 mmol) to maintain the temperature below 6° C. The reaction mixture was allowed to warm to room temperature and stirred for 48 hours. The reaction mixture was then concentrated in vacuo, acidified with 1N HCl, and extracted three times with EtOAc. After drying over anhydrous magnesium sulfate and filtering, the organic solvent was removed under reduced pressure and to give a white solid T19.2 (0.90 g, 95% yield).

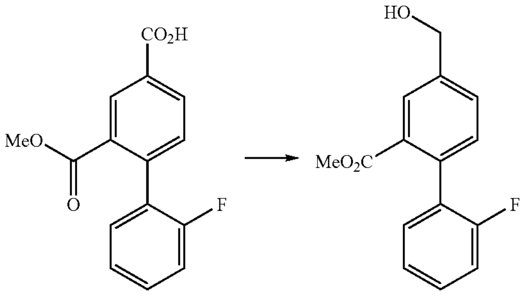

T19.2 T19.3

Methyl 2'-fluoro-4-(hydroxymethyl)-1,1'-biphenyl-2-carboxylate (T19.3)

To a stirred solution of T19.2 (0.90 g, 3 mmol) in THF (33 mL) at 0° C. was added borane-THF complex (7 mL, 7 mmol, 1.0M). The reaction was allowed to warm to 23° C. and stirred for 7 hours. The reaction mixture was then concentrated in vacuo. The reaction was diluted with 1N HCl and extracted three times with EtOAc. After drying over anhydrous magnesium sulfate and filtering, the organic solvent was removed under reduced pressure and the product was then purified on silica gel (0-40% EtOAc in hexanes) to yield T19.3 as a colorless solid (0.850 g, 100% yield).

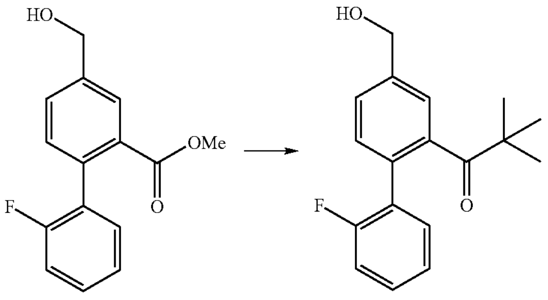

T19.3 T19.4

1-(2'-Fluoro-4-(hydroxymethyl)-1,1'-biphenyl-2-yl)-2,2-dimethyl-1-propanone (T19.4)

To a stirred solution of T19.3 (0.850 g, 3 mmol) in THF (33 mL) at −78° C. was added tert-butyllithium (6 mL, 10 mmol, 1.7M). The reaction was stirred for 5 hours and then a saturated solution of ammonium chloride was added and the mixture was extracted three times with EtOAc. After drying over anhydrous magnesium sulfate and filtering, the organic solvent was removed under reduced pressure and the product was then purified on silica gel (0-40% EtOAc in hexanes) to yield T19.4 as a colorless oil (0.670 g, 72% yield).

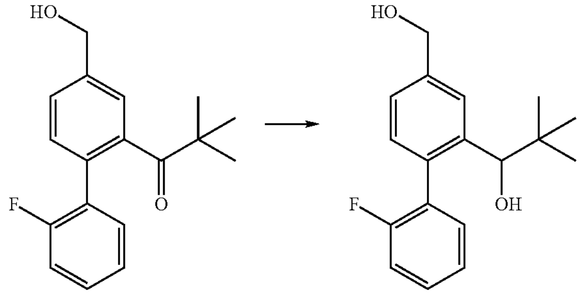

T19.4 T19.5

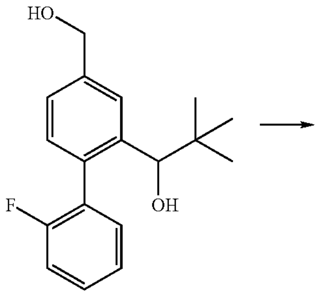

T19.5

-continued

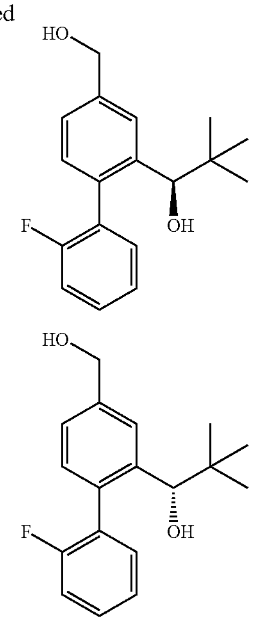

T19.6 and 19.7

(1R)-1-(2'-Fluoro-4-(hydroxymethyl)-1,1'-biphenyl-2-yl)-2,2-dimethyl-1-propanol and (1S)-1-(2'-fluoro-4-(hydroxymethyl)-1,1'-biphenyl-2-yl)-2,2-dimethyl-1-propanol (T19.6 and T19.7)

To a stirred solution of T19.4 (0.670 g, 2 mmol) in THF (6 mL) at 0° C. was added LAH in THF (5 mL, 5 mmol, 1.0M). The reaction was stirred for 1.5 hours and then 1N NaOH(aq) was added to quench the reaction mixture. The reaction was then extracted three times with EtOAc. After drying over anhydrous magnesium sulfate and filtering, the organic solvent was removed under reduced pressure and the product was purified on silica gel (0-20% EtOAc in hexanes) to yield T19.5 as a colorless oil (0.450 g, 67% yield). Chiral separation of T19.5 was accomplished on Chiracel-OD (3% IPA in hexane) to provide T19.6 and T19.7.

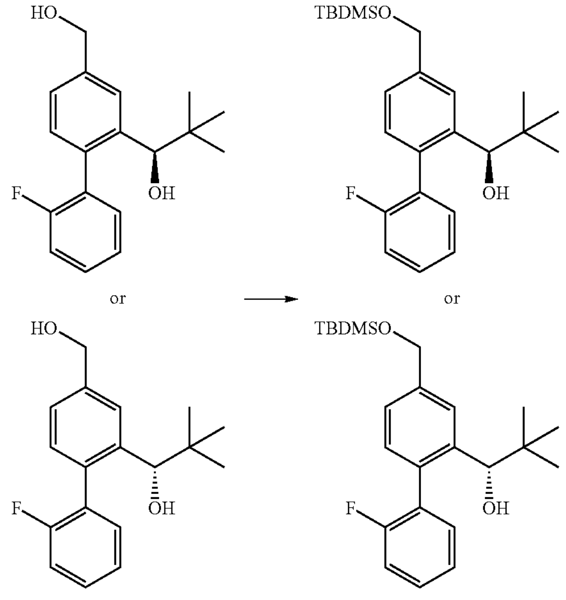

or or

T19.6 or T19.7 T19.8 or T19.9

(1R)-1-(4-((((1,1-Dimethylethyl)(dimethyl)silyl)oxy)methyl)-2'-fluoro-1,1'-biphenyl-2-yl)-2,2-dimethyl-1-propanol or (1S)-1-(4-((((1,1-dimethylethyl)(dimethyl)silyl)oxy)methyl)-2'-fluoro-1,1'-biphenyl-2-yl)-2,2-dimethyl-1-propanol (T19.8 or T19.9)

To a stirred solution of T19.6 or T19.7 (0.200 g, 0.7 mmol) in DCM (10.00 mL) at 23° C. was added tert-butyldimethylsilyl chloride (0.1 mL, 0.8 mmol), followed by TEA (0.1 mL, 0.8 mmol) and DMAP (0.008 g, 0.07 mmol). The reaction was stirred for 14 hours and then concentrated in vacuo. The product was then purified on silica gel (0-10% EtOAc in hexanes) to yield T19.8 or T19.9 as a colorless oil (0.250 g, 90% yield).

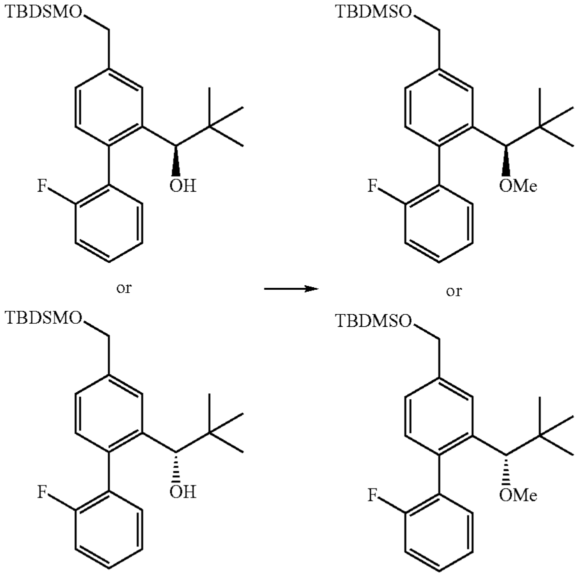

or or

T19.8 or T19.9 T19.10 or T19.11

(1,1-Dimethylethyl)(((2-((1R)-2,2-dimethyl-1-(methyloxy)propyl)-2'-fluoro-1,1'-biphenyl-4-yl)methyl)oxy)dimethylsilane or (1,1-dimethylethyl)(((2-((1S)-2,2-dimethyl-1-(methyloxy)propyl)-2'-fluoro-1,1'-biphenyl-4-yl)methyl)oxy)dimethylsilane (T19.10 or T19.11)

To a stirred solution of T19.8 or T19.9 (0.060 g, 0.15 mmol) in DMF (2.00 mL) at 23° C. was added iodomethane (0.025 g, 0.18 mmol), followed by sodium hydride (0.0043 g, 0.18 mmol). The reaction was stirred at 60° C. for 19 hours, diluted with water, and the mixture was extracted three times with EtOAc. After drying over anhydrous magnesium sulfate and filtering, the organic solvent was removed under reduced pressure and the product was then purified on silica gel (0-5% EtOAc in hexanes) to yield T19.10 or T19.11 as a colorless oil (0.062 g, 100% yield).

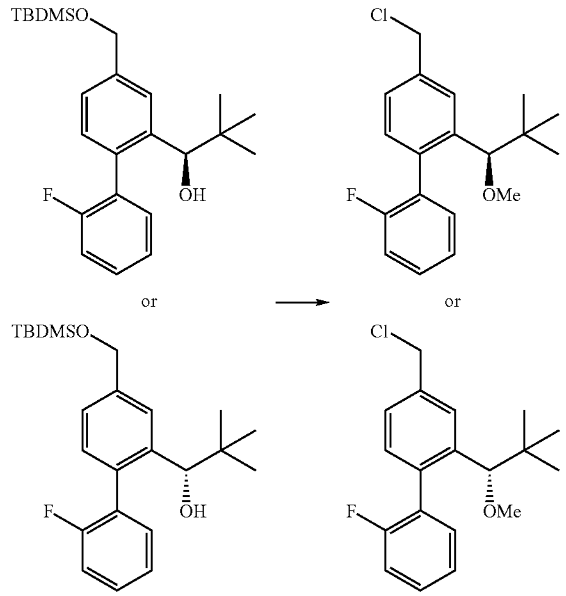

T19.10 or T19.11 T19A or T19B 4-(Chloromethyl)-2-((1R)-2,2-dimethyl-1-(methyloxy)propyl)-2'-fluoro-1,1'-biphenyl or 4-(chloromethyl)-2-((1S)-2,2-dimethyl-1-(methyloxy)propyl)-2'-fluoro-1,1'-biphenyl (T19A or T19B)

To a stirred solution of T19.10 or T19.11 (0.071 g, 0.17 mmol) in DCM (1.7 mL) and DMF (0.013 mL) at 0° C. was added thionyl chloride (0.025 mL, 0.34 mmol). The reaction was stirred at room temperature for 1.5 hours and then concentrated in vacuo. The product was then purified on silica gel (0-5% EtOAc in hexanes) to yield T19A or T19B as a colorless oil (0.036 g, 66% yield).

Example T20

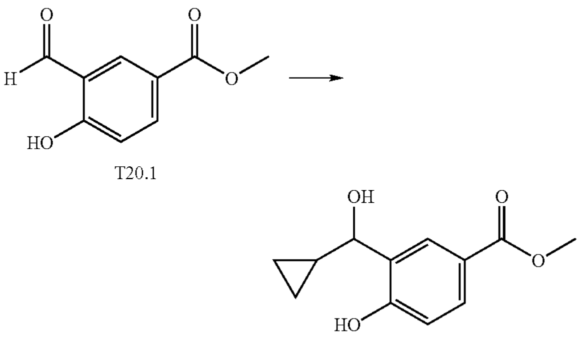

T20.1

T20.2

Methyl 3-(cyclopropyl(hydroxy)methyl)-4-hydroxybenzoate (T20.2)

In an ice-bath, methyl 3-formyl-4-hydroxybenzoate T20.1 (900 mg, 5 mmol) (commercially available from Aldrich) was dissolved in 5 mL THF. Then cyclopropylmagnesium bromide, 0.5 m in THF (22000 μL, 11 mmol) (commercially available from Aldrich) was added slowly. The reaction was raised to room temperature immediately and stirred at room temperature for 2 hours. After quenching with 1N HCl 11 mL, the reaction was extracted with EtOAc and dried. Silica gel chromatography afforded 950 mg of the product T20.2 (85%).

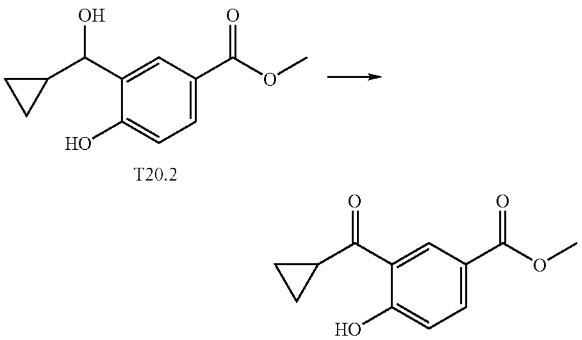

T20.2

T20.3

Methyl 3-(cyclopropanecarbonyl)-4-hydroxybenzoate (T20.3)

To a flask with methyl 3-(cyclopropyl(hydroxy)methyl)-4-hydroxybenzoate (T20.2) (845 mg, 0.38 mmol) was added manganese (IV) oxide (1.65 g, 1.9 mmol). Then dioxane 3.5 mL was added and the reaction was heated at reflux for 4 hours. The reaction was filtered and concentrated and silica gel chromatography afforded 693 mg of T20.3 (83%).

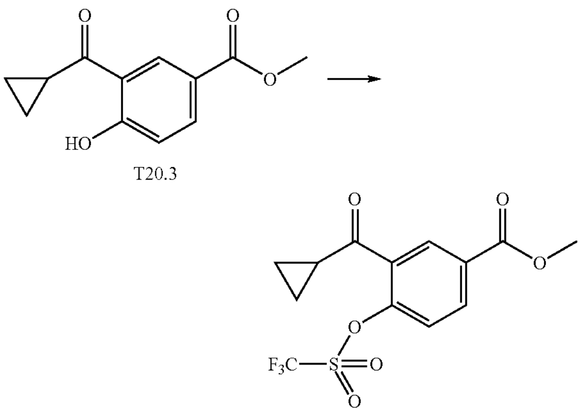

T20.3

T20.4

Methyl 3-(cyclopropanecarbonyl)-4-(trifluoromethylsulfonyloxy)benzoate (T20.4)

To a flask with methyl 3-(cyclopropanecarbonyl)-4-hydroxybenzoate T20.3 (693 mg, 3.1 mmol) was added DMAP (38 mg, 0.31 mmol), and the mixture was flushed with nitrogen. DCM was then added followed by TEA (0.88 mL, 6.3 mmol). After stirring at room temperature for 20 minutes, PhN(Tf)2 (1.2 g, 3.5 mmol) was added. The reaction gradually turned red and was stirred for another hour. The mixture was concentrated and purified by silica gel chromatography to afford 1.077 g of T20.4 as a colorless oil (97%).

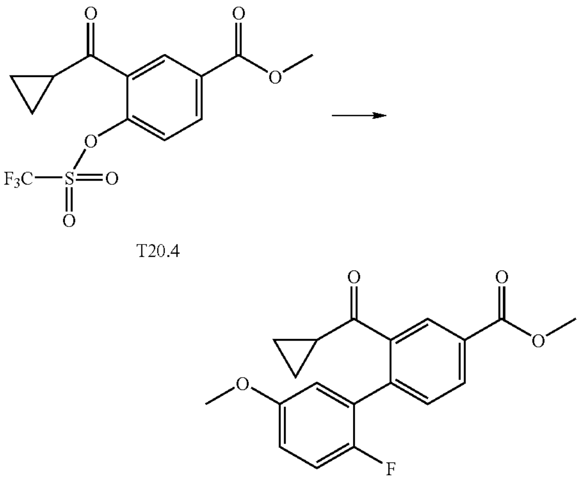

T20.4

T20.5

Methyl 3-(cyclopropanecarbonyl)-4-(2-fluoro-5-methoxyphenyl))benzoate (T20.5)

Methyl 3-(cyclopropanecarbonyl)-4-(trifluoromethylsulfonyloxy)benzoate (T20.4) (1.077 g, 3.1 mmol) was dried under vacuum. To a second flask was added 2-fluoro-5-methoxyphenylboronic acid (1.5 g, 8.9 mmol) (commercially available from Aldrich), cesium carbonate (3.5 g, 11 mmol), and tetrakis(triphenylphosphine)Palladium (0) (0.35 g, 0.31 mmol). Both flasks were flushed with nitrogen followed by vacuum. Degassed DME was then added to the flask with T20.4 (3 mL). Another 17 mL DME was added to the flask with the palladium catalyst followed by the DME solution of T20.4. The resulting slurry was stirred overnight in a 95° C. oil-bath. The reaction was filtered, concentrated, and purified by silica gel chromatography to afford 0.94 g of the desired product T20.5 (94%).

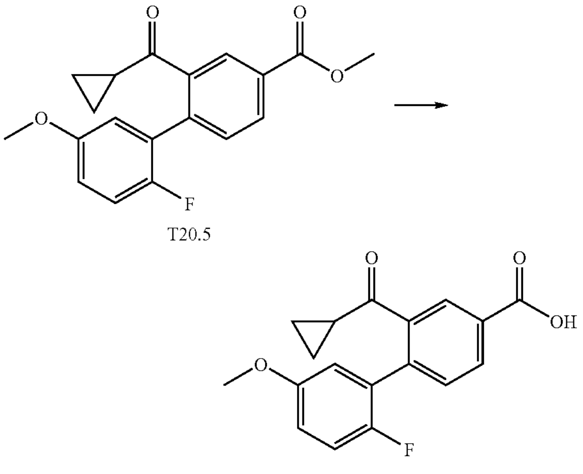

T20.5

T20.6

3-(Cyclopropanecarbonyl)-4-(2-fluoro-5-methoxyphenyl))benzoic acid (T20.6)

To a flask with methyl 3-(cyclopropanecarbonyl)-4-(2-fluoro-5-methoxyphenyl))benzoate (T20.5) (523 mg, 1593 μmol) was added 9.6 mL of MeOH and 1N NaOH (3186 μL, 3186 μmol). The reaction was heated to 55 C for 2 hours. The mixture was then acidified with 1N HCl, concentrated, and extracted with EtOAc. Removal of the solvent afforded 500 mg of T20.6 (100%).

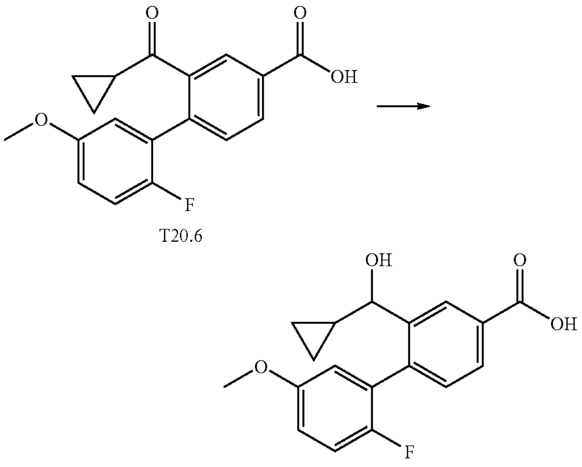

T20.6

T20.7

3-(Cyclopropyl(hydroxy)methyl)-4-(2-fluoro-5-methoxyphenyl))benzoic acid (T20.7)

To a flask with 3-(cyclopropanecarbonyl)-4-(2-fluoro-5-methoxyphenyl))benzoic acid (T20.6) (500 mg, 1591 μmol) was added anhydrous EtOH 10 mL, followed by addition of sodium borohydride (361 mg, 0.95 mmol). The reaction mixture was stirred overnight, quenched with water, and extracted with EtOAc. Removal of solvent gave 503 mg of T20.7 in racemic form.

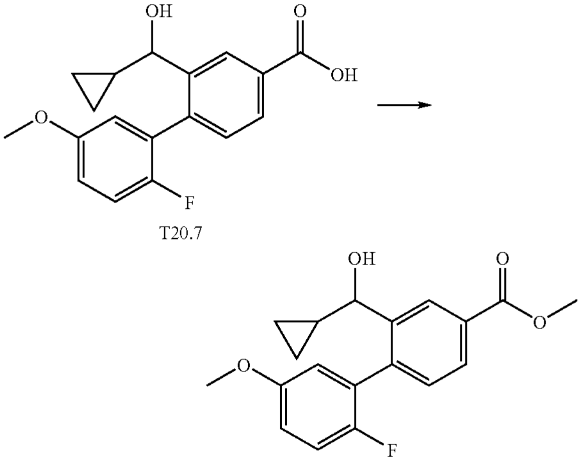

T20.7

T20.8

Methyl 3-(cyclopropyl(hydroxy)methyl)-4-(2-fluoro-5-methoxyphenyl))benzoate (T20.8)

To a flask with 3-(cyclopropyl(hydroxy)methyl)-4-(2-fluoro-5-methoxyphenyl))benzoic acid (T20.7), (503 mg, 1.6 mmol) was added 10 mL DCM and 2 mL MeOH. TMS diazomethane (795 μL, 1590 μmol) in ether was then added, and the reaction was stirred at room temperature for 1 hour, and then quenched with a acetic acid. Water was added, and the reaction was extracted with EtOAc. Purification by silica gel chromatography afforded 484 mg of T20.8 (92%) in racemic form.

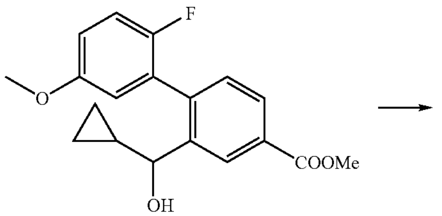

T20.8

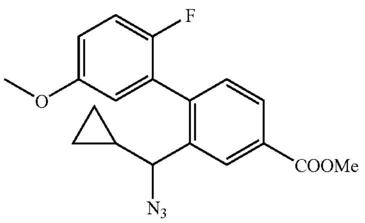

T20.9

Methyl 3-(azido(cyclopropyl)methyl)-4-(2-fluoro-5-methoxyphenyl))benzoate (T20.9)

To methyl 3-(cyclopropyl(hydroxy)methyl)-4-(2-fluoro-5-methoxyphenyl))benzoate (T20.8) (235 mg, 711 μmol) was added DMF 4 mL, then 1,8-diazabicyclo[5.4.0]undec-7-ene (160 μL, 1067 μmol), and diphenylphosphoryl azide (231 μL, 1067 μmol). The mixture was heated to 80° C. After 3 hours, 1.5 equivalents more of each of the 1,8-diazabicyclo[5.4.0]undec-7-ene and diphenylphosphoryl azide were added. The reaction was heated for two more hours and water was then added followed by EtOAc extraction. Purification by silica gel chromatography afforded 260 mg of T20.9 mixed with a non-polar side product. The product thus obtained was carried to the next step without further purification.

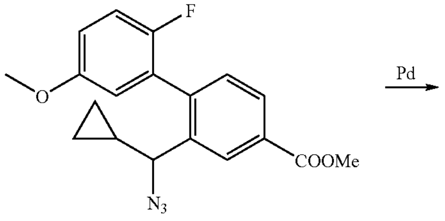

T20.9

-continued

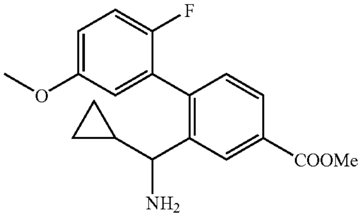

T20.10

Methyl 3-(amino(cyclopropyl)methyl)-4-(2-fluoro-5-methoxyphenyl))benzoate (T20.10)

To a flask with methyl 3-(azido(cyclopropyl)methyl)-4-(2-fluoro-5-methoxyphenyl))benzoate (T20.9) (260 mg, 732 μmol) was added 10% Pd/C (78 mg, 732 μmol), and then 6 mL of MeOH was added. The reaction was purged with hydrogen and stirred under a hydrogen balloon for about 6 hours. The reaction was filtered through a pad of Celite® filter aid, concentrated, and purified by silica gel chromatography to afford 76 mg of the desired product T20.10 (32% for 2 steps).

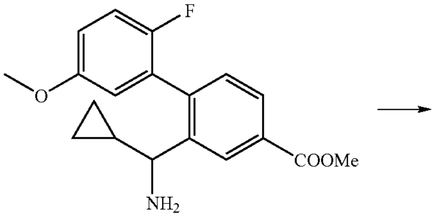

T20.10

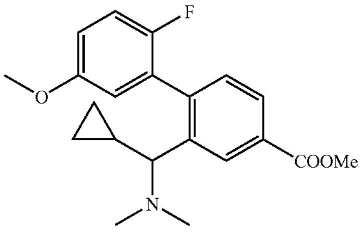

T20.11

Methyl 3-(cyclopropyl(dimethylamino)methyl)-4-(2-fluoro-5-methoxyphenyl)benzoate (T20.11)

To a flask with methyl 3-(amino(cyclopropyl)methyl)-4-(2-fluoro-5-methoxyphenyl))benzoate (T20.10) (76 mg, 231 μmol) were added 2 mL DCM, formaldehyde (70 μL, 923 μmol), and acetic acid (26 μL, 461 μmol). Sodium triacetoxyborohydride (245 mg, 1154 μmol) was then added to the reaction mixture. The reaction was stirred for 1.5 hours and worked up with water and EtOAc. Silica gel chromatography afforded 35 mg of T20.11 (43%).

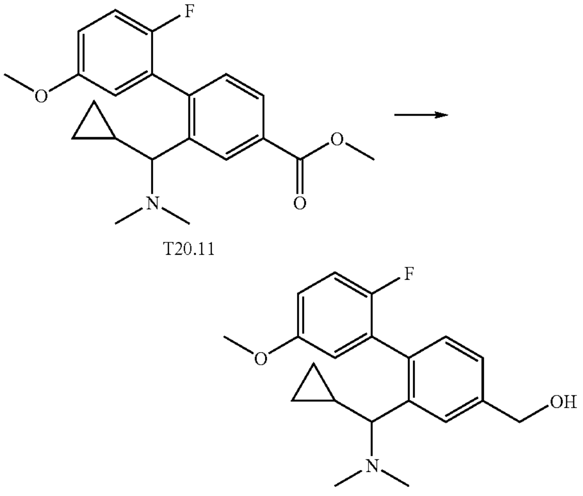

T20.11

T20.12

(3-(Cyclopropyl(dimethylamino)methyl))-4-(2-fluoro-5-methoxyphenyl)phenyl)methanol (T20.12)

To a flask with methyl 3-(amino(cyclopropyl)methyl)-4-(2-fluoro-5-methoxyphenyl))benzoate (T20.11) (35 mg, 98 μmol) was added THF (1.5 mL). The mixture was cooled to 0° C. and then 1M LAH (196 μL, 196 μmol, 1M solution in THF) was added. The temperature was slowly raised to room temperature over 1 hour. Water and a small amount of Rochelle's salt solution were added to quench the reaction and it was then extracted with EtOAc. Silica gel chromatography afforded 26 mg of T20.12 (81%).

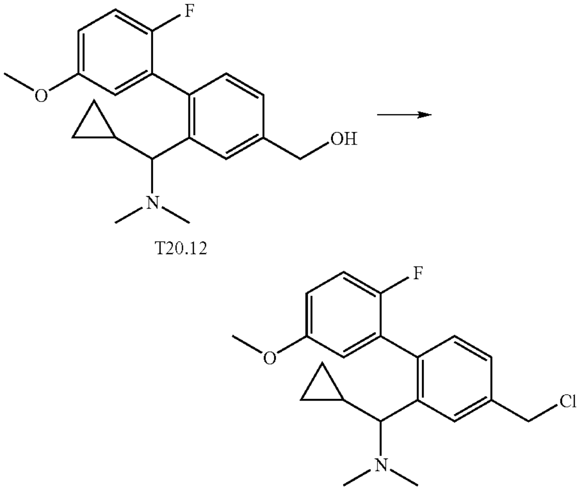

T20.12

T20

(5-(Chloromethyl)-2-(2-fluoro-5-methoxyphenyl)phenyl)(cyclopropyl)-N,N-dimethylmethanamine (T20)

To a flask with (3-(cyclopropyl(dimethylamino)methyl))-4-(2-fluoro-5-methoxyphenyl)phenyl)methanol (T20.12) (26 mg, 79 μmol) was added DCM. The mixture was cooled in an ice-bath and then thionyl chloride (12 μL, 158 μmol) and DMF (6 μL, 79 μmol) were added. The reaction was stirred at room temperature for 1 hour, and then it was concentrated and purified by silica gel chromatography to afford 28 mg of T20 (102%).

Example T21

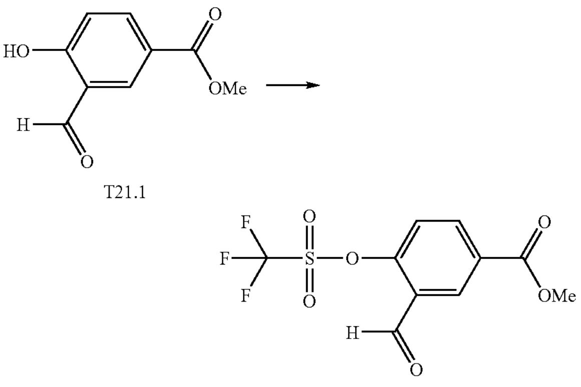

T21.1

T21.2

Methyl 3-formyl-4-(trifluoromethylsulfonyloxy)benzoate (T21.2)

Compound T21.2 was synthesized from methyl 3-formyl-4-hydroxybenzoate T21.1 (commercially available from Aldrich) using a method analogous to the method used to prepare compound T6.9 from T6.8. MS ESI m/e: 313.2 $(M+H)^+$.

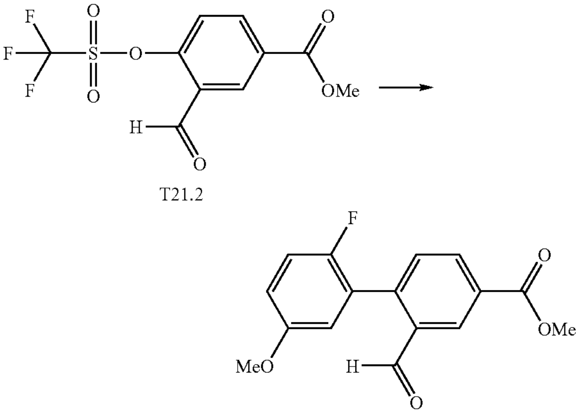

T21.2

T21.3

2'-Fluoro-2-formyl-5'-methoxy-biphenyl-4-carboxylic acid methyl ester (T21.3)

To a round bottle flask, was added methyl 3-formyl-4-(trifluoromethylsulfonyloxy)benzoate (6300 mg, 20 mmol), 2-fluoro-5-methoxyphenylboronic acid (10 g, 61 mmol) (commercially available from Aldrich), potassium phosphate tribasic (6.6 mL, 81 mmol) (granular) and tetrakis(triphenylphosphine)palladium (2.3 g, 2.0 mmol). The flask was flushed with nitrogen, DME was added, and the mixture was heated at 90° C. for 6 hours. The reaction mixture was diluted with EtOAc and water. The organic phase was washed with water and brine and then dried over anhydrous sodium sulfate. After filtration, the organic solvent was removed in vacuo to give a residue which was purified by chromatography to give the product as a yellow solid (5.80 g, 100%). MS ESI m/e: 289.2 $(M+H)^+$.

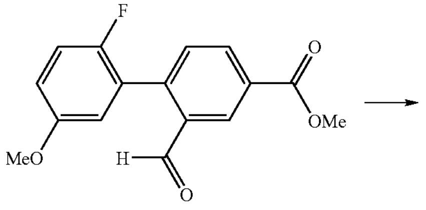

T21.3

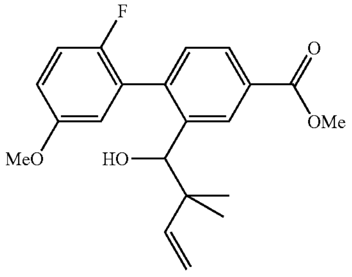

T21.4

2'-Fluoro-2-(1-hydroxy-2,2-dimethyl-but-3-enyl)-5'-methoxy-biphenyl-4-carboxylic acid methyl ester (T21.4)

To a mixed solution of sodium iodide (2080 mg, 13876 μmol), indium (2000 mg, 6938 μmol) and 1-bromo-3-methylbut-2-ene (1616 μL, 13876 μmol) in DMF (30 mL), was added T21.3 (1593 mg, 13876 μmol). The mixture was stirred at room temperature for 1 hour, and then was diluted with EtOAc and water. The organic phase was washed with water and brine and then dried over anhydrous sodium sulfate. After filtration, the organic solvent was removed in vacuo to give a residue which was purified by chromatography to give the product as an oil (2.30 g, 92%). MS ESI m/e: 376.1 $(M+18)^+$.

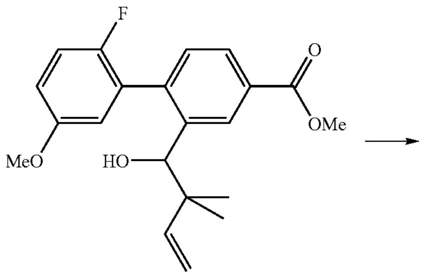

T21.4

-continued

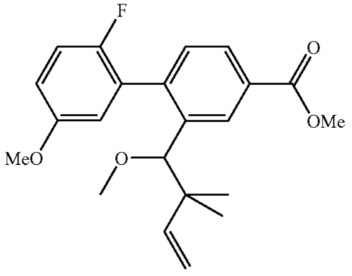

T21.5

2'-Fluoro-5'-methoxy-2-(1-methoxy-2,2-dimethyl-but-3-enyl)-biphenyl-4-carboxylic acid methyl ester (T21.5)

To a solution of T21.4 (1530 mg, 4269 μmol) in DMF (40 mL), was added sodium hydride (60% in oil) (213 μL, 8538 μmol). The mixture was stirred at room temperature for 10 minutes and then methyl iodide (530 μL, 8538 μmol) was added in one portion and the mixture was stirred at room temperature for 30 minutes. Water was added and the mixture was, extracted with EtOAc. The organic phase was washed with water and brine and then dried over anhydrous sodium sulfate. After filtration, the organic solvent was removed in vacuo to give the product as a residue which was purified by chromatography to give the product as an oil (0.75 g, 47%). MS ESI m/e: 373.2 $(M+18)^+$.

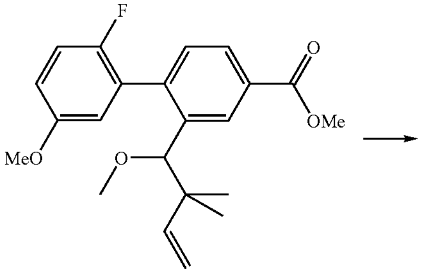

T21.5

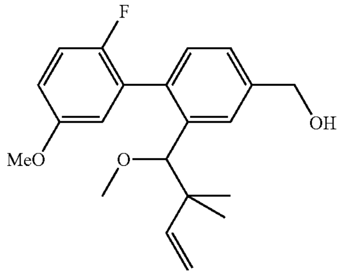

T21.6

[2'-Fluoro-5'-methoxy-2-(1-methoxy-2,2-dimethyl-but-3-enyl)-biphenyl-4-yl]methanol (T21.6)

Compound T21.6 was synthesized from T21.5 by a method analogous to that used to prepare compound T3.4 from T3.3. MS ESI m/e: 345.2 $(M+H)^+$.

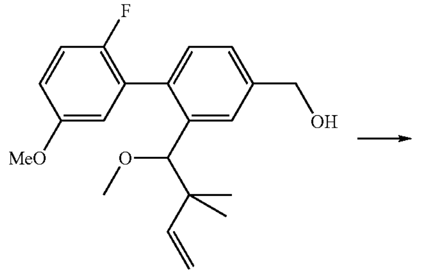

T21.6

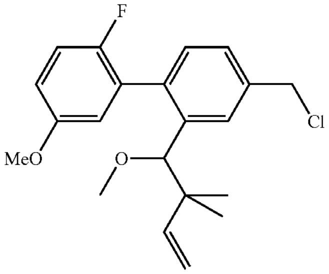

T21

4-Chloromethyl-2'-fluoro-5'-methoxy-2-(1-methoxy-2,2-dimethyl-but-3-enyl)-biphenyl (T21)

Compound T21 was synthesized from T21.6 by a method analogous to the method used to prepare compound T3 from T3.4. MS ESI m/e: 363.2 $(M+H)^+$.

Example T22

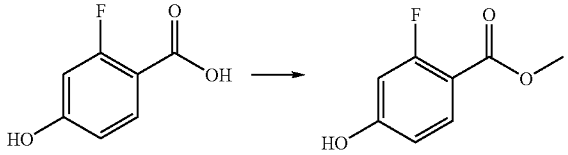

T22.1

Methyl 2-fluoro-4-hydroxybenzoate (T22.1)

To a round bottom containing 2-fluoro-4-hydroxybenzoic acid (5.34 g, 34.19 mmol) (commercially available from Matrix Scientific and TCI America) was added a cold solution of MeOH (50 mL) and sulfuric acid (2.0 mL). The mixture was heated to 80° C. and monitored with TLC. After 20.5 hours, the solvent was removed, and the mixture was diluted with diethyl ether. The organic phase was washed carefully two times with saturated. aqueous $NaHCO_3$, once with brine, and then dried over anhydrous sodium sulfate. After filtration, the organic solvent was removed in vacuo to yield T22.1 as a white solid (5.82, 85% yield). $^1$H NMR (400 MHz, DMSO-$d_6$) δ ppm 10.79 (1H, s), 7.75 (1H, t, J=8.8 Hz), 6.69 (1H, dd, J=8.6, 2.3 Hz), 6.62 (1H, dd, J=13.1, 2.2 Hz), 3.78 (3H, s).

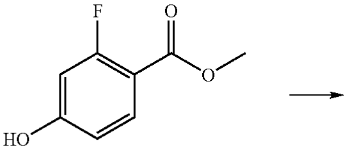

T22.1

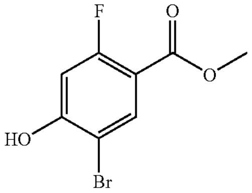

T22.2

Methyl 5-bromo-2-fluoro-4-hydroxybenzoate (T22.2)

To a solution of T22.1 (2.03 g, 11.9 mmol) in acetic acid (65 mL) was added a pre-mixed solution of bromine (0.67 mL, 13.1 mmol) in acetic acid (10 mL). The mixture was stirred at 45° C. and monitored with TLC and LC-MS. After 18 hours, the reaction mixture was concentrated under reduced pressure. Brine was added to the residue, and the mixture was extracted three times with EtOAc. The combined organic layers were dried over anhydrous magnesium sulfate, filtered and concentrated to provide T22.2 as a white solid (2.12 g, 71% yield). $^1$H NMR (400 MHz, $CDCl_3$) δ ppm 8.13 (1H, d, J=7.4 Hz), 6.82 (1H, d, J=11.3 Hz), 6.04 (1H, s), 3.92 (3H, s).

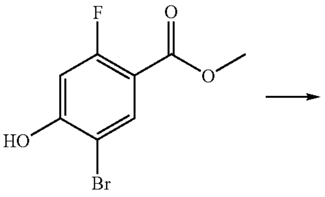

T22.2

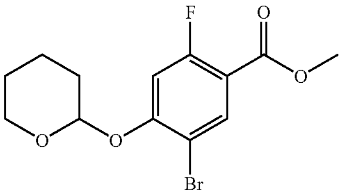

T22.3

Methyl 5-bromo-2-fluoro-4-(tetrahydro-2H-pyran-2-yloxy)benzoate (T22.3)

To a round bottom containing T22.2 (13.15 g, 52.8 mmol) in dry DCM (90 mL) was added 3,4-dihydro-2H-pyran (10 mL, 110 mmol) followed by PPTS (0.13 g, 0.53 mmol). The reaction mixture was heated to a gentle reflux (50° C.) and monitored with TLC and LC-MS. After 24 hours, the reaction was concentrated under reduced pressure and then diluted with MeOH. After concentration, the residue was heated in a round bottom flask containing MeOH on the rotary evaporator (without vacuum.) at 40° C. After about 30 minutes, the solution was concentrated to a volume of about 5 mL. After cooling to room temperature, the white solid was filtered and rinsed once with MeOH to yield T22.3 (13.35 g, 76% yield). $^1$H NMR (400 MHz, $CDCl_3$) δ ppm 8.25 (1H, m), 6.96 (1H, d, J=12.5 Hz), 5.56 (1H, m), 3.91 (3H, s), 3.79 (1H, td, J=11.1, 2.5 Hz), 3.65 (1H, d, J=10.6 Hz), 2.23 (2H, m), 1.96 (3H, m), 1.68 (1H, m).

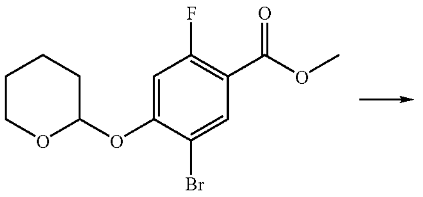

T22.3

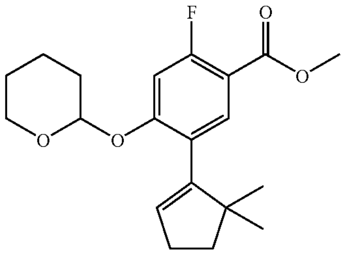

T22.4

Methyl 5-(5,5-dimethylcyclopent-1-enyl)-2-fluoro-4-(tetrahydro-2H-pyran-2-yloxy)benzoate (T22.4)

A stirred mixture of T22.3 (10.33 g, 31.0 mmol), ground S-Phos (2.55 g, 6.21 mmol), palladium acetate (0.70 g, 3.11 mmol), and potassium phosphate, tribasic (16.49 g, 77.7 mmol) in DMF (75 mL) and water (4 mL) was purged with argon and placed under vacuum and the process repeated three times. Before heating, 2-(5,5-dimethylcyclopent-1-enyl)-4,4,5,5-tetramethyl-1,3,2-dioxaborolane (T6.3) (8.96 g, 40.4 mmol) was added via syringe. The mixture was then heated at 75° C. After 21 hours, the reaction was cooled to room temperature, diluted with water, and extracted three times with EtOAc. The organic layers were combined and washed twice with brine. After drying over anhydrous sodium sulfate and filtration, the organic solvent was removed under reduced pressure. The residue was purified by silica gel flash chromatography (0-10% EtOAc/hexane) to yield T22.4 (5.65 g, 52% yield). $^1$H NMR (400 MHz, $CDCl_3$) δ ppm 7.63 (1H, d, J=8.6 Hz), 6.93 (1H, d, J=13.3 Hz), 5.55 (1H, t, J=2.3 Hz), 5.43 (1H, t, J=2.7 Hz), 3.90 (3H, s), 3.82 (1H, m), 3.67 (1H, m), 2.41 (2H, td, J=7.0, 2.3 Hz), 1.97 (5H, m), 1.79 (3H, m), 1.07 (6H, d, J=13.7 Hz).

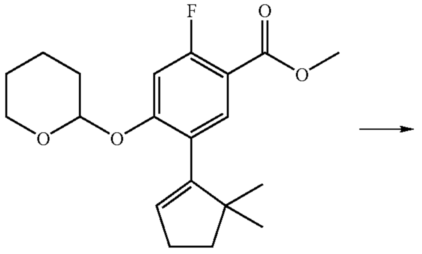

T22.4

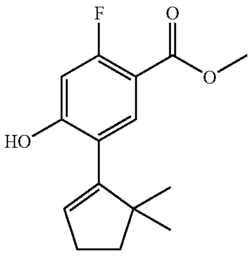

T22.5

Methyl 5-(5,5-dimethylcyclopent-1-enyl)-2-fluoro-4-hydroxybenzoate (T22.5)

To a stirred mixture of T22.4 (5.65 g, 16.2 mmol) in MeOH (60 mL) was added PPTS (0.42 g, 1.69 mmol). The mixture was heated to 50° C. and monitored with TLC and LCMS. After 19 hours, the organic solvent was removed under reduced pressure, and the residue was then purified on silica gel (0-15% EtOAc in hexanes) to yield T22.5 as a white solid (3.47 g, 81% yield). $^1$H NMR (500 MHz, $CDCl_3$) δ ppm 7.69 (1H, d, J=8.3 Hz), 6.71 (1H, d, J=12.0 Hz), 5.93 (1H, d, J=1.7 Hz), 5.80 (1H, t, J=2.4 Hz), 3.90 (3H, s), 2.54 (2H, m), 1.93 (2H, t, J=7.1 Hz), 1.11 (6H, s).

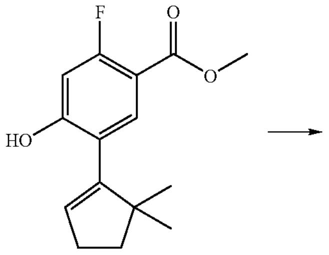

T22.5

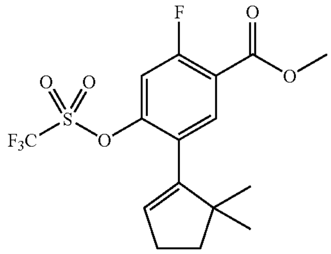

T22.6

Methyl 5-(5,5-dimethylcyclopent-1-enyl)-2-fluoro-4-(trifluoromethylsulfonyloxy)benzoate (T22.6)

To a stirred solution of T22.5 (0.80 g, 3.02 mmol) in dry DCM (15 mL) was added TEA (1.0 mL, 7.19 mmol) and 4-dimethylaminopyridine (38.1 mg, 0.312 mmol). After about 20 minutes, N-phenyl-bis(trifluoromethanesulfonimide) (1.30 g, 3.64 mmol) was added in portions. Upon complete addition, the solution was stirred at room temperature and monitored with TLC and LC-MS. After 19 hours, the organic solvent was removed under reduced pressure and the resulting residue was purified with silica gel chromatography using 0-10% EtOAc in hexanes to yield T22.6 as a colorless oil (1.05 g, 88% yield). $^1$H NMR (400 MHz, $CDCl_3$) δ ppm 7.84 (1H, d, J=7.8 Hz), 7.13 (1H, d, J=10.2 Hz), 5.79 (1H, t, J=2.3 Hz), 3.96 (3H, s), 2.47 (2H, td, J=7.0, 2.3 Hz), 1.91 (2H, t, J=7.0 Hz), 1.08 (6H, s).

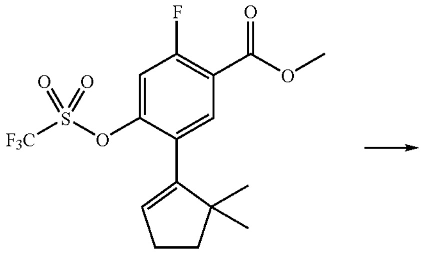

T22.6

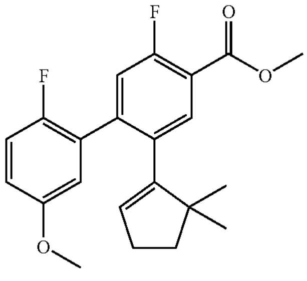

T22.7

Methyl 2-(5,5-dimethyl-1-cyclopenten-1-yl)-2',5-difluoro-5'-(methyloxy)-1,1'-biphenyl-4-carboxylate (T22.7)

To a stirred solution of T22.6 (1.05 g, 2.65 mmol) in DMF (5 mL) at 23° C. was added 2-fluoro-5-methoxyphenylboronic acid (0.90 g, 5.32 mmol) (commercially available from Aldrich) and potassium carbonate (1.10 g, 7.96 mmol) followed by tetrakis(triphenylphosphine)palladium (0.31 g, 0.27 mmol). The mixture was heated to 90° C. After 17 hours, the mixture was cooled to room temperature and then diluted with water. After extracting three times with EtOAc, the mixture was concentrated in vacuo and then purified on silica gel (0%-10% EtOAc/hexane) to give T22.7 as a clear oil that was used without further purification (0.92 g, 93% yield). $^1$H NMR (400 MHz, $CDCl_3$) δ ppm 7.79 (1H, d, J=7.4 Hz), 7.13 (1H, d, J=11.3 Hz), 6.99 (1H, t, J=9.0 Hz), 6.84 (1H, dt, J=8.7, 3.7 Hz), 6.78 (1H, dd, J=5.9, 3.1 Hz), 5.55 (1H, s), 3.96 (3H, s), 3.79 (3H, s), 2.27 (2H, td, J=7.1, 2.5 Hz), 1.67 (2H, t, J=7.0 Hz), 0.84 (6H, s).

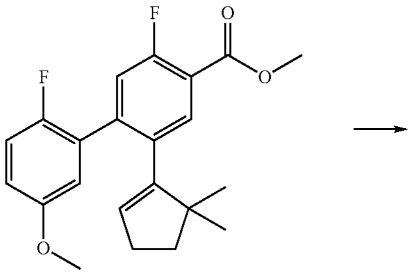

T22.7

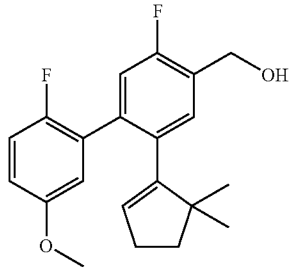

T22.8

(2-(5,5-Dimethyl-1-cyclopenten-1-yl)-2',5-difluoro-5'-(methyloxy)-1,1'-biphenyl-4-yl)methanol (T22.8)

To a cooled solution of T22.7 (0.92 g, 2.47 mmol) in dry THF (15 mL) at 0° C. was added LAH (1.0 M in THF) (5.0 mL, 5.0 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by flash chromatography (silica gel 60, eluted with 0%-50% EtOAc in hexanes). Fractions containing the desired product were combined and concentrated to provide T22.8 as a colorless oil (0.70 g, 82% yield). $^1$H NMR (500 MHz, $CDCl_3$) δ ppm 7.30 (1H, m), 7.05 (1H, dd, J=10.6, 1.1 Hz), 6.97 (1H, t, J=8.9 Hz), 6.83 (2H, m), 5.52 (1H, td, J=2.4, 0.9 Hz), 4.81 (2H, s), 3.76 (3H, s), 2.25 (2H, td, J=7.1, 2.4 Hz), 1.76 (1H, br. s.), 1.69 (2H, m), 0.85 (6H, s).

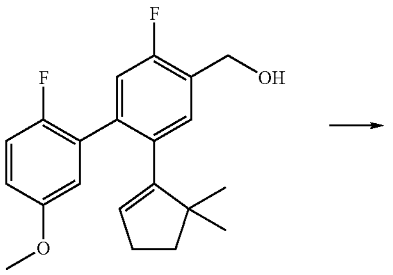

T22.8

-continued

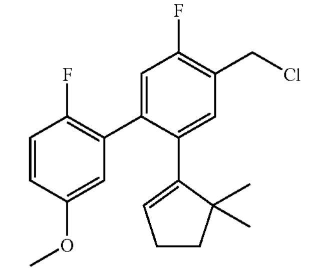

T22

4-(Chloromethyl)-2-(5,5-dimethyl-1-cyclopenten-1-yl)-2',5-difluoro-5'-(methyloxy)-1,1'-biphenyl (T22)

To a solution of T22.8 (0.17 g, 0.48 mmol) in dry DCM (2.0 mL) and dry DMF (0.020 mL) was added thionyl chloride (0.080 mL, 1.1 mmol) dropwise at 0° C. The resulting solution was warmed to room temperature and monitored with TLC and LCMS. After 45 minutes, the reaction was concentrated and then purified by silica gel flash chromatography (0-5% EtOAc/hexane) to afford T22 as a colorless oil (0.16 g, 93% yield). $^1$H NMR (400 MHz, $CDCl_3$) δ ppm 7.29 (1H, d, J=7.8 Hz), 7.08 (1H, d, J=10.2 Hz), 6.98 (1H, t, J=9.0 Hz), 6.85 (2H, m), 5.56 (1H, s), 4.69 (2H, s), 3.77 (3H, s), 2.27 (2H, td, J=7.0, 2.7 Hz), 1.68 (2H, t, J=7.0 Hz), 0.86 (6H, s).

Example T23

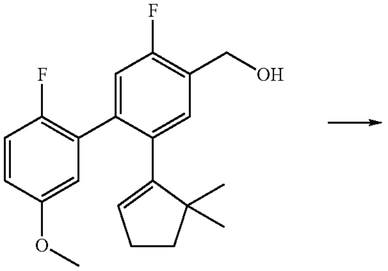

T22.8

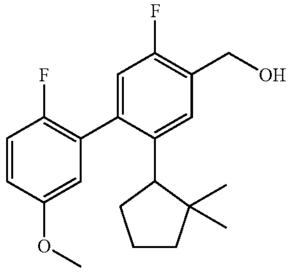

T23.1

-continued

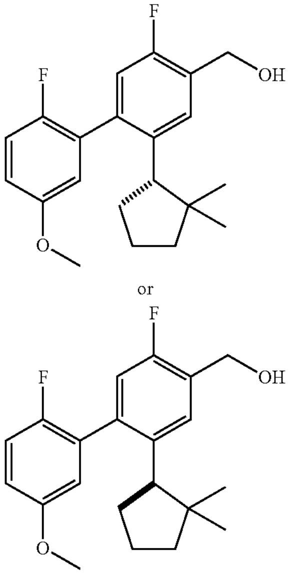

or

T23.2 and T23.3

(2-(2,2-Dimethylcyclopentyl)-2',5-difluoro-5'-(methyloxy)-1,1'-biphenyl-4-yl)methanol (T23.1)

To a dry flask containing T22.8 (0.70 g, 2.03 mmol) in dry MeOH (5 mL) and EtOAc (3 mL) was added palladium, 10 wt. % on activated carbon (77.2 mg). After purging, the mixture was stirred under an atmosphere of hydrogen at room temperature. After 4.5 hours, the mixture was filtered through Celite® filter aid. After concentration, the residue was identified as T23.1 as a mixture of enantiomers and rotamers (0.31 g, 45% yield). Chiral separation of T23.1 was accomplished on Chiracel-OJ (2% IPA in hexane) to provide T23.2 (peak 1) and T23.3 (peak 2).

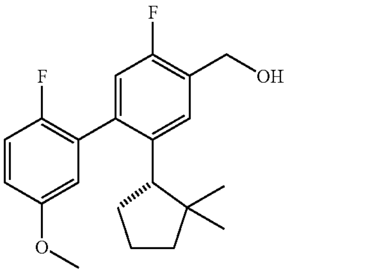

or

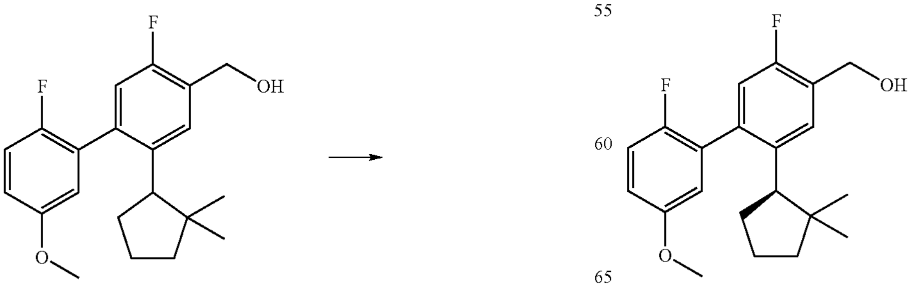

T23.1

T23.2

-continued

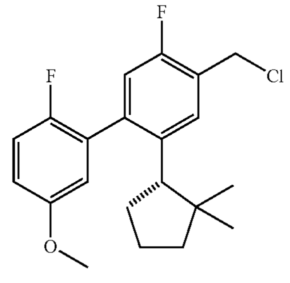

or

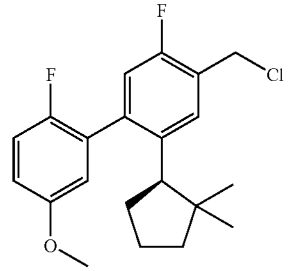

T23

4-(Chloromethyl)-2-((1S)-2,2-dimethylcyclopentyl)-2',5-difluoro-5'-(methyloxy)-1,1'-biphenyl or 4-(chloromethyl)-2-((1R)-2,2-dimethylcyclopentyl)-2',5-difluoro-5'-(methyloxy)-1,1'-biphenyl (T23)

To a solution of T23.2 (0.71 g, 2.05 mmol) in dry DCM (23 mL) and dry DMF (0.18 mL) was added thionyl chloride (0.3 mL, 4.1 mmol) dropwise at 0° C. The resulting solution was warmed to room temperature and monitored with TLC and LCMS. After 45 minutes, the reaction was concentrated and then purified by silica gel flash chromatography (0-5% EtOAc/hexane) to yield T23 as a colorless oil (0.73 g, 97% yield). $^1$H NMR (400 MHz, $CDCl_3$) δ ppm 7.46 (1H, m), 7.11 (3H, m), 6.75 (1H, m), 4.78 (2H, m), 3.80 (3H, s), 2.91 (1H, m), 2.20 (2H, m), 1.87 (2H, m), 1.59 (1H, m), 1.43 (1H, m), 0.77 (3H, m), 0.64 (3H, m).

Asymmetric Synthesis of T23.2 or T23.3

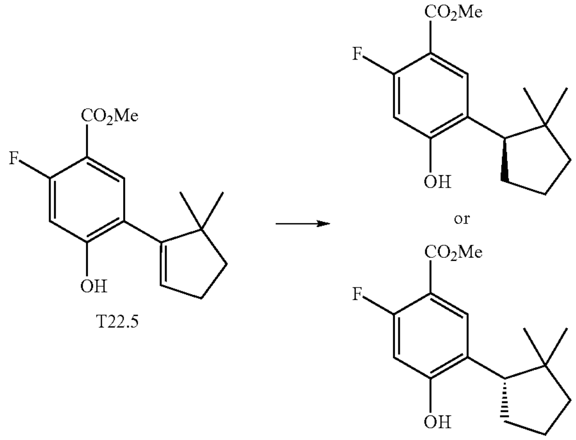

T22.5 or

T23.4 or T23.5

(R)-Methyl 5-(2,2-dimethylcyclopentyl)-2-fluoro-4-hydroxybenzoate or (S)-methyl 5-(2,2-dimethylcyclopentyl)-2-fluoro-4-hydroxybenzoate (T23.4 or T23.5)

A mixture of $Rh(COD)_2BF_4$ (Stern Chemical) 35138-22-8, 36.95 mg, 0.091 mmol) and (R)-1-[(S)-2-(R)-(Ditertbutylphosphino)ferrocenyl]ethyl-bis-(3,5-bistrifluoromethylphenyl)phosphine (Solvias, SL-J210-1, 81.5 mg, 0.100 mmol), was stirred in THF (75 mL) under $N_2$ for 60 minutes and a dark red solution formed. To the resulting solution was added T22.5 (8.2 g, 45.4 mmol) and TEA (10 mol %, 0.63 mL, 4.54 mmol). The resulting solution was filled with $H_2$ (200 psi) three times and stirred at room temperature under 200 psi $H_2$ for 2 hours. The resulting mixture was passed through a short plug of silica gel, eluting with 1:1 hexane/EtOAc and then concentrated affording the desired product as a white solid (83% yield (6.8 g), 99.3% ee). The other enantiomer may be obtained as the majority product using the enantiomer of the ferrocenyl compound.

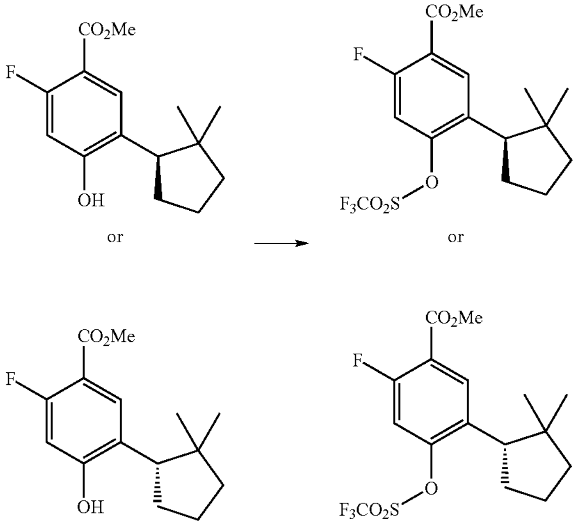

or or

T23.4 or T23.5 T23.6 or T23.7

(R)-Methyl 5-(2,2-dimethylcyclopentyl)-2-fluoro-4-(trifluoromethylsulfonyloxy)benzoate or (S)-methyl 5-(2,2-dimethylcyclopentyl)-2-fluoro-4-(trifluoromethylsulfonyloxy)benzoate (T23.6 or T23.7)

To a stirred solution of T23.4 or T23.5 (4.02 g, 15.1 mmol) in dry DCM (50 mL) was added TEA (4.2 mL, 30.2 mmol) and DMAP (0.19 g, 1.52 mmol). After 20 minutes, N-phenyl-bis(trifluoromethanesulfonimide) (5.94 g, 16.6 mmol) was added in portions. Upon complete addition, the solution was stirred at room temperature and monitored with TLC and LC-MS. After 4 hours, the mixture was washed twice with brine, dried over anhydrous magnesium sulfate. After filtration and concentration, the residue was purified with silica gel chromatography (0-10% EtOAc in hexanes) to yield T23.6 or T23.7 as a colorless oil (5.51, 92%). $^1$H NMR (500 MHz, $CDCl_3$) δ ppm 7.97 (1H, d, J=7.8 Hz), 7.14 (1H, d, J=10.0 Hz), 3.96 (3H, s), 3.13 (1H, dd, J=10.1, 8.2 Hz), 2.14 (2H, m), 1.96 (2H, m), 1.70 (2H, m), 1.00 (3H, s), 0.69 (3H, s).

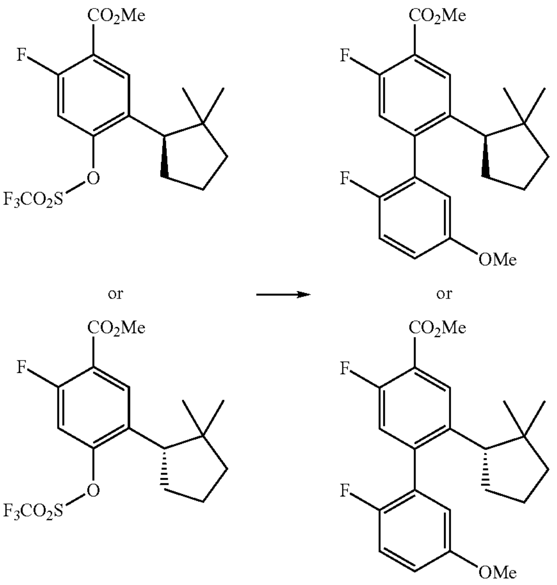

or or

T23.6 or T23.7

T23.8 or T23.9

Methyl 2-((1R)-2,2-dimethylcyclopentyl)-2',5-difluoro-5'-(methyloxy)-1,1'-biphenyl-4-carboxylate or methyl 2-((1S)-2,2-dimethylcyclopentyl)-2',5-difluoro-5'-(methyloxy)-1,1'-biphenyl-4-carboxylate (T23.8 or T23.9)

To a stirred solution of T23.6 or T23.7 (5.51 g, 13.8 mmol) in DMF (25 mL) at 23° C. was added 2-fluoro-5-methoxyphenylboronic acid (4.71 g, 27.7 mmol) (commercially available from Aldrich and potassium carbonate (5.74 g, 41.6 mmol) followed by tetrakis(triphenylphosphine)palladium (1.60 g, 1.39 mmol). The mixture was heated to 90° C. After 3.5 hours, the mixture was cooled to room temperature and then diluted with water. After extracting three times with EtOAc, the mixture was concentrated in vacuo and then purified on silica gel (0%-10% EtOAc/hexane) to yield T23.8 or T23.9 as an oil that solidified (5.11 g, 99%).

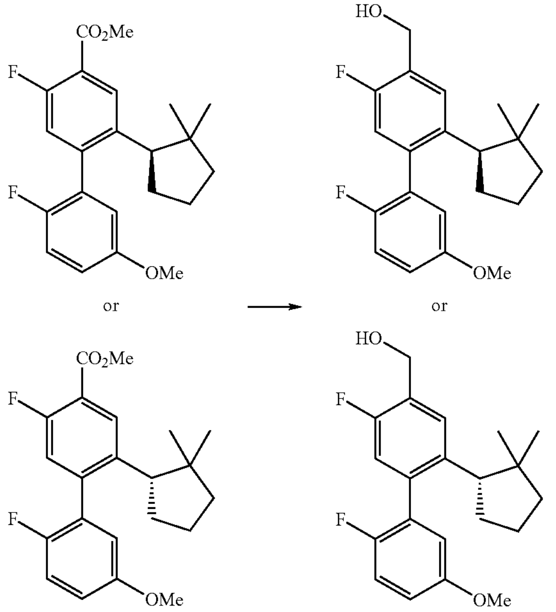

or or

T23.8 or T23.9

T23.2 or T23.3

(2-((1R)-2,2-Dimethylcyclopentyl)-2',5-difluoro-5'-(methyloxy)-1,1'-biphenyl-4-yl)methanol or (2-((1S)-2,2-dimethylcyclopentyl)-2',5-difluoro-5'-(methyloxy)-1,1'-biphenyl-4-yl)methanol (T23.2 or T23.3)

To a cooled solution of T23.8 or T23.9 (5.11 g, 13.6 mmol) in dry THF (40 mL) at 0° C. was added LAH, (1.0 M in THF) (27.3 mL, 27.30 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by silica gel chromatography (0-25% EtOAc in hexanes) to yield T23.2 or T23.3 (this enantiomer corresponds to peak one from the chiral separation of T23.1 on the OJ column) as a colorless oil (3.94 g, 83%). $^{1}$H NMR (400 MHz, $CDCl_3$) δ ppm 7.50 (1H, m), 7.11 (3H, m), 6.85 (1H, m), 4.81 (2H, s), 3.80 (3H, s), 2.92 (1H, m), 2.19 (2H, m), 1.83 (1H, m), 1.72 (1H, m), 1.59 (2H, m), 1.42 (1H, m), 0.82 (3H, m), 0.65 (3H, m).

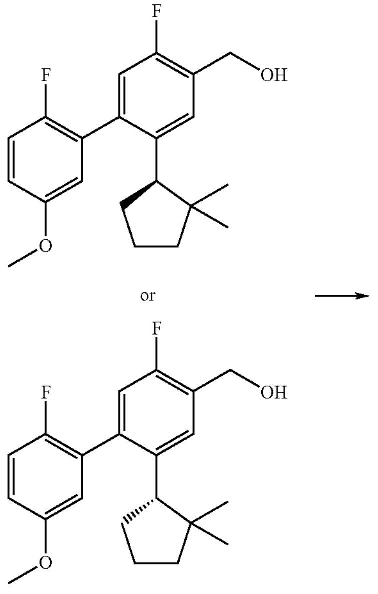

or

T23.2 or T23.3

-continued

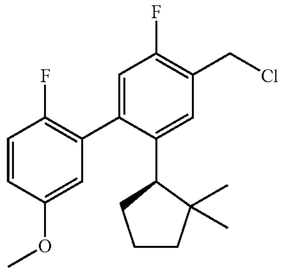

or

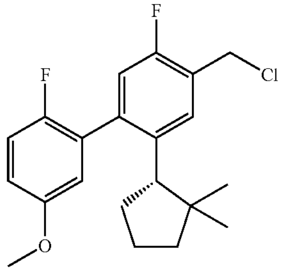

T23A or T23B 4-(Chloromethyl)-2-((1R)-2,2-dimethylcyclopentyl)-2',5-difluoro-5'-(methyloxy)-1,1'-biphenyl or 4-(chloromethyl)-2-((1S)-2,2-dimethylcyclopentyl)-2',5-difluoro-5'-(methyloxy)-1,1'-biphenyl (T23A or T23B)

To a solution of T23.2 or T23.3 (40.0 mg, 0.12 mmol) in dry DCM (2.0 mL) and dry DMF (0.010 mL) was added thionyl chloride (0.020 mL, 0.27 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T23A or T23B as a colorless oil (39.9 mg, 95% yield). $^1$H NMR (400 MHz, $CDCl_3$) δ ppm 7.46 (1H, m), 7.11 (3H, m), 6.75 (1H, m), 4.78 (2H, m), 3.80 (3H, s), 2.91 (1H, m), 2.20 (2H, m), 1.87 (2H, m), 1.59 (1H, m), 1.43 (1H, m), 0.77 (3H, m), 0.64 (3H, m).

Example T24

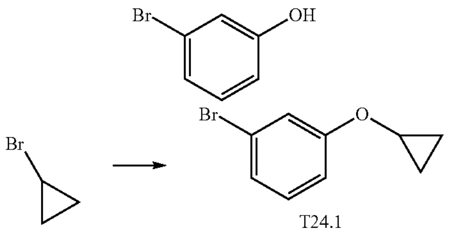

T24.1

3-Bromophenyl cyclopropyl ether (T24.1)

To a solution of 3-bromophenol (0.57 g, 3.29 mmol) (commercially available from Aldrich) in dry DMF (5.0 mL) was added cyclopropyl bromide (0.53 mL, 6.62 mmol) (commercially available from Aldrich), sodium iodide (50.1 mg, 0.334 mmol), and cesium carbonate (3.2 g, 9.86 mmol). The reaction mixture was heated in a pressure tube to 150° C. After 19 hours, the reaction was cooled to room temperature then diluted with EtOAc, washed with water, and extracted three times with EtOAc. The combined organic layers were dried over sodium sulfate, filtered, and concentrated. The residue was purified by silica gel flash chromatography (0-5% EtOAc/hexane) to afford T24.1 as a colorless oil (144 mg, 21% yield). $^1$H NMR (400 MHz, $CDCl_3$) δ ppm 7.29 (1H, m), 7.19 (2H, m), 6.99 (1H, d, J=7.8 Hz), 3.74 (1H, ddd, J=8.9, 5.8, 3.3 Hz), 0.81 (4H, ddd, J=11.2, 9.0, 8.8 Hz.).

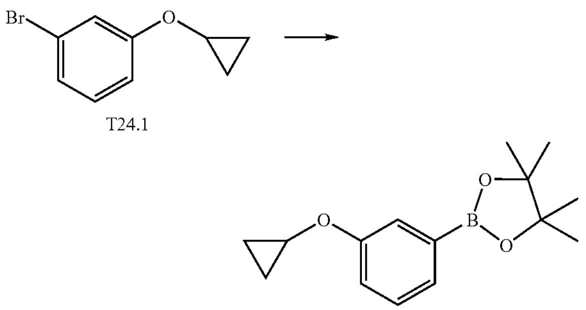

T24.1

T24.2

2-(3-(Cyclopropyloxy)phenyl)-4,4,5,5-tetramethyl-1,3,2-dioxaborolane (T24.2)

A stirred mixture of T24.1 (0.144 g, 0.676 mmol), bis(pinacolato)diboron (0.189 g, 0.745 mmol), potassium acetate (0.2007 g, 2.04 mmol), and dichloro[1,1'-bis(diphenylphosphino)ferrocene]palladium (II) DCM adduct (25.3 mg, 0.0346 mmol) in dry 1,4-dioxane (3.0 mL) was purged three times with argon and placed under vacuum three times. The mixture was heated to 100° C., and monitored with LC-MS and TLC. After 21 hours, the reaction was cooled to room temperature and filtered through Celite® filter aid. The organic solvent was removed under reduced pressure. The residue was purified by silica gel flash chromatography (0-10% EtOAc/hexane) to afford T24.2 as a colorless oil (72 mg, 41% yield). $^1$H NMR (400 MHz, $CDCl_3$) δ ppm 7.51 (1H, d, J=2.7 Hz), 7.44 (1H, d, J=7.0 Hz), 7.34 (1H, m), 7.14 (1H, dd, J=7.6, 2.2 Hz), 3.80 (1H, ddd, J=8.8, 5.9, 3.3 Hz), 1.36 (12H, s), 0.82 (4H, m).

T7.6

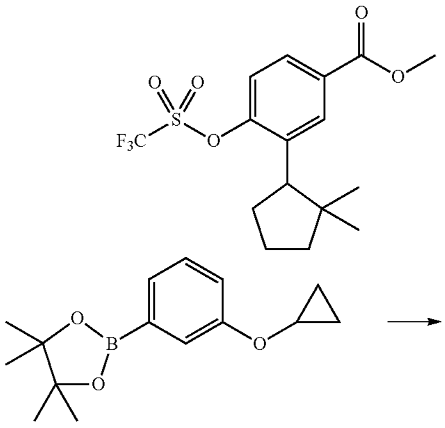

T24.2

-continued

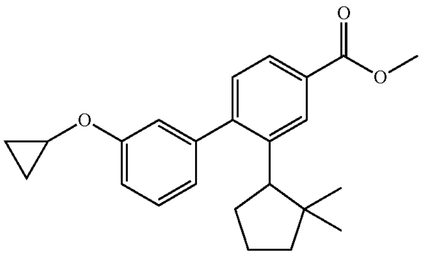

T24.3

Methyl 3'-(cyclopropyloxy)-2-(2,2-dimethylcyclopentyl)-1,1'-biphenyl-4-carboxylate (T24.3)

To a stirred solution of T7.6F (438.2 mg, 1.15 mmol) in dry DMF (5.0 mL) at 23° C. was added potassium carbonate (480.3 mg, 3.47 mmol) followed by tetrakis(triphenylphosphine)palladium (140.2 mg, 0.121 mmol). The mixture was purged three times with argon and placed under vacuum three times. Before heating, T24.2 (523.1 mg, 2.01 mmol) was added via syringe and then the mixture was heated to 90° C. After 19 hours, LCMS showed reaction was complete. The mixture was cooled to room temperature and then diluted with water. After extracting three times with EtOAc, the mixture was concentrated in vacuo and then purified on silica gel (0%-10% EtOAc/hexane) to afford T24.3 as a colorless oil that was used without further purification (411.5 mg, 98% yield). MS ESI (pos.) m/e: 365.0 $(M+H)^+$.

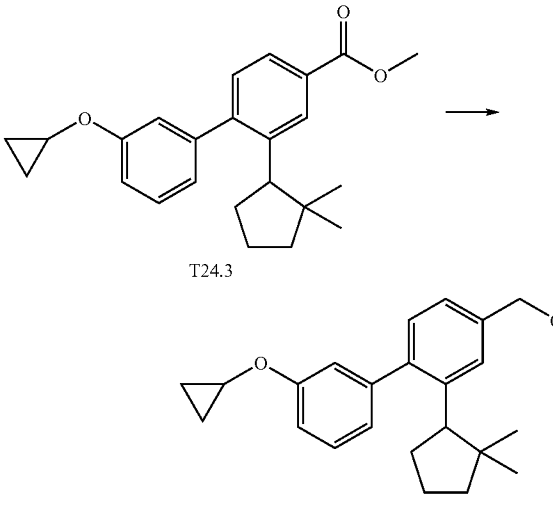

T24.3

T24.4

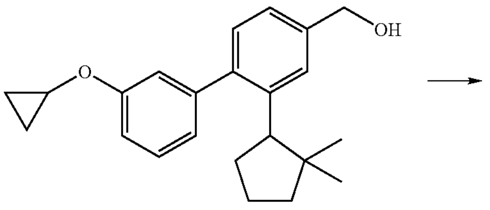

T24.4

-continued

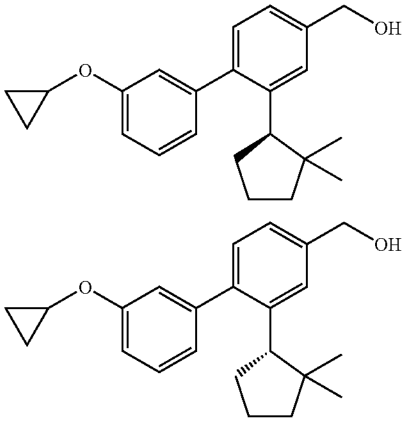

T24.5 and T24.6

(3'-(Cyclopropyloxy)-2-(2,2-dimethylcyclopentyl)-1,1'-biphenyl-4-yl)methanol (T24.4)

To a cooled solution of T24.3 (0.4115 g, 1.129 mmol) in dry THF (10 mL) at 0° C. was added LAH (1.0M in THF) (2.30 mL, 2.3 mmol) dropwise. Upon complete addition, the reaction was maintained at 0° C. and was monitored by TLC and LCMS. After 45 minutes, 1N NaOH was added to quench the reaction. The resulting mixture was extracted three times with EtOAc. After drying over anhydrous magnesium sulfate, filtration, and concentration, the residue was purified by flash chromatography ($SiO_2$ gel 60, eluted with 0%-50% EtOAc in hexanes). Fractions containing the desired product were combined and concentrated to a colorless oil as T24.4 (317.1 mg, 83% yield). MS ESI (pos.) m/e: 319.0 $(M-H_2O)^+$. Chiral separation of T24.4 was accomplished on Chiracel-OD (3% IPA in hexane) to provide T24.5 (peak 1) and T24.6 (peak 2).

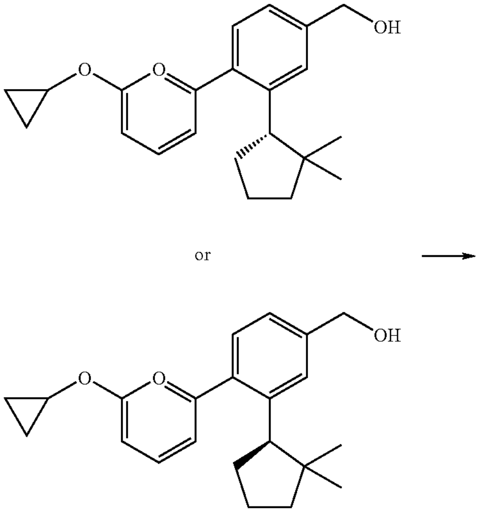

or

T24.6

-continued

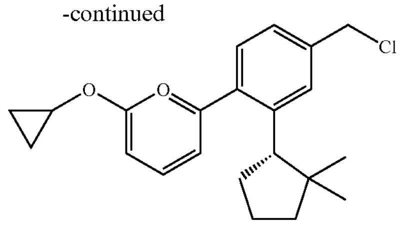

or

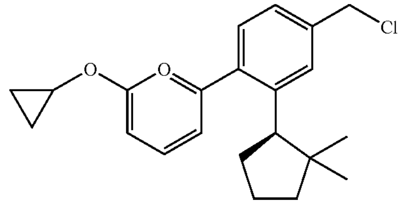

T24.7

4-(Chloromethyl)-3'-(cyclopropyloxy)-2-((1S)-2,2-dimethylcyclopentyl)-1,1'-biphenyl or 4-(chloromethyl)-3'-(cyclopropyloxy)-2-((1R)-2,2-dimethylcyclopentyl)-1,1'-biphenyl (T24.7)

To a solution of T24.6 (0.1335 g, 0.397 mmol) in dry DCM (4 mL) and dry DMF (0.03 mL) was added thionyl chloride (0.07 mL, 0.96 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T24.7 as a colorless oil (118.3 mg, 84% yield). $^1$H NMR (400 MHz, $CDCl_3$) δ ppm 7.39 (1H, d, J=1.6 Hz), 7.34 ( ), 3.78 (1H, m), 3.15 (1H, dd, J=10.4, 3H, m), 7.01 (1H, dd, J=7.8, 3.1 Hz), 6.98 (1H, m), 6.85 (1H, d, J=7.4 Hz), 4.69 (2H, m 8.4 Hz), 2.13 (2H, m), 1.88 (1H, m), 1.72 (1H, m), 1.59 (1H, m), 1.41 (1H, m), 0.82 (6H, m), 0.58 (3H, s).

Example T25

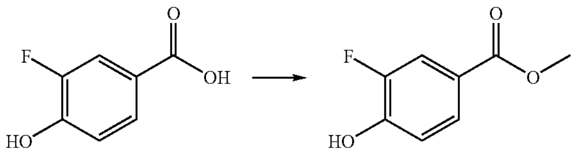

T25.1

Methyl 3-fluoro-4-hydroxybenzoate (T25.1)

To a round bottom flask containing 3-fluoro-4-hydroxybenzoic acid (5.03 g, 32.22 mmol) (commercially available from Aldrich) was added a cold solution of MeOH (50.0 mL) and sulfuric acid (2.0 mL). The mixture was heated to 80° C. and monitored with TLC. After 20.5 hours, the solvent was removed and the mixture was diluted with diethyl ether. The organic phase was washed carefully twice with saturated aqueous $NaHCO_3$ and once with brine. The organic phase was then dried over anhydrous sodium sulfate. After filtration, the organic solvent was removed in vacuo to afford T25.1 as a white solid (4.79 g, 87% yield). $^1$H NMR (400 MHz, $CDCl_3$) δ ppm 7.81 (2H, m), 7.06 (1H, t, J=8.4 Hz), 5.62 (1H, d, J=4.3 Hz), 3.91 (3H, s).

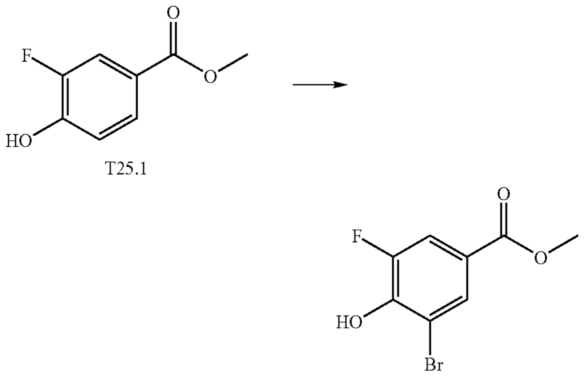

T25.1

T25.2

Methyl 3-bromo-5-fluoro-4-hydroxybenzoate (T25.2)

Bromine (1.60 mL, 31.1 mmol) was added dropwise with stirring over 30 minutes to an ice-cooled solution of T25.1 (4.79 g, 28.1 mmol) in a 1:1 mixture of DCM (20 mL) and acetic acid (20 mL). Upon complete addition, the reaction mixture was allowed to warm to room temperature and monitored with TLC and LC-MS. After stirring at room temperature for 40 hours, the mixture was diluted with EtOAc, and then the resulting solution was washed twice with aqueous saturated $Na_2SO_3$, once with water, and once with brine. After drying over anhydrous magnesium sulfate, filtration, and concentration, the white solid T25.2 was obtained 6.69 g, 95% yield). $^1$H NMR (400 MHz, $CDCl_3$) δ ppm 8.05 (1H, m), 7.75 (1H, dd, J=10.6, 2.0 Hz), 6.12 (1H, s), 3.94 (3H, s).

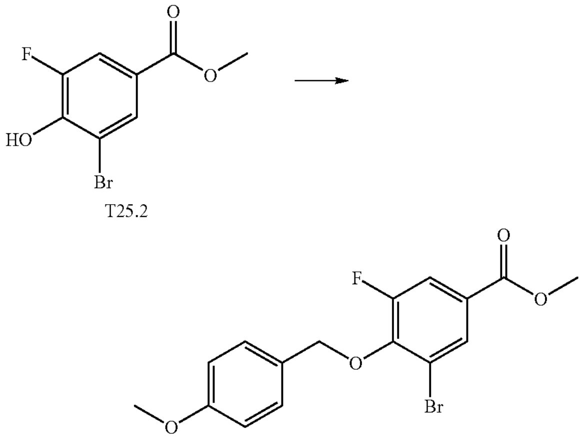

T25.2

T25.3

Methyl 3-bromo-5-fluoro-4-(((4-(methyloxy)phenyl) methyl)oxy)benzoate (T25.3)

To a vial containing T25.2 (0.64 g, 2.58 mmol) in 5.0 mL dry DMF was added cesium carbonate (1.10 g, 3.36 mmol).

The mixture was stirred at room temperature for 10 minutes and then 4-methoxybenzyl bromide (0.45 mL, 3.1 mmol) was added. After 4 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-40% EtOAc/hexane) to afford T25.3 as a white solid (679.1 mg, 71% yield). $^1$H NMR (400 MHz, $CDCl_3$) δ ppm 8.02 (1H, t, J=2.0 Hz), 7.72 (1H, dd, J=11.5, 2.2 Hz), 7.42 (2H, m, J=8.6 Hz), 6.90 (2H, m), 5.20 (2H, s), 3.91 (3H, s), 3.82 (3H, s).

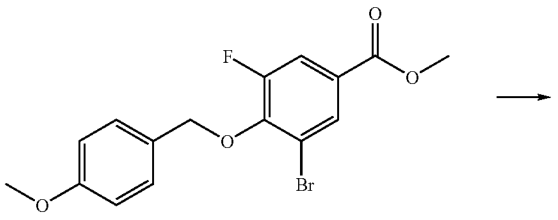

T25.3

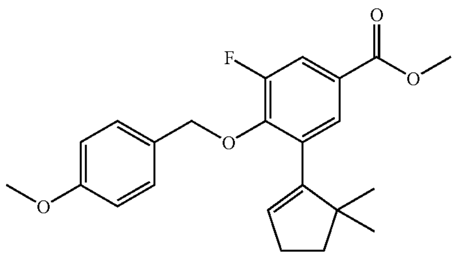

T25.4

Methyl 3-(5,5-dimethyl-1-cyclopenten-1-yl)-5-fluoro-4-(((4-(methyloxy)phenyl)methyl)oxy)benzoate (T25.4)

A stirred mixture of T25.3 (1.63 g, 4.420 mmol), ground S-Phos (0.36 g, 0.88 mmol), palladium acetate (0.10 g, 0.45 mmol), and potassium phosphate tribasic (2.35 g, 11.06 mmol) in DMF (13 mL) and water (0.4 mL) was purged with argon and placed under vacuum and the process repeated three times. Before heating, 2-(5,5-dimethylcyclopent-1-enyl)-4,4,5,5-tetramethyl-1,3,2-dioxaborolane (T6.3) (1.47 g, 6.63 mmol) was added via syringe and then the mixture was heated to 75° C. After 18 hours, the reaction was cooled to room temperature, diluted with water, and extracted three times with EtOAc. The organic layers were combined and washed twice with brine. After drying over anhydrous sodium sulfate and filtration, the organic solvent was removed under reduced pressure. The residue was purified on a 40 g column of silica gel (0-10% EtOAc in hexanes) to afford T25.4 as a white solid (1.12 g, 66% yield). $^1$H NMR (400 MHz, $CDCl_3$) δ ppm 7.69 (1H, dd, J=11.7, 2.3 Hz), 7.57 (1H, dd, J=2.0, 1.2 Hz), 7.31 (2H, m), 6.88 (2H, m), 5.56 (1H, t, J=2.5 Hz), 5.01 (2H, s), 3.91 (3H, s), 3.82 (3H, s), 2.42 (2H, td, J=7.0, 2.7 Hz), 1.86 (2H, t, J=7.2 Hz), 1.06 (6H, s).

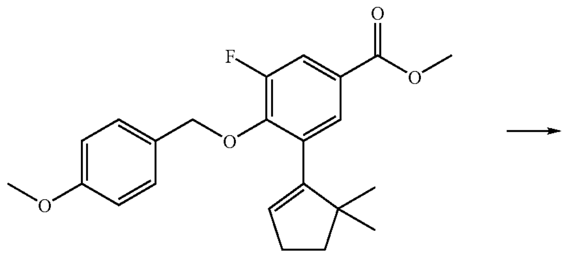

T25.4

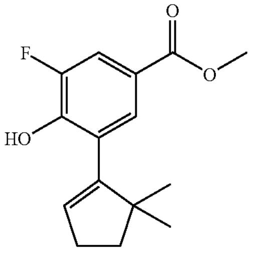

T25.5

Methyl 3-(5,5-dimethyl-1-cyclopenten-1-yl)-5-fluoro-4-hydroxybenzoate (T25.5)

To a flask containing T25.4 (1.12 g, 2.93 mmol) was added a premixed solution of DCM (14 mL) and TFA (1 mL). The mixture was stirred at room temperature and monitored with TLC and LC-MS. After 1 hour, the reaction was diluted with DCM and then washed once with saturated aqueous sodium bicarbonate solution and brine. After washing, the organic layer was dried over anhydrous sodium sulfate, filtered, and concentrated in vacuo. The residue was purified by flash chromatography ($SiO_2$ gel 60, eluted with 0%-50% EtOAc in hexanes). Fractions containing the desired product were combined and concentrated to provide a colorless oil that solidified as T25.5 and which was used without further purification (732.6 mg, 95% yield).

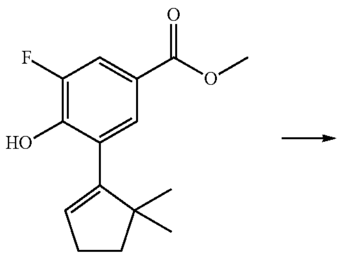

T25.5

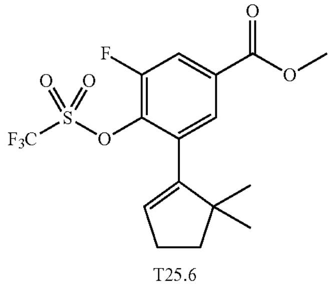

T25.6

Methyl 3-(5,5-dimethyl-1-cyclopenten-1-yl)-5-fluoro-4-(((trifluoromethyl)sulfonyl)oxy)benzoate (T25.6)

To a stirred solution of T25.5 (0.7326 g, 2.77 mmol) in dry DCM (15 mL) was added TEA (0.78 mL, 5.60 mmol) and 4-(dimethylamino)pyridine (0.0354 g, 0.29 mmol). After about 20 minutes, N-phenyl-bis(trifluoromethanesulfonimide) (1.20 g, 3.36 mmol) was added in portions. Upon complete addition, the solution was stirred at room temperature and monitored with TLC and LC-MS. After 19 hours, the organic solvent was removed under reduced pressure and the product thus obtained was then purified with silica gel chromatography using 0-10% EtOAc in hexanes to afford T25.6 as a colorless oil (946.4 mg, 86% yield). $^1$H NMR (400 MHz, $CDCl_3$) δ ppm 7.82 (1H, dd, J=9.9, 2.1 Hz), 7.75 (1H, m), 5.87 (1H, t, J=2.4 Hz), 3.95 (3H, s), 2.49 (2H, td, J=7.1, 2.4 Hz), 1.92 (2H, t, J=7.0 Hz), 1.11 (6H, s).

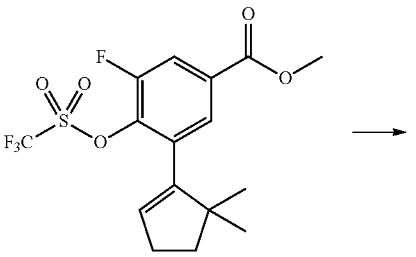

T25.6

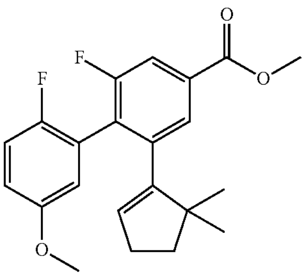

T25.7

Methyl 2-(5,5-dimethyl-1-cyclopenten-1-yl)-2',6-difluoro-5'-(methyloxy)-1,1'-biphenyl-4-carboxylate (T25.7)

A stirred mixture of T25.6 (0.9464 g, 2.39 mmol), ground S-Phos (0.1977 g, 0.482 mmol), palladium acetate (0.0555 g, 0.247 mmol), 2-fluoro-5-methoxyphenylboronic acid (0.8114 g, 4.77 mmol) (commercially available from Aldrich), and potassium phosphate tribasic (1.2888 g, 6.072 mmol) in dry DMF (7.000 mL) was purged with argon and placed under vacuum and the process repeated three times. The mixture was then heated to 75° C. and the reaction was stirred for 21 hours. The reaction was then cooled to room temperature, diluted with water and extracted three times with EtOAc. The organic layers were combined and washed twice with brine. After drying over anhydrous sodium sulfate and filtration, the organic solvent was removed under reduced pressure. The residue was purified on an 80 g column of silica gel (0-20% EtOAc in hexanes) to afford T25.7 as a colorless oil that was used without further purification (850.5 mg, 95% yield). MS ESI (pos.) m/e: 373.0 (M+H)$^+$.

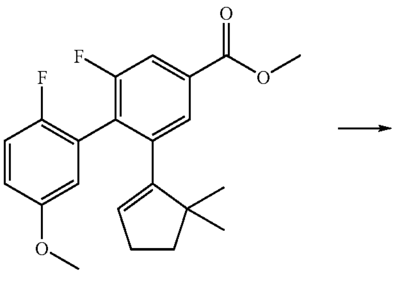

T25.7

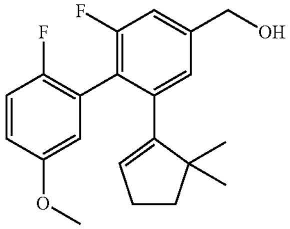

T25.8

(2-(5,5-Dimethyl-1-cyclopenten-1-yl)-2',6-difluoro-5'-(methyloxy)-1,1'-biphenyl-4-yl)methanol (T25.8)

To a cooled solution of T25.7 (0.1435 g, 0.385 mmol) in dry THF (9 mL) at 0° C. was added LAH (1.0 M in THF) (0.8 mL, 0.80 mmol) dropwise. Upon complete addition, the reaction was maintained at 0° C. and was monitored by TLC and LCMS. After 45 minutes, 1N NaOH was added to quench the reaction (gas evolution occurred), and the resulting solution was extracted three times with EtOAc. After drying over anhydrous magnesium sulfate, filtration, and concentration, the residue was purified by flash chromatography ($SiO_2$ gel 60, eluted with 0%-50% EtOAc in hexanes). Fractions containing the desired product were combined and concentrated to provide T25.8 as a colorless oil (114.9 mg, 87% yield). $^1$H NMR (400 MHz, $CDCl_3$) δ ppm 7.12 (1H, dd, J=9.8, 1.6 Hz), 7.04 (2H, m), 6.84 (1H, dt, J=9.0, 3.5 Hz), 6.74 (1H, dd, J=5.5, 3.1 Hz), 5.50 (1H, t, J=2.3 Hz), 4.74 (2H, s), 3.76 (3H, s), 2.24 (2H, td, J=7.0, 2.3 Hz), 1.75 (5H, m), 0.97 (3H, s), 0.78 (3H, s).

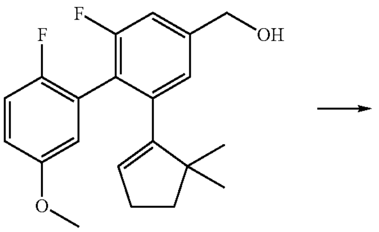

T25.8

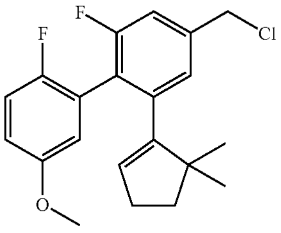

T25

4-(Chloromethyl)-2-(5,5-dimethyl-1-cyclopenten-1-yl)-2',6-difluoro-5'-(methyloxy)-1,1'-biphenyl (T25)

To a solution of T25.8 (0.1149 g, 0.334 mmol) in dry DCM (4 mL) and dry DMF (0.03 mL) was added thionyl chloride (0.05 mL, 0.685 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T25 as a colorless oil (35.6 mg, 29% yield). $^1$H NMR (400 MHz, $CDCl_3$) δ ppm 7.14 (1H, dd, J=9.4, 1.6 Hz), 7.06 (1H, s), 7.00 (1H, t, J=9.0 Hz), 6.85 (1H, dt, J=9.0, 3.7 Hz), 6.74 (1H, dd, J=5.5, 3.1 Hz), 5.53 (1H, t, J=2.3 Hz), 4.61 (2H, s), 3.76 (3H, s), 2.25 (2H, td, J=7.1, 2.5 Hz), 1.73 (2H, m), 0.97 (3H, s), 0.78 (3H, s).

Example T26

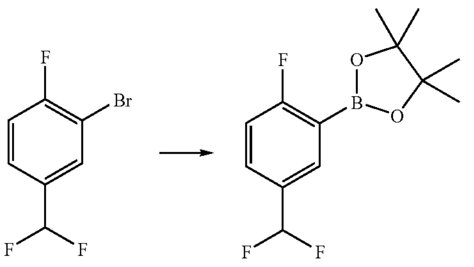

T26.1

2-(5-(Difluoromethyl)-2-fluorophenyl)-4,4,5,5-tetramethyl-1,3,2-dioxaborolane (T26.1)

A stirred mixture of 1-bromo-5-difluoromethyl-2-fluorobenzene (commercially available from Oakwood Products, Inc.) (2.0231 g, 8.991 mmol), bis(pinacolato)diboron (2.5123 g, 9.893 mmol), dichloro[1,1'-bis(diphenylphosphino)ferrocene]palladium (II) DCM adduct (0.3688 g, 0.4516 mmol), and potassium acetate (2.6504 g, 27.01 mmol) in dry 1,4-dioxane (35 mL) was purged with argon and placed under vacuum and the purging vacuum process repeated three times. The mixture was heated to 90° C. and monitored with LC-MS and TLC. After 18 hours, the reaction was cooled to room temperature and then filtered through Celite® filter aid. The organic solvent was removed under reduced pressure, and the residue was purified on a 40 g column of silica gel (0-10% EtOAc in hexanes) to afford T26.1 as a colorless oil that was used without further purification (1.6019 g, 65% yield). $^1$H NMR (400 MHz, $CDCl_3$) δ ppm 7.89 (1H, td, J=2.7, 1.2 Hz), 7.63 (1H, m), 7.09 (1H, t, J=8.6 Hz), 6.62 (1H, t), 1.35 (12H, s).

-continued

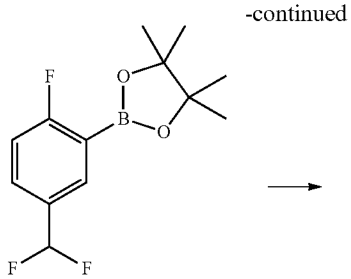

T26.1

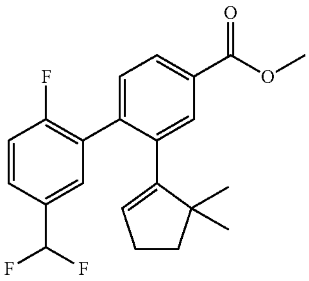

T26.2

Methyl 5'-(difluoromethyl)-2-(5,5-dimethyl-1-cyclopenten-1-yl)-2'-fluoro-1,1'-biphenyl-4-carboxylate (T26.2)

To a stirred solution of T6.9 (1.1209 g, 2.962 mmol) in dry DMF (10 mL) at 23° C. was added potassium carbonate (1.2262 g, 8.872 mmol) and then tetrakis(triphenylphosphine)palladium (0.3408 g, 0.2949 mmol). The mixture was purged with argon and placed under vacuum and the purging and vacuum process repeated three times. Before heating, T26.1 (1.6019 g, 5.888 mmol) was added via syringe and then the mixture was heated to 90° C. After 19 hours, LC-MS showed that the reaction was complete. The mixture was cooled to room temperature and then diluted with water. After extracting three times with EtOAc, the mixture was concentrated in vacuo and then purified on silica gel (0%-10% EtOAc/hexane) to afford T26.2 as a clear oil (994.4 mg, 90% yield). $^1$H NMR (400 MHz, $CDCl_3$) δ ppm 8.00 (1H, dd, J=8.0, 1.8 Hz), 7.94 (1H, d, J=1.6 Hz), 7.50 (3H, m), 7.16 (1H, t, J=9.0 Hz), 6.63 (1H, t), 5.53 (1H, s), 3.96 (3H, s), 2.25 (2H, td, J=7.0, 2.3 Hz), 1.65 (2H, t, J=7.0 Hz), 0.85 (6H, s).

T6.9

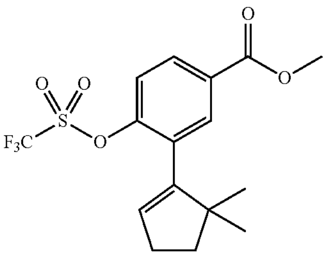

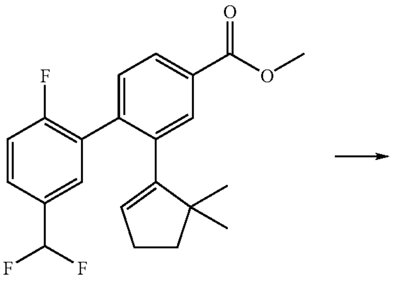

T26.2

-continued

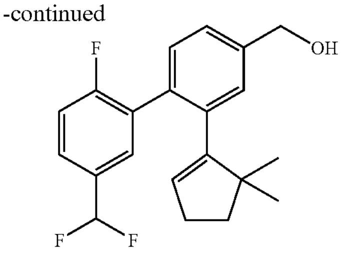

T26.3

(5'-(Difluoromethyl)-2-(5,5-dimethyl-1-cyclopenten-1-yl)-2'-fluoro-1,1'-biphenyl-4-yl)methanol (T26.3)

To a cooled solution of T26.2 (0.2349 g, 0.6274 mmol) in dry THF (5 mL) at 0° C. was added LAH (1.0 M in THF) (1.3 mL, 1.3 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was then purified by flash chromatography ($SiO_2$ gel 60, eluted with 0%-50% EtOAc in hexanes). Fractions containing the desired product were combined and concentrated to a colorless oil as T26.3 (166.6 mg, 77% yield). $^1$H NMR (400 MHz, $CDCl_3$) δ ppm 7.47 (2H, m), 7.38 (2H, m), 7.14 (1H, t, J=9.0 Hz), 6.62 (1H, t), 5.50 (1H, td, J=2.4, 1.0 Hz), 4.76 (2H, s), 2.23 (2H, td, J=7.0, 2.3 Hz), 1.74 (3H, m), 0.85 (6H, s).

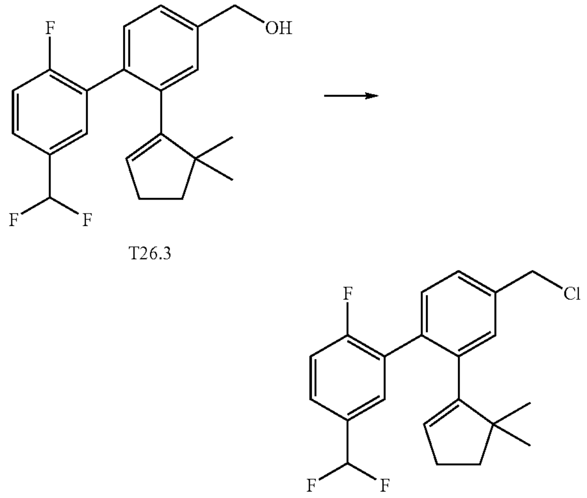

T26.3

T26

4-(Chloromethyl)-5'-(difluoromethyl)-2-(5,5-dimethyl-1-cyclopenten-1-yl)-2'-fluoro-1,1'-biphenyl (T26)

To a solution of T26.3 (0.1666 g, 0.481 mmol) in dry DCM (3 mL) and dry DMF (0.06 mL) was added thionyl chloride (0.07 mL, 0.96 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T26 (172.1 mg, 98% yield). $^1$H NMR (500 MHz, $CDCl_3$) δ ppm 7.46 (2H, m), 7.39 (1H, m), 7.33 (1H, m), 7.28 (1H, d, J=1.7 Hz), 7.17 (1H, m), 6.62 (1H, t), 5.51 (1H, td, J=2.3, 1.0 Hz), 4.64 (2H, s), 2.24 (2H, td, J=7.1, 2.4 Hz), 1.68 (2H, m), 0.85 (6H, s).

Examples T27A and T27B

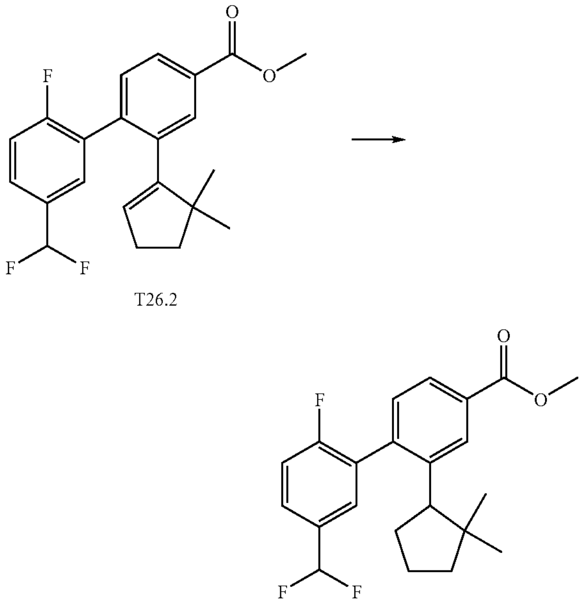

T26.2

T27.1

Methyl 5'-(difluoromethyl)-2-(2,2-dimethylcyclopentyl)-2'-fluoro-1,1'-biphenyl-4-carboxylate (T27.1)

To a dry flask containing T26.2 (0.8621 g, 2.303 mmol) in dry MeOH (10 mL) and EtOAc (2 mL) was added palladium (10% wt. on activated carbon) (0.2455 g, 0.2307 mmol). After purging, the mixture was stirred under an atmosphere of hydrogen at room temperature. The reaction was monitored with TLC and LC-MS. After 22.5 hours, the reaction was filtered through Celite® filter aid. After concentration, the residue was identified as T27.1 and was used without purification (863 mg, 99% yield). MS ESI (pos.) m/e: 376.9 $(M+H)^+$.

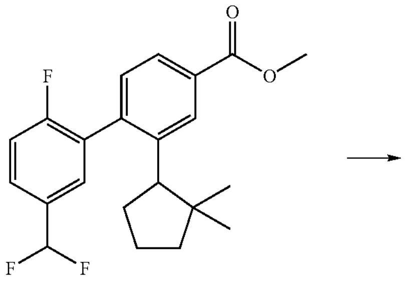

T27.1

-continued

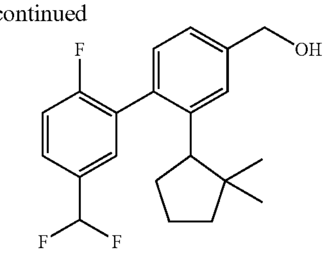

T27.2

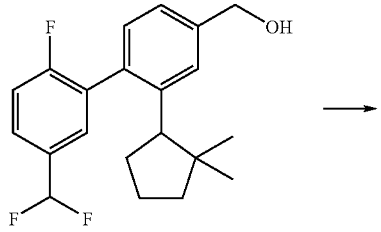

T27.2

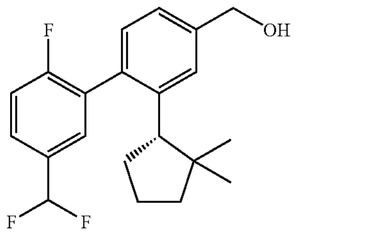

or

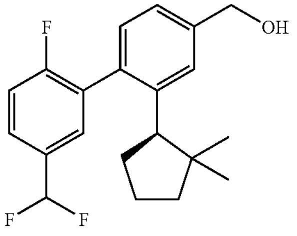

T27.4

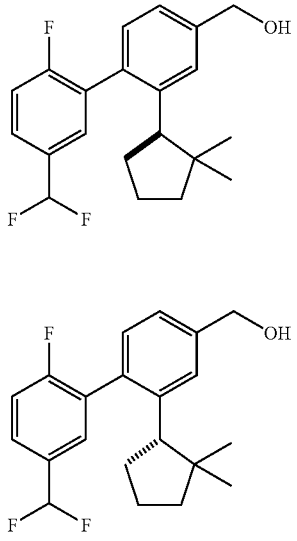

T27.3 and T27.4

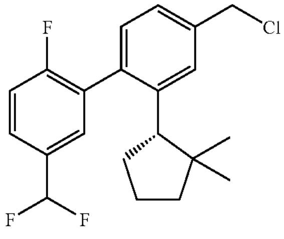

or

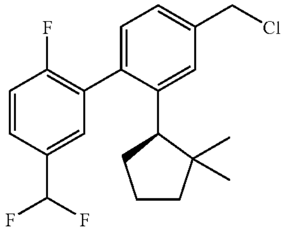

T27A (5'-(Difluoromethyl)-2-(2,2-dimethylcyclopentyl)-2'-fluoro-1,1'-biphenyl-4-yl)methanol (T27.2)

To a cooled solution of T27.1 (0.8631 g, 2.293 mmol) in dry THF (15.4 mL) at 0° C. was added LAH (1.0 M in THF) (4.6 mL, 4.6 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was then purified by flash chromatography ($SiO_2$ gel 60, eluted with 0%-100% EtOAc in hexanes). Fractions containing the desired product were combined and concentrated to a colorless oil as T27.2 (617.1 mg, 77% yield). MS ESI (pos.) m/e: 331.0 $(M-H_2O)^+$. Chiral separation of T27.2 was accomplished on a Chiracel-OD column (4% IPA in hexane) to provide T27.3 (peak 1) and T27.4 (peak 2). Both enantiomers were used to synthesize example compounds, and both enantiomers gave active compounds.

4-(Chloromethyl)-5'-(difluoromethyl)-2-((1S)-2,2-dimethylcyclopentyl)-2'-fluoro-1,1'-biphenyl or 4-(chloromethyl)-5'-(difluoromethyl)-2-((1R)-2,2-dimethylcyclopentyl)-2'-fluoro-1,1'-biphenyl (T27A)

To a solution of T27.4 (0.2882 g, 0.827 mmol) in dry DCM (10.5 mL) and dry DMF (0.08 mL) was added thionyl chloride (0.12 mL, 1.65 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T27A. (272.1 mg, 90% yield).

4-(Chloromethyl)-5'-(difluoromethyl)-2-((1S)-2,2-dimethylcyclopentyl)-2'-fluoro-1,1'-biphenyl or 4-(chloromethyl)-5'-(difluoromethyl)-2-((1R)-2,2-dimethylcyclopentyl)-2'-fluoro-1,1'-biphenyl (T27B)

To a solution of T27.3 (0.2798 g, 0.803 mmol) in dry DCM (10 mL) and dry DMF (0.076 mL) was added thionyl chloride (0.12 mL, 1.65 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T27B (282.5 mg, 96% yield).

Example T28

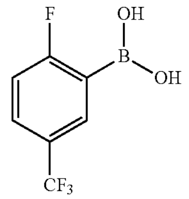

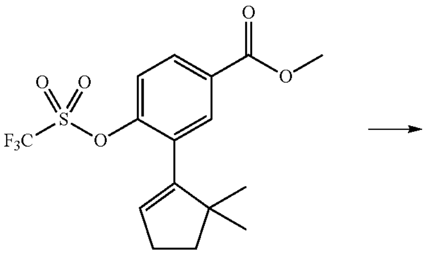

T6.9

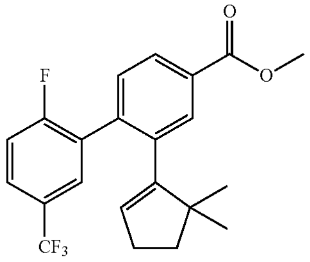

T28.1

Methyl 2-(5,5-dimethyl-1-cyclopenten-1-yl)-2'-fluoro-5'-(trifluoromethyl)-1,1'-biphenyl-4-carboxylate (T28.1)

To a stirred solution of T6.9 (0.7595 g, 2.007 mmol) in DMF (5 mL) at 23° C. was added 2-fluoro-5-(trifluoromethyl)phenylboronic acid (commercially available from Aldrich Chemical Company, Inc.) (0.8352 g, 4.017 mmol) and potassium carbonate (0.8357 g, 6.047 mmol) followed by tetrakis(triphenylphosphine)palladium (0.2364 g, 0.2046 mmol). The mixture was heated to 90° C. After 17 hours, LCMS-showed that the reaction was complete. The mixture was cooled to room temperature and then diluted with water. After extracting three times with EtOAc, the mixture was concentrated in vacuo and then purified on silica gel (0%-10% EtOAc/hexane) to afford T28.1 as a clear oil that was used without further purification (414.2 mg, 53% yield).

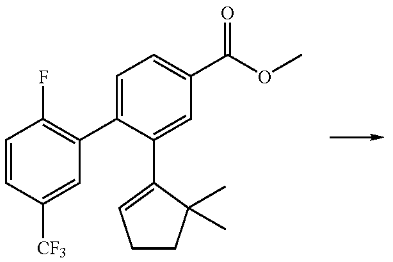

T28.1

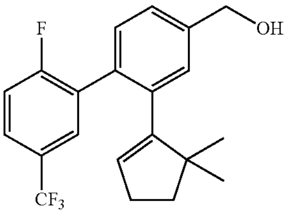

T28.2

(2-(5,5-Dimethyl-1-cyclopenten-1-yl)-2'-fluoro-5'-(trifluoromethyl)-1,1'-biphenyl-4-yl)methanol (T28.2)

To a cooled solution of T28.1 (0.4142 g, 1.056 mmol) in dry THF (7.8 mL) at 0° C. was added LAH (1.0 M in THF) (2.2 mL, 2.200 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by flash chromatography ($SiO_2$ gel 60, eluted with 0%-100% EtOAc in hexanes). Fractions containing the desired product were combined and concentrated to afford T28.2 as a colorless oil (257.4 mg, 67% yield). $^1H$ NMR (400 MHz, $CDCl_3$) δ ppm 7.61 (2H, m), 7.40 (2H, m), 7.17 (1H, t, J=8.8 Hz), 5.52 (1H, m), 4.77 (2H, s), 2.24 (2H, td, J=7.0, 2.3 Hz), 1.71 (3H, m), 0.84 (6H, s).

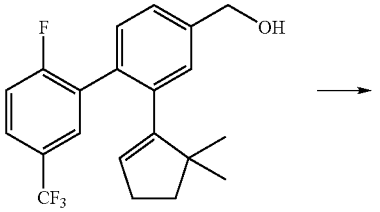

T28.2

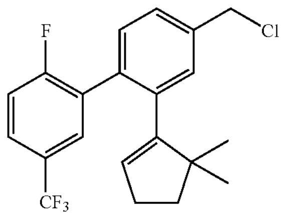

T28

4-(Chloromethyl)-2-(5,5-dimethyl-1-cyclopenten-1-yl)-2'-fluoro-5'-(trifluoromethyl)-1,1'-biphenyl (T28)

To a solution of T28.2 (0.2574 g, 0.706 mmol) in dry DCM (10 mL) and dry DMF (0.07 mL) was added thionyl chloride (0.11 mL, 1.51 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford T28 (242.8 mg, 90% yield). $^1$H NMR (400 MHz, $CDCl_3$) δ ppm 7.60 (2H, m), 7.40 (1H, m), 7.35 (2H, m), 7.21 (1H, m), 5.52 (1H, td, J=2.4, 0.9 Hz), 4.66 (2H, m), 2.24 (2H, td, J=7.0, 2.3 Hz), 1.68 (2H, m), 0.84 (6H, s).

Example T29

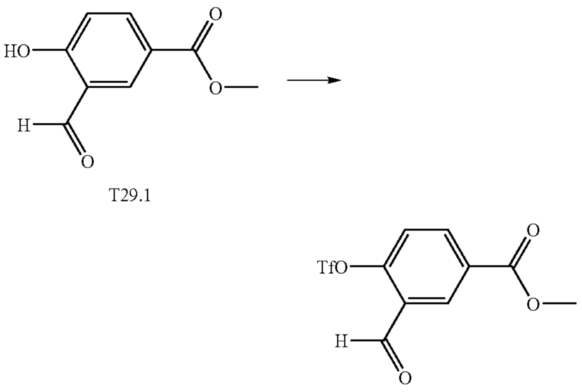

T29.1

T29.2

Methyl 3-formyl-4-(trifluoromethylsulfonyloxy)benzoate (T29.2)

TEA (6.81 mL, 48.8 mmol), and N,N-dimethylpyridin-4-amine (0.298 g, 2.44 mmol) were added to a solution of methyl 3-formyl-4-hydroxybenzoate (T29.1) (commercially available from Aldrich) (4.40 g, 24.4 mmol) in DCM (26 mL). The resulting mixture was stirred at room temperature for 20 minutes and then N-phenyltrifluoromethanesulfonimide (9.60 g, 26.9 mmol) was added in one portion. The mixture was then stirred at room temperature for 30 minutes. After removing solvent, the residue was purified by flash chromatography (silica gel, 1:1 EtOAc/hexane) and gave T29.2, a colorless oil, in 99% yield (7.57 g).

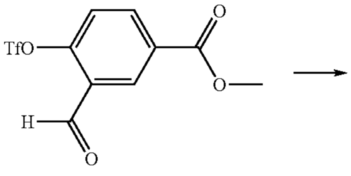

T29.2

-continued

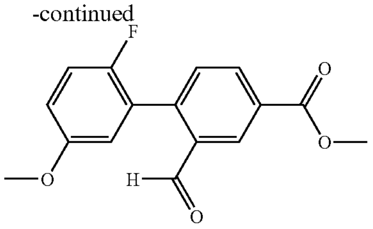

T29.3

Methyl 2'-fluoro-2-formyl-5'-(methyloxy)-1,1'-biphenyl-4-carboxylate (T29.3)

A mixture of methyl 3-formyl-4-(trifluoromethyl-sulfonyloxy)benzoate (T29.2) (7.57 g, 24.2 mmol), 2-fluoro-5-methoxy-phenylboronic acid (commercially available from Aldrich) (12.4 g, 72.7 mmol), cesium carbonate (27.6 g, 84.9 mmol), and tetrakis(triphenylphosphine) palladium (2.80 g, 2.42 mmol) in 1,2-dimethoxyethane (DME) (75 mL) was degassed with $N_2$ at room temperature The mixture was heated at 95° C. for 9 hours. After removing solvent, the residue was purified by flash chromatography (silica gel, 1:19 EtOAc/hexane) and gave T29.3, a white solid, in 56% yield (2.9 g). $^1$H NMR (400 MHz, DMSO-d6) δ ppm 9.88 (dd, J=4 Hz, 1H), 8.45 (s, 1H), 8.28 (m, 1H), 7.69 (d, j=8 Hz, 1H), 7.29 (t, J=9 HZ, 1H), 7.08 (m, 2H), 3.92 (s, 3H), 3.79 (s, 3H).

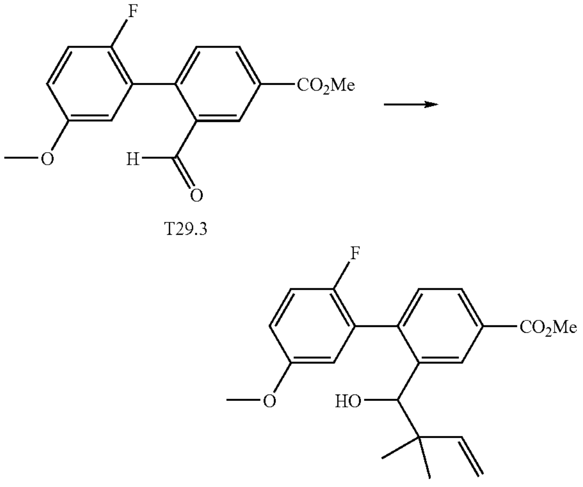

T29.3

T29.4

Methyl 2'-fluoro-2-(1-hydroxy-2,2-dimethyl-3-butenyl)-5'-(methyloxy)-1,1'-biphenyl-4-carboxylate (T29.4)

To a mixture of T29.3 (0.38 g, 1.3 mmol), 1-bromo-3-methylbut-2-ene (commercially available from Aldrich) (0.31 mL, 2.6 mmol) and sodium iodide (0.40 g, 2.6 mmol) in DMF (8 mL), was added indium (0.30 g, 2.6 mmol). The resulting mixture was stirred at room temperature for 1 hour and then additional 1-bromo-3-methylbut-2-ene (100 mg) and indium (100 mg) were added and the mixture was stirred at room temperature for one more hour. The reaction was quenched with water (20 mL) and extracted with EtOAc (200 mL). The organic phase was washed with brine, dried over anhydrous sodium sulfate, and filtered. After removing solvent, the residue was purified by flash chromatography (silica gel, 1:4 EtOAc/hexane) and gave product (T29.4), in 94% yield.

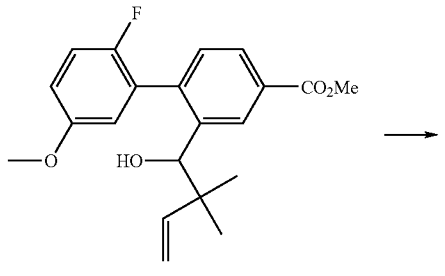

T29.4

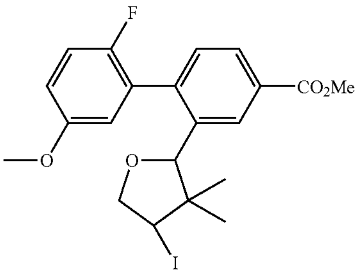

T29.5

Methyl 2'-fluoro-2-(3-iodo-2,2-dimethylcyclopentyl)-5'-(methyloxy)-1,1'-biphenyl-4-carboxylate (T29.5)

To a mixture of $NaHCO_3$ (0.035 g, 0.42 mmol) and T29.4 (0.050 g, 0.14 mmol) in ACN (2 mL), was added iodine (0.12 g, 0.49 mmol). The mixture was then stirred at room temperature for 16 hours. Next, the mixture was poured into a 0.2 M solution of $Na_2S_2O_3$ and extracted with EtOAc. The organic phase was dried over anhydrous $Na_2SO_4$ and filtered. After removing solvent, the residue was purified by flash chromatography (silica gel, 1:19 EtOAc/hexane) and gave product T29.5, a white solid, in 84% yield.

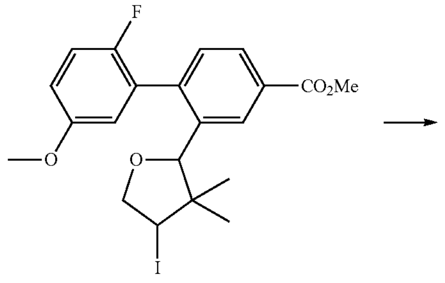

T29.5

-continued

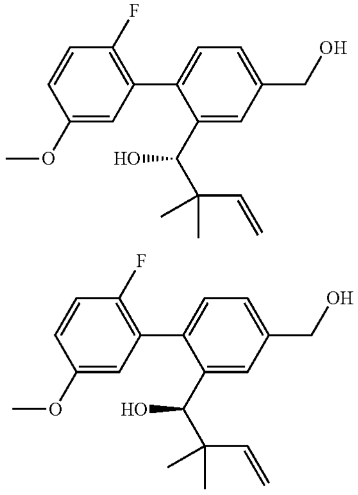

T29.7 and T29.6

(1S)-1-(2'-Fluoro-4-(hydroxymethyl)-5'-(methyloxy)-1,1'-biphenyl-2-yl)-2,2-dimethyl-3-buten-1-ol and (1R)-1-(2'-fluoro-4-(hydroxymethyl)-5'-(methyloxy)-1,1'-biphenyl-2-yl)-2,2-dimethyl-3-buten-1-ol (T29.6 and T29.7)

To a mixture of T29.5 (0.460 g, 0.950 mmol) in THF (12 mL), was added LAH (0.108 g, 2.85 mmol), and the mixture was stirred at room temperature for 45 minutes. The reaction mixture was then poured into water and extracted with EtOAc. The organic phase was dried over anhydrous $Na_2SO_4$ and filtered. After removing solvent, the residue was purified by flash chromatography (silica gel, 1:2 EtOAc/hexane) and gave racemic product, which was separated by chiral chromatography (column: OD-H; solvent: 6% i-PrOH/hexane) to yield T29.6 (72 mg) (retention time=12.9 min) and T29.7 (74 mg) (retention time=18.2 min).

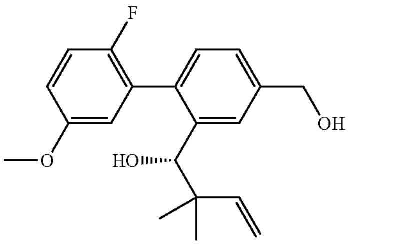

or

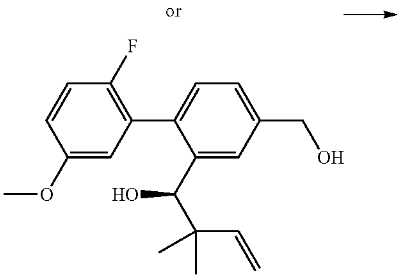

T29.6

-continued

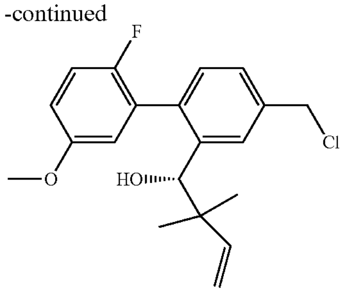

or

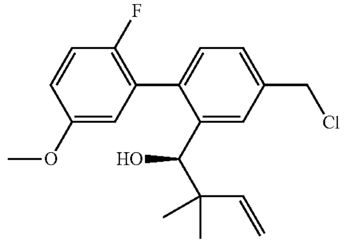

T29

(1S)-1-(4-(Chloromethyl)-2'-fluoro-5'-(methyloxy)-1,1'-biphenyl-2-yl)-2,2-dimethyl-3-buten-1-ol or (1R)-1-(4-(chloromethyl)-2'-fluoro-5'-(methyloxy)-1,1'-biphenyl-2-yl)-2,2-dimethyl-3-buten-1-ol (T29)

Thionyl chloride (0.27 g, 2.2 mmol) was added to a solution of T29.6 (0.074 g, 0.22 mmol) in DCM (2 mL), and the mixture was stirred at room temperature for 40 minutes. After removing solvent, T29 was obtained.

Example T30

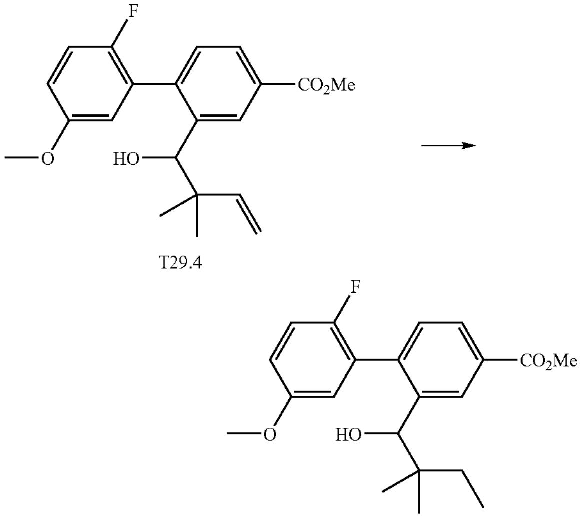

T29.4

T30.1

Methyl 2'-fluoro-2-(1-hydroxy-2,2-dimethylbutyl)-5'-(methyloxy)-1,1'-biphenyl-4-carboxylate (T30.1)

To a solution of T29.4 (0.453 g, 1.26 mmol) in MeOH (10 mL) (degassed by $N_2$), was added palladium on carbon (0.135 g, 1.26 mmol). The resulting mixture was stirred at room temperature under $H_2$ for 18 hrs. The reaction mixture was then filtered through silica gel. After removing solvent, T30.1 (394 mg) was obtained as a colorless oil.

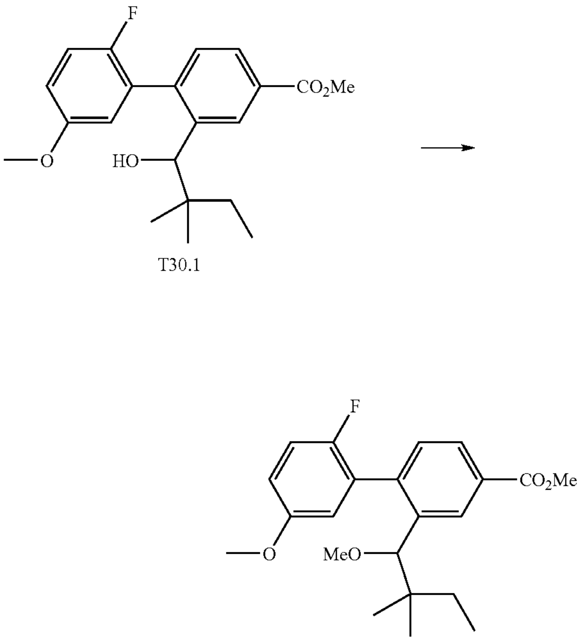

T30.1

T30.2

Methyl 2-(2,2-dimethyl-1-(methyloxy)butyl)-2'-fluoro-5'-(methyloxy)-1,1'-biphenyl-4-carboxylate (T30.2)

To a solution of T30.1 (0.39 g, 1.1 mmol) in DMF (5 mL), was added NaH (0.034 g, 1.4 mmol). The mixture was stirred at room temperature for 10 minutes and then iodomethane (0.20 mL, 3.2 mmol) was added. The mixture was stirred at room temperature for 60 minutes and then it was diluted with EtOAc, washed with water and brine, and dried over anhydrous $Na_2SO_4$. After removing solvent, the residue was purified by flash chromatography (silica gel, 1:9 EtOAc/hexane) and gave T30.2, colorless oil, in 64% yield (260 mg).

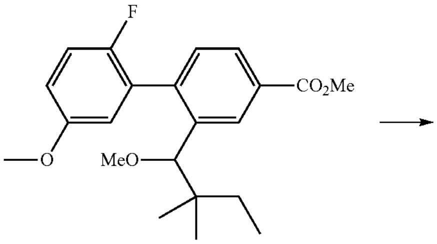

T30.2

-continued

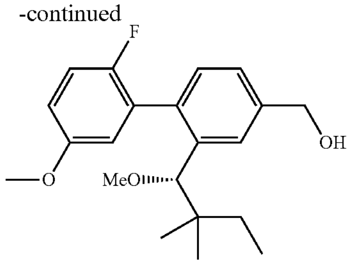

or

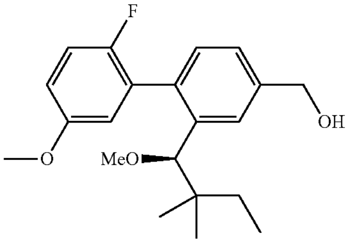

T30.3 and T30.4

(2-((1S)-2,2-Dimethyl-1-(methyloxy)butyl)-2'-fluoro-5'-(methyloxy)-1,1'-biphenyl-4-yl)methanol and (2-((1R)-2,2-dimethyl-1-(methyloxy)butyl)-2'-fluoro-5'-(methyloxy)-1,1'-biphenyl-4-yl)methanol (T30.3 and T30.4)

To a solution of T30.2 (0.26 g, 0.69 mmol) in THF (4 mL), was added LAH (0.026 g, 0.69 mmol). The resulting mixture was stirred at room temperature for 10 minutes and then was poured into to water and extracted with EtOAc. The combined organic layers were dried over anhydrous $Na_2SO_4$. After removing solvent, the residue was purified by flash chromatography (silica gel, 1:6 EtOAc/hexane) and gave racemic product (157 mg) as a colorless oil, which was separated by chiral chromatography (column: OD; solvent: 6% i-PrOH/hexane) to yield T30.3 (68 mg) (retention time=11.8 min) and T30.4 (70 mg) (retention time=15.1 min).

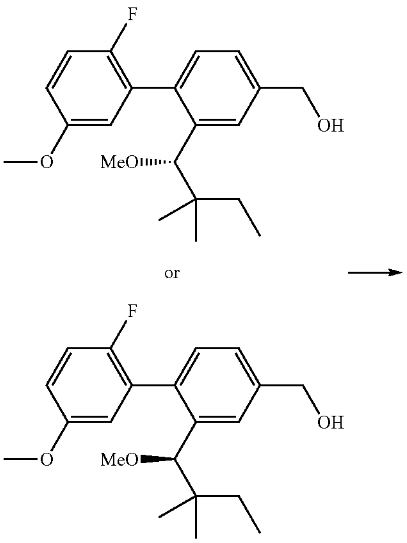

or

T30.3

-continued

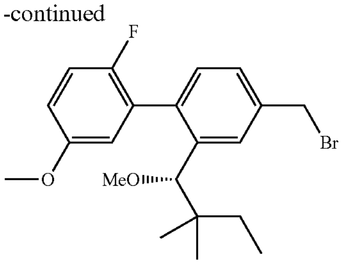

or

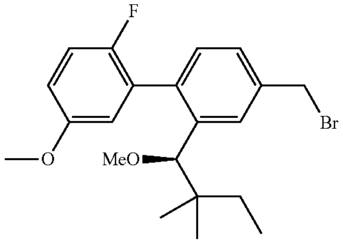

T30

4-(Bromomethyl)-2-((1S)-2,2-dimethyl-1-(methyloxy)butyl)-2'-fluoro-5'-(methyloxy)-1,1'-biphenyl or 4-(bromomethyl)-2-((1R)-2,2-dimethyl-1-(methyloxy)butyl)-2'-fluoro-5'-(methyloxy)-1,1'-biphenyl (T30)

To a solution of T30.3 (0.070 g, 0.20 mmol) in THF (2 mL), was added triphenylphosphine (0.11 g, 0.40 mmol) and 1-bromopyrrolidine-2,5-dione (0.072 g, 0.40 mmol). The resulting mixture was stirred at room temperature for 10 minutes. After removing solvent, the residue was purified by flash chromatography (silica gel, 1:6 EtOAc/hexane) and gave T30 (73 mg).

Example T31

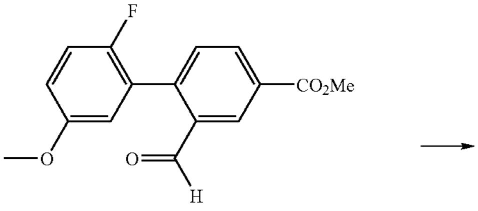

T29.3

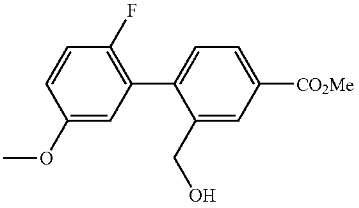

T31.1

Methyl 2'-fluoro-2-(hydroxymethyl)-5'-(methyloxy)-1,1'-biphenyl-4-carboxylate (T31.1)

Sodium tetrahydroborate (available from Aldrich) (0.656 g, 17.3 mmol) was added portion by portion slowly to T29.3

(1.00 g, 3.47 mmol) in MeOH (20 mL). The resulting mixture was stirred at room temperature for 25 minutes. After removing solvent, the residue was purified by flash chromatography (silica gel, 1:2 EtOAc/hexane) and gave T31.1 (725 mg) in 72% yield.

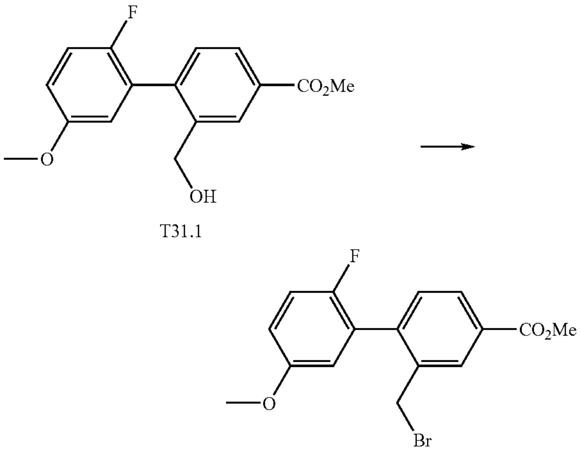

T31.1

T31.2

Methyl 2-(bromomethyl)-2'-fluoro-5'-(methyloxy)-1,1'-biphenyl-4-carboxylate (T31.2)

To a solution of T31.1 (0.725 g, 2.50 mmol) and triphenylphosphine (2.62 g, 9.99 mmol) in THF (20 mL) was added portion by portion 1-bromopyrrolidine-2,5-dione (available from Aldrich) (1.78 g, 9.99 mmol). The resulting mixture was stirred at room temperature for 20 minutes. After removing solvent, the residue was purified by flash chromatography (silica gel, 1:9 EtOAc/hexane) and gave T31.2 (882 mg) in 100% yield.

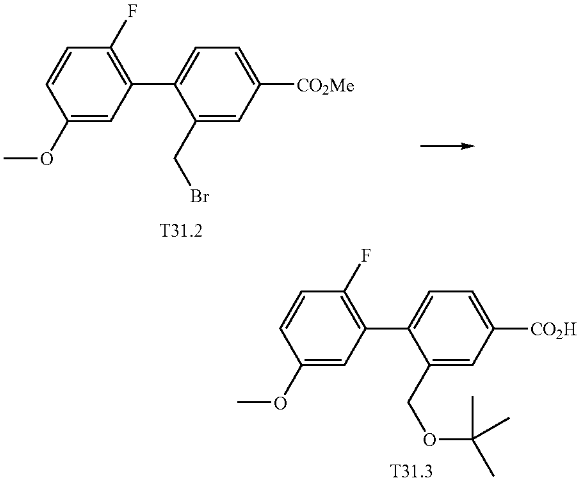

T31.2

T31.3

2-(((1,1-Dimethylethyl)oxymethyl)-2'-fluoro-5'-(methyloxy)-1,1'-biphenyl-4-carboxylic acid (T31.3)

A mixture of T31.2 (0.245 g, 0.69 mmol) and sodium 2-methylpropan-2-olate (0.20 g, 2.1 mmol) in DMF (6 mL)

was stirred at room temperature for 28 minutes. The mixture was acidified with 1N HCl to pH 3-4 and then was extracted with EtOAc (100 mL). The organic phase was washed with brine and dried over anhydrous $Na_2SO_4$. After removing solvent, the residue was purified by flash chromatography (silica gel, 1:4 EtOAc/hexane) and gave T31.3 (49 mg) in 20% yield.

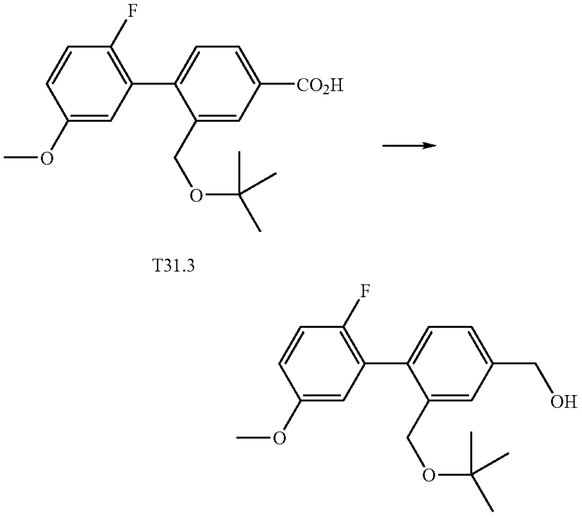

T31.3

T31.4

(2-(((1,1-Dimethylethyl)oxymethyl)-2'-fluoro-5'-(methyloxy)-1,1'-biphenyl-4-yl)methanol (T31.4)

LAH (0.15 mL, 0.15 mmol) was added to a solution of T31.3 (0.049 g, 0.15 mmol) in THF (2 mL). The resulting mixture was stirred at room temperature for 10 minutes and then was poured slowly into brine (5 mL). The mixture was extracted with EtOAc (2×50 mL). The organic phase was dried over anhydrous sodium sulfate. After filtering and removing solvent, the residue was purified by flash chromatography (silica gel, 1:2 EtOAc/hexane) and gave T31.4 (6 mg).

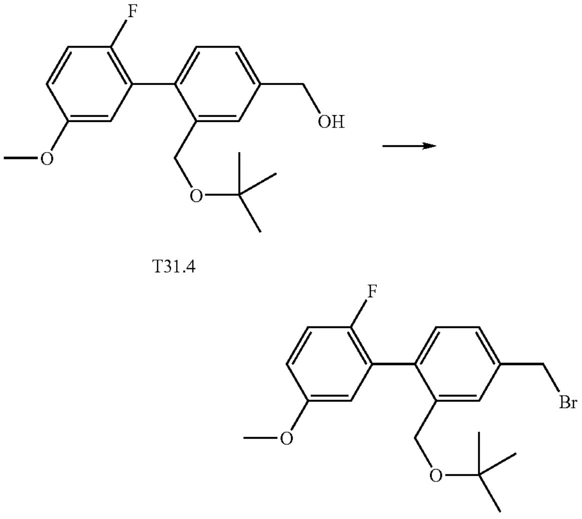

T31.4

T31

4-(Bromomethyl)-2-(((1,1-dimethylethyl)oxy)methyl)-2'-fluoro-5'-(methyloxy)-1,1'-biphenyl (T31)

Bromomethyl compound T31 was prepared using an analogous procedure to that set forth for the synthesis of T31.2.

Example T32

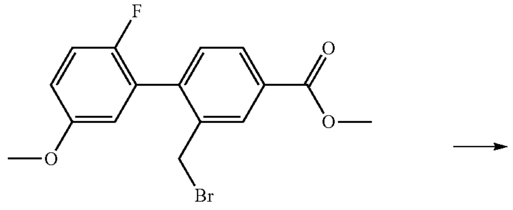

T31.2

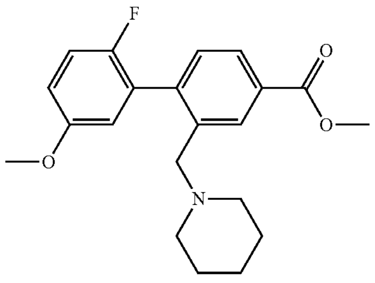

T32.1

Methyl 2'-fluoro-5'-(methyloxy)-2-(1-piperidinylmethyl)-1,1'-biphenyl-4-carboxylate (T32.1)

Piperidine (commercially available from Aldrich) (0.038 g, 0.44 mmol) was added to a solution of T31.2 (0.13 g, 0.37 mmol) in DMSO (3 mL). $Cs_2CO_3$ (0.18 g, 0.55 mmol) was then added to the reaction and it was stirred at room temperature for 1 hour. EtOAc (100 mL) was added and the organic phase was washed with water and brine and dried over anhydrous sodium sulfate. After removing solvent, the residue was purified by flash chromatography (silica gel, 1:1 EtOAc/DCM) and gave T32.1 (100 mg) in 76% yield. MS ESI (pos.) m/e: 358 $(M+H)^+$.

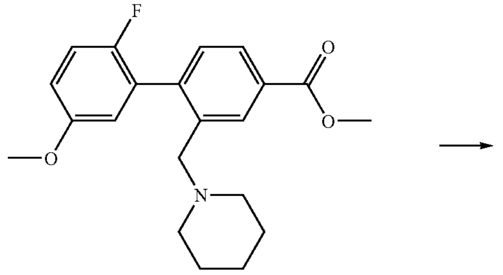

T32.1

-continued

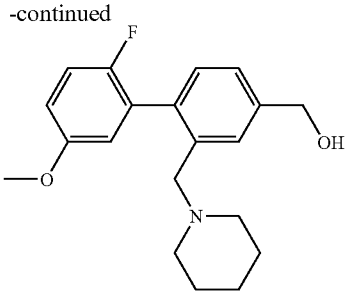

T32.2

(2'-Fluoro-5'-(methyloxy)-2-(1-piperidinylmethyl)-1,1'-biphenyl-4-yl)methanol (T32.2)

LAH (1.0 M solution in THF) (0.55 mL, 0.55 mmol) was added to a solution of T32.1 (0.098 g, 0.27 mmol) in THF (5 mL). The resulting mixture was stirred at room temperature for 1 hour and then it was diluted with EtOAc, washed with water and brine, and dried over anhydrous $Na_2SO_4$. After removing solvent, T32.2 was obtained as a colorless oil in 100% yield.

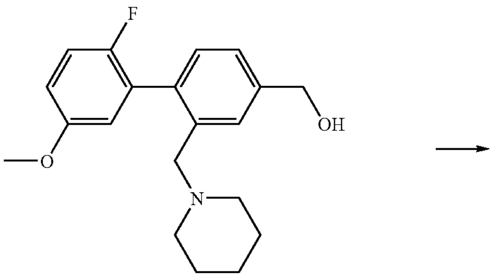

T32.2

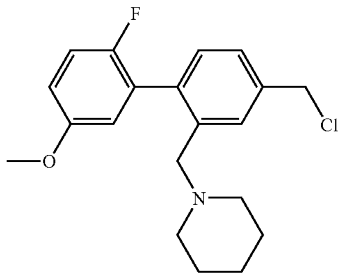

T32

1-((4-(Chloromethyl)-2'-fluoro-5'-(methyloxy)-1,1'-biphenyl-2-yl)methyl)piperidine (T32)

Thionyl chloride (0.066 g, 0.56 mmol) was added to a solution of T32.2 (0.023 g, 0.070 mmol) in DCM (1 mL). The resulting mixture was stirred at room temperature for 2 hours. After removing solvent, T32 was obtained in 100% yield.

Example T33

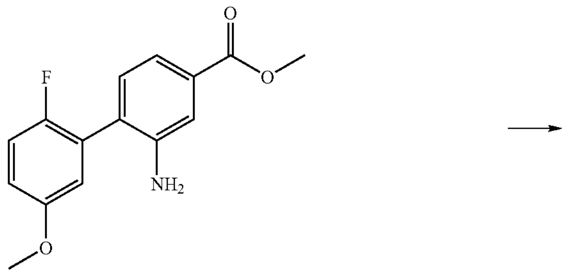

T10.3

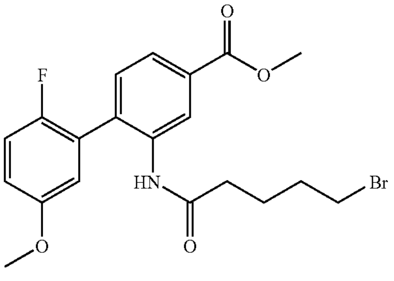

T33.1

Methyl 2-((5-bromopentanoyl)amino)-2'-fluoro-5'-(methyloxy)-1,1'-biphenyl-4-carboxylate (T33.1)

To a dry round bottom flask containing T10.3 (0.7779 g, 2.83 mmol) was added dry chloroform (8 mL) at 0° C. After five minutes, 5-bromovaleryl chloride (0.5 mL, 3.73 mmol) (commercially available from Aldrich) was added followed by dropwise addition of dry pyridine (0.31 mL, 3.80 mmol). The reaction mixture was allowed to warm to room temperature and monitored with TLC and LC-MS. After 3 hours, the reaction was diluted with DCM and washed twice with saturated aqueous sodium bicarbonate solution, twice with water, and once with brine. The organic layer was dried over anhydrous sodium sulfate then filtered and concentrated. The residue was purified by recrystallization from isopropanol to afford T33.1 as an off white solid (726.2 mg, 59% yield). $^{1}H$ NMR (400 MHz, $CDCl_3$) δ ppm 8.78 (1H, s), 7.91 (1H, d, J=7.8 Hz), 7.36 (1H, d, J=7.8 Hz), 7.15 (1H, t, J=9.2 Hz), 7.08 (1H, s), 6.97 (1H, dt, J=9.0, 3.7 Hz), 6.81 (1H, dd, J=5.9, 3.1 Hz), 3.94 (3H, s), 3.83 (3H, s), 3.39 (2H, t, J=6.3 Hz), 2.28 (2H, t, J=7.0 Hz), 1.89 (2H, m), 1.82 (2H, m).

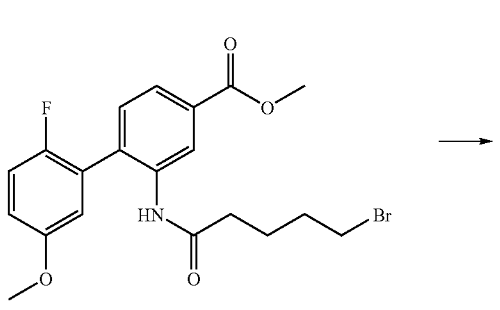

T33.1

-continued

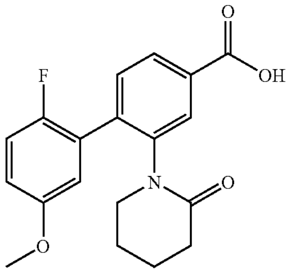

T33.2

2'-Fluoro-5'-(methyloxy)-2-(2-oxo-1-piperidinyl)-1,1'-biphenyl-4-carboxylic acid (T33.2)

To a dry vial containing T33.1 (0.5858 g, 1.337 mmol) was added dry DMF (25 mL). The mixture was stirred at 0° C. for about 15 minutes, then potassium tert-butoxide (0.3766 g, 3.356 mmol) was carefully added in portions. The mixture was heated to 145° C. and monitored with TLC and LC-MS. After 2.5 hours, the reaction was cooled to room temperature and then carefully quenched with 2 M aqueous citric acid solution. After extracting three times with DCM, the organic layer was dried over anhydrous magnesium sulfate, filtered and concentrated. The residue was purified with silica gel flash chromatography (0-25% MeOH in DCM) to afford T33.2 as an oil (440.1 mg, 96% yield). MS ESI (neg.) m/e: 342.0 $(M-H)^+$.

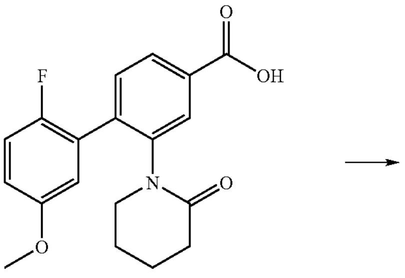

T33.2

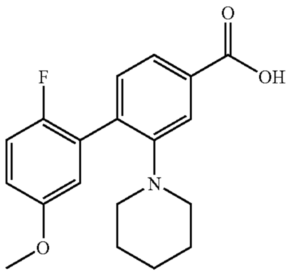

T33.3

2'-Fluoro-5'-(methyloxy)-2-(1-piperidinyl)-1,1'-biphenyl-4-carboxylic acid (T33.3)

To a cooled solution of T33.2 (0.4401 g, 1.282 mmol) in dry THF (8 mL) at 0° C. was added borane.THF complex, 1.0 M in THF (2.5 mL, 2.5 mmol) dropwise. Upon complete addition, the reaction was maintained at 0° C. and monitored by TLC and LCMS. After 3 hours, water was added to quench the reaction, and the resulting solution was extracted three times with EtOAc. The organic extractions were combined and washed successively with saturated aqueous sodium bicarbonate, water, and then brine. After drying over anhydrous magnesium sulfate, filtration, and concentration, the residue was purified with silica gel flash chromatography (0-25% MeOH in DCM) to afford T33.3 as an oil (292.9 mg, 69% yield). $^1$H NMR (400 MHz, $CDCl_3$) δ ppm 7.85 (2H, m), 7.36 (1H, d, J=7.8 Hz), 7.11 (2H, m), 6.86 (1H, dt, J=8.9, 3.6 Hz), 3.83 (3H, s), 2.85 (4H, m), 1.46 (6H, m).

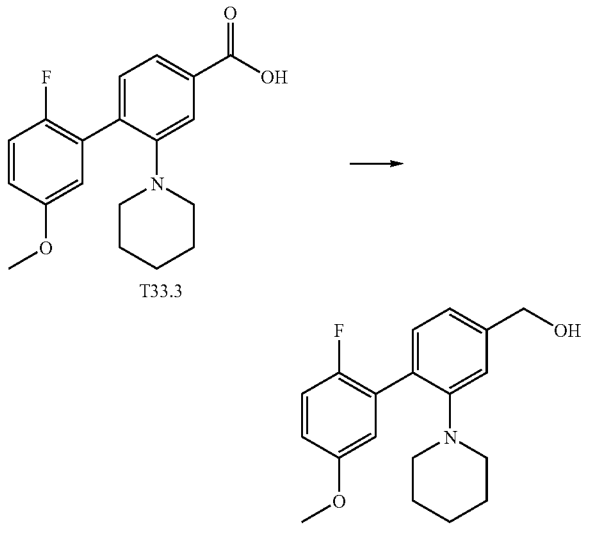

T33.3

T33.4

(2'-Fluoro-5'-(methyloxy)-2-(1-piperidinyl)-1,1'-biphenyl-4-yl)methanol (T33.4)

To a cooled solution of T33.3 (0.2929 g, 0.8893 mmol) in dry THF (10 mL) at 0° C. was added LAH (1M in THF) (1.8 mL, 1.8 mmol). Upon complete addition, the reaction was maintained at 0° C. and was monitored by TLC and LCMS. After 2 hours, 1N NaOH was added to quench the reaction (gas evolution occurred). The resulting solution was extracted three times with EtOAc. After drying over anhydrous magnesium sulfate, filtration, and concentration, the residue was purified by flash chromatography ($SiO_2$ gel 60, eluted with 0%-50% EtOAc in hexanes). Fractions containing the desired product were combined and concentrated to afford T33.4 as a colorless oil (231.8 mg, 83% yield). $^1$H NMR (400 MHz, $CDCl_3$) δ ppm 7.25 (1H, d, J=9.0 Hz), 7.11 (4H, m), 6.82 (1H, dt, J=9.0, 3.5 Hz), 4.71 (2H, d, J=5.5 Hz), 3.81 (3H, s), 2.81 (4H, m), 1.69 (1H, s), 1.43 (6H, m).

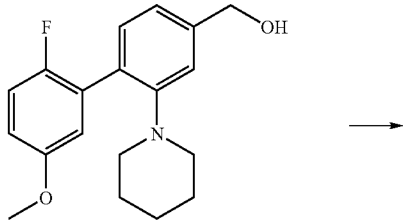

T33.4

-continued

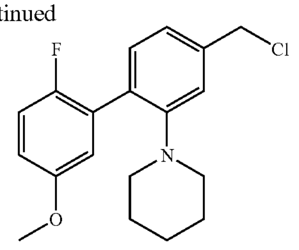

T33

1-(4-(Chloromethyl)-2'-fluoro-5'-(methyloxy)-1,1'-biphenyl-2-yl)piperidine (T33)

To a solution of T33.4 (0.2318 g, 0.73 mmol) in dry DMF (0.03 mL) and dry DCM (3 mL) was added thionyl chloride (0.13 mL, 1.8 mmol) at 0° C. The resulting solution was warmed to room temperature and monitored with TLC and LCMS. After 45 minutes, the reaction was diluted with DCM and then washed once with saturated aqueous sodium bicarbonate and once with brine. After drying over anhydrous magnesium sulfate, filtering, and removing the solvent under reduced pressure, the residue was purified by silica gel flash chromatography (0-5% EtOAc/hexane) to afford T33 (86.3 mg, 35% yield). $^1$H NMR (400 MHz, $CDCl_3$) δ ppm 7.16 (1H, m), 7.00 (4H, m), 6.72 (1H, dt, J=9.0, 3.5 Hz), 4.50 (2H, s), 3.71 (3H, s), 2.71 (4H, m), 1.34 (6H, m).

Example T34

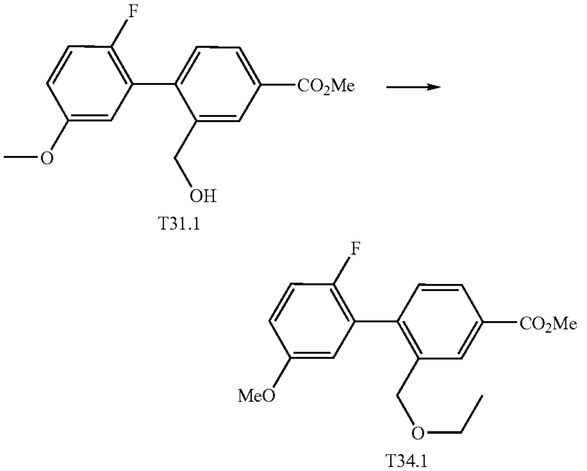

T31.1

T34.1

Methyl 2-((ethyloxy)methyl)-2'-fluoro-5'-(methyloxy)-1,1'-biphenyl-4-carboxylate (T34.1)

To a solution of T31.1 (0.200 g, 0.689 mmol) in DMF (5 mL), was added NaH (0.0198 g, 0.827 mmol). The reaction was stirred at room temperature fort 0 minutes. Ethyl iodide was then added and the reaction was stirred at room temperatures for 1 hour. The mixture was diluted with EtOAc, washed with water and brine, and dried over anhydrous $Na_2SO_4$. After removing solvent, the residue was purified by flash chromatography (silica gel, 1:1 EtOAc/hexane) and gave T34.1 in 79% yield. MS ESI (pos.) m/e: 336 $(M+18)^+$.

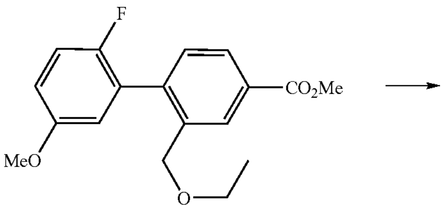

T34.1

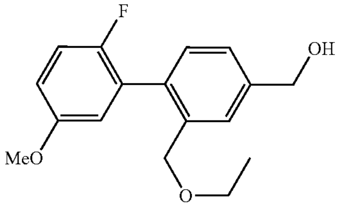

T34.2

(2-((Ethyloxy)methyl)-2'-fluoro-5'-(methyloxy)-1,1'-biphenyl-4-yl)methanol (T34.2)

Example T34.1 was reduced using LAH using a procedure analogous to that of Example T6 to yield T34.2.

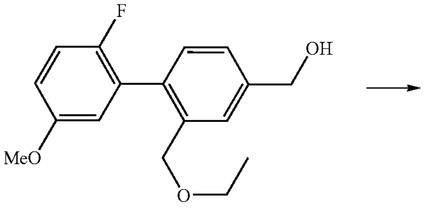

T34.2

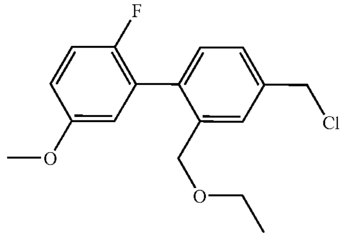

T34

4-(Chloromethyl)-2-((ethyloxy)methyl)-2'-fluoro-5'-(methyloxy)-1,1'-biphenyl (T34)

Compound T34.2 was converted to the chloromethyl compound T34 using a procedure analogous to that described in Example T6.

Example T35

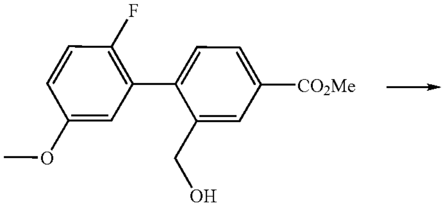

T31.1

-continued

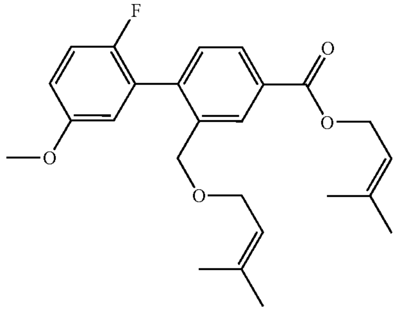

T35.1

3-Methyl-2-butenyl 2'-fluoro-2-(((3-methyl-2-butenyl)oxy)methyl)-5'-(methyloxy)-1,1'-biphenyl-4-carboxylate (T35.1)

To a solution of T31.1 (0.322 mmol) in DMF (4 mL), was added NaH (0.0100 g, 0.419 mmol). The resulting mixture was stirred at room temperature for 10 minutes. 1-Bromo-3-methylbut-2-ene (0.240 g, 1.61 mmol) (commercially available from Aldrich) was added and the mixture was stirred at room temperature for 2 hours. After removing solvent, the residue was purified by flash chromatography (silica gel, 1:6 EtOAc/hexane) and gave T35.1 as a colorless oil, in 77% yield. MS ESI (pos.) m/e: 430 $(M+18)^+$.

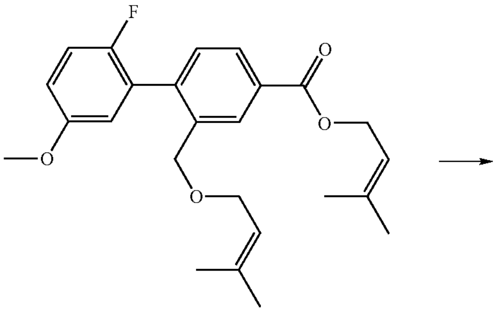

T35.1

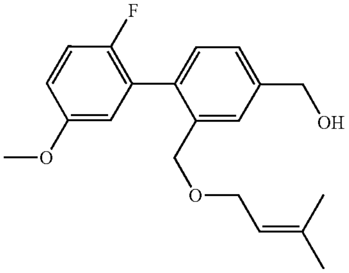

T35.2

(2'-Fluoro-2-(((3-methyl-2-butenyl)oxy)methyl)-5'-(methyloxy)-1,1'-biphenyl-4-yl)methanol (T35.2)

The conversion of ester T35.1 to hydroxymethyl compound T35.2 was conducted using a procedure analogous to that described in Example T31.4.

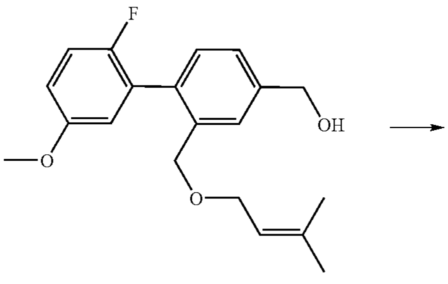

T35.2

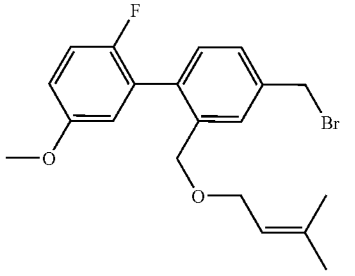

T35

4-(Bromomethyl)-2'-fluoro-2-(((3-methyl-2-butenyl) oxy)methyl)-5'-(methyloxy)-1,1'-biphenyl (T35)

Hydroxymethyl compound T35.2 was converted to bromomethyl T35 using a procedure analogous to that of Example T30.

Example T36

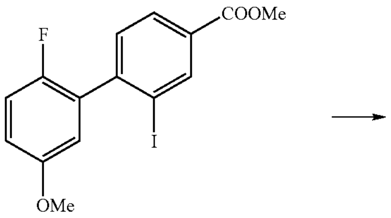

T10.4

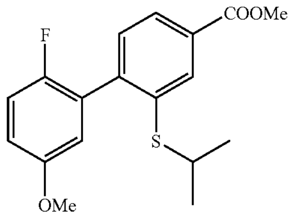

T36.1

2'-Fluoro-2-isopropylsulfanyl-5'-methoxy-biphenyl-4-carboxylic acid methyl ester (T36.1)

A tube was charged with T10.4 (213 mg, 552 μmol), N-ethyl-N-isopropylpropan-2-amine (143 mg, 1103 μmol) and toluene, evacuated and back-filled with nitrogen three times. $Pd_2(dba)_3$, 4,5-bis(diphenylphosphino)-9,9-dimethyl-9H-xanthene (31.9 mg, 55.2 μmol) and propane-2-thiol (63.0 mg, 827 μmol) were added to the mixture and then the mixture was degassed three times. The suspension was refluxed overnight, filtered, and concentrated to give a residue which was purified by silica gel chromatography to give T36.1 as a pale yellow solid (164 mg, 89%). MS ESI m/e: 335.2 $(M+1)^+$.

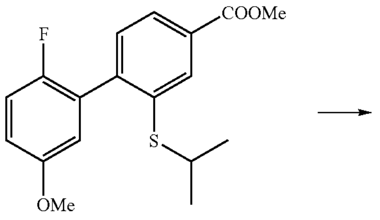

T36.1

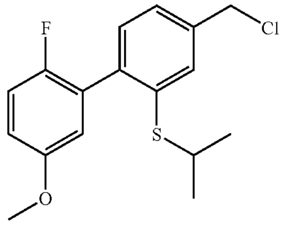

T36

4-Chloromethyl-2'-fluoro-2-isopropylsulfanyl-5'-methoxy-biphenyl (T36)

The reduction and chlorination of T36.1 was conducted in an analogous manner to that used to synthesize T3. MS ESI m/e: 325.10 $(M+H)^+$.

Examples T37A and T37B

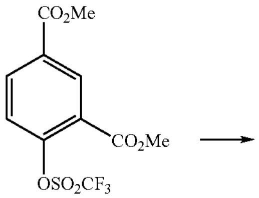

T9.2

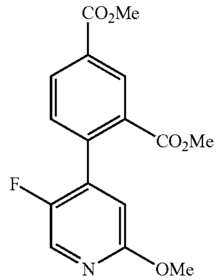

T37.1

Dimethyl 4-(5-fluoro-2-(methyloxy)-4-pyridinyl)-1,3-benzenedicarboxylate (T37.1)

To a stirred solution of T9.2 (1.00 g, 2.9 mmol) in DMF (12 mL) at 23° C. was added 5-fluoro-2-methoxypyridin-4-ylboronic acid (0.75 g, 4.4 mmol) (commercially available from Asymchem), potassium carbonate (1.2 g, 8.8 mmol), followed by tetrakis(triphenylphosphine)palladium (0.24 g, 0.20 mmol). The mixture was heated to 90° C. The reaction mixture was then stirred for 17 hours and then cooled to room temperature. The reaction was diluted with brine and extracted three times with EtOAc. After drying over anhydrous magnesium sulfate and filtering, the organic solvent was removed under reduced pressure and the product was then purified on silica gel (0-30% EtOAc in hexanes) to yield T37.1 as a colorless solid (0.860 g, 92% yield).

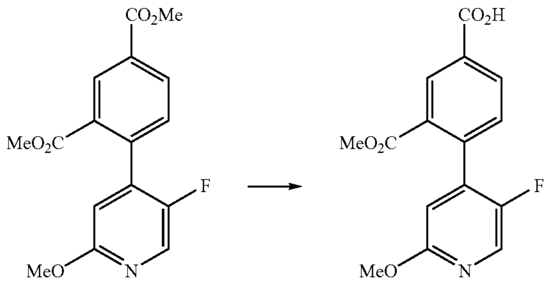

T37.1 T37.2

4-(5-Fluoro-2-(methyloxy)-4-pyridinyl)-3-((methyloxy)carbonyl)benzoic acid (T37.2)

To a stirred solution of T37.1 (0.860 g, 2.7 mmol) in THF (7.00 mL) and MeOH (7.00 mL) at 0° C. was added potassium hydroxide (1.5 mL, 3.0 mmol) slowly to maintain the temperature below 6° C. The reaction mixture was allowed to warm to room temperature and stirred for 17 hours. After which, the reaction was acidified with 1N HCl and extracted three times with EtOAc. After drying over anhydrous magnesium sulfate and filtering, the organic solvent was removed under reduced pressure to yield T37.2 as a colorless solid (0.82 g, 100% yield).

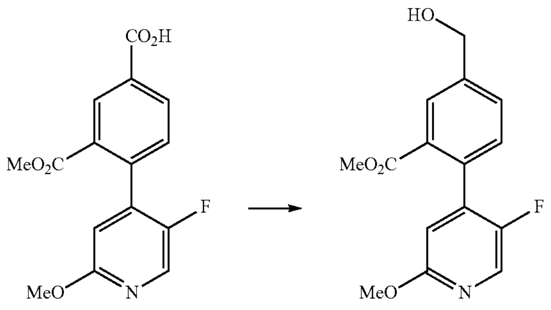

T37.2 T37.3

Methyl 2-(5-fluoro-2-(methyloxy)-4-pyridinyl)-5-(hydroxymethyl)benzoate (T37.3)

To a stirred solution of 4-(5-fluoro-2-methoxypyridin-4-yl)-3-(methoxycarbonyl)benzoic acid T37.2 (0.416 g, 1 mmol) in THF (14 mL) at 0° C. was added borane-THF (3 mL, 3 mmol, 1.0M). The reaction was warmed to 23° C. and stirred for 46 hours. The reaction was then concentrated in vacuo. The reaction was diluted with 1N HCl and extracted three times with EtOAc. After drying over anhydrous magnesium sulfate and filtering, the organic solvent was removed under reduced pressure and the product was then purified on silica gel (0-40% EtOAc in hexanes) to yield T37.3 as a colorless solid (0.307 g, 77% yield).

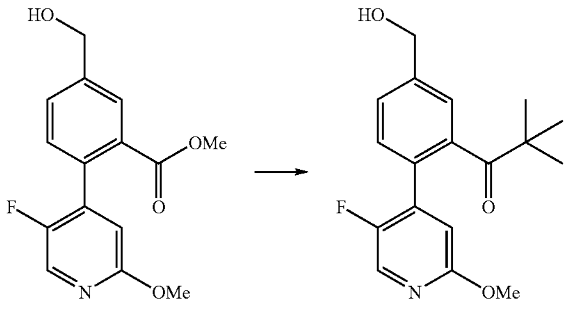

T37.3 T37.4

1-(2-(5-Fluoro-2-(methyloxy)-4-pyridinyl)-5-(hydroxymethyl)phenyl)-2,2-dimethyl-1-propanone (T37.4)

To a stirred solution of methyl 2-(5-fluoro-2-methoxypyridin-4-yl)-5-(hydroxymethyl)benzoate T37.3 (0.307 g, 1 mmol) in THF (11 mL) at −78° C. was added tert-butyl lithium (2 mL, 3 mmol). The reaction mixture was stirred for one hour and then quenched with a saturated solution of ammonium chloride and extracted three times with EtOAc. After drying over anhydrous magnesium sulfate and filtering, the organic solvent was removed under reduced pressure and the product was then purified on silica gel (0-40% EtOAc in hexanes) to yield T37.4 as a colorless solid (0.28 g, 84% yield).

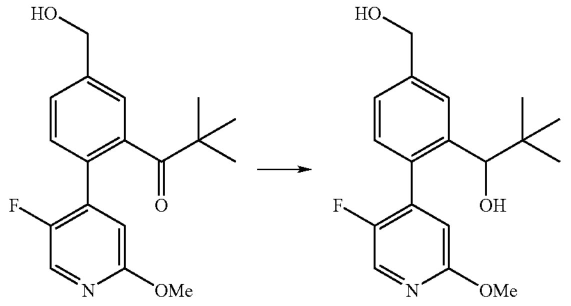

T37.4 T37.5

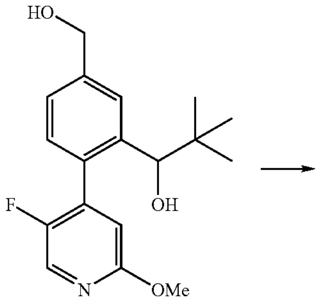

T37.5

-continued

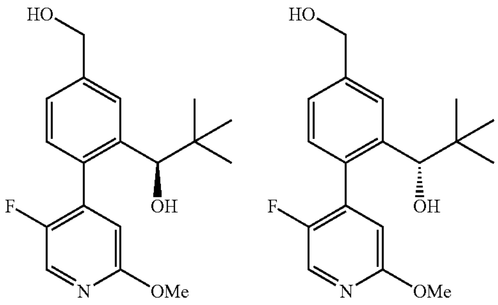

T37.6 and T37.7

(1R)-1-(2-(5-Fluoro-2-methoxypyridin-4-yl)-5-(hydroxymethyl)phenyl)-2,2-dimethylpropan-1-ol or (1S)-1-(2-(5-fluoro-2-methoxypyridin-4-yl)-5-(hydroxymethyl)phenyl)-2,2-dimethylpropan-1-ol (T37.6 and T37.7)

To a stirred solution of 1-(2-(5-fluoro-2-methoxypyridin-4-yl)-5-(hydroxymethyl)phenyl)-2,2-dimethylpropan-1-one T37.4 (0.130 g, 0.4 mmol) in THF (2 mL) at 0° C. was added LAH (0.6 mL, 0.6 mmol, 1.0M). The reaction was stirred for 3 hours. 1N NaOH(aq) was then added to quench the reaction mixture. The reaction was extracted three times with EtOAc. After drying over anhydrous magnesium sulfate and filtering, the organic solvent was removed under reduced pressure and the product was then purified on silica gel (0-20% EtOAc in hexanes) to yield T37.5 as a colorless solid (0.120 g, 92% yield). Chiral separation of T37.5 was accomplished on Chiracel-OD (4% IPA in hexane) to provide T37.6 (peak one—23.87 mins) and T37.7 (peak two—29.04 mins).[1]

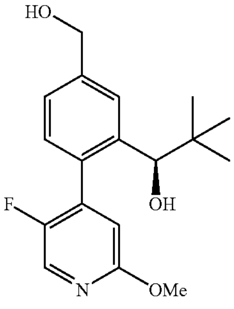

or

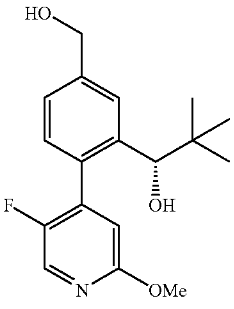

T37.6 or T37.7

-continued

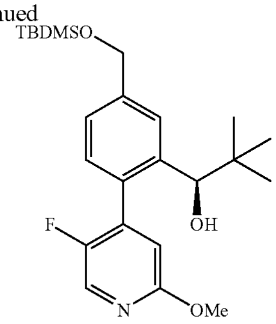

or

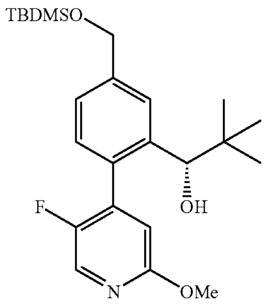

T37.8 or T37.9

(1R)-1-(5-((((1,1-Dimethylethyl)(dimethyl)silyl)oxy)methyl)-2-(5-fluoro-2-(methyloxy)-4-pyridinyl)phenyl)-2,2-dimethyl-1-propanol or (1S)-1-(5-((((1,1-dimethylethyl)(dimethyl)silyl)oxy)methyl)-2-(5-fluoro-2-(methyloxy)-4-pyridinyl)phenyl)-2,2-dimethyl-1-propanol (T37.8 or 8 T37.9)

To a stirred solution of T37.6 or T37.7 (0.050 g, 0.2 mmol) in DCM (2 mL) at 23° C. was added tert-butyldimethylsilyl chloride (0.03 mL, 0.2 mmol), followed by TEA (0.03 mL, 0.2 mmol) and DMAP (0.002 g, 0.02 mmol). The reaction was then stirred for 24 hours and then concentrated in vacuo. The reaction was extracted three times with EtOAc. After drying over anhydrous magnesium sulfate and filtering, the organic solvent was removed under reduced pressure and the product was then purified on silica gel (0-20% EtOAc in hexanes) to yield T37.8 or T37.9 as a colorless oil (0.062 g, 91% yield).

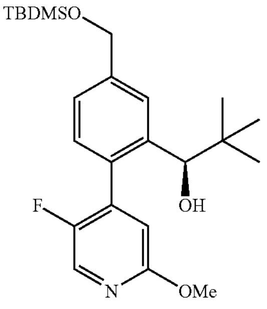

or

-continued

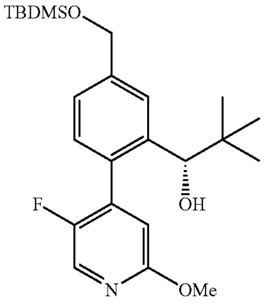

T37.8 or T37.9

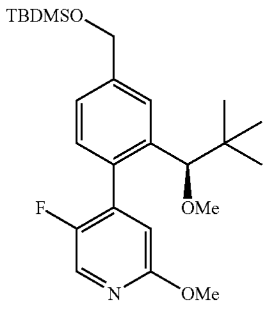

or

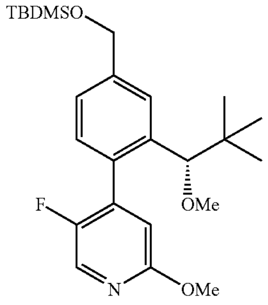

T37.10 or T37.11

4-(4-((((1,1-Dimethylethyl)(dimethyl)silyl)oxy)methyl)-2-((1R)-2,2-dimethyl-1-(methyloxy)propyl)phenyl)-5-fluoro-2-(methyloxy)pyridine or 4-(4-((((1,1-dimethylethyl)(dimethyl)silyl)oxy)methyl)-2-((1S)-2,2-dimethyl-1-(methyloxy)propyl)phenyl)-5-fluoro-2-(methyloxy)pyridine (T37.10 or T37.11)

To a stirred solution of T37.8 or T37.9 (0.062 g, 0.14 mmol) in DMF (1.4 mL) at 23° C. was added iodomethane (0.018 mL, 0.29 mmol), followed by sodium hydride (0.0069 g, 0.29 mmol). The reaction was then stirred at 50° C. for 15 hours, diluted with water and extracted three times with EtOAc. After drying over anhydrous magnesium sulfate and filtering, the organic solvent was removed under reduced pressure and the product was then purified on silica gel (0-40% EtOAc in hexanes) to yield T37.10 or T37.11 as a colorless oil (0.047 g, 73% yield).

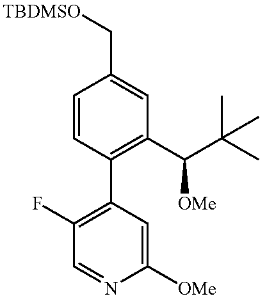

or

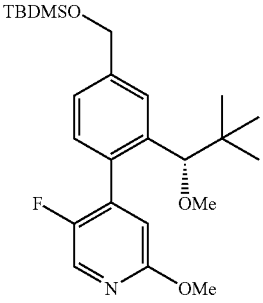

T37.10 or T37.11

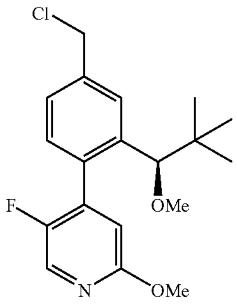

or

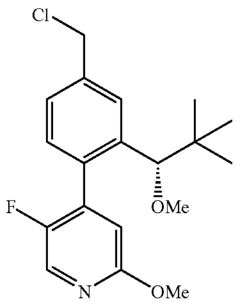

T37A or T37B 4-(4-(Chloromethyl)-2-((1R)-2,2-dimethyl-1-(methyloxy)propyl)phenyl)-5-fluoro-2-(methyloxy)pyridine or 4-(4-(chloromethyl)-2-((1S)-2,2-dimethyl-1-(methyloxy)propyl)phenyl)-5-fluoro-2-(methyloxy)pyridine (T37A or T37B)

To a stirred solution of T37.10 or T37.11 (0.047 g, 0.10 mmol) in DCM (1.0 mL) and DMF (0.0081 mL) at 0° C. was added thionyl chloride (0.015 mL, 0.21 mmol). The reaction was then stirred at room temperature for one hour and concentrated in vacuo. The product was then purified on silica gel (0-10% EtOAc in hexanes) to yield T37A or T37B as a colorless solid (0.032 g, 87% yield).

Example T38

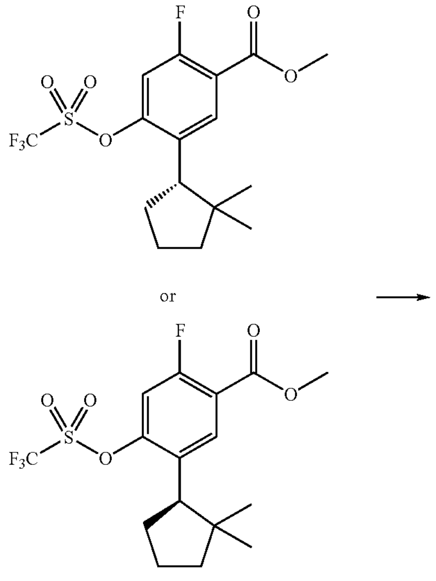

or

T23.6

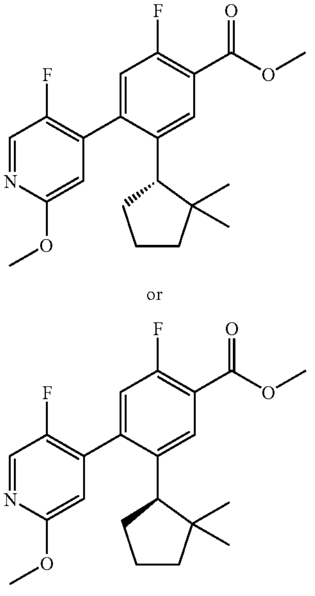

or

T38.1

Methyl 5-((1S)-2,2-dimethylcyclopentyl)-2-fluoro-4-(5-fluoro-2-(methyloxy)-4-pyridinyl)benzoate or methyl 5-((1R)-2,2-dimethylcyclopentyl)-2-fluoro-4-(5-fluoro-2-(methyloxy)-4-pyridinyl)benzoate (T38.1)

To a stirred solution of T23.6 (0.7937 g, 1.992 mmol) in DMF (4 mL) at 23° C. was added 5-fluoro-2-methoxypyridine boronic acid (commercially available from Asymchem) (0.5115 g, 2.992 mmol) and potassium carbonate (0.8279 g, 5.990 mmol) followed by tetrakis(triphenylphosphine)palladium (0.2374 g, 0.2054 mmol). The mixture was heated to 90° C. After 2 hours, LCMS-showed the reaction was complete. The mixture was cooled to room temperature and then diluted with water. After extracting three times with EtOAc, the mixture was concentrated in vacuo and then purified on silica gel (0%-20% EtOAc/hexane) to afford T38.1 (601.2 mg, 80% yield). MS ESI (pos.) m/e: 376.1 $(M+H)^+$.

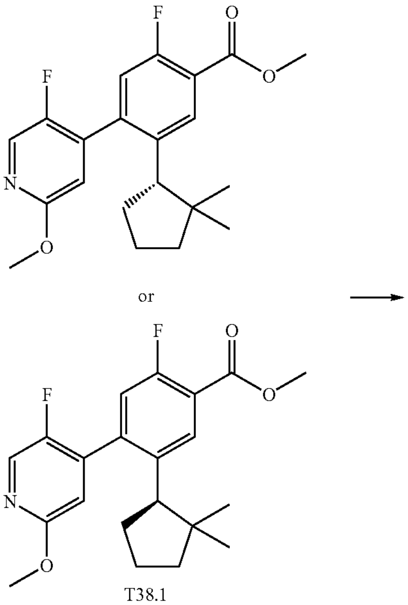

or

T38.1

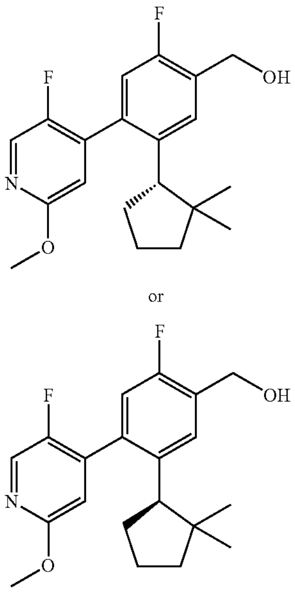

or

T38.2

(5-((1S)-2,2-Dimethylcyclopentyl)-2-fluoro-4-(5-fluoro-2-(methyloxy)-4-pyridinyl)phenyl)methanol or (5-((1R)-2,2-dimethylcyclopentyl)-2-fluoro-4-(5-fluoro-2-(methyloxy)-4-pyridinyl)phenyl)methanol (T38.2)

To a cooled solution of T38.1 (0.6012 g, 1.601 mmol) in dry THF (15 mL) at 0° C. was added LAH (1.0M in THF) (3.2 mL, 3.2 mmol) dropwise. Upon complete addition, the reaction was maintained at 0° C. and was monitored by TLC and LCMS. After 45 minutes, 1N NaOH was added to quench the reaction. Gas evolved. The resulting solution was extracted three times with EtOAc. After drying over anhydrous magnesium sulfate, filtration, and concentration, the residue was purified on silica gel (0%-20% EtOAc/hexane) to afford T38.2 (449.9 mg, 81% yield). MS ESI (pos.) m/e: 348.1 $(M+H)^+$.

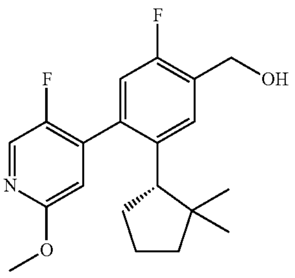

or

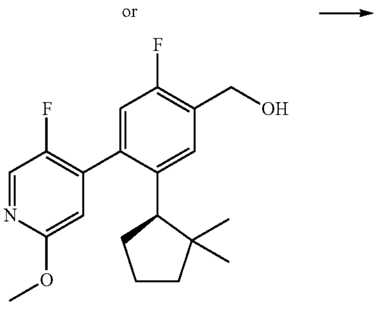

T38.2

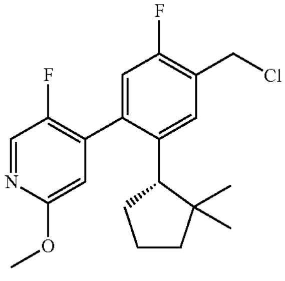

or

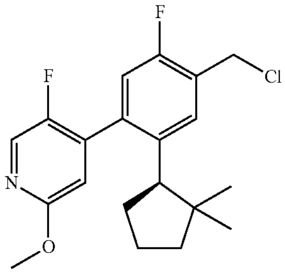

T38.3

4-(4-(Chloromethyl)-2-((1S)-2,2-dimethylcyclopentyl)-5-fluorophenyl)-5-fluoro-2-(methyloxy)pyridine or 4-(4-(chloromethyl)-2-((1R)-2,2-dimethylcyclopentyl)-5-fluorophenyl)-5-fluoro-2-(methyloxy)pyridine (T38.3)

To a solution of T38.2 (0.4463 g, 1.285 mmol) in dry DCM (17 mL) and dry DMF (0.12 mL) was added thionyl chloride (0.19 mL, 2.605 mmol) at 0° C. The resulting solution was warmed to room temperature and monitored with TLC and LCMS. After 1.5 hours, the reaction was concentrated. The residue was diluted with EtOAc and washed once with saturated aqueous $NaHCO_3$ solution and once with brine. The organic layer was subsequently dried over anhydrous sodium sulfate, filtered, concentrated, and purified by silica gel flash chromatography (0-15% EtOAc/hexane) to afford T38.3 (446.9 mg, 95% yield). MS ESI (pos.) m/e: 366.1 $(M+H)^+$.

Example T39

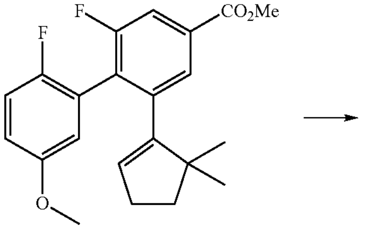

T 25.7

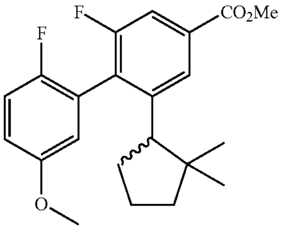

T 39.1

Methyl 2-(2,2-dimethylcyclopentyl)-2',6-difluoro-5'-(methyloxy)-1,1'-biphenyl-4-carboxylate (T39.1)

To a flask containing T25.7 (0.7168 g, 1.925 mmol) in dry MeOH (8 mL) and EtOAc (5 mL) was added palladium, 10 wt. % on activated carbon (0.2103 g, 0.1976 mmol). After purging, the mixture was stirred under an atmosphere of hydrogen at room temperature. After 18.5 hours, the mixture was filtered through Celite® filter aid. After concentration, hydrogenated product T39.1 (703.6 mg, 98% yield) was obtained. $^1H$ NMR (400 MHz, $CDCl_3$) δ ppm 7.88 (1H, s), 7.65 (1H, dd, J=9.4, 1.6 Hz), 7.13 (2H, m), 6.96 (2H, m), 6.77 (1H, dd, J=5.5, 3.1 Hz), 3.95 (3H, s), 3.80 (3H, s), 2.76 (1H, ddd, J=10.3, 8.3, 1.8 Hz), 2.19 (1H, m), 2.08 (1H, m), 1.91 (1H, m), 1.75 (2H, m), 1.45 (1H, m), 0.78 (3H, s), 0.64 (3H, s).

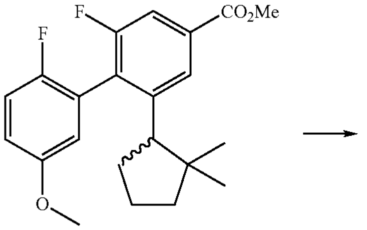

T39.1

-continued

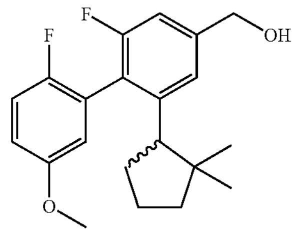

T39.2

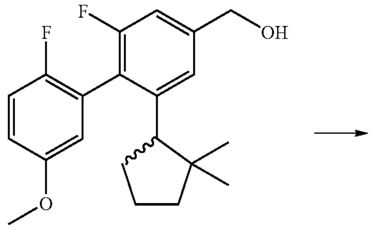

T39.2

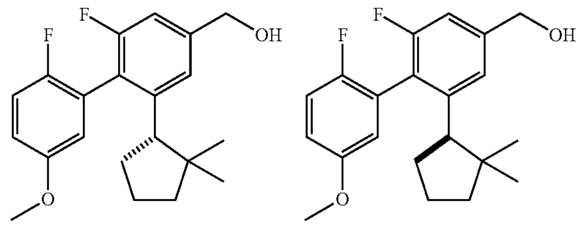

T39.3 and T39.4

(2-((1S)-2,2-Dimethylcyclopentyl)-2',6-difluoro-5'-(methyloxy)-1,1'-biphenyl-4-yl)methanol and (2-((1R)-2,2-dimethylcyclopentyl)-2',6-difluoro-5'-(methyloxy)-1,1'-biphenyl-4-yl)methanol (T39.3 or T 39.4)

To a cooled solution of T39.1 (0.7036 g, 1.879 mmol) in dry THF (15 mL) at 0° C. was added LAH, 1.0 M in THF (4 mL, 4.0 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by flash chromatography ($SiO_2$ gel 60, eluted with 0%-50% EtOAc in hexanes). Fractions containing the desired product were combined and concentrated providing a colorless oil that solidified as T39.2 (300.5 mg, 46% yield). $^1H$ NMR (400 MHz, $CDCl_3$) δ ppm 7.16 (1H, s), 7.10 (2H, m), 6.92 (1H, m), 6.77 (1H, dd, J=5.9, 3.1 Hz), 4.74 (2H, s), 3.81 (3H, m), 2.73 (1H, ddd, J=10.3, 8.3, 1.8 Hz), 2.17 (1H, m), 2.04 (1H, m), 1.87 (1H, m), 1.73 (3H, m), 1.42 (1H, m), 0.78 (3H, s), 0.64 (3H, s). Chiral separation of T39.2 was accomplished on Chiracel-OJ (2% IPA in hexane) to provide T39.3 (peak 1) and T39.4 (peak 2). Both enantiomers were used to synthesize example compounds, and both enantiomers gave active compounds.

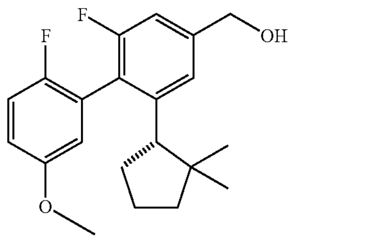

or

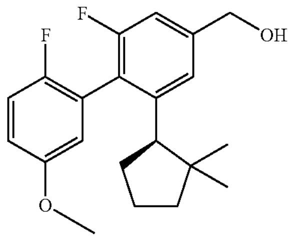

T39.3

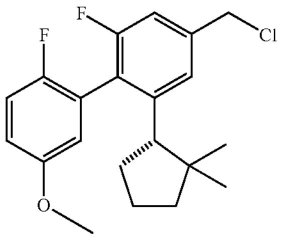

or

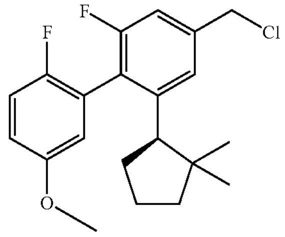

T39

4-(Chloromethyl)-2-((1S)-2,2-dimethylcyclopentyl)-2',6-difluoro-5'-(methyloxy)-1,1'-biphenyl or 4-(chloromethyl)-2-((1R)-2,2-dimethylcyclopentyl)-2',6-difluoro-5'-(methyloxy)-1,1'-biphenyl (T39 A or T39B)

To a solution of T39.3 (0.1171 g, 0.338 mmol) in dry DCM (4.5 mL) and dry DMF (0.03 mL) was added thionyl chloride (0.05 mL, 0.685 mmol) at 0° C. The resulting solution was warmed to room temperature and monitored with TLC and LCMS. After 19 hours, the reaction was concentrated and then purified by silica gel flash chromatography (0-5% EtOAc/hexane) to afford T39 (99.7 mg, 81% yield). $^1H$ NMR (400 MHz, $CDCl_3$) δ ppm 7.18 (1H, d, J=1.6 Hz), 7.13 (2H, m), 6.95 (1H, m), 6.77 (1H, dd, J=5.9, 3.1 Hz), 4.68 (2H, m), 3.84 (3H, m), 2.73 (1H, ddd, J=10.3, 8.3, 1.8 Hz), 2.18 (1H, m), 2.01 (1H, m), 1.88 (1H, m), 1.73 (3H, m), 1.44 (1H, m), 0.78 (3H, s), 0.64 (3H, s).

Synthesis of Example Compounds

Example 1

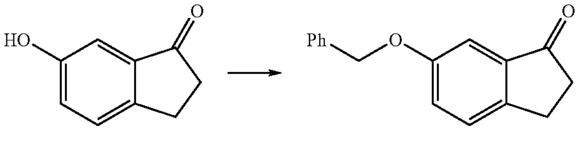

1.1 1.2

6-(Benzyloxy)-2,3-dihydroinden-1-one (1.2)

A mixture of 6-hydroxy-2,3-dihydroinden-1-one (available from Aldrich) (5.0 g, 34 mmol), 1-(bromomethyl)benzene (1.1) (available from Aldrich) (4.4 mL, 37 mmol) and cesium carbonate (25 g, 78 mmol) in DMF were stirred at room temperature for 23 hours. The reaction mixture was diluted with EtOAc (400 mL). The mixture was washed with brine and dried over anhydrous sodium sulfate. After removing solvent by rotary evaporation, the residue was purified by column chromatography (1:4 EtOAc/hexane). Product 1.2 was obtained in 67% yield as a white solid.

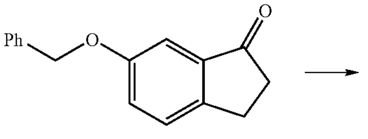

1.2

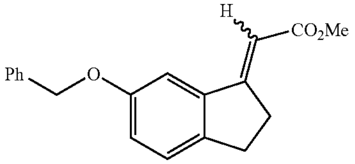

1.3

(E)-Methyl 2-(6-(benzyloxy)-2,3-dihydroinden-1-ylidene)acetate (1.3)

At −78° C., lithium bis(trimethylsilyl)amide (1.0 M in hexanes) (4 mL, 26 mmol) was added slowly to a solution of methyl 2-(trimethylsilyl)acetate (4 g, 26 mmol) in THF (20 mL). The reaction mixture was maintained at −78° C. for 22 minutes. 1.2 (3.5 g, 15 mmol) in THF (20 mL) was then added slowly to the mixture. The mixture was stirred at −78° C. and allowed to warm to room temperature overnight. The reaction mixture was then poured into water (30 mL) and extracted with EtOAc (300 mL). The organic layers were washed with brine and dried over anhydrous sodium sulfate. After removing solvent by rotary evaporation, the residue was purified by column chromatography (1:4 EtOAc/hexane). The Product 1.3 was obtained in 38% yield as a white solid.

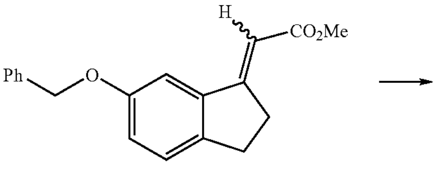

1.3

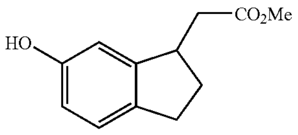

1.4

Methyl 2-(6-hydroxy-2,3-dihydro-1H-inden-1-yl) acetate (1.4)

Under hydrogen, a mixture of (E)-methyl 2-(6-(benzyloxy)-2,3-dihydroinden-1-ylidene)acetate (1.3) (1.64 g, 5.57 mmol), palladium on carbon (10%) (0.462 g, 3.90 mmol) in MeOH (30 mL) were stirred for 24 hours. The mixture was then filtered through silica gel to remove the Pd—C, eluting with EtOAc. After removing solvent by rotary evaporation, the residue was purified using column chromatography (1:1 EtOAc/hexane). Product 1.4 was obtained in 68% yield as a colorless oil.

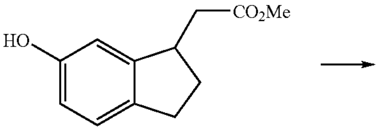

1.4

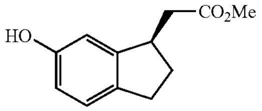

or

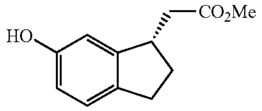

1.5

(R)-Methyl 2-(6-hydroxy-2,3-dihydro-1H-inden-1-yl)acetate or (S)-methyl 2-(6-hydroxy-2,3-dihydro-1H-inden-1-yl)acetate (1.5)

Chiral separation was achieved using a chiral separation column: OJ; solvent: 14% IPA: hexane. One of the enantiomers 1.5 (0.36 g) was obtained in optical purity >99%.

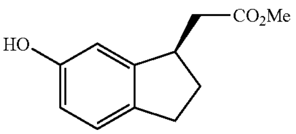

or

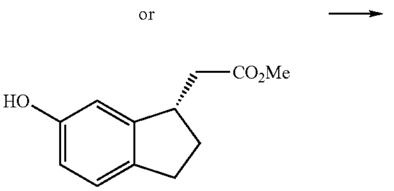

1.5

-continued

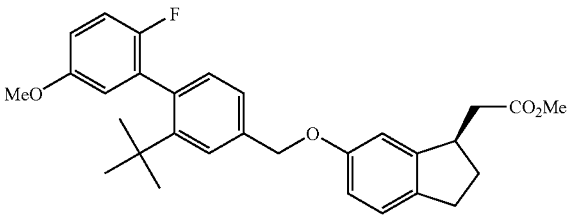

or

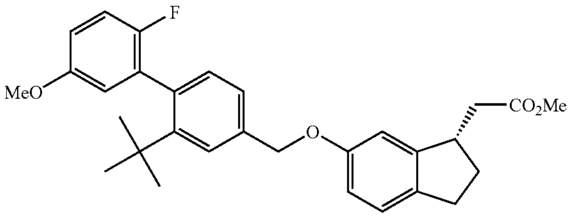

1.6

-continued

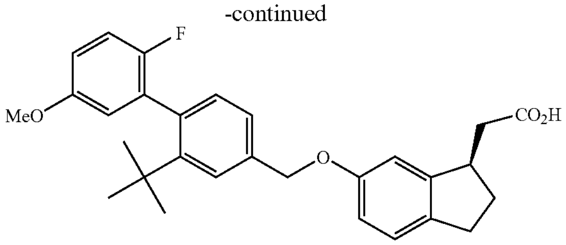

or

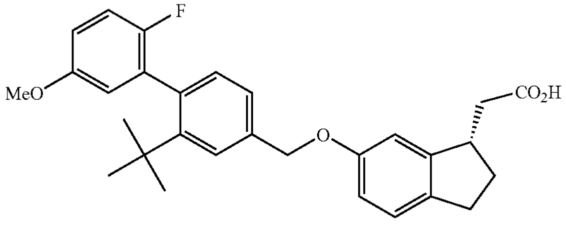

1

(R)-2-(6-(Aryloxy)-2,3-dihydro-1H-inden-1-yl)acetic acids or (S)-2-(6-(aryloxy)-2,3-dihydro-1H-inden-1-yl)acetic acids (1.6)

A mixture of 1.5 (0.050 g, 0.24 mmol), 4-(chloromethyl)-2-(1,1-dimethylethyl)-2'-fluoro-5'-(methyloxy)-1,1'-biphenyl (Method A) (0.061 g, 0.24 mmol) and cesium carbonate in DMF were stirred at room temperature overnight. The reaction mixture was then diluted with EtOAc (400 mL). The mixture was washed with brine and dried over anhydrous sodium sulfate. After removing solvent by rotary evaporation, the residue was purified using column chromatography (1:7 EtOAc:hexane) to obtain product 1.6.

((1R)-6-(((2-(1,1-Dimethylethyl)-2'-fluoro-5'-(methyloxy)-1,1'-biphenyl-4-yl)methyl)oxy)-2,3-dihydro-1H-inden-1-yl)acetic acid or ((1S)-6-(((2-(1,1-Dimethylethyl)-2'-fluoro-5'-(methyloxy)-1,1'-biphenyl-4-yl)methyl)oxy)-2,3-dihydro-1H-inden-1-yl)acetic acid (1)

A mixture of 1.6, NaOH (10% aq) (1 mL), EtOH (3 mL) was stirred at room temperature for 4 hours. The mixture was concentrated by removing EtOH and water (2 mL) was added. The mixture was then acidified with 1 N HCl to a pH of 3-5. The mixture was extracted with EtOAc (150 mL), washed with water and brine, and dried over anhydrous sodium sulfate. After removing solvent, the residue was purified by chromatography (silica gel, 1% MeOH/DCM) to give 1. MS ESI (neg.) M/E: 461 (M−H). $^1$HNMR (DMSO-$d_6$) δ 7.63 (d, J=1 Hz, 1H), 7.29 (m, 1H), 7.12-7.19 (m, 2H), 6.98 (m, 3H), 6.81-6.84 (m, 2H), 5.09 (s, 2H), 3.75 (s, 3H), 3.40 (m, 1H), 2.78 (m, 3H), 2.31 (m, 2H), 1.65 (m, 1H), 1.18 (s, 9H).

Example 2

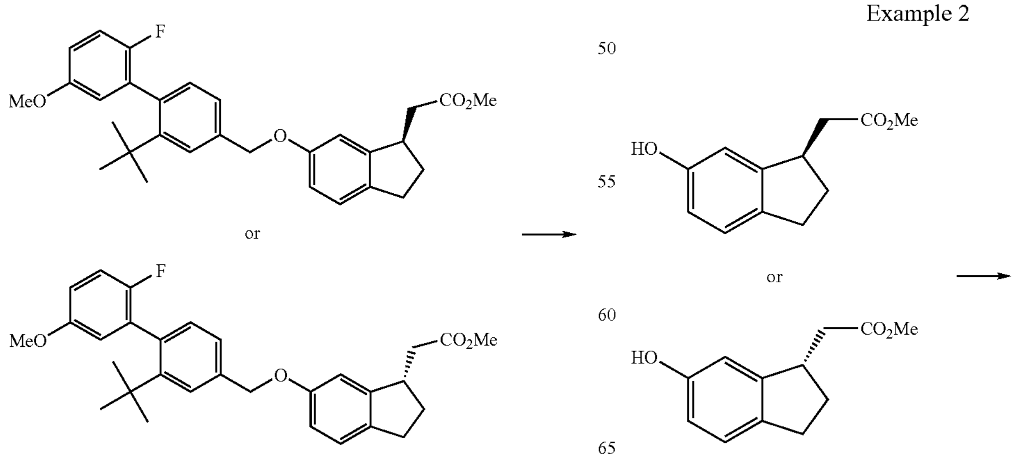

or 1.6 or 1.5

-continued

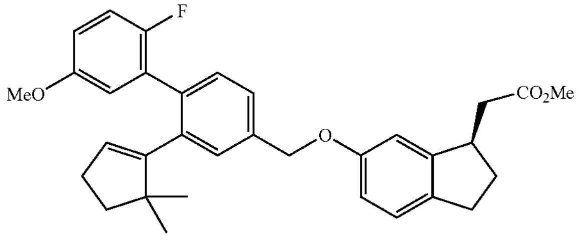

or

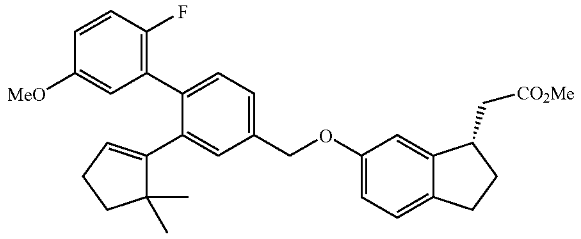

2.1

Methyl ((1R)-6-(((2-(5,5-dimethyl-1-cyclopenten-1-yl)-2'-fluoro-5'-(methyloxy)-1,1'-biphenyl-4-yl)methyl)oxy)-2,3-dihydro-1H-inden-1-yl)acetate or methyl ((1S)-6-(((2-(5,5-dimethyl-1-cyclopenten-1-yl)-2'-fluoro-5'-(methyloxy)-1,1'-biphenyl-4-yl)methyl)oxy)-2,3-dihydro-1H-inden-1-yl)acetate (2.1)

The title compound was synthesized from 1.5 and 4-(chloromethyl)-2-(5,5-dimethyl-1-cyclopenten-1-yl)-2'-fluoro-5'-(methyloxy)-1,1'-biphenyl (B.9) using a procedure analogous to that described for synthesizing 1.6 from 1.5.

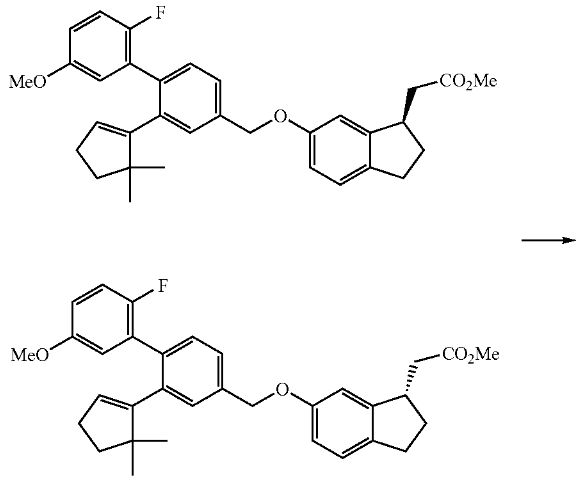

2.1

-continued

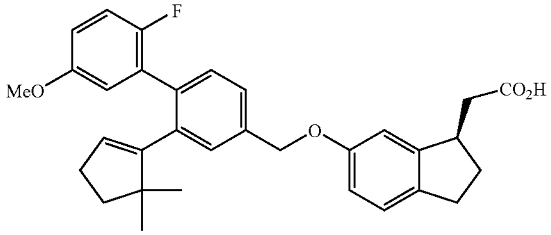

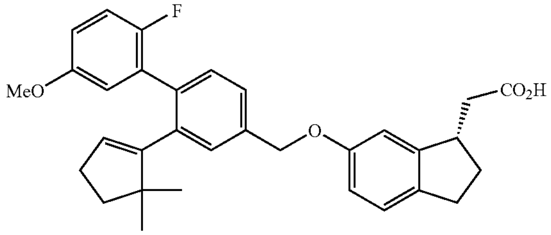

2

((1R)-6-(((2-(5,5-Dimethyl-1-cyclopenten-1-yl)-2'-fluoro-5'-(methyloxy)-1,1'-biphenyl-4-yl)methyl)oxy)-2,3-dihydro-1H-inden-1-yl)acetic acid or ((1S)-6-(((2-(5,5-Dimethyl-1-cyclopenten-1-yl)-2'-fluoro-5'-(methyloxy)-1,1'-biphenyl-4-yl)methyl)oxy)-2,3-dihydro-1H-inden-1-yl)acetic acid (2)

The title compound was synthesized from 2.1 using a procedure analogous to that described for synthesizing 1 from 1.6. MS ESI (neg.) M/E: 499 (M−H). $^1$HNMR (DMSO-$d_6$) δ 7.56 (d, J=10 Hz, 1H), 7.41 (m, 1H), 7.28.7.31 (m, 2H), 7.10-7.13 (m, 2H), 6.95 (d, J=2 Hz, 1H), 6.90 (m, 1H), 6.81-6.85 (m, 2H), 5.51 (s, 1H), 5.13 (s, 2H), 3.72 (s, 3H), 2.71-2.78 (m, 3H), 2.29 (m, 2H), 2.20 (m, 2H), 1.65-1.70 (m, 1H), 1.60 (m, 2H), 0.80 (d, 6H).

Example 3

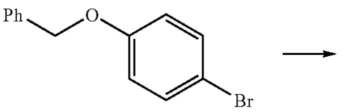

3.1

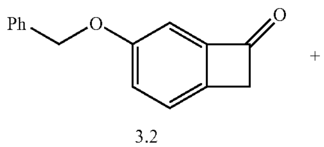

3.2

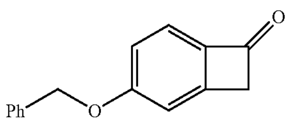

3.3

5-(Benzyloxy)cyclobutabenzen-1(2H)-one (3.2) and 4-(benzyloxy)cyclobutabenzen-1(2H)-one (3.3)

A mixture of 1-(benzyloxy)-4-bromobenzene 3.1 (available from Aldrich) (5.00 g, 19 mmol), ketene diethyl acetal (5.0 mL, 38 mmol) and sodium amide (1.5 g, 38 mmol) in THF (20 mL) were stirred in a sealed tube at 76° C. for 19 hours. After cooling to room temperature, the reaction mixture was diluted with EtOAc (280 mL), washed with water, brine, dried over anhydrous $Na_2SO_4$. The solvent was removed by rotary evaporation and the residue was mixed with acetone (70 mL) and 1N HCL (10 mL). After it was stirred at room temperature for 1 hour, it was neutralized with $NaHCO_3$ solution. The mixture was concentrated, extracted with EtOAc (300 mL). The organic phase was washed with brine and dried over anhydrous sodium sulfate. The residue was purified by chromatography (1:1 DCM/hexane) to give product 3.2 as a pale yellow solid, in 41% yield and 3.3 as a brown oil in 12% yield.

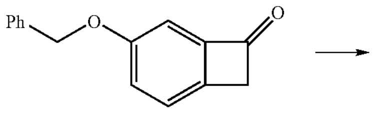

3.2

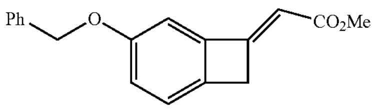

3.4

(E)-Methyl 2-(5-(benzyloxy)cyclobutabenzen-1(2H)-ylidene)acetate (3.4)

At −78° C., Lithium bis(trimethylsilyl)amide (1.0 M in THF) (7.1 mL, 7.1 mmol) was added slowly to a solution of methyl 2-(trimethylsilyl)acetate (1.2 mL, 7.1 mmol) in THF (6 mL). It was maintained at −78° C. for 12 min. 5-(Benzyloxy)cyclobutabenzen-1(2H)-one (3.2) (0.88 g, 3.9 mmol) in THF (3 mL) was added in one portion. It was stirred at −78° C. and allowed to r.t. overnight. EtOAc (300 mL) was added and it was washed with brine and dried over $Na_2SO_4$. After removing solvent, the residue was purified by chromatography (silica gel, 1:6 EtOAc/hexane) to give 3.4 in 14% yield.

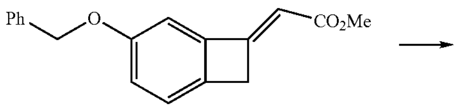

3.4

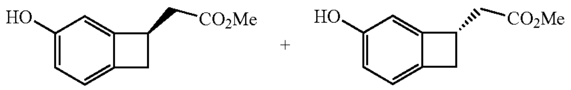

3.5 and 3.6

(R)-Methyl 2-(5-hydroxy-1,2-dihydrocyclobutabenzen-1-yl)acetate and (S)-methyl 2-(5-hydroxy-1,2-dihydrocyclobutabenzen-1-yl)acetate (3.5 and 3.6)

Under hydrogen, a mixture of 3.4, palladium-carbon in MeOH (10 mL) was stirred for 1 hour. The mixture was then filtered through silica gel to remove the palladium-carbon. After removing solvent, the residue was purified by chromatography (silica gel, 1:4 EtOAc/hexane) to give a racemic methyl 2-(5-hydroxy-1,2-dihydrocyclobutabenzen-1-yl)acetate. The racemate was separated by chiral HPLC (column: OD-H; 4% IPA/hexane) to give 58 mg (>99% ee) of one enantiomer and 44 mg (>99% ee) of the other. One of 3.5 and 3.6 is the R enantiomer and the other is the S enantiomer.

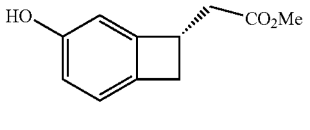

or

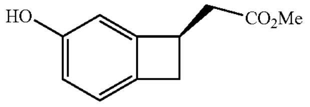

3.6

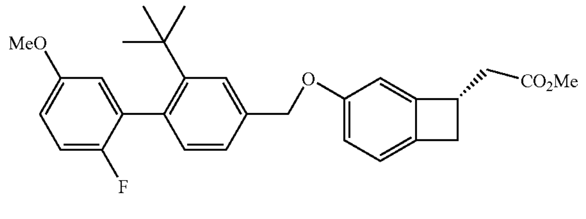

or

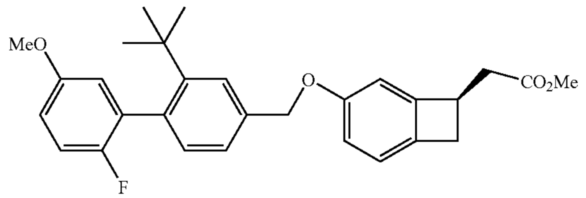

3.7

(R)-Methyl 2-(5-(3-t-butyl-4-(2-fluoro-5-methoxyphenyl)benzyloxy)-1,2-dihydrocyclobutabenzen-1-yl)acetate or (S)-methyl 2-(5-(3-t-butyl-4-(2-fluoro-5-methoxyphenyl)benzyloxy)-1,2-dihydrocyclobutabenzen-1-yl)acetate (3.7)

The title compound was prepared from 3.6 and 4-(chloromethyl)-2-(1,1-dimethylethyl)-2'-fluoro-5'-(methyloxy)-1,1'-biphenyl (Method A) using the method described for the synthesis of 1.6.

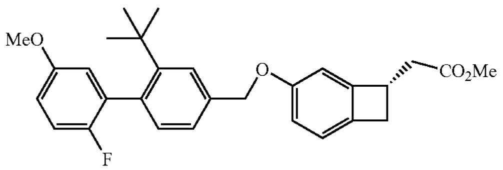

or

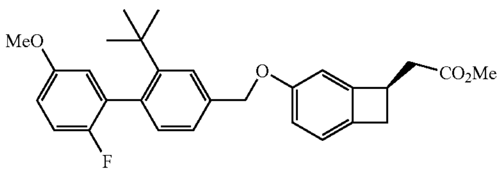

3.7

-continued

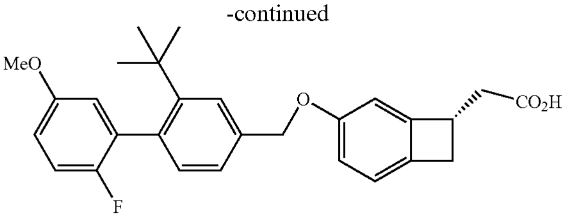

or

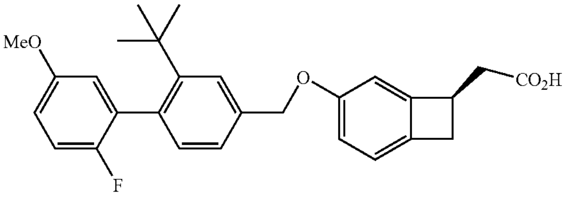

3

(R)-2-(5-(3-t-Butyl-4-(2-fluoro-5-methoxyphenyl)benzyloxy)-1,2-dihydrocyclobutabenzen-1-yl)acetic acid or (S)-2-(5-(3-t-butyl-4-(2-fluoro-5-methoxyphenyl)benzyloxy)-1,2-dihydrocyclobutabenzen-1-yl)acetic acid (3)

The title compound was synthesized from 3.7 using a procedure analogous to that described for synthesizing 1 from 1.6. MS ESI (neg.) M/E: 447 (M−H). $^1$HNMR (DMSO-$d_6$) δ 7.56 (d, J=10 Hz, 1H), 7.41 (m, 1H), 7.16 (m, 1H), 7.02 (d, J=2 Hz, 1H), 6.95-6.99 (m, 2H), 6.82 (m, 2H), 6.78 (m, 1H), 4.98 (s, 2H), 3.74 (s, 3H), 3.62 (m, 1H), 3.22 (m, 1H), 2.70 (m, 1H), 2.59 (m, 2H), 1.17 (s, 9H).

Example 4

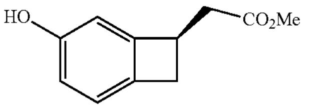

or

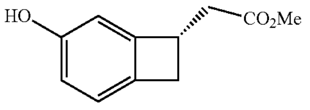

3.5

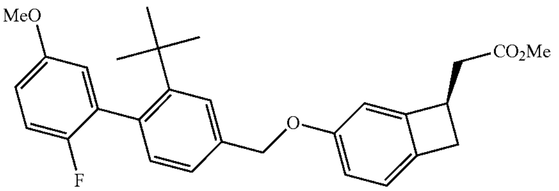

or

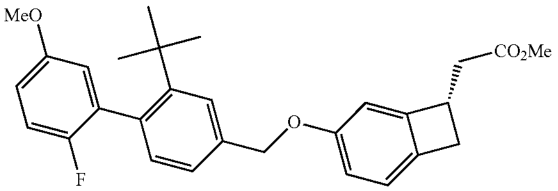

4.1

Methyl ((7R)-4-(((2-(1,1-dimethylethyl)-2'-fluoro-5'-(methyloxy)-1,1'-biphenyl-4-yl)methyl)oxy)bicyclo[4.2.0]octa-1,3,5-trien-7-yl)acetate (4.1) or methyl ((7S)-4-(((2-(1,1-dimethylethyl)-2'-fluoro-5'-(methyloxy)-1,1'-biphenyl-4-yl)methyl)oxy)bicyclo[4.2.0]octa-1,3,5-trien-7-yl)acetate (4.1)

A mixture of 3.5 (0.018 g, 0.094 mmol), 4-(chloromethyl)-2-(1,1-dimethylethyl)-2'-fluoro-5'-(methyloxy)-1,1'-biphenyl (Method A) (0.029 g, 0.094 mmol) and cesium carbonate (0.20 mmol) in DMF (2 mL) was stirred at room temperature for 21 hours. The was then diluted with EtOAc (150 mL), washed with water and brine, and dried over anhydrous sodium sulfate. The solvent was then removed and the residue was purified by flash chromatography (silica gel, eluting with 1:4 EtOAc/hexane) providing 4.1. MS ESI (pos.) M/E: 462 (M+18).

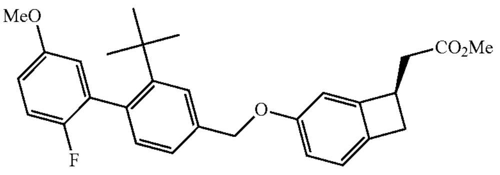

or

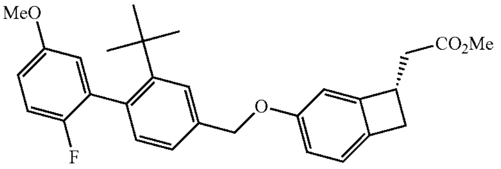

4.1

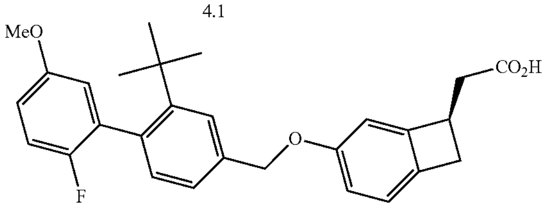

or

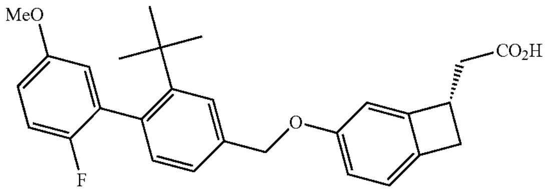

4

((7R)-4-(((2-(1,1-Dimethylethyl)-2'-fluoro-5'-(methyloxy)-1,1'-biphenyl-4-yl)methyl)oxy)bicyclo[4.2.0]octa-1,3,5-trien-7-yl)acetic acid or ((7R)-4-(((2-(1,1-dimethylethyl)-2'-fluoro-5'-(methyloxy)-1,1'-biphenyl-4-yl)methyl)oxy)bicyclo[4.2.0]octa-1,3,5-trien-7-yl)acetic acid (4)

The title compound was synthesized from 4.1 using a procedure analogous to that described for synthesizing 1 from 1.6. MS ESI (neg.) M/E: 447 (M−H). $^1$HNMR (DMSO-$d_6$) δ 7.61 (d, J=1 Hz, 1H), 7.28 (m, 1H), 7.16 (m, 1H), 7.01 (m, 1H), 6.93-6.98 (m, 2H), 6.85-6.87 (m, 1H), 6.80-6.84 (m, 2H), 5.06 (s, 2H), 3.74 (s, 3H), 3.64-3.68 (m, 1H), 3.24-3.28 (m, 1H), 2.61 (m, 2H), 2.68 (m, 1H), 1.17 (s, 9H).

Example 5

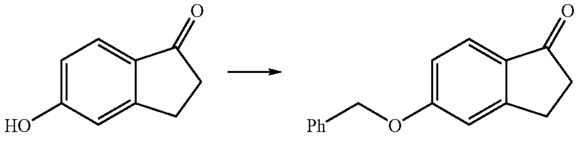

5.1 5.2

5-(Benzyloxy)-2,3-dihydroinden-1-one (5.2)

A mixture of 5-hydroxy-1-indanone 5.1 (available from Aldrich) (5 g, 34 mmol), 1-(bromomethyl)benzene (available from Aldrich) (4 mL, 37 mmol) and cesium carbonate (16 g, 51 mmol) in DMF (40 mL) was stirred at room temperature for 17 hours. EtOAc (400 mL) was added, and the mixture was washed with water and brine, and dried over anhydrous sodium sulfate. After removing solvent, the residue was purified by chromatography (silica gel, 1:4 EtOAc/hexane) to give 5.2 in 75% yield.

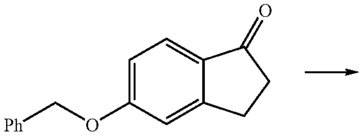

5.2

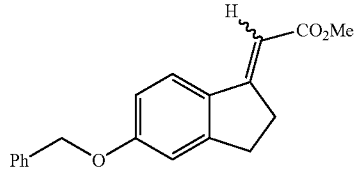

5.3

Methyl 2-(5-(benzyloxy)-2,3-dihydroinden-1-ylidene)acetate (5.3)

At −78° C., lithium bis(trimethylsilyl)amide (1.0 M in THF) (30 mL, 30 mmol) was added slowly to a solution of methyl 2-(trimethylsilyl)acetate (5.0 mL, 30 mmol) in THF (20 mL). The reaction was maintained at −78° C. for 11 minutes and then 5-(benzyloxy)-2,3-dihydroinden-1-one (5.2) (4.0 g, 17 mmol) in 10 mL of THF was added in one portion. The resulting mixture was stirred at −78° C. and allowed to warm to room temperature overnight. EtOAc (400 mL) was added, and the mixture was washed with water and brine, and dried over anhydrous sodium sulfate. After removing solvent, the residue was purified by chromatography (silica gel, 1:4 EtOAc/hexane) to give 5.3 in 70% yield.

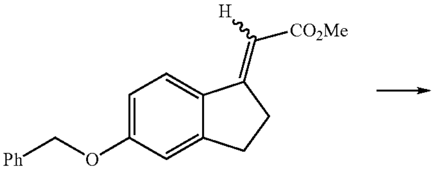

5.3

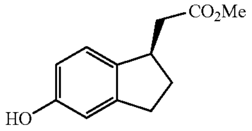

or

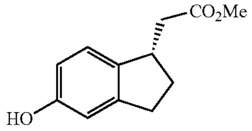

5.4

(R)-Methyl 2-(5-hydroxy-2,3-dihydro-1H-inden-1-yl)acetate or (S)-methyl 2-(5-hydroxy-2,3-dihydro-1H-inden-1-yl)acetate (5.4)

Under hydrogen, a mixture of methyl 2-(5-(benzyloxy)-2,3-dihydroinden-1-ylidene)acetate 5.3 (3.44 g, 11.7 mmol), Pd—C (1.38 g, 11.7 mmol) in MeOH (35 mL) was stirred for 3 hours. The resulting mixture was then filtered through silica gel to remove the Pd—C. After removing solvent, the residue was purified by chromatography (silica gel, 1:2 EtOAc/hexane) to give a racemate in 47% yield. The racemate was separated by chiral chromatography (column: OD, 4% IPA/hexane) to give 5.4 (>99% ee).

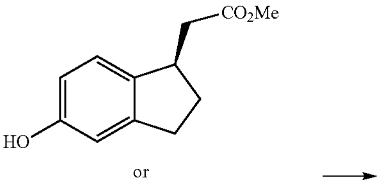

or

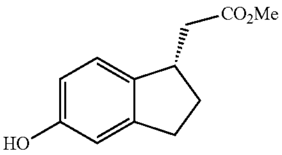

5.4

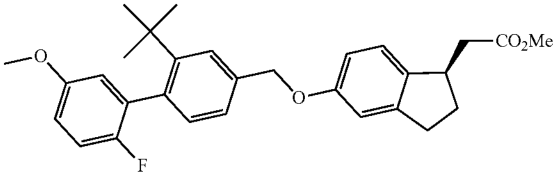

or

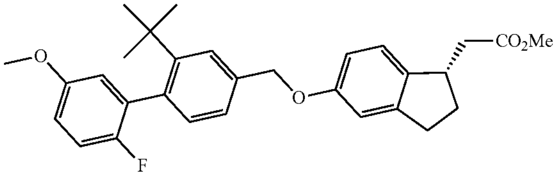

5.5

(R)-Methyl 2-(5-(3-t-butyl-4-(2-fluoro-5-methoxyphenyl)benzyloxy)-2,3-dihydro-1H-inden-1-yl) acetate or (S)-Methyl 2-(5-(3-t-butyl-4-(2-fluoro-5-methoxyphenyl)benzyloxy)-2,3-dihydro-1H-inden-1-yl)acetate (5.5)

The title compound was prepared from 5.4 and 4-(chloromethyl)-2-(1,1-dimethylethyl)-2'-fluoro-5'-(methyloxy)-1,1'-biphenyl (Method A) using the method described for the synthesis of 1.6.

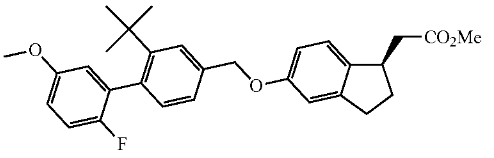

or

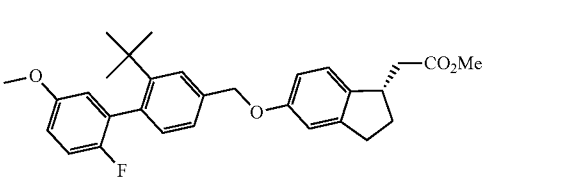

5.5

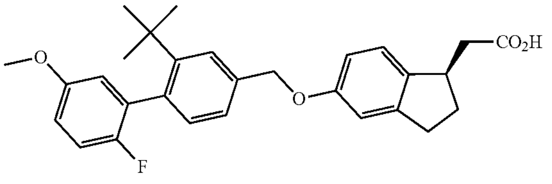

or

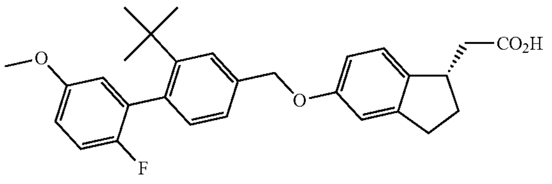

5

(R)-Methyl 2-(5-(3-t-butyl-4-(2-fluoro-5-methoxyphenyl)benzyloxy)-2,3-dihydro-1H-inden-1-yl) acetic acid or (S)-methyl 2-(5-(3-t-butyl-4-(2-fluoro-5-methoxyphenyl)benzyloxy)-2,3-dihydro-1H-inden-1-yl)acetic acid (5)

The title compound was synthesized from 5.5 using a procedure analogous to that described for synthesizing 1 from 1.6. MS ESI (neg.) M/E: 461 (M−H). $^1$HNMR (DMSO-$d_6$) δ 7.62 (d, J=1 Hz, 1H), 7.29 (m, 1H), 7.16 (m, 2H), 7.98 (m, 2H), 6.93 (m, 1H), 6.82 (m, 2H), 5.10 (s, 2H), 3.75 (s, 3H), 3.40 (m, 1H), 2.86 (m, 1H), 2.78 (m, 1H), 2.68 (m, 1H), 2.31 (m, 2H), 1.67 (m, 1H), 1.18 (s, 9H).

Example 6

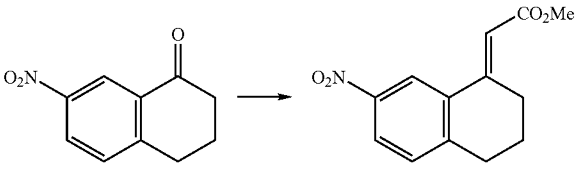

6.1 6.2

(E)-Methyl 2-(7-nitro-3,4-dihydronaphthalen-1(2H)-ylidene)acetate (6.2)

At −78° C., lithium bis(trimethylsilyl)amide, (1.0 M in hexanes) (5 mL, 28 mmol) was added slowly to a solution of methyl 2-(trimethylsilyl)acetate (4 g, 28 mmol) in THF (30 mL). The reaction was maintained at −78° C. for 16 minutes and then 7-nitro-1-tetralone 6.1 (available from Astratech) (3 g, 16 mmol) was added in one portion, and the resulting mixture was stirred at −78° C. and allowed to warm to room temperature for 20 hours. The resulting mixture was poured into water (30 mL) and then extracted with EtOAc (300 mL). The combined organic layers were washed with brine and dried over anhydrous sodium sulfate. After removing solvent, the residue was purified by chromatography (silica gel, 1:4 EtOAc/hexane) to give 6.2 in 83% yield.

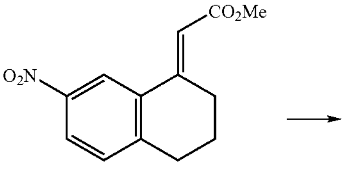

6.2

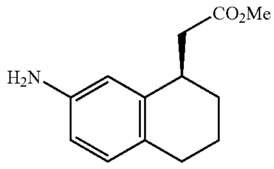

or

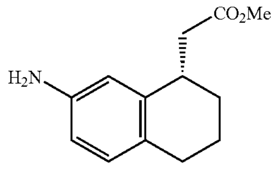

6.3

(R)-Methyl 2-(7-amino-1,2,3,4-tetrahydronaphthalen-1-yl)acetate or (S)-methyl 2-(7-amino-1,2,3,4-tetrahydronaphthalen-1-yl)acetate (6.3)

Under hydrogen, a mixture of (E)-methyl 2-(7-nitro-3,4-dihydronaphthalen-1(2H)-ylidene)acetate 6.2 (3.2 g, 13 mmol), palladium on carbon (10%) (1.1 g, 9.1 mmol) in MeOH (50 mL) was stirred for 16 hours. The resulting mixture was filtered through silica gel to remove the palladium on carbon. After removing solvent, the residue was purified by chromatography (silica gel, 1:19 EtOAc/hexane) to give the racemic product as a brown oil in 54%. yield. The racemate was separated by chiral chromatography (column: OD, 20% IPA/hexane) to give 6.3 (>99% ee).

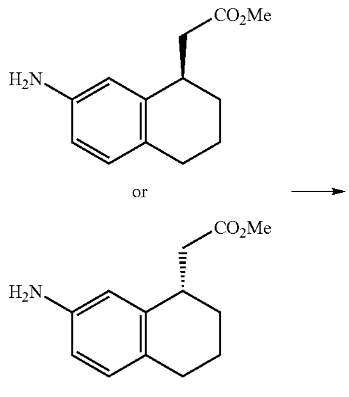

or 6.3

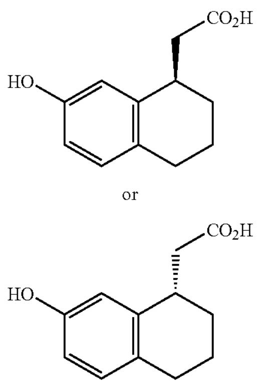

or 6.4

(R)-2-(7-Hydroxy-1,2,3,4-tetrahydronaphthalen-1-yl)acetic acid or (S)-2-(7-hydroxy-1,2,3,4-tetrahydronaphthalen-1-yl)acetic acid (6.4)

At 0-5° C., $NaNO_2$ (aq) solution (1.1 mL) (1.98 mmol) was added dropwise to a solution of (R)-methyl 2-(7-amino-1,2,3,4-tetrahydronaphthalen-1-yl)acetate or (S)-methyl 2-(7-amino-1,2,3,4-tetrahydronaphthalen-1-yl)acetate 6.3 (0.394 g, 1.80 mmol) in 1,4-dioxane (3 mL) and $H_2SO_4$ (aq., 15%) (3 mL). The resulting mixture was stirred at 0-5° C. for 7 minutes. The reaction mixture was then added slowly to a solution of 15% $H_2SO_4$ (aq) (5 mL) at reflux (bath temperature of 110° C.). The resulting mixture was refluxed for 48 minutes. The reaction mixture was then cooled to room temperature and extracted with EtOAc (2×100 mL). The combined organic layers were washed with brine and dried over anhydrous sodium sulfate. After removing solvent, the residue was purified by chromatography (silica gel, 1:19 MeOH/DCM) to give 6.4 in 44% yield.

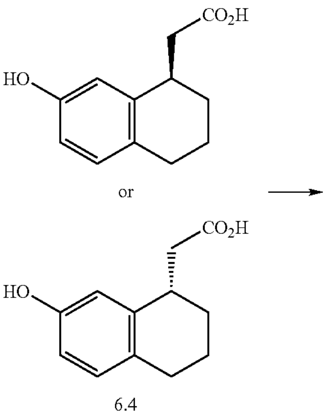

or 6.4

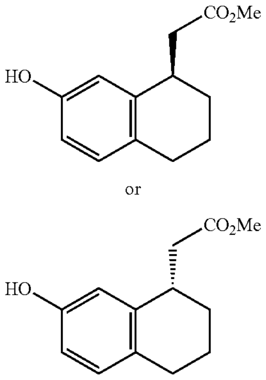

or 6.5

(R)-Methyl 2-(7-hydroxy-1,2,3,4-tetrahydronaphthalen-1-yl)acetate or (S)-methyl 2-(7-hydroxy-1,2,3,4-tetrahydronaphthalen-1-yl)acetate (6.5)

One drop of concentrated $H_2SO_4$ was added to 25 mL of MeOH and mixed with (R)-2-(7-hydroxy-1,2,3,4-tetrahydronaphthalen-1-yl)acetic acid or (S)-2-(7-hydroxy-1,2,3,4-tetrahydronaphthalen-1-yl)acetic acid 6.4 (0.162 g, 0.786 mmol). The mixture was then stirred at 75° C. for 24 hours. The resulting mixture was then neutralized with sodium bicarbonate solution and concentrated by rotary evaporation. The mixture was extracted with EtOAc (150 mL), washed with brine, and dried over anhydrous sodium sulfate. After removing solvent, the residue was purified by chromatography (silica gel, 1:4 EtOAc/hexane) to give 6.5 in 66% yield.

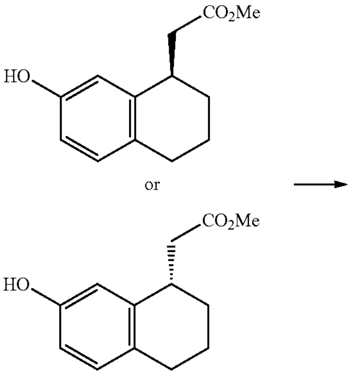

or 6.5

-continued

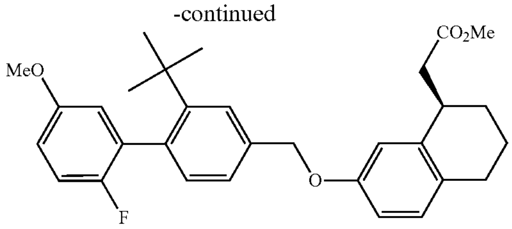

or

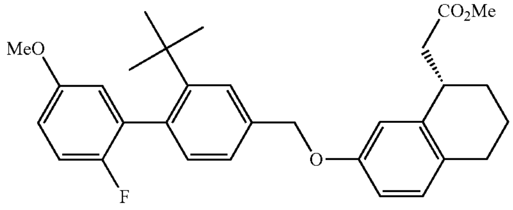

6.6

(R)-Methyl 2-(7-(3-t-butyl-4-(2-fluoro-5-methoxyphenyl)benzyloxy)-1,2,3,4-tetrahydronaphthalen-1-yl)acetate or (S)-methyl 2-(7-(3-t-butyl-4-(2-fluoro-5-methoxyphenyl)benzyloxy)-1,2,3,4-tetrahydronaphthalen-1-yl)acetate (6.6)

The title compound was prepared from 6.5 and 4-(chloromethyl)-2-(1,1-dimethylethyl)-2'-fluoro-5'-(methyloxy)-1,1'-biphenyl (Method A) using the method described for the synthesis of 1.6.

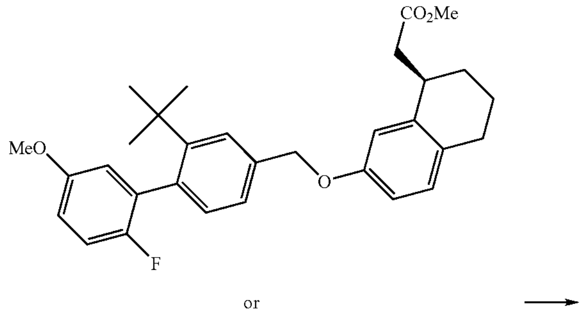

or

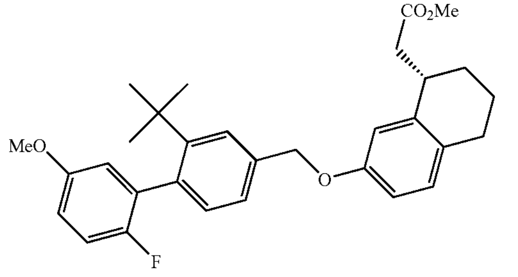

6.6

-continued

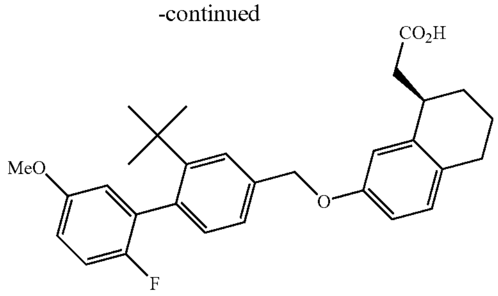

or

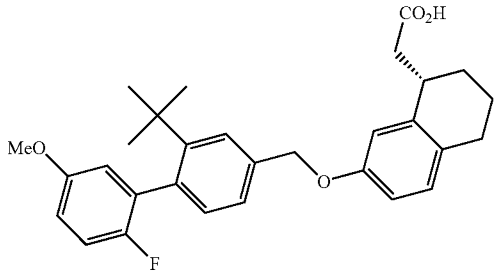

6

(R)-2-(7-(3-t-Butyl-4-(2-fluoro-5-methoxyphenyl)benzyloxy)1,2,3,4-tetrahydronaphthalen-1-yl)acetic acid or (S)-2-(7-(3-t-butyl-4-(2-fluoro-5-methoxyphenyl)benzyloxy)1,2,3,4-tetrahydronaphthalen-1-yl)acetic acid (6)

The title compound was synthesized from 6.6 using a procedure analogous to that described for synthesizing 1 from 1.6. MS ESI (neg.) M/E: 475 (M−H). $^1$HNMR (DMSO-$d_6$) δ 7.62 (s, 1H), 7.28 (d, J=8 Hz, 1H), 7.17 (t, J=8 Hz, 1H), 6.97 (m, 3H), 6.89 (m, 1H), 6.78-6.83 (m, 2H), 5.10 (s, 2H), 3.75 (s, 3H), 3.16 (m, 1H), 3.17 (m, 1H), 2.65 (m, 3H), 2.38 (m, 1H), 1.74-1.83 (m, 2H), 1.60-1.66 (m, 2H), 1.18 (s, 9H).

Example 7

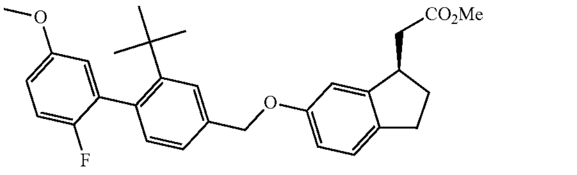

or

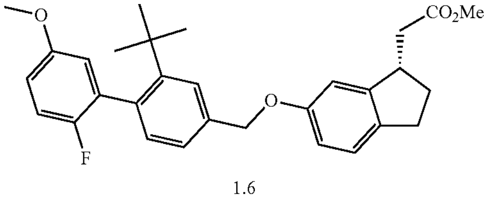

1.6

-continued

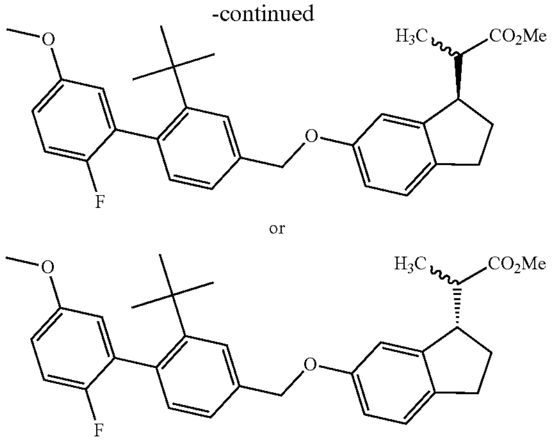

or 7.1

(S)-Methyl 2-(6-(3-t-butyl-4-(2-fluoro-5-methoxyphenyl)benzyloxy)-2,3-dihydro-1H-inden-1-yl)propanoate or (R)-methyl 2-(6-(3-t-butyl-4-(2-fluoro-5-methoxyphenyl)benzyloxy)-2,3-dihydro-1H-inden-1-yl)propanoate (7.1)

At −78° C., lithium bis(trimethylsilyl)amide (1M in hexane) (0.25 mL) was added to a solution of 1.6 (0.117 g, 0.245 mmol) in THF (5 mL). The resulting mixture was stirred at −78° C. for 5 minutes. Methyl iodide (70 mg, 0.5 mmol) was then added, and the mixture was stirred at −78° C. for 3 hours. The resulting mixture was extracted with EtOAc (150 mL), washed with brine, and dried over anhydrous sodium sulfate. After removing solvent, the residue was purified by chromatography (silica gel, 1:6 EtOAc/hexane) to give 7.1 in 70% yield.

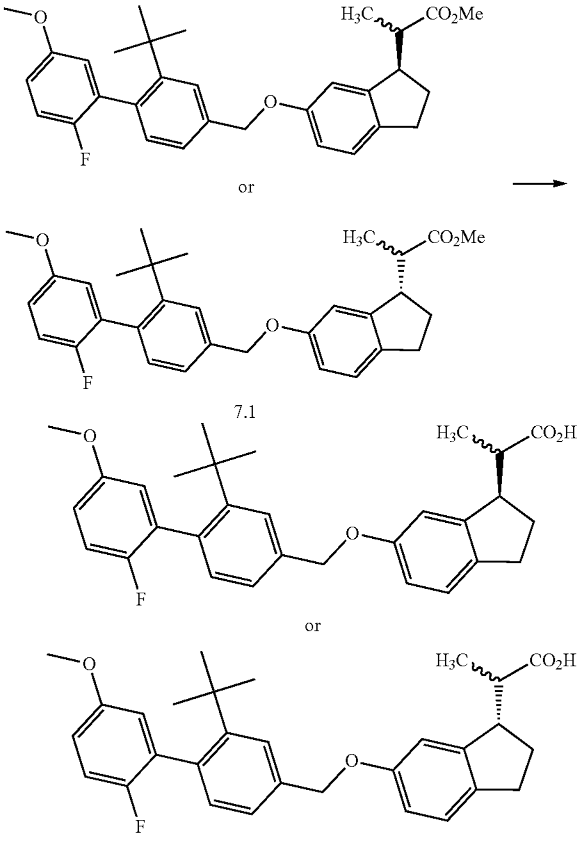

or 7.1 or

7

(S)-2-(6-(3-t-Butyl-4-(2-fluoro-5-methoxyphenyl)benzyloxy)-2,3-dihydro-1H-inden-1-yl)propanoic acid or (R)-2-(6-(3-t-butyl-4-(2-fluoro-5-methoxyphenyl)benzyloxy)-2,3-dihydro-1H-inden-1-yl)propanoic acid (7)

The title compound was synthesized from 7.1 using a procedure analogous to that described for synthesizing 1 from 1.6. MS ESI (neg.) M/E: 475 (M−H). $^1$HNMR (DMSO-$d_6$) δ 7.61 (s, 1H), 7.41 (m, 1H), 7.27 (m, 1H), 7.16 (m, 2H), 6.95-6.98 (m, 2H), 6.89 (m, 1H), 6.78-6.83 (m, 2H), 5.09 (s, 2H), 3.74 (s, 3H), 3.46 (m, 1H), 2.80 (m, 3H), 2.05 (m, 1H), 1.75 (m, 1H), 1.17 (s, 9H), 0.88-0.89 (d, 3H).

Example 8

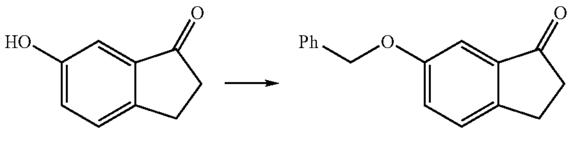

8.1 8.2

6-(Benzyloxy)-2,3-dihydroinden-1-one (8.2)

A mixture of 6-hydroxy-2,3-dihydroinden-1-one (8.1) (available from Aldrich) (5.0 g, 34 mmol), 1-(bromomethyl)benzene (available from Aldrich) (4.4 mL, 37 mmol) and cesium carbonate (25 g, 78 mmol) in DMF (40 mL) was stirred at room temperature for 23 hours. The resulting mixture was diluted with EtOAc (400 mL), washed with water and brine, and dried over anhydrous sodium sulfate. After removing solvent, the residue was purified by chromatography (silica gel, 1:4 EtOAc/hexane) to give product 8.2 in 67% yield.

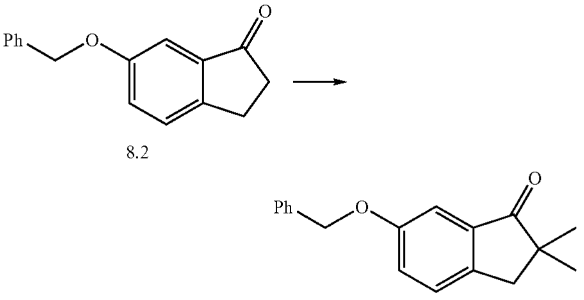

8.2

8.3

6-(Benzyloxy)-2,2-dimethyl-2,3-dihydroinden-1-one (8.3)

At −78° C., lithium bis(trimethylsilyl)amide (1.0 M in THF) (14 mL, 14 mmol) was added dropwise to a solution of 6-(benzyloxy)-2,3-dihydroinden-1-one (8.2) (1.7 g, 7 mmol) in THF (15 mL). After the mixture was stirred at −78° C. for 16 minutes, iodomethane (1.6 mL, 29 mmol) was slowly added. The resulting mixture was stirred at −78° C. for 4 hours and was then allowed to warm to room temperature overnight. The mixture was then diluted with EtOAc (300 mL), washed with water and brine, and dried over anhydrous sodium sulfate. After removing solvent, the residue was purified by chromatography (silica gel, 1:6 EtOAc/hexane) to give product 8.3 in 28% yield.

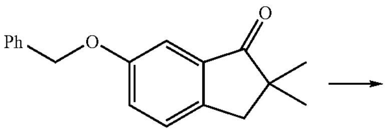

8.3

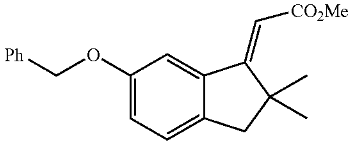

8.4

(E)-Methyl 2-(6-(benzyloxy)-2,2-dimethyl-2,3-dihydroinden-1-ylidene)acetate (8.4)

At −78° C., lithium bis(trimethylsilyl)amide (1.0 M in THF) (3.6 mL, 3.6 mmol) was added slowly to a solution of methyl 2-(trimethylsilyl)acetate (0.59 mL, 3.6 mmol) in THF (20 mL). The mixture was maintained at −78° C. for 7 minutes and then 6-(benzyloxy)-2,2-dimethyl-2,3-dihydroinden-1-one (8.3) (0.535 g, 2.0 mmol) was added in one portion. The resulting mixture was stirred at −78° C. and allowed to warm to room temperature overnight. The reaction mixture was then diluted with EtOAc (200 mL), washed with water and brine, and dried over anhydrous sodium sulfate. After removing solvent, the residue was purified by chromatography (silica gel, 1:5 EtOAc/hexane) to give product 8.4 in 45% yield.

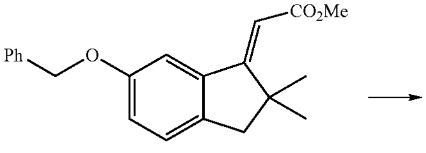

8.4

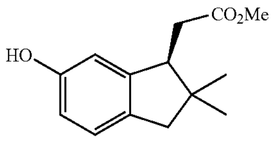

+

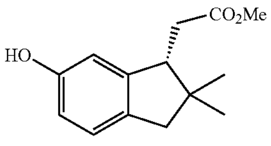

8.5 and 8.6

(S)-Methyl 2-(6-hydroxy-2,2-dimethyl-2,3-dihydro-1H-inden-1-yl)acetate and (R)-methyl 2-(6-hydroxy-2,2-dimethyl-2,3-dihydro-1H-inden-1-yl)acetate (8.5 and 8.6)

Under hydrogen, a mixture of (E)-methyl 2-(6-(benzyloxy)-2,2-dimethyl-2,3-dihydroinden-1-ylidene)acetate (8.4) (0.29 g, 0.90 mmol), Pd—C (0.11 g, 0.90 mmol) in MeOH (10 mL) was stirred fort 8 hours. The resulting mixture was filtered through silica gel to remove Pd—C. The filtrate was concentrated, and the residue was purified by chromatography (silica gel, 1:2 EtOAc/hexane) to give 0.169 g racemic product which was separated by OJ-H column to give 0.080 g of one enantiomer and 0.082 g of the other enantiomer. One of 8.5 and 8.6 is the R enantiomer and the other is the S enantiomer.

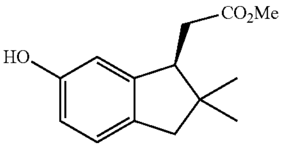

or

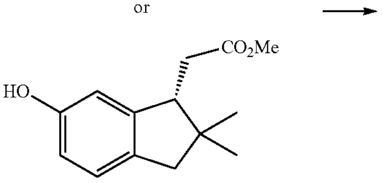

8.5

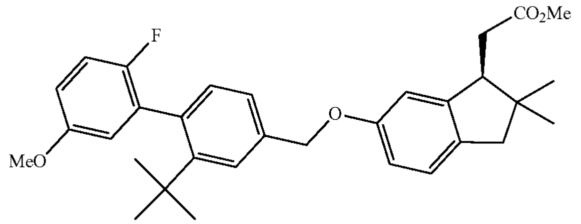

or

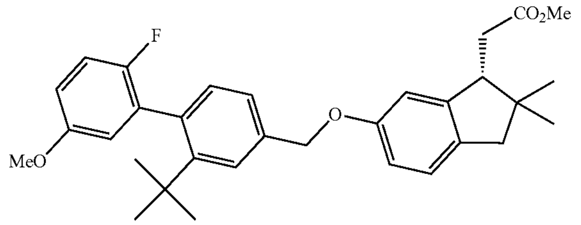

8.7

Methyl ((1S)-6-(((2-(1,1-dimethylethyl)-2'-fluoro-5'-(methyloxy)-1,1'-biphenyl-4-yl)methyl)oxy)-2,2-dimethyl-2,3-dihydro-1H-inden-1-yl)acetate or methyl ((1R)-6-(((2-(1,1-dimethylethyl)-2'-fluoro-5'-(methyloxy)-1,1'-biphenyl-4-yl)methyl)oxy)-2,2-dimethyl-2,3-dihydro-M-inden-1-yl)acetate (8.7)

A mixture of (S)-methyl 2-(6-hydroxy-2,2-dimethyl-2,3-dihydro-1H-inden-1-yl)acetate or (R)-methyl 2-(6-hydroxy-2,2-dimethyl-2,3-dihydro-1H-inden-1-yl)acetate (8.5) (0.026 g, 0.11 mmol), 4-(chloromethyl)-2-(1,1-dimethylethyl)-2'-fluoro-5'-(methyloxy)-1,1'-biphenyl (Method A) (0.034 g, 0.11 mmol) and cesium carbonate (0.072 g, 0.22 mmol) in DMF (2 mL) was stirred at room temperature for 24 hours. The mixture was diluted with EtOAc (150 mL), washed with water and brine, and dried over anhydrous sodium sulfate. After removing solvent, the residue was purified by chromatography (silica gel, 1:5 EtOAc/hexane) to give 0.029 g of 8.7.

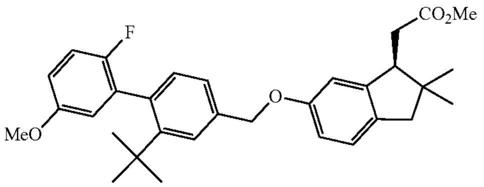

or

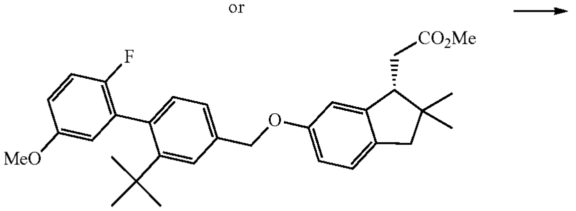

8.7

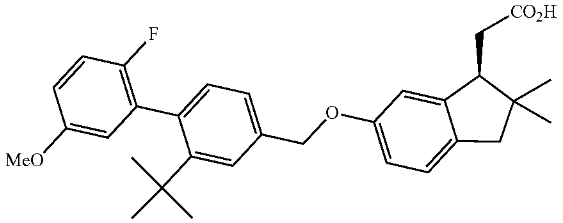

or

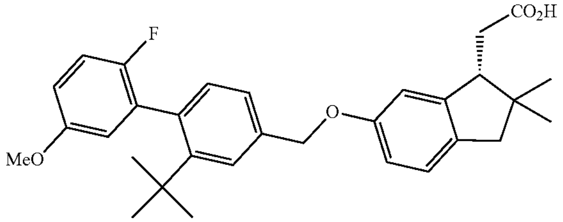

8

((1S)-6-(((2-(1,1-Dimethylethyl)-2'-fluoro-5'-(methyloxy)-1,1'-biphenyl-4-yl)methyl)oxy)-2,2-dimethyl-2,3-dihydro-1H-inden-1-yl)acetic acid or ((1R)-6-(((2-(1,1-dimethylethyl)-2'-fluoro-5'-(methyloxy)-1,1'-biphenyl-4-yl)methyl)oxy)-2,2-dimethyl-2,3-dihydro-1H-inden-1-yl)acetic acid (8)

A mixture of 8.7 (0.029 g), NaOH (aq, 10%) (1 mL) and EtOH (2 mL) was stirred at room temperature for 24 hours. Water (5 mL) was added, and the mixture was acidified with 1N HCl to pH 3-5 and then extracted with EtOAc (150 mL). The organic layer was washed with brine and dried over sodium sulfate. After removing solvent, the residue was purified by chromatography (silica gel, eluting with DCM to give 0.018 g of 8. MS ESI (neg.) M/E: 489 (M−H). $^1$HNMR (DMSO-$d_6$) δ 7.61 (d, J=2 Hz, 1H), 7.27-7.30 (m, 1H), 7.14-7-19 (m, 1H), 7.08-7.10 (d, J=8 Hz, 1H), 6.95-6.99 (m, 2H), 6.78-6.83 (m, 3H), 5.06 (s, 2H), 3.75 (s, 3H), 3.11 (m, 1H), 2.60 (m, 2H), 2.35-2.45 (m, 2H), 1.17 (s, 9H), 1.13 (s, 3H), 0.86 (s, 3H).

Example 9

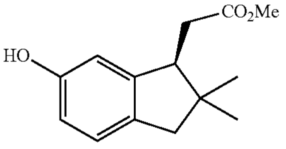

or

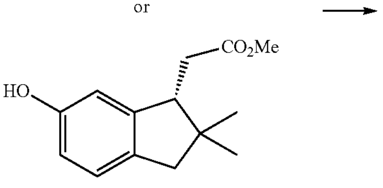

8.5

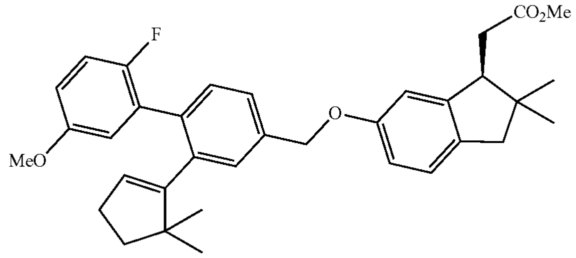

or

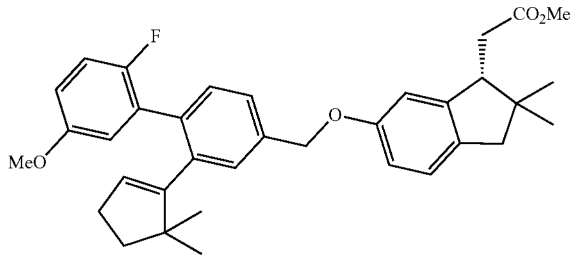

9.1

1-((1S)-6-(((2-(5,5-Dimethyl-1-cyclopenten-1-yl)-2'-fluoro-5'-(methyloxy)-1,1'-biphenyl-4-yl)methyl)oxy)-2,2-dimethyl-2,3-dihydro-1H-inden-1-yl)-2-propanone or 1-((1R)-6-(((2-(5,5-dimethyl-1-cyclopenten-1-yl)-2'-fluoro-5'-(methyloxy)-1,1'-biphenyl-4-yl)methyl)oxy)-2,2-dimethyl-2,3-dihydro-1H-inden-1-yl)-2-propanone (9.1)

The title compound was synthesized from 8.5 and 4-(chloromethyl)-2-(5,5-dimethyl-1-cyclopenten-1-yl)-2'-fluoro-5'-(methyloxy)-1,1'-biphenyl (B.9) using the method described for the synthesis of 8.7.

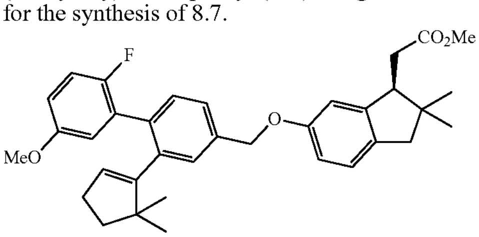

or

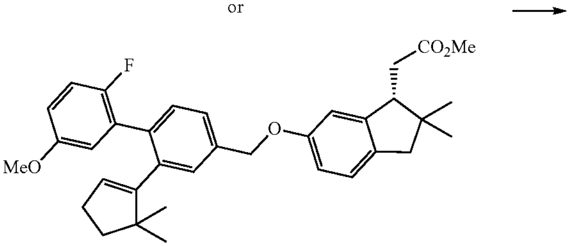

9.1

-continued

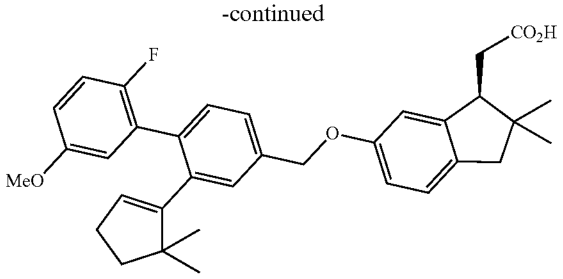

or

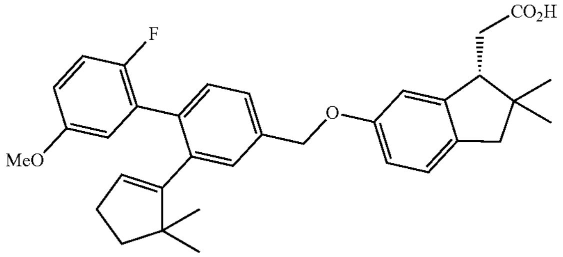

9

((1S)-6-(((2-(5,5-Dimethyl-1-cyclopenten-1-yl)-2'-fluoro-5'-(methyloxy)-1,1'-biphenyl-4-yl)methyl)oxy)-2,2-dimethyl-2,3-dihydro-1H-inden-1-yl)acetic acid or ((1R)-6-(((2-(5,5-dimethyl-1-cyclopenten-1-yl)-2'-fluoro-5'-(methyloxy)-1,1'-biphenyl-4-yl)methyl)oxy)-2,2-dimethyl-2,3-dihydro-1H-inden-1-yl)acetic acid (9)

The title compound was synthesized from 9.1 using a procedure analogous to that described for synthesizing 8 from 8.7. MS ESI (neg.) M/E: 527 (M−H). $^{1}$HNMR (DMSO-$d_6$) δ 7.39-7.41 (m, 1H), 7.28-7.30 (d, J=7 Hz, 1H), 7.26 (d, J=2 Hz, 1H), 7.06-7.12 (m, 2H), 6.87-6.89 (m, 1H), 6.81-6.84 (m, 2H), 6.77-6.79 (m, 1H), 5.50 (m, 1H), 5.09 (s, 2H), 3.71 (s, 3H), 3.11 (m, 1H), 2.56-2.60 (m, 2H), 2.42-2.45 (m, 1H), 2.30-2.36 (m, 1H), 2.19 (m, 2H), 1.59 (t, J=7 Hz, 2H), 1.14 (s, 3H), 1.12 (s, 3H), 0.84 (s, 3H), 0.78 (s, 3H).

Example 10

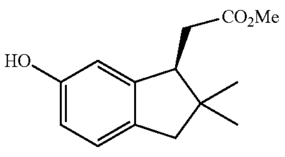

or

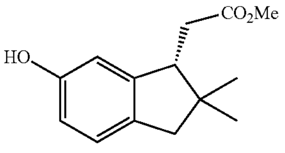

8.6

-continued

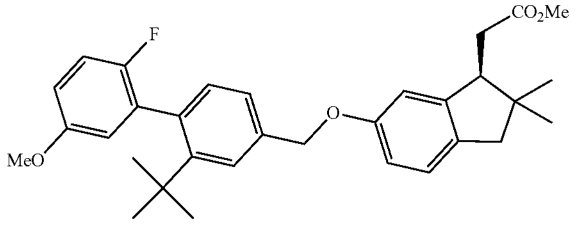

or

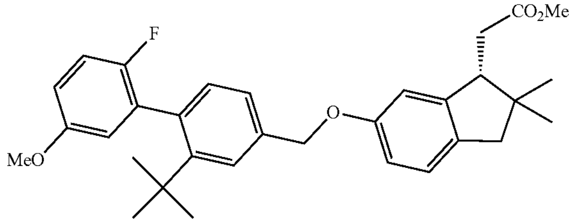

10.1

Methyl ((1R)-6-(((2-(1,1-dimethylethyl)-2'-fluoro-5'-(methyloxy)-1,1'-biphenyl-4-yl)methyl)oxy)-2,2-dimethyl-2,3-dihydro-1H-inden-1-yl)acetate or methyl ((1S)-6-(((2-(1,1-dimethylethyl)-2'-fluoro-5'-(methyloxy)-1,1'-biphenyl-4-yl)methyl)oxy)-2,2-dimethyl-2,3-dihydro-1H-inden-1-yl)acetate (10.1)

A mixture of (R)-methyl 2-(6-hydroxy-2,2-dimethyl-2,3-dihydro-1H-inden-1-yl)acetate or (S)-methyl 2-(6-hydroxy-2,2-dimethyl-2,3-dihydro-1H-inden-1-yl)acetate (8.6) (0.026 g, 0.11 mmol), 4-(chloromethyl)-2-(1,1-dimethylethyl)-2'-fluoro-5'-(methyloxy)-1,1'-biphenyl (Method A) (0.034 g, 0.11 mmol) and cesium carbonate (0.072 g, 0.22 mmol) in DMF (2 mL) was stirred at room temperature for 24 hours. The reaction mixture was diluted with EtOAc (150 mL), washed with water and brine, and dried over anhydrous sodium sulfate. After removing solvent, the residue was purified by chromatography (silica gel, 1:5 EtOAc/hexane) to give 0.028 g of product 10.1.

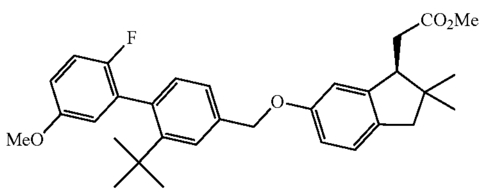

or

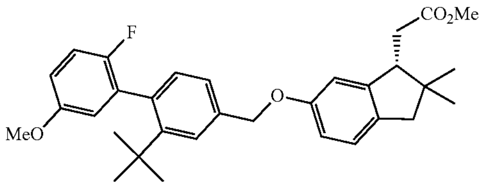

10.1

-continued

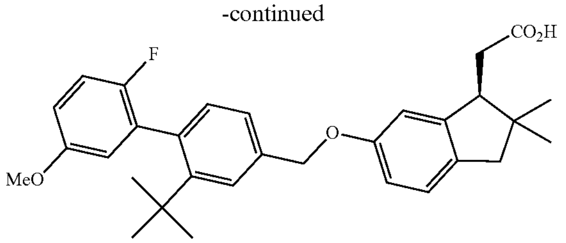

or

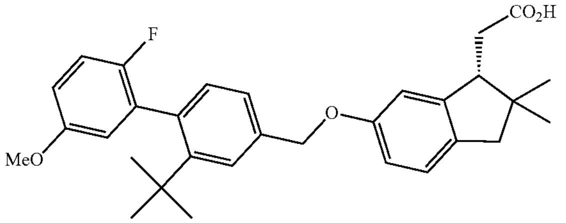

10

((1R)-6-(((2-(1,1-Dimethylethyl)-2'-fluoro-5'-(methyloxy)-1,1'-biphenyl-4-yl)methyl)oxy)-2,2-dimethyl-2,3-dihydro-1H-inden-1-yl)acetic acid or ((1S)-6-(((2-(1,1-dimethylethyl)-2'-fluoro-5'-(methyloxy)-1,1'-biphenyl-4-yl)methyl)oxy)-2,2-dimethyl-2,3-dihydro-1H-inden-1-yl)acetic acid (10)

The title compound was synthesized from 10.1 using a procedure analogous to that described for synthesizing 8 from 8.7. MS ESI (neg.) M/E: 489 (M−H). $^1$HNMR (DMSO-$d_6$) δ 7.61 (d, J=2 Hz, 1H), 7.27-7.30 (m, 1H), 7.14-7-19 (m, 1H), 7.08-7.10 (d, J=8 Hz, 1H), 6.95-6.99 (m, 2H), 6.78-6.83 (m, 3H), 5.06 (s, 2H), 3.75 (s, 3H), 3.11 (m, 1H), 2.60 (m, 2H), 2.35-2.45 (m, 2H), 1.17 (s, 9H), 1.13 (s, 3H), 0.86 (s, 3H).

Example 11

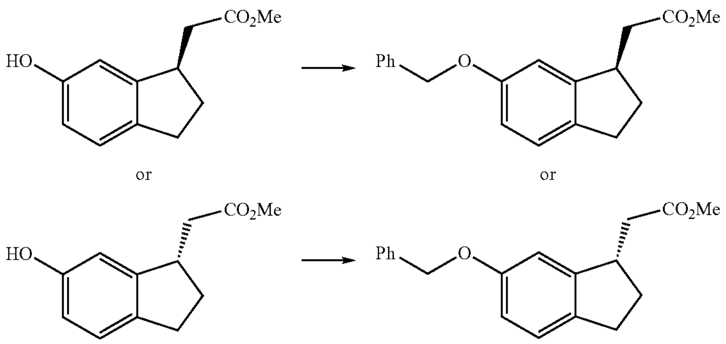

1.5 11.1

1-((1R)-6-((Phenylmethyl)oxy)-2,3-dihydro-1H-inden-1-yl)-2-propanone or 1-((1S)-6-((phenylmethyl)oxy)-2,3-dihydro-1H-inden-1-yl)-2-propanone (11.1)

A mixture of (R)-methyl 2-(6-hydroxy-2,3-dihydro-1H-inden-1-yl)acetate or (S)-methyl 2-(6-hydroxy-2,3-dihydro-1H-inden-1-yl)acetate (1.5) (1.37 g, 6.64 mmol), 1-(bromomethyl)benzene (0.790 mL, 6.64 mmol) and cesium carbonate (4.33 g, 13.3 mmol) in DMF (15 mL) was stirred at room temperature for 19 hours. The reaction mixture was then diluted with EtOAc (250 mL), washed with water and brine, and dried over anhydrous sodium sulfate. After removing solvent, the residue was purified by chromatography (silica gel, 1:5 EtOAc/hexane) to give 1.49 g of product 11.1 in 76% yield.

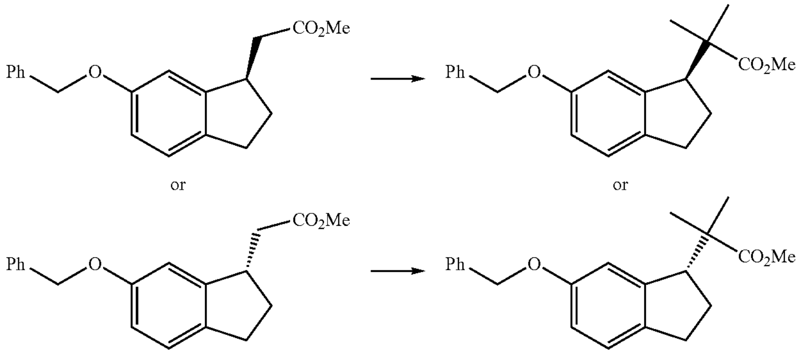

11.1 11.2

(S)-Methyl 2-(6-(benzyloxy)-2,3-dihydro-1H-inden-1-yl)-2-methylpropanoate or (R)-methyl 2-(6-(benzyloxy)-2,3-dihydro-1H-inden-1-yl)-2-methylpropanoate (11.2)

At −78° C., LDA (2.0 M solution in heptane/THF/ethylbenzene) (1.1 mL, 2.2 mmol) was added dropwise to a solution of (R)-methyl 2-(6-(benzyloxy)-2,3-dihydro-1H-inden-1-yl)acetate (11.1) (0.43 g, 1.5 mmol) in THF (10 mL). The reaction mixture was stirred at −78° C. for 11 minutes and then HMPA (0.20 mL) and iodomethane (0.18 mL, 2.9 mmol) were added. The resulting mixture was stirred at −78° C. for 16 minutes. Additional LDA (1.1 mL, 2.2 mmol) was added, and the reaction was stirred at −78° C. for 9 minutes and then additional HMPA (0.20 mL) and iodomethane (0.4 mL) were added. The reaction mixture was then stirred at −78° C. for 83 minutes. The reaction mixture was quenched with $NH_4Cl$ solution and extracted with EtOAc, washed with brine, and dried over sodium sulfate. After removing solvent, the residue was purified by chromatography (silica gel, 1:6 EtOAc/hexane) to give 0.47 g product 11.2 in 64% yield.

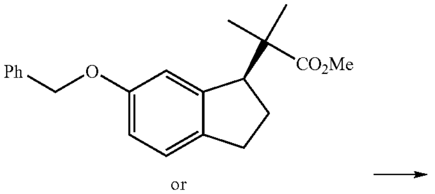

or

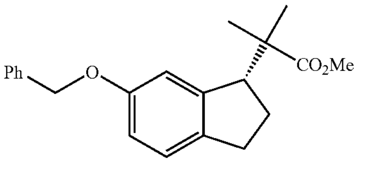

11.2

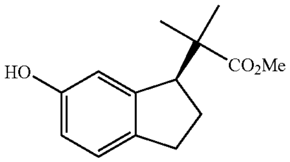

or

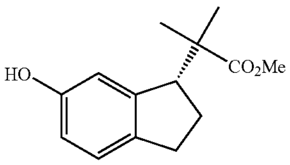

11.3

(S)-Methyl 2-(6-hydroxy-2,3-dihydro-1H-inden-1-yl)-2-methylpropanoate or (R)-methyl 2-(6-hydroxy-2,3-dihydro-1H-inden-1-yl)-2-methylpropanoate (11.3)

Under hydrogen, a mixture of (S)-methyl 2-(6-(benzyloxy)-2,3-dihydro-1H-inden-1-yl)-2-methylpropanoate or (R)-methyl 2-(6-(benzyloxy)-2,3-dihydro-1H-inden-1-yl)-2-methylpropanoate (11.2) (0.296 g, 0.91 mmol) and palladium, 10 wt. % on activated carbon (0.019 g, 0.18 mmol) in MeOH (15 mL) was stirred at room temperature for 22 hours. The reaction mixture was then filtered to remove Pd—C. After removing solvent, the residue was purified by chromatography (silica gel, 1:2 EtOAc/hexane) to give 0.21 g product 11.3 in 98% yield.

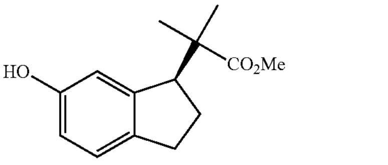

or

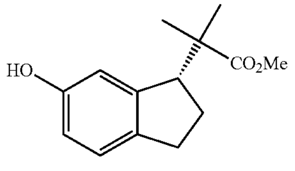

11.3

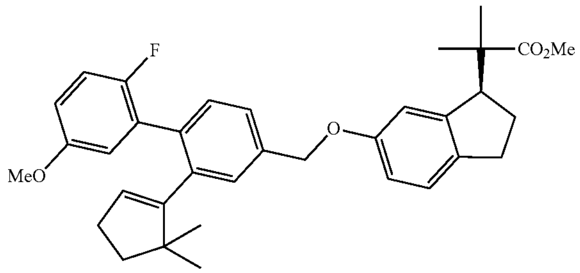

or

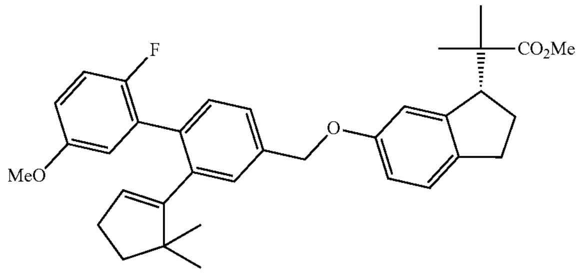

11.4

Methyl 2-((1S)-6-(((2-(5,5-dimethyl-1-cyclopenten-1-yl)-2'-fluoro-5'-(methyloxy)-1,1'-biphenyl-4-yl)methyl)oxy)-2,3-dihydro-1H-inden-1-yl)-2-methylpropanoate or methyl 2-((1R)-6-(((2-(5,5-dimethyl-1-cyclopenten-1-yl)-2'-fluoro-5'-(methyloxy)-1,1'-biphenyl-4-yl)methyl)oxy)-2,3-dihydro-1H-inden-1-yl)-2-methylpropanoate (11.4)

The title compound was synthesized from 11.3 and 4-(chloromethyl)-2-(5,5-dimethyl-1-cyclopenten-1-yl)-2'-fluoro-5'-(methyloxy)-1,1'-biphenyl (B.9) using the method described for the synthesis of 8.7.

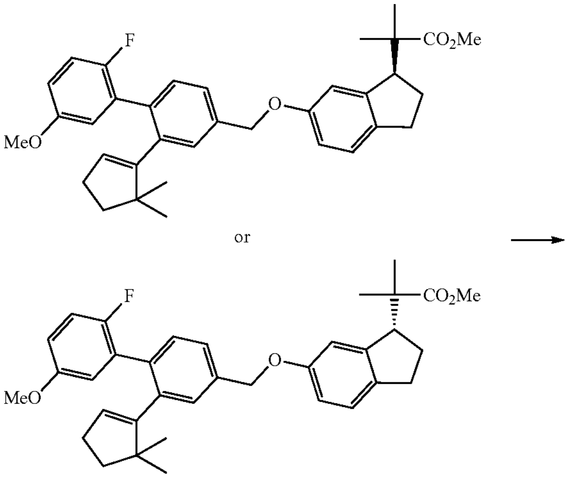

or 11.4

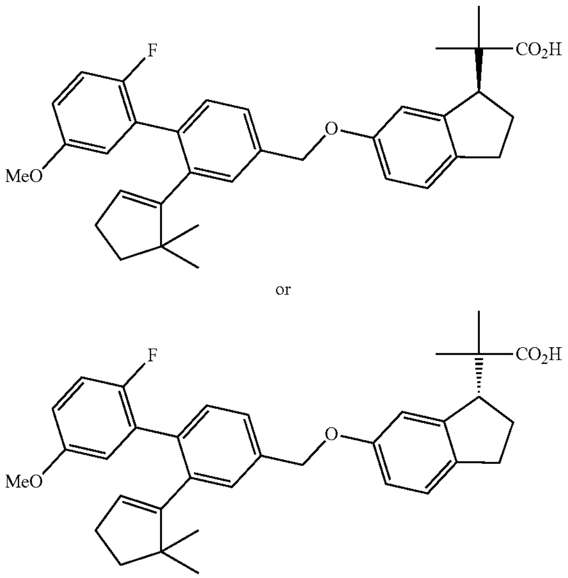

or

11

2-((1S)-6-(((2-(5,5-Dimethyl-1-cyclopenten-1-yl)-2'-fluoro-5'-(methyloxy)-1,1'-biphenyl-4-yl)methyl)oxy)-2,3-dihydro-1H-inden-1-yl)-2-methylpropanoic acid or 2-((1R)-6-(((2-(5,5-dimethyl-1-cyclopenten-1-yl)-2'-fluoro-5'-(methyloxy)-1,1'-biphenyl-4-yl)methyl)oxy)-2,3-dihydro-1H-inden-1-yl)-2-methylpropanoic acid (11)

The title compound was synthesized from 11.4 using a procedure analogous to that described for synthesizing 8 from 8.7. MS ESI (neg.) M/E: 527 (M−H). $^{1}$HNMR (DMSO-$d_6$) δ 7.38-7.40 (m, 1H), 7.24-7.29 (m, 2H), 7.08-7.12 (m, 2H), 6.86-6.90 (m, 1H), 6.80-6.83 (m, 2H), 6.78 (m, 1H), 5.49 (m, 1H), 5.10 (m, 1H), 3.70 (s, 3H), 3.47 (m, 1H), 2.76 (m, 1H), 2.66 (m, 1H), 2.11-2.20 (m, 3H), 1.81-1.90 (m, 1H), 1.58 (m, 2H), 1.10 (s, 3H), 0.96 (s, 3H), 0.77 (d, J=6 Hz, 6H).

Example 12

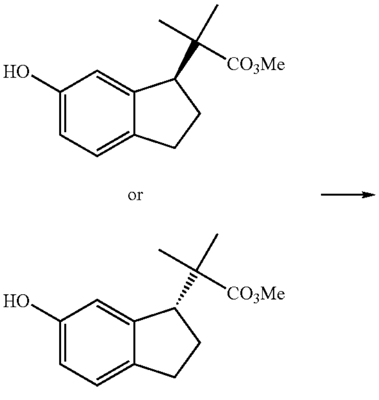

or 11.3

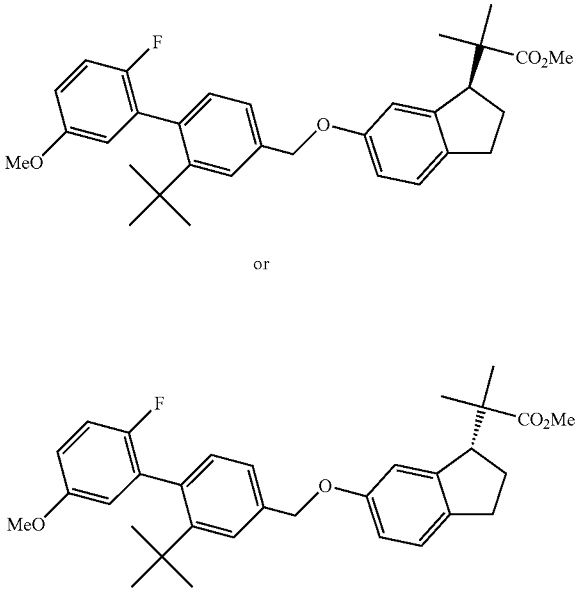

or 12.1

Methyl 2-((1S)-6-(((2-(1,1-dimethylethyl)-2'-fluoro-5'-(methyloxy)-1,1'-biphenyl-4-yl)methyl)oxy)-2,3-dihydro-1H-inden-1-yl)-2-methylpropanoate or methyl 2-((1R)-6-(((2-(1,1-dimethylethyl)-2'-fluoro-5'-(methyloxy)-1,1'-biphenyl-4-yl)methyl)oxy)-2,3-dihydro-1H-inden-1-yl)-2-methylpropanoate (12.1)

The title compound was synthesized from 11.3 and 4-(chloromethyl)-2-(1,1-dimethylethyl)-2'-fluoro-5'-(methyloxy)-1,1'-biphenyl (Method A) using the method described for the synthesis of 8.7.

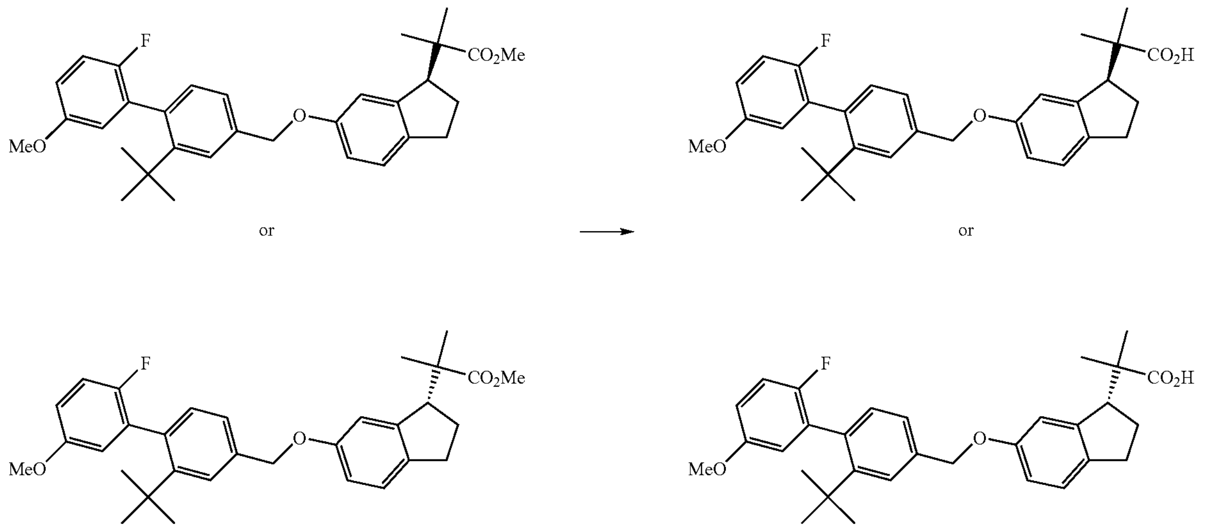

or or 12.1

12

2-((1S)-6-(((2-(1,1-Dimethylethyl)-2'-fluoro-5'-(methyloxy)-1,1'-biphenyl-4-yl)methyl)oxy)-2,3-dihydro-1H-inden-1-yl)-2-methylpropanoic acid or 2-((1R)-6-(((2-(1,1-Dimethylethyl)-2'-fluoro-5'-(methyloxy)-1,1'-biphenyl-4-yl)methyl)oxy)-2,3-dihydro-1H-inden-1-yl)-2-methylpropanoic acid (12)

The title compound was synthesized from 12.1 using a procedure analogous to that described for synthesizing 8 from 8.7. MS ESI (neg.) M/E: 489 (M−H). $^{1}$HNMR (DMSO-$d_6$) δ 7.60 (s, 1H), 7.27-7.29 (m, 1H), 7.12-7.17 (m, 2H), 6.97-6.99 (m, 2H), 6.86 (m, 1H), 6.79 (m, 2H), 5.08 (m, 2H), 3.75 (s, 3H), 3.51 (m, 1H), 2.78 (m, 1H), 2.68 (m, 1H), 2.3 (m, 3H), 1.84 (m, 1H), 1.17 (m, 9H), 1.04 (s, 3H), 0.97 (s, 3H).

Example 13

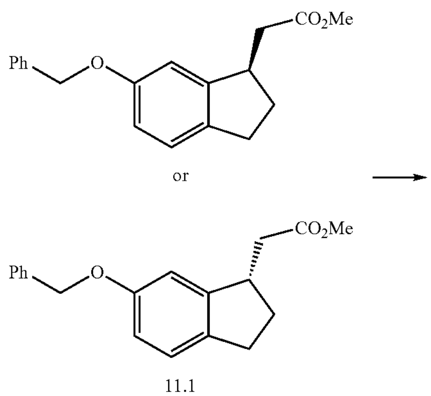

or 11.1

-continued

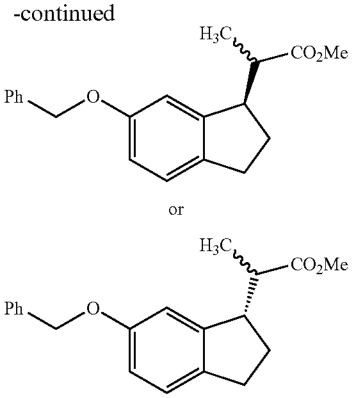

or 13.1

Methyl 2-((R)-6-(benzyloxy)-2,3-dihydro-1H-inden-1-yl)propanoate or methyl 2-((S)-6-(benzyloxy)-2,3-dihydro-1H-inden-1-yl)propanoate (13.1)

At −78° C., lithium bis(trimethylsilyl)amide (1M in hexane) (0.25 mL) was added to a solution of (R)-methyl 2-(6-(benzyloxy)-2,3-dihydro-1H-inden-1-yl)acetate or (S)-methyl 2-(6-(benzyloxy)-2,3-dihydro-1H-inden-1-yl)acetate (11.1) (0.93 g, 3.1 mmol) in THF (10 mL). After stirring for 5 minutes, iodomethane (0.98 mL, 16 mmol) was added. The reaction was stirred at −78° C. for 60 minutes and then it was diluted with EtOAc (150 mL), washed with water and brine, and dried over anhydrous sodium sulfate. After removing solvent, the residue was purified by chromatography (silica gel, 1:6 EtOAc/hexane) to give 0.79 g product 13.1 in 81% yield.

(R)-Methyl 2-((R)-6-hydroxy-2,3-dihydro-1H-inden-1-yl)propanoate and (S)-methyl 2-((R)-6-hydroxy-2,3-dihydro-1H-inden-1-yl)propanoate or (R)-methyl 2-((S)-6-hydroxy-2,3-dihydro-1H-inden-1-yl)propanoate and (S)-methyl 2-((S)-6-hydroxy-2,3-dihydro-1H-inden-1-yl)propanoate (13.2 and 13.3)

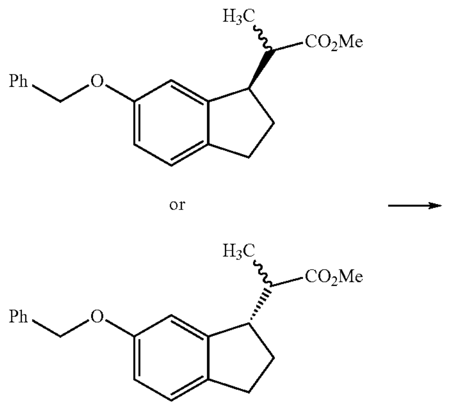

or 13.1

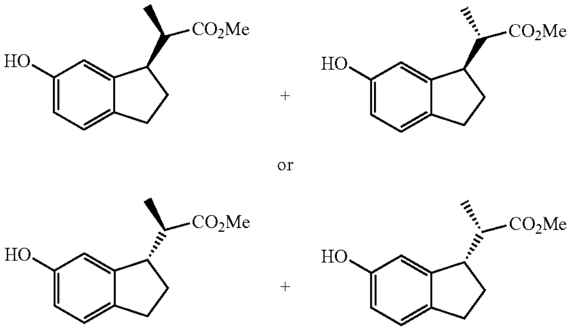

+ or

+

13.2 and 13.3

Under hydrogen, a mixture of 13.1 (0.77 g, 2 mmol) and palladium-carbon (10 wt. % on activated carbon) (0.3 mL, 2 mmol) in MeOH (20 mL) was stirred at room temperature for 20 hours. The reaction mixture was then filtered to remove Pd—C. After removing solvent, the residue was purified by chromatography (silica gel, 1:2 EtOAc/hexane) to give a mixture of diastereomers 13.2 and 13.3 in 85% yield. The mixture was separated by chiral HPLC (column: AD; solvent: 6% IPA/hexane) to give 0.032 g of 13.2 or 13.3 one compound (retention time 21.1 min), and 0.43 g of the other compound (retention time 34.2 min) One of 13.2 and 13.3 has the R stereochemistry at the α carbon and the other has the S stereochemistry at the α carbon.

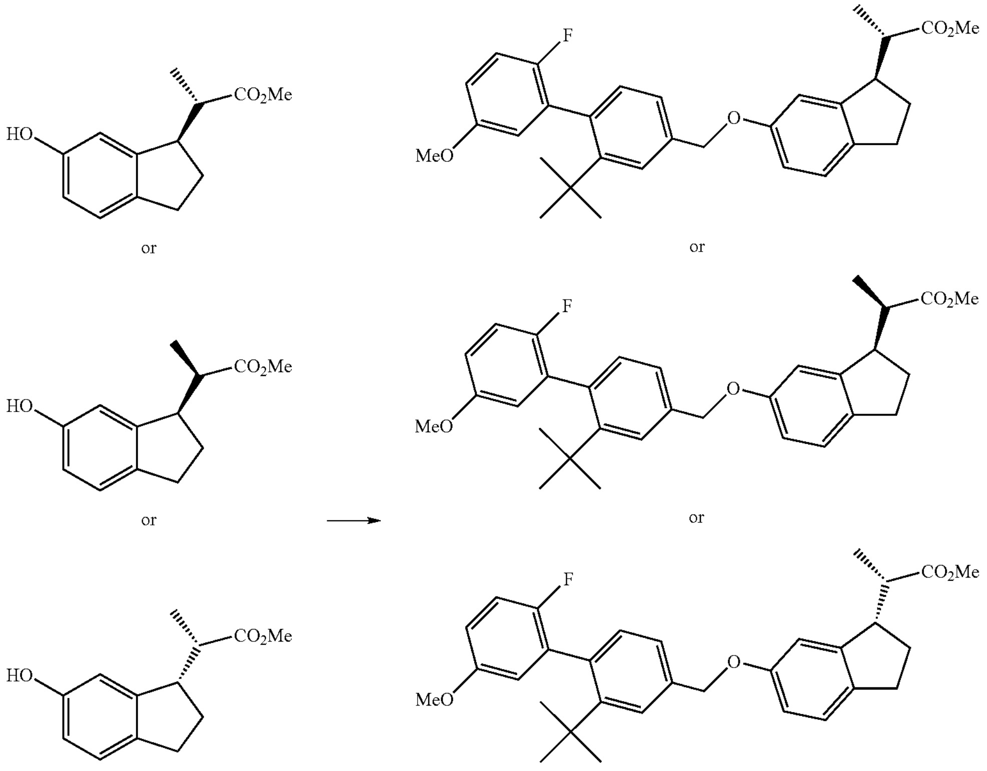

or or or or or or

-continued

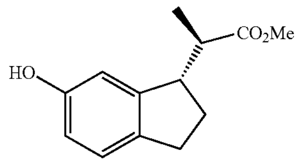

13.3

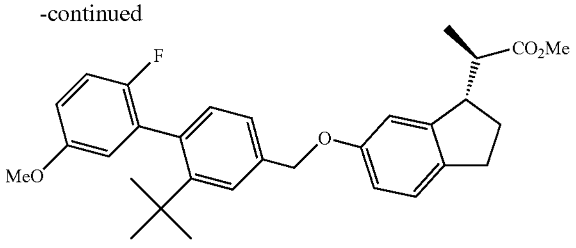

13.4

Synthesis of 13.4

The title compound was synthesized from 13.3 and 4-(chloromethyl)-2-(1,1-dimethylethyl)-2'-fluoro-5'-(methyloxy)-1,1'-biphenyl (Method A) using the method described for the synthesis of 8.7.

Synthesis of 13

The title compound was synthesized from 13.4 using a procedure analogous to that described for synthesizing 8 from 8.7. MS ESI (neg.) M/E: 475 (M−H). $^1$HNMR (DMSO-$d_6$) δ 7.59 (s, 1H), 7.25-7.27 (m, 1H), 7.09-7.16 (m, 2H), 6.93-6.96 (m, 2H), 6.88 (m, 1H), 6.77-6.82 (m, 2H), 5.08 (s, 2H), 3.72 (s, 3H), 3.47 (m, 1H), 2.72-2.79 (m, 3H), 2.07 (m, 1H), 2.03 (m, 1H), 1.15 (s, 9H), 0.88 (d, J=7 Hz, 3H).

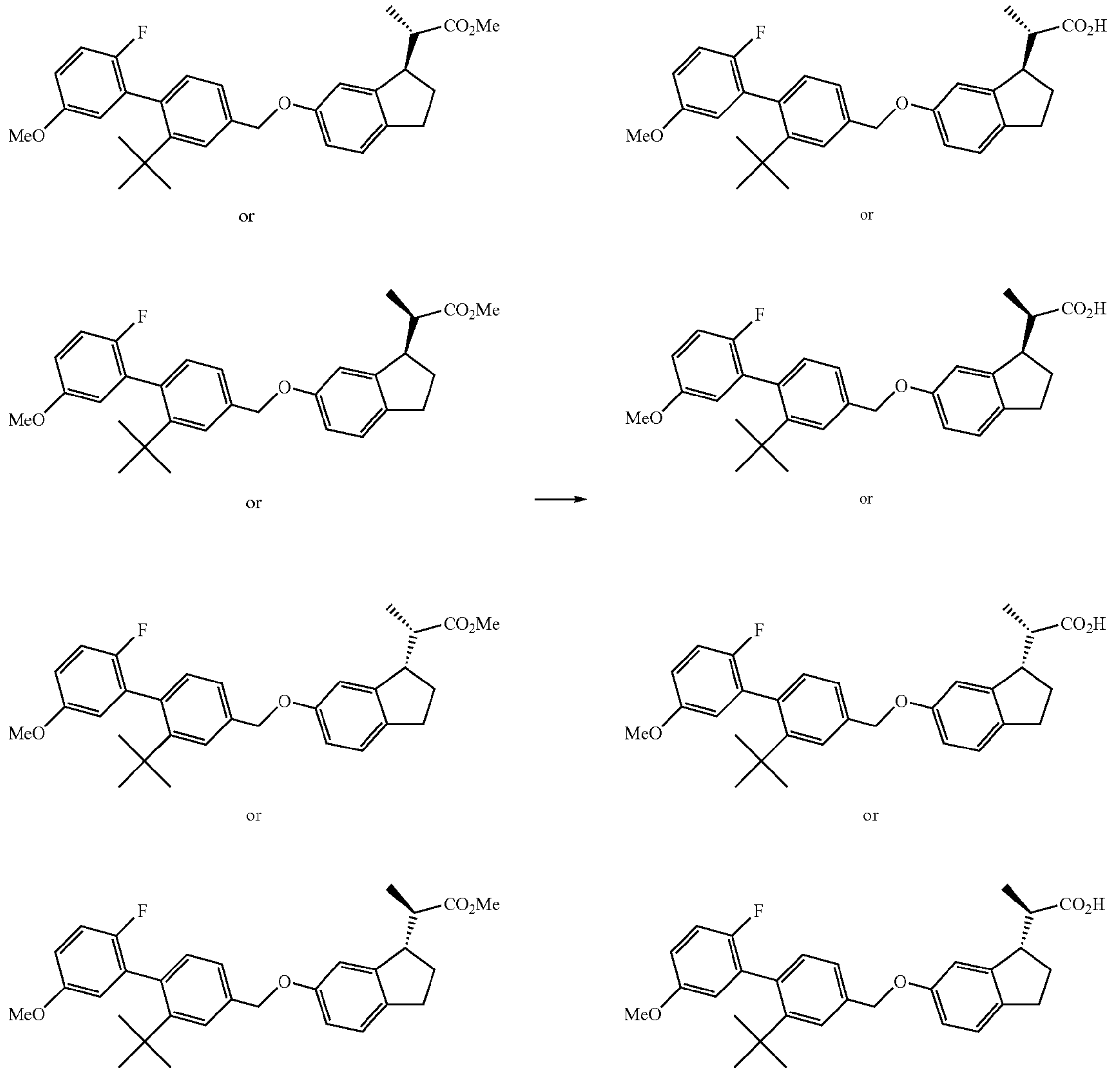

13.4 13

Example 14
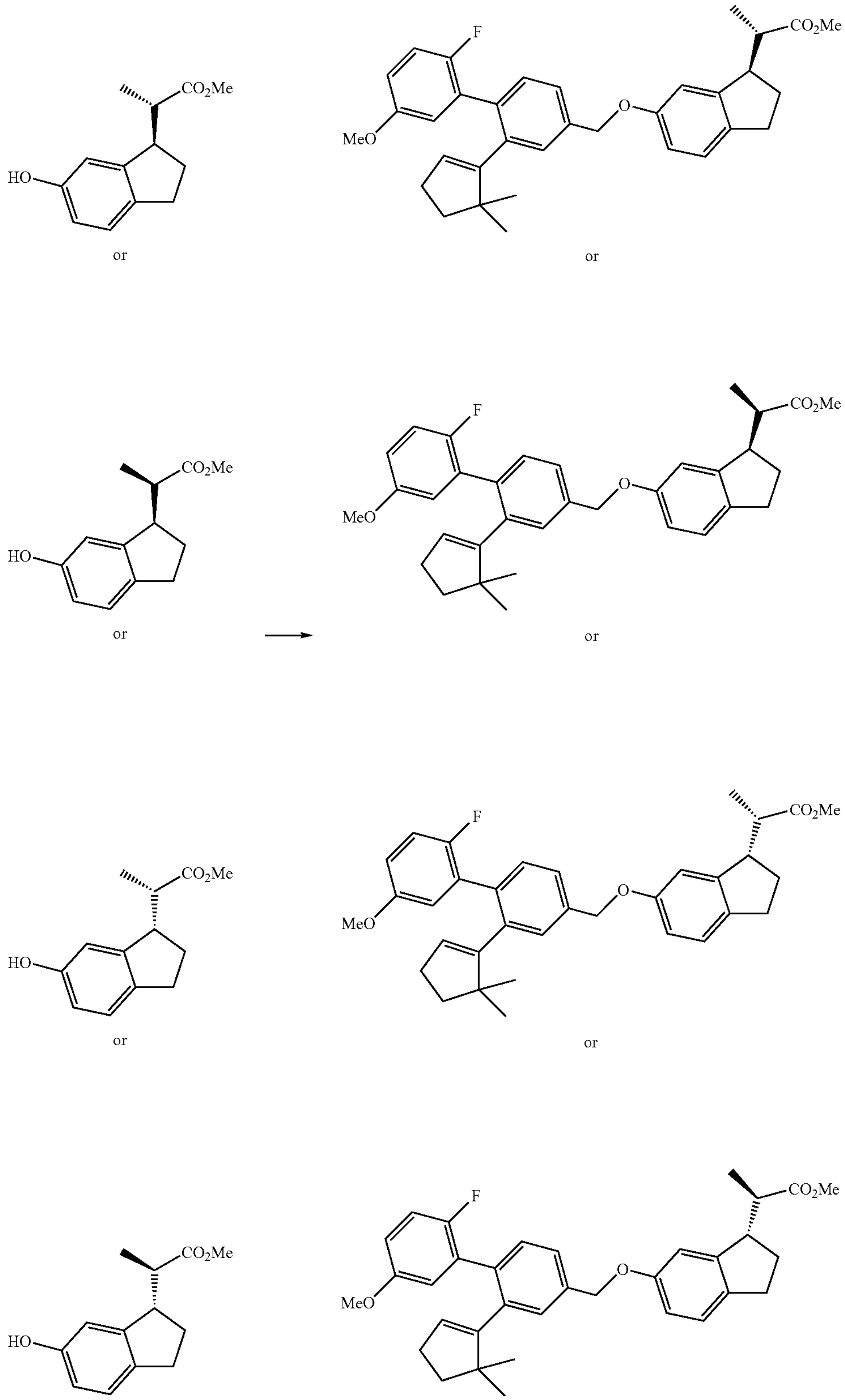
or or
or or
or or
13.3 14.1

Synthesis of 14.1

The title compound was synthesized from 13.3 and 4-(chloromethyl)-2-(5,5-dimethyl-1-cyclopenten-1-yl)-2'-fluoro-5'-(methyloxy)-1,1'-biphenyl (B.9) using the method described for the synthesis of 8.7.

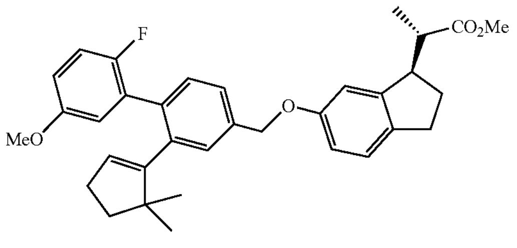

or

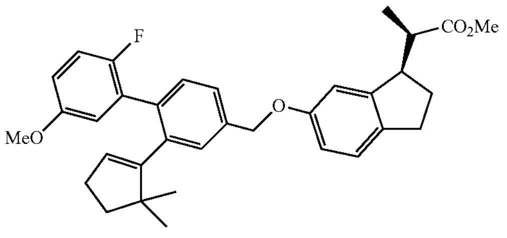

or

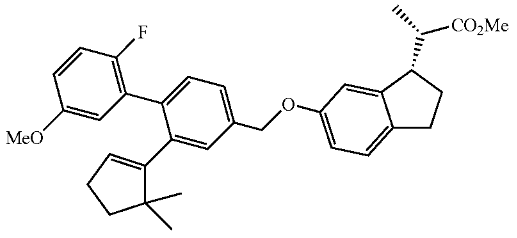

or

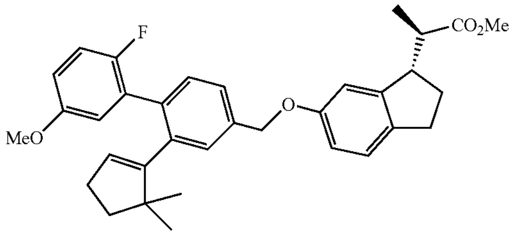

14.1

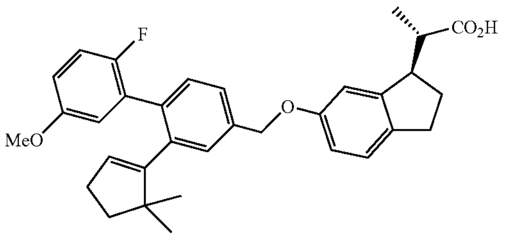

or

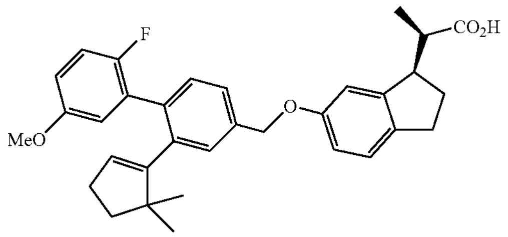

or

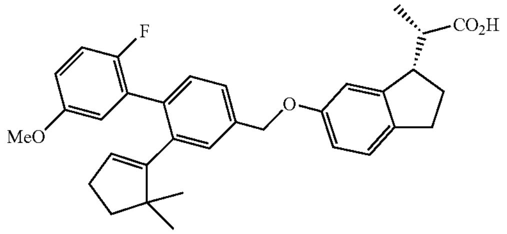

or

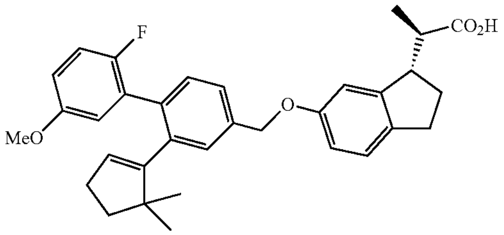

14

Synthesis of 14

The title compound was synthesized from 14.1 using a procedure analogous to that described for synthesizing 8 from 8.7. MS ESI (neg.) M/E: 513 (M−H). $^{1}$HNMR (DMSO-$d_6$) δ 7.37-7.39 (m, 1H), 7.24-7.28 (m, 2H), 7.07-7.11 (m, 2H), 6.85-6.88 (m, 2H), 6.78-6.81 (m, 2H), 5.48 (m, 1H), 5.10 (s, 1H), 3.69 (s, 3H), 3.46 (m, 1H), 2.76-2.78 (m, 3H), 2.16 (m, 2H), 2.03 (m, 1H), 1.78 (m, 1H), 1.57 (m, 2H), 0.87 (d, J=3 Hz, 3H), 0.77 (d, J=6 Hz, 6H).

Example 15
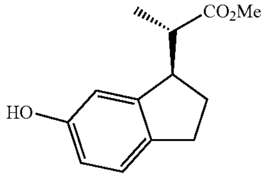
or
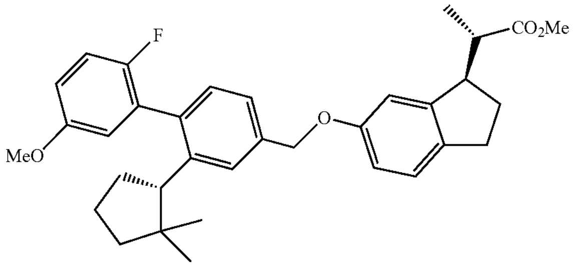
or
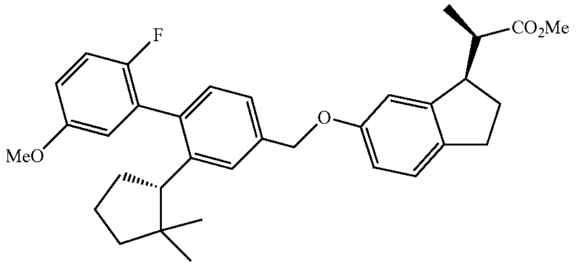
or
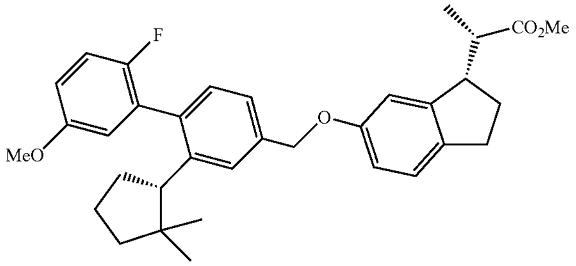
or
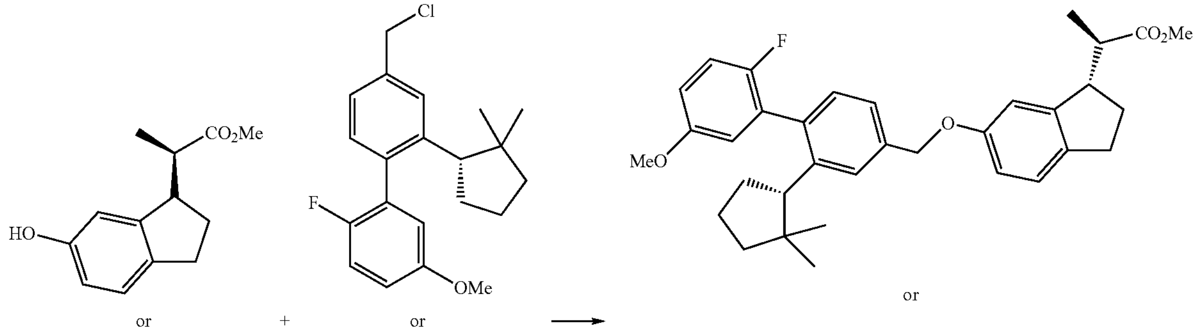
or
+
or
or -continued
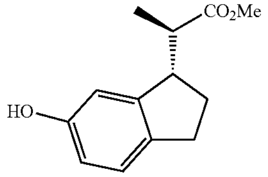
or
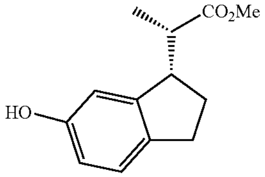
13.3
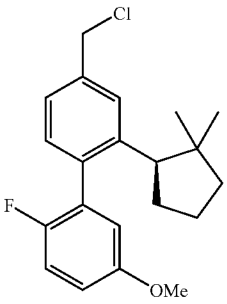
C
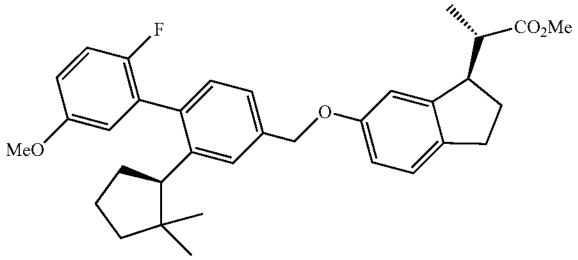
or
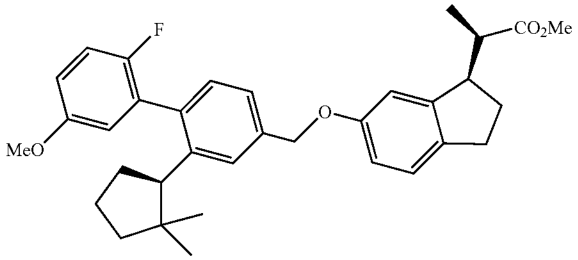
or
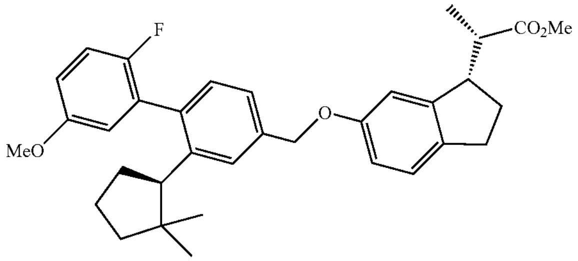
or
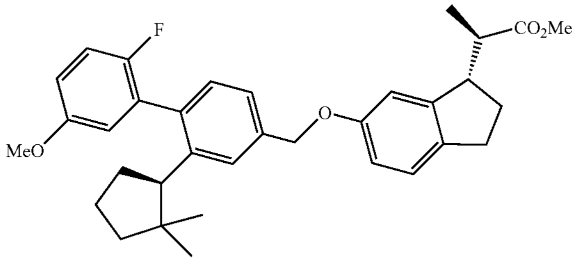
15.1
Synthesis of 15.1
The title compound was synthesized from 13.3 and C using the method described for the synthesis of 8.7.
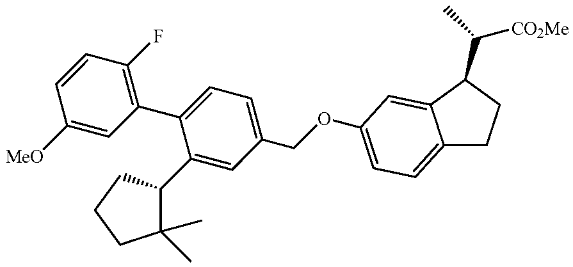
or
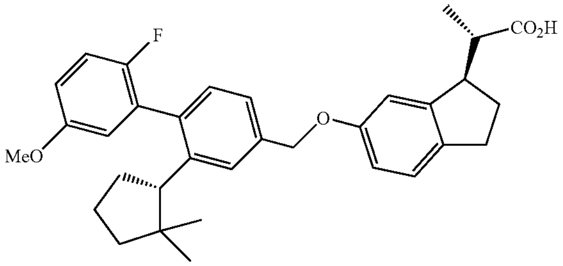
or -continued
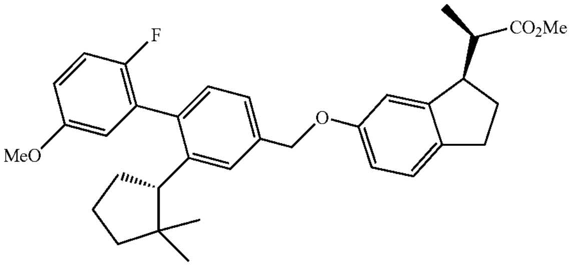
or
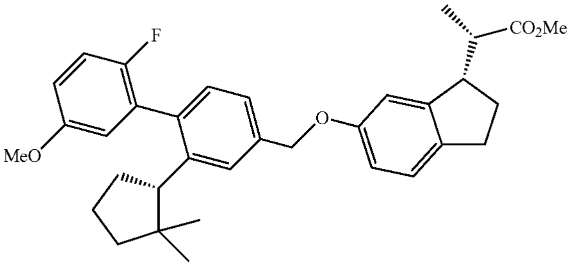
or
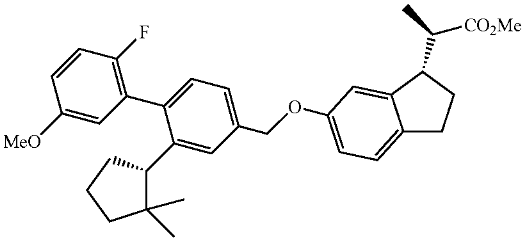
or
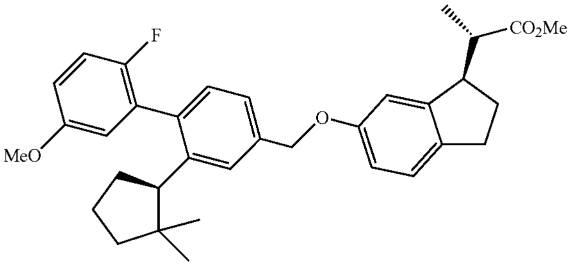
or
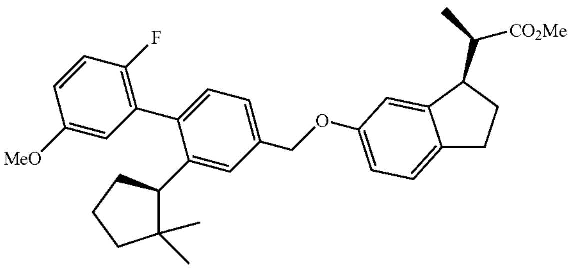
or
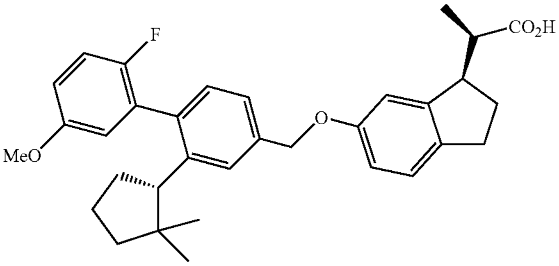
or
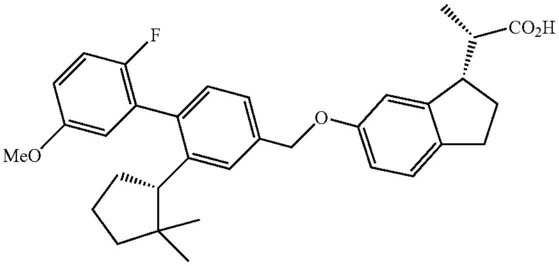
or
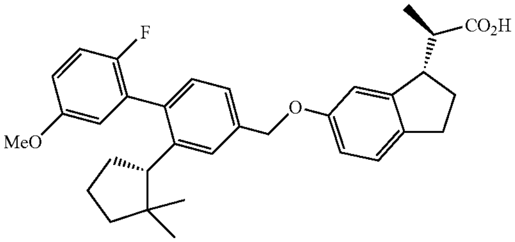
or
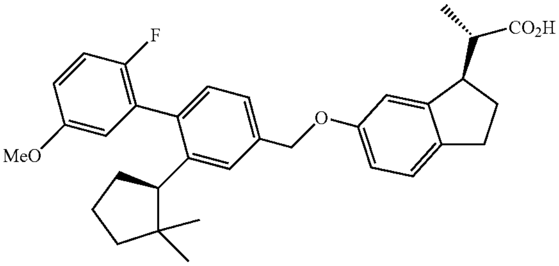
or
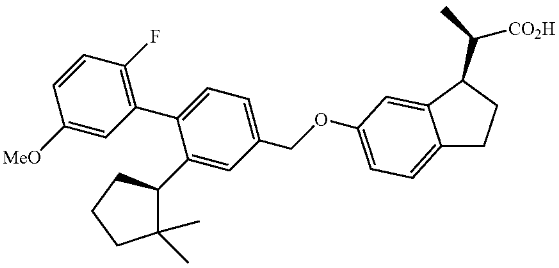
or -continued
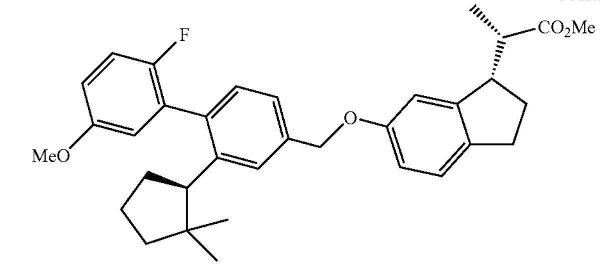
or
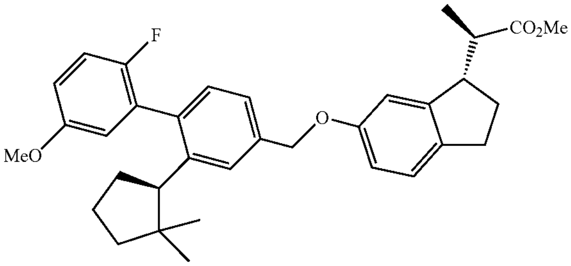
15.1
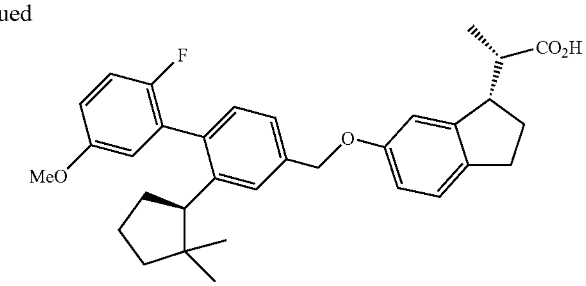
or
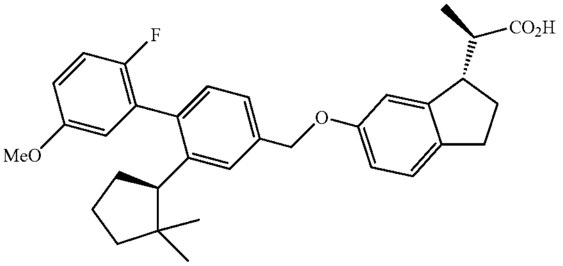
15
Synthesis of 15
The title compound was synthesized from 15.1 using a procedure analogous to that described for synthesizing 8 from 8.7. MS ESI (neg.) M/E: 515 (M−H). $^1$HNMR (DMSO-$d_6$) δ 7.43-7.47 (m, 1H), 7.27-7.33 (m, 2H), 7.14-7.22 (m, 2H), 7.09 (m, 1H), 6.93-6.96 (m, 1H), 6.86 (m, 1H), 6.79-6.81 (m, 2H), 5.10 (s, 2H), 3.74 (s, 3H), 3.47 (m, 1H), 2.73-2.78 (m, 3H), 1.97-2.08 (m, 2H), 1.79 (m, 2H), 1.77 (m, 1H), 1.47 (m, 1H), 1.23-1.30 (m, 2H), 0.88 (d, J=7 Hz, 3H), 0.62 (m, 3H), 0.48 (m, 3H).
Example 16
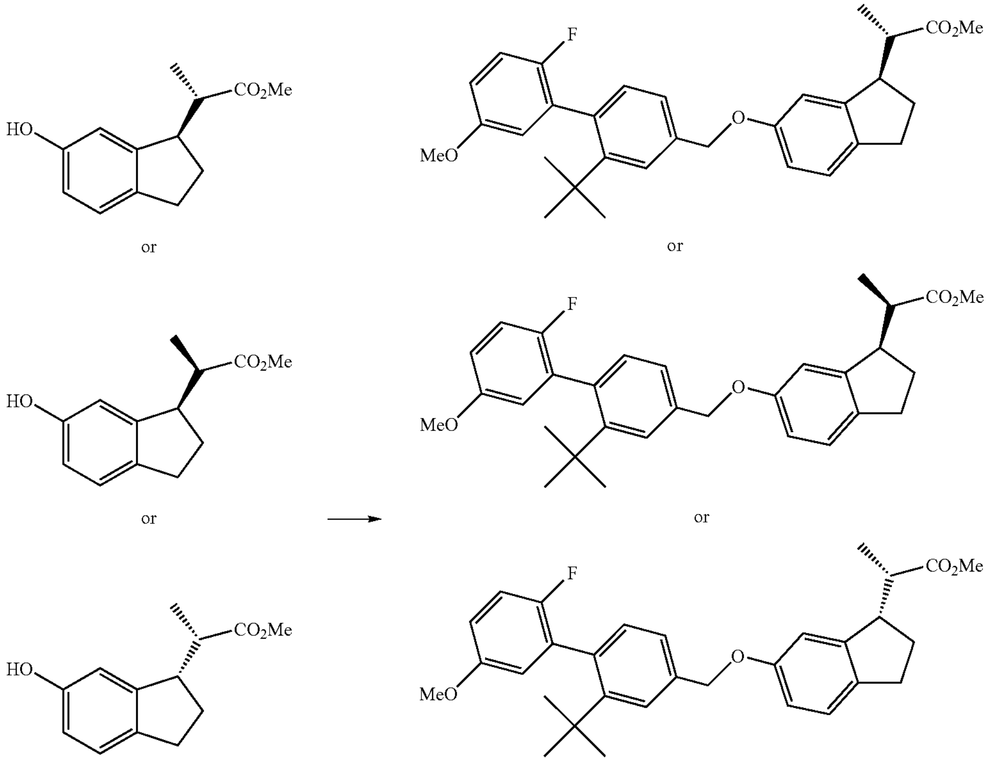
or
or
or
or
or
or -continued

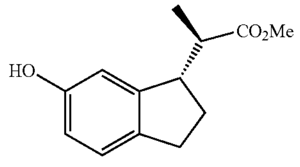

13.2

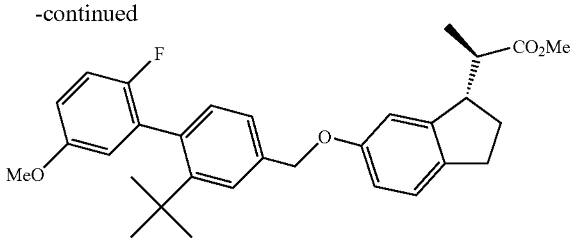

16.1

Synthesis of 16.1

The title compound was synthesized from 13.2 and 4-(chloromethyl)-2-(1,1-dimethylethyl)-2'-fluoro-5'-(methyloxy)-1,1'-biphenyl (Method A) using the method described for the synthesis of 8.7.

Synthesis of 16

The title compound was synthesized from 16.1 using a procedure analogous to that described for synthesizing 8 from 8.7. MS ESI (neg.) M/E: 475 (M−H). $^1$HNMR (DMSO-$d_6$) δ 7.60 (m, 1H), 7.28-7.29 (m, 1H), 7.11-7.19 (m, 2H), 6.95-

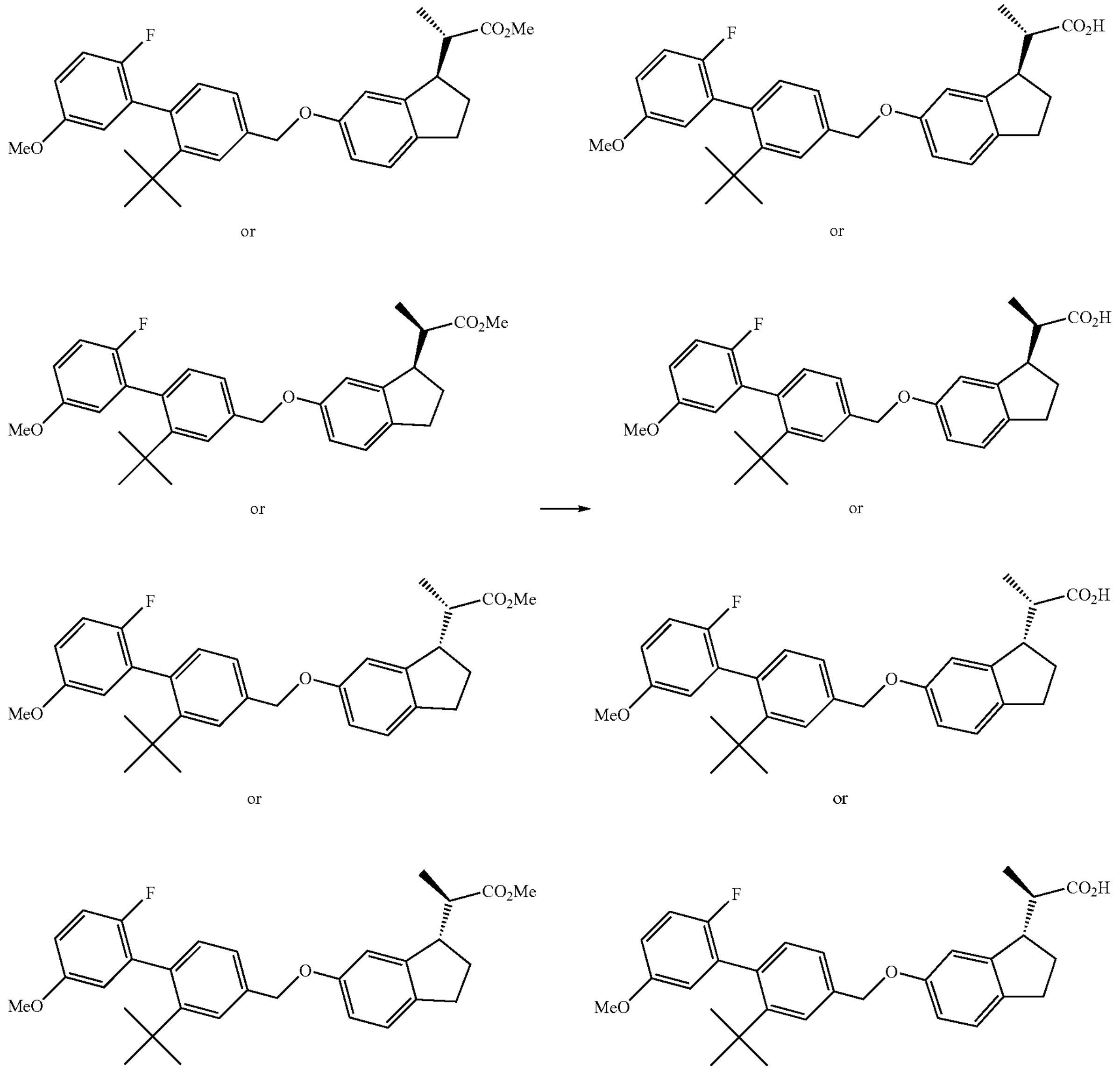

or or or or or or 16.1

16

6.99 (m, 2H), 6.88 (m, 1H), 6.80-6.85 (m, 2H), 5.09 (s, 2H), 3.75 (s, 3H), 3.36 (m, 1H), 2.84 (m, 1H), 2.69 (m, 1H), 2.59 (m, 1H), 2.16 (m, 1H), 1.90 (m, 1H), 1.18 (s, 9H), 1.02 (d, J=7 Hz, 3H).

Example 17

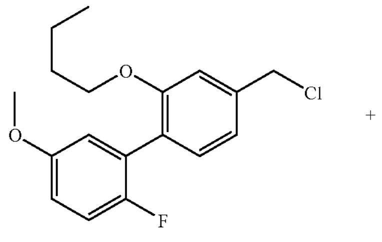

D

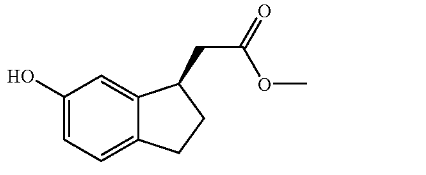

or

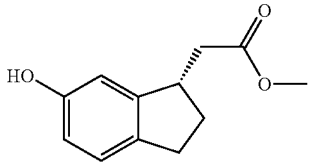

1.5

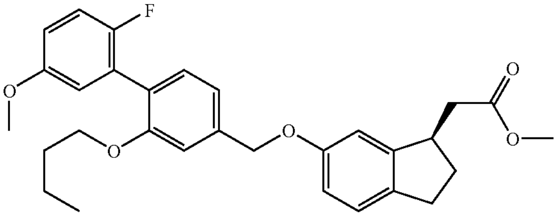

or

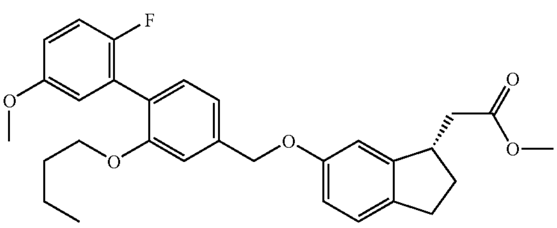

17.1

-continued

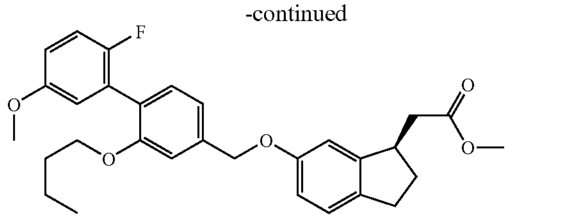

or

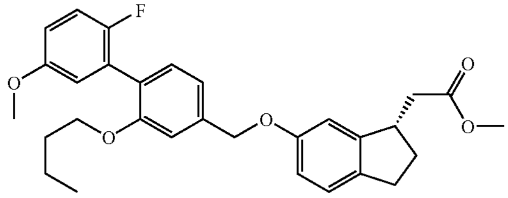

17.1

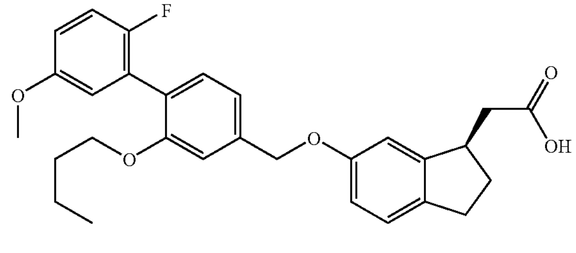

or

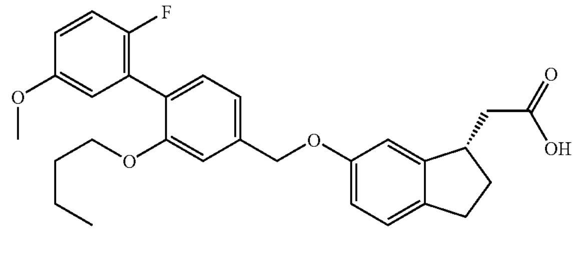

17

Synthesis of 17.1 and 17

To flask containing (R) or (S)-methyl 2-(6-hydroxy-2,3-dihydro-1H-inden-1-yl)acetate (1.5) (0.0100 g, 0.0485 mmol) and cesium carbonate (0.0205 g, 0.0630 mmol) in DMF (1 mL) was added 2-(butyloxy)-4-(chloromethyl)-2'-fluoro-5'-(methyloxy)-1,1'-biphenyl (D) (0.0188 g, 0.0582 mmol). The reaction was then stirred overnight, diluted with water, and extracted with EtOAc. The combined organic layers were washed with brine, dried over anhydrous $Na_2SO_4$, filtered, concentrated, and then purified by silica gel chromatography (0 to 20% EtOAc/Hexane) to provide methyl ((1R)-6-(((2-(butyloxy)-2'-fluoro-5'-(methyloxy)-1,1'-biphenyl-4-yl)methyl)oxy)-2,3-dihydro-1H-inden-1-yl)acetate or methyl ((1S)-6-(((2-(butyloxy)-2'-fluoro-5'-(methyloxy)-1,1'-biphenyl-4-yl)methyl)oxy)-2,3-dihydro-1H-inden-1-yl) acetate 17.1.

To a solution of 17.1 (0.024 g, 0.0485 mmol) in THF/MeOH (2/1) (1.5 mL) was added lithium hydroxide (0.50 mL, 0.50 mmol). The resulting mixture was stirred overnight at 23° C., quenched with excess 1N HCl, and extracted with EtOAc. The combined organic layers were dried over anhydrous $Na_2SO_4$ and concentrated. The residue was purified by silica gel chromatography (0 to 40% EtOAc/hexanes) to afford ((1R)-6-(((2-(butyloxy)-2'-fluoro-5'-(methyloxy)-1,1'-biphenyl-4-yl)methyl)oxy)-2,3-dihydro-1H-inden-1-yl) acetic acid or ((1S)-6-(((2-(butyloxy)-2'-fluoro-5'-(methyloxy)-1,1'-biphenyl-4-yl)methyl)oxy)-2,3-dihydro-1H-inden-1-yl)acetic acid 17 (0.0098 g, 42% yield). $^1H$ NMR (400 MHz, $CDCl_3$) δ ppm 7.26-7.31 (1H, m), 7.15 (1H, d, J=7.8 Hz), 7.00-7.09 (3H, m), 6.81-6.90 (4H, m), 5.07 (2H, s), 4.00 (2H, t, J=6.5 Hz), 3.80 (3H, s), 3.59 (1H, m), 2.78-2.94 (3H, m), 2.55-2.40 (2H, m), 1.86-1.76 (1H, m), 1.64-1.71 (2H, m), 1.33-1.43 (2H, m), 0.89 (3H, t, J=7.4 Hz).

Example 18

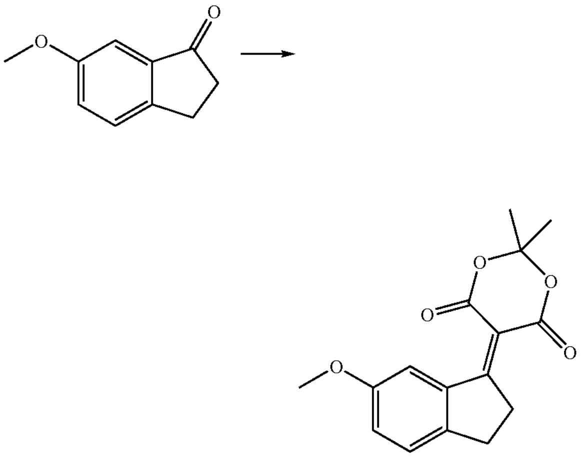

18.1

5-(6-Methoxy-indan-1-ylidene)-2,2-dimethyl-[1,3]dioxane-4,6-dione (18.1)

This compound was synthesized using essentially the same procedure described in Fillion, E.; Wilsily, A.; *J. Am. Chem. Soc.,* 2006, 128, pp. 2774-2775 to give 5-((6-methoxy-2,3-dihydroinden-1-ylidene)-2,2-dimethyl-1,3-dioxane-4,6-dione (12.2 g, 72% yield) from the commercially available 6-methoxy-1-indanone (Aldrich). LCMS ESI (neg.) m/e: 287.0 $(M-1)^-$.

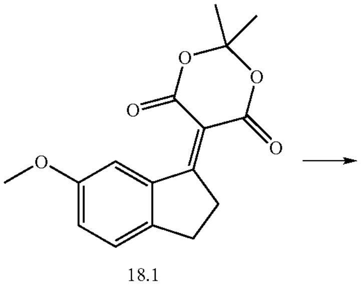

18.1

-continued

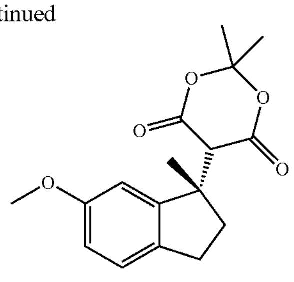

18.2

5-((S)-6-Methoxy-1-methyl-indan-1-yl)-2,2-dimethyl-[1,3]dioxane-4,6-dione (18.2)

This compound was synthesized using essentially the same procedure described in Fillion, E.; Wilsily, A.; *J. Am. Chem. Soc.,* 2006, 128, pp. 2774-2775. The initially obtained product was purified by flash chromatography (silica, 0 to 100% EtOAc:hexanes) to give (S)-5-(6-methoxy-1-methyl-2,3-dihydro-1H-inden-1-yl)-2,2-dimethyl-1,3-dioxane-4,6-dione (290 mg, 57% yield). LCMS ESI (neg.) m/e: 303.1 $(M-1)^-$.

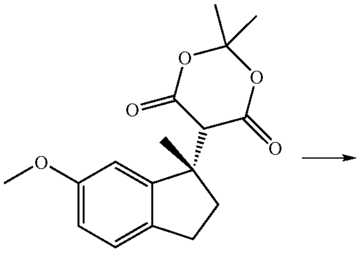

18.2

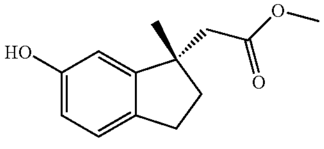

18.3

((S)-6-Hydroxy-1-methyl-indan-1-yl)-acetic acid methyl ester (18.3)

(S)-5-(6-Methoxy-1-methyl-2,3-dihydro-1H-inden-1-yl)-2,2-dimethyl-1,3-dioxane-4,6-dione (290 mg, 960 μmol) was dissolved in N-methylpyrrolidinone (2 mL). Water (17.2 μL, 960 μmol) was added, and the reaction was heated and stirred at 125° C. for one hour to give the intermediate anisole carboxylic acid. The reaction was cooled and NaOH (170 mg, 4.3 mmol) and 1-dodecanethiol (0.80 mmol, 3.3 mmol) were added. The reaction was reheated to 125° C. and stirred for 2.5 days. Another 2.25 equivalents of NaOH was added along with 1.75 equivalents of the thiol. The resulting mixture was stirred at 125° C. for an additional 16 hours. The reaction was then cooled to room temperature and diluted with water (about 25 mL). The resulting mixture was extracted with diethyl ether (2×50 mL) and then the aqueous layer was acidified with hydrochloric acid. The aqueous layer was extracted with EtOAc (2×75 mL). The combined EtOAc layers were washed with water (2×75 mL) and brine (1×25 mL) and dried over magnesium sulfate. The organic layer was filtered and the solvent was removed. The residue was used directly in the next step (S)-2-(6-hydroxy-1-methyl-2,3-dihydro-1H-inden-1-yl)acetic acid (370 mg, 190% yield) (contains residual NMP). The (S)-2-(6-hydroxy-1-methyl-2,3-dihydro-1H-inden-1-yl)acetic acid (197 mg, 955 mmol) was dissolved in MeOH (10 mL) and a catalytic amount of sulfuric acid was added. The mixture was heated at reflux and stirred for three hours. The reaction was cooled, basified with saturated sodium bicarbonate, and the solvent was removed. The residue was then partitioned between EtOAc and water, and the layers were separated. The aqueous layer was extracted with EtOAc (1×50 mL), and the combined organic layers were washed with brine (1×25 mL) and dried over magnesium sulfate. After filtration and solvent removal, the residue was purified by medium pressure chromatography (silica, 0 to 15% EtOAc:DCM) to give (S)-methyl 2-(6-hydroxy-1-methyl-2,3-dihydro-1H-inden-1-yl)acetate (141 mg, 67% yield). LCMS ESI (neg.) m/e: 219.1 $(M-1)^-$. Chiral Analytical HPLC (ChiralPak AD-H column, 8% isopropanol: hexanes): retention time=18.1 minutes (second peak).

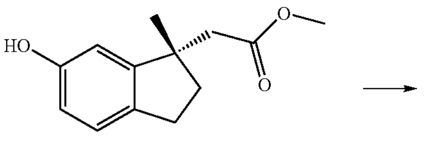

18.3

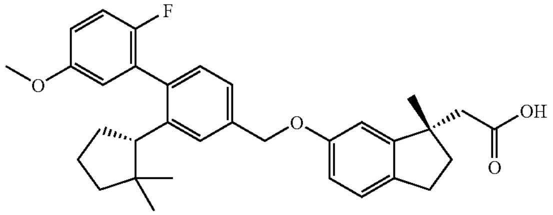

or

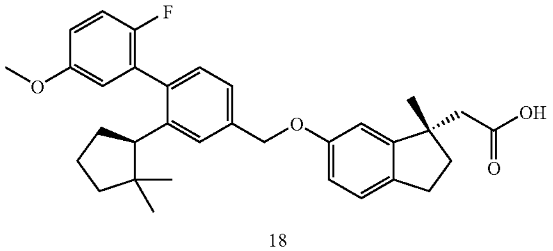

18

{(S)-6-[2-((S)-2,2-Dimethyl-cyclopentyl)-2'-fluoro-5'-methoxy-biphenyl-4-ylmethoxy]-1-methyl-indan-1-yl}-acetic acid or diastereomer thereof (18)

Example 18 was prepared from 18.3 using essentially the same procedure described in Example 3 (31 mg, 44% yield). LCMS ESI (pos.) m/e: 548.2 $(M+H_20)^+$.

Example 19

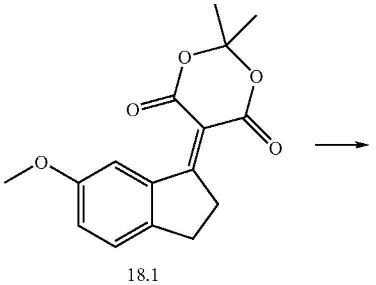

18.1

-continued

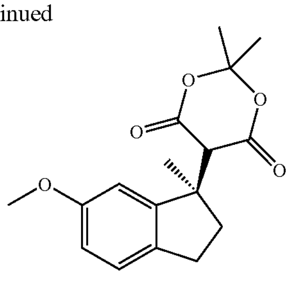

19.1

5-((R)-6-Methoxy-1-methyl-indan-1-yl)-2,2-dimethyl-[1,3]dioxane-4,6-dione (19.1)

The title compound was synthesized from 18.1 using essentially the same procedure described in Fillion, E.; Wilsily, A.; *J. Am. Chem. Soc.,* 2006, 128, pp. 2774-2775, except the chiral phosphorimidate ligand referenced was substituted for (R)-2,2'-binapthyl-(R,R)-di(1-phenylethyl)aminoylphosphine which was prepared using essentially the same procedure outlined in RajanBabu, T. V.; Smith, C. R.; *Org. Lett;* 2008, 10(8); pp. 1657-1659. The residue was purified by flash chromatography (silica, 0 to 100% EtOAc: hexanes) to give (R)-5-(6-methoxy-1-methyl-2,3-dihydro-1H-inden-1-yl)-2,2-dimethyl-1,3-dioxane-4,6-dione (1370 mg, 81.1% yield). LCMS ESI (neg.) m/e: 303.1 $(M+1)^-$.

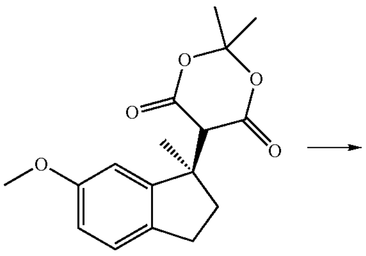

19.1

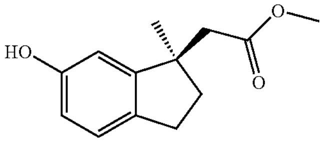

19.2

((R)-6-Hydroxy-1-methyl-indan-1-yl)-acetic acid methyl ester (19.2)

This compound was synthesized from 19.1 using essentially the same procedure described in Example 18 to give ((R)-6-hydroxy-1-methyl-indan-1-yl)-acetic acid methyl ester (19.2). LCMS ESI (pos.) m/e: 219.1 $(M-1)^-$. Chiral Analytical HPLC (ChiralPak AD-H column, 8% isopropanol: hexanes): retention time=14.6 minutes (first peak). 1H NMR (400 MHz, $CDCl_3$) δ ppm 7.05 (1H, d, J=7.8 Hz), 6.60-6.70 (2H, m), 5.58 (1H, s), 3.65 (3H, s), 2.83 (2H, t, J=7.0 Hz), 2.45-2.63 (2H, m), 2.22-2.33 (1H, m), 1.89-2.01 (1H, m), 1.35 (3H, s).

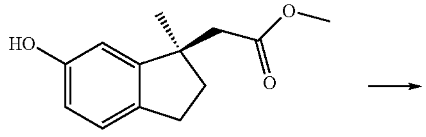

19.2

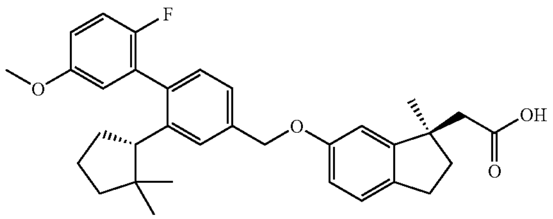

or

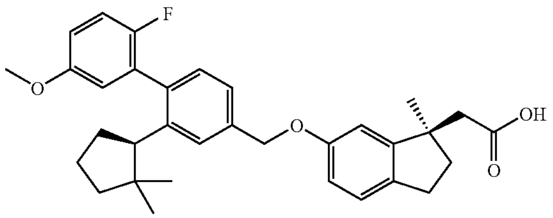

19

{(R)-6-[2-((S)-2,2-Dimethyl-cyclopentyl)-2'-fluoro-5'-methoxy-biphenyl-4-ylmethoxy]-1-methyl-indan-1-yl}-acetic acid or diastereomer thereof (19)

Example 19 was synthesized from 19.2 using essentially the same procedure described in Example 20 (28 mg, 40% yield). LCMS ESI (pos.) m/e: 548.2 $(M+H_20)^+$.

Example 20

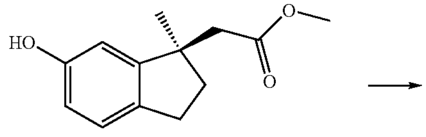

19.2

-continued

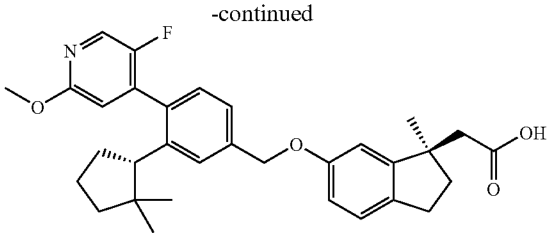

or

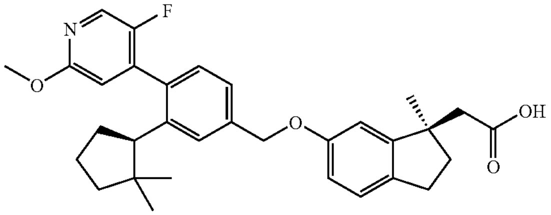

20

{(R)-6-[3-((S)-2,2-Dimethyl-cyclopentyl)-4-(5-fluoro-2-methoxy-pyridin-4-yl)-benzyloxy]-1-methyl-indan-1-yl}-acetic acid or diastereomer thereof (R)-Methyl 2-(6-hydroxy-1-methyl-2,3-dihydro-1H-inden-1-yl)acetate (46 mg, 210 μmol) was dissolved in DMF (2 mL) and cesium carbonate (140 mg, 420 μmol) was added followed by 4-(4-(chloromethyl)-2-(S)-2,2-dimethylcyclopentyl)phenyl)-5-fluoro-2-methoxypyridine or its enantiomer (73 mg, 210 μmol). The resulting slurry was stirred overnight, diluted with water (15 mL), and extracted with EtOAc (10 mL). The organic layer was removed and concentrated. The residue was purified by medium pressure chromatography (silica, 0 to 15% EtOAc:hexanes) to give methyl 2-((R)-6-((8S)-3-((S)-2,2-dimethylcyclopentyl)-4-(5-fluoro-2-methoxypyridin-4-yl)benzyloxy)-1-methyl-2,3-dihydro-1H-inden-1-yl)acetate or the diastereomer thereof (90 mg, 81% yield). The ester (39 mg, 73 μmol) was dissolved in 1:1 MeOH:THF (4 mL) and shaken overnight. The reaction mixture was then acidified using TFA, and the mixture was concentrated. The residue was purified by reverse phase chromatography (C18, 5 to 95% ACN:water (+0.1% TFA)) to give {(R)-6-[3-((S)-2,2-dimethyl-cyclopentyl)-4-(5-fluoro-2-methoxy-pyridin-4-yl)-benzyloxy]-1-methyl-indan-1-yl}-acetic acid or the diastereomer thereof (20). (28 mg, 74% yield). LCMS ESI (pos.) m/e: 518.2 $(M+1)^+$.

Example 21

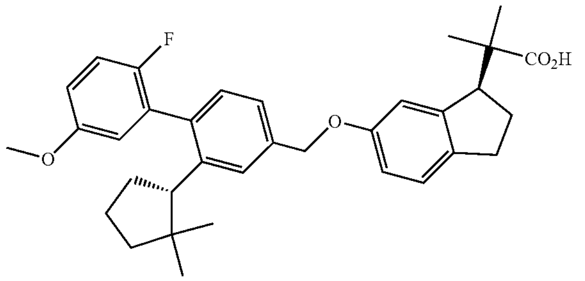

or

-continued

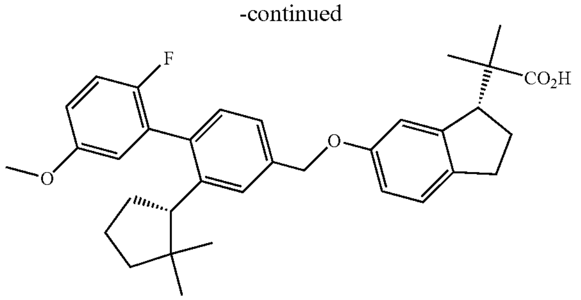

or

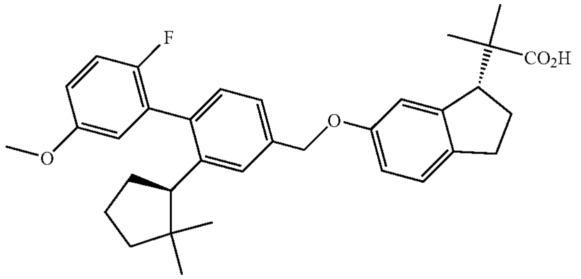

or

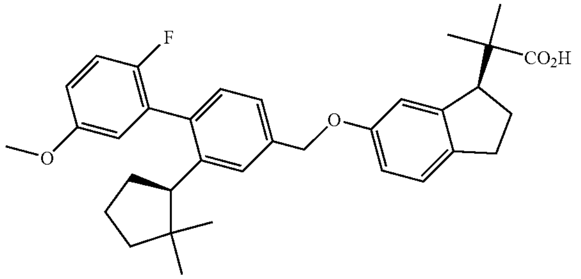

21

2-((1S)-6-(((2-((1S)-2,2-Dimethylcyclopentyl)-2'-fluoro-5'-(methyloxy)-1,1'-biphenyl-4-yl)methyl)oxy)-2,3-dihydro-1H-inden-1-yl)-2-methylpropanoic acid or 2-((1R)-6-(((2-((1S)-2,2-dimethylcyclopentyl)-2'-fluoro-5'-(methyloxy)-1,1'-biphenyl-4-yl)methyl)oxy)-2,3-dihydro-1H-inden-1-yl)-2-methylpropanoic acid or 2-((1S)-6-(((2-(((1R)-2,2-dimethylcyclopentyl)-2'-fluoro-5'-(methyloxy)-1,1'-biphenyl-4-yl)methyl)oxy)-2,3-dihydro-1H-inden-1-yl)-2-methylpropanoic acid or 2-((1R)-6-(((2-((1R)-2,2-dimethylcyclopentyl)-2'-fluoro-5'-(methyloxy)-1,1'-biphenyl-4-yl)methyl)oxy)-2,3-dihydro-1H-inden-1-yl)-2-methylpropanoic acid (21)

The title compound was prepared from the appropriate reagents using the methods described herein. MS ESI (neg.) m/e: 529 $(M-H)^+$. $^1H$ NMR (400 MHz, DMSO-d6) δ ppm 7.42-7.46 (m, 1H), 7.26-7.33 (m, 1H), 7.14-7.20 (m, 2H), 7.08-7.10 (m, 1H), 6.93-6.96 (m, 1H), 6.76-6.83 (m, 3H), 5.08 (s, 2H), 3.73 (s, 3H), 3.49 (m, 1H), 2.60-2.80 (m, 2H), 1.90-2.20 (m, 2H), 1.70-1.85 (m, 2H), 1.45-1.60 (m, 2H), 1.20-1.29 (m, 3H), 1.03 (s, 3H), 0.96 (s, 3H), 0.46 (m, 1H), 0.62 (m, 3H), 0.50 (m, 3H).

Example 22

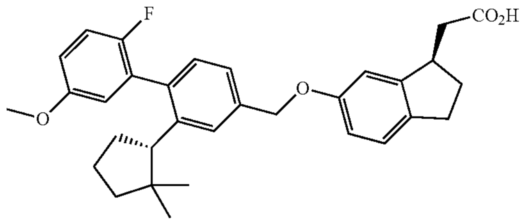

or

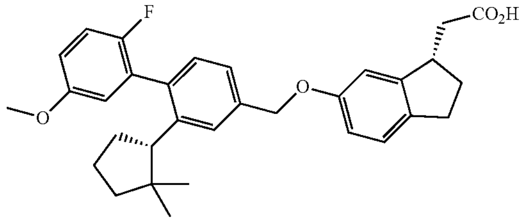

or

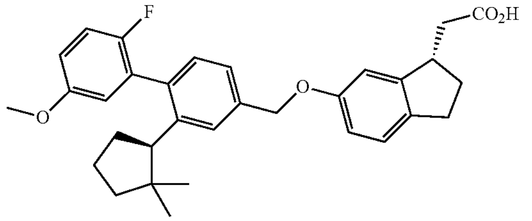

or

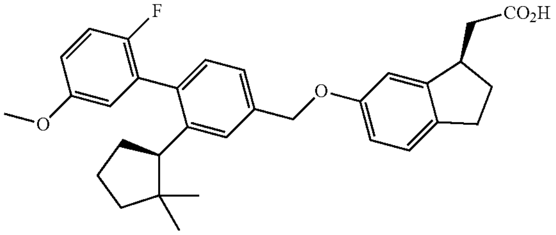

22

((1R)-6-(((2-((1S)-2,2-Dimethylcyclopentyl)-2'-fluoro-5'-(methyloxy)-1,1'-biphenyl-4-yl)methyl)oxy)-2,3-dihydro-1H-inden-1-yl)acetic acid or ((1S)-6-(((2-((1S)-2,2-dimethylcyclopentyl)-2'-fluoro-5'-(methyloxy)-1,1'-biphenyl-4-yl)methyl)oxy)-2,3-dihydro-1H-inden-1-yl)acetic acid or ((1R)-6-(((2-((1R)-2,2-dimethylcyclopentyl)-2'-fluoro-5'-(methyloxy)-1,1'-biphenyl-4-yl)methyl)oxy)-2,3-dihydro-1H-inden-1-yl)acetic acid or ((1S)-6-(((2-((1R)-2,2-dimethylcyclopentyl)-2'-fluoro-5'-(methyloxy)-1,1'-biphenyl-4-yl)methyl)oxy)-2,3-dihydro-1H-inden-1-yl)acetic acid (22)

The title compound was prepared from the appropriate reagents using the methods described herein. MS ESI (neg.) m/e: 501 $(M-H)^+$. $^1H$ NMR (400 MHz, DMSO-d6) δ ppm 7.44-7.48 (m, 1H), 7.28-7.36 (m, 1H), 7.15-7.25 (m, 2H), 7.09-7.11 (m, 1H), 6.93-6.96 (m, 2H), 6.79-6.82 (m, 2H), 5.11 (s, 2H), 3.74 (s, 3H), 2.72-2.77 (m, 4H), 2.24-2.31 (m, 2H), 1.95-2.00 (m, 2H), 1.70-1.80 (m, 1H), 1.55-1.70 (m, 1H), 1.20-1.26 (m, 2H), 0.63 (m, 3H), 0.50 (m, 3H).

Example 23

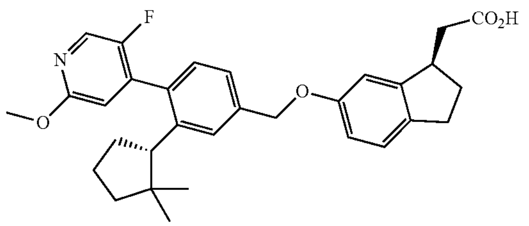

or

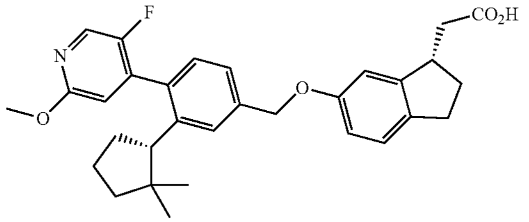

or

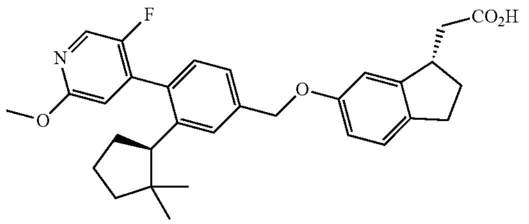

or

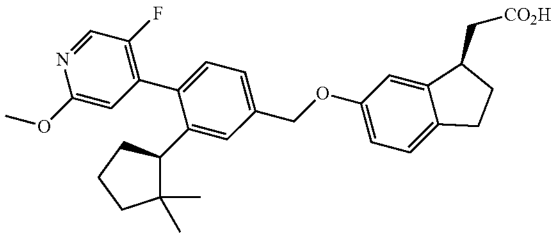

23

((1R)-6-(((3-((1S)-2,2-Dimethylcyclopentyl)-4-(5-fluoro-2-(methyloxy)-4-pyridinyl)phenyl)methyl)oxy)-2,3-dihydro-1H-inden-1-yl)acetic acid or ((1S)-6-(((3-((1S)-2,2-dimethylcyclopentyl)-4-(5-fluoro-2-(methyloxy)-4-pyridinyl)phenyl)methyl)oxy)-2,3-dihydro-1H-inden-1-yl)acetic acid or ((1R)-6-(((3-((1R)-2,2-dimethylcyclopentyl)-4-(5-fluoro-2-(methyloxy)-4-pyridinyl)phenyl)methyl)oxy)-2,3-dihydro-1H-inden-1-yl)acetic acid or ((1S)-6-(((3-((1R)-2,2-dimethylcyclopentyl)-4-(5-fluoro-2-(methyloxy)-4-pyridinyl)phenyl)methyl)oxy)-2,3-dihydro-1H-inden-1-yl)acetic acid (23)

The title compound was prepared from the appropriate reagents using the methods described herein. MS ESI (neg.) m/e: 502 $(M-H)^+$. $^1H$ NMR (400 MHz, DMSO-d6) δ ppm 12.20 (s, 1H), 8.19 (m, 1H), 7.49 (m, 1H), 7.37 (m, 1H), 7.20 (m, 1H), 7.10 (m, 1H), 6.93 (m, 1H), 6.70-6.81 (m, 2H), 5.12 (s, 2H), 3.40 (m, 1H), 2.60-2.77 (m, 4H), 2.24-2.31 (m, 2H), 1.99 (m, 1H), 1.75 (m, 1H), 1.62-1.67 (m, 1H), 1.49 (m, 1H), 1.24-1.33 (m, 2H), 0.61 (m, 3H), 0.50 (m, 3H).

Example 24

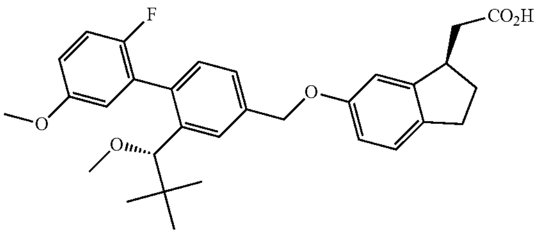

or

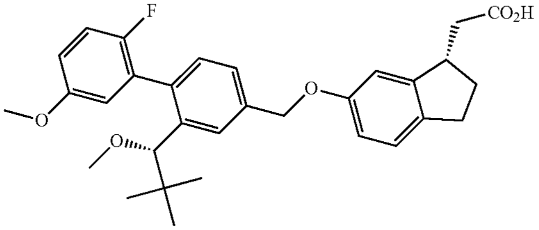

or

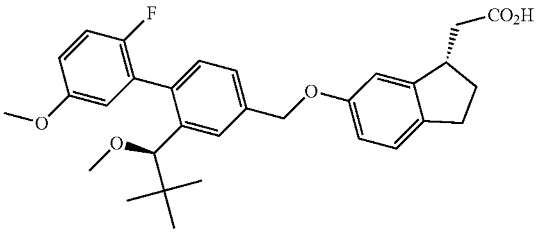

or

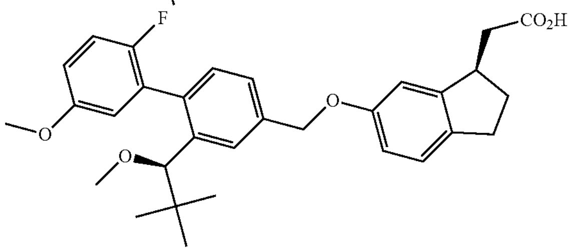

24

((1R)-6-(((2-((1S)-2,2-Dimethyl-1-(methyloxy)propyl)-2'-fluoro-5'-(methyloxy)-1,1'-biphenyl-4-yl)methyl)oxy)-2,3-dihydro-1H-inden-1-yl)acetic acid or ((1S)-6-(((2-((1S)-2,2-dimethyl-1-(methyloxy)propyl)-2'-fluoro-5'-(methyloxy)-1,1'-biphenyl-4-yl)methyl)oxy)-2,3-dihydro-1H-inden-1-yl)acetic acid or ((1R)-6-(((2-((1R)-2,2-dimethyl-1-(methyloxy)propyl)-2'-fluoro-5'-(methyloxy)-1,1'-biphenyl-4-yl)methyl)oxy)-2,3-dihydro-1H-inden-1-yl)acetic acid or ((1S)-6-(((2-((1R)-2,2-dimethyl-1-(methyloxy)propyl)-2'-fluoro-5'-(methyloxy)-1,1'-biphenyl-4-yl)methyl)oxy)-2,3-dihydro-1H-inden-1-yl)acetic acid (24)

The title compound was prepared from the appropriate reagents using the methods described herein. MS ESI (neg.) m/e: 505 $(M-H)^+$. $^1H$ NMR (400 MHz, DMSO-d6) δ ppm 7.49-7.54 (m, 1H), 7.39-7.45 (m, 1H), 7.19-7.24 (m, 2H), 7.10 (m, 1H), 7.00 (m, 1H), 6.92 (m, 1H), 6.78-6.81 (m, 2H), 5.15 (s, 2H), 3.88-4.11 (m, 1H), 3.75 (m, 3H), 3.15-3.22 (m, 3H), 2.70-2.876 (m, 3H), 2.23-2.29 (m, 2H), 1.64 (m, 1H), 1.24 (m, 1H), 0.63 (s, 9H).

Example 25

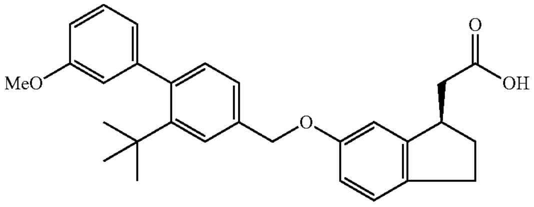

or

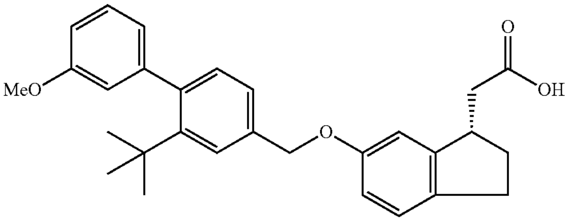

25

((1R)-6-(((2-(1,1-Dimethylethyl)-3'-(methyloxy)-1,1'-biphenyl-4-yl)methyl)oxy)-2,3-dihydro-1H-inden-1-yl)acetic acid or ((1S)-6-(((2-(1,1-dimethylethyl)-3'-(methyloxy)-1,1'-biphenyl-4-yl)methyl)oxy)-2,3-dihydro-1H-inden-1-yl)acetic acid (25)

The title compound was prepared from the appropriate reagents using the methods described herein. MS ESI (neg.) m/e: 443 (M−H)$^+$. $^1$H NMR (400 MHz, DMSO-d6) δ ppm 7.58 (m, 1H), 7.27-7.30 (m, 1H), 7.23-7.25 (m, 1H), 7.11 (m, 1H), 6.91-6.95 (m, 3H), 6.80-6.82 (m, 2H), 6.77-6.78 (m, 1H), 5.07 (s, 2H), 3.76 (s, 3H), 3.39 (m, 1H), 2.75-2.78 (m, 3H), 2.27-2.32 (m, 2H), 1.65-1.68 (m, 1H).

Example 26

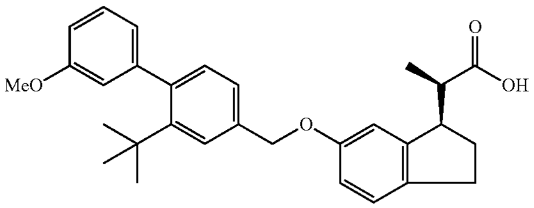

or

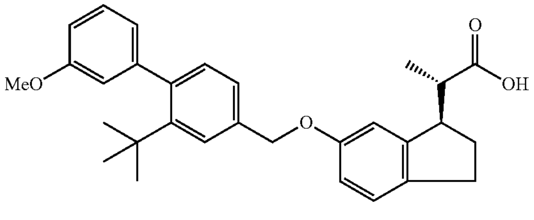

or

-continued

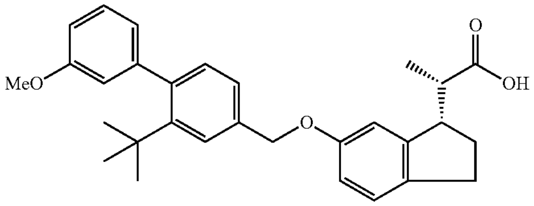

or

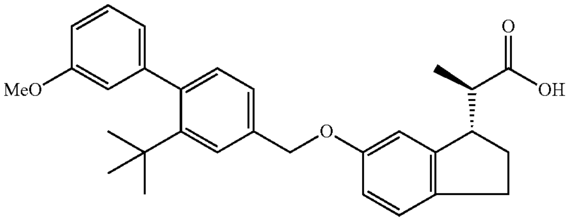

26

2-((1R)-6-(((2-(1,1-dimethylethyl)-3'-(methyloxy)-1,1'-biphenyl-4-yl)methyl)-oxy)-2,3-dihydro-1H-inden-1-yl)propanoic acid or stereoisomer thereof (26)

The title compound was prepared from the appropriate reagents using the methods described herein. MS ESI (neg.) m/e: 457 (M−H)$^+$. $^1$H NMR (400 MHz, DMSO-d6) δ ppm 7.57 (m, 1H), 7.27-7.30 (m, 1H), 7.23-7.24 (m, 1H), 7.11 (d, 1H), 6.92-6.95 (m, 2H), 6.89 (m, 1H), 6.80-6.83 (m, 2H), 6.77 (m, 1H), 5.08 (s, 2H), 3.75 (s, 3H), 3.49 (m, 1H), 2.72-2.80 (m, 3H), 2.05-2.10 (m, 1H), 1.75-1.85 (m, 1H), 1.16 9 m, 9H), 0.89 (m, 3H).

Example 27

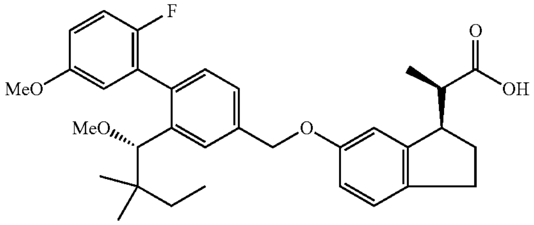

or

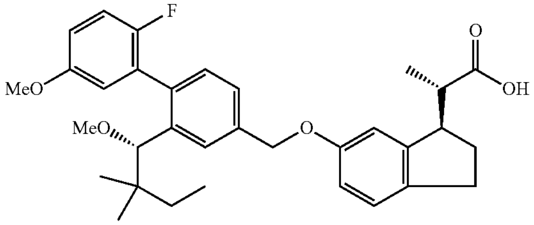

or

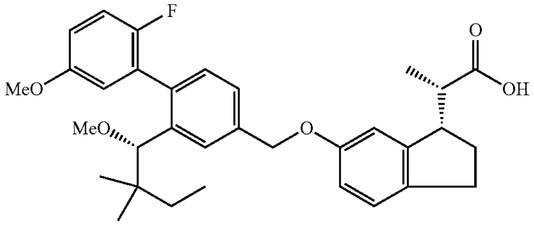

or

-continued

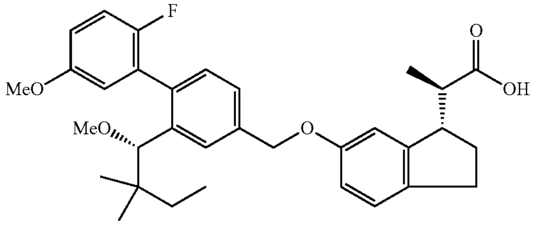

or

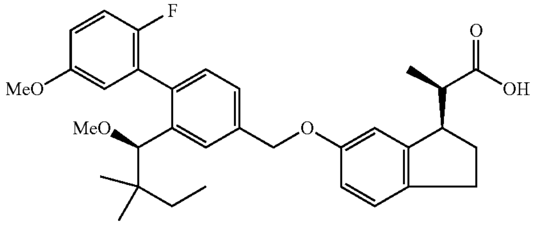

or

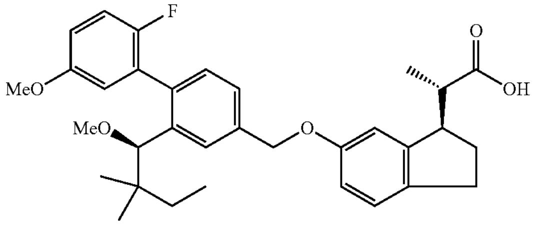

or

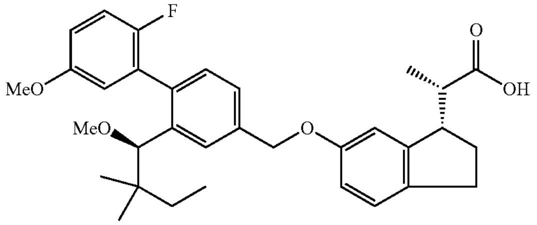

or

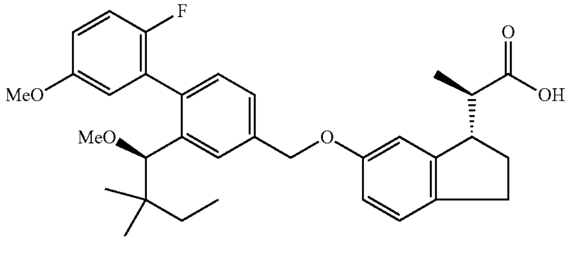

27

2-((1R)-6-(((2-((1R)-2,2-Dimethyl-1-(methyloxy)butyl)-2'-fluoro-5'-(methyloxy)-1,1'-biphenyl-4-yl)methyl)oxy)-2,3-dihydro-1H-inden-1-yl)propanoic acid (27) or stereoisomer thereof (27)

The title compound was prepared from the appropriate reagents using the methods described herein. MS ESI (neg.) m/e: 533 (M−H)$^+$. $^1$H NMR (400 MHz, CDCl3) δ ppm 7.59-7.63 (m, 1H), 7.42-7.44 (m, 1H), 7.17-7.19 (m, 1H), 7.00-7.13 (m, 2H), 6.82-6.88 (m, 3H), 6.73-6.75 (m, 1H), 5.13 (s, 2H), 4.05-4.29 (m, 1H), 3.80 (s, 3H), 3.62 (m, 1H), 3.25-3.30

(m, 3H), 2.81-2.90 (m, 3H), 2.18-2.23 (m, 1H), 1.93-1.97 (m, 1H), 1.25-1.30 (m, 1H), 1.05-1.09 (m, 4H), 0.72 (s, 3H), 0.61 (t, 3H), 0.59 (m, 3H).

Example 28

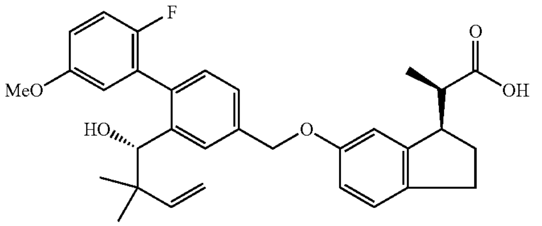

or

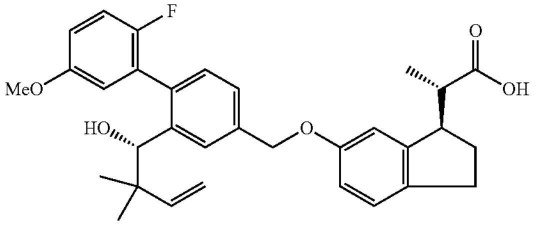

or

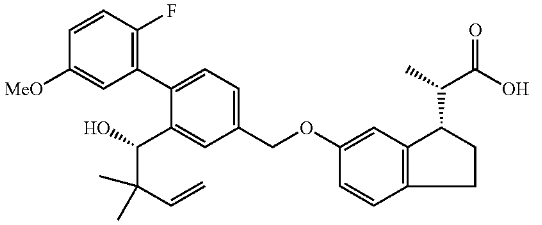

or

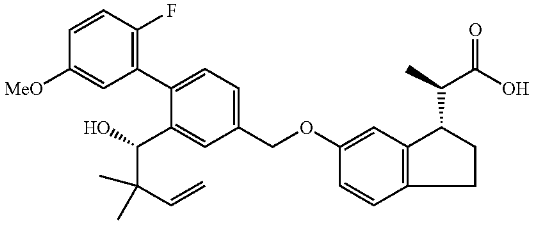

or

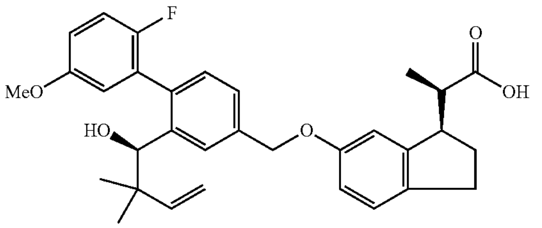

or

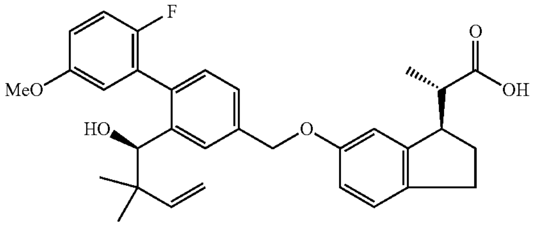

or

-continued

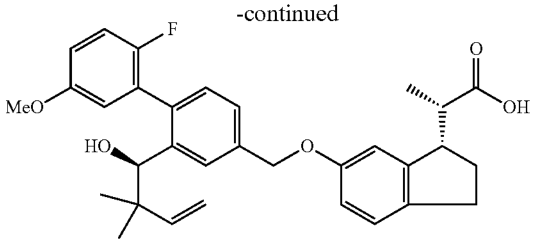

or

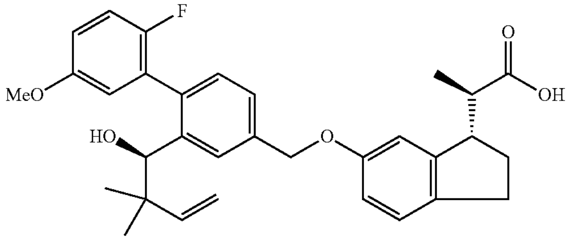

28

2-((1R)-6-(((2'-Fluoro-2-((1S)-1-hydroxy-2,2-dimethyl-3-butenyl)-5'-(methyloxy)-1,1'-biphenyl-4-yl)methyl)oxy)-2,3-dihydro-1H-inden-1-yl)propanoic acid or stereoisomer thereof (28)

The title compound was prepared from the appropriate reagents using the methods described herein. MS ESI (neg.) m/e: 517 $(M-H)^+$. $^1H$ NMR (400 MHz, CD3OD) δ ppm 7.64-7.70 (m, 1H), 7.17-7.33 (m, 1H), 7.07-7.14 (m, 3H), 6.79-6.93 (m, 4H), 5.79 (m, 1H), 5.10 (s, 2H), 4.69-4.73 (m, 2H), 4.52 (m, 1H), 3.79 (s, 3H), 3.50-3.54 (m, 1H), 2.76-2.84 (m, 3H), 2.10-2.28 (m, 1H), 1.80-1.92 (m, 1H), 1.03 (m, 3H), 0.82 (s, 3H), 0.73 (m, 3H).

Example 29

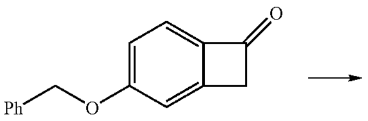

3.3

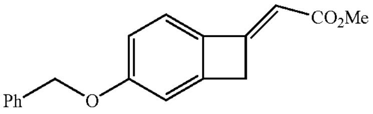

29.1

3-(Benzyloxy)-7-(2-methylperoxy)ethylidene)bicyclo[4.2.0]octa-1,3,5-triene (29.1)

At −78° C., lithium bis(trimethylsilyl)amide (1.0 M in THF) (4.2 mL, 4.2 mmol) was added slowly to a solution of methyl 2-(trimethylsilyl)acetate (4.2 mmol) in THF (6 mL). The mixture was maintained at −78° C. for 8 minutes. Ketone 3.3 (2.3 mmol) in THF (3 mL) was then added in one portion. The resulting mixture was stirred at −78° C., allowed to warm to room temperature and stirred overnight. EtOAc (300 mL) was added to the reaction mixture and the mixture was washed with water and brine and then was dried over anhydrous sodium sulfate. After removing solvent, the residue was purified by chromatography (silica gel, 1:4 EtOAc/hexane) to give 29.1 in 52% yield. MS ESI (pos.) M/E: 282 (M+1).

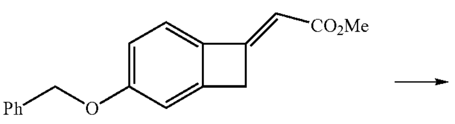

29.1

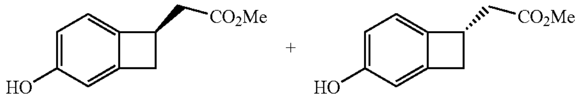

29.2 and 29.3

(7S)-7-(2-(Methylperoxy)ethyl)bicyclo[4.2.0]octa-1,3,5-trien-3-ol or (7R)-7-(2-(Methylperoxy)ethyl)bicyclo[4.2.0]octa-1,3,5-trien-3-ol (29.2 or 29.3)

Under hydrogen, a mixture of 29.1 (335 mg), Pd—C (0.042 g, 0.36 mmol) in MeOH (22 mL) was stirred for 1 hour. The resulting mixture was then filtered through silica gel to remove the solid. The filtrate was concentrated and the residue was purified by chromatography (silica gel, eluting with 1:3 EtOAc/hexane) to yield racemic product (189 mg). MS ESI (pos.) M/E: 193 (M+1). The racemic product was separated by chiral chromatography (OD-H column; 5% i-PrOH/hexane) to give 29.2 (67 mg, retention time 20.9 minutes) and 29.3 (67 mg, retention time 31.6 minutes).

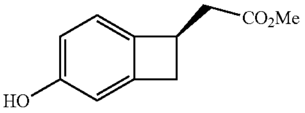

or

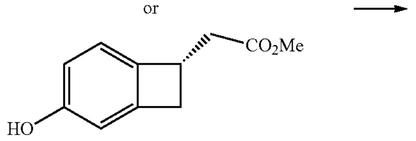

29.2

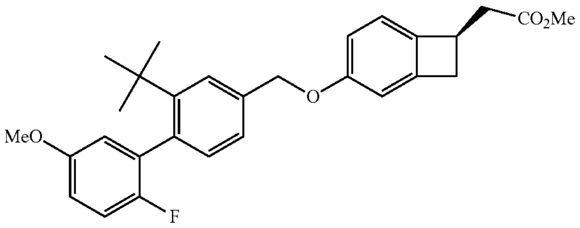

or

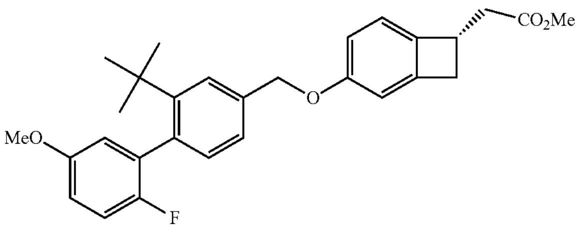

29.4

((7S)-3-((2'-Fluoro-5'-methoxy-2-(2-methyl-2-propanyl)-4-biphenylyl)methoxy)bicycle[4.2.0]octa-1,3,5-trien-7-yl)acetic acid methyl ester or ((7R)-3-((2'-fluoro-5'-methoxy-2-(2-methyl-2-propanyl)-4-biphenylyl)methoxy)bicycle[4.2.0]octa-1,3,5-trien-7-yl)acetic acid methyl ester (29.4)

The title compound was prepared from 29.2 and 4-(chloromethyl)-2-(1,1-dimethylethyl)-2'-fluoro-5'-(methyloxy)-1,1'-biphenyl (Method A) using the method described for the synthesis of 1.6.

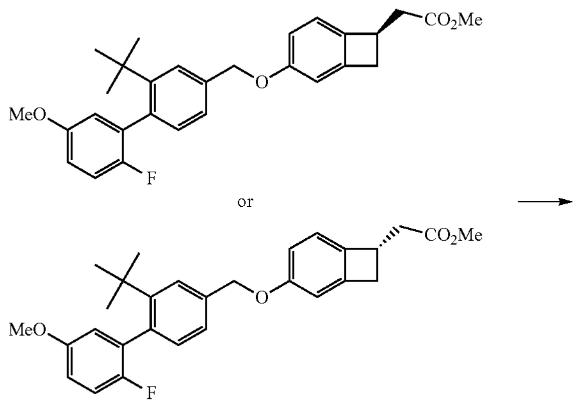

or 29.4

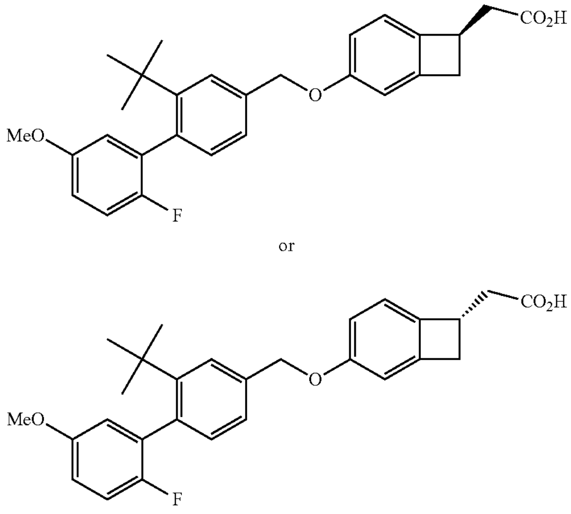

or

29

((7S)-3-((2'-Fluoro-5'-methoxy-2-(2-methyl-2-propanyl)-4-biphenylyl)methoxy)bicycle[4.2.0]octa-1,3,5-trien-7-yl)acetic acid or ((7R)-3-((2'-fluoro-5'-methoxy-2-(2-methyl-2-propanyl)-4-biphenylyl)methoxy)bicycle[4.2.0]octa-1,3,5-trien-7-yl)acetic acid (29)

The title compound was prepared from 29.4 using the method described for the synthesis of 1 from 1.6. MS ESI (neg.) m/e: 447 $(M-H)^+$. $^1H$ NMR (500 MHz, DMSO-d6) δ ppm 7.60 (m, 1H), 7.26-7.28 (m, 1H), 7.16 (m, 1H), 6.95-6.99

(m, 3H), 6.80-6.84 (m, 3H), 5.08 (s, 2H), 3.74 (s, 3H), 3.60 (m, 1H), 3.28 (m, 1H), 2.75 (m, 1H), 2.58 (m, 2H), 1.14-1.17 (m, 9H).

Example 30

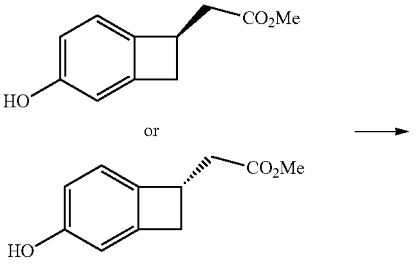

or 29.3

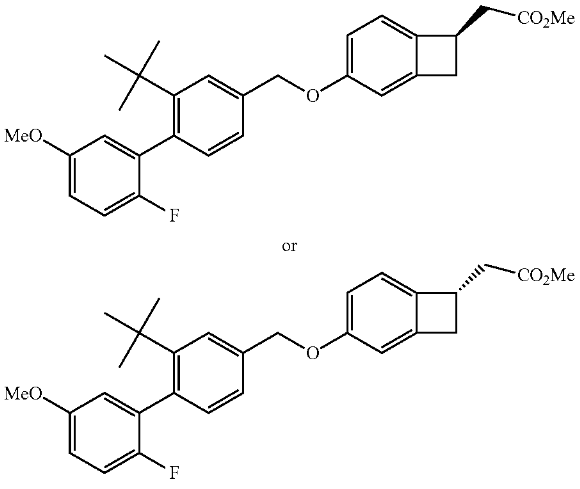

or 30.1

((7S)-3-((2'-Fluoro-5'-methoxy-2-(2-methyl-2-propanyl)-4-biphenylyl)methoxy)bicycle[4.2.0]octa-1,3,5-trien-7-yl)acetic acid methyl ester or ((7R)-3-((2'-fluoro-5'-methoxy-2-(2-methyl-2-propanyl)-4-biphenylyl)methoxy)bicycle[4.2.0]octa-1,3,5-trien-7-yl)acetic acid methyl ester (30.1)

The title compound was prepared from 29.3 and 4-(chloromethyl)-2-(1,1-dimethylethyl)-2'-fluoro-5'-(methyloxy)-1,1'-biphenyl (Method A) using the method described for the synthesis of 1.6.

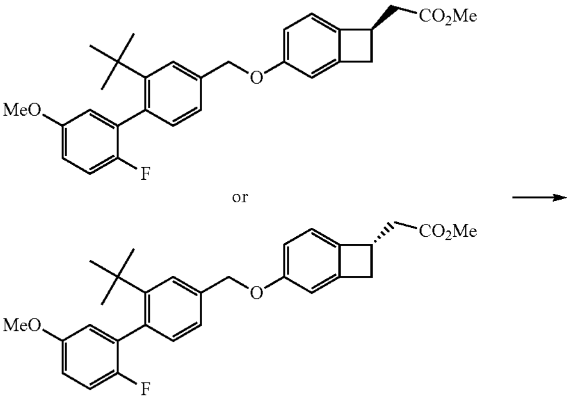

or 30.1

-continued

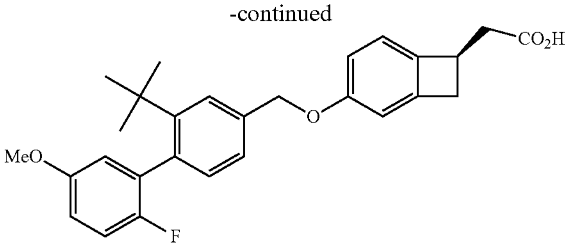

or

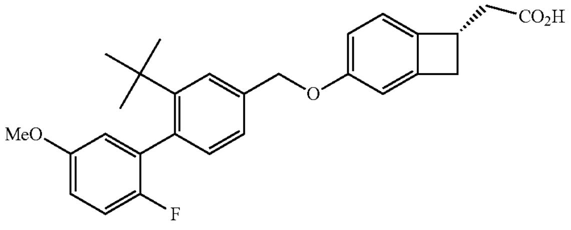

30

((7S)-3-((2'-Fluoro-5'-methoxy-2-(2-methyl-2-propanyl)-4-biphenylyl)methoxy)bicycle[4.2.0]octa-1,3,5-trien-7-yl)acetic acid or ((7R)-3-((2'-fluoro-5'-methoxy-2-(2-methyl-2-propanyl)-4-biphenylyl)methoxy) bicycle[4.2.0]octa-1,3,5-trien-7-yl)acetic acid (30)

The title compound was prepared from 30.1 using the method described for the synthesis of 1 from 1.6. MS ESI (neg.) m/e: 447 $(M-H)^-$. $^1H$ NMR (500 MHz, DMSO-d6) δ ppm 7.60 (m, 1H), 7.26-7.28 (m, 1H), 7.16 (m, 1H), 6.95-6.99 (m, 3H), 6.80-6.84 (m, 3H), 5.08 (s, 2H), 3.74 (s, 3H), 3.60 (m, 1H), 3.28 (m, 1H), 2.75 (m, 1H), 2.58 (m, 2H), 1.14-1.17 (m, 9H).

Example 31

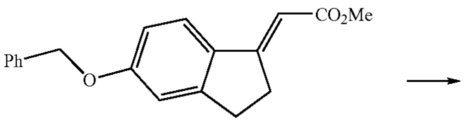

5.3

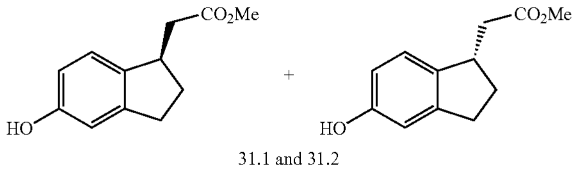

31.1 and 31.2

(R)-Methyl 2-(5-hydroxy-2,3-dihydro-1H-inden-1-yl)acetate or (S)-methyl 2-(5-hydroxy-2,3-dihydro-1H-inden-1-yl)acetate (31.1 or 31.2)

Under hydrogen, a mixture of methyl 2-(5-(benzyloxy)-2,3-dihydroinden-1-ylidene)acetate 5.3 (3.44 g, 11.7 mmol), Pd—C (1.38 g, 11.7 mmol) in MeOH (35 mL) was stirred for 3 hours. The resulting mixture was then filtered through silica gel to remove the Pd—C. After removing solvent, the residue was purified by chromatography (silica gel, 1:2 EtOAc/hexane) to give racemic product in 47% yield. The racemate was separated by chiral chromatography (column: OD, 4% IPA/hexane) to give 31.1 (0.324 g, retention time: 23.9 minutes, >99% ee) and 31.2 (0.315 g, retention time: 30.4 minutes, >99% ee).

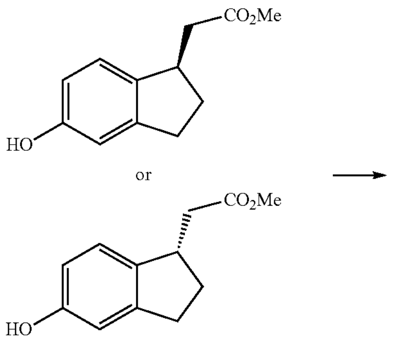

or 31.1

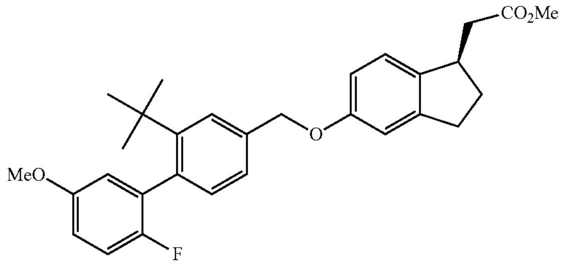

or

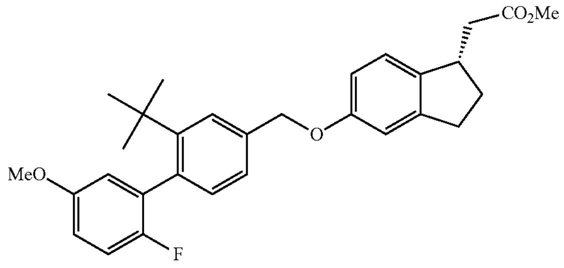

31.3

((1S)-5-((2'-Fluoro-5'-methoxy-2-(2-methyl-2-propanyl)-4-biphenylyl)methoxy)-2,3-dihydro-1H-inden-1-yl)acetic acid methyl ester or ((1R)-5-((2'-fluoro-5'-methoxy-2-(2-methyl-2-propanyl)-4-biphenylyl) methoxy)-2,3-dihydro-1H-inden-1-yl)acetic acid methyl ester (31.3)

The title compound was prepared from 31.1 and 4-(chloromethyl)-2-(1,1-dimethylethyl)-2'-fluoro-5'-(methyloxy)-1,1'-biphenyl (Method A) using the method described for the synthesis of 1.6.

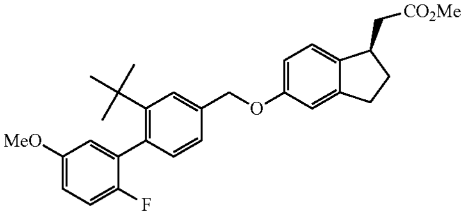

or

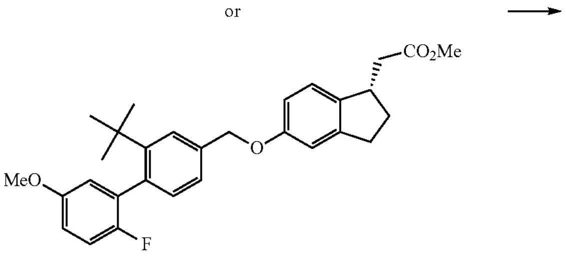

31.3

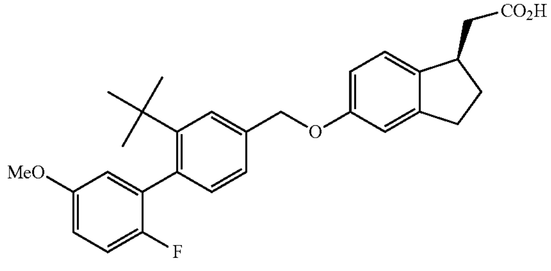

or

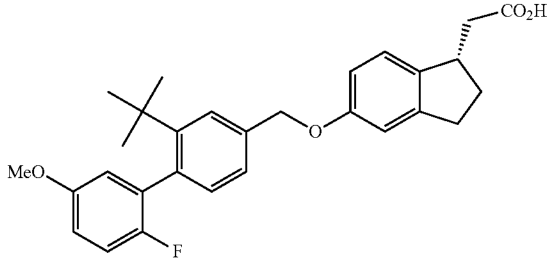

31

((1S)-5-((2'-Fluoro-5'-methoxy-2-(2-methyl-2-propanyl)-4-biphenylyl)methoxy)-2,3-dihydro-1H-inden-1-yl)acetic acid or ((1R)-5-((2'-fluoro-5'-methoxy-2-(2-methyl-2-propanyl)-4-biphenylyl)methoxy)-2,3-dihydro-1H-inden-1-yl)acetic acid (31)

The title compound was prepared from 31.3 using the method described for the synthesis of 1 from 1.6. MS ESI (neg.) m/e: 461 $(M-H)^+$. $^1H$ NMR (500 MHz, DMSO-d6) δ ppm 7.61 (m, 1H), 7.27-7.29 (m, 1H), 7.12-7.18 (m, 2H), 6.96-6.99 (m, 2H), 6.93 (m, 1H), 6.81-6.83 (m, 2H), 5.10 (s, 2H), 3.75 (s, 3H), 3.37 (m, 1H), 2.83-2.90 (m, 1H), 2.74-2.82 (m, 1H), 2.66-2.70 (m, 1H), 2.26-2.32 (m, 2H), 1.63-1.68 (m, 1H), 1.14-1.17 (m, 9H).

Example 32

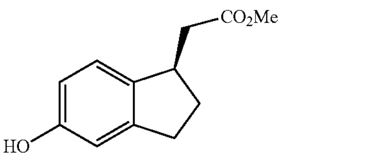

or

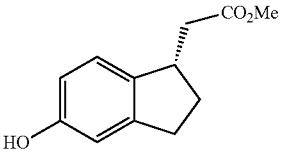

31.2

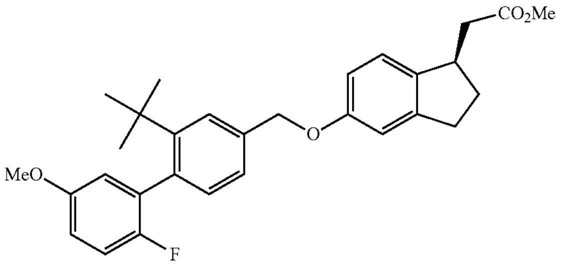

or

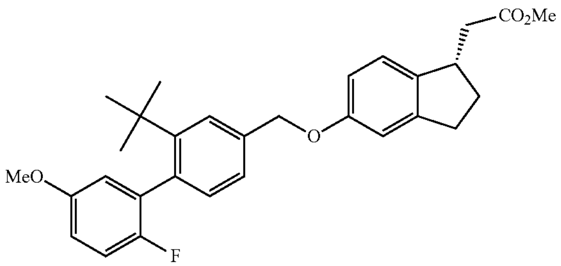

32.1

((1S)-5-((2'-Fluoro-5'-methoxy-2-(2-methyl-2-propanyl)-4-biphenylyl)methoxy)-2,3-dihydro-1H-inden-1-yl)acetic acid methyl ester or ((1R)-5-((2'-fluoro-5'-methoxy-2-(2-methyl-2-propanyl)-4-biphenylyl)methoxy)-2,3-dihydro-1H-inden-1-yl)acetic acid methyl ester (32.1)

The title compound was prepared from 31.2 and 4-(chloromethyl)-2-(1,1-dimethylethyl)-2'-fluoro-5'-(methyloxy)-1,1'-biphenyl (Method A) using the method described for the synthesis of 1.6.

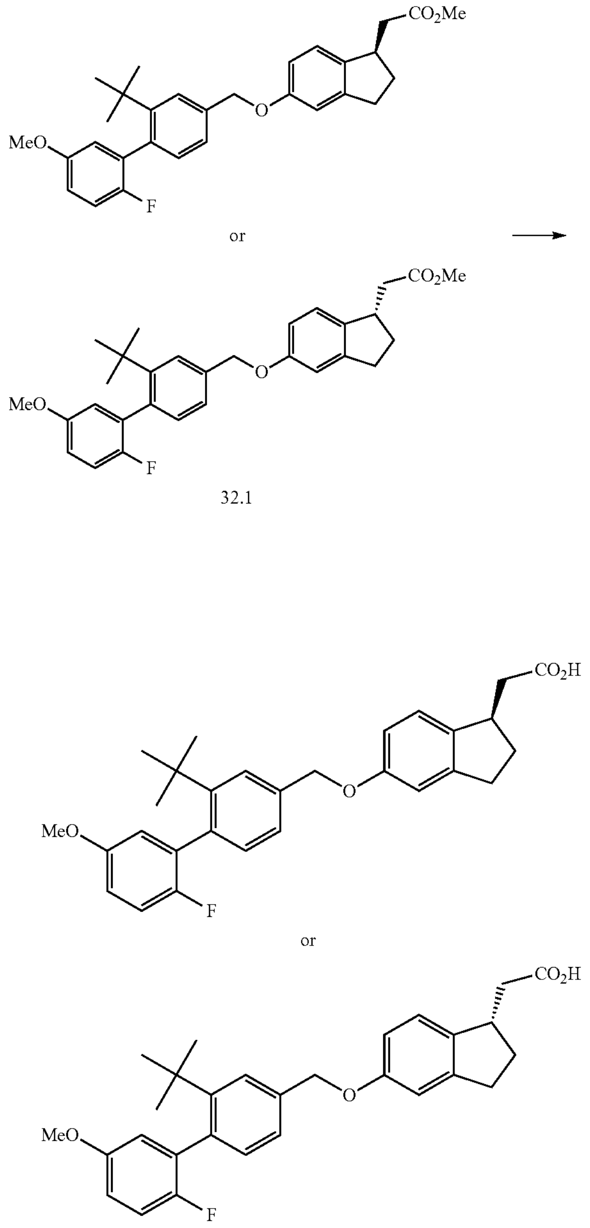

or 32.1 or

32

((1S)-5-((2'-Fluoro-5'-methoxy-2-(2-methyl-2-propanyl)-4-biphenylyl)methoxy)-2,3-dihydro-1H-inden-1-yl)acetic acid or ((1R)-5-((2'-fluoro-5'-methoxy-2-(2-methyl-2-propanyl)-4-biphenylyl)methoxy)-2,3-dihydro-1H-inden-1-yl)acetic acid (32)

The title compound was prepared from 32.1 using the method described for the synthesis of 1 from 1.6. MS ESI (neg.) m/e: 461 $(M-H)^+$. $^1H$ NMR (500 MHz, DMSO-d6) δ ppm 7.62 (m, 1H), 7.28-7.30 (m, 1H), 7.13-7.19 (m, 2H), 6.96-6.99 (m, 2H), 6.93 (m, 1H), 6.81-6.83 (m, 2H), 5.10 (s, 2H), 3.75 (s, 3H), 3.37 (m, 1H), 2.83-2.90 (m, 1H), 2.74-2.82 (m, 1H), 2.66-2.70 (m, 1H), 2.27-2.32 (m, 2H), 1.64-1.71 (m, 1H), 1.15-1.18 (m, 9H).

Example 33

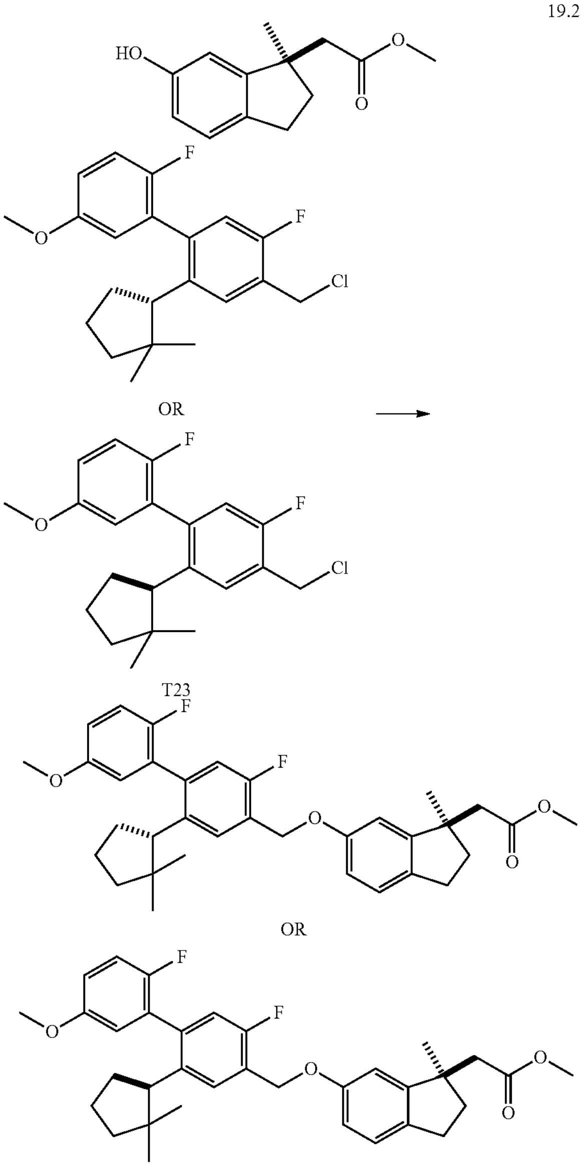

19.2

OR

T23

OR 33.1

Methyl ((1R)-6-((2-((1S)-2,2-dimethylcyclopentyl)-2',5-difluoro-5'-methoxy-4-biphenylyl)methoxy)-1-methyl-2,3-dihydro-1H-inden-1-yl)acetate or Methyl ((1R)-6-((2-((1R)-2,2-dimethylcyclopentyl)-2',5-difluoro-5'-methoxy-4-biphenylyl)methoxy)-1-methyl-2,3-dihydro-1H-inden-1-yl)acetate (33.1)

To a vial containing 19.2 (0.0329 g, 0.149 mmol) in dry DMF (1.00 mL) was added cesium carbonate (0.0607 g, 0.186 mmol). The mixture was stirred at 23° C. for 10 minutes, then T23 (0.0611 g, 0.167 mmol) was added. After 18 hours, the reaction was diluted with water and then was extracted five times with EtOAc. The combined organic extracts were then washed one time with brine and dried over anhydrous magnesium sulfate. The solid was filtered off, and the solvent was concentrated. The residue was purified with silica gel chromatography 0-15% EtOAc in hexanes to yield a film of compound 33.1 (0.0743 g, 0.135 mmol, 91% yield). $^1$H NMR (500 MHz, $CDCl_3$) δ ppm 7.53 (1H, m), 7.15 (3H, m), 6.90 (4H, m), 5.23 (2H, m), 3.81 (3H, s), 3.66 (3H, s), 2.96 (2H, m), 2.78 (1H, ddd, J=10.4, 8.2, 2.0 Hz), 2.65 (1H, m), 2.56 (1H, m), 2.36 (1H, m), 2.06 (2H, m), 1.85 (1H, m), 1.71 (1H, m), 1.50 (1H, ddd, J=12.7, 8.3, 4.4 Hz), 1.41 (4H, m), 0.69 (3H, m), 0.60 (1H, s), 0.56 (2H, s).

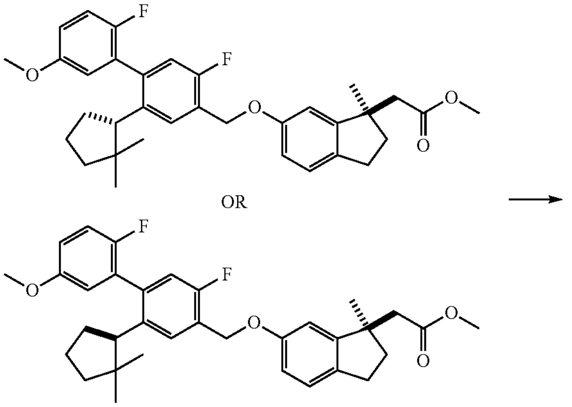

OR 33.1

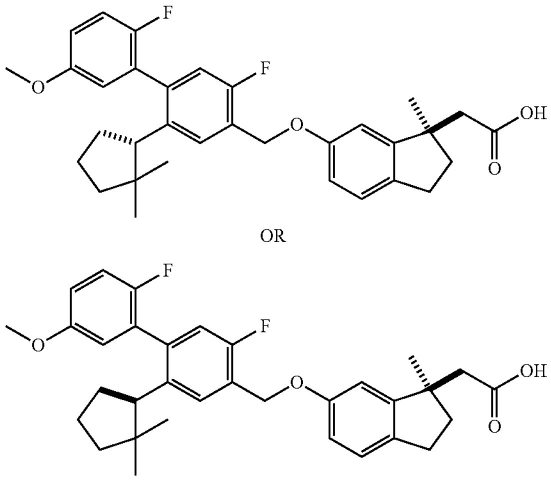

OR

33

((1R)-6-((2-((1S)-2,2-Dimethylcyclopentyl)-2',5-difluoro-5'-methoxy-4-biphenylyl)methoxy)-1-methyl-2,3-dihydro-1H-inden-1-yl)acetic acid or ((1R)-6-((2-((1R)-2,2-dimethylcyclopentyl)-2',5-difluoro-5'-methoxy-4-biphenylyl)methoxy)-1-methyl-2,3-dihydro-1H-inden-1-yl)acetic acid (33)

A pre-mixed solution of 2M sodium hydroxide (0.50 mL, 1.00 mmol), THF (1.00 mL), and MeOH (1.00 mL) was added to a vial containing 33.1 (0.0743 g, 0.135 mmol). The resulting solution was stirred at 23° C. and monitored with TLC and LC-MS. After 24 hours, the mixture was diluted with water and acidified with 1M aqueous HCl solution. The resulting mixture was then extracted five times with EtOAc. The combined organic layers were dried over anhydrous magnesium sulfate, filtered and concentrated. The residue was purified with silica gel chromatography 0-95% EtOAc in hexanes to yield a film of compound 33 (0.0666 g, 0.125 mmol, 92% yield). $^1$H NMR (400 MHz, $CDCl_3$) δ ppm 7.56 (1H, m), 7.19 (3H, m), 6.91 (3H, m), 6.78 (1H, dd, J=5.9, 3.1 Hz), 5.27 (2H, m), 3.81 (3H, s), 2.98 (2H, m), 2.84 (1H, m), 2.72 (1H, m), 2.61 (1H, m), 2.35 (1H, dt, J=13.4, 6.8 Hz), 2.20 (3H, m), 1.87 (2H, m), 1.51 (1H, qd, J=8.3, 3.7 Hz), 1.44 (4H, m), 0.73 (6H, m). MS ESI (neg.) m/e: 533.2 (M−H)$^+$.

Example 34

19.2

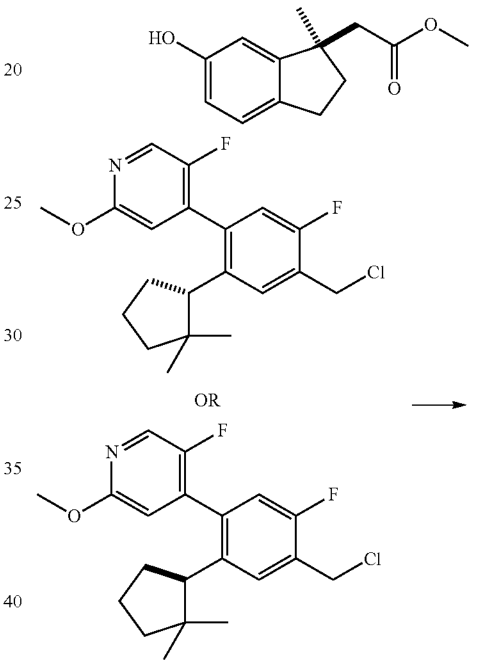

OR

T38.3

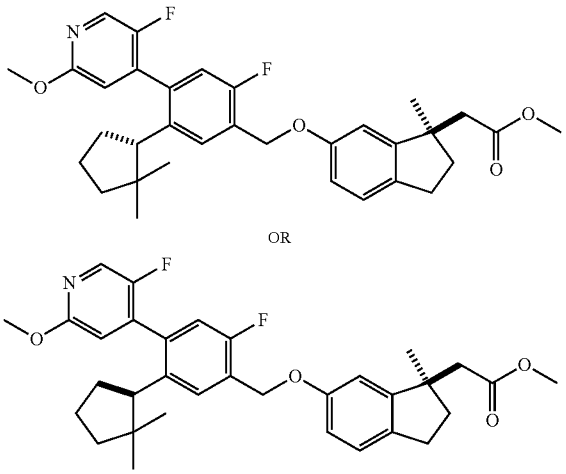

OR 34.1

Methyl ((1R)-6-((5-((1S)-2,2-dimethylcyclopentyl)-2-fluoro-4-(5-fluoro-2-methoxy-4-pyridinyl)benzyl)oxy)-1-methyl-2,3-dihydro-1H-inden-1-yl)acetate or methyl ((1R)-6-((5-((1R)-2,2-dimethylcyclopentyl)-2-fluoro-4-(5-fluoro-2-methoxy-4-pyridinyl)benzyl)oxy)-1-methyl-2,3-dihydro-1H-inden-1-yl)acetate (34.1)

34.1 was synthesized from 19.2 and T38.3 using the procedure described in Example 33 (0.0629 g, 0.114 mmol, 86% yield). MS ESI (pos.) m/e: 550.3 (M+H)$^+$.

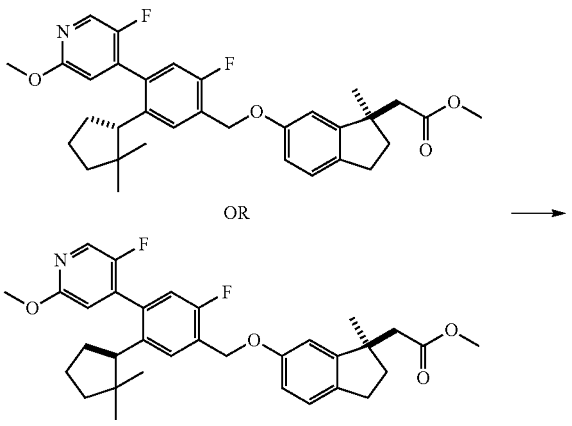

OR 34.1

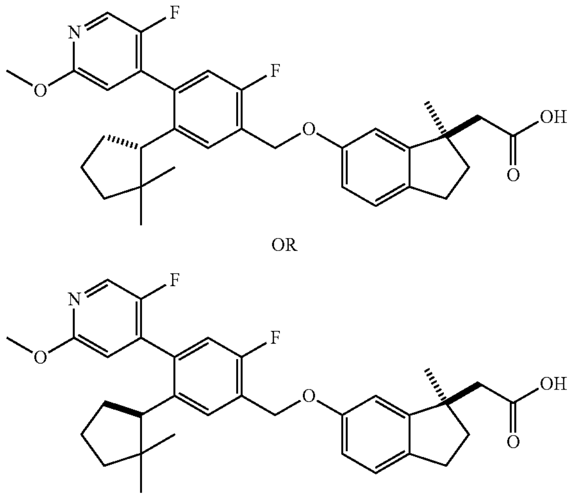

OR

34

((1R)-6-((5-((1S)-2,2-Dimethylcyclopentyl)-2-fluoro-4-(5-fluoro-2-methoxy-4-pyridinyl)benzyl)oxy)-1-methyl-2,3-dihydro-1H-inden-1-yl)acetic acid or ((1R)-6-((5-((1R)-2,2-dimethylcyclopentyl)-2-fluoro-4-(5-fluoro-2-methoxy-4-pyridinyl)benzyl)oxy)-1-methyl-2,3-dihydro-1H-inden-1-yl)acetic acid (34)

Compound 34 was synthesized from 34.1 using the procedure described in Example 33 (0.0532 g, 0.099 mmol, 87% yield). $^1$H NMR (400 MHz, $CDCl_3$) δ ppm 8.20 (1H, m), 7.51 (1H, d, J=7.0 Hz), 7.13 (1H, d, J=8.2 Hz), 6.98 (3H, m), 6.66 (1H, br. s.), 5.28 (2H, m), 3.96 (3H, s), 2.95 (2H, m), 2.74 (2H, m), 2.60 (1H, m), 2.34 (1H, ddd, J=13.2, 7.0, 6.7 Hz), 2.19 (3H, m), 1.86 (1H, m), 1.67 (1H, br. s.), 1.51 (1H, ddd, J=12.7, 8.2, 4.5 Hz), 1.44 (4H, m), 0.71 (6H, m). MS ESI (pos.) m/e: 536.2 (M+H)$^+$. MS ESI (neg.) m/e: 534.2 (M−H)$^+$.

Example 35

19.2

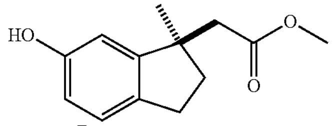

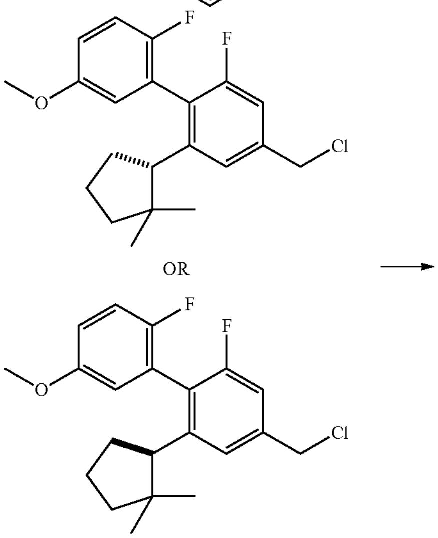

OR

T39

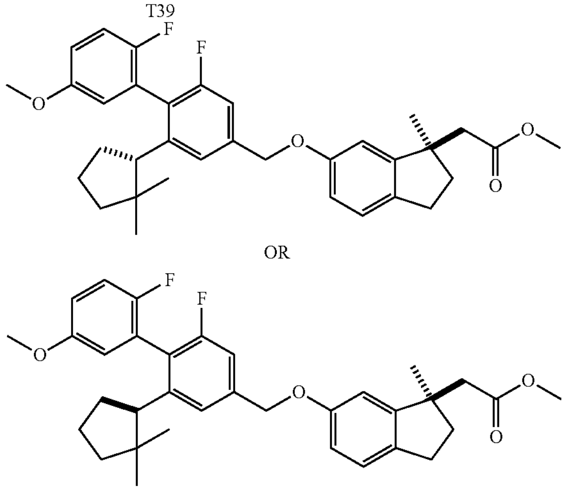

OR 35.1

Methyl ((1R)-6-((2-((1S)-2,2-dimethylcyclopentyl)-2',6-difluoro-5'-methoxy-4-biphenylyl)methoxy)-1-methyl-2,3-dihydro-1H-inden-1-yl)acetate or methyl ((1R)-6-((2-((1R)-2,2-dimethylcyclopentyl)-2',6-difluoro-5'-methoxy-4-biphenylyl)methoxy)-1-methyl-2,3-dihydro-1H-inden-1-yl)acetate (35.1)

35.1 was synthesized from 19.2 and T39 using essentially the same procedure described in Example 33 (0.0340 g, 0.062 mmol, 66.6% yield). $^1$H NMR (500 MHz, $CDCl_3$) δ ppm 7.21 (1H, s), 7.15 (2H, m), 7.10 (1H, m), 6.90 (1H, dt, J=9.0, 3.5 Hz), 6.85 (3H, m), 5.08 (2H, s), 3.83 (3H, m), 3.65 (3H, s), 2.86 (2H, t, J=6.8 Hz), 2.74 (1H, ddd, J=10.2, 8.4, 1.7 Hz), 2.64 (1H, m), 2.56 (1H, m), 2.36 (1H, m), 2.18 (1H, m), 2.03 (2H, m), 1.85 (1H, m), 1.72 (2H, m), 1.44 (4H, m), 0.75 (3H, s), 0.69 (3H, m).

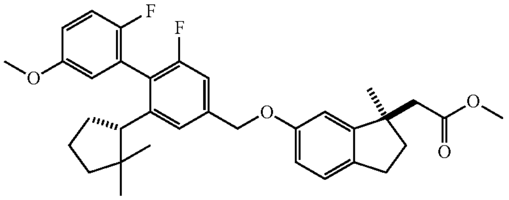

OR

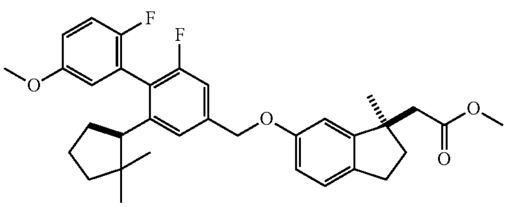

35.1

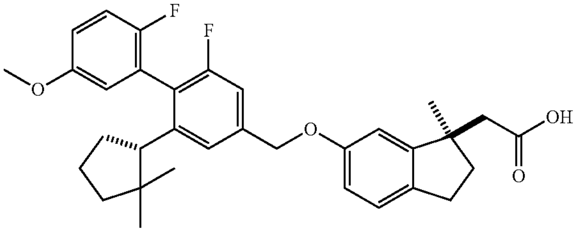

OR

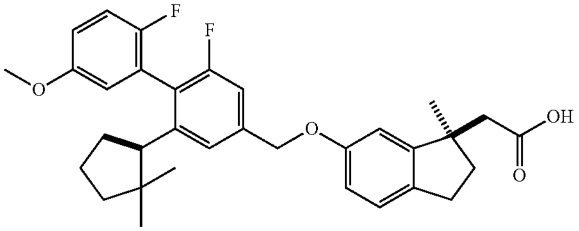

35

((1R)-6-((2-((1S)-2,2-Dimethylcyclopentyl)-2',6-difluoro-5'-methoxy-4-biphenylyl)methoxy)-1-methyl-2,3-dihydro-1H-inden-1-yl)acetic acid or ((1R)-6-((2-((1R)-2,2-dimethylcyclopentyl)-2',6-difluoro-5'-methoxy-4-biphenylyl)methoxy)-1-methyl-2,3-dihydro-1H-inden-1-yl)acetic acid (35)

Example 35 was synthesized from 35.1 using essentially the same procedure described in Example 33 (0.0326 g, 0.061 mmol, 98% yield). $^{1}H$ NMR (500 MHz, $CDCl_3$) δ ppm 7.21 (1H, s), 7.16 (2H, m), 7.10 (1H, m), 6.90 (1H, ddd, J=8.9, 3.7, 3.5 Hz), 6.86 (3H, m), 5.08 (2H, s), 3.84 (3H, m), 2.87 (2H, t, J=7.1 Hz), 2.78 (1H, m), 2.68 (1H, m), 2.60 (1H, m), 2.34 (1H, ddd, J=13.1, 6.8, 6.7 Hz), 2.18 (1H, m), 2.06 (2H, m), 1.85 (1H, m), 1.73 (1H, m), 1.54 (1H, ddd, J=12.8, 8.1, 5.0 Hz), 1.45 (4H, m), 0.75 (3H, m), 0.57-0.68 (3H, m). MS ESI (neg.) m/e: 533.2 $(M-H)^{+}$.

Example 36

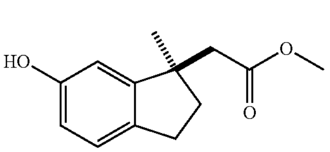

19.2

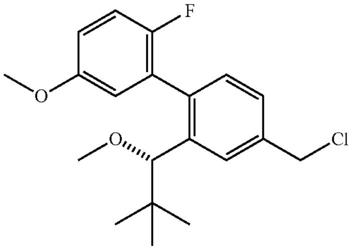

OR

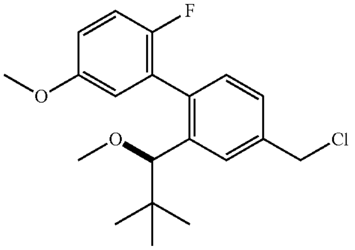

T9A or T9B

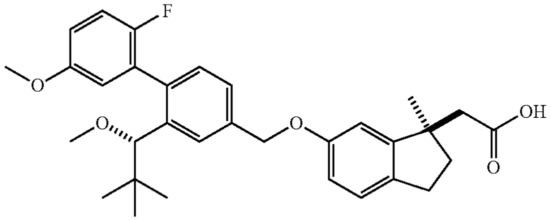

OR

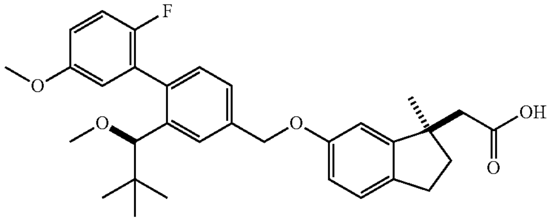

36

((1R)-6-((2'-Fluoro-5'-methoxy-2-((1S)-1-methoxy-2,2-dimethylpropyl)-4-biphenylyl)methoxy)-1-methyl-2,3-dihydro-1H-inden-1-yl)acetic acid or ((1R)-6-((2'-fluoro-5'-methoxy-2-((1R)-1-methoxy-2,2-dimethylpropyl)-4-biphenylyl)methoxy)-1-methyl-2,3-dihydro-1H-inden-1-yl)acetic acid (36)

Example 36 was synthesized from 19.2 and T9A or T9B using essentially the same procedure described in Example 24 (0.0444 g, 75% yield). MS ESI (neg.) m/e: 519.2 (M−H)$^+$.

Example 37

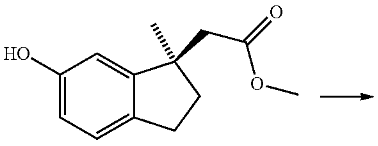

19.2

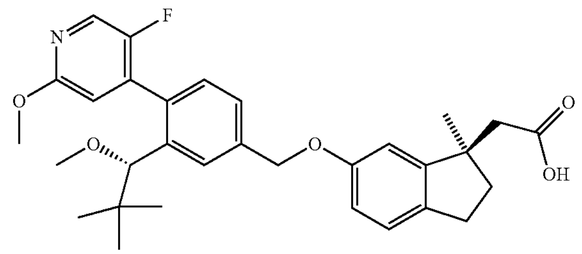

or

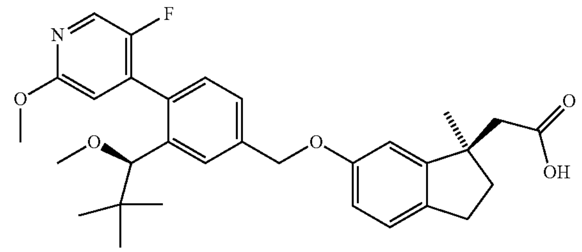

37

2-((1R)-6-(4-(5-Fluoro-2-methoxypyridin-4-yl)-3-((S)-1-methoxy-2,2-dimethylpropyl)benzyloxy)-1-methyl-2,3-dihydro-1H-inden-1-yl)acetic acid or 2-((1R)-6-(4-(5-fluoro-2-methoxypyridin-4-yl)-3-(R)-1-methoxy-2,2-dimethylpropyl)benzyloxy)-1-methyl-2,3-dihydro-1H-inden-1-yl)acetic acid (37)

The title compound was prepared from 19.2 and T37B according to methods analogous to those described for the synthesis of compound 20. $^1$H NMR (400 MHz, $CDCl_3$) δ ppm 0.58-0.81 (s, 9H), 1.39 (s, 3H), 1.91-2.09 (m, 1H), 2.34 (ddd, J=13.20, 7.04, 6.75 Hz, 1H), 2.49-2.58 (m, 1H), 2.58-2.70 (m, 1H), 2.86 (t, J=7.24 Hz, 2H), 3.28 (br. s., 3H), 3.88 (br. s., 1H), 3.96 (s, 3H), 4.13 (q, J=7.17 Hz, 1H), 5.13 (s, 2H), 6.64 (br. s., 1H), 6.79-6.87 (m, 2H), 7.12 (d, J=8.61 Hz, 1H), 7.16 (d, J=7.04 Hz, 1H), 7.47 (d, J=7.43 Hz, 1H), 7.62 (br. s., 1H), 8.06 (br. s., 1H). MS ESI (neg.) m/e: 520.9 (M−H).

Example 38

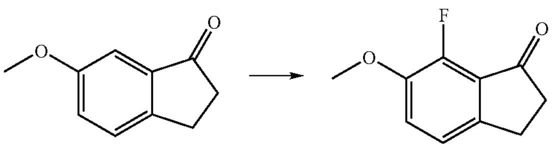

38.1

7-Fluoro-6-methoxy-indan-1-one (38.1)

A solution of Accufluor™ fluorinating reagent (6.75 g, 9.00 mmol) and 6-methoxy-indan-1-one (500 mg, 3.00 mmol) in ACN (600 mL) was heated at 80° C. for six hours. The reaction was concentrated under reduced pressure, and the residue was purified by medium pressure chromatography (silica, 10 to 25% EtOAc:hexanes) to yield 38.1. $^1$H NMR (400 MHz, $CDCl_3$) δ ppm 7.21-7.29 (m, 1H), 7.12-7.18 (m, 1H), 3.92 (s, 3H), 3.04-3.12 (m, 2H), 2.70-2.76 (m, 2H).

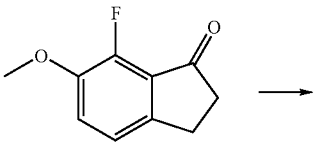

38.1

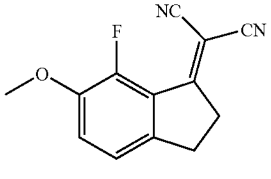

38.2

2-(7-Fluoro-6-methoxy-indan-1-ylidene)-malononitrile (38.2)

To a solution of 38.1 (740 mg, 4.13 mmol) and malononitrile (0.275 mL, 4.96 mmol) in toluene (10.0 mL), was added ammonium acetate (79.6 mg, 1.03 mmol) followed by acetic acid (0.284 mL, 4.96 mmol). The resulting mixture was heated at reflux at 140° C. with a Dean-Stark trap for 18 hours. The reaction was concentrated under reduced pressure, and the residue was purified by medium pressure chromatography to yield 38.2 (260 mg, 27% yield). MS ESI (neg.) m/e: 227.1 (M−H)$^-$.

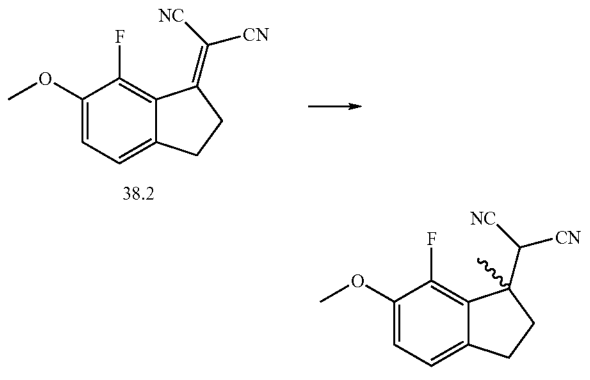

38.2

38.3

2-(7-Fluoro-6-methoxy-1-methyl-indan-1-yl)-malononitrile (38.3)

To a solution of 38.2 (260 mg, 1.1 mmol) in THF (7.0 mL) was added copper(I) iodide (260 mg, 1.4 mmol) followed by a 3.0M solution of methylmagnesium bromide in diethyl ether (0.45 mL, 1.4 mmol). The mixture was heated to reflux and stirred for one hour. The reaction was then cooled to room temperature and quenched with a saturated ammonium chloride solution. The mixture was extracted with EtOAc (2×) and the combined organic layers were dried over magnesium sulfate. The residue was purified by medium pressure chromatography (silica, 25 to 50% EtOAc:hexanes) to yield 38.3 (190 mg, 68% yield). MS ESI (neg.) m/e: 243.1 $(M-H)^-$.

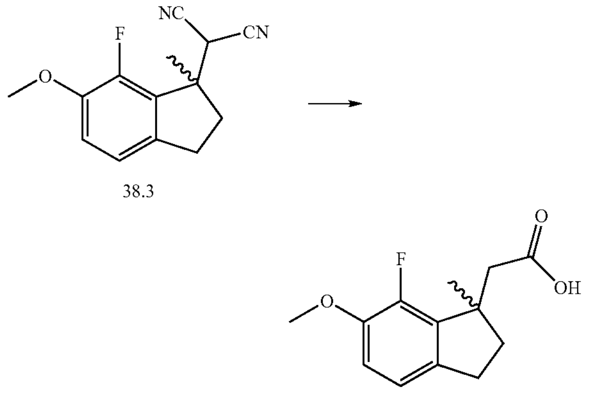

38.3

38.4

(7-Fluoro-6-methoxy-1-methyl-indan-1-yl)-acetic acid (38.4)

A solution of 38.3 (190 mg, 0.78 mmol) and potassium hydroxide (860 mg, 15 mmol) in water (0.5 mL) and ethylene glycol (1.0 mL) was heated in a sealed tube and stirred at 133° C. overnight. The reaction was cooled and then acidified with hydrochloric acid to pH ~1. The mixture was extracted with EtOAc (5×), and the combined organic layers were dried over magnesium sulfate. The filtrate was concentrated to yield crude 38.4 and taken directly to the next step. MS ESI (neg.) m/e: 237.1 $(M-H)^-$.

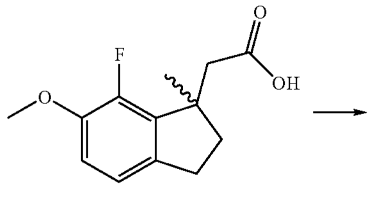

38.4

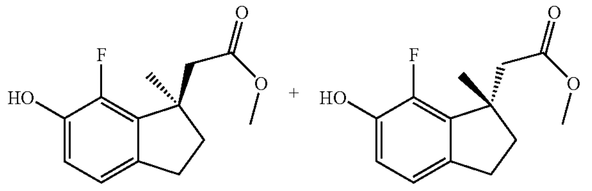

38.5 and 38.6

((R)-7-Fluoro-6-hydroxy-1-methyl-indan-1-yl)-acetic acid methyl ester and ((S)-7-Fluoro-6-hydroxy-1-methyl-indan-1-yl)-acetic acid methyl ester (38.5 and 38.6)

The racemic carboxylic acid 38.4 (180 mg, 0.77 mmol) was dissolved in MeOH (40 mL) and a catalytic amount of concentrated sulfuric acid was added. The solution was heated to reflux and stirred for 4 hours. The reaction was concentrated under reduced pressure and diluted with EtOAc, washed with water, and washed with a saturated sodium bicarbonate solution. The organic layer was dried over sodium sulfate to give the racemic (7-fluoro-6-methoxy-1-methyl-indan-1-yl)-acetic acid methyl ester (194 mg, 0.77 mmol). The racemic methyl ester was subsequently dissolved in dichloroethane (8.0 mL) and cooled to 0° C. To the solution was added ethanethiol (0.17 mL, 2.4 mmol) followed by aluminum chloride (310 mg, 2.3 mmol). The reaction mixture was then warmed to room temperature and stirred for one hour. The reaction was diluted with DCM (300 mL) and washed with saturated sodium bicarbonate solution (200 mL). The aqueous layer was extracted with DCM (3×300 mL). The combined organic layers were dried over sodium sulfate and concentrated. The residue was then passed through a plug of silica using an EtOAc:DCM mixture to give racemic 7-fluoro-6-hydroxy-1-methyl-indan-1-yl)-acetic acid methyl ester (170 mg, 93%). The racemic material was then purified by chiral HPLC (column: AD; solvent: 5% IPA/hexane) to yield 38.5 (64 mg, 38%) (retention time 30 minutes) and 38.6 (61 mg, 36%) (retention time 55 minutes). One of either 38.5 or 38.6 has the R stereochemistry at the β carbon and the other has the S stereochemistry at the β carbon. MS ESI (pos.) m/e: 239.1 $(M+H)^+$. $^1H$ NMR (400 MHz, $CDCl_3$) δ ppm 6.75-6.87 (m, 2H), 5.20 (br. s., 1H), 3.64 (s, 3H), 2.87 (t, J=7.2 Hz, 2H), 2.66-2.84 (m, 2H), 2.33 (dt, J=12.9 Hz, 7.4 Hz, 1H), 1.99 (dt, J=13.0 Hz, 7.4 Hz, 1H), 1.46 (s, 3H).

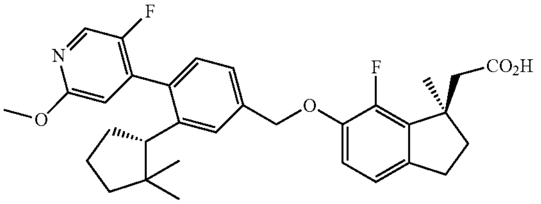

or

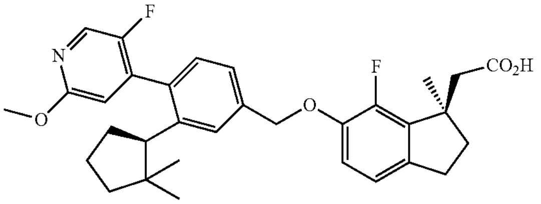

or

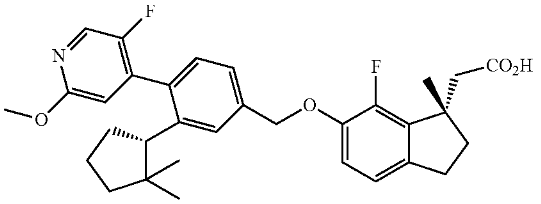

or

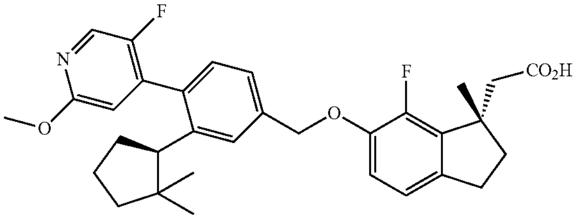

{(R)-6-[3-((S)-2,2-Dimethyl-cyclopentyl)-4-(5-fluoro-2-methoxy-pyridin-4-yl)-benzyloxy]-7-fluoro-1-methyl-indan-1-yl}-acetic acid or stereoisomer thereof (38)

The title compound was prepared from the appropriate reagents (from Example 38.5 and Method L) using the methods described herein. MS ESI (pos.) m/e: 536.2 $(M+H)^+$.

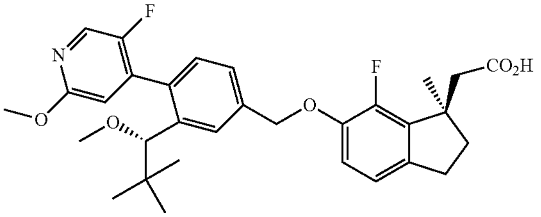

or

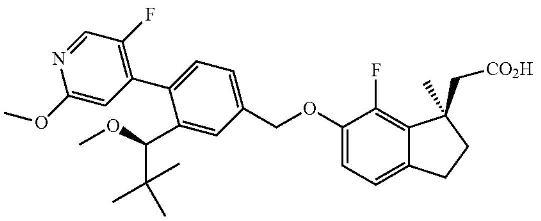

or

-continued

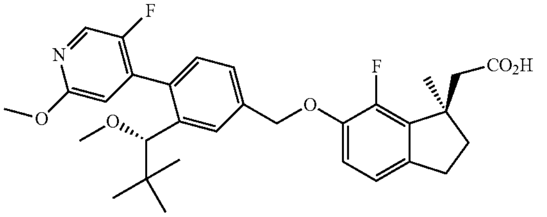

or

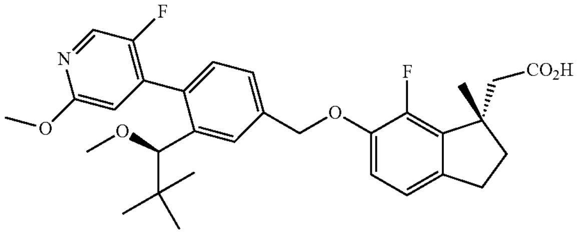

{(R)-7-Fluoro-6-[4-(5-fluoro-2-methoxy-pyridin-4-yl)-3-((S)-1-methoxy-2,2-dimethyl-propyl)-benzyloxy]-1-methyl-indan-1-yl}-acetic acid or stereoisomer thereof (39)

The title compound was prepared from the appropriate reagents (from Example 38.5 and Example T37A or T37B) using the methods described herein. MS ESI (pos.) m/e: 540.3 $(M+H)^+$.

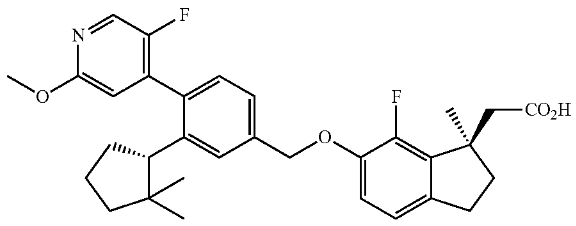

or

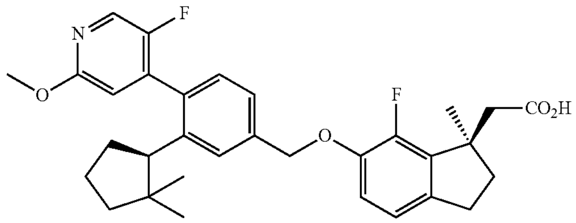

or

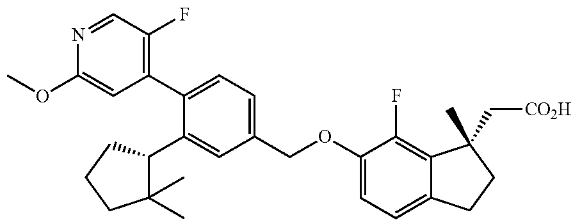

or

-continued

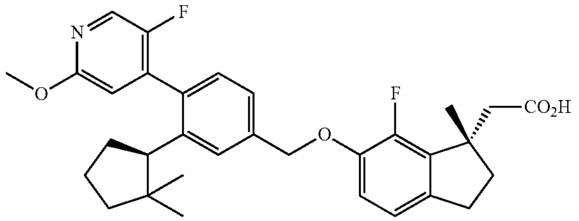

{(S)-6-[3-((S)-2,2-Dimethyl-cyclopentyl)-4-(5-fluoro-2-methoxy-pyridin-4-yl)-benzyloxy]-7-fluoro-1-methyl-indan-1-yl}-acetic acid or stereoisomer thereof (40)

The title compound was prepared from the appropriate reagents (38.6 and L) using the methods described herein. MS ESI (pos.) m/e: 536.2 $(M+H)^+$.

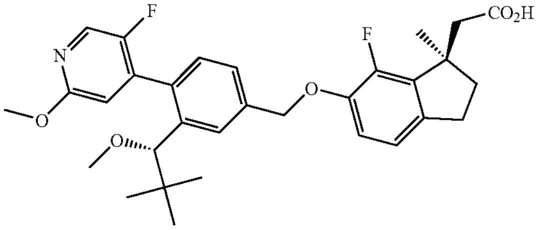

or

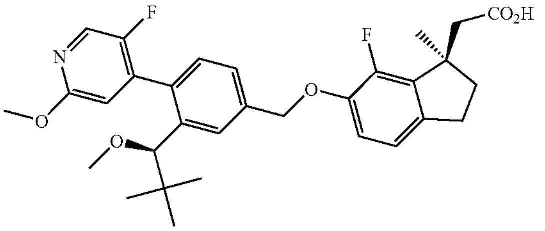

or

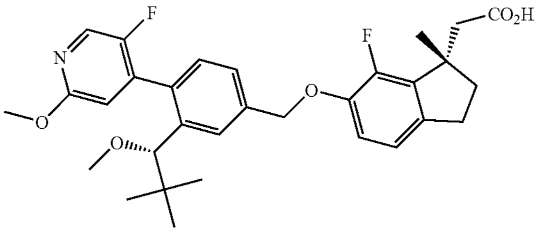

or

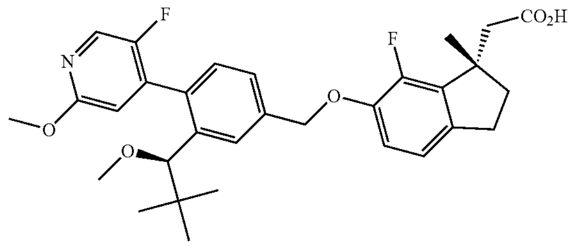

{(S)-7-Fluoro-6-[4-(5-fluoro-2-methoxy-pyridin-4-yl)-3-((S)-1-methoxy-2,2-dimethyl-propyl)-benzyloxy]-1-methyl-indan-1-yl}-acetic acid or stereoisomer thereof (41)

The title compound was prepared from the appropriate reagents (38.6 and T37A or T37B) using the methods described herein. MS ESI (pos.) m/e: 540.3 $(M+H)^+$.

Example 42

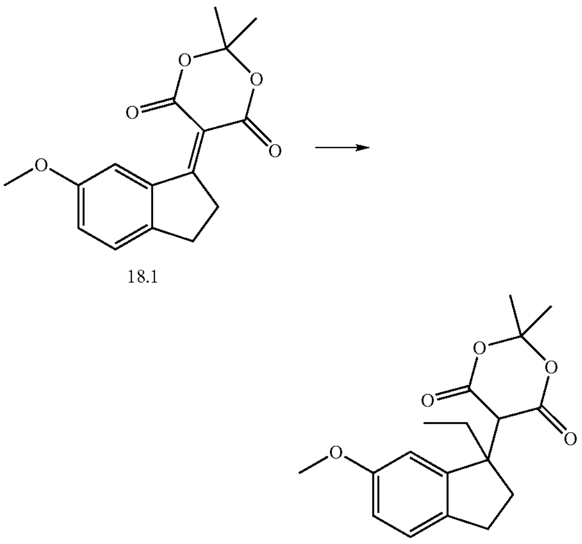

18.1

42.1

5-(1-Ethyl-6-methoxy-2,3-dihydro-1H-inden-1-yl)-2,2-dimethyl-1,3-dioxane-4,6-dione (42.1)

A 200 mL round bottom flask was charged with copper(II) trifluoromethanesulfonate (0.087 g, 0.24 mmol) and DME (12 mL), cooled to −40° C. (dry ice/acetone), and subjected to 3 cycles of evacuation/back-filling with $N_2$. To the cold solution were added diethylzinc (1.0 M solution in hexanes, commercially available from Aldrich) (12 mL, 12 mmol) and a solution of 18.1 (0.694 g, 2.4 mmol) in DME (12 mL) slowly under $N_2$. The mixture was warmed to room temperature and stirred for 2 days. The reaction was carefully quenched with 1 N HCl (15 mL) and diluted with EtOAc. The organic layer was washed with water and brine, dried ($MgSO_4$) and concentrated. The residue was purified by silica gel flash chromatography (0-30% EtOAc/hexanes) to afford 42.1 (0.31 g, 40% yield) as a yellow oil.

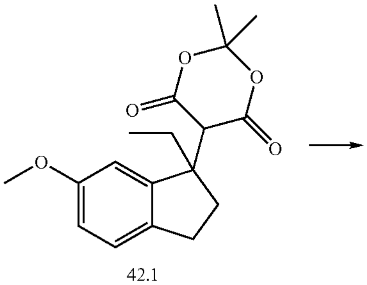

42.1

-continued

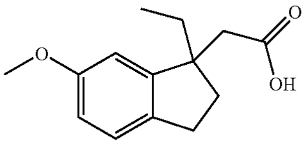

42.2

2-(1-Ethyl-6-methoxy-2,3-dihydro-1H-inden-1-yl) acetic acid (42.2)

A 100 mL round bottom flask was charged with 42.1 (0.30 g, 0.94 mmol) and 10:1 DMF/water (5 mL). The solution was stirred overnight at 90° C., cooled to room temperature, and diluted with EtOAc. The organic layer was washed with water and brine, dried ($MgSO_4$) and concentrated. The residue was purified by silica gel flash chromatography (0-30% EtOAc/hexanes) to afford 42.2 (0.204 g, 92% yield) as a yellow oil.

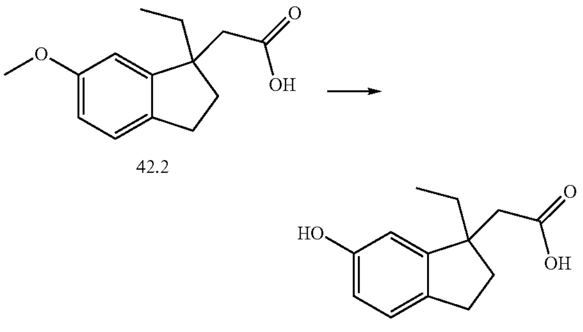

42.2

42.3

2-(1-Ethyl-6-hydroxy-2,3-dihydro-1H-inden-1-yl) acetic acid (42.3)

A screw-cap vial was charged with 42.2 (0.195 g, 0.832 mmol), NMP (0.8 mL), sodium hydroxide (0.150 g, 3.75 mmol), and 1-dodecanethiol (available from Aldrich) (0.699 mL, 2.91 mmol). The mixture was stirred overnight at 125° C. (sealed vial) and cooled to room temperature. Additional NMP (0.8 mL), sodium hydroxide (0.150 g, 3.75 mmol), and 1-dodecanethiol (0.699 mL, 2.91 mmol) were added, and the mixture was stirred for 72 hours at 125° C. and cooled to room temperature. The solidified mixture was fractured with a spatula, diluted with 1 N HCl, and extracted with EtOAc. The combined organic layers were washed with water and brine, dried ($MgSO_4$), and concentrated. The residue was purified by silica gel flash chromatography (20-50% EtOAc/hexanes) to afford 42.3 (0.119 g, 65% yield) as a brown oil.

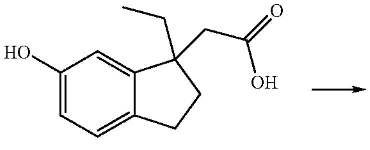

42.3

-continued

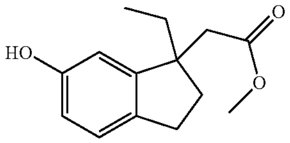

42.4

Methyl 2-(1-ethyl-6-hydroxy-2,3-dihydro-1H-inden-1-yl)acetate (42.4)

A 25 mL conical flask was charged with 42.3 (0.11 g, 0.50 mmol) and 10:1 DCM/MeOH (5 mL). To the orange solution was added (trimethylsilyl)diazomethane (2.0 M solution in diethyl ether, commercially available from Aldrich) (0.30 mL, 0.60 mmol) dropwise (vigorous gas evolution). The resulting solution was stirred for 15 minutes at room temperature, quenched with acetic acid (0.029 mL, 0.50 mmol), and concentrated. The residue was purified by silica gel flash chromatography (0-30% EtOAc/hexanes) to afford 42.4 (0.104 g, 89% yield) as a yellow oil.

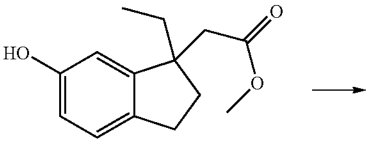

42.4

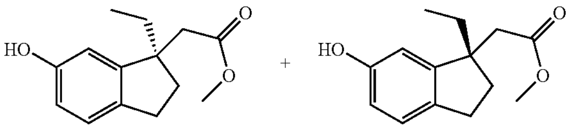

42.5 and 42.6

(R)-Methyl 2-(1-ethyl-6-hydroxy-2,3-dihydro-1H-inden-1-yl)acetate or (S)-methyl 2-(1-ethyl-6-hydroxy-2,3-dihydro-1H-inden-1-yl)acetate and (S)-methyl 2-(1-ethyl-6-hydroxy-2,3-dihydro-1H-inden-1-yl)acetate (42.5 and 42.6)

Racemic 42.4 (0.10 g, 0.43 mmol) was resolved by chiral HPLC (Chiralcel OJ column, isocratic elution with 8% IPA/hexanes, detection at 220 nm) to afford (in order of elution) 42.5 (0.045 g, 90% yield, >99% e.e.) and 42.6 (0.047 g, 94% yield, >99% e.e.) as yellow oils. 42.5 was the first eluting enantiomer; 42.6 was the second eluting enantiomer.

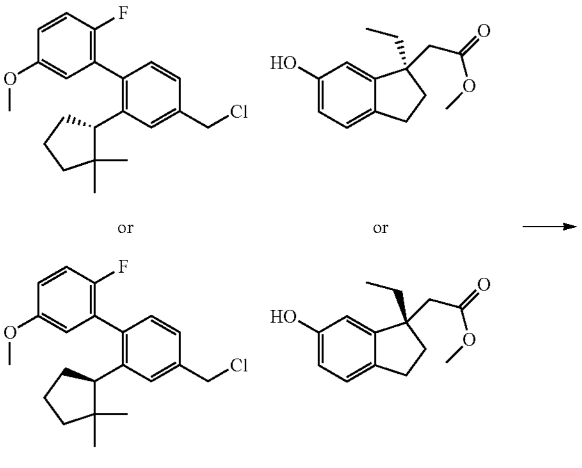

or or

C 42.5

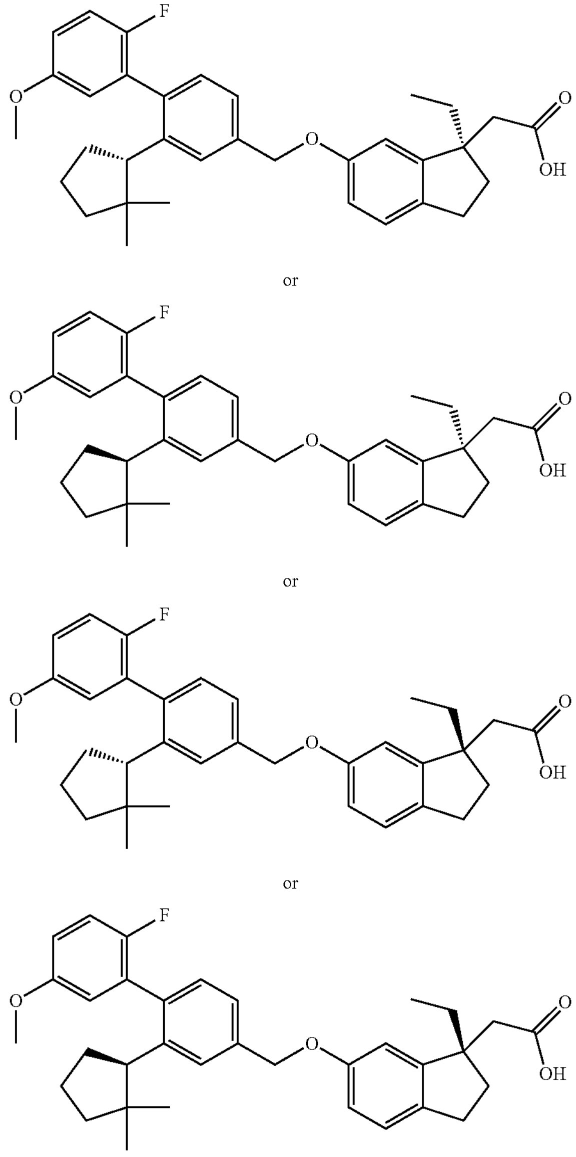

or or or

42

2-((1R)-6-((2-((S)-2,2-Dimethylcyclopentyl)-2'-fluoro-5'-methoxybiphenyl-4-yl)methoxy)-1-ethyl-2,3-dihydro-1H-inden-1-yl)acetic acid or 2-((1R)-6-((2-((R)-2,2-dimethylcyclopentyl)-2'-fluoro-5'-methoxybiphenyl-4-yl)methoxy)-1-ethyl-2,3-dihydro-1H-inden-1-yl)acetic acid or 2-((1S)-6-((2-((S)-2,2-dimethylcyclopentyl)-2'-fluoro-5'-methoxybiphenyl-4-yl)methoxy)-1-ethyl-2,3-dihydro-1H-inden-1-yl)acetic acid or 2-((1S)-6-((2-((R)-2,2-dimethylcyclopentyl)-2'-fluoro-5'-methoxybiphenyl-4-yl)methoxy)-1-ethyl-2,3-dihydro-1H-inden-1-yl)acetic acid (42)

A screw-cap vial was charged with 42.5 (0.013 g, 0.055 mmol), C (0.021 g, 0.061 mmol), DMF (1 mL), and cesium carbonate (0.027 g, 0.083 mmol). The mixture was stirred overnight at room temperature, diluted with water, and extracted with EtOAc. The combined organic layers were dried ($MgSO_4$), concentrated, and chromatographed on silica gel (0-10% EtOAc/hexanes) to afford a colorless oil. The oil thus obtained was dissolved in 2:1 THF/MeOH (1.5 mL) and treated with 1 N LiOH (0.500 mL, 0.50 mmol). The mixture was stirred overnight at 45° C., concentrated, quenched with a slight excess of 1 N HCl (0.60 mL), and extracted with EtOAc. The combined organic layers were dried ($MgSO_4$) and concentrated to afford 42 (0.0208 g, 71% yield) as a white solid. MS ESI (neg.) m/e: 529.3 (M−H).

Example 43

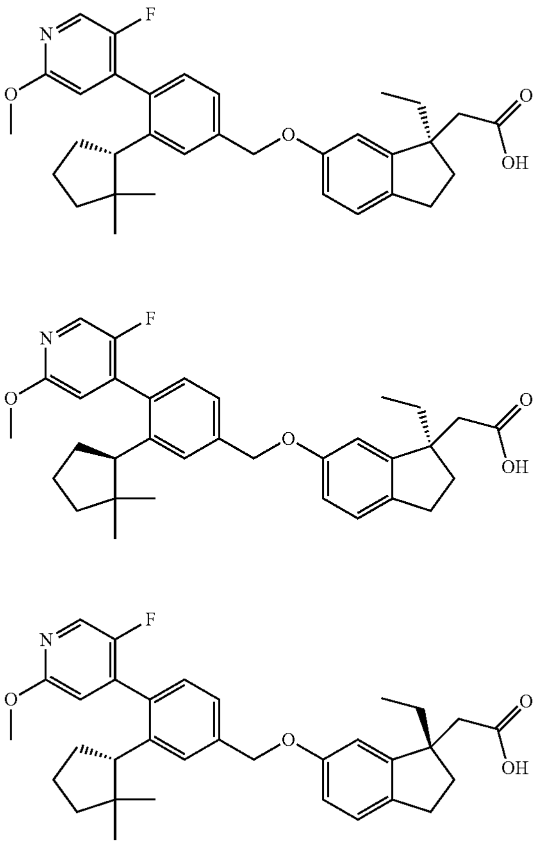

or or or

-continued

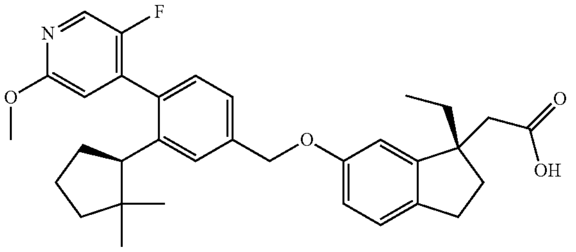

43

2-((1R)-6-(3-((S)-2,2-Dimethylcyclopentyl)-4-(5-fluoro-2-methoxypyridin-4-yl)benzyloxy)-1-ethyl-2,3-dihydro-1H-inden-1-yl)acetic acid or 2-((1R)-6-(3-((R)-2,2-dimethylcyclopentyl)-4-(5-fluoro-2-methoxypyridin-4-yl)benzyloxy)-1-ethyl-2,3-dihydro-1H-inden-1-yl)acetic acid or 2-((1S)-6-(3-((S)-2,2-dimethylcyclopentyl)-4-(5-fluoro-2-methoxypyridin-4-yl)benzyloxy)-1-ethyl-2,3-dihydro-1H-inden-1-yl)acetic acid or 2-((1S)-6-(3-((R)-2,2-dimethylcyclopentyl)-4-(5-fluoro-2-methoxypyridin-4-yl)benzyloxy)-1-ethyl-2,3-dihydro-1H-inden-1-yl)acetic acid (43)

The title compound was prepared from 42.5 and L according to the analogous methods described for the synthesis of compound 42. MS ESI (neg.) m/e: 530.3 (M−H).

Example 44

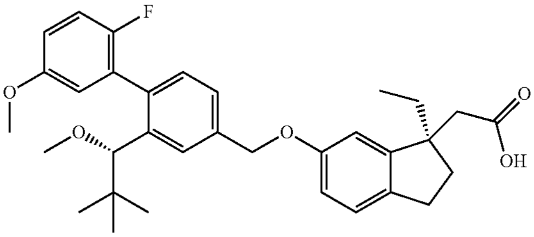

or

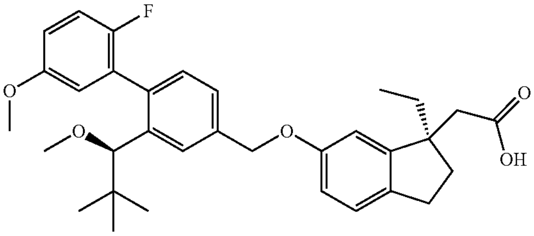

or

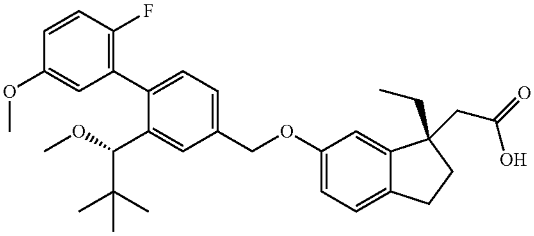

or

-continued

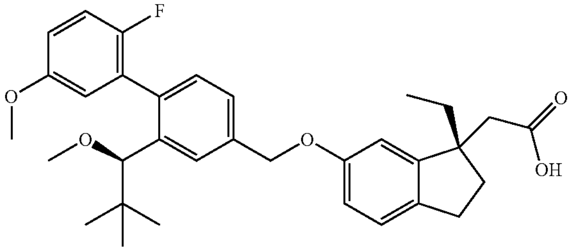

44

2-((1R)-1-Ethyl-6-((2'-fluoro-5'-methoxy-2-((S)-1-methoxy-2,2-dimethylpropyl)biphenyl-4-yl)methoxy)-2,3-dihydro-1H-inden-1-yl)acetic acid or 2-((1R)-1-ethyl-6-((2'-fluoro-5'-methoxy-2-((R)-1-methoxy-2,2-dimethylpropyl)biphenyl-4-yl)methoxy)-2,3-dihydro-1H-inden-1-yl)acetic acid or 2-((1S)-1-ethyl-6-((2'-fluoro-5'-methoxy-2-((S)-1-methoxy-2,2-dimethylpropyl)biphenyl-4-yl)methoxy)-2,3-dihydro-1H-inden-1-yl)acetic acid or 2-((1S)-1-ethyl-6-((2'-fluoro-5'-methoxy-2-((R)-1-methoxy-2,2-dimethylpropyl)biphenyl-4-yl)methoxy)-2,3-dihydro-1H-inden-1-yl)acetic acid (44)

The title compound was prepared from 42.5 and either T9A or T9B according to the analogous methods described for the synthesis of compound 42. MS ESI (neg.) m/e: 533.3 (M−H).

Example 45

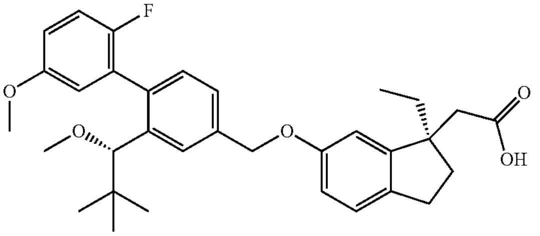

or

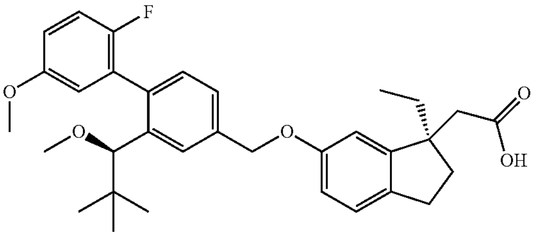

or

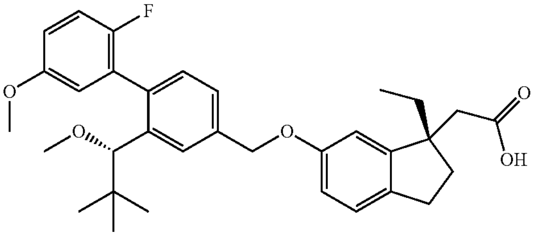

or

-continued

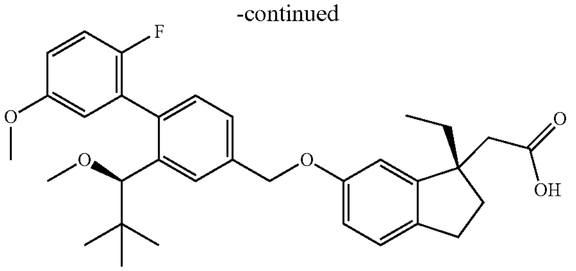

45

2-((1R)-1-Ethyl-6-((2'-fluoro-5'-methoxy-2-((S)-1-methoxy-2,2-dimethylpropyl)biphenyl-4-yl)methoxy)-2,3-dihydro-1H-inden-1-yl)acetic acid or 2-((1R)-1-ethyl-6-((2'-fluoro-5'-methoxy-2-((R)-1-methoxy-2,2-dimethylpropyl)biphenyl-4-yl)methoxy)-2,3-dihydro-1H-inden-1-yl)acetic acid or 2-((1S)-1-ethyl-6-((2'-fluoro-5'-methoxy-2-((S)-1-methoxy-2,2-dimethylpropyl)biphenyl-4-yl)methoxy)-2,3-dihydro-1H-inden-1-yl)acetic acid or 2-((1S)-1-ethyl-6-((2'-fluoro-5'-methoxy-2-((R)-1-methoxy-2,2-dimethylpropyl)biphenyl-4-yl)methoxy)-2,3-dihydro-1H-inden-1-yl)acetic acid (45)

The title compound was prepared from 42.6 and either T9A or T9B according to the analogous methods described for the synthesis of compound 42. MS ESI (neg.) m/e: 533.3 (M−H).

Example 46

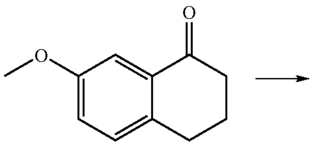

46.1

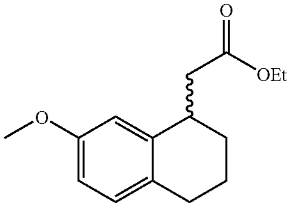

46.2

Ethyl 2-(7-methoxy-1,2,3,4-tetrahydronaphthalen-1-yl)acetate (46.2)

To a solution of 7-methoxy-3,4-dihydronaphthalen-1(2H)-one 46.1 (10.0 g, 56.7 mmol, Aldrich) and triethyl phosphonoacetate (13.6 mL, 68.1 mmol) in THF (250 mL) was added potassium tert-butoxide (1.0M solution in THF (68.1 mL, 68.1 mmol)) via addition funnel over 15 minutes. The resulting mixture was stirred at room temperature for 16 hours (LC-MS showed no difference between 15 minutes and 16 hours) after addition. The mixture was concentrated and re-suspended in hexanes (250 mL). The mixture was passed through a silica gel plug (50 g silica) and rinsed with 1 L of hexanes. The resulting mixture was concentrated to give two pure products (535 mg and 267 mg). Both products were dissolved in EtOH and stirred with Pd/C under $H_2$ for 16 hours. LC-MS showed that both gave the same desired product. The mixture was combined, filtered, and concentrated to give 46.2 (0.77 g, 5.5% yield). MS ESI (pos.) M/E: 249 (M+H).

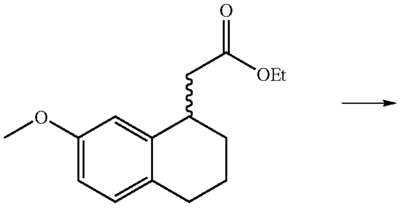

46.2

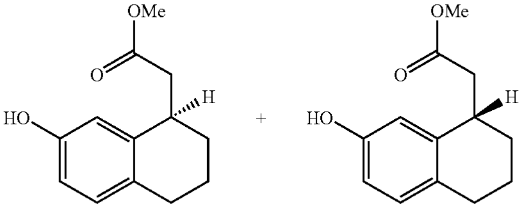

46.4 and 46.3

(S)-Methyl 2-(7-hydroxy-1,2,3,4-tetrahydronaphthalen-1-yl)acetate and (R)-methyl 2-(7-hydroxy-1,2,3,4-tetrahydronaphthalen-1-yl)acetate (46.3 and 46.4)

A 100 mL flask was charged with 46.2 (0.770 g, 3101 mmol), NMP (20 mL), sodium hydroxide (558 mg, 13954 mmol), and 1-dodecanethiol (2.60 mL, 10853 μmol). The mixture was stirred for 16 hours at 125° C., cooled to room temperature, diluted with 1N HCl (200 mL) and ether (300 mL). The organic layer was washed with water and brine, dried over $MgSO_4$, and concentrated. Column purification (10-40% EtOAc/hex) gave the desired acid (0.51 g, 80% yield). The acid was dissolved in 40 mL of benzene and 10 mL of MeOH, treated with (trimethylsilyl)diazomethane (2.0 M in diethyl ether (3.10 mL, 6202 μmol)) at room temperature for 1 hour. The resulting mixture was concentrated to give the methyl ester, which was separated on an OJ column (5 cm, 10% IPA/hex then 20% IPA/hex after the first major peak, 500 mg per injection) to give 46.4 (first peak, >99% ee, 209 mg) and 46.3 (second peak, >99% ee, 212 mg). MS ESI (pos.) M/E: 243 (M+Na).

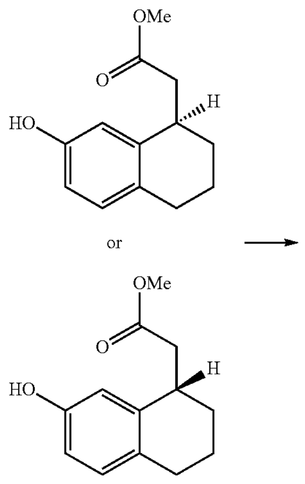

46.3

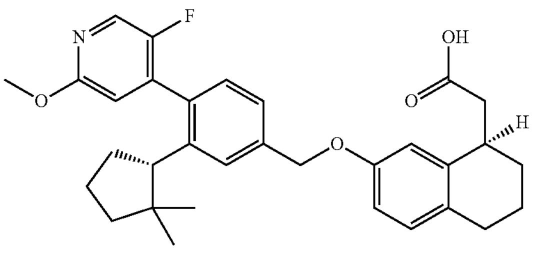

or

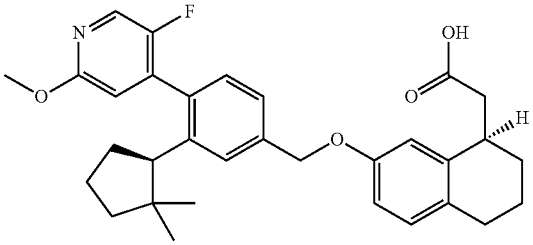

or

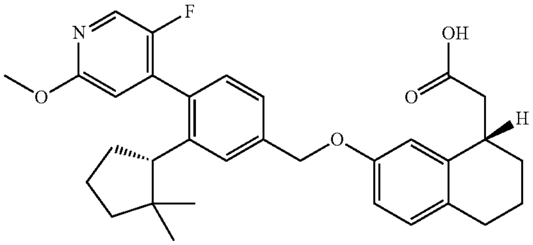

or

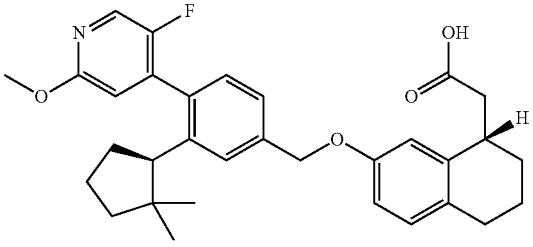

46

((1R)-7-((3-((1S)-2,2-Dimethylcyclopentyl)-4-(5-fluoro-2-methoxy-4-pyridinyl)benzyl)oxy)-1,2,3,4-tetrahydro-1-naphthalenyl)acetic acid or ((1R)-7-((3-((1R)-2,2-dimethylcyclopentyl)-4-(5-fluoro-2-methoxy-4-pyridinyl)benzyl)oxy)-1,2,3,4-tetrahydro-1-naphthalenyl)acetic acid or ((1S)-7-((3-((1S)-2,2-dimethylcyclopentyl)-4-(5-fluoro-2-methoxy-4-pyridinyl)benzyl)oxy)-1,2,3,4-tetrahydro-1-naphthalenyl)acetic acid or ((1S)-7-((3-((1R)-2,2-dimethylcyclopentyl)-4-(5-fluoro-2-methoxy-4-pyridinyl)benzyl)oxy)-1,2,3,4-tetrahydro-1-naphthalenyl)acetic acid (46)

To a stirred solution of 46.3 (13.0 mg, 0.063 mmol) and 4-(4-(chloromethyl)-2-(S)-2,2-dimethylcyclopentyl)phenyl)-5-fluoro-2-methoxypyridine L (20.0 mg, 0.057 mmol) in DMSO (1 mL) was added cesium carbonate (6.9 mg, 0.115 mmol). The resulting mixture was then stirred at 50° C. for 2 hours. After addition of 2N LiOH (0.5 mL) and MeOH (1 mL), the mixture was stirred for 15 hours at 50° C. The resulting mixture was acidified with 2N HCl (0.8 mL), diluted with ACN, filtered and purified by HPLC to give desired product 46 as the TFA salt (30.4 mg, 84% yield). MS ESI (pos.) M/E: 518 (M+H). 1H NMR (400 MHz, $CDCl_3$) δ ppm 8.06-8.12 (1H, s), 7.43-7.46 (1H, m), 7.32-7.37 (1H, m), 7.16 (1H, d, J=7.8 Hz), 7.02 (1H, d, J=9.4 Hz), 6.79-6.83 (2H, m), 6.59-6.71 (1H, m), 5.08 (2H, s), 3.97 (3H, s), 3.33 (1H, dq, J=9.9, 4.9 Hz), 2.79 (2H, br. s.), 2.57-2.91 (4H, m), 1.71-2.17 (8H, m), 1.54 (1H, ddd, J=12.7, 8.4, 4.7 Hz), 1.38-1.43 (1H, m), 0.69 (3H, br. s.), 0.57-0.66 (3H, m)

Example 47

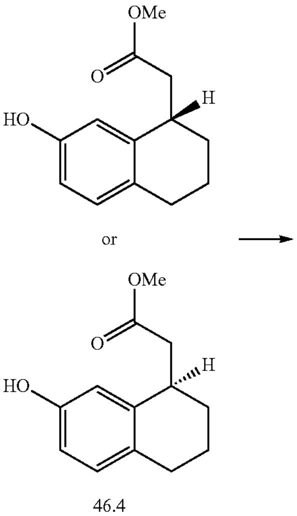

46.4

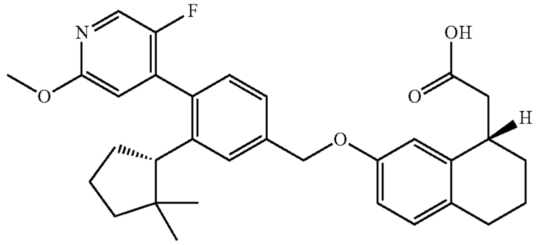

or

-continued

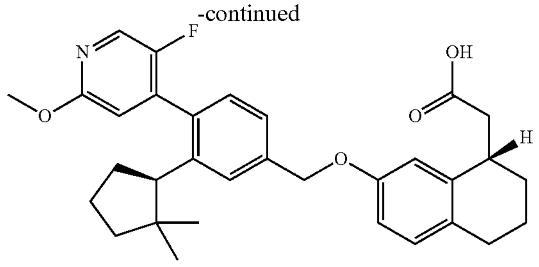

or

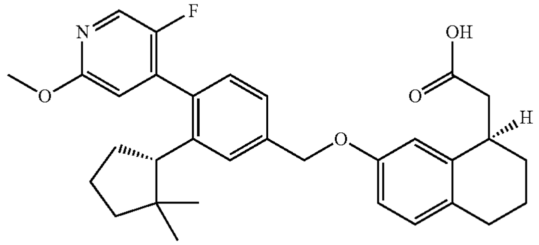

or

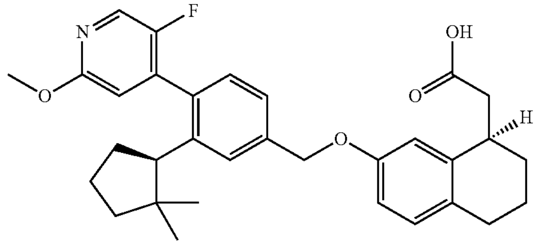

47

((1S)-7-((3-((1S)-2,2-Dimethylcyclopentyl)-4-(5-fluoro-2-methoxy-4-pyridinyl)benzyl)oxy)-1,2,3,4-tetrahydro-1-naphthalenyl)acetic acid or ((1S)-7-((3-((1R)-2,2-dimethylcyclopentyl)-4-(5-fluoro-2-methoxy-4-pyridinyl)benzyl)oxy)-1,2,3,4-tetrahydro-1-naphthalenyl)acetic acid or ((1R)-7-((3-((1S)-2,2-dimethylcyclopentyl)-4-(5-fluoro-2-methoxy-4-pyridinyl)benzyl)oxy)-1,2,3,4-tetrahydro-1-naphthalenyl)acetic acid or ((1R)-7-((3-((1R)-2,2-dimethylcyclopentyl)-4-(5-fluoro-2-methoxy-4-pyridinyl)benzyl)oxy)-1,2,3,4-tetrahydro-1-naphthalenyl)acetic acid (47)

The title compound was prepared from the 46.4 and L using the methods described for example 46. HPLC purification gave desired product 47 as the TFA salt (32.4 mg, 89% yield). MS ESI (pos.) M/E: 518 (M+H). $^1$H NMR (400 MHz, $CDCl_3$) δ ppm 8.15-8.19 (1H, m), 7.45-7.48 (1H, m), 7.34-7.38 (1H, m), 7.15-7.19 (1H, m), 7.02 (1H, d, J=9.0 Hz), 6.64-6.82 (3H, m), 5.75 (2H, br. s.), 5.10 (2H, s), 4.00 (3H, s), 3.33 (1H, dq, J=10.0, 5.0 Hz), 2.56-2.87 (4H, m), 1.69-2.22 (8H, m), 1.55 (1H, ddd, J=12.7, 8.2, 4.5 Hz), 1.36-1.45 (1H, m), 0.67 (1H, br. s), 0.59-0.63 (1H, m)

Example 48

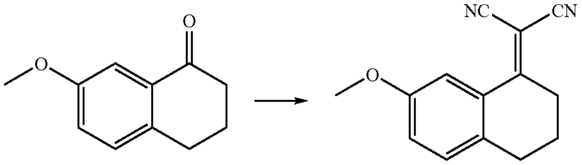

46.1

48.1

2-(7-Methoxy-3,4-dihydronaphthalen-1(2H)-ylidene)malononitrile (48.1)

To a solution of 7-methoxy-3,4-dihydronaphthalen-1(2H)-one 46.1 (10.0 g, 56.7 mmol, Aldrich) and malononitrile (4.07 mL, 64.7 mmol) in toluene (40.0 mL, 378 mmol) was added ammonium acetate (0.938 mL, 13.1 mmol) and acetic acid (3.90 mL, 68.1 mmol). The mixture was refluxed vigorously for 17 hours and water was removed using a Dean Stark trap under the reflux condenser. The resulting mixture was concentrated and purified by silica gel column chromatography to give 48.1 (9.32 g, 73.2% yield). MS ESI (pos.) M/E: 225 (M+H).

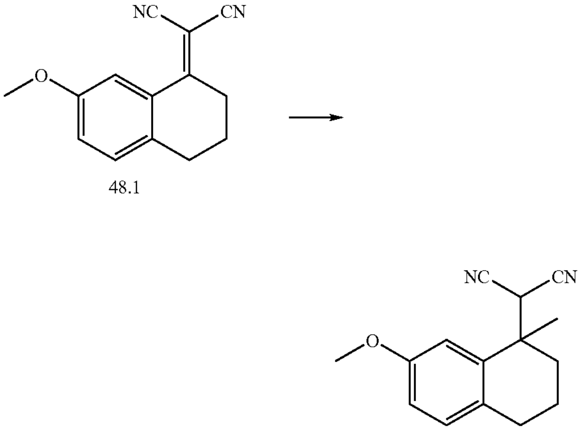

48.1

48.2

2-(7-Methoxy-1-methyl-1,2,3,4-tetrahydronaphthalen-1-yl)malononitrile (48.2)

To a solution of methylmagnesium bromide (3.0 M in diethyl ether (12.0 mL, 36.0 mmol)) and copper(I) iodide (6.86 g, 36.0 mmol) in THF (100 mL) was added 48.1 (6.73 g, 30.0 mmol) at room temperature. The resulting mixture was refluxed for 4 hours. The mixture was then cooled in an ice-bath, quenched with aqueous $NH_4Cl$ (200 mL), extracted with ether, concentrated, and purified by silica gel column chromatography to give 48.2 (4.8 g, 66% yield). MS ESI (pos.) M/E: 241 (M+H).

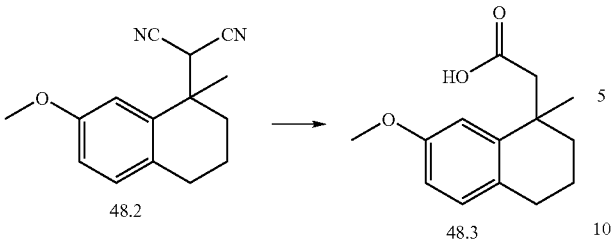

48.2

48.3

2-(7-Methoxy-1-methyl-1,2,3,4-tetrahydronaphthalen-1-yl)acetic acid (48.3)

To a solution of 48.2 (4.80 g, 20 mmol) in ethylene glycol (200 mL) was added potassium hydroxide (5.0 g, 90 mmol) at room temperature. The resulting mixture was refluxed for 4 hours. The reaction was then cooled in an ice-bath, acidified with 12N HCl, and refluxed for 4 hours. The resulting mixture was extracted with water/ether and concentrated. Column purification gave the desired di-acid, which was heated in 3 mL of ethylene glycol at 130° C. for 16 hours, cooled to room temperature, diluted with water and extracted with EtOAc. The combined extracts were washed with water and brine and then dried over $Na_2SO_4$. Removal of the solvent afforded 48.3 (2.05 g, 44% yield). MS ESI (neg.) M/E: 233 (M−H).

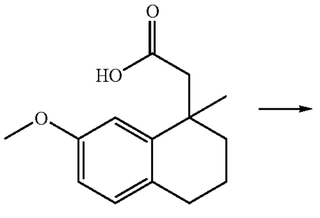

48.3

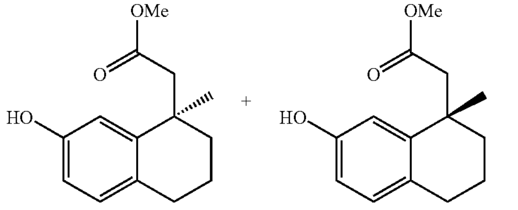

48.5 and 48.4

(R)-Methyl 2-(7-hydroxy-1-methyl-1,2,3,4-tetrahydronaphthalen-1-yl)acetate and (S)-methyl 2-(7-hydroxy-1-methyl-1,2,3,4-tetrahydronaphthalen-1-yl) acetate (48.5 and 48.4)

A 500 mL flask was charged with 48.3 (2.05 g, 8.75 mmol), NMP (50 mL), sodium hydroxide (1.57 g, 39.4 mmol) and dodecane-1-thiol (7.34 mL, 30.6 mmol). The mixture was stirred for 16 hours at 125° C., cooled to room temperature, diluted with 1 N HCl (200 mL) and ether (300 mL). The organic layer was washed with water and brine, dried ($MgSO_4$), and concentrated. Column purification (10-40% EtOAc/hex) gave the desired hydroxy compound (1.26 g, 65% yield). The hydroxy compound was dissolved in 40 mL of benzene and 10 mL of MeOH, treated with (trimethylsilyl) diazomethane, 2.0 M in diethyl ether (5.80 mL, 11.60 mmol) at room temperature for 1 hour. The resulting mixture was then concentrated to give the methyl ester, which was separated on an OJ column (5 cm, 10% IPA/hex then 20% IPA/hex after the first major peak, 500 mg per injection) to give 48.5 (first peak, >99% ee) and 48.4 (second peak, >99% ee). MS ESI (neg.) M/E: 233 (M−H).

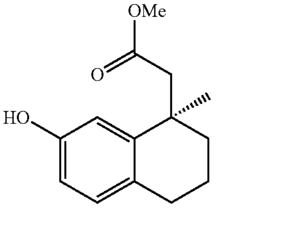

or

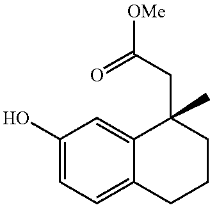

48.5

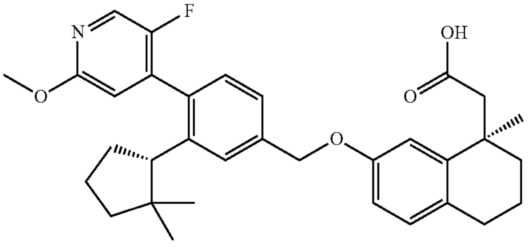

or

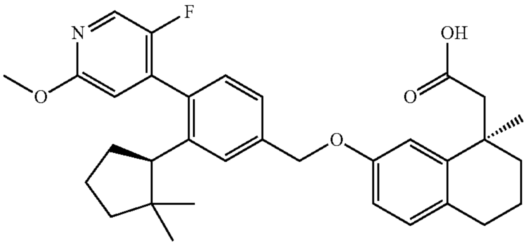

or

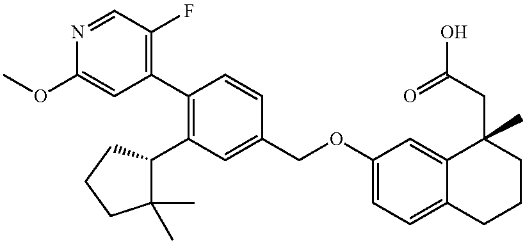

or

-continued

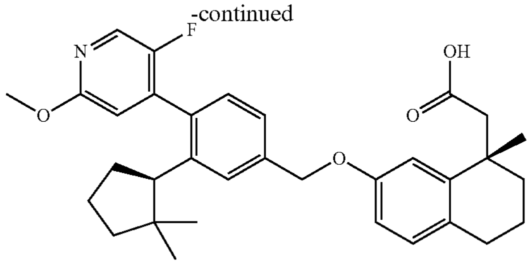

48

((1R)-7-((3-((1S)-2,2-Dimethylcyclopentyl)-4-(5-fluoro-2-methoxy-4-pyridinyl)benzyl)oxy)-1-methyl-1,2,3,4-tetrahydro-1-naphthalenyl)acetic acid or ((1R)-7-((3-((1R)-2,2-dimethylcyclopentyl)-4-(5-fluoro-2-methoxy-4-pyridinyl)benzyl)oxy)-1-methyl-1,2,3,4-tetrahydro-1-naphthalenyl)acetic acid or ((1S)-7-((3-((1S)-2,2-dimethylcyclopentyl)-4-(5-fluoro-2-methoxy-4-pyridinyl)benzyl)oxy)-1-methyl-1,2,3,4-tetrahydro-1-naphthalenyl)acetic acid or ((1S)-7-((3-((1R)-2,2-dimethylcyclopentyl)-4-(5-fluoro-2-methoxy-4-pyridinyl)benzyl)oxy)-1-methyl-1,2,3,4-tetrahydro-1-naphthalenyl)acetic acid (48)

The title compound was prepared from the 48.5 and L using the methods described for example 46. HPLC purification gave desired product 48 as the TFA salt (32.2 mg, 87% yield). MS ESI (pos.) M/E: 532 (M+H). 1H NMR (400 MHz, $CDCl_3$) δ ppm 8.12-8.17 (1H, m), 7.36-7.47 (1H, m), 7.15-7.19 (1H, m), 7.01 (1H, d, J=8.6 Hz), 6.89 (1H, d, J=2.7 Hz), 6.79 (1H, dd, J=8.2, 2.7 Hz), 6.62-6.75 (1H, m), 5.09 (2H, s), 5.06 (2H, br. s), 3.99 (3H, s), 2.61-2.90 (4H, m), 1.97-2.22 (3H, m), 1.71-1.89 (5H, m), 1.55 (1H, ddd, J=12.7, 8.2, 4.5 Hz), 1.35-1.46 (1H, m), 1.40 (3H, s), 0.68 (3H, s), 0.55-0.66 (3H, m)

Example 49

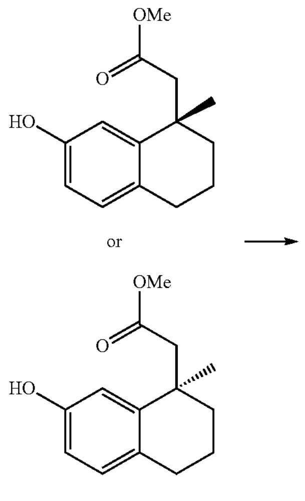
or 48.4

-continued

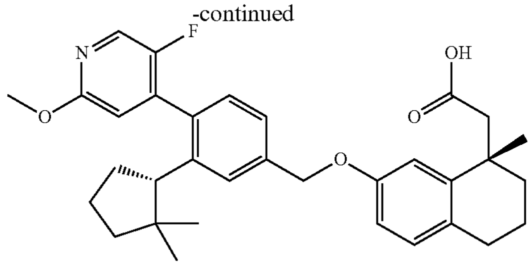

or

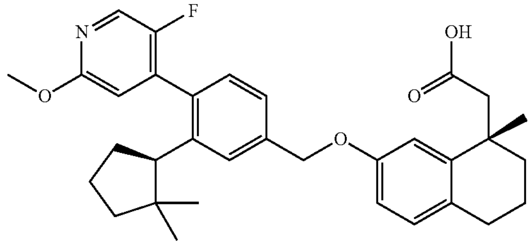

or

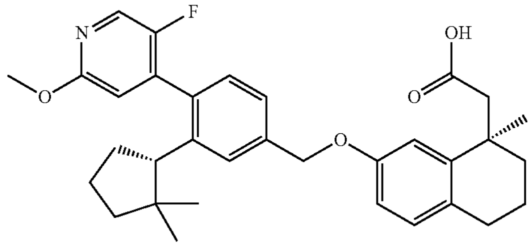

or

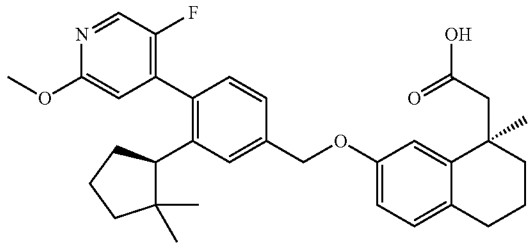

49

((1S)-7-((3-((1S)-2,2-Dimethylcyclopentyl)-4-(5-fluoro-2-methoxy-4-pyridinyl)benzyl)oxy)-1-methyl-1,2,3,4-tetrahydro-1-naphthalenyl)acetic acid or ((1S)-7-((3-((1R)-2,2-dimethylcyclopentyl)-4-(5-fluoro-2-methoxy-4-pyridinyl)benzyl)oxy)-1-methyl-1,2,3,4-tetrahydro-1-naphthalenyl)acetic acid or ((1R)-7-((3-((1S)-2,2-dimethylcyclopentyl)-4-(5-fluoro-2-methoxy-4-pyridinyl)benzyl)oxy)-1-methyl-1,2,3,4-tetrahydro-1-naphthalenyl)acetic acid or ((1R)-7-((3-((1R)-2,2-dimethylcyclopentyl)-4-(5-fluoro-2-methoxy-4-pyridinyl)benzyl)oxy)-1-methyl-1,2,3,4-tetrahydro-1-naphthalenyl)acetic acid (49)

The title compound was prepared from the 48.4 and L using the methods described for example 46. HPLC purification gave the desired product 49 as the TFA salt (36.0 mg, 97% yield). MS ESI (pos.) M/E: 532 (M+H). 1H NMR (400 MHz, $CDCl_3$) δ ppm 8.08-8.13 (1H, m), 7.42-7.48 (1H, m), 7.33-7.36 (1H, m), 7.16 (1H, m,), 7.00 (1H, d, J=8.2 Hz), 6.90

(1H, d, J=2.7 Hz), 6.78 (1H, dd, J=8.4, 2.5 Hz), 6.60-6.72 (1H, m), 5.09 (2H, s), 3.98 (3H, s), 3.28 (2H, br. s.), 2.59-2.92 (4H, m), 1.98-2.20 (3H, m), 1.64-1.88 (5H, m), 1.54 (1H, ddd, J=12.6, 8.1, 4.7 Hz), 1.35-1.46 (1H, m), 1.42 (3H, s), 0.68 (3H, s), 0.57-0.65 (3H, m)

Competition binding assays were performed on A9 membranes expressing GPR40. The membranes were incubated with different concentrations of Comparative Compound 1 and Example 1 in the presence of 5 nM [$^3$H] labeled Comparative Compound 1 for 4 hours at room temperature. [$^3$H] labeled Comparative Compound 1 was displaced completely by the unlabeled Comparative Compound 1 exhibiting homologous competition such that the unlabeled Comparative Compound 1 competes for the same site on the receptor as does the [$^3$H] labeled compound. However, surprisingly and unexpectedly, Example 1 did not displace the bound [$^3$H] labeled Comparative Compound 1. Rather, even more surprisingly, addition of Example 1 enhanced the binding of the radioligand (Comparative Compound 1) to the receptor. The non-competitive behavior displayed shows positive allostery of these compounds in the presence of Comparative Compound 1. The positive cooperativity of these compounds is greater than 1 when the receptor is bound to Comparative Compound 1. Thus, competition binding assays show that the compounds of the present invention agonists bind to a distinct site on the GPR40 receptor compared to other GPR40 agonists.

In GPR40 cell signaling assays, the compounds of the present invention displayed surprisingly enhanced activity compared with previously described GPR40 agonists. In aequorin assays, using a cell lines stably expressing GPR40, the $E_{max}$ of the compounds of the present invention was greater than that of previously described GPR40 agonists and believed to be similar to that of the GPR40 natural ligands, fatty acids. Thus, the compounds of the present invention appear to be full agonists while the previously described GPR40 compounds were partial agonists. Briefly, the Aequorin assays were performed on doubly stable CHO cells expressing GPR40 and Aequorin DNA. Ligand-induced calcium mobilization was observed as indicated by an increase in the Aequorin luminescence which is in proportion to the calcium released upon activation of the receptor. The luminescence was recorded over a period of 20 seconds with a Microlumat luminometer (Berthold). The efficacy of the compounds of the present invention was surprisingly and unexpectedly improved over Comparative Compound 1.

The enhanced activity of the compounds of the present invention will also be observed in primary cell culture experiments. Islets are isolated from rodents and insulin secretion in response to the compounds of the present invention and certain previously described GPR40 agonists is measured. More specifically, islets are isolated from the pancreas of mice using collagenase digestion followed by purification on a histopaque gradient. Islets are hand-picked and then incubated for one hour in KRBH medium containing 16.7 mM dextrose, 0.1% human serum albumin, and test compounds are diluted to a specified concentration. Insulin secreted into the culture supernatant is measured using an insulin ELISA. Dose response plots are graphed using Graphpad Prism software. The compounds of the present invention are found to secrete unexpectedly greater levels of insulin compared with the previously described GPR40 agonists. The enhanced activity of the compounds of the present invention indicates that these compounds are more effective than previously described GPR40 agonists in treating type 2 diabetes, metabolic syndrome, and other conditions where enhanced GPR40 activity may result in therapeutic utility. The structure of Comparative Compound I is shown below.

Comparative Compound 1

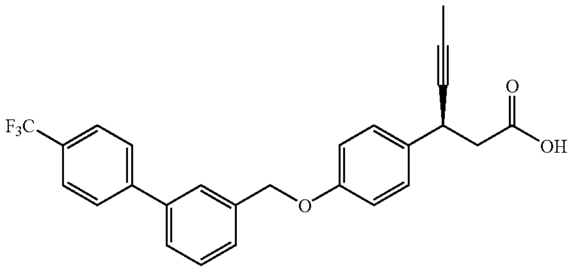

The synthesis of Comparative Compound 1 is set forth in Example 2 of US Patent Publication No. US2006/0004012 which is hereby incorporated herein by reference.

Cell-Based Aequorin Assay

Cell-based aequorin assays were employed to characterize the modulatory activity of compounds on the GPR40 signaling pathway. In an exemplary assay, CHO cells were stably transfected with both GPR40 and Aequorin (Euroscreen). Cells were detached from the tissue culture dish with 2 mL of trypsin (0.25% (w/v)). Trypsinization was halted with 28 mL of Hanks Buffered Salt Solution containing 20 mM Hepes (H/HBSS) and 0.01% fatty acid-free human serum albumin (HSA). Coelantrazine is added to 1 ug/mL, and the cells were incubated for 2 hours at room temperature. Compounds were dissolved in DMSO for preparation of 10 mM stock solutions. Compounds were diluted in H/HBSS containing 0.01% HSA. Serial dilutions of the test compounds were prepared to determine dose response.

Aequorin luminescence measurements were made using an EG&G Berthold 96-well luminometer, and the response was measured over a 20 second interval after cells and compounds were mixed. The maximum relative light units was plotted to determine dose response. The $EC_{50}$ (effective concentration to reach 50% maximal response) was determined from the dose response plot.

The following table presents representative data ($EC_{50}$ values) obtained for exemplary compounds of the invention for the activation of human GPR40.

Inositol Phosphate Accumulation Assay

An A9 cell line stably transfected with GPR40 (A9_GPR40) was used in IP accumulation assays. A9_GPR40 cells were plated in 96-well plates containing 20,000 cells/well in DMEM containing 10% FBS. After the cells attached to the well surface, the media was replaced with inositol free DMEM containing 10% dialyzed FBS and 1 μCi, mL $^3$H-inositol and incubated for 16 hours. Compounds were diluted in HBSS/10 mM LiCl containing a desired amount of HSA and added directly to cells. Following 1 hour incubation at 37° C., the media was replaced with 100 μl of 20 mM formic acid to quench the reaction. 50 μL of the extract was then added to 100 μL of SPA beads, incubated overnight, and measured on a TopCount the following day.

The stereoisomers in the following Table are as specified, i.e., S-enantiomers or R-enantiomers, and if not specified, or if shown with wavy bonds, are mixtures of S-enantiomers and R-enantiomers. In addition, the present invention provides the S-enantiomers, the R-enantiomers, and mixtures of both S-enantiomers and R-enantiomers including racemates of each compound prepared according to the synthetic methods described herein or adapted with the necessary minor modifications from these methods.

Insulin Secretion Assay

Human islets are isolated from cadaveric donors. Islets are treated with trypsin (0.25% (w/v) and cells are seeded in 96-well plates containing 3,000 cells per well. Cells are cultured in Roswell Park Memorial Institute (RMPI) media containing 10% fetal bovine serum.

For determination of insulin secretion, media is removed from islet cells and replaced with Krebs-Ringer bicarbonate buffer containing 10 mM HEPES (KRBH) and 2 mM glucose. After one hour incubation, media is replaced with KRBH containing 11.2 mM glucose and test compounds. Insulin released into the medium from the islet cells is measured using a scintillation proximity assay (SPA).

For determination of insulin secretion from rodent islets, C57/Bl6 mice are euthanized with carbon dioxide gas. The pancreatic bile duct is clamped proximal to the duodenum and then cannulated. H/HBSS containing 0.75 mg/mL collagenase XI (Sigma) is then infused into the pancreas through the cannula. The pancreas is excised and then incubated at 37° C. for 13 minutes to complete enzymatic digestion. The collagenase digestion is quenched in H/HBSS containing 1% BSA and washed once in the same buffer. Islets can be purified using density gradient centrifugation using Histopaque (Sigma) and are hand-picked under a stereomicroscope.

Islets are cultured overnight in Roswell Park Memorial Institute (RMPI) media containing 10% fetal bovine serum and 50 uM beta-mercaptoethanol. Following overnight culture, islets are incubated in KRBH containing 2.8 mM glucose for one hour.

For determination of insulin secretion, islets are incubated in DMEM containing 12.5 mM glucose and test compounds for one hour. Insulin released into the culture medium from the islets is measured using an insulin ELISA.

TABLE

Assay Data For Human GPR40

| No. | Structure[a] | Aequorin $Ec_{50}^{b,c}$ | IP3 $EC_{50}^{c,d}$ |
|---|---|---|---|
| 1 | 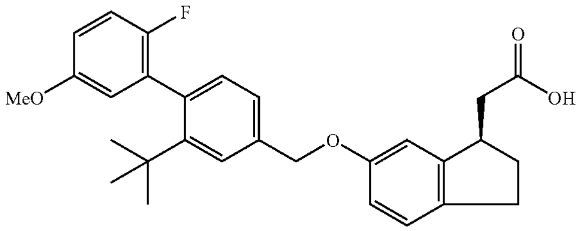 or 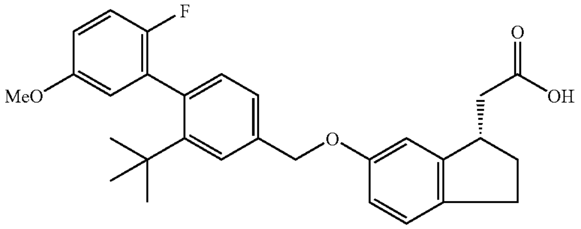 [SMILES: COc1ccc(F)c(-c2ccc(COc3ccc4c(c3)[C@H](CC(=O)O)CC4)cc2C(C)(C)C)c1] | ++ | ND[e] |
| 2 | 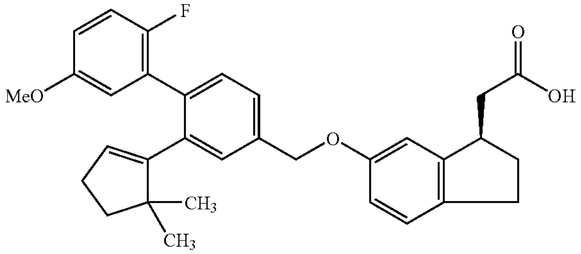 or 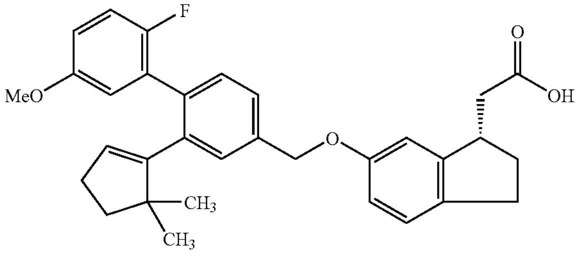 [SMILES: COc1ccc(F)c(-c2ccc(COc3ccc4c(c3)[C@H](CC(=O)O)CC4)cc2C2=CCCC2(C)C)c1] | +++ | ND |

TABLE-continued
Assay Data For Human GPR40
| No. | Structure[a] | Aequorin $Ec_{50}$[b,c] | IP3 $EC_{50}$[c,d] |
|---|---|---|---|
| 3 | 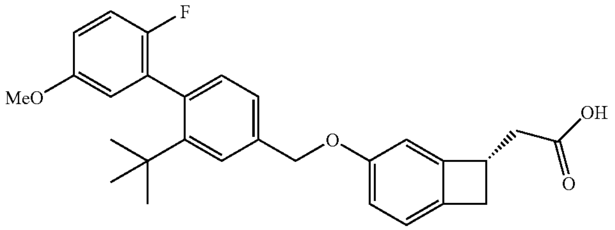 or 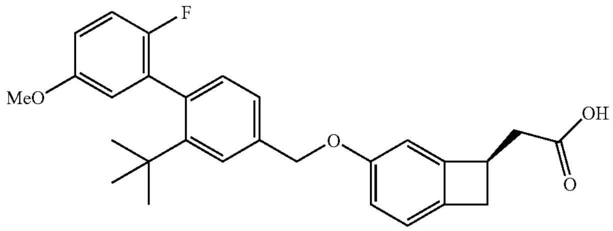 [SMILES: COc1ccc(F)c(-c2ccc(COc3ccc4c(c3)[C@@H](CC(=O)O)C4)cc2C(C)(C)C)c1] | ++ | ND |
| 4 | Enantiomer of Example 3 | + | ND |
| 5 | 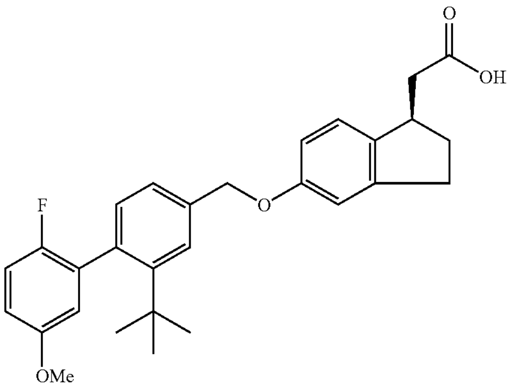 or 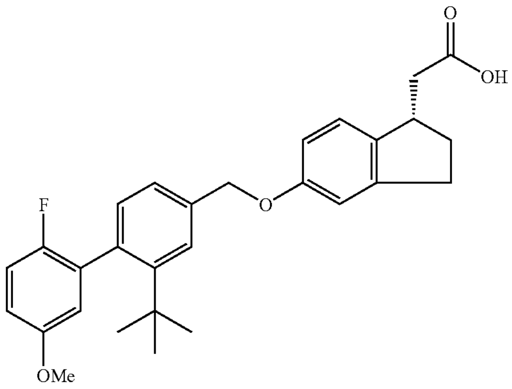 [SMILES: COc1ccc(F)c(-c2ccc(COc3ccc4c(c3)CC[C@H]4CC(=O)O)cc2C(C)(C)C)c1] | ++ | ND |
| 6 | 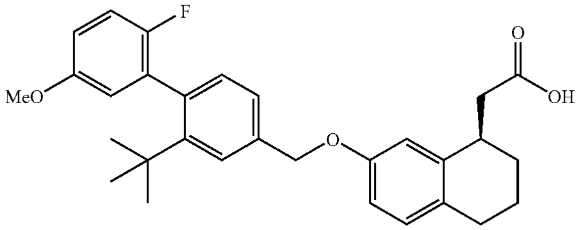 or | +++ | +++ |

TABLE-continued
Assay Data For Human GPR40
| No. | Structure[a] | Aequorin $Ec_{50}$[b,c] | IP3 $EC_{50}$[c,d] |
|---|---|---|---|
| | 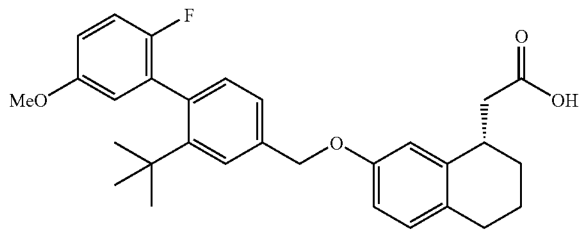 [SMILES: COc1ccc(F)c(-c2ccc(COc3ccc4c(c3)[C@H](CC(=O)O)CCC4)cc2C(C)(C)C)c1] | | |
| 7 | 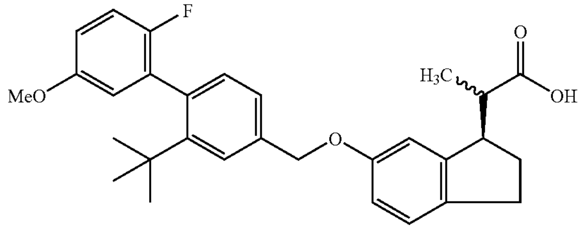 or 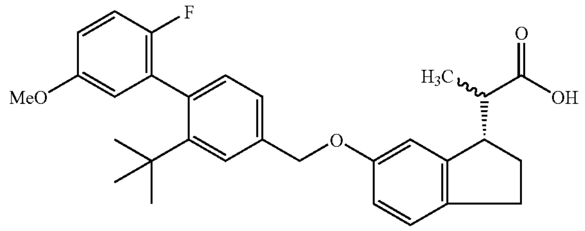 [SMILES: COc1ccc(F)c(-c2ccc(COc3ccc4c(c3)[C@H](C(C)C(=O)O)CC4)cc2C(C)(C)C)c1] | +++ | +++ |
| 8 | 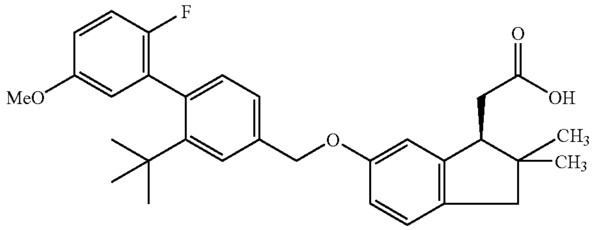 or 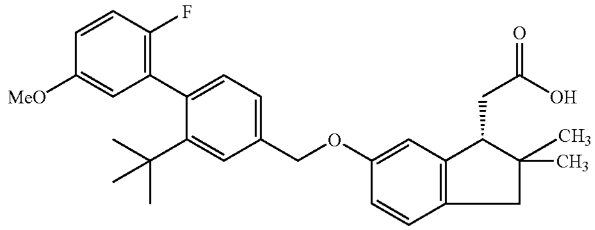 [SMILES: COc1ccc(F)c(-c2ccc(COc3ccc4c(c3)[C@H](CC(=O)O)C(C)(C)C4)cc2C(C)(C)C)c1] | ++ | ND |
| 9 | 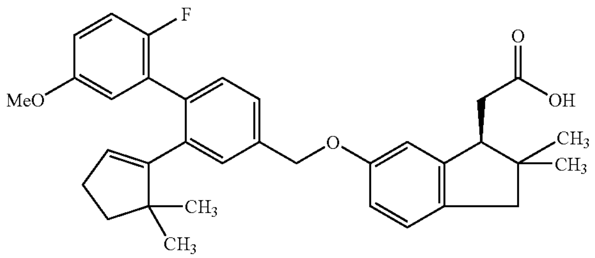 or | +++ | ND |

TABLE-continued
| Assay Data For Human GPR40 | | | |
|---|---|---|---|
| No. | Structure[a] | Aequorin Ec$_{50}$[b,c] | IP3 EC$_{50}$[c,d] |
| | 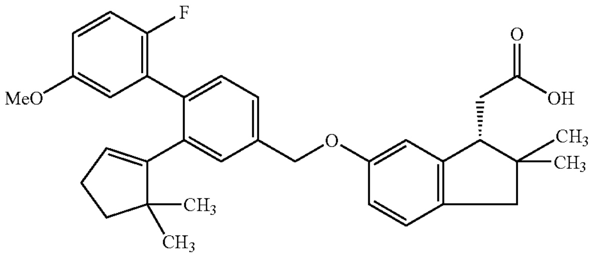 [SMILES: COc1ccc(F)c(-c2ccc(COc3ccc4c(c3)[C@H](CC(=O)O)C(C)(C)C4)cc2C2=CCCC2(C)C)c1] | | |
| 10 | Enantiomer of Example 8 | ++ | ND |
| 11 | 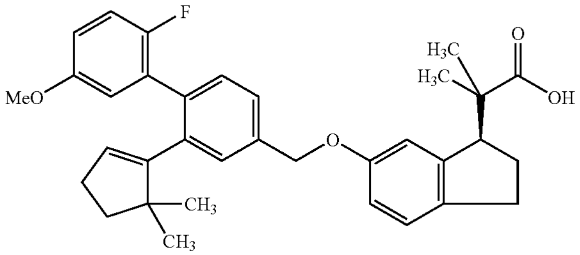 or 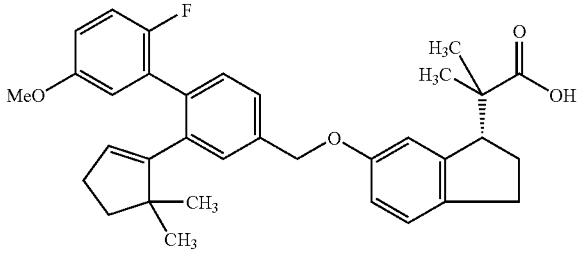 [SMILES: COc1ccc(F)c(-c2ccc(COc3ccc4c(c3)[C@H](C(C)(C)C(=O)O)CC4)cc2C2=CCCC2(C)C)c1] | +++ | ND |
| 12 | 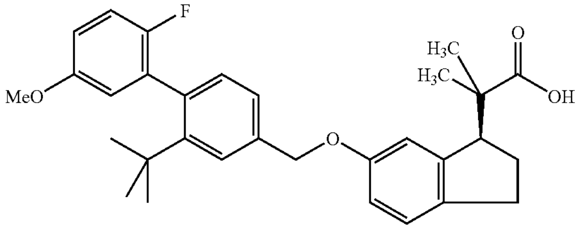 or 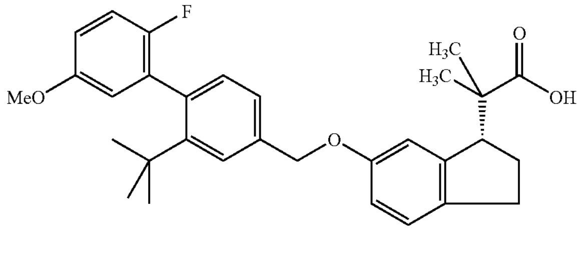 [SMILES: COc1ccc(F)c(-c2ccc(COc3ccc4c(c3)[C@H](C(C)(C)C(=O)O)CC4)cc2C(C)(C)C)c1] | +++ | ND |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 13 | 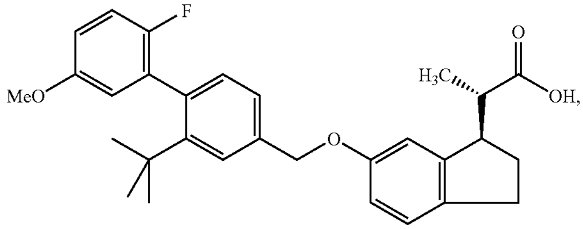, | +++ | ND |
| | 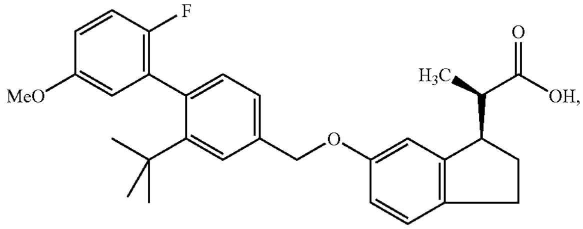, | | |
| | 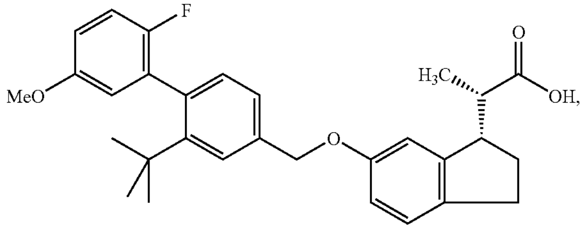, or | | |
| | 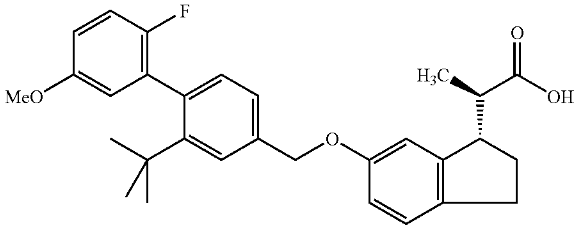 [SMILES: COc1ccc(F)c(-c2ccc(COc3ccc4c(c3)[C@H]([C@@H](C)C(=O)O)CC4)cc2C(C)(C)C)c1] | | |
| 14 | 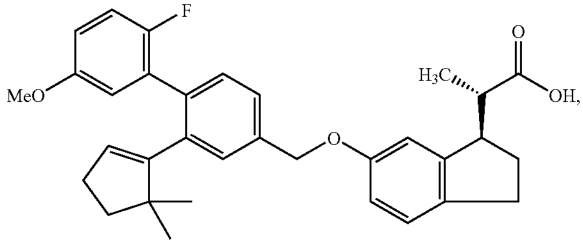, | +++ | ++++ |
| | 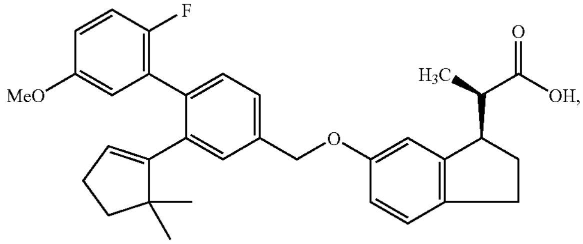, | | |

TABLE-continued
Assay Data For Human GPR40
| No. | Structure[a] | Aequorin $Ec_{50}$[b,c] | IP3 $EC_{50}$[c,d] |
|---|---|---|---|
| | 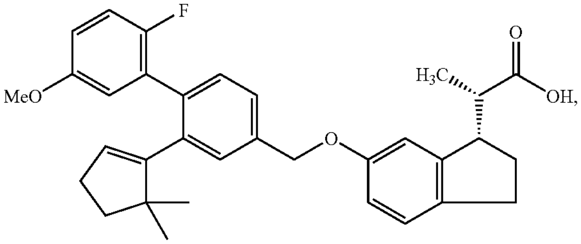 or | | |
| | 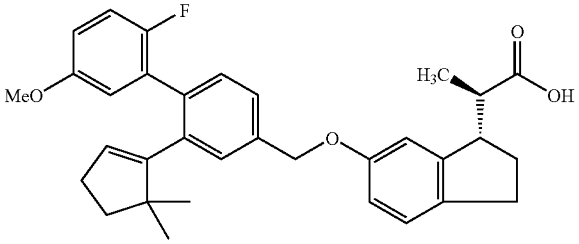 [SMILES: COc1ccc(F)c(-c2ccc(COc3ccc4c(c3)[C@H]([C@@H](C)C(=O)O)CC4)cc2C2=CCCC2(C)C)c1] | | |
| 15 | 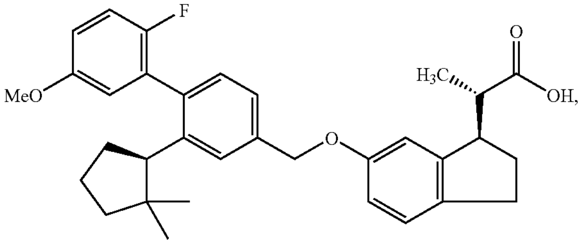 | +++ | ++++ |
| | 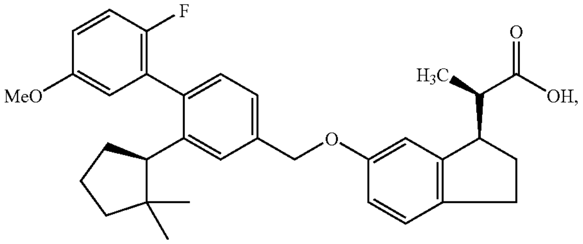 | | |
| | 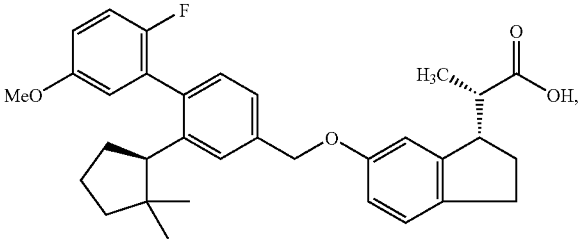 | | |
| | 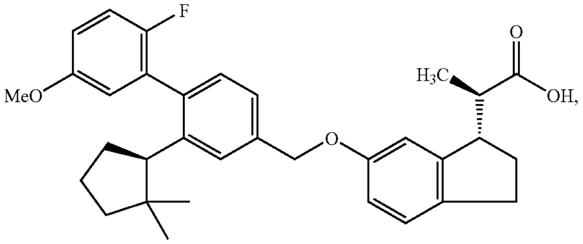 | | |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| | 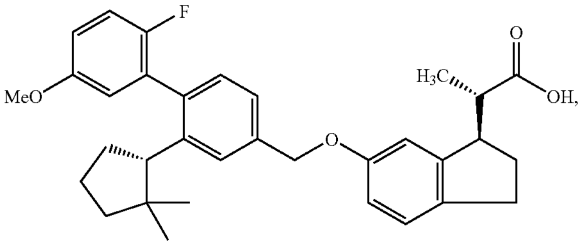 | | |
| | 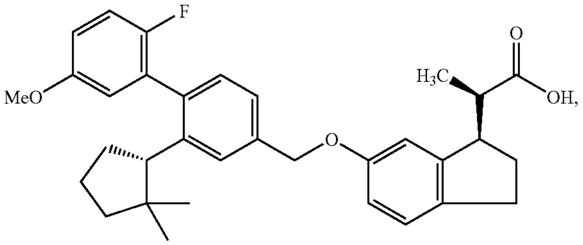 | | |
| | 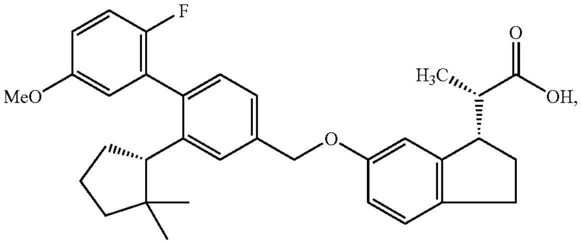 or | | |
| | 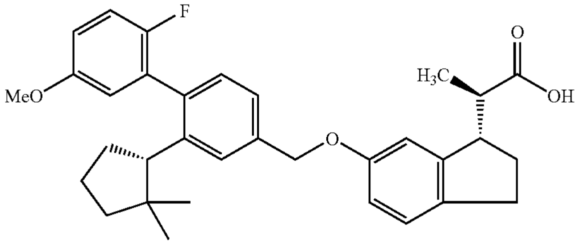 | | |
| 16 | One of the 4 Diastereomers shown for Example 13, but not the same one as Example 13 | +++ | ND |
| 17 | 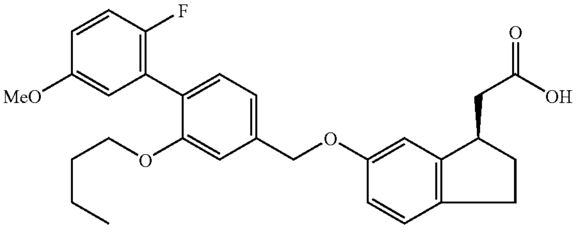 [SMILES: CCCCOc1cc(COc2ccc3c(c2)[C@H](CC(=O)O)CC3)ccc1-c1cc(OC)ccc1F] or | +++ | ++ |

TABLE-continued
Assay Data For Human GPR40
| No. | Structure[a] | Aequorin $Ec_{50}^{b,c}$ | IP3 $EC_{50}^{c,d}$ |
|---|---|---|---|
| | 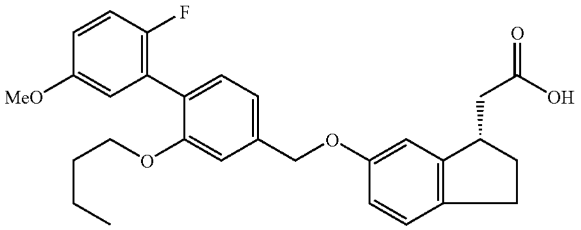 | | |
| 18 | 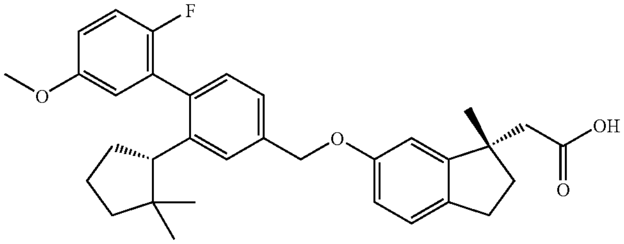 or | +++ | ++++ |
| | 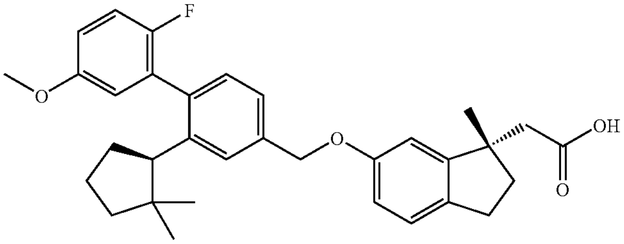 [SMILES: COc1ccc(F)c(-c2ccc(COc3ccc4c(c3)[C@](C)(CC(=O)O)CC4)cc2[C@@H]2CCCC2(C)C)c1] | | |
| 19 | 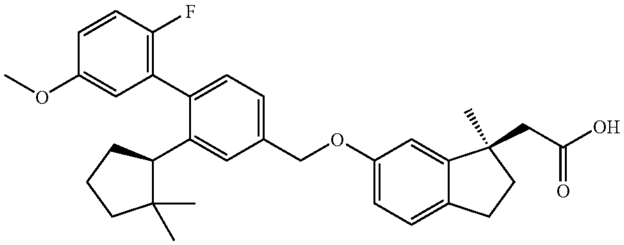 or | +++ | +++++ |
| | 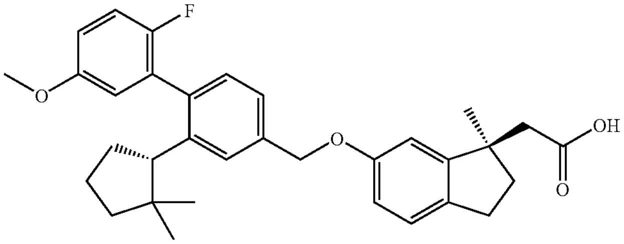 | | |
| 20 | 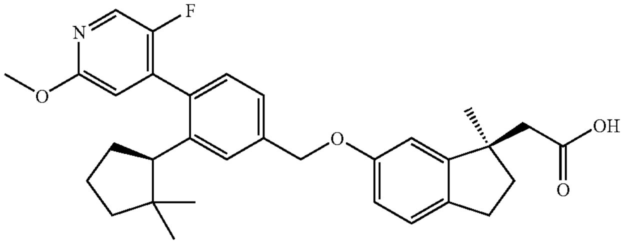 or | +++ | +++++ |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| | 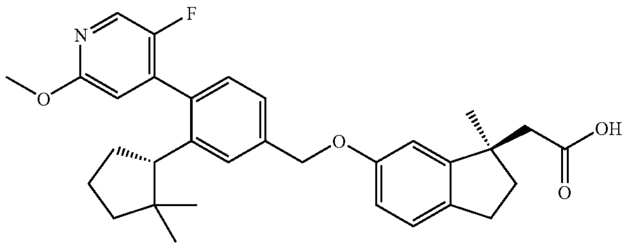 [SMILES: COc1ccc(F)c(-c2ccc(COc3ccc4c(c3)[C@@](C)(CC(=O)O)CC4)cc2[C@H]2CCCC2(C)C)c1] | | |
| 21 | 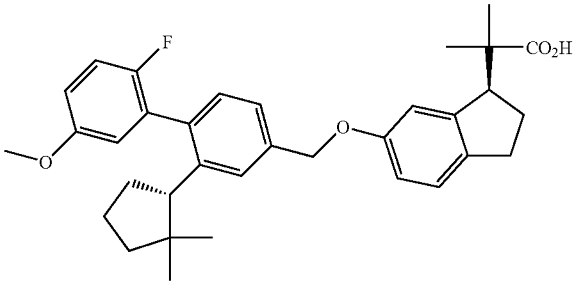 or | +++ | ++++ |
| | 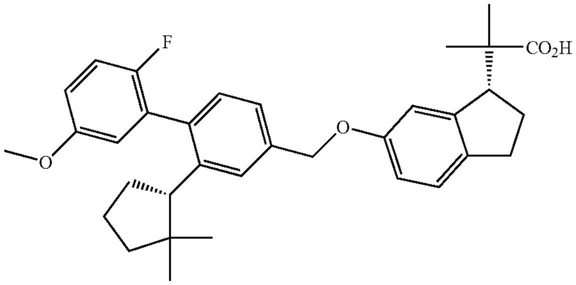 or | | |
| | 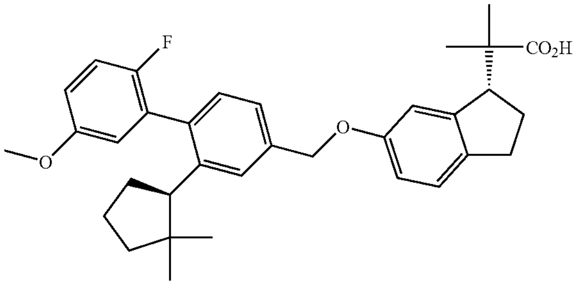 or | | |
| | 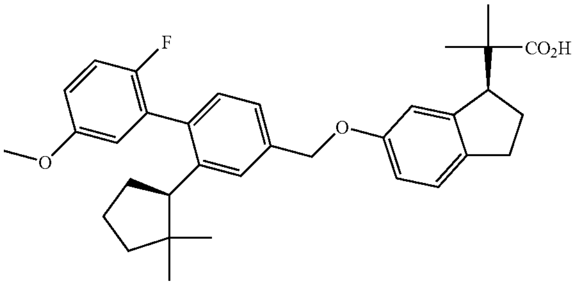 [SMILES: COc1ccc(F)c(-c2ccc(COc3ccc4c(c3)[C@@H](C(C)(C)C(=O)O)CC4)cc2[C@@H]2CCCC2(C)C)c1] | | |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 22 | 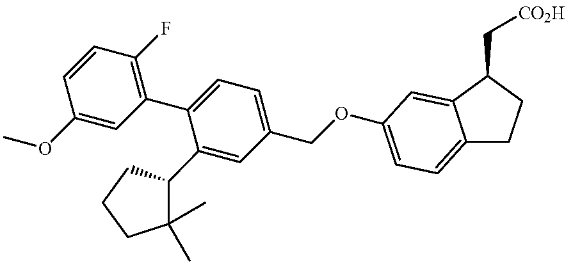 or | +++ | ++++ |
| | 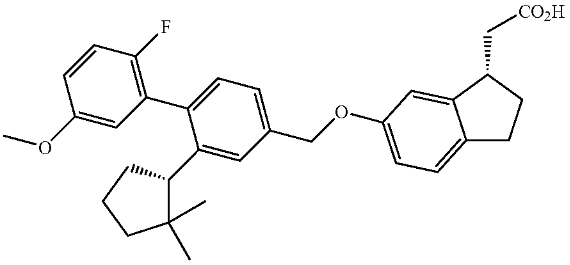 or | | |
| | 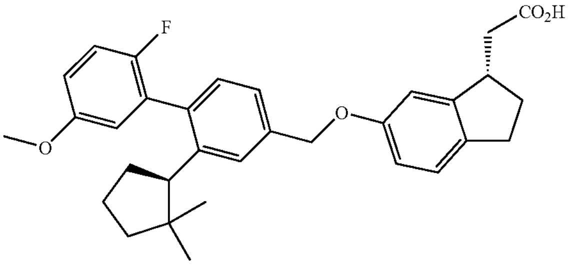 or | | |
| | 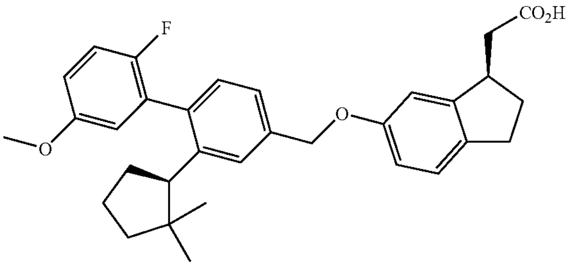 [SMILES: COc1ccc(F)c(-c2ccc(COc3ccc4c(c3)[C@@H](CC(=O)O)CC4)cc2[C@@H]2CCCC2(C)C)c1] | | |
| 23 | 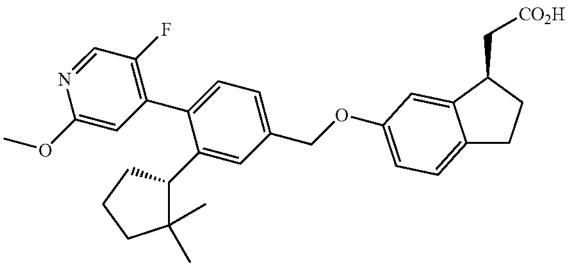 or | +++ | ++++ |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| | 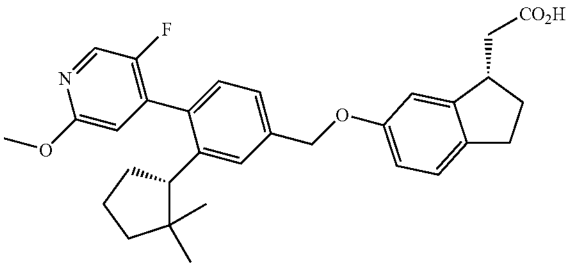 or | | |
| | 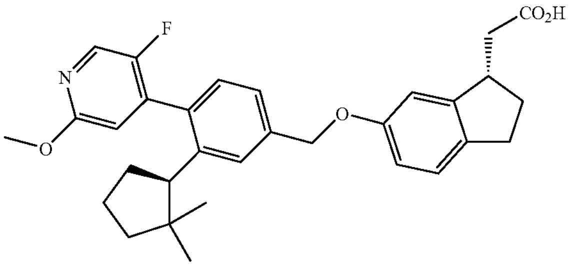 or | | |
| | 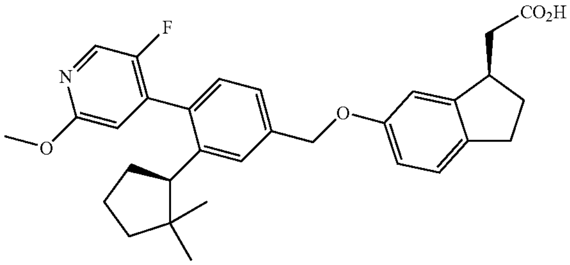 | | |
| 24 | 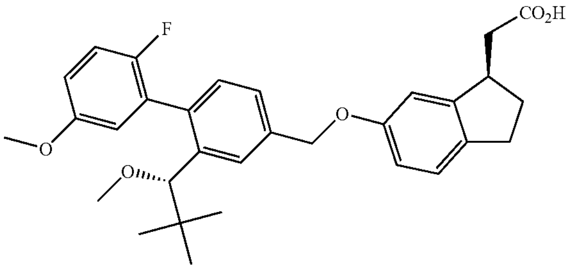 or | +++ | ++++ |
| | 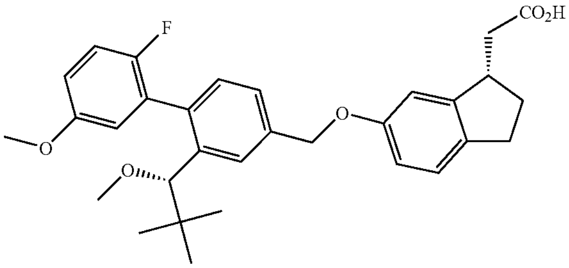 or | | |

TABLE-continued
Assay Data For Human GPR40
| No. | Structure[a] | Aequorin $Ec_{50}$[b,c] | IP3 $EC_{50}$[c,d] |
|---|---|---|---|
| | 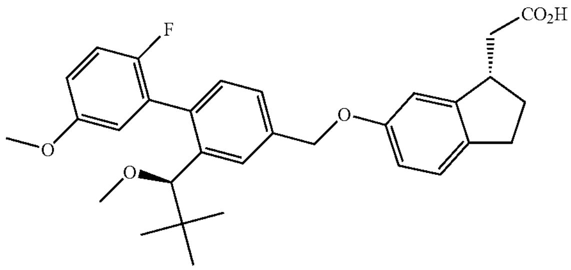 or | | |
| | 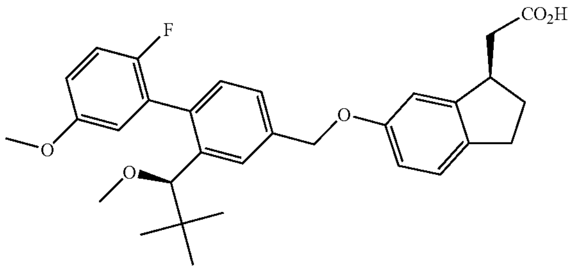 [SMILES: COc1ccc(F)c(-c2ccc(COc3ccc4c(c3)[C@@H](CC(=O)O)CC4)cc2[C@H](OC)C(C)(C)C)c1] | | |
| 25 | 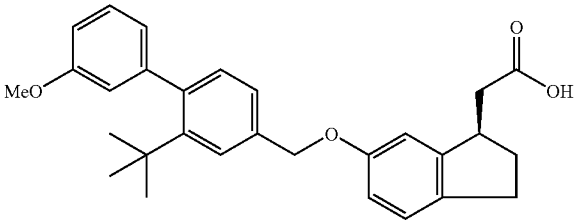 or | ++ | ND |
| | 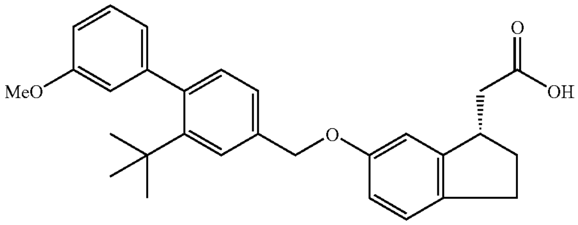 [SMILES: COc1cccc(-c2ccc(COc3ccc4c(c3)[C@H](CC(=O)O)CC4)cc2C(C)(C)C)c1] | | |
| 26 | 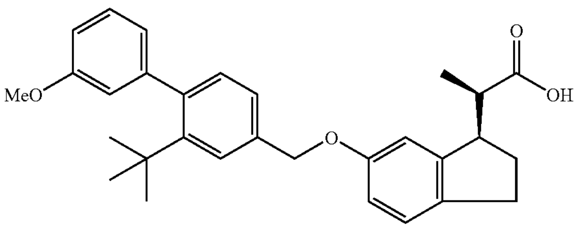 or | ++ | ND |
| | 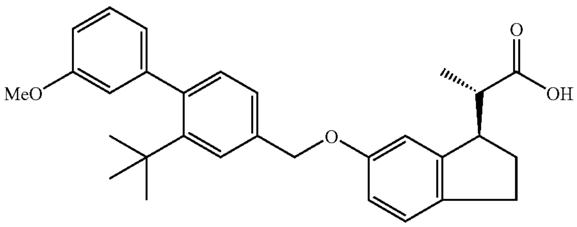 or | | |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| | 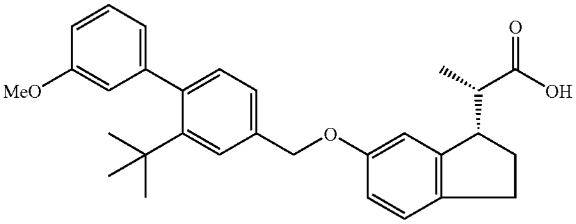 or | | |
| | 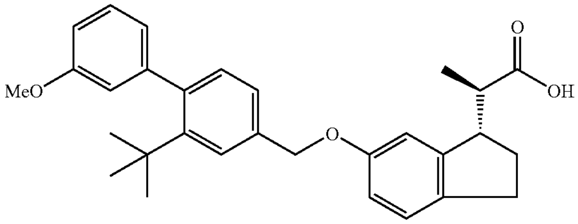 [SMILES: COc1cccc(-c2ccc(COc3ccc4c(c3)[C@H]([C@@H](C)C(=O)O)CC4)cc2C(C)(C)C)c1] | | |
| 27 | 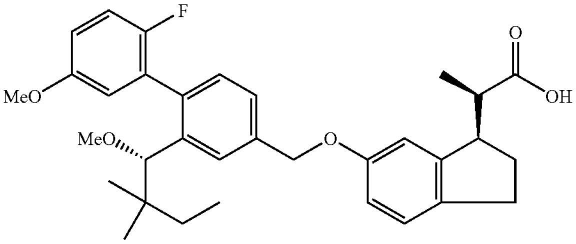 or | ++ | ND |
| | 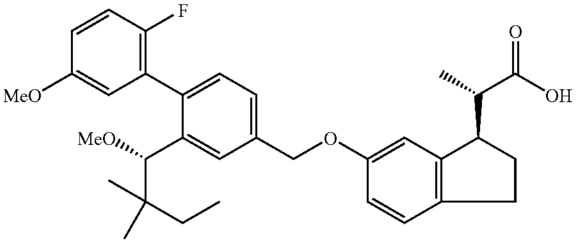 or | | |
| | 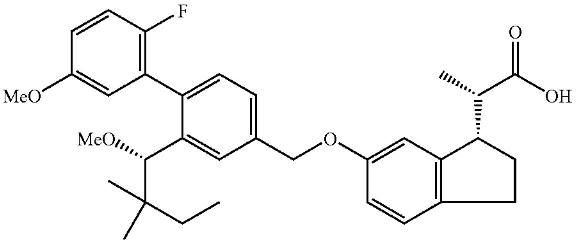 or | | |
| | 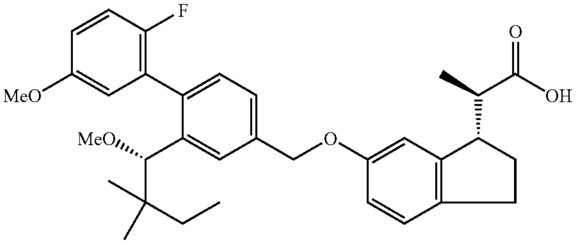 or | | |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| | 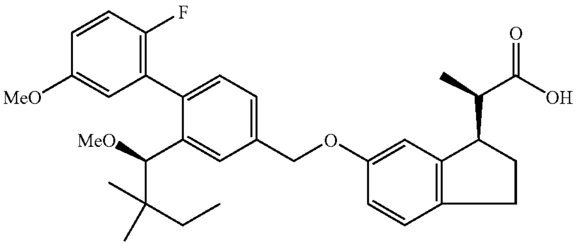 or | | |
| | 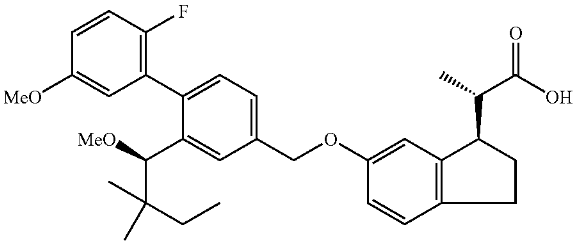 or | | |
| | 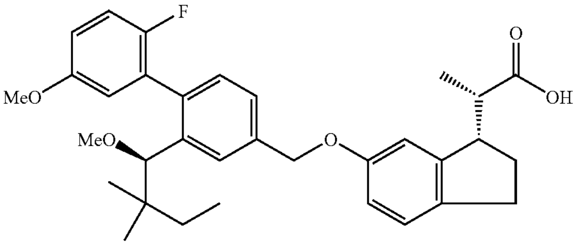 or | | |
| | 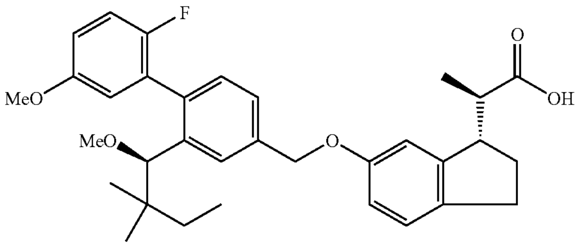 [SMILES: CCC(C)(C)[C@@H](OC)c1cc(COc2ccc3c(c2)[C@H]([C@@H](C)C(=O)O)CC3)ccc1-c1cc(OC)ccc1F] | | |
| 28 | 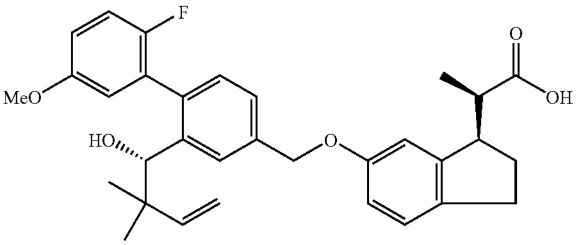 or | ++ | ND |
| | 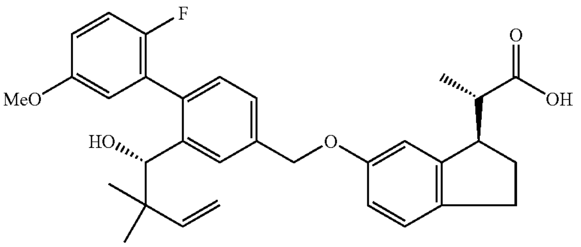 or | | |

TABLE-continued
Assay Data For Human GPR40
| No. | Structure[a] | Aequorin $Ec_{50}$[b,c] | IP3 $EC_{50}$[c,d] |
|---|---|---|---|
| | 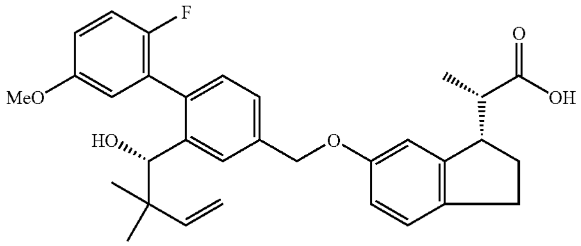 or | | |
| | 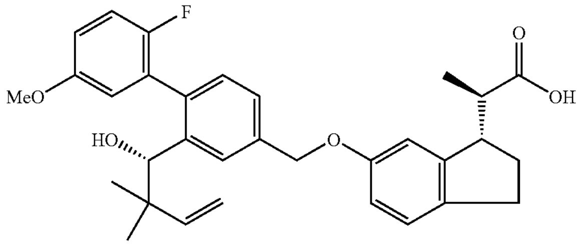 or | | |
| | 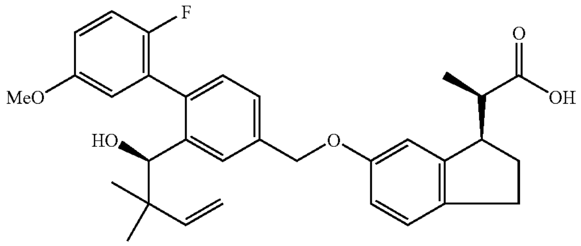 or | | |
| | 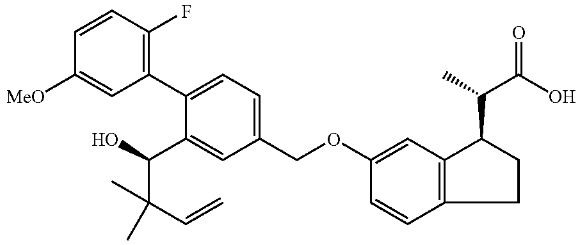 or | | |
| | 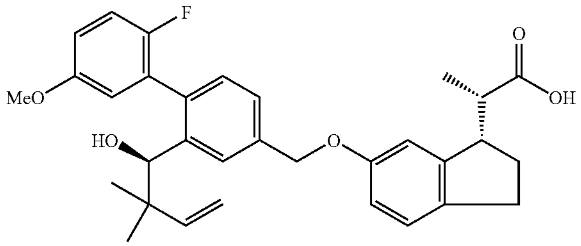 or | | |
| | 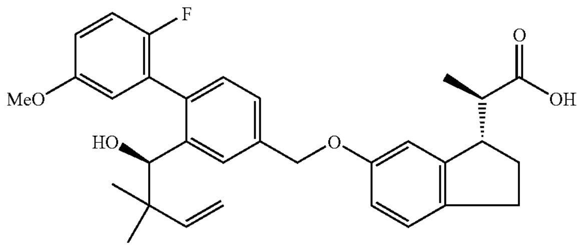 [SMILES: C=CC(C)(C)[C@@H](O)c1cc(COc2ccc3c(c2)[C@H]([C@@H](C)C(=O)O)CC3)ccc1-c1cc(OC)ccc1F] | | |

TABLE-continued
Assay Data For Human GPR40
| No. | Structure[a] | Aequorin $Ec_{50}$[b,c] | IP3 $EC_{50}$[c,d] |
|---|---|---|---|
| 29 | 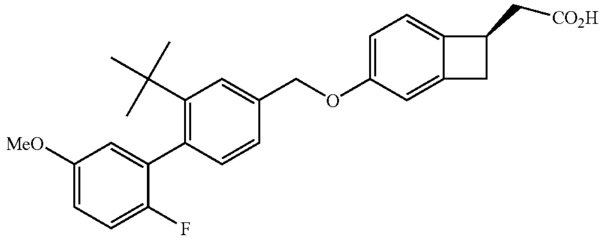 or 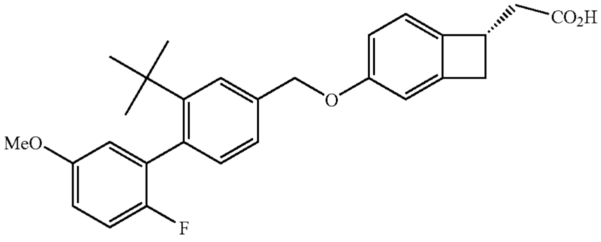 [SMILES: COc1ccc(F)c(-c2ccc(COc3ccc4c(c3)C[C@H]4CC(=O)O)cc2C(C)(C)C)c1] | ++ | ND |
| 30 | Enantiomer of 29 | ++ | ND |
| 31 | 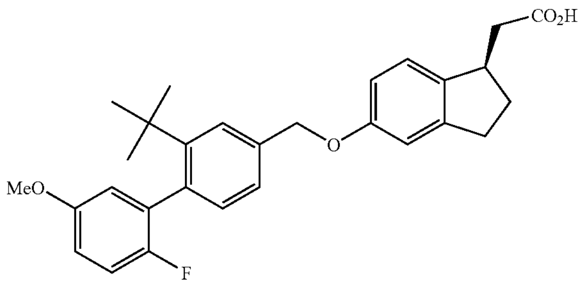 or 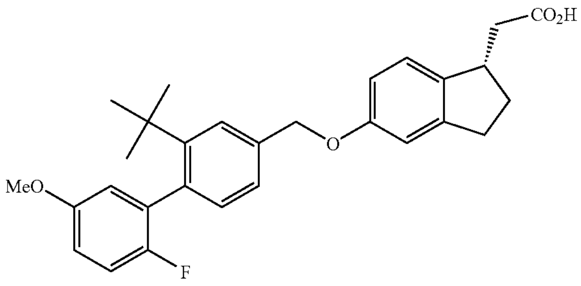 [SMILES: COc1ccc(F)c(-c2ccc(COc3ccc4c(c3)CC[C@H]4CC(=O)O)cc2C(C)(C)C)c1] | ++ | ND |
| 32 | Enantiomer of 31 | ++ | ND |
| 33 | 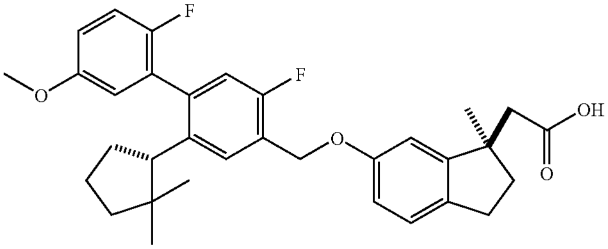 OR | ++++ | +++++ |

TABLE-continued
Assay Data For Human GPR40
| No. | Structure[a] | Aequorin $Ec_{50}$[b,c] | IP3 $EC_{50}$[c,d] |
|---|---|---|---|
| | 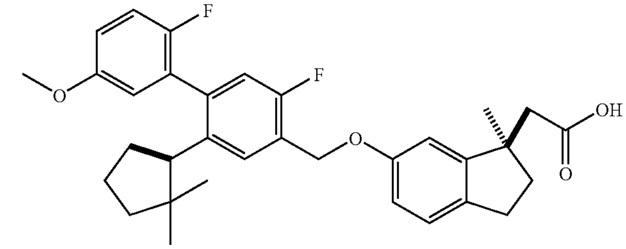 [SMILES: COc1ccc(F)c(-c2cc(F)c(COc3ccc4c(c3)[C@@](C)(CC(=O)O)CC4)cc2[C@@H]2CCCC2(C)C)c1] | | |
| 34 | 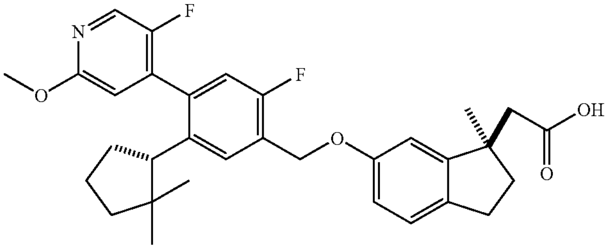 OR | +++ | +++++ |
| | 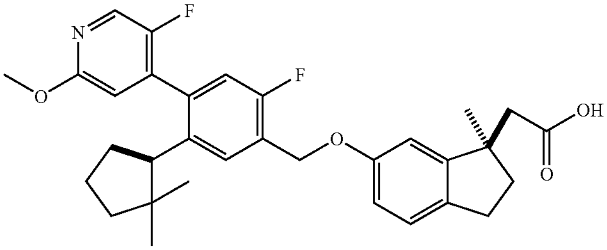 | | |
| 35 | 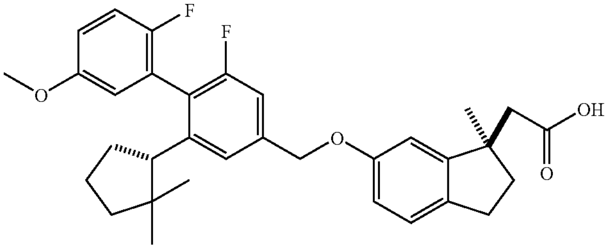 OR | +++ | +++++ |
| | 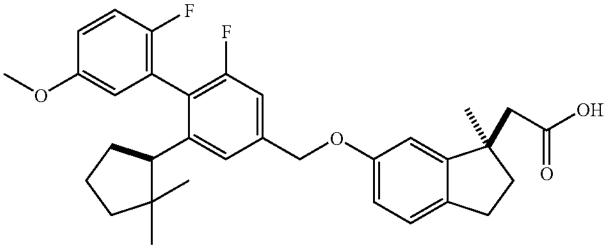 | | |
| 36 | 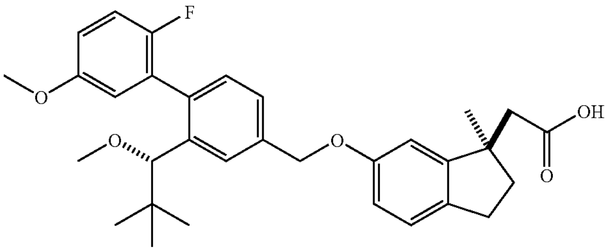 OR | +++ | +++++ |

TABLE-continued
| Assay Data For Human GPR40 | | | |
|---|---|---|---|
| No. | Structure[a] | Aequorin $Ec_{50}^{b,c}$ | IP3 $EC_{50}^{c,d}$ |
| | 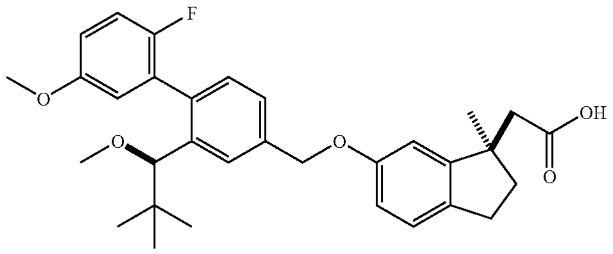 [SMILES: COc1ccc(F)c(-c2ccc(COc3ccc4c(c3)[C@@](C)(CC(=O)O)CC4)cc2[C@H](OC)C(C)(C)C)c1] | | |
| 37 | 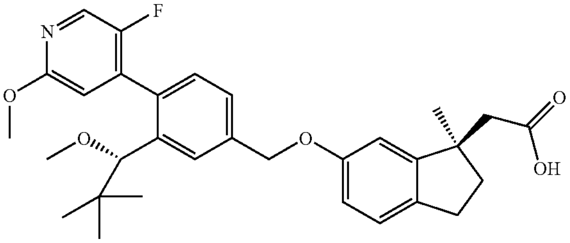 or | +++ | +++++ |
| | 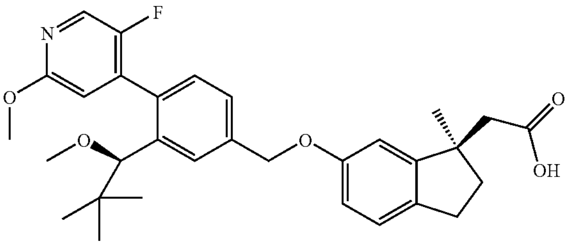 [SMILES: COc1cc(-c2ccc(COc3ccc4c(c3)[C@@](C)(CC(=O)O)CC4)cc2[C@H](OC)C(C)(C)C)c(F)cn1] | | |
| 38 | 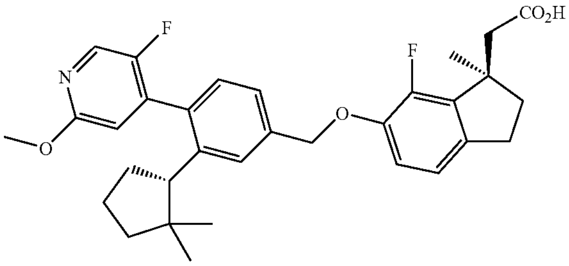 or | +++ | ++++ |
| | 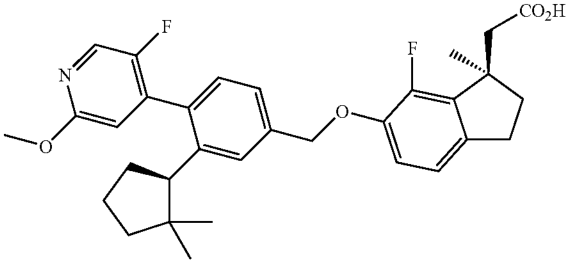 or | | |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| | 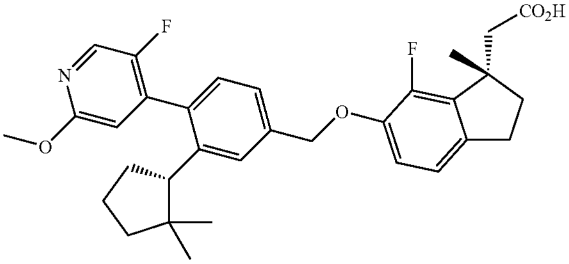 or | | |
| | 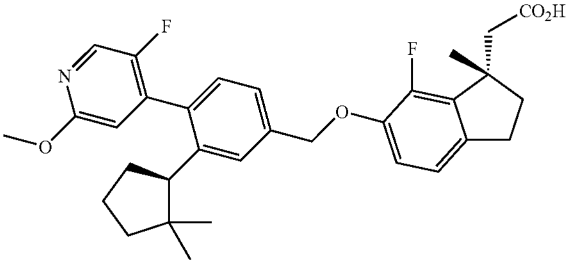 [SMILES: COc1cc(-c2ccc(COc3ccc4c(c3F)[C@](C)(CC(=O)O)CC4)cc2[C@@H]2CCCC2(C)C)c(F)cn1] | | |
| 39 | 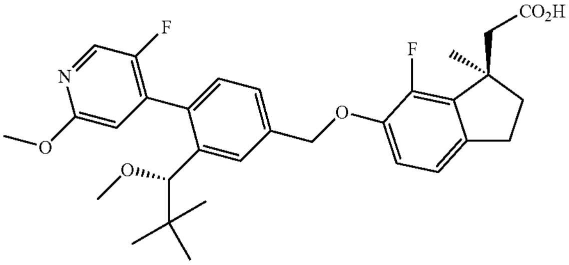 or | +++ | ++++ |
| | 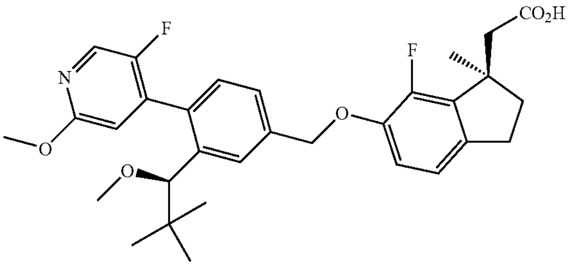 or | | |
| | 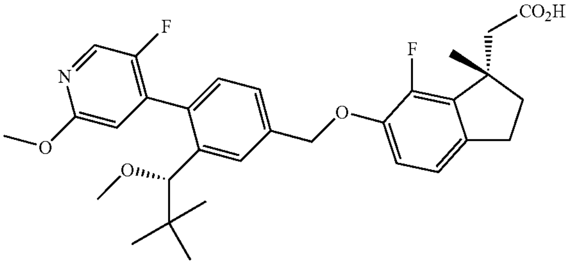 or | | |

TABLE-continued
Assay Data For Human GPR40
| No. | Structure[a] | Aequorin $Ec_{50}$[b,c] | IP3 $EC_{50}$[c,d] |
|---|---|---|---|
| | 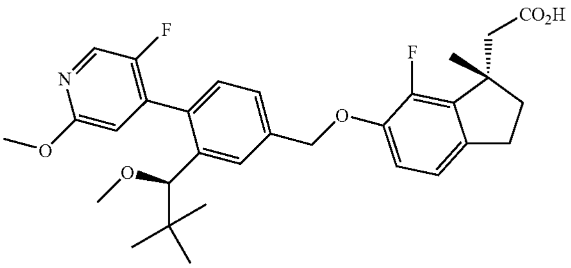 [SMILES: COc1cc(-c2ccc(COc3ccc4c(c3F)[C@](C)(CC(=O)O)CC4)cc2[C@H](OC)C(C)(C)C)c(F)cn1] | | |
| 40 | Diastereomer of 38 | +++ | +++ |
| 41 | Diastereomer of 39 | ++ | ND |
| 42 | 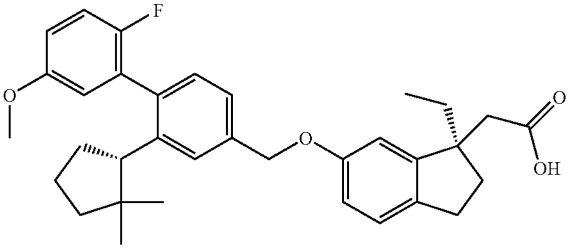 or 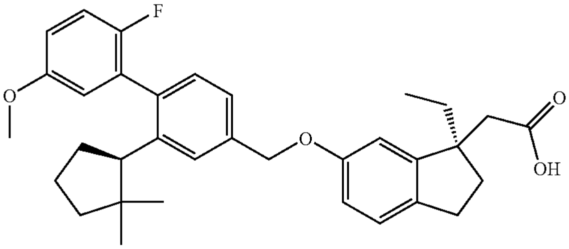 or 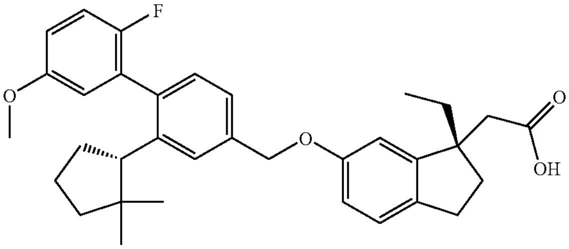 or 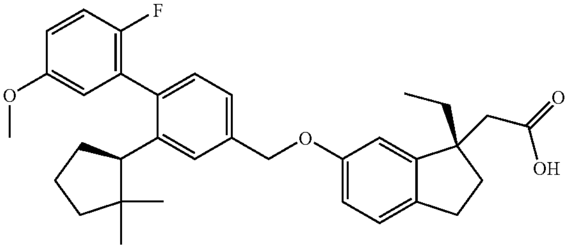 [SMILES: CC[C@@]1(CC(=O)O)CCc2ccc(OCc3ccc(-c4cc(OC)ccc4F)c([C@@H]4CCCC4(C)C)c3)cc21] | +++ | ++++ |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 43 | 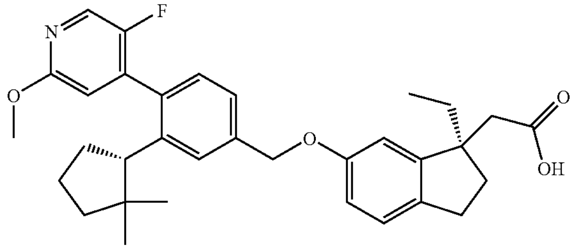 or 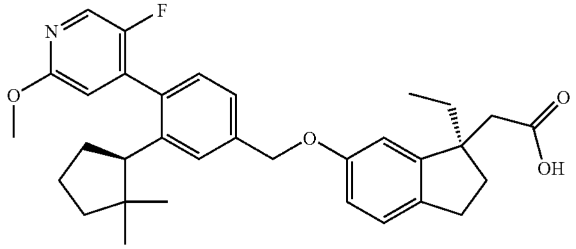 or 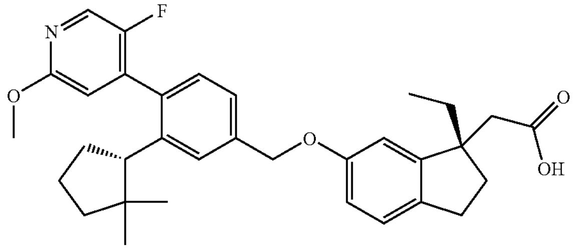 or 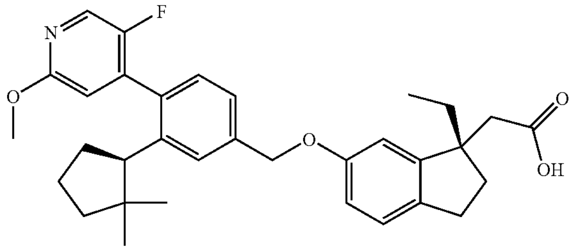 [SMILES: CC[C@@]1(CC(=O)O)CCc2ccc(OCc3ccc(-c4cc(OC)ncc4F)c([C@@H]4CCCC4(C)C)c3)cc21] | +++ | ++++ |
| 44 | 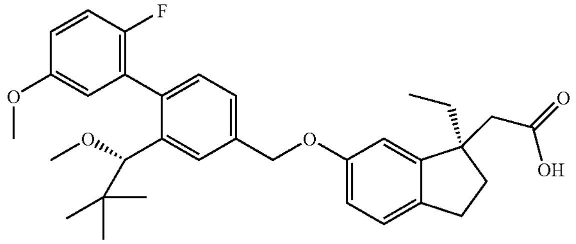 or 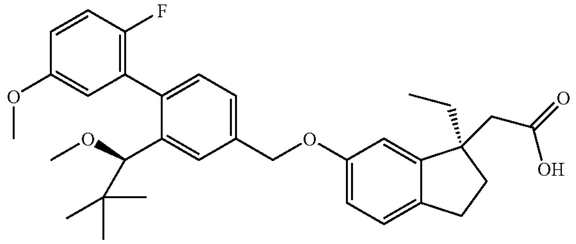 or | +++ | ++++ |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| | 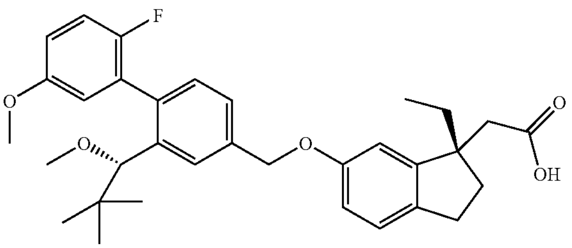 or | | |
| | 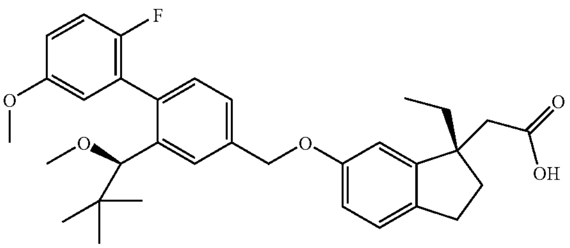 [SMILES: CC[C@@]1(CC(=O)O)CCc2ccc(OCc3ccc(-c4cc(OC)ccc4F)c([C@H](OC)C(C)(C)C)c3)cc21] | | |
| 45 | Diastereomer of 44 | +++ | +++ |
| 46 | 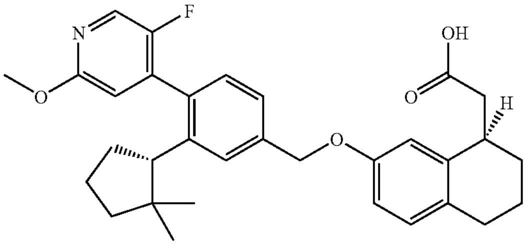 or | +++ | ++++ |
| | 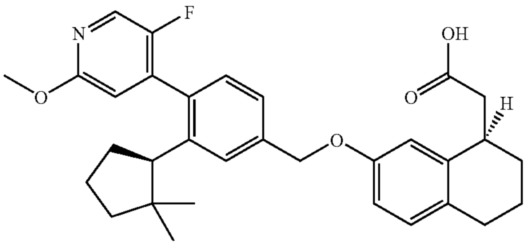 or | | |
| | 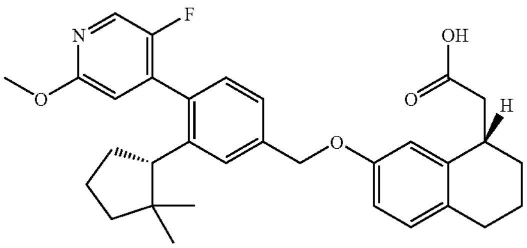 or | | |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| | 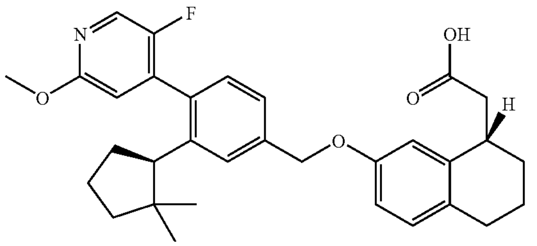 [SMILES: COc1cc(-c2ccc(COc3ccc4c(c3)[C@H](CC(=O)O)CCC4)cc2[C@@H]2CCCC2(C)C)c(F)cn1] | | |
| 47 | Diastereomer of 46 | ++ | ND |
| 48 | 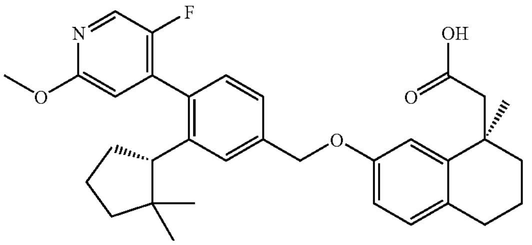 or 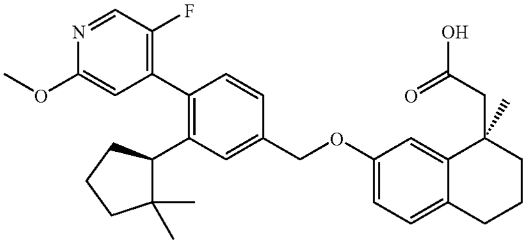 or 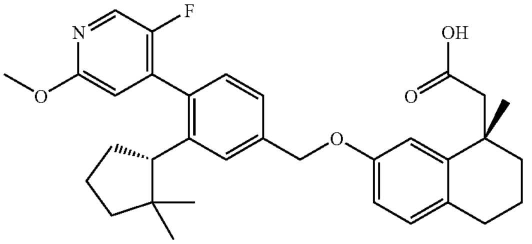 or 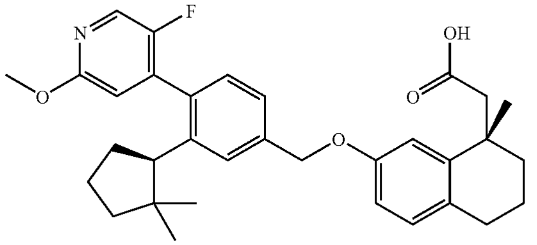 [SMILES: COc1cc(-c2ccc(COc3ccc4c(c3)[C@](C)(CC(=O)O)CCC4)cc2[C@@H]2CCCC2(C)C)c(F)cn1] | +++ | ++++ |

TABLE-continued

| Assay Data For Human GPR40 | | | |
|---|---|---|---|
| No. | Structure[a] | Aequorin $Ec_{50}$[b,c] | IP3 $EC_{50}$[c,d] |
| 49 | Diastereomer of 48 | +++ | ND |
| | The following compounds are synthesized using the methodology described herein from the intermediates described herein or synthesized using intermediates analogous to those described herein and synthesized using analogous routes from commercially available starting materials. | | |
| 50 | 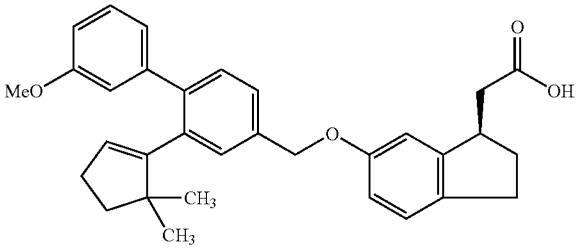 | ND | ND |
| 51 | 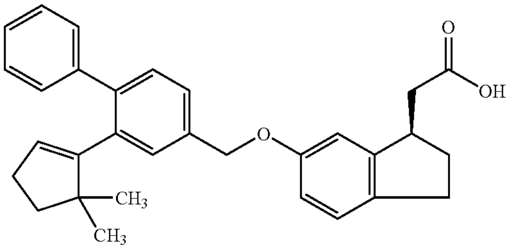 [SMILES: CC1(C)CCC=C1c1cc(COc2ccc3c(c2)[C@@H](CC(=O)O)CC3)ccc1-c1ccccc1] | ND | ND |
| 52 | 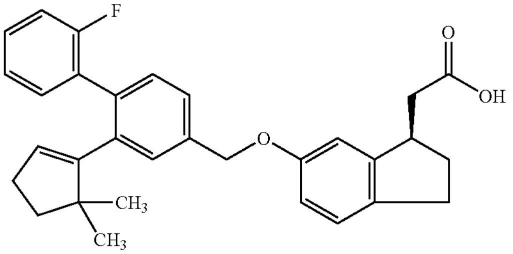 [SMILES: CC1(C)CCC=C1c1cc(COc2ccc3c(c2)[C@@H](CC(=O)O)CC3)ccc1-c1ccccc1F] | ND | ND |
| 53 | 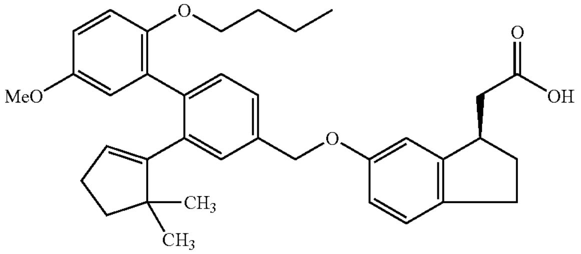 [SMILES: CCCCOc1ccc(OC)cc1-c1ccc(COc2ccc3c(c2)[C@@H](CC(=O)O)CC3)cc1C1=CCCC1(C)C] | ND | ND |
| 54 | 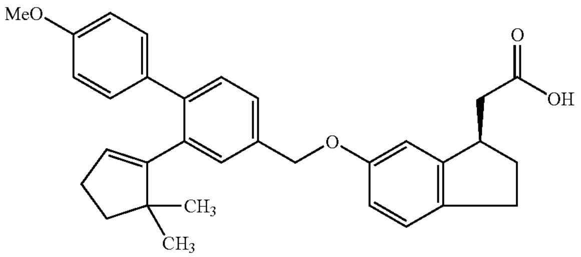 [SMILES: COc1ccc(-c2ccc(COc3ccc4c(c3)[C@@H](CC(=O)O)CC4)cc2C2=CCCC2(C)C)cc1] | ND | ND |

TABLE-continued
Assay Data For Human GPR40
| No. | Structure[a] | Aequorin $Ec_{50}$[b,c] | IP3 $EC_{50}$[c,d] |
|---|---|---|---|
| 55 | 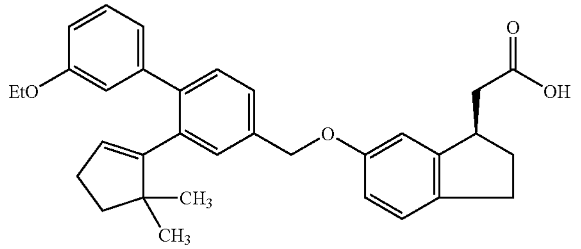 [SMILES: CCOc1cccc(-c2ccc(COc3ccc4c(c3)[C@@H](CC(=O)O)CC4)cc2C2=CCCC2(C)C)c1] | ND | ND |
| 56 | 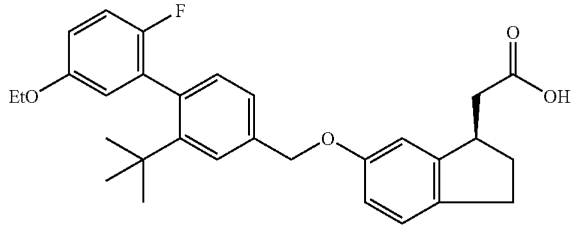 [SMILES: CCOc1ccc(F)c(-c2ccc(COc3ccc4c(c3)[C@@H](CC(=O)O)CC4)cc2C(C)(C)C)c1] | ND | ND |
| 57 | 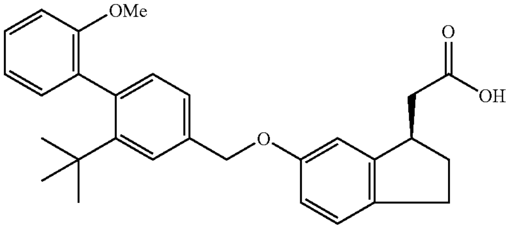 [SMILES: COc1ccccc1-c1ccc(COc2ccc3c(c2)[C@@H](CC(=O)O)CC3)cc1C(C)(C)C] | ND | ND |
| 58 | 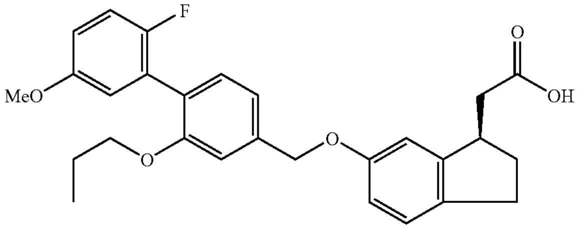 [SMILES: CCCOc1cc(COc2ccc3c(c2)[C@@H](CC(=O)O)CC3)ccc1-c1cc(OC)ccc1F] | ND | ND |
| 59 | 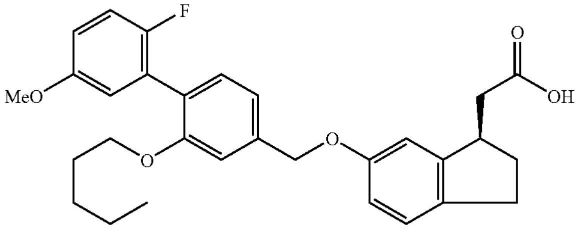 [SMILES: CCCCCOc1cc(COc2ccc3c(c2)[C@@H](CC(=O)O)CC3)ccc1-c1cc(OC)ccc1F] | ND | ND |
| 60 | 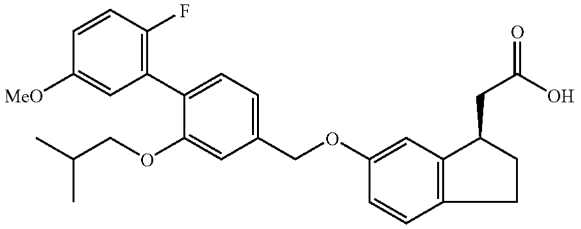 | ND | ND |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 61 | 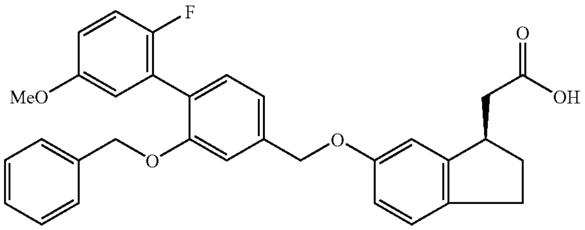 [SMILES: COc1ccc(F)c(-c2ccc(COc3ccc4c(c3)[C@@H](CC(=O)O)CC4)cc2OCc2ccccc2)c1] | ND | ND |
| 62 | 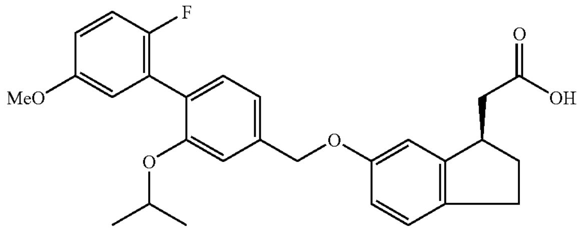 [SMILES: COc1ccc(F)c(-c2ccc(COc3ccc4c(c3)[C@@H](CC(=O)O)CC4)cc2OC(C)C)c1] | ND | ND |
| 63 | 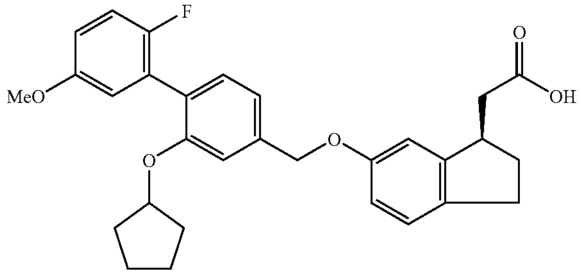 [SMILES: COc1ccc(F)c(-c2ccc(COc3ccc4c(c3)[C@@H](CC(=O)O)CC4)cc2OC2CCCC2)c1] | ND | ND |
| 64 | 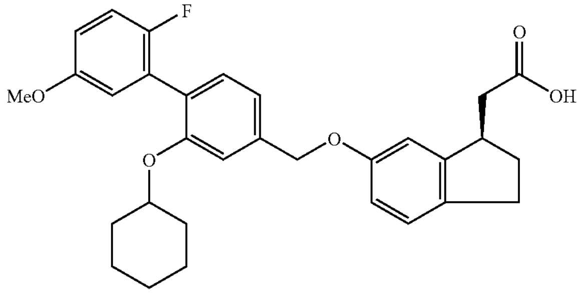 [SMILES: COc1ccc(F)c(-c2ccc(COc3ccc4c(c3)[C@@H](CC(=O)O)CC4)cc2OC2CCCCC2)c1] | ND | ND |
| 65 | 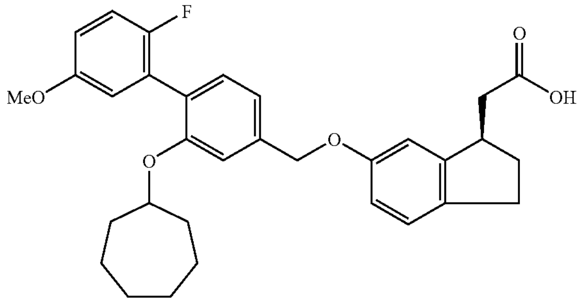 [SMILES: COc1ccc(F)c(-c2ccc(COc3ccc4c(c3)[C@@H](CC(=O)O)CC4)cc2OC2CCCCCC2)c1] | ND | ND |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 66 | 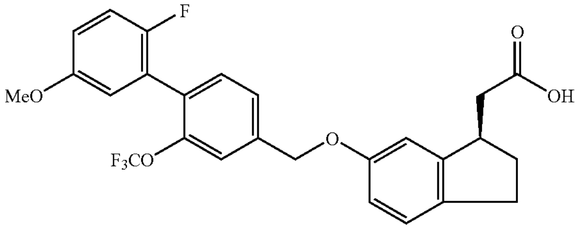 [SMILES: COc1ccc(F)c(-c2ccc(COc3ccc4c(c3)[C@@H](CC(=O)O)CC4)cc2OC(F)(F)F)c1] | ND | ND |
| 67 | 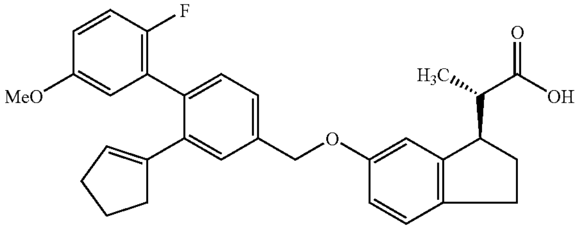 [SMILES: COc1ccc(F)c(-c2ccc(COc3ccc4c(c3)[C@@H]([C@H](C)C(=O)O)CC4)cc2C2=CCCC2)c1] | ND | ND |
| 68 | 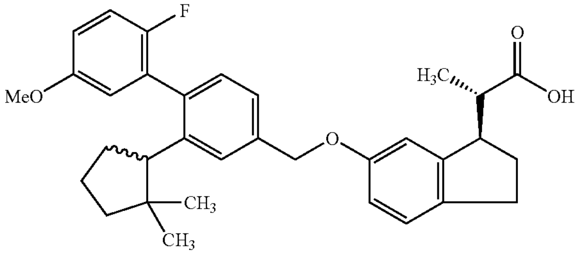 [SMILES: COc1ccc(F)c(-c2ccc(COc3ccc4c(c3)[C@@H]([C@H](C)C(=O)O)CC4)cc2C2CCCC2(C)C)c1] | ND | ND |
| 69 | 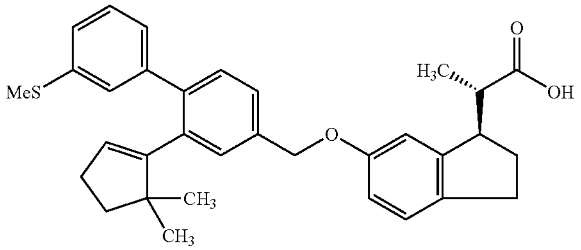 [SMILES: CSc1cccc(-c2ccc(COc3ccc4c(c3)[C@@H]([C@H](C)C(=O)O)CC4)cc2C2=CCCC2(C)C)c1] | ND | ND |
| 70 | 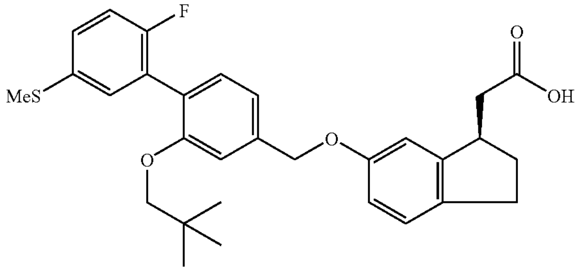 [SMILES: CSc1ccc(F)c(-c2ccc(COc3ccc4c(c3)[C@@H](CC(=O)O)CC4)cc2OCC(C)(C)C)c1] | ND | ND |
| 71 | 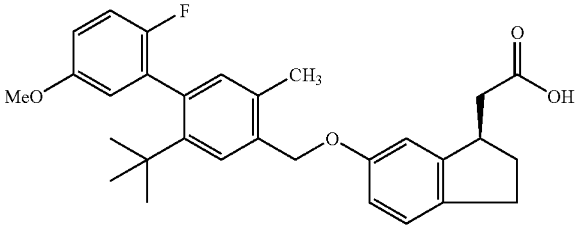 [SMILES: COc1ccc(F)c(-c2cc(C)c(COc3ccc4c(c3)[C@@H](CC(=O)O)CC4)cc2C(C)(C)C)c1] | ND | ND |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 72 | 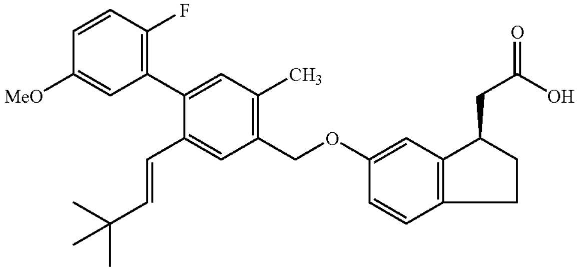 [SMILES: COc1ccc(F)c(-c2cc(C)c(COc3ccc4c(c3)[C@@H](CC(=O)O)CC4)cc2/C=C/C(C)(C)C)c1] | ND | ND |
| 73 | 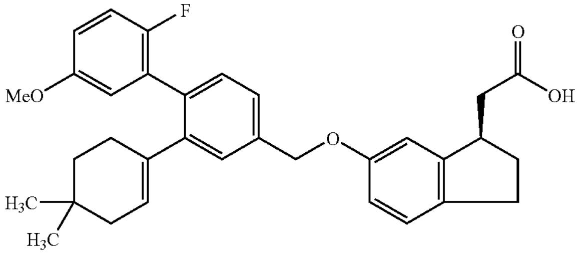 | ND | ND |
| 74 | 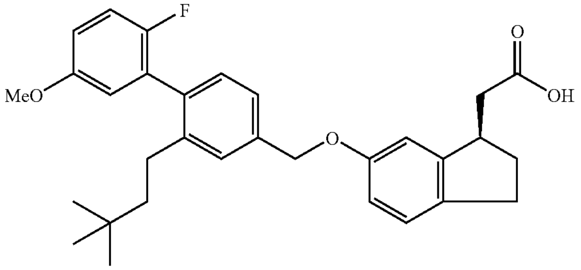 [SMILES: COc1ccc(F)c(-c2ccc(COc3ccc4c(c3)[C@@H](CC(=O)O)CC4)cc2CCC(C)(C)C)c1] | ND | ND |
| 75 | 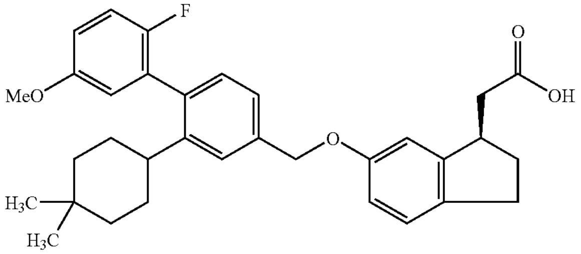 [SMILES: COc1ccc(F)c(-c2ccc(COc3ccc4c(c3)[C@@H](CC(=O)O)CC4)cc2C2CCC(C)(C)CC2)c1] | ND | ND |
| 76 | 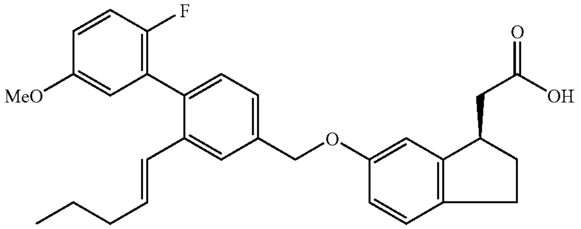 [SMILES: CCC/C=C/c1cc(COc2ccc3c(c2)[C@@H](CC(=O)O)CC3)ccc1-c1cc(OC)ccc1F] | ND | ND |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 77 | 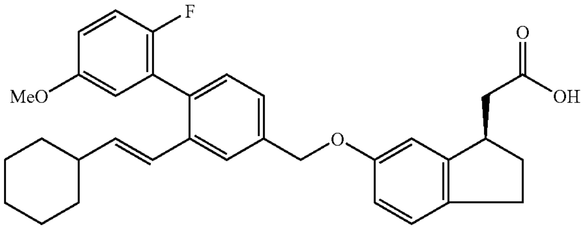 [SMILES: COc1ccc(F)c(-c2ccc(COc3ccc4c(c3)[C@@H](CC(=O)O)CC4)cc2/C=C/C2CCCCC2)c1] | ND | ND |
| 78 | 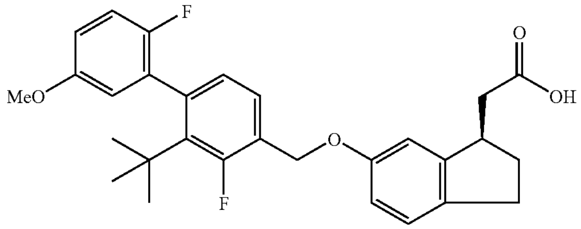 [SMILES: COc1ccc(F)c(-c2ccc(COc3ccc4c(c3)[C@@H](CC(=O)O)CC4)c(F)c2C(C)(C)C)c1] | ND | ND |
| 79 | 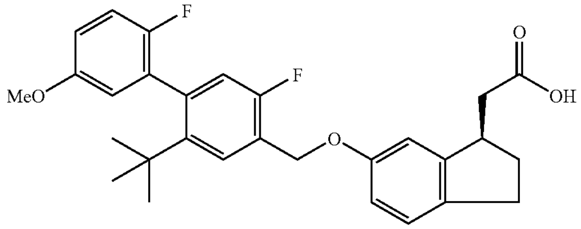 [SMILES: COc1ccc(F)c(-c2cc(F)c(COc3ccc4c(c3)[C@@H](CC(=O)O)CC4)cc2C(C)(C)C)c1] | ND | ND |
| 80 | 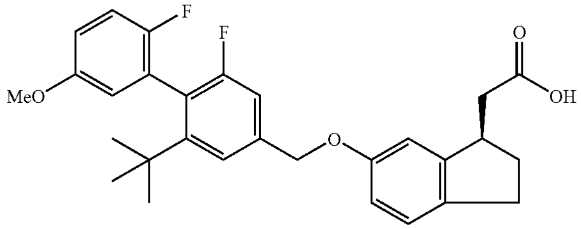 [SMILES: COc1ccc(F)c(-c2c(F)cc(COc3ccc4c(c3)[C@@H](CC(=O)O)CC4)cc2C(C)(C)C)c1] | ND | ND |
| 81 | 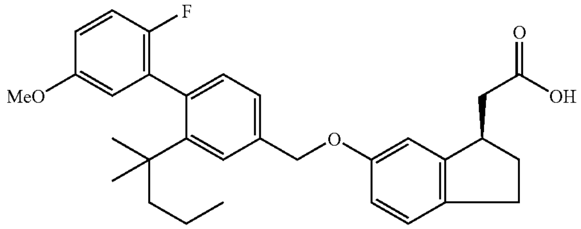 [SMILES: CCCC(C)(C)c1cc(COc2ccc3c(c2)[C@@H](CC(=O)O)CC3)ccc1-c1cc(OC)ccc1F] | ND | ND |
| 82 | 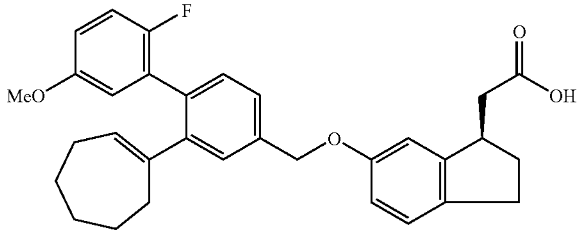 | ND | ND |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 83 | 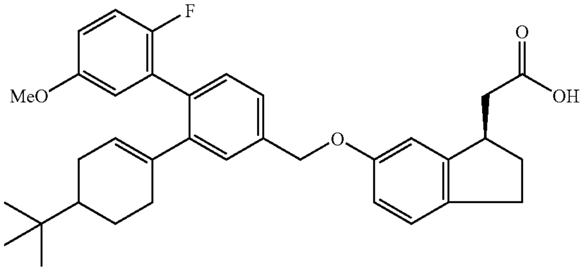 [SMILES: COc1ccc(F)c(-c2ccc(COc3ccc4c(c3)[C@@H](CC(=O)O)CC4)cc2C2=CCC(C(C)(C)C)CC2)c1] | ND | ND |
| 84 | 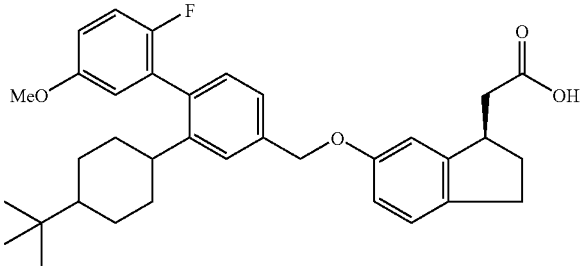 | ND | ND |
| 85 | 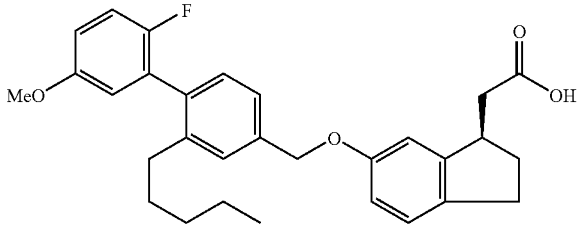 [SMILES: CCCCCc1cc(COc2ccc3c(c2)[C@@H](CC(=O)O)CC3)ccc1-c1cc(OC)ccc1F] | ND | ND |
| 86 | 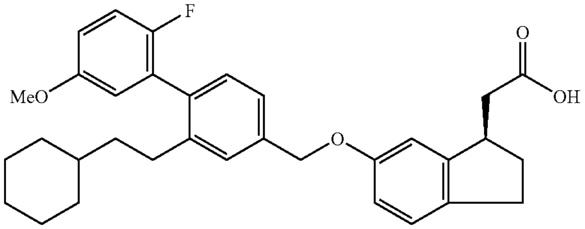 [SMILES: COc1ccc(F)c(-c2ccc(COc3ccc4c(c3)[C@@H](CC(=O)O)CC4)cc2CCC2CCCCC2)c1] | ND | ND |
| 87 | 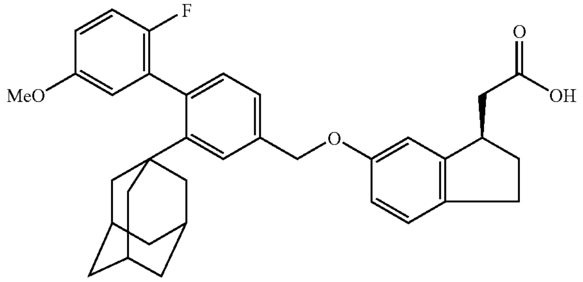 [SMILES: COc1ccc(F)c(-c2ccc(COc3ccc4c(c3)[C@@H](CC(=O)O)CC4)cc2C23CC4CC(CC(C4)C2)C3)c1] | ND | ND |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 88 | 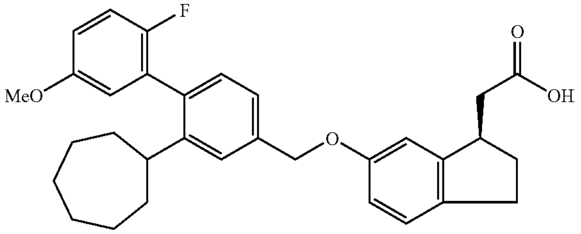 [SMILES: COc1ccc(F)c(-c2ccc(COc3ccc4c(c3)[C@@H](CC(=O)O)CC4)cc2C2CCCCCC2)c1] | ND | ND |
| 89 | 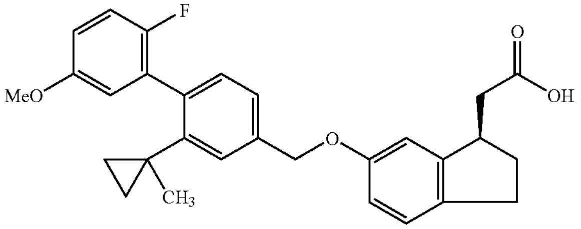 [SMILES: COc1ccc(F)c(-c2ccc(COc3ccc4c(c3)[C@@H](CC(=O)O)CC4)cc2C2(C)CC2)c1] | ND | ND |
| 90 | 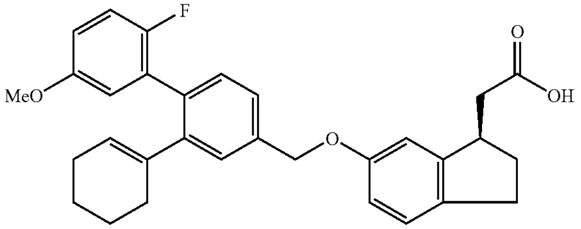 [SMILES: COc1ccc(F)c(-c2ccc(COc3ccc4c(c3)[C@@H](CC(=O)O)CC4)cc2C2=CCCCC2)c1] | ND | ND |
| 91 | 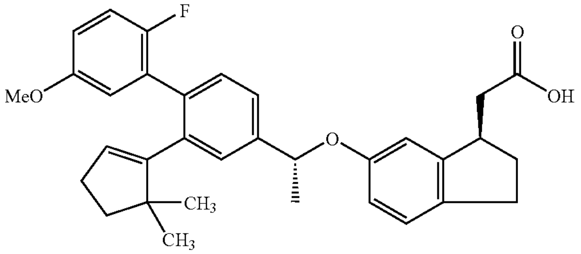 [SMILES: COc1ccc(F)c(-c2ccc([C@@H](C)Oc3ccc4c(c3)[C@@H](CC(=O)O)CC4)cc2C2=CCCC2(C)C)c1] | ND | ND |
| 92 | 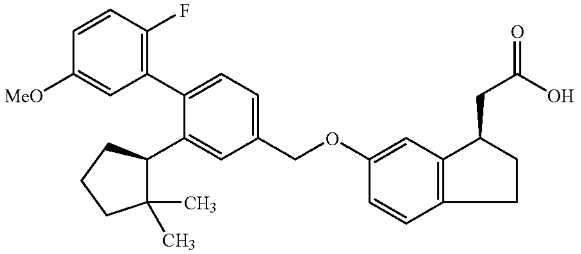 [SMILES: COc1ccc(F)c(-c2ccc(COc3ccc4c(c3)[C@@H](CC(=O)O)CC4)cc2[C@@H]2CCCC2(C)C)c1] | ND | ND |
| 93 | 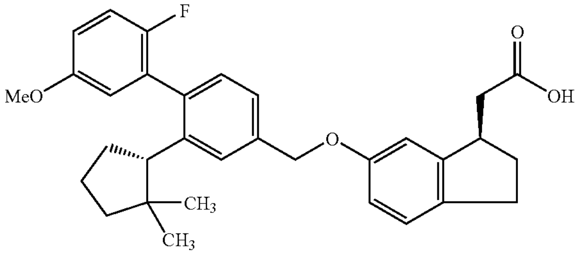 [SMILES: COc1ccc(F)c(-c2ccc(COc3ccc4c(c3)[C@@H](CC(=O)O)CC4)cc2[C@H]2CCCC2(C)C)c1] | ND | ND |

TABLE-continued
| Assay Data For Human GPR40 | | | |
|---|---|---|---|
| No. | Structure[a] | Aequorin $Ec_{50}$[b,c] | IP3 $EC_{50}$[c,d] |
| 94 | 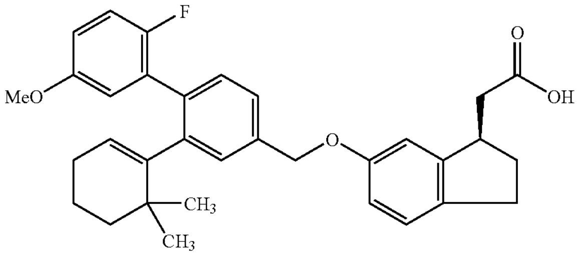 [SMILES: COc1ccc(F)c(-c2ccc(COc3ccc4c(c3)[C@@H](CC(=O)O)CC4)cc2C2=CCCCC2(C)C)c1] | ND | ND |
| 95 | 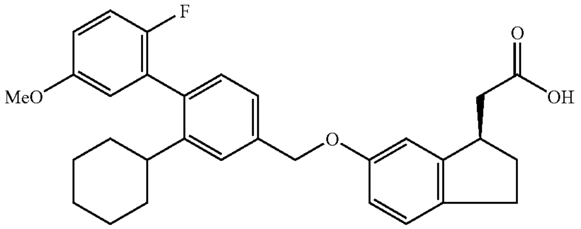 [SMILES: COc1ccc(F)c(-c2ccc(COc3ccc4c(c3)[C@@H](CC(=O)O)CC4)cc2C2CCCCC2)c1] | ND | ND |
| 96 | 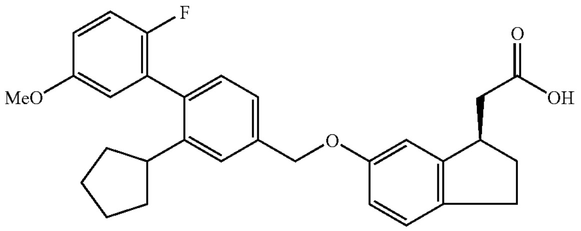 [SMILES: COc1ccc(F)c(-c2ccc(COc3ccc4c(c3)[C@@H](CC(=O)O)CC4)cc2C2CCCC2)c1] | ND | ND |
| 97 | 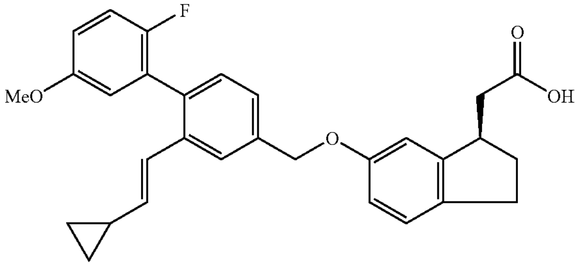 [SMILES: COc1ccc(F)c(-c2ccc(COc3ccc4c(c3)[C@@H](CC(=O)O)CC4)cc2/C=C/C2CC2)c1] | ND | ND |
| 98 | 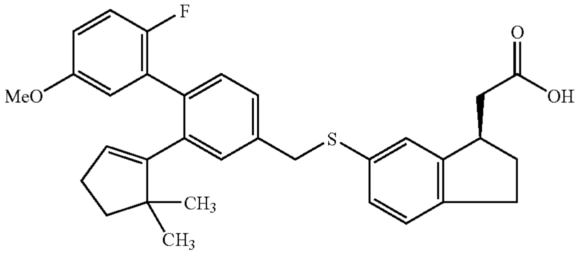 | ND | ND |
| 99 | 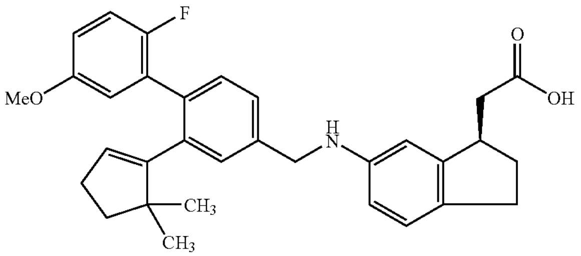 [SMILES: COc1ccc(F)c(-c2ccc(CSc3ccc4c(c3)[C@@H](CC(=O)O)CC4)cc2C2=CCCC2(C)C)c1] | ND | ND |

TABLE-continued
| No. | Structure[a] | Aequorin $Ec_{50}$[b,c] | IP3 $EC_{50}$[c,d] |
|---|---|---|---|
| | Assay Data For Human GPR40 | | |
| 100 | 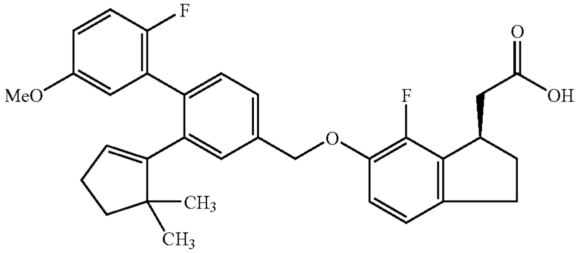 [SMILES: COc1ccc(F)c(-c2ccc(COc3ccc4c(c3F)[C@@H](CC(=O)O)CC4)cc2C2=CCCC2(C)C)c1] | ND | ND |
| 101 | 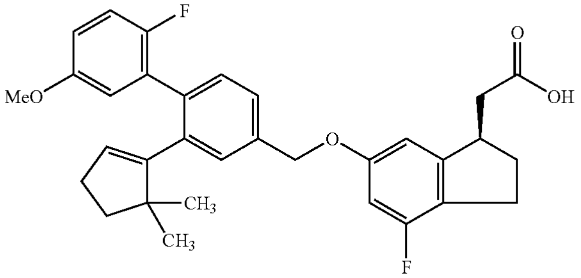 [SMILES: COc1ccc(F)c(-c2ccc(COc3cc(F)c4c(c3)[C@@H](CC(=O)O)CC4)cc2C2=CCCC2(C)C)c1] | ND | ND |
| 102 | 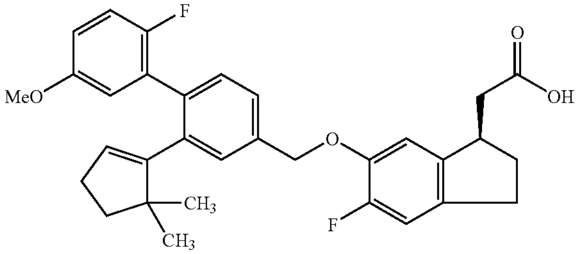 [SMILES: COc1ccc(F)c(-c2ccc(COc3cc4c(cc3F)CC[C@@H]4CC(=O)O)cc2C2=CCCC2(C)C)c1] | ND | ND |
| 103 | 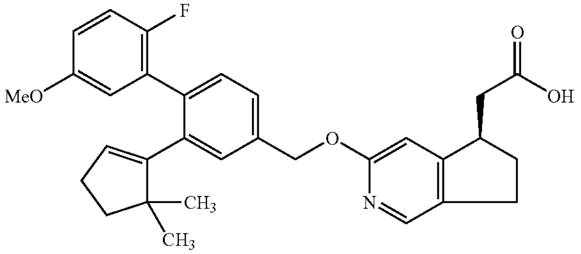 | ND | ND |
| 104 | 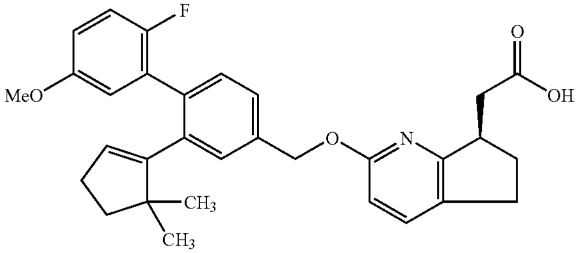 | ND | ND |

TABLE-continued

| Assay Data For Human GPR40 | | | |
|---|---|---|---|
| No. | Structure[a] | Aequorin $Ec_{50}$[b,c] | IP3 $EC_{50}$[c,d] |
| 105 | 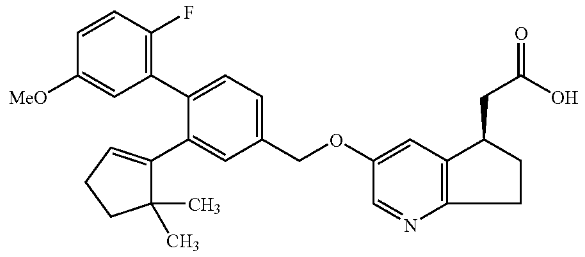 [SMILES: COc1ccc(F)c(-c2ccc(COc3cnc4c(c3)[C@@H](CC(=O)O)CC4)cc2C2=CCCC2(C)C)c1] | ND | ND |

[a]When present, the "〰" bond indicates a mixture of stereoisomers are present in the exemplary compound or indicates a mixture of cis and trans isomers when attached to a double bond.
[b]Aequorin assay data
[c]$EC_{50}$ Ranges:
+ $EC_{50}$ >10 μM
++ 1 μM ≦ $EC_{50}$ ≦ 10 μM
+++ 0.1 μM ≦ $EC_{50}$ < 1 μM
++++ 0.01 μM ≦ $EC_{50}$ < 0.1 μM
+++++ $EC_{50}$ < 0.01 μM
[d]Inositol phosphate assay data
[e]ND means not determined All publications and patent applications cited in this specification are hereby incorporated by reference as if each individual publication or patent application were specifically and individually indicated to be incorporated by reference. Each publication and patent application cited herein is incorporated in its entirety as if fully set forth herein. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of formula I or formula III:

I

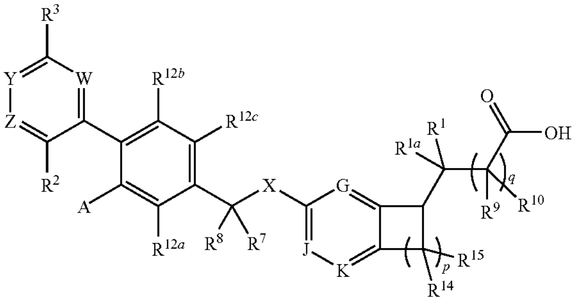

III

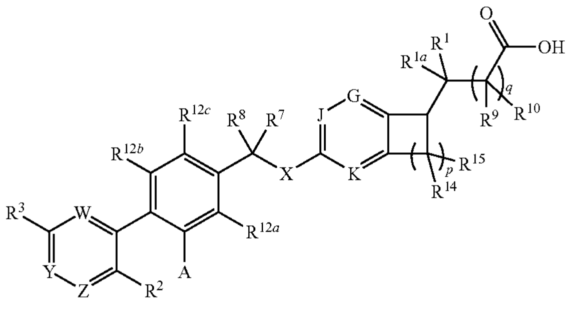

or a pharmaceutically acceptable salt, stereoisomer, or $C_1$-$C_6$ alkyl ester thereof; or a tautomer or a pharmaceutically acceptable salt, stereoisomer, or $C_1$-$C_6$ alkyl ester thereof; or a mixture thereof, wherein G is $CR^{11a}$;

J is $CR^{11b}$;

K is $CR^{11c}$;

A is an optionally substituted $C_5$-cycloalkyl or an optionally substituted $C_5$-cycloalkenyl group;

X is O;

W is C—H;

Y is C—H;

Z is C—H;

$R^1$ is selected from H or ($C_1$-$C_6$)alkyl;

$R^{1a}$ is selected from H or ($C_1$-$C_4$)alkyl;

$R^2$ is F;

$R^3$ is methoxy;

$R^7$ and $R^8$ are H;

$R^{14}$, and $R^{15}$ are, in each instance independently selected from H or ($C_1$-$C_4$)alkyl;

Each of $R^{11a}$, $R^{11b}$, and $R^{11c}$ is H;

Each of $R^{12a}$, $R^{12b}$, and $R^{12c}$ is H;

q is 0; and p is 1, 2, or 3.

2. The compound of claim 1, wherein $R^1$ is selected from H or ($C_1$-$C_4$)alkyl.

3. The compound of claim 2, wherein $R^1$ and $R^{1a}$ are independently selected from H or $CH_3$.

4. The compound of claim 1, wherein each instance of $R^{14}$ and $R^{15}$ is selected from H or $CH_3$.

5. The compound of claim 1, wherein A is a group of formula

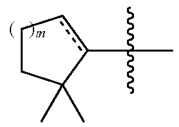

wherein m is 1, and the dashed line indicates a single or double bond.

6. The compound of claim 1, wherein the compound is a compound of formula I.

7. The compound of claim 6, wherein the compound of formula I is a compound of formula IIA, IIB, or IIC

IIA

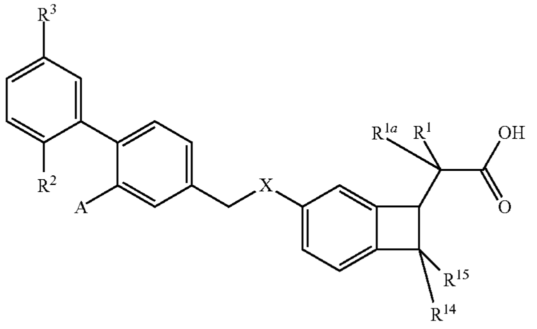

IIB

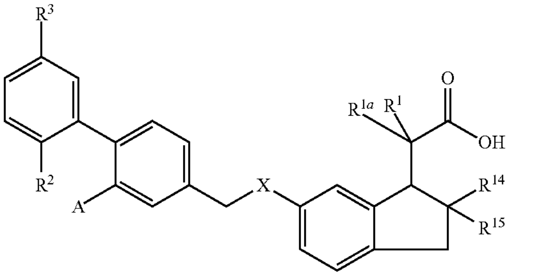

IIC

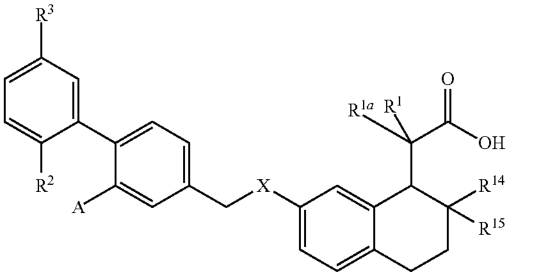

or a pharmaceutically acceptable salt, or $C_1$-$C_6$ alkyl ester thereof; or a tautomer or a pharmaceutically acceptable salt, or $C_1$-$C_6$ alkyl ester thereof; or a mixture thereof.

8. A pharmaceutical composition, comprising: a pharmaceutically acceptable carrier, diluent, or excipient, and the compound of claim 1.

9. A method for treating a disease or condition, comprising: administering to a subject in need thereof, a therapeutically effective amount of the compound of claim 1, wherein the disease or condition is type II diabetes.

10. The compound of claim 1, wherein the compound does not displace a compound of the following formula that is bound to the GPR40 receptor:

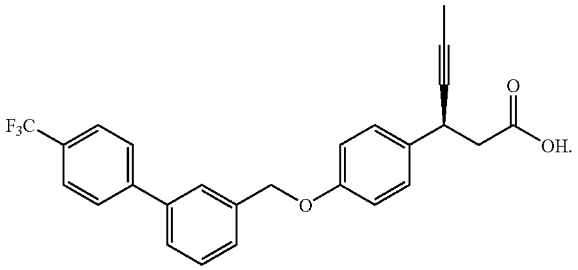 [SMILES: CC#C[C@@H](CC(=O)O)c1ccc(OCc2cccc(-c3ccc(C(F)(F)F)cc3)c2)cc1]

11. The compound of claim 1, wherein the compound is

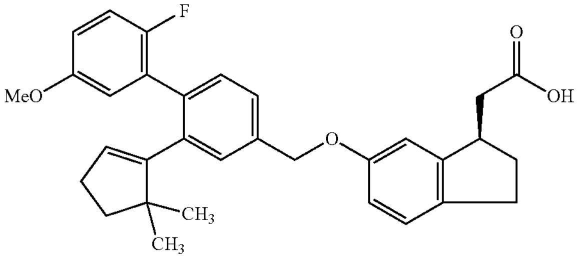

or

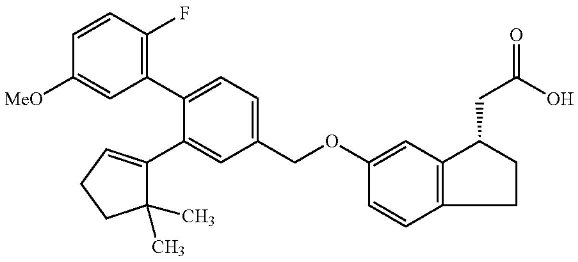

or the pharmaceutically acceptable salt thereof.

12. The compound of claim 1, wherein the compound is

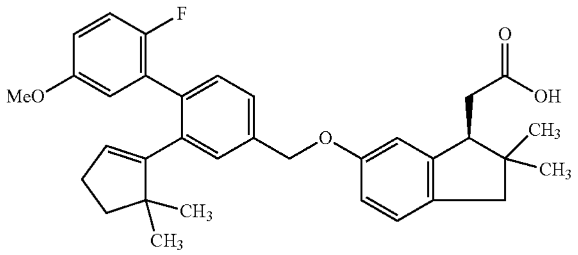

or

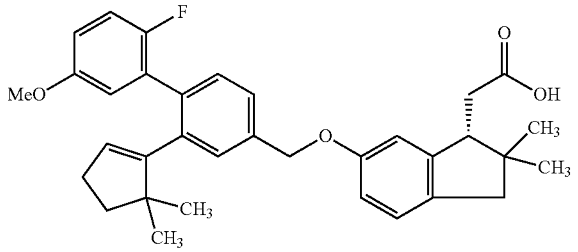

or the pharmaceutically acceptable salt thereof.

13. The compound of claim 1, wherein the compound is
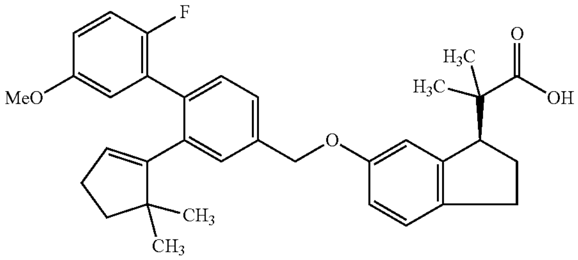
or
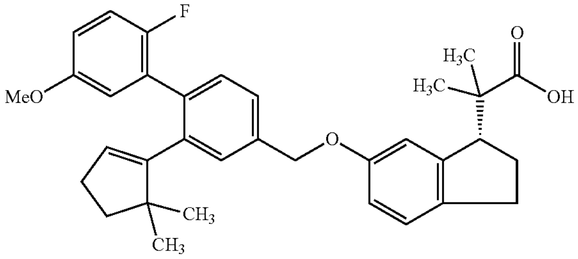
or the pharmaceutically acceptable salt thereof.
14. The compound of claim 1, wherein the compound is
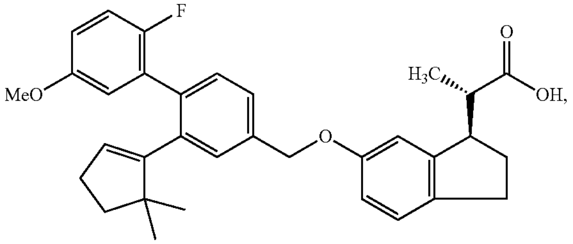
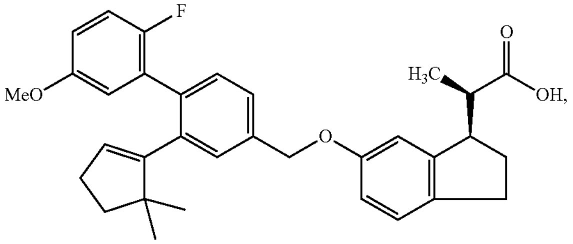
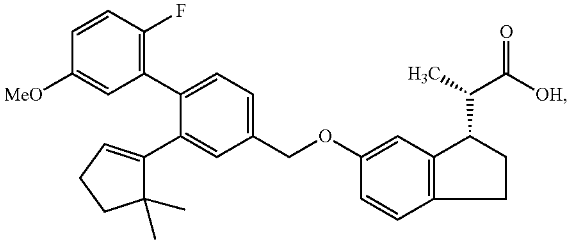
-continued
or
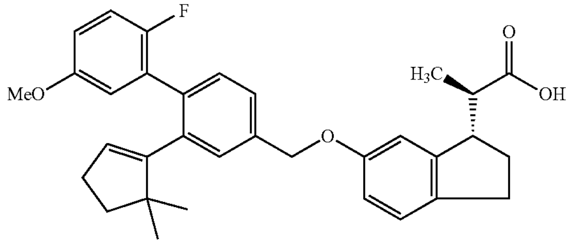
or the pharmaceutically acceptable salt thereof.
15. The compound of claim 1, wherein the compound is
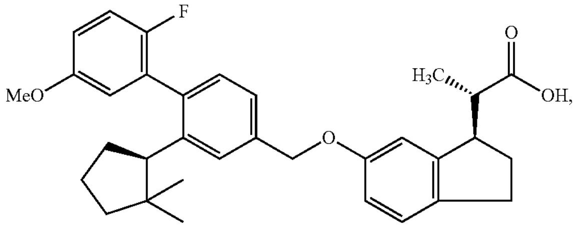
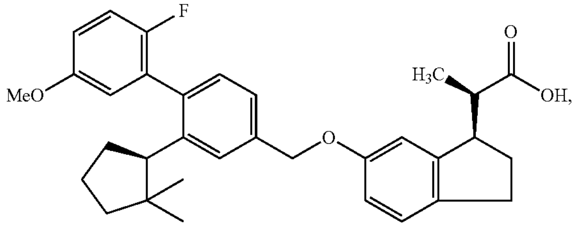
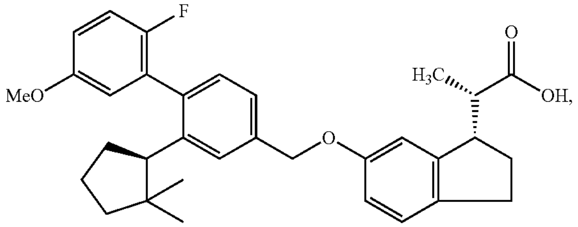
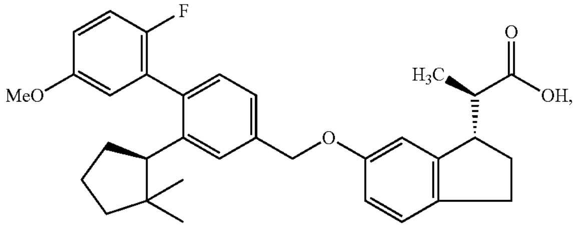
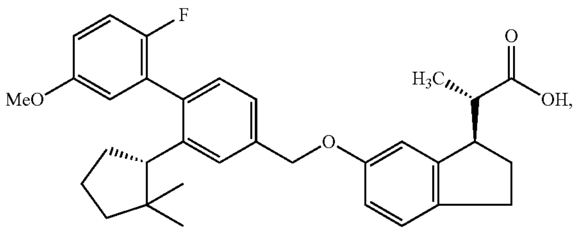

-continued
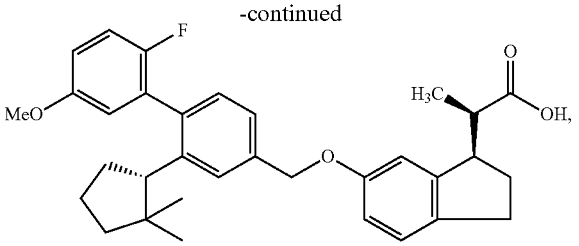
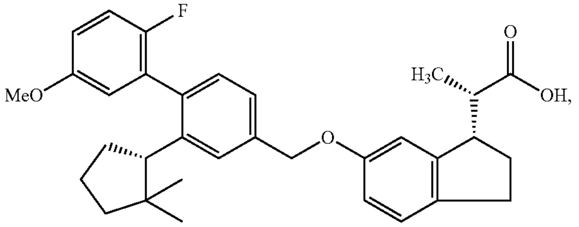
or
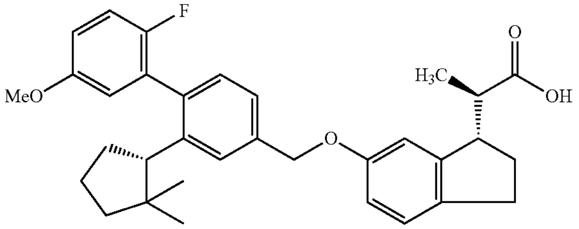
or the pharmaceutically acceptable salt thereof.
16. The compound of claim 1, wherein the compound is
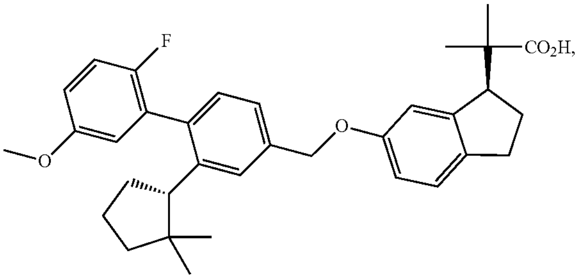
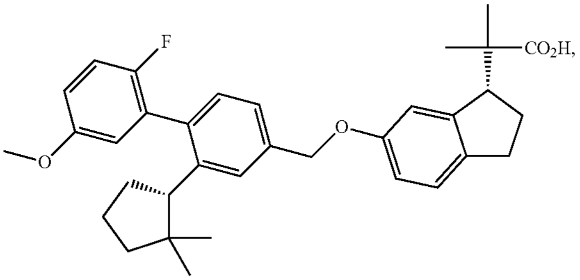
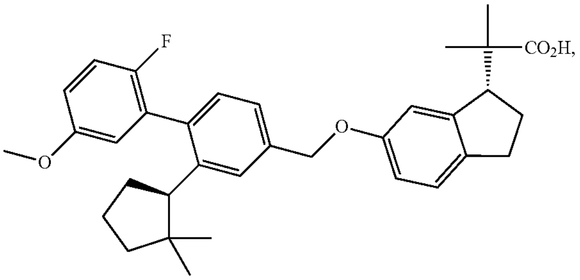
-continued
or
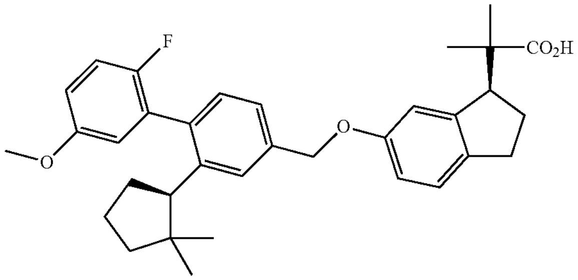
or the pharmaceutically acceptable salt thereof.
17. The compound of claim 1, wherein the compound is
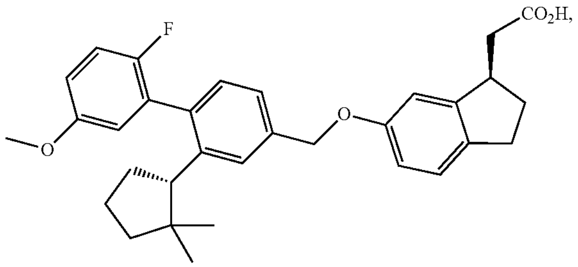
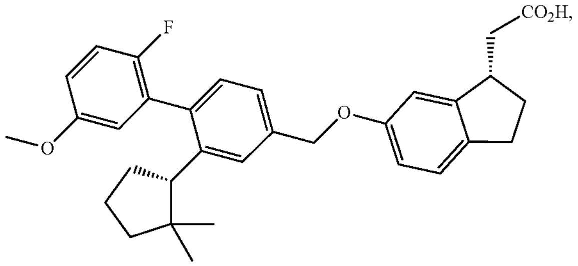
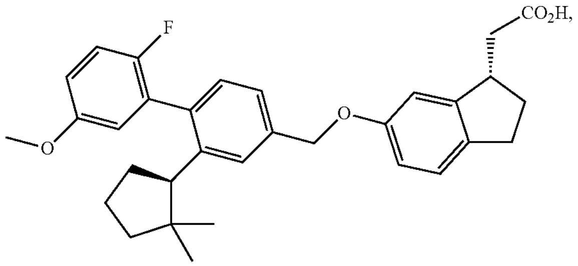
or
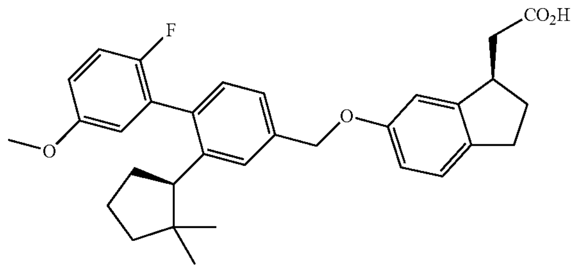
or the pharmaceutically acceptable salt thereof.
* * * * *